(12) United States Patent
Ioannidis et al.

(10) Patent No.: US 12,018,030 B2
(45) Date of Patent: Jun. 25, 2024

(54) PYRROLO AND PYRAZOLOPYRIMIDINES AS UBIQUITIN-SPECIFIC PROTEASE 7 INHIBITORS

(71) Applicant: Valo Health, Inc., Boston, MA (US)

(72) Inventors: Stephanos Ioannidis, Natick, MA (US); Adam Charles Talbot, Watertown, MA (US); Bruce Follows, Littleton, MA (US); Alexandre Joseph Buckmelter, Acton, MA (US); Minghua Wang, Acton, MA (US); Ann-Marie Campbell, Monroe, CT (US); Darby Rye Schmidt, Arlington, MA (US); David Joseph Guerin, Natick, MA (US); Justin Andrew Caravella, Cambridge, MA (US); R. Bruce Diebold, Waltham, MA (US); Anna Ericsson, Shrewsbury, MA (US); David R. Lancia, Jr., Boston, MA (US)

(73) Assignee: VALO HEALTH, INC., Boston, MA (US)

( * ) Notice: Subject to any disclaimer, the term of this patent is extended or adjusted under 35 U.S.C. 154(b) by 58 days.

(21) Appl. No.: 17/186,915

(22) Filed: Feb. 26, 2021

(65) Prior Publication Data

US 2021/0332052 A1 Oct. 28, 2021

Related U.S. Application Data

(63) Continuation of application No. 16/517,149, filed on Jul. 19, 2019, now Pat. No. 10,934,299, which is a continuation of application No. 15/874,163, filed on Jan. 18, 2018, now Pat. No. 10,377,760, which is a continuation of application No. 14/982,127, filed on Dec. 29, 2015, now Pat. No. 9,902,728.

(60) Provisional application No. 62/098,141, filed on Dec. 30, 2014.

(51) Int. Cl.
C07D 487/04 (2006.01)
A61K 31/519 (2006.01)
C07D 519/00 (2006.01)

(52) U.S. Cl.
CPC .......... *C07D 487/04* (2013.01); *A61K 31/519* (2013.01); *C07D 519/00* (2013.01)

(58) Field of Classification Search
CPC .......................... C07D 487/04; A61K 31/519
USPC ............................. 544/280; 514/265.1, 262.1
See application file for complete search history.

(56) References Cited

U.S. PATENT DOCUMENTS

| 4,895,841 | A | 1/1990 | Sugimoto et al. |
| 5,100,901 | A | 3/1992 | Sugimoto et al. |
| 5,124,335 | A | 6/1992 | Patchett et al. |
| 5,656,627 | A | 8/1997 | Bemis et al. |
| 5,716,929 | A | 2/1998 | Bemis et al. |
| 5,756,466 | A | 5/1998 | Bemis et al. |
| 5,847,135 | A | 12/1998 | Bemis et al. |
| 5,874,424 | A | 2/1999 | Batchelor et al. |
| 5,973,111 | A | 10/1999 | Bemis et al. |
| 5,985,863 | A | 11/1999 | Su et al. |
| 6,008,217 | A | 12/1999 | Batchelor et al. |
| 6,103,711 | A | 8/2000 | Bemis et al. |
| 6,204,261 | B1 | 3/2001 | Batchelor et al. |
| 6,258,948 | B1 | 7/2001 | Batchelor et al. |
| 6,420,522 | B1 | 7/2002 | Bemis et al. |
| 6,423,840 | B1 | 7/2002 | Batchelor et al. |
| 6,432,964 | B1 | 8/2002 | Atherall et al. |
| 6,444,816 | B1 | 9/2002 | Das et al. |
| 6,482,838 | B2 | 11/2002 | Pratt |
| 6,506,771 | B2 | 1/2003 | Pinto et al. |
| 6,541,630 | B1 | 4/2003 | Atherall et al. |
| 6,576,646 | B1 | 6/2003 | Pratt |
| 6,632,815 | B2 | 10/2003 | Zhu et al. |
| 6,686,368 | B1 | 2/2004 | Zhu et al. |

(Continued)

FOREIGN PATENT DOCUMENTS

CN 103833646 A 6/2014
EP 1460077 A1 9/2004

(Continued)

OTHER PUBLICATIONS

Banker, et. al., Modern Pharmaceuticals, 596 (1996).
Corrected Petition for Post Grant Review of U.S. Pat. No. 9,840,491 (PGR2018-00098, dated Oct. 1, 2018, Paper No. 4).
Database Registry [Online] Chemical Abstracts Service, Columbus, Ohio; Mar. 23, 2009, XP002755482, Data base accession No. 1125429-24-4, the whole document.
Database Registry [Online] Chemical Abstracts Service, Columbus, Ohio; Mar. 23, 2009, XP002755483, Database accession No. 1125419-46-6, the whole document.
Database Registry [Online] Chemical Abstracts Service, Columbus, Ohio; Jul. 4, 2012 (Jul. 4, 2012), XP002755481, Database accession No. 1381357-58-9.

(Continued)

*Primary Examiner* — Jeffrey H Murray
(74) *Attorney, Agent, or Firm* — Dechert LLP; Nicholas J. Pace; Steven M. Swick

(57) ABSTRACT

The invention relates to inhibitors of USP7 inhibitors useful in the treatment of cancers, neurodegenerative diseases, immunological disorders, inflammatory disorders, cardiovascular diseases, ischemic diseases, viral infections and diseases, and bacterial infections and diseases, having the Formula:

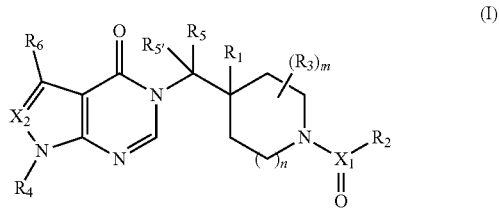

(I)

where m, n, $X_1$, $X_2$, $R_1$-$R_5$, $R_{5'}$ and $R_6$ are described herein.

16 Claims, No Drawings

(56) References Cited

U.S. PATENT DOCUMENTS

| | | | |
|---|---|---|---|
| 6,689,795 B2 | 2/2004 | Pratt | |
| 6,720,317 B1 | 4/2004 | Zhu et al. | |
| 6,943,253 B2 | 9/2005 | Vidal Juan et al. | |
| 6,960,595 B2 | 11/2005 | Pinto et al. | |
| 6,964,957 B2 | 11/2005 | Abreo et al. | |
| 7,253,204 B2 | 8/2007 | Delorme et al. | |
| 7,285,565 B2 | 10/2007 | Zhu et al. | |
| 7,288,624 B2 | 10/2007 | Bemis et al. | |
| 7,557,113 B2 | 7/2009 | Tsutsumi et al. | |
| 7,563,808 B2 | 7/2009 | Pratt | |
| 7,601,728 B2 | 10/2009 | Nakahira et al. | |
| 7,745,447 B2 | 6/2010 | Washburn et al. | |
| 7,772,366 B2 | 8/2010 | Bemis et al. | |
| 7,790,713 B2 | 9/2010 | Batchelor et al. | |
| 7,816,363 B2 | 10/2010 | Angibaud et al. | |
| 7,868,205 B2 | 1/2011 | Moradei et al. | |
| 7,932,246 B2 | 4/2011 | Moffat et al. | |
| 7,989,445 B2 | 8/2011 | Murata et al. | |
| 8,084,459 B2 | 12/2011 | Kok et al. | |
| 8,088,805 B2 | 1/2012 | Delorme et al. | |
| 8,119,631 B2 | 2/2012 | Batchelor et al. | |
| 8,133,998 B2 | 3/2012 | Pajouhesh et al. | |
| 8,268,833 B2 | 9/2012 | Angibaud et al. | |
| 8,343,988 B2 | 1/2013 | Angibaud et al. | |
| 8,575,114 B2 | 11/2013 | Liu et al. | |
| 8,586,619 B2 | 11/2013 | Wu et al. | |
| 8,618,115 B2 | 12/2013 | Washburn et al. | |
| 8,642,609 B2 | 2/2014 | Makings et al. | |
| 8,765,773 B2 | 7/2014 | England et al. | |
| 8,841,289 B2 | 9/2014 | Ratcliffe et al. | |
| 8,859,566 B2 | 10/2014 | Palle et al. | |
| 8,927,718 B2 | 1/2015 | Sasaki et al. | |
| 9,260,448 B2 | 2/2016 | Choo et al. | |
| 9,273,068 B2 | 3/2016 | Geneste et al. | |
| 9,284,297 B2 | 3/2016 | Keller et al. | |
| 9,546,150 B2 | 1/2017 | Colland et al. | |
| 9,840,491 B2 | 12/2017 | Ioannidis et al. | |
| 9,902,728 B2* | 2/2018 | Ioannidis | C07D 519/00 |
| 9,932,351 B2 | 4/2018 | Ioannidis et al. | |
| 9,938,300 B2 | 4/2018 | Ioannidis et al. | |
| 10,000,495 B2 | 6/2018 | Ioannidis et al. | |
| 10,351,571 B2 | 7/2019 | Ioannidis et al. | |
| 10,377,760 B2* | 8/2019 | Ioannidis | A61P 9/00 |
| 10,377,767 B2 | 8/2019 | Ioannidis et al. | |
| 10,377,773 B2 | 8/2019 | Ioannidis et al. | |
| 10,508,098 B2 | 12/2019 | Ioannidis et al. | |
| 10,513,507 B2 | 12/2019 | Ioannidis et al. | |
| 10,513,508 B2 | 12/2019 | Ioannidis et al. | |
| 10,519,127 B2 | 12/2019 | Ioannidis et al. | |
| 10,519,128 B2 | 12/2019 | Ioannidis et al. | |
| 10,519,129 B2 | 12/2019 | Ioannidis et al. | |
| 10,519,130 B2 | 12/2019 | Ioannidis et al. | |
| 10,836,741 B2 | 11/2020 | Ioannidis et al. | |
| 10,906,916 B2 | 2/2021 | Ioannidis et al. | |
| 10,927,130 B2 | 2/2021 | Ioannidis et al. | |
| 10,934,299 B2* | 3/2021 | Ioannidis | A61P 25/28 |
| 10,981,915 B2 | 4/2021 | Ioannidis et al. | |
| 2002/0035128 A1 | 3/2002 | Pratt | |
| 2002/0132319 A1 | 9/2002 | Abreo et al. | |
| 2002/0169175 A1 | 11/2002 | Gaddam et al. | |
| 2003/0153598 A1 | 8/2003 | Pratt | |
| 2003/0225269 A1 | 12/2003 | Batchelor et al. | |
| 2004/0038994 A1 | 2/2004 | Wilson | |
| 2004/0039012 A1 | 2/2004 | Wilson | |
| 2004/0116399 A1 | 6/2004 | Zhu et al. | |
| 2004/0132732 A1 | 7/2004 | Han et al. | |
| 2004/0180931 A1 | 9/2004 | Pratt | |
| 2004/0192732 A1 | 9/2004 | Pratt et al. | |
| 2004/0214863 A1 | 10/2004 | Pratt | |
| 2005/0143436 A1 | 6/2005 | Batchelor et al. | |
| 2005/0148534 A1 | 7/2005 | Castellino et al. | |
| 2005/0153992 A1 | 7/2005 | Tsutsumi et al. | |
| 2005/0250812 A1 | 11/2005 | Pratt | |
| 2006/0018839 A1 | 1/2006 | Ieni et al. | |
| 2006/0135507 A1 | 6/2006 | Yokoyama et al. | |
| 2006/0172992 A1 | 8/2006 | Yokoyama et al. | |
| 2006/0183776 A9 | 8/2006 | Pratt | |
| 2006/0234909 A1 | 10/2006 | Newman et al. | |
| 2007/0053976 A1 | 3/2007 | Sakai et al. | |
| 2008/0045500 A1 | 2/2008 | Teramoto et al. | |
| 2008/0064680 A1 | 3/2008 | Bamdad | |
| 2008/0119457 A1 | 5/2008 | Huang et al. | |
| 2008/0167343 A1 | 7/2008 | Ieni et al. | |
| 2008/0312189 A1 | 12/2008 | Pratt | |
| 2008/0318922 A1 | 12/2008 | Nakahira et al. | |
| 2009/0042939 A1 | 2/2009 | Ieni et al. | |
| 2009/0042940 A1 | 2/2009 | Ieni et al. | |
| 2009/0118261 A1 | 5/2009 | Aquila et al. | |
| 2009/0192129 A1 | 7/2009 | Nakahira et al. | |
| 2009/0192138 A1 | 7/2009 | Baeschlin et al. | |
| 2009/0253704 A1 | 10/2009 | Koltun et al. | |
| 2011/0015193 A1 | 1/2011 | Eickmeier et al. | |
| 2011/0015371 A1 | 1/2011 | Bemis et al. | |
| 2011/0053981 A1 | 3/2011 | Ieni et al. | |
| 2011/0082158 A1 | 4/2011 | Gangjee et al. | |
| 2011/0184000 A1 | 7/2011 | Giovannini et al. | |
| 2011/0263532 A1 | 10/2011 | Keller et al. | |
| 2012/0122889 A1 | 5/2012 | Yuan et al. | |
| 2012/0165319 A1 | 6/2012 | Batchelor et al. | |
| 2012/0238749 A1 | 9/2012 | Bemis et al. | |
| 2013/0085133 A1 | 4/2013 | Severson et al. | |
| 2013/0116241 A1 | 5/2013 | Geneste et al. | |
| 2013/0303551 A1 | 11/2013 | Adams et al. | |
| 2014/0024657 A1 | 1/2014 | Yuan et al. | |
| 2014/0213779 A1 | 7/2014 | Dixon et al. | |
| 2016/0185785 A1 | 6/2016 | Ioannidis et al. | |
| 2016/0185786 A1 | 6/2016 | Ioannidis et al. | |
| 2016/0229833 A1 | 8/2016 | Ioannidis et al. | |
| 2016/0229864 A1 | 8/2016 | Ioannidis et al. | |
| 2016/0229872 A1 | 8/2016 | Ioannidis et al. | |
| 2018/0162835 A1 | 6/2018 | Ioannidis et al. | |
| 2018/0339988 A1 | 11/2018 | Ioannidis et al. | |
| 2018/0339991 A1 | 11/2018 | Ioannidis et al. | |
| 2018/0346480 A1 | 12/2018 | Ioannidis et al. | |
| 2018/0346485 A1 | 12/2018 | Ioannidis et al. | |
| 2019/0071418 A1 | 3/2019 | Ioannidis et al. | |
| 2019/0071419 A1 | 3/2019 | Ioannidis et al. | |
| 2019/0071420 A1 | 3/2019 | Ioannidis et al. | |
| 2019/0071421 A1 | 3/2019 | Ioannidis et al. | |
| 2019/0071422 A1 | 3/2019 | Ioannidis et al. | |
| 2019/0071423 A1 | 3/2019 | Ioannidis et al. | |
| 2019/0308980 A1 | 10/2019 | Ioannidis et al. | |
| 2019/0359629 A1 | 11/2019 | Ioannidis et al. | |
| 2019/0359635 A1 | 11/2019 | Ioannidis et al. | |
| 2019/0367525 A1 | 12/2019 | Ioannidis et al. | |
| 2020/0087280 A1 | 3/2020 | Ioannidis et al. | |
| 2021/0130321 A1 | 5/2021 | Ioannidis et al. | |
| 2021/0292337 A1 | 9/2021 | Ioannidis et al. | |
| 2021/0323978 A1 | 10/2021 | Ioannidis et al. | |
| 2022/0033403 A1 | 2/2022 | Ioannidis et al. | |

FOREIGN PATENT DOCUMENTS

| | | |
|---|---|---|
| EP | 2 565 186 A1 | 3/2013 |
| IN | 151496 B | 5/1983 |
| JP | H02-169569 A | 6/1990 |
| JP | 2002105081 A | 4/2002 |
| JP | 2006176503 A | 7/2006 |
| WO | WO-98/02162 A1 | 1/1998 |
| WO | WO-99/08501 A2 | 2/1999 |
| WO | WO-02/16365 A1 | 2/2002 |
| WO | WO-2003/024456 A1 | 3/2003 |
| WO | WO-2003/092606 A2 | 11/2003 |
| WO | WO-2004/037176 A2 | 5/2004 |
| WO | WO-2004/058727 A1 | 7/2004 |
| WO | WO-2005/019219 A1 | 3/2005 |
| WO | WO-2005/030704 A1 | 4/2005 |
| WO | WO-2007/053135 A1 | 5/2007 |
| WO | WO-2008/094909 A2 | 8/2008 |
| WO | WO-2008/113255 A1 | 9/2008 |
| WO | WO-2008/116053 A2 | 9/2008 |
| WO | WO-2009/010925 A2 | 1/2009 |
| WO | WO-2009/011617 A2 | 1/2009 |
| WO | WO-2012/075393 A2 | 6/2012 |

(56) References Cited

FOREIGN PATENT DOCUMENTS

| WO | WO-2013/030218 A1 | 3/2013 |
| --- | --- | --- |
| WO | WO-2013/130660 A1 | 9/2013 |
| WO | WO-2013/140189 A1 | 9/2013 |
| WO | WO-2014/105952 A2 | 7/2014 |
| WO | WO-2016/109480 A1 | 7/2016 |
| WO | WO-2016/109515 A1 | 7/2016 |
| WO | WO-2016/126926 A1 | 8/2016 |
| WO | WO-2016/126929 A1 | 8/2016 |
| WO | WO-2016/126935 A1 | 8/2016 |

OTHER PUBLICATIONS

Database Registry [Online] Chemical Abstracts Service, Columbus, Ohio; Jul. 4, 2012 (Jul. 4, 2012), XP002755499, Database accession No. 1381443-55-5.
Database Registry [Online] Chemical Abstracts Service, Columbus, Ohio; Jul. 4, 2012 (Jul. 4, 2012), XP002755500, Database accession No. 1381443-96-4.
Database Registry [Online] Chemical Abstracts Service, Columbus, Ohio; Jul. 4, 2012 (Jul. 4, 2012), XP002755501, Database accession No. 1381349-35-4.
Database Registry [Online] Chemical Abstracts Service, Columbus, Ohio; Jul. 4, 2012 (Jul. 4, 2012), XP002755502, Database accession No. 1381291-44-6.
Database Registry [Online] Chemical Abstracts Service, Columbus, Ohio; Jul. 4, 2012 (Jul. 4, 2012), XP002755503, Database accession No. 1381280-64-3.
Database Registry [Online] Chemical Abstracts Service, Columbus, Ohio; Jul. 4, 2012 (Jul. 4, 2012), XP002755504, Database accession No. 1381443-88-4.
Du, Z. et al. DNMT1 stability is regulated by proteins coordinating deubiquitination and acetylation-driven ubiquitination, Sci. Signal. 3(146) (2010).
Epping M.T., et al. TSPYL5 suppresses p53 levels and function by physical interaction with USP7, Nat. Cell Biol. 13(1):102-108 (2011).
Everett R.D. et al. A novel ubiquitin-specific protease is dynamically associated with the PML nuclear domain and binds to a herpes virus regulatory protein, EMBO J 16(7): 1519-1530 (1997).
Faustrup H. et al. USP7 counteracts SCFβTrCP—but not APC Cdh1—mediated proteolysis of Claspin, J Cell Biol. 184(1):13-19 (2009).
Finley D. Recognition and processing of ubiquitin-protein conjugates by the proteasome Annu. Rev. Biochem. 78:477-513, (2009).
Gao Y. et al. Early adipogenesis is regulated through USP7-mediated deubiquitination of the hi stone acetyltransferase TIP60, Nat. Commun. 4:2656 (2013).
Gavory, G., et al., Discovery and characterization of highly potent and selective allosteric USP7 inhibitors, Nature chemical biology, 14: 118-125, (2018).
Holowaty M.N. et al. Protein profiling with Epstein-Barr nuclear antigen-I reveals an interaction with the herpesvirus-associated ubiquitin-specific protease HAUSP/USP7, J Biol. Chem. 278(32):29987-29994 (2003).
International Search Report for PCT/US2015/067781, 4 pages (dated Mar. 8, 2016).
International Search Report for PCT/US2015/067831, 4 pages (dated Mar. 23, 2016).
International Search Report for PCT/US2016/016542, 6 pages (dated Apr. 15, 2016).
International Search Report for PCT/US2016/016548, 4 pages (dated Apr. 5, 2016).
International Search Report for PCT/US2016/016556, 3 pages (dated Mar. 23, 2016).
Kessler, B., Selective and reversible inhibitors of ubiquitin-specific protease 7: a patent evaluation, Expert Opinion on Therapeutic Patents, 24(5): 597-602 (2014).
Komander D. The emerging complexity of protein ubiquitination, Biochem. Soc. Trans. 37(Pt 5):937-953 (2009).
Li M. et al. A dynamic role of HAUSP in the p53-Mdm2 pathway, Mal. Cell. 13(6):879-886 (2004).
Li M. et al. Deubiquitination of p53 by HAUSP is an important pathway for p53 stabilization, Nature 416(6881):648-653 (2002).
McMahon et al., VEGF Receptor Signaling in Tumor Angiogenesis, The Oncologist 2000; 5 (suppl 1): 3-10.
Petition for Post Grant Review of U.S. Pat. No. 9,840,491 (PGR2018-00098, dated Sep. 12, 2018, Paper No. 1).
Pinedo et al. Translational Research: The Role of VEGF in Tumor Angiogenesis, The Oncologist 2000; 5 (Suppl 1):1-2.
Saridakis V., et al. Structure of the p53 binding domain of HAUSP/USP7 bound to Epstein-Barr nuclear antigen 1 implications for EBY-mediated immortalization, Mal. Cell. 18(1):25-36 (2005).
Sarkari F. et al. EBNAI-mediated recruitment of a histone H2B deubiquitylating complex to the Epstein-Barr virus latent origin of DNA replication, PLoS pathoKens 5(10):el 000624 (2009).
Sep. 11, 2018 Declaration of Remi Delansorne, part 1 of 2 (PGR2018-00098, EX-1005).
Sep. 11, 2018 Declaration of Remi Delansorne, part 2 of 2 (PGR2018-00098, EX-1006).
Sheng Y. et al. Molecular recognition of p53 and MDM2 by USP7/HAUSP, Nat. Struct. Mal. Biol. 13(3):285-291 (2006).
Sippl, W. et al. Ubiquitin-specific proteases as cancer drug targets, Future Oncology, vol. (7)5,1:619-632, (2011).
Song M.S. et al. The deubiquitinylation and localization of PTEN are regulated by a HAUSP-PML network, Nature 455(7214):813-817 (2008).
Trotman L.C., et al. Ubiquitination regulates PTEN nuclear import and tumor suppression, Cell 128(1): 141-156 (2007).
Turnbull, A.P. et al., Molecular basis of USP7 inhibition by selective small-molecule inhibitors, Nature, 550: 481-486 (2017), 24 pages.
Van der Horst A et al. FOX04 transcriptional activity is regulated by monoubiquitination and USP7/HAUSP, Nat. Cell Biol. 8(10): 1064-1073 (2006).
Vippagunta et al. Crystalline Solids, Advanced Drug Delivery Reviews, 48 (2001) 3-26.
West, A.R., Solid State Chemistry and Its Applications, Wiley, New York, Chapter 10: 358 (1988).
Wolff et. al., Burger's Medicinal Chemistry and Drug Discovery, 5th Ed. Part 1: 975-977 (1995).
Written Opinion for PCT/US2015/067781 (Publication WO2016/109480), 6 pages (dated Jul. 7, 2016).
Written Opinion for PCT/US2015/067831 (Publication WO2016/109515), 6 pages (dated Mar. 23, 2016).
Written Opinion for PCT/US2016/016542 (Publication WO2016/126926), 9 pages (dated Aug. 11, 2016).
Written Opinion for PCT/US2016/016548 (Publication WO2016/126929), 9 pages (dated Apr. 15, 2016).
Written Opinion for PCT/US2016/016556, (Publication WO2016/126935), 6 pages (dated Mar. 23, 2016).

* cited by examiner

PYRROLO AND PYRAZOLOPYRIMIDINES AS UBIQUITIN-SPECIFIC PROTEASE 7 INHIBITORS

RELATED APPLICATIONS

This application is a continuation of U.S. application Ser. No. 16/517,149, now U.S. Patent No. 10,934,299, filed Jul. 19, 2019, which is a continuation of U.S. application Ser. No. 15/874,163, now U.S. Pat. No. 10,377,760, filed Jan. 18, 2018, which is a continuation application of U.S. application Ser. No. 14/982,127, now U.S. Pat. No. 9,902,728, filed Dec. 29, 2015, which claims the benefit of and priority to U.S. provisional application No. 62/098,141 filed Dec. 30, 2014, the entire contents of each of which are incorporated herein by reference in its entirety.

FIELD OF INVENTION

The present invention is directed to inhibitors of ubiquitin-specific protease 7 (USP7) useful in the treatment of diseases or disorders associated with USP7 enzymes. Specifically, the invention is concerned with compounds and compositions inhibiting USP7, methods of treating diseases or disorders associated with USP7, and methods of synthesis of these compounds.

BACKGROUND OF THE INVENTION

Ubiquitination is a post translational modification initially identified as a crucial component of proteasomal degradation in the ubiquitin proteasome system (UPS). Chains of Ubiquitin (Ub(s)), an 8.5 kDa highly conserved protein, are covalently attached to substrates to be degraded in the proteasome (Finley D. "Recognition and processing of ubiquitin-protein conjugates by the proteasome." *Annual review of biochemistry* 78:477-513, (2009)) The molecular mechanisms by which the UPS acts are also varied, with different chain linkages of ubiquitination controlling protein turnover, enzymatic activity, subcellular localization, and protein-protein interactions of substrate proteins. (Komander D., et. al. "The emerging complexity of protein ubiquitination," *Biochem. Soc. Trans.* 37(Pt 5):937-53 (2009))

Ubiquitin-specific protease 7 (USP7) is a Ubiquitin Specific Protease (USP) family deubiquitinase (DUB) that was originally identified as an enzyme that interacted with virally-encoded proteins of the Herpes simplex virus and later the Epstein-Barr virus (Everett R. D., Meredith M., Orr A., Cross A, Kathoria M., Parkinson J. "A novel ubiquitin-specific protease is dynamically associated with the PML nuclear domain and binds to a herpes virus regulatory protein," *EMBO J.* 16(7):1519-30 (1997); Holowaty M. N., Zeghouf M., Wu H., et al. "Protein profiling with Epstein-Barr nuclear antigen-1 reveals an interaction with the herpesvirus-associated ubiquitin-specific protease HAUSP/USP7," *J. Biol. Chem.* 278(32):29987-94 (2003)) Ubiquitin Specific Proteases (USPs) specifically cleave the isopeptide bond at the carboxy terminus of ubiquitin. In contrast to other DUB classes, which are thought to generally regulate ubiquitin homeostasis or to be involved in pre-processing of linear ubiquitin chains, USPs remove ubiquitin from specific targets. Given this substrate specificity combined with the numerous roles ubiquitination has in the cell, USPs are important regulators of a multitude of pathways, ranging from preventing the proteolysis of ubiquitinated substrates, to controlling their nuclear localization.

USP7 deubiquitinates a variety of cellular targets involved in different processes related to cancer and metastasis, neurodegenerative diseases, immunological disorders, osteoporosis, arthritis inflammatory disorders, cardiovascular diseases, ischemic diseases, viral infections and diseases, and bacterial infections and diseases.

For example, USP7 has been shown to stabilize DNMT1, a DNA methyltransferase that maintain epigenetic silencing, to maintain higher steady state-levels of Claspin, a protein involved in ataxia telangiectasia and Rad3-related (ATR) phosphorylation of Chk1, and to regulate Tip60 protein levels, a histone acetyltransferase and transcriptional coregulator involved in adipogenesis. (Zhanwen du, Song J., Wang Y., et al. "DNMT1 stability is regulated by proteins coordinating deubiquitination and acetylation-driven ubiquitination," *Science Signaling* 3(146) (2010); Faustrup H., Bekker-Jensen S., Bartek J., Lukas J., Mail N., Mailand N. "USP7 counteracts SCFbetaTrCP—but not APCCdh1-mediated proteolysis of Claspin," *The Journal of cell biology* 184(1):13-9 (2009); Gao Y., Koppen A., Rakhsh M., et al. "Early adipogenesis is regulated through USP7-mediated deubiquitination of the histone acetyltransferase TIP60," *Nature Communications* 4:2656 (2013)

In addition to regulating the protein stability of poly-ubiquitinated targets, USP7 also acts to control the subcellular localization of proteins. Mono-ubiquitination of PTEN has been shown to effect its cytoplasmic/nuclear partitioning, where nuclear localization of PTEN is important for its tumor suppression activity. (Trotman L. C., Wang X., Alimonti A., et al. "Ubiquitination regulates PTEN nuclear import and tumor suppression," *Cell* 128(1):141-56 (2007); Song M. S., Salmena L., Carracedo A., et al. "The deubiquitinylation and localization of PTEN are regulated by a HAUSP-PML network," *Nature* 455(7214):813-7 (2008)) USP7 has also been shown to bind and deubiquitinate FOXO4, a member of the FOXO subfamily of transcription factors involved in a variety of cell processes including metabolism, cell cycle regulation apoptosis, and response to oxidative stress, decreasing its nuclear localization and transcriptional activity. (van der Horst A., van der Horst O., de Vries-Smits A. M. M., et al. "FOXO4 transcriptional activity is regulated by monoubiquitination and USP7/HAUSP," *Nat. Cell Biol.* 8(10):1064-73 (2006))

Cellular targets of USP7 also include the tumor suppressor p53 and its major E3 ligase, MDM2, stabilizing p53 via the degradation of MDM2. (Li M., Chen D., Shiloh A., et al. "Deubiquitination of p53 by HAUSP is an important pathway for p53 stabilization," *Nature* 416(6881):648-53 (2002); Li M., Brooks C. L., Kon N., Gu W. "A dynamic role of HAUSP in the p53-Mdm2 pathway," *Mol. Cell.* 13(6):879-86 (2004)) Structural studies have also shown that the EBNA1 protein encoded by the Epstein-Barr virus interacts at the same binding surface as USP7 on p53, preventing USP7 endogenous cellular activity while recruiting USP7 to viral promoters in order to activate latent viral gene expression. (Saridakis V., et al. "Structure of the p53 binding domain of HAUSP/USP7 bound to Epstein-Barr nuclear antigen 1 implications for EBV-mediated immortalization," *Mol. Cell.* 18(1):25-36 (2005); Sarkari F., Sanchez-Alcaraz T., Wang S., Holowaty M. N., Sheng Y., Frappier L. "EBNA1-mediated recruitment of a histone H2B deubiquitylating complex to the Epstein-Barr virus latent origin of DNA replication," *PLoS pathogens* 5(10) (2009); Sheng Y., et al. "Molecular recognition of p53 and MDM2 by USP7/HAUSP," *Nat. Struct. Mol. Biol.* 13(3):285-91 (2006)) Similarly, the gene product of TSPYL5, a gene frequently amplified in breast cancer and associated with poor clinical outcome, alters the ubiquitination status of p53 via its interaction with USP7. (Epping M. T., et al. "TSPYL5 suppresses p53 levels and function by physical interaction with USP7," *Nat. Cell Biol.* 13(1):102-8 (2011))

Inhibition of USP7 with small molecule inhibitors therefore has the potential to be a treatment for cancers and other disorders. For this reason, there remains a considerable need for novel and potent small molecule inhibitors of USP7.

SUMMARY OF THE INVENTION

A first aspect of the invention relates to compounds of Formula (I):

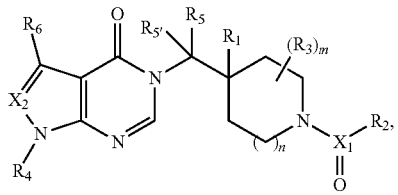

and pharmaceutically acceptable salts, hydrates, solvates, prodrugs, stereoisomers, and tautomers thereof, wherein:
$X_1$ is C, S, or S(O);
$X_2$ is $CR_7$ or N;
$R_1$ is H, D, —OH, —SH, —NH$_2$, —NH($C_1$-$C_4$) alkyl, —N(($C_1$-$C_4$) alkyl)$_2$, or F; $R_2$ is ($C_2$-$C_6$) alkyl, aryl, heteroaryl, ($C_3$-$C_8$) cycloalkyl, heterocyclyl, —NR$_{10}$R$_{11}$, or —OR$_{10}$, wherein alkyl, aryl, cycloalkyl, and heterocyclyl are optionally substituted with one or more $R_8$;
each $R_3$ is independently at each occurrence selected from D, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, aryl, heteroaryl, ($C_3$-$C_8$) cycloalkyl, heterocyclyl, —CN, —OH, —C(O)R$_{17}$, —C(O)OR$_{17}$, —OC(O)OR$_{17}$, —OC(O)NR$_{17}$R$_{18}$, —NR$_{17}$R$_{18}$, —NR$_{17}$C(O)R$_{18}$, —NR$_{17}$C(O)OR$_{18}$, —C(O)NR$_{17}$R$_{18}$, —NR$_{17}$C(O)NR$_{17}$R$_{18}$, —S(O)$_q$NR$_{17}$R$_{18}$, —S(O)$_q$R$_{17}$R$_{18}$, —NR$_{17}$S(O)$_q$R$_{17}$R$_{18}$, or halogen, wherein alkyl is optionally substituted with one or more substituents independently selected from —OH or —NH$_2$;
or two $R_3$ together when on adjacent carbons form a ($C_3$-$C_8$) cycloalkyl optionally substituted with one or more $R_{19}$; or two $R_3$ together form a ($C_3$-$C_8$) spirocycloalkyl optionally substituted with one or more $R_{19}$; or two $R_3$ together form a spiroheterocyclyl optionally substituted with one or more $R_{19}$; or two $R_3$ together when on adjacent carbons form an aryl ring optionally substituted with one or more $R_{19}$, or two $R_3$ together when on adjacent carbons form an heteroaryl ring optionally substituted with one or more $R_{19}$;
$R_4$ is ($C_1$-$C_6$) alkyl, —($C_0$-$C_3$) alkylene-aryl, heteroaryl, ($C_3$-$C_8$) cycloalkyl, CD$_3$ or heterocyclyl, wherein aryl, heteroaryl, heterocyclyl and cycloalkyl are optionally substituted with one or more $R_{12}$;
$R_5$ and $R_{5'}$ are independently H, D, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, or halogen; or
$R_5$ and $R_{5'}$ together form a ($C_3$-$C_6$) cycloalkyl or heterocyclyl ring optionally substituted with one or more substituents independently selected from halogen, —CN, ($C_1$-$C_6$) alkyl, —OH, —CH$_2$OH, —($C_0$-$C_2$)-alkylene-O($C_1$-$C_6$) alkyl, or —($C_0$-$C_2$)-alkylene-NR$_{17}$R$_{18}$;
$R_6$ is independently H, D, halogen, —CN, —NR$_{17}$R$_{18}$, ($C_1$-$C_6$) alkyl, ($C_1$-$C_6$) alkoxy, or —OH when $X_2$ is N;
$R_7$ is H, D, ($C_1$-$C_6$) alkyl, ($C_2$-$C_6$) alkenyl, ($C_2$-$C_6$) alkynyl, ($C_1$-$C_6$) alkoxy, ($C_1$-$C_6$) haloalkyl, ($C_1$-$C_6$) haloalkoxy, halogen, aryl, heteroaryl, —CN, or —NR$_{10}$R$_{11}$, wherein aryl and heteroaryl is optionally substituted with one or more $R_{10}$;
each $R_8$ is independently at each occurrence selected from D, ($C_1$-$C_6$) alkyl, ($C_1$-$C_6$) alkoxy, ($C_1$-$C_6$) haloalkyl, ($C_1$-$C_6$) haloalkoxy, —($C_1$-$C_3$)-alkylene-O($C_1$-$C_6$) alkyl, —($C_0$-$C_4$)-alkylene-aryl, —($C_0$-$C_4$)-alkylene-heteroaryl, ($C_3$-$C_{10}$) cycloalkyl, heterocyclyl, —($C_0$-$C_4$)-alkylene-O-aryl, —($C_0$-$C_4$)-alkylene-O-heteroaryl, —O—($C_3$-$C_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —($C_0$-$C_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)(($C_1$-$C_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more $R_9$;
or two $R_8$ together when on adjacent carbons form an aryl ring optionally substituted with one or more $R_9$; or two $R_8$ together when on adjacent carbons form a heteroaryl ring optionally substituted with one or more $R_9$; or two $R_8$ together when on adjacent carbons form a heterocyclyl ring optionally substituted with one or more $R_9$;
each $R_9$ is independently at each occurrence selected from D, ($C_1$-$C_6$) alkyl, ($C_1$-$C_6$) alkoxy, ($C_3$-$C_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)(($C_1$-$C_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from ($C_1$-$C_6$) alkyl, ($C_1$-$C_6$) alkoxy, ($C_1$-$C_6$) haloalkyl, halogen, aryl, —NR$_{14}$C(O)R$_{15}$, —NR$_{14}$S(O)$_q$R$_{15}$, —OH or —CN;
or two $R_9$ together when on adjacent carbons form an aryl ring; or two $R_9$ together when on adjacent carbons form a heteroaryl ring; or two $R_9$ together when on adjacent carbons form a ($C_3$-$C_{10}$) cycloalkyl ring;
each $R_{10}$ and $R_{11}$ is independently at each occurrence selected from H, ($C_1$-$C_6$) alkyl, ($C_2$-$C_6$) alkenyl, ($C_2$-$C_6$) alkynyl, —($C_0$-$C_3$) alkylene-aryl, —($C_0$-$C_4$) alkylene-($C_3$-$C_8$) cycloalkyl, —($C_0$-$C_4$) alkylene-heterocyclyl, —($C_0$-$C_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from ($C_1$-$C_6$) alkyl, ($C_1$-$C_6$) alkoxy, ($C_1$-$C_6$) haloalkyl, ($C_1$-$C_6$) haloalkoxy, ($C_3$-$C_8$) cycloalkyl, heterocyclyl, aryl, —S(O)$_q$($C_1$-$C_3$) alkyl, —S(O)$_q$NR$_{14}$R$_{15}$, —NR$_{14}$R$_{15}$, —NR$_{14}$C(O)R$_{15}$, halogen, —OH, or —CN;
or $R_{10}$ and $R_{11}$ together form a heterocyclyl ring optionally substituted with one or more substituents selected from oxo, —C(O)($C_1$-$C_3$) alkyl or —NR$_{14}$NR$_{15}$;
each $R_{12}$ is independently at each occurrence selected from D, ($C_1$-$C_6$) alkyl, ($C_1$-$C_6$) alkoxy, ($C_1$-$C_6$) haloalkyl, ($C_3$-$C_8$) cycloalkyl, aryl, heteroaryl, —O-aryl, —O-heteroaryl, —O-heterocyclyl, —O—($C_3$-$C_8$)cycloalkyl, —S(O)$_q$R$_{10}$, —(CH$_2$)$_p$C(O)OR$_{10}$, —C(O)

NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, heterocyclyl, and cycloalkyl are optionally substituted with one or more R$_{13}$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)NR$_{14}$R$_{15}$, —NR$_{14}$C(O)NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_{13}$ together when on adjacent carbons form a heteroaryl ring optionally substituted with one or more R$_{16}$; or two R$_{13}$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

each R$_{17}$ and R$_{18}$ is at each occurrence independently H or (C$_1$-C$_6$) alkyl;

R$_{19}$ is independently at each occurrence H, D, (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, halogen, —CN, or —NR$_{17}$R$_{18}$;

m is 0, 1 or 2;
n is 0, 1, 2 or 3;
p is 0, 1, or 2; and
each q is 0, 1, or 2.

Another aspect of the invention relates to a method of treating a disease or disorder associated with modulation of USP7. The method comprises administering to a patient in need of a treatment for diseases or disorders associated with modulation of USP7 an effective amount of a compound of Formula (I), or a pharmaceutically acceptable salt, hydrate, solvate, prodrug, stereoisomer, or tautomer thereof.

Another aspect of the invention is directed to a method of inhibiting USP7. The method involves administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating cancer. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a neurodegenerative disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating a viral infection or disease. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of treating an inflammatory disease or condition. The method comprises administering to a patient in need thereof an effective amount of a compound of Formula (I), or a pharmaceutically acceptable salt, hydrate, solvate, prodrug, stereoisomer, or tautomer thereof.

Another aspect of the invention relates to a method of inducing cell cycle arrest, apoptosis in tumor cells and/or enhanced tumor-specific T-cell immunity. The method comprises contacting the cells with an effective amount of a compound of Formula (I), or a pharmaceutically acceptable salt, hydrate, solvate, prodrug, stereoisomer, or tautomer thereof.

Another aspect of the invention is directed to pharmaceutical compositions comprising a compound of Formula (I), or a pharmaceutically acceptable salt, hydrate, solvate, prodrug, stereoisomer, or tautomer thereof and a pharmaceutically acceptable carrier. The pharmaceutical acceptable carrier may further include an excipient, diluent, or surfactant.

Another aspect of the present invention relates to a compound of Formula (I), or a pharmaceutically acceptable salt, hydrate, solvate, prodrug, stereoisomer, or tautomer thereof, for use in the manufacture of a medicament for treating a disease associated with inhibiting USP7.

Another aspect of the present invention relates to the use of a compound of Formula (I), or a pharmaceutically acceptable salt, hydrate, solvate, prodrug, stereoisomer, or tautomer thereof, in the treatment of a disease associated with inhibiting USP7.

The present invention further provides methods of treating a disease or disorder associated with modulation of USP7 including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I), or a pharmaceutically acceptable salt, hydrate, solvate, prodrug, stereoisomer, or tautomer thereof.

The present invention provides inhibitors of USP7 that are therapeutic agents in the treatment of diseases such as cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention further provides compounds and compositions with an improved efficacy and safety profile relative to known USP7 inhibitors. The present disclosure also provides agents with novel mechanisms of action toward USP7 enzymes in the treatment of various types of diseases including cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases. Ultimately the present invention provides the medical community with a novel pharmacological strategy for the treatment of diseases and disorders associated with USP7 enzymes.

DETAILED DESCRIPTION OF THE INVENTION

The present invention relates to compounds and compositions that are capable of inhibiting the activity USP7. The invention features methods of treating, preventing or ameliorating a disease or disorder in which USP7 plays a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of USP7 dependent diseases and disorders by inhibiting the activity of USP7 enzymes. Inhibition of USP7 provides a novel approach to the treatment, prevention, or amelioration of diseases including, but not limited to, cancer and metastasis, neurodegenerative diseases, immunological disorders, osteoporosis, arthritis inflammatory disorders, cardiovascular diseases, ischemic diseases, viral infections and diseases, and bacterial infections and diseases.

In a first aspect of the invention, the compounds of Formula (I) are described:

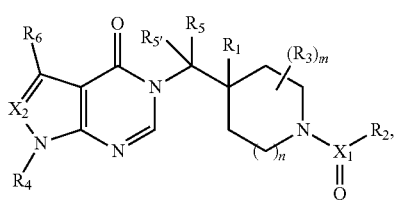

(I)

and pharmaceutically acceptable salts, hydrates, solvates, prodrugs, stereoisomers, and tautomers thereof, wherein m, n, $X_1$, $X_2$, $R_1$-$R_5$, $R_{5'}$ and $R_6$ are as described herein above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —CH$_2$CN, —O—($C_1$-$C_6$) alkyl, ($C_1$-$C_6$) alkyl, $C_1$-$C_6$ alkoxy, $C_1$-$C_6$ haloalkyl, $C_1$-$C_6$ haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, —NH$_2$, —NH(($C_1$-$C_6$) alkyl), —N(($C_1$-$C_6$) alkyl)$_2$, —NHC(O)($C_1$-$C_6$) alkyl, —C(O)NH($C_1$-$C_6$) alkyl, —S(O)$_2$($C_1$-$C_6$) alkyl, —S(O)NH($C_1$-$C_6$) alkyl, and S(O)N(($C_1$-$C_6$) alkyl)$_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)(OH)$_2$, —OC(O)($C_1$-$C_6$) alkyl, —C(O)($C_1$-$C_6$) alkyl, —OC(O)O($C_1$-$C_6$) alkyl, NH$_2$, NH(($C_1$-$C_6$) alkyl), N(($C_1$-$C_6$) alkyl)$_2$, —S(O)$_2$—($C_1$-$C_6$) alkyl, —S(O)NH($C_1$-$C_6$) alkyl, and S(O)N(($C_1$-$C_6$) alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

Halogen or "halo" refers to fluorine, chlorine, bromine, or iodine.

Alkyl refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Cycloalkylalkyl" means monocyclic saturated carbon rings containing 3-24 carbon atoms further substituted with ($C_1$-$C_6$) alkyl groups. In general cycloalkylalkyl groups herein described display the following formula

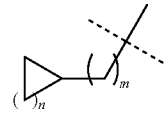

where m is an integer from 1 to 6 and n is an integer from 1 to 16. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

"Heterocyclyl" or "heterocycloalkyl" monocyclic rings containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl.

The term "hydroxyalkyl" means an alkyl group as defined above, where the alkyl group is substituted with one or more OH groups. Examples of hydroxyalkyl groups include HO—CH$_2$—, HO—CH$_2$—CH$_2$— and CH$_3$—CH(OH)—.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—NH$_2$, R≠H), secondary (R$_2$—NH, R$_2$≠H) and tertiary (R$_3$—N, R≠H) amines. A substituted amine is intended to mean an amine where at least one of the hydrogen atoms has been replaced by the substituent.

The term "amino" as used herein means a substituent containing at least one nitrogen atom. Specifically, NH$_2$, —NH(alkyl) or alkylamino, —N(alkyl)$_2$ or dialkylamino, amide-, carbamide-, urea, and sulfamide substituents are included in the term "amino".

The term "dialkylamino" as used herein refers to an amino or NH$_2$ group where both of the hydrogens have been replaced with alkyl groups, as defined herein above, i.e., —N(alkyl)$_2$. The alkyl groups on the amino group can be the same or different alkyl groups. Example of alkylamino groups include, but are not limited to, dimethylamino (i.e., —N(CH$_3$)$_2$), diethylamino, dipropylamino, diiso-propylamino, di-n-butylamino, di-sec-butylamino, di-tert-butylamino, methyl(ethyl)amino, methyl(butylamino), etc.

"Spirocycloalkyl" or "spirocyclyl" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A (C$_3$-C$_{12}$) spirocycloalkyl is a spirocycle containing between 3 and 12 carbon atoms. One or more of the carbon atoms can be substituted with a heteroatom.

The term "spiroheterocycloalkyl" or "spiroheterocyclyl" is understood to mean a spirocycle wherein at least one of the rings is a heterocycle (e.g., at least one of the rings is furanyl, morpholinyl, or piperadinyl).

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting USP7, which are useful for the treatment of diseases and disorders associated with modulation of a USP7 enzyme. The invention further relates to compounds, or pharmaceutically acceptable salts, hydrates, solvates, prodrugs, stereoisomers, or tautomers thereof, which are useful for inhibiting USP7.

In one embodiment, the compounds of Formula (I) have the structure of Formula (Ia):

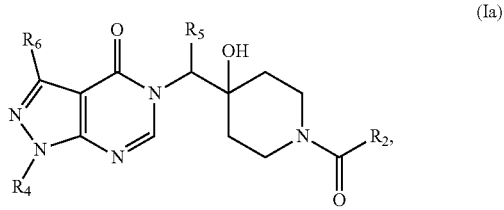

(Ia)

and pharmaceutically acceptable salts, hydrates, solvates, prodrugs, stereoisomers, and tautomers thereof,
wherein:
- $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$; $R_4$ is $(C_1-C_6)$ alkyl, $-(C_0-C_3)$ alkylene-aryl, heteroaryl, $(C_3-C_8)$ cycloalkyl, $CD_3$, or heterocyclyl, wherein aryl, heteroaryl, heterocyclyl and cycloalkyl are optionally substituted with one or more $R_{12}$;
- $R_5$ is H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen; or
- $R_6$ is independently H, D, halogen, $-CN$, $-NR_{17}R_{18}$, $(C_1-C_6)$ alkyl, $(C_1-C_6)$ alkoxy, or $-OH$;
- each $R_8$ is independently at each occurrence selected from D, $(C_1-C_6)$ alkyl, $(C_1-C_6)$ alkoxy, $(C_1-C_6)$ haloalkyl, $(C_1-C_6)$ haloalkoxy, $-(C_1-C_3)$-alkylene-$O(C_1-C_6)$ alkyl, $-(C_0-C_4)$-alkylene-aryl, $-(C_0-C_4)$-alkylene-heteroaryl, $(C_3-C_{10})$ cycloalkyl, heterocyclyl, $-(C_0-C_4)$-alkylene-O-aryl, $-(C_0-C_4)$-alkylene-O-heteroaryl, $-O-(C_3-C_8)$cycloalkyl, $-S$-heteroaryl, halogen, $-CN$, $-C(O)R_{10}$, $-CO(O)R_{10}$, $-C(O)NR_{10}R_{11}$, $-S(O)_qR_{10}$, $-S(O)_qNR_{10}R_{11}$, $-NR_{10}S(O)_qR_{11}$, $-(C_0-C_3)$-alkylene-$NR_{10}R_{11}$, $-NR_{10}C(O)R_{11}$, $-NR_{10}C(O)C(O)R_{11}$, $-NR_{10}C(O)NR_{10}R_{11}$, $-P(O)((C_1-C_6)alkyl)_2$, $-P(O)(aryl)_2$, $-SiMe_3$, $SF_5$, or $-OH$, wherein alkyl, alkylene, aryl, heteroaryl, and heterocyclyl are optionally substituted with one or more $R_9$;
- or two $R_8$ together when on adjacent carbons form an aryl ring optionally substituted with one or more $R_9$; or two $R_8$ together when on adjacent carbons form a heteroaryl ring optionally substituted with one or more $R_9$; or two $R_8$ together when on adjacent carbons form a heterocyclyl ring optionally substituted with one or more $R_9$;
- each $R_9$ is independently at each occurrence selected from D, $(C_1-C_6)$ alkyl, $(C_1-C_6)$ alkoxy, $(C_3-C_8)$ cycloalkyl, halogen, aryl, $-OH$, $-CN$, $-C(O)R_{10}$, $-C(O)NR_{10}R_{11}$, $-NR_{10}C(O)R_{11}$, $-NR_{10}R_{11}$, $-S(O)_qR_{10}$, $-S(O)_qNR_{10}R_{11}$, $-NR_{10}S(O)_qR_{11}$, oxo, $-P(O)((C_1-C_6)alkyl)_2$, $-P(O)(aryl)_2$, $-SiMe_3$, $SF_5$, $-O$-aryl, $CN$, or $-O$-heteroaryl, wherein alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, $-NR_{14}C(O)R_{15}$, $-NR_{14}S(O)_qR_{15}$, $-OH$ or $-CN$;
- or two $R_9$ together when on adjacent carbons form an aryl ring; or two $R_9$ together when on adjacent carbons form a heteroaryl ring; or two $R_9$ together when on adjacent carbons form a $(C_3-C_{10})$ cycloalkyl ring;
- each $R_{10}$ and $R_{11}$ is independently at each occurrence selected from H, $(C_1-C_6)$ alkyl, $(C_2-C_6)$ alkenyl, $(C_2-C_6)$ alkynyl, $-(C_0-C_3)$ alkylene-aryl, $-(C_0-C_4)$ alkylene-$(C_3-C_8)$ cycloalkyl, $-(C_0-C_4)$ alkylene-heterocyclyl, $-(C_0-C_4)$ alkylene-heteroaryl, or $-CN$, wherein alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, $-S(O)_q(C_1-C_3)$ alkyl, $-S(O)_qNR_{14}R_{15}$, $-NR_{14}R_{15}$, $-NR_{14}C(O)R_{15}$, halogen, $-OH$, or $-CN$;
- or $R_{10}$ and $R_{11}$ together form a heterocyclyl ring optionally substituted with one or more substituents selected from oxo, $-C(O)(C_1-C_3)$ alkyl or $-NR_{14}NR_{15}$;
- each $R_{12}$ is independently at each occurrence selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, $-O$-aryl, $-O$-heteroaryl, $-O$-heterocyclyl, $-O-(C_3-C_8)$cycloalkyl, $-S(O)_qR_{10}$, $-(CH_2)_pC(O)OR_{10}$, $-C(O)NR_{14}R_{15}$, $-S(O)_qNR_{14}R_{15}$, $-NR_{14}R_{15}$, $-NR_{14}C(O)NR_{14}R_{15}$, $-NR_{14}C(O)OR_{10}$, $-NR_{14}SO_qR_{10}$, $-NR_{14}COR_{10}$, halogen, $-P(O)((C_1-C_6)alkyl)_2$, $-P(O)(aryl)_2$, $-SiMe_3$, $SF_5$ or $-OH$, wherein alkyl, aryl, heteroaryl, and cycloalkyl are optionally substituted with one or more $R_{13}$;
- each $R_{13}$ is independently at each occurrence selected from D, $(C_1-C_6)$ alkyl, $(C_1-C_6)$ haloalkyl, $(C_1-C_6)$ alkoxy, halogen, $(C_1-C_6)$ haloalkoxy, $(C_1-C_6)$ hydroxyalkyl, heterocyclyl, heteroaryl, aryl, $-OR_{14}$, $-C(O)R_{14}$, $-C(O)NR_{14}R_{15}$, $-NR_{14}R_{15}$, $-S(O)_qR_{14}$, $-NR_{14}S(O)_qR_{15}$, $-S(O)_qNR_{14}R_{15}$, $-NR_{14}C(O)NR_{14}R_{15}$, $-NR_{14}C(O)OR_{15}$, $-P(O)((C_1-C_6)alkyl)_2$, $-P(O)(aryl)_2$, $-SiMe_3$, $SF_5$ or $-CN$, wherein alkyl, cycloalkyl, aryl, heterocyclyl, and heteroaryl are substituted with one or more substituents independently selected from $(C_1-C_6)$ alkyl, $-NR_{14}C(O)R_{15}$, $-OH$, $-CN$, $-C(O)R_{14}$, or $-NR_{14}R_{15}$;
- each $R_{14}$ and $R_{15}$ are independently at each occurrence selected from H, $(C_1-C_6)$ alkyl, $(C_2-C_6)$ alkenyl, $(C_2-C_6)$ alkynyl, $-(C_1-C_4)$ alkylene-$(C_3-C_8)$ cycloalkyl, $-(C_0-C_4)$ alkylene-heterocyclyl, $-(C_0-C_4)$ alkylene-aryl, $-(C_0-C_4)$ alkylene-heteroaryl, or $-CN$, wherein alkyl, alkenyl, alkynyl, alkylene, cycloalkyl, heterocyclyl, aryl, and heteroaryl are optionally substituted with one or more $R_{16}$;
- or $R_{14}$ and $R_{15}$ together form a heterocyclyl ring optionally substituted with one or more $R_{16}$;
- each $R_{16}$ is independently at each occurrence selected from D, $(C_1-C_6)$ alkyl, $(C_2-C_6)$ alkenyl, $(C_2-C_6)$ alkynyl, $(C_1-C_6)$ haloalkyl, $(C_1-C_6)$ alkoxy, $(C_1-C_6)$ haloalkoxy, $-C(O)(C_1-C_3)$ alkyl, $-NHC(O)(C_1-C_4)$ alkyl, $-CN$, $-CH_2CN$, $-CR_{10}R_{11}NR_{10}R_{11}$, oxo, $-NR_{10}R_{11}$, $-S(O)_Q(C_1-C_6)$ alkyl, $-C(O)NR_{10}R_{11}$, $-S(O)_qNR_{10}R_{11}$, $-NR_{10}C(O)R_{10}R_{11}$, $-NR_{10}C(O)NR_{10}R_{11}$, or $-OH$;
- or two $R_{16}$ together when on adjacent carbons form an aryl ring; or two $R_{16}$ together when on adjacent carbons form a spiroheterocyclyl ring;
- each $R_{17}$ and $R_{18}$ is independently at each occurrence H or $(C_1-C_6)$ alkyl;
- p is 0, 1, or 2; and
- each q is 0, 1, or 2.

In another embodiment, the compounds of Formula (I) have the structure of Formula (Ib):

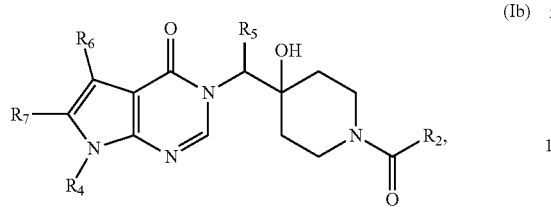

(Ib)

and pharmaceutically acceptable salts, hydrates, solvates, prodrugs, stereoisomers, and tautomers thereof,
wherein:
$R_2$ is $(C_1-C_8)$ alkyl, aryl, heteroaryl, $(C_3-C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$;
$R_4$ is $(C_1-C_6)$ alkyl, —$(C_0-C_3)$ alkylene-aryl, heteroaryl, $(C_3-C_8)$ cycloalkyl, $CD_3$, or heterocyclyl, wherein aryl, heteroaryl, heterocyclyl and cycloalkyl are optionally substituted with one or more $R_{12}$;
$R_5$ is H, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen; or
$R_6$ is independently H, D, halogen, —CN, —$NR_{17}R_{18}$, $(C_1-C_6)$ alkyl, $(C_1-C_6)$ alkoxy, or —OH when $X_2$ is N;
$R_7$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, aryl, heteroaryl, —CN, or —$NR_{10}R_{11}$, wherein aryl and heteroaryl is optionally substituted with one or more $R_{10}$;
each $R_8$ is independently at each occurrence selected from D, $(C_1-C_6)$ alkyl, $(C_1-C_6)$ alkoxy, $(C_1-C_6)$ haloalkyl, $(C_1-C_6)$ haloalkoxy, —$(C_1-C_3)$-alkylene-O$(C_1-C_6)$ alkyl, —$(C_0-C_4)$-alkylene-aryl, —$(C_0-C_4)$-alkylene-heteroaryl, $(C_3-C_{10})$ cycloalkyl, heterocyclyl, —$(C_0-C_4)$-alkylene-O-aryl, —$(C_0-C_4)$-alkylene-O-heteroaryl, —O—$(C_3-C_8)$cycloalkyl, —S-heteroaryl, halogen, —CN, —$C(O)R_{10}$, —$CO(O)R_{10}$, —$C(O)NR_{10}R_{11}$, —$S(O)_qR_{10}$, —$S(O)_qNR_{10}R_{11}$, —$NR_{10}S(O)_qR_{11}$, —$(C_0-C_3)$-alkylene-$NR_{10}R_{11}$, —$NR_{10}C(O)R_{11}$, —$NR_{10}C(O)C(O)R_{11}$, —$NR_{10}C(O)NR_{10}R_{11}$, —$P(O)((C_1-C_6)alkyl)_2$, —$P(O)(aryl)_2$, —$SiMe_3$, $SF_5$, or —OH, wherein alkyl, alkylene, aryl, heteroaryl, and heterocyclyl are optionally substituted with one or more $R_9$;
or two $R_8$ together when on adjacent carbons form an aryl ring optionally substituted with one or more $R_9$, or two $R_8$ together when on adjacent carbons form a heteroaryl ring optionally substituted with one or more $R_9$; or two $R_8$ together when on adjacent carbons form a heterocyclyl ring optionally substituted with one or more $R_9$;
each $R_9$ is independently at each occurrence selected from D, $(C_1-C_6)$ alkyl, $(C_1-C_6)$ alkoxy, $(C_3-C_8)$ cycloalkyl, halogen, aryl, —OH, —CN, —$C(O)R_{10}$, —$C(O)NR_{10}R_{11}$, —$NR_{10}C(O)R_{11}$, —$NR_{10}R_{11}$, —$S(O)_qR_{10}$, —$S(O)_qNR_{10}R_{11}$, —$NR_{10}S(O)_qR_{11}$, oxo, —$P(O)((C_1-C_6)alkyl)_2$, —$P(O)(aryl)_2$, —$SiMe_3$, $SF_5$, —O-aryl, CN, or —O-heteroaryl, wherein alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, —$NR_{14}C(O)R_{15}$, —$NR_{14}S(O)_qR_{15}$, —OH or —CN;
or two $R_9$ together when on adjacent carbons form an aryl ring; or two $R_9$ together when on adjacent carbons form a heteroaryl ring; or two $R_9$ together when on adjacent carbons form a $(C_3-C_{10})$ cycloalkyl ring;
each $R_{10}$ and $R_{11}$ is independently at each occurrence selected from H, $(C_1-C_6)$ alkyl, $(C_2-C_6)$ alkenyl, $(C_2-C_6)$ alkynyl, —$(C_0-C_3)$ alkylene-aryl, —$(C_0-C_4)$ alkylene-$(C_3-C_8)$ cycloalkyl, —$(C_0-C_4)$ alkylene-heterocyclyl, —$(C_0-C_4)$ alkylene-heteroaryl, or —CN, wherein alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, —$S(O)_q(C_1-C_3)$ alkyl, —$S(O)_qNR_{14}R_{15}$, —$NR_{14}R_{15}$, —$NR_{14}C(O)R_{15}$, halogen, —OH, or —CN;
or $R_{10}$ and $R_{11}$ together form a heterocyclyl ring optionally substituted with one or more substituents selected from oxo, —$C(O)(C_1-C_3)$ alkyl or —$NR_{14}NR_{15}$;
each $R_{12}$ is independently at each occurrence selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, —O-aryl, —O-heteroaryl, —O-heterocyclyl, —O—$(C_3-C_8)$cycloalkyl, —$S(O)_qR_{10}$, —$(CH_2)_pC(O)OR_{10}$, —$C(O)NR_{14}R_{15}$, —$S(O)_qNR_{14}R_{15}$, —$NR_{14}R_{15}$, —$NR_{14}C(O)NR_{14}R_{15}$, —$NR_{14}C(O)OR_{10}$, —$NR_{14}SO_qR_{10}$, —$NR_{14}COR_{10}$, halogen, —$P(O)((C_1-C_6)alkyl)_2$, —$P(O)(aryl)_2$, —$SiMe_3$, $SF_5$ or —OH, wherein alkyl, aryl, heteroaryl, and cycloalkyl are optionally substituted with one or more $R_1$;
each $R_{13}$ is independently at each occurrence selected from D, $(C_1-C_6)$ alkyl, $(C_1-C_6)$ haloalkyl, $(C_1-C_6)$ alkoxy, halogen, $(C_1-C_6)$ haloalkoxy, $(C_1-C_6)$ hydroxyalkyl, heterocyclyl, heteroaryl, aryl, —$OR_{14}$, —$C(O)R_{14}$, —$C(O)NR_{14}R_{15}$, —$NR_{14}R_{15}$, —$S(O)_qR_{14}$, —$NR_{14}S(O)_qR_{15}$, —$S(O)_qNR_{14}R_{15}$, —$NR_{14}C(O)NR_{14}R_{15}$, —$NR_{14}C(O)OR_{15}$, —$P(O)((C_1-C_6)alkyl)_2$, —$P(O)(aryl)_2$, —$SiMe_3$, $SF_5$ or —CN, wherein alkyl, cycloalkyl, aryl, heterocyclyl, and heteroaryl are substituted with one or more substituents independently selected from $(C_1-C_6)$ alkyl, —$NR_{14}C(O)R_{15}$, —OH, —CN, —$C(O)R_{14}$, or —$NR_{14}R_{15}$;
or two $R_{13}$ together when on adjacent carbons form a heterocyclyl ring optionally substituted with one or more $R_{16}$; or two $R_3$ together when on adjacent carbons form a heteroaryl ring optionally substituted with one or more $R_{16}$; or two $R_3$ together with the carbon to which they are attached can form a spiroheterocyclyl optionally substituted with one or more $R_{16}$;
each $R_{14}$ and $R_{15}$ are independently at each occurrence selected from H, $(C_1-C_6)$ alkyl, $(C_2-C_6)$ alkenyl, $(C_2-C_6)$ alkynyl, —$(C_1-C_4)$ alkylene-$(C_3-C_8)$ cycloalkyl, —$(C_0-C_4)$ alkylene-heterocyclyl, —$(C_0-C_4)$ alkylene-aryl, —$(C_0-C_4)$ alkylene-heteroaryl, or —CN, wherein alkyl, alkenyl, alkynyl, alkylene, cycloalkyl, heterocyclyl, aryl, and heteroaryl are optionally substituted with one or more $R_{16}$;
or $R_{14}$ and $R_{15}$ together form a heterocyclyl ring optionally substituted with one or more $R_{16}$;
each $R_{16}$ is independently at each occurrence selected from D, $(C_1-C_6)$ alkyl, $(C_2-C_6)$ alkenyl, $(C_2-C_6)$ alkynyl, $(C_1-C_6)$ haloalkyl, $(C_1-C_6)$ alkoxy, $(C_1-C_6)$ haloalkoxy, —$C(O)(C_1-C_3)$ alkyl, —$NHC(O)(C_1-C_4)$ alkyl, —CN, —$CH_2CN$, —$CR_{10}R_{11}NR_{10}R_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

each R$_{17}$ and R$_{18}$ is at each occurrence independently H or (C$_1$-C$_6$) alkyl;

p is 0, 1, or 2; and each q is 0, 1, or 2.

In another embodiment, the compounds of Formula (I) have the structure of Formula (Ic):

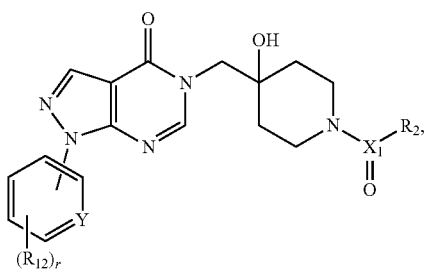

(Ic)

and pharmaceutically acceptable salts, hydrates, solvates, prodrugs, stereoisomers, and tautomers thereof, wherein.

X$_1$ is C, S, or S(O);

Y is CH or N;

R$_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more R$_8$;

each R$_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heterocyclyl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$ R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two R$_8$ together when on adjacent carbons form an aryl ring optionally substituted with one or more R$_9$; or two R$_8$ together when on adjacent carbons form a heteroaryl ring optionally substituted with one or more R$_9$; or two R$_8$ together when on adjacent carbons form a heterocyclyl ring optionally substituted with one or more R$_9$;

each R$_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;

or two R$_9$ together when on adjacent carbons form an aryl ring; or two R$_9$ together when on adjacent carbons form a heteroaryl ring; or two R$_9$ together when on adjacent carbons form a (C$_3$-C$_{10}$) cycloalkyl ring;

each R$_{10}$ and R$_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN;

or R$_{10}$ and R$_{11}$ together form a heterocyclyl ring optionally substituted with one or more substituents selected from oxo, —C(O)(C$_1$-C$_3$) alkyl or —NR$_{14}$NR$_{15}$;

each R$_{12}$ is independently at each occurrence selected from D, (C$_1$-C$_6$) alkyl, (C$_1$-C$_6$) alkoxy, (C$_1$-C$_6$) haloalkyl, (C$_3$-C$_8$) cycloalkyl, aryl, heteroaryl, —O-aryl, —O-heteroaryl, —O-heterocyclyl, —O—(C$_3$-C$_8$)cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, and cycloalkyl are optionally substituted with one or more R$_3$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O)NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_3$ together when on adjacent carbons form a heteroaryl ring optionally substituted with one or more R$_{11}$; or two R$_{13}$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O) NR$_{10}$R$_{11}$, or —OH;

or two R$_{16}$ together when on adjacent carbons form an aryl ring; or two R$_{16}$ together when on adjacent carbons form a spiroheterocyclyl ring;

p is 0, 1, or 2;

each q is 0, 1, or 2; and r is 1, 2, 3, 4, or 5.

In another embodiment, the compounds of Formula (I) have the structure of Formula (Id):

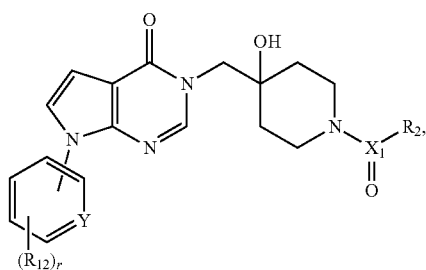

(Id)

and pharmaceutically acceptable salts, hydrates, solvates, prodrugs, stereoisomers, and tautomers thereof, wherein:

X$_1$ is C, S, or S(O);

Y is CH or N;

R$_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more R$_8$;

each R$_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O) R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two R$_8$ together when on adjacent carbons form an aryl ring optionally substituted with one or more R$_9$; or two R$_8$ together when on adjacent carbons form a heteroaryl ring optionally substituted with one or more R$_9$; or two R$_8$ together when on adjacent carbons form a heterocyclyl ring optionally substituted with one or more R$_9$;

each R$_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O) NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;

or two R$_9$ together when on adjacent carbons form an aryl ring; or two R$_9$ together when on adjacent carbons form a heteroaryl ring; or two R$_9$ together when on adjacent carbons form a (C$_3$-C$_{10}$) cycloalkyl ring;

each R$_{10}$ and R$_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$ NR$_{14}$R$_{15}$, —NR$_{14}$R$_{15}$, —NR$_{14}$C(O)R$_{15}$, halogen, —OH, or —CN;

or R$_{10}$ and R$_{11}$ together form a heterocyclyl ring optionally substituted with one or more substituents selected from oxo, —C(O)(C$_1$-C$_3$) alkyl or —NR$_{14}$NR$_{15}$;

each R$_{12}$ is independently at each occurrence selected from D, (C$_1$-C$_6$) alkyl, (C$_1$-C$_6$) alkoxy, (C$_1$-C$_6$) haloalkyl, (C$_3$-C$_8$) cycloalkyl, aryl, heteroaryl, —O-aryl, —O-heteroaryl, —O-heterocyclyl, —O—(C$_3$-C$_8$)cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O) NR$_{14}$R$_{15}$, —NR$_{14}$C(O)OR$_{10}$, —NR$_4$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, and cycloalkyl are optionally substituted with one or more R$_{13}$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O) R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O) NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_{13}$ together when on adjacent carbons form a heteroaryl ring optionally substituted with one or more R$_{16}$; or two R$_{13}$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

p is 0, 1, or 2;

each q is 0, 1, or 2; and r is 1, 2, 3, 4, or 5.

In another embodiment, the compounds of Formula (I) have the structure of Formula (Ie):

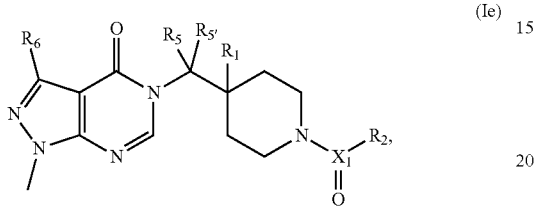

(Ie)

and pharmaceutically acceptable salts, hydrates, solvates, prodrugs, stereoisomers, and tautomers thereof, wherein:

X$_1$ is C, S, or S(O);

R$_1$ is H, D, —OH, —SH, —NH$_2$, —NH(C$_1$-C$_4$) alkyl, —N((C$_1$-C$_4$) alkyl)$_2$, or F;

R$_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more R$_8$;

R$_5$ and R$_{5'}$ are independently H, D, (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, or halogen; or R$_5$ and R$_{5'}$ together form a (C$_3$-C$_6$) cycloalkyl or heterocyclyl ring optionally substituted with one or more substituents independently selected from halogen, —CN, (C$_1$-C$_6$) alkyl, —OH, —CH$_2$OH, —(C$_0$-C$_2$)-alkylene-O(C$_1$-C$_6$) alkyl, or —(C$_0$-C$_2$)-alkylene-NR$_{17}$R$_{18}$;

R$_6$ is independently H, D, halogen, —CN, —NR$_{17}$R$_{18}$, (C$_1$-C$_6$) alkyl, (C$_1$-C$_6$) alkoxy, or —OH when X$_2$ is N;

each R$_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two R$_R$ together when on adjacent carbons form an aryl ring optionally substituted with one or more R$_9$; or two R$_8$ together when on adjacent carbons form a heteroaryl ring optionally substituted with one or more R$_9$; or two R$_R$ together when on adjacent carbons form a heterocyclyl ring optionally substituted with one or more R$_9$;

each R$_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;

or two R$_9$ together when on adjacent carbons form an aryl ring; or two R$_9$ together when on adjacent carbons form a heteroaryl ring; or two R$_9$ together when on adjacent carbons form a (C$_3$-C$_{10}$) cycloalkyl ring;

each R$_{10}$ and R$_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN;

or R$_{10}$ and R$_{11}$ together form a heterocyclyl ring optionally substituted with one or more substituents selected from oxo, —C(O)(C$_1$-C$_3$) alkyl or —NR$_{14}$NR$_{15}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

each R$_{17}$ and R$_{18}$ is at each occurrence independently H or (C$_1$-C$_6$) alkyl;

p is 0, 1, or 2; and each q is 0, 1, or 2.

In another embodiment, the compounds of Formula (I) have the structure of Formula (If):

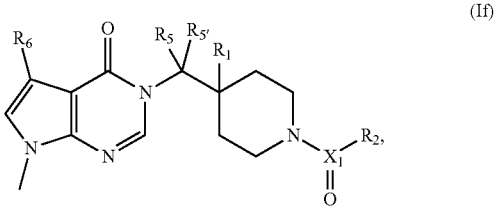

(If)

and pharmaceutically acceptable salts, hydrates, solvates, prodrugs, stereoisomers, and tautomers thereof,
wherein,
$X_1$ is C, S, or S(O);
$R_1$ is H, D, —OH, —SH, —NH$_2$, —NH(C$_1$-C$_4$) alkyl, —N((C$_1$-C$_4$) alkyl)$_2$, or F;
$R_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more $R_R$;
$R_5$ and $R_{5'}$ are independently H, D, (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, or halogen; or
$R_5$ and $R_{5'}$ together form a (C$_3$-C$_6$) cycloalkyl or heterocyclyl ring optionally substituted with one or more substituents independently selected from halogen, —CN, (C$_1$-C$_6$) alkyl, —OH, —CH$_2$OH, —(C$_0$-C$_2$)-alkylene-O(C$_1$-C$_6$) alkyl, or —(C$_0$-C$_2$)-alkylene-NR$_{17}$R$_{18}$;
$R_6$ is independently H, D, halogen, —CN, —NR$_{17}$R$_{18}$, (C$_1$-C$_6$) alkyl, (C$_1$-C$_6$) alkoxy, or —OH when $X_2$ is N;
each $R_R$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more $R_9$;
or two $R_R$ together when on adjacent carbons form an aryl ring optionally substituted with one or more $R_9$; or two $R_8$ together when on adjacent carbons form a heteroaryl ring optionally substituted with one or more $R_9$; or two $R_8$ together when on adjacent carbons form a heterocyclyl ring optionally substituted with one or more $R_9$;
each $R_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;
or two $R_9$ together when on adjacent carbons form an aryl ring; or two $R_9$ together when on adjacent carbons form a heteroaryl ring; or two $R_9$ together when on adjacent carbons form a (C$_3$-C$_{10}$) cycloalkyl ring;
each $R_{10}$ and $R_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN;
or $R_{10}$ and $R_{11}$ together form a heterocyclyl ring optionally substituted with one or more substituents selected from oxo, —C(O)(C$_1$-C$_3$) alkyl or —NR$_{14}$NR$_{15}$;
each $R_{14}$ and $R_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more $R_{16}$;
or $R_{14}$ and $R_{15}$ together form a heterocyclyl ring optionally substituted with one or more $R_{16}$;
each $R_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{11}$C(O)NR$_{10}$R$_{11}$, or —OH;
or two $R_{16}$ together when on adjacent carbons form an aryl ring; or two $R_{16}$ together when on adjacent carbons form a spiroheterocyclyl ring;
each $R_{17}$ and $R_{18}$ is at each occurrence independently H or (C$_1$-C$_6$) alkyl;
p is 0, 1, or 2; and
each q is 0, 1, or 2.
In another embodiment, the compounds of Formula (I) have the structure of Formula (Ig):

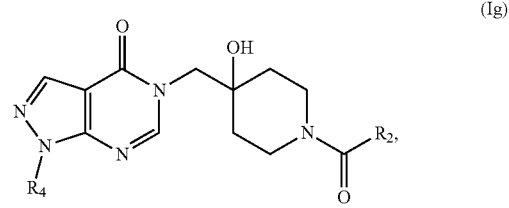

(Ig)

and pharmaceutically acceptable salts, hydrates, solvates, prodrugs, stereoisomers, and tautomers thereof,
wherein:
$R_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more $R_8$;
$R_4$ is (C$_1$-C$_6$) alkyl, —(C$_0$-C$_3$) alkylene-aryl, heteroaryl, (C$_3$-C$_8$) cycloalkyl, CD$_3$, or heterocyclyl, wherein aryl, heteroaryl, heterocyclyl and cycloalkyl are optionally substituted with one or more $R_{12}$;
each $R_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two R$_8$ together when on adjacent carbons form an aryl ring optionally substituted with one or more R$_9$; or two R$_8$ together when on adjacent carbons form a heteroaryl ring optionally substituted with one or more R$_9$; or two R$_8$ together when on adjacent carbons form a heterocyclyl ring optionally substituted with one or more R$_9$;

each R$_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;

or two R$_9$ together when on adjacent carbons form an aryl ring; or two R$_9$ together when on adjacent carbons form a heteroaryl ring; or two R$_9$ together when on adjacent carbons form a (C$_3$-C$_{10}$) cycloalkyl ring;

each R$_{10}$ and R$_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN; or R$_{10}$ and R$_{11}$ together form a heterocyclyl ring optionally substituted with one or more substituents selected from oxo, —C(O)(C$_1$-C$_3$) alkyl or —NR$_{14}$NR$_{15}$;

each R$_{12}$ is independently at each occurrence selected from D, (C$_1$-C$_6$) alkyl, (C$_1$-C$_6$) alkoxy, (C$_1$-C$_6$) haloalkyl, (C$_3$-C$_8$) cycloalkyl, aryl, heteroaryl, —O-aryl, —O-heteroaryl, —O-heterocyclyl, —O—(C$_3$-C$_8$)cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, and cycloalkyl are optionally substituted with one or more R$_{13}$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O)NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_{13}$ together when on adjacent carbons form a heteroaryl ring optionally substituted with one or more R$_{16}$; or two R$_3$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

p is 0, 1, or 2; and each q is 0, 1, or 2.

In another embodiment, the compounds of Formula (I) have the structure of Formula (Ih):

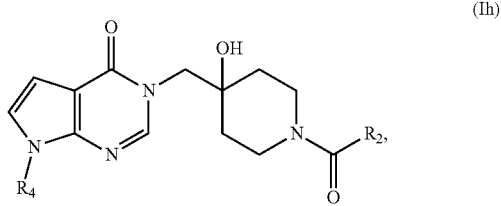

(Ih)

and pharmaceutically acceptable salts, hydrates, solvates, prodrugs, stereoisomers, and tautomers thereof, wherein:

R$_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more R$_8$;

R$_4$ is (C$_1$-C$_6$) alkyl, —(C$_0$-C$_3$) alkylene-aryl, heteroaryl, (C$_3$-C$_8$) cycloalkyl, CD$_3$, or heterocyclyl, wherein aryl, heteroaryl, heterocyclyl and cycloalkyl are optionally substituted with one or more R$_{12}$;

each R$_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two $R_8$ together when on adjacent carbons form an aryl ring optionally substituted with one or more $R_9$; or two $R_8$ together when on adjacent carbons form a heteroaryl ring optionally substituted with one or more $R_9$; or two $R_8$ together when on adjacent carbons form a heterocyclyl ring optionally substituted with one or more $R_9$;

each $R_9$ is independently at each occurrence selected from D, $(C_1-C_6)$ alkyl, $(C_1-C_6)$ alkoxy, $(C_3-C_8)$ cycloalkyl, halogen, aryl, —OH, —CN, —C(O)$R_{10}$, —C(O)NR$_{10}$R$_{11}$, —NR$_{10}$C(O)R$_{11}$, NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)(($C_1$-$C_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, —NR$_{14}$C(O)R$_{15}$, —NR$_{14}$S(O)$_q$R$_{15}$, —OH or —CN;

or two $R_9$ together when on adjacent carbons form an aryl ring; or two $R_9$ together when on adjacent carbons form a heteroaryl ring; or two $R_9$ together when on adjacent carbons form a $(C_3-C_{10})$ cycloalkyl ring;

each $R_{10}$ and $R_{11}$ is independently at each occurrence selected from H, $(C_1-C_6)$ alkyl, $(C_2-C_6)$ alkenyl, $(C_2-C_6)$ alkynyl, —$(C_0-C_3)$ alkylene-aryl, —$(C_0-C_4)$ alkylene-$(C_3-C_8)$ cycloalkyl, —$(C_0-C_4)$ alkylene-heterocyclyl, —$(C_0-C_4)$ alkylene-heteroaryl, or —CN, wherein alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, —S(O)$_q$($C_1$-$C_3$) alkyl, —S(O)$_q$NR$_{14}$R$_{15}$, —NR$_{14}$R$_{15}$, —NR$_{14}$C(O)R$_{15}$, halogen, —OH, or —CN;

or $R_{10}$ and $R_{11}$ together form a heterocyclyl ring optionally substituted with one or more substituents selected from oxo, —C(O)($C_1$-$C_3$) alkyl or —NR$_{14}$NR$_{15}$;

each $R_{12}$ is independently at each occurrence selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, —O-aryl, —O-heteroaryl, —O-heterocyclyl, —O—$(C_3-C_8)$cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)(($C_1$-$C_6$)alkyl)$_2$, —P(O)(aryl)$_2$, —SiMe$_3$, SF$_5$ or —OH, wherein alkyl, aryl, heteroaryl, and cycloalkyl are optionally substituted with one or more $R_{13}$;

each $R_{13}$ is independently at each occurrence selected from D, $(C_1-C_6)$ alkyl, $(C_1-C_6)$ haloalkyl, $(C_1-C_6)$ alkoxy, halogen, $(C_1-C_6)$ haloalkoxy, $(C_1-C_6)$ hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O)NR$_{14}$R$_{15}$, —NR$_{14}$C(O)OR$_{15}$, —P(O)(($C_1$-$C_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from $(C_1-C_6)$ alkyl, —NR$_{14}$C(O)R$_{15}$, —OH, —CN, —C(O)R$_{14}$, or —NR$_{14}$R$_{15}$;

or two $R_{13}$ together when on adjacent carbons form a heterocyclyl ring optionally substituted with one or more $R_{16}$; or two $R_{13}$ together when on adjacent carbons form a heteroaryl ring optionally substituted with one or more $R_{16}$; or two $R_{13}$ together with the carbon to which they are attached can form a spiroheterocyclyl optionally substituted with one or more $R_{16}$;

each $R_{14}$ and $R_{15}$ are independently at each occurrence selected from H, $(C_1-C_6)$ alkyl, $(C_2-C_6)$ alkenyl, $(C_2-C_6)$ alkynyl, —$(C_1-C_4)$ alkylene-$(C_3-C_8)$ cycloalkyl, —$(C_0-C_4)$ alkylene-heterocyclyl, —$(C_0-C_4)$ alkylene-aryl, —$(C_0-C_4)$ alkylene-heteroaryl, or —CN, wherein alkyl, alkenyl, alkynyl, alkylene, cycloalkyl, heterocyclyl, aryl, and heteroaryl are optionally substituted with one or more $R_{16}$;

or $R_{14}$ and $R_{15}$ together form a heterocyclyl ring optionally substituted with one or more $R_{16}$;

each $R_{16}$ is independently at each occurrence selected from D, $(C_1-C_6)$ alkyl, $(C_2-C_6)$ alkenyl, $(C_2-C_6)$ alkynyl, $(C_1-C_6)$ haloalkyl, $(C_1-C_6)$ alkoxy, $(C_1-C_6)$ haloalkoxy, —C(O)($C_1$-$C_3$) alkyl, —NHC(O)($C_1$-$C_4$) alkyl, —CN, —CH$_2$CN, —CR$_{10}$R$_{11}$NR$_{10}$R$_{11}$, oxo, —NR$_{10}$R$_{11}$, —S(O)$_q$($C_1$-$C_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two $R_{16}$ together when on adjacent carbons form an aryl ring; or two $R_{16}$ together when on adjacent carbons form a spiroheterocyclyl ring;

p is 0, 1, or 2; and each q is 0, 1, or 2.

In another embodiment, the compounds of Formula (I) have the structure of Formula (Ii):

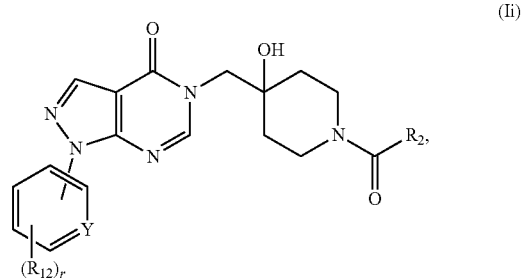

(Ii)

and pharmaceutically acceptable salts, hydrates, solvates, prodrugs, stereoisomers, and tautomers thereof, wherein:

Y is CH or N;

$R_2$ is $(C_1-C_8)$ alkyl, aryl, heteroaryl, $(C_3-C_8)$ cycloalkyl, heterocyclyl, —NR$_{10}$R$_{11}$, or —OR$_{10}$, wherein alkyl, aryl, cycloalkyl, and heterocyclyl are optionally substituted with one or more $R_8$;

each $R_8$ is independently at each occurrence selected from D, $(C_1-C_6)$ alkyl, $(C_1-C_6)$ alkoxy, $(C_1-C_6)$ haloalkyl, $(C_1-C_6)$ haloalkoxy, —$(C_1-C_3)$-alkylene-O($C_1-C_6)$ alkyl, —$(C_0-C_4)$-alkylene-aryl, —$(C_0-C_4)$-alkylene-heteroaryl, $(C_3-C_{10})$ cycloalkyl, heterocyclyl, —$(C_0-C_4)$-alkylene-O-aryl, —$(C_0-C_4)$-alkylene-O-heteroaryl, —O—$(C_3-C_8)$cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —$(C_0-C_3)$-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)(($C_1$-$C_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more $R_9$;

or two $R_8$ together when on adjacent carbons form an aryl ring optionally substituted with one or more $R_9$; or two $R_8$ together when on adjacent carbons form a heteroaryl ring optionally substituted with one or more $R_9$; or two R$_8$ together when on adjacent carbons form a heterocyclyl ring optionally substituted with one or more R$_9$;

each R$_9$ is independently at each occurrence selected from D, (C$_1$-C$_6$) alkyl, (C$_1$-C$_6$) alkoxy, (C$_3$-C$_8$) cycloalkyl, halogen, aryl, —OH, —CN, —C(O)R$_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from (C$_1$-C$_6$) alkyl, (C$_1$-C$_6$) alkoxy, (C$_1$-C$_6$) haloalkyl, halogen, aryl, —NR$_{14}$C(O)R$_{15}$, —NR$_{14}$S(O)$_q$R$_{15}$, —OH or —CN;

or two R$_9$ together when on adjacent carbons form an aryl ring; or two R$_9$ together when on adjacent carbons form a heteroaryl ring; or two R$_9$ together when on adjacent carbons form a (C$_3$-C$_{10}$) cycloalkyl ring;

each R$_{10}$ and R$_{11}$ is independently at each occurrence selected from H, (C$_1$-C$_6$) alkyl, (C$_2$-C$_6$) alkenyl, (C$_2$-C$_6$) alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from (C$_1$-C$_6$) alkyl, (C$_1$-C$_6$) alkoxy, (C$_1$-C$_6$) haloalkyl, (C$_1$-C$_6$) haloalkoxy, (C$_3$-C$_8$) cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN;

or R$_{10}$ and R$_{11}$ together form a heterocyclyl ring optionally substituted with one or more substituents selected from oxo, —C(O)(C$_1$-C$_3$) alkyl or —NR$_{14}$NR$_{15}$;

each R$_{12}$ is independently at each occurrence selected from D, (C$_1$-C$_6$) alkyl, (C$_1$-C$_6$) alkoxy, (C$_1$-C$_6$) haloalkyl, (C$_3$-C$_8$) cycloalkyl, aryl, heteroaryl, —O-aryl, —O-heteroaryl, —O-heterocyclyl, —O—(C$_3$-C$_8$)cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, and cycloalkyl are optionally substituted with one or more R$_{13}$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O)NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_{13}$ together when on adjacent carbons form a heteroaryl ring optionally substituted with one or more R$_{16}$; or two R$_{13}$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, —CR$_1$OR$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two R$_{16}$ together when on adjacent carbons form an aryl ring; or two R$_{16}$ together when on adjacent carbons form a spiroheterocyclyl ring;

p is 0, 1, or 2;

each q is 0, 1, or 2 and r is 0, 1, 2, 3, 4, or 5.

In another embodiment, the compounds of Formula (I) have the structure of Formula (Ij):

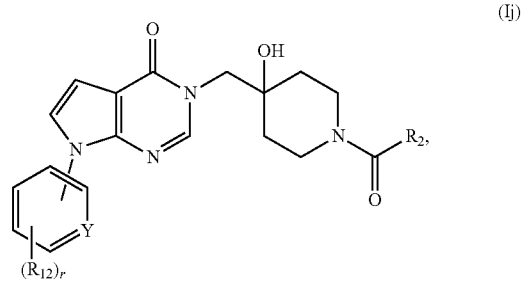

(Ij)

and pharmaceutically acceptable salts, hydrates, solvates, prodrugs, stereoisomers, and tautomers thereof, wherein:

Y is CH or N;

R$_2$ is (C$_1$-C$_8$) alkyl, aryl, heteroaryl, (C$_3$-C$_8$) cycloalkyl, heterocyclyl, —NR$_{10}$R$_{11}$, or —OR$_{10}$, wherein alkyl, aryl, cycloalkyl, and heterocyclyl are optionally substituted with one or more R$_R$;

each R$_8$ is independently at each occurrence selected from D, (C$_1$-C$_6$) alkyl, (C$_1$-C$_6$) alkoxy, (C$_1$-C$_6$) haloalkyl, (C$_1$-C$_6$) haloalkoxy, —(C$_1$-C$_3$)-alkylene-O(C$_1$-C$_6$) alkyl, —(C$_0$-C$_4$)-alkylene-aryl, —(C$_0$-C$_4$)-alkylene-heteroaryl, (C$_3$-C$_{10}$) cycloalkyl, heterocyclyl, —(C$_0$-C$_4$)-alkylene-O-aryl, —(C$_0$-C$_4$)-alkylene-O-heteroaryl, —O—(C$_3$-C$_8$)cycloalkyl, —S-heteroaryl, halogen, —CN, —C(O)R$_{10}$, —CO(O)R$_{10}$, —C(O)NR$_{10}$R$_{11}$, —S(O)$_q$R$_{10}$, —S(O)$_q$NR$_{10}$R$_{11}$, —NR$_{10}$S(O)$_q$R$_{11}$, —(C$_0$-C$_3$)-alkylene-NR$_{10}$R$_{11}$, —NR$_{10}$C(O)R$_{11}$, —NR$_{10}$C(O)C(O)R$_{11}$, —NR$_{10}$C(O)NR$_{10}$R$_{11}$, —P(O)((C$_1$-C$_6$)alkyl)$_2$, —P(O)(aryl)$_2$, —SiMe$_3$, SF$_5$, or —OH, wherein alkyl, alkylene, aryl, heteroaryl, and heterocyclyl are optionally substituted with one or more R$_9$;

or two R$_8$ together when on adjacent carbons form an aryl ring optionally substituted with one or more R$_9$; or two R$_8$ together when on adjacent carbons form a heteroaryl ring optionally substituted with one or more R$_9$; or two R$_8$ together when on adjacent carbons form a heterocyclyl ring optionally substituted with one or more R$_9$;

each $R_9$ is independently at each occurrence selected from D, $(C_1-C_6)$ alkyl, $(C_1-C_6)$ alkoxy, $(C_3-C_8)$ cycloalkyl, halogen, aryl, —OH, —CN, —C(O)$R_{10}$, —C(O)NR$_{10}$R$_{11}$, —NR$_{10}$C(O)R$_{11}$, —NR$_{10}$R$_{11}$, —S(O)$_q$R$_{10}$, —S(O)$_q$NR$_{10}$R$_{11}$, —NR$_{10}$S(O)$_q$R$_{11}$, oxo, —P(O)((C$_1$-C$_6$)alkyl)$_2$, —P(O)(aryl)$_2$, —SiMe$_3$, SF$_5$, —O-aryl, CN, or —O-heteroaryl, wherein alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, —NR$_{14}$C(O)R$_{15}$, —NR$_4$S(O)$_q$R$_{15}$, —OH or —CN;

or two $R_9$ together when on adjacent carbons form an aryl ring; or two $R_9$ together when on adjacent carbons form a heteroaryl ring; or two $R_9$ together when on adjacent carbons form a $(C_3-C_{10})$ cycloalkyl ring;

each $R_{10}$ and $R_{11}$ is independently at each occurrence selected from H, $(C_1-C_6)$ alkyl, $(C_2-C_6)$ alkenyl, $(C_2-C_6)$ alkynyl, —(C$_0$-C$_3$) alkylene-aryl, —(C$_0$-C$_4$) alkylene-(C$_3$-C$_8$) cycloalkyl, —(C$_0$-C$_4$) alkylene-heterocyclyl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, —S(O)$_q$(C$_1$-C$_3$) alkyl, —S(O)$_q$NR$_{14}$R$_{15}$, —NR$_{14}$R$_{15}$, —NR$_{14}$C(O)R$_{15}$, halogen, —OH, or —CN;

or $R_{10}$ and $R_{11}$ together form a heterocyclyl ring optionally substituted with one or more substituents selected from oxo, —C(O)(C$_1$-C$_3$) alkyl or —NR$_{14}$NR$_{15}$;

each $R_{12}$ is independently at each occurrence selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, —O-aryl, —O-heteroaryl, —O-heterocyclyl, —O—(C$_3$-C$_8$)cycloalkyl, —S(O)$_q$R$_{10}$, —(CH$_2$)$_p$C(O)OR$_{10}$, —C(O)NR$_{14}$R$_{15}$, —S(O)$_q$NR$_{14}$R$_{15}$, —NR$_{14}$R$_{15}$, —NR$_{14}$C(O)NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein alkyl, aryl, heteroaryl, and cycloalkyl are optionally substituted with one or more R$_3$;

each $R_{13}$ is independently at each occurrence selected from D, $(C_1-C_6)$ alkyl, $(C_1-C_6)$ haloalkyl, $(C_1-C_6)$ alkoxy, halogen, $(C_1-C_6)$ haloalkoxy, $(C_1-C_6)$ hydroxyalkyl, heterocyclyl, heteroaryl, aryl, —OR$_{14}$, —C(O)R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O)NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from $(C_1-C_6)$ alkyl, —NR$_{14}$C(O)R$_{15}$, —OH, —CN, —C(O)R$_{14}$, or —NR$_{14}$R$_{15}$;

or two $R_{13}$ together when on adjacent carbons form a heterocyclyl ring optionally substituted with one or more R$_{16}$; or two $R_{13}$ together when on adjacent carbons form a heteroaryl ring optionally substituted with one or more R$_{16}$; or two $R_{13}$ together with the carbon to which they are attached can form a spiroheterocyclyl optionally substituted with one or more R$_{16}$;

each $R_{14}$ and $R_{15}$ are independently at each occurrence selected from H, $(C_1-C_6)$ alkyl, $(C_2-C_6)$ alkenyl, $(C_2-C_6)$ alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or $R_{14}$ and $R_{15}$ together form a heterocyclyl ring optionally substituted with one or more R$_{16}$;

each $R_{16}$, is independently at each occurrence selected from D, $(C_1-C_6)$ alkyl, $(C_2-C_6)$ alkenyl, $(C_2-C_6)$ alkynyl, $(C_1-C_6)$ haloalkyl, $(C_1-C_6)$ alkoxy, $(C_1-C_6)$ haloalkoxy, —C(O)(C$_1$-C$_3$) alkyl, —NHC(O)(C$_1$-C$_4$) alkyl, —CN, —CH$_2$CN, —CR$_{10}$R$_{11}$NR$_{10}$R$_{11}$, oxo, —NR$_{10}$R$_{11}$, —S(O)$_q$(C$_1$-C$_6$) alkyl, —C(O)NR$_{10}$R$_{11}$, —S(O)$_q$NR$_{10}$R$_{11}$, —NR$_{10}$C(O)R$_{10}$R$_{11}$, —NR$_{10}$C(O)NR$_{10}$R$_{11}$, or —OH;

or two $R_{16}$ together when on adjacent carbons form an aryl ring; or two $R_{16}$ together when on adjacent carbons form a spiroheterocyclyl ring;

p is 0, 1, or 2;

each q is 0, 1, or 2 and r is 0, 1, 2, 3, 4, or 5.

In some embodiments of the Formulae above, $X_1$ is C, S, or S(O). In another embodiment, $X_1$ is C. In yet another embodiment, $X_1$ is S. In another embodiment, $X_1$ is S(O).

In some embodiments of the Formulae above, $X_2$ is N. In another embodiment, $X_2$ is CR$_7$.

In some embodiments of the Formulae above, $R_1$ is H, D, —OH, —SH, —NH$_2$, —NH(C$_1$-C$_4$) alkyl, —N((C$_1$-C$_4$) alkyl)$_2$, or F. In another embodiment, $R_1$ is —OH, —SH, —NH$_2$, —NH(C$_1$-C$_2$) alkyl, —N((C$_1$-C$_2$) alkyl)$_2$, or F. In yet another embodiment, $R_1$ is —OH, —SH, —NH$_2$, —NHCH$_3$, —NHCH$_2$CH$_3$, —N(CH$_3$)$_2$, —N(CH$_2$CH$_3$)$_2$ or F. In another embodiment, $R_1$ is —OH, —NH$_2$, —NHCH$_3$, —N(CH$_3$)$_2$, or F. In yet another embodiment, $R_1$ is —OH, —NH$_2$, or F.

In some embodiments of the Formulae above embodiment, $R_2$ is $(C_1-C_8)$ alkyl, aryl, heteroaryl, $(C_3-C_8)$ cycloalkyl, heterocyclyl, —NR$_{10}$R$_{11}$, or OR$_{10}$. In this embodiment, alkyl, aryl, cycloalkyl, and heterocyclyl are optionally substituted with one or more R$_8$.

In some embodiments of the Formulae above, $R_3$ is D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, aryl, heteroaryl, $(C_3-C_8)$ cycloalkyl, heterocyclyl, —CN, —OH, —C(O)R$_{17}$, C(O)OR$_{17}$, —OC(O)OR$_{17}$, —OC(O)NR$_{17}$R$_{18}$, —NR$_{17}$R$_{18}$, —NR$_{17}$C(O)R$_{18}$, —NR$_{17}$C(O)OR$_{18}$, —C(O)NR$_{17}$R$_{18}$, —NR$_{17}$C(O)NR$_{17}$R$_{18}$, —S(O)$_q$NR$_{17}$R$_{18}$, —S(O)$_q$ R$_{17}$R$_{18}$, —NR$_{17}$S(O)$_q$R$_{17}$R$_{18}$, or halogen. In another embodiment, $R_3$ is selected from $(C_1-C_6)$ alkyl, $(C_1-C_6)$ alkenyl, $(C_2-C_6)$ alkynyl, $(C_1-C_6)$ alkoxy, $(C_1-C_6)$ haloalkyl, $(C_1-C_6)$ haloalkoxy, aryl, heteroaryl, $(C_3-C_8)$ cycloalkyl, heterocyclyl, or —OH In yet another embodiment, $R_3$ is selected from $(C_1-C_6)$ alkyl, $(C_1-C_6)$ alkoxy, $(C_1-C_6)$ haloalkyl, $(C_1-C_6)$ haloalkoxy, or —OH. In yet another embodiment, $R_3$ is selected from $(C_1-C_3)$ alkyl, $(C_1-C_3)$ alkoxy, $(C_1-C_3)$ haloalkyl, $(C_1-C_3)$ haloalkoxy, or —OH In another embodiment, $R_3$ is selected from $(C_1-C_3)$ alkyl, $(C_1-C_3)$ alkoxy, or —OH. In another embodiment, $R_3$ is selected from methyl, ethyl, propyl, isopropyl, methoxy, ethoxy, isopropoxy, or —OH.

In some embodiments of the Formulae above, two $R_3$ together when on adjacent carbons can form a $(C_3-C_8)$ cycloalkyl optionally substituted with one or more R$_{19}$. In another embodiment, two $R_3$ together when on adjacent carbons can form a $(C_3-C_8)$ spirocycloalkyl optionally substituted with one or more R$_{19}$. In another embodiment, two $R_3$ together when on adjacent carbons can form a spiroheterocyclyl optionally substituted with one or more R$_{19}$. In yet another embodiment, two $R_3$ together when on adjacent carbons can form an aryl ring optionally substituted with one or more $R_{19}$. In another embodiment, two $R_3$ together when on adjacent carbons can form a heteroaryl ring optionally substituted with one or more $R_{19}$.

In some embodiments of the Formulae above, $R_4$ is $(C_1-C_6)$ alkyl, $-(C_0-C_3)$ alkylene-aryl, heteroaryl, $(C_3-C_8)$ cycloalkyl, $CD_3$, or heterocyclyl, where the aryl, heteroaryl, heterocyclyl and cycloalkyl are optionally substituted with one or more $R_{12}$.

In some embodiments of the Formulae above, $R_5$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen. In another embodiment, $R_5$ is H, D, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or halogen. In yet another embodiment, $R_5$ is H, $(C_1-C_3)$ alkyl, $(C_1-C_3)$ alkoxy, $(C_1-C_3)$ haloalkyl, or halogen. In another embodiment, $R_5$ is H or $(C_1-C_3)$ alkyl. In yet another embodiment, $R_5$ is H, methyl, ethyl, propyl, or isopropyl.

In some embodiments of the Formulae above, $R_5$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen. In another embodiment, $R_{5'}$ is H, D, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or halogen. In yet another embodiment, $R_{5'}$ is H, D, $(C_1-C_3)$ alkyl, $(C_1-C_3)$ alkoxy, $(C_1-C_3)$ haloalkyl, or halogen. In another embodiment, $R_{5'}$ is H or $(C_1-C_3)$ alkyl. In yet another embodiment, $R_{5'}$ is H, methyl, ethyl, propyl, or isopropyl.

In some embodiments of the Formulae above, $R_5$ and $R_{5'}$ together can form a $(C_3-C_6)$ cycloalkyl or heterocyclyl ring optionally substituted. The optional substituents can be halogen, —CN, $(C_1-C_6)$ alkyl, —OH, —CH$_2$OH, $-(C_0-C_2)$-alkylene-O$(C_1-C_6)$ alkyl, or $-(C_0-C_2)$-alkylene-$NR_{17}R_{18}$.

In some embodiments of the Formulae above, $R_6$ is H, D, halogen, —CN, $-NR_{17}R_{18}$, $(C_1-C_6)$ alkyl, $(C_1-C_6)$ alkoxy, or —OH. In another embodiment, $R_6$ is H, D, halogen, —CN, $(C_1-C_4)$ alkyl, $(C_1-C_4)$ alkoxy, or —OH. In yet another embodiment, $R_6$ is H, halogen, or $(C_1-C_3)$ alkyl In another embodiment, $R_6$ is H, F, Cl, methyl, ethyl, propyl, or isopropyl.

In some embodiments of the Formulae above, $R_7$ is H, D, $(C_1-C_6)$ alkyl, $(C_1-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, optionally substituted aryl, optionally substituted heteroaryl, —CN, or $-NR_{10}R_{11}$. In another embodiment, $R_7$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, or halogen. In yet another embodiment, $R_7$ is H, D, $(C_1-C_3)$ alkyl, $(C_2-C_3)$ alkenyl, $(C_2-C_3)$ alkynyl, $(C_1-C_3)$ alkoxy, $(C_1-C_3)$ haloalkyl, $(C_1-C_3)$ haloalkoxy, or halogen. In another embodiment, $R_7$ is H, D, $(C_1-C_3)$ alkyl, $(C_1-C_3)$ alkoxy, $(C_1-C_3)$ haloalkyl, $(C_1-C_3)$ haloalkoxy, or halogen. In yet another embodiment, $R_7$ is H, D, $(C_1-C_3)$ alkyl, $(C_1-C_3)$ alkoxy, $(C_1-C_3)$ haloalkyl, or halogen. In another embodiment, $R_7$ is H, $(C_1-C_3)$ alkyl, or halogen. In yet another embodiment, $R_7$ is H, methyl, ethyl, propyl, isopropyl, F or Cl. In another embodiment, $R_7$ is H or methyl.

In some embodiments of the Formulae above, $R_8$ is D, $(C_1-C_6)$ alkyl, $(C_1-C_6)$ alkoxy, $(C_1-C_6)$ haloalkyl, $(C_1-C_6)$ haloalkoxy, $-(C_1-C_3)$-alkylene-O$(C_1-C_6)$ alkyl, $-(C_0-C_4)$-alkylene-aryl, $-(C_0-C_4)$-alkylene-heteroaryl, $(C_3-C_{10})$ cycloalkyl, heterocyclyl, $-(C_0-C_4)$-alkylene-O-aryl, $-(C_0-C_4)$-alkylene-O-heteroaryl, —O—$(C_3-C_8)$cycloalkyl, —S-heteroaryl, halogen, —CN, $-C(O)R_{10}$, $-CO(O)R_{10}$, $-C(O)NR_{10}R_{11}$, $-S(O)_qR_{10}$, $-S(O)_qNR_{10}R_{11}$, $-NR_{10}S$ (O)$_qR_{11}$, $-(C_0-C_3)$-alkylene-$NR_{10}R_{11}$, $-NR_{10}C(O)R_{11}$, $-NR_{10}C(O)C(O)R_{11}$, $-NR_{10}C(O)NR_{10}R_{11}$, $-P(O)((C_1-C_6)alkyl)_2$, $-P(O)(aryl)_2$, $-SiMe_3$, $SF_5$, or —OH. In this embodiment, alkyl, alkylene, aryl, heteroaryl, and heterocyclyl can be optionally substituted with one or more $R_9$.

In some embodiments of the Formulae above, two $R_8$ together when on adjacent carbons can form an aryl ring optionally substituted with one or more $R_9$. In yet another embodiment, two $R_q$ together when on adjacent carbons can form a heteroaryl ring optionally substituted with one or more $R_9$. In another embodiment, two $R_8$ together when on adjacent carbons can form a heterocyclyl ring optionally substituted with one or more $R_9$.

In some embodiments of the Formulae above, $R_9$ is D, $(C_1-C_6)$ alkyl, $(C_1-C_6)$ alkoxy, $(C_3-C_8)$ cycloalkyl, halogen, aryl, —OH, —CN, $-C(O)R_{10}$, $-C(O)NR_{10}R_{11}$, $-NR_{10}C$ (O)$R_{11}$, $-NR_{10}R_{11}$, $-S(O)_qR_{10}$, $-S(O)_qNR_{10}R_{11}$, $-NR_{10}S(O)_qR_{11}$, oxo, $-P(O)((C_1-C_6)alkyl)_2$, $-P(O)(aryl)_2$, $-SiMe_3$, $SF_5$, —O-aryl, or —O-heteroaryl. The alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, $-NR_{14}C(O)R_{15}$, $-NR_{14}S(O)_qR_{15}$, —OH or —CN.

In some embodiments of the Formulae above, two $R_9$ together when on adjacent carbons can form an aryl ring. In another embodiment, two $R_9$ together when on adjacent carbons can form a heteroaryl ring. In another embodiment, two $R_9$ together when on adjacent carbons can form a $(C_3-C_{10})$ cycloalkyl ring.

In some embodiments of the Formulae above, $R_{10}$ is H, $(C_1-C_6)$ alkyl, $(C_2-C_6)$ alkenyl, $(C_2-C_6)$ alkynyl, $-(C_0-C_3)$ alkylene-aryl, $-(C_0-C_4)$ alkylene-$(C_3-C_8)$ cycloalkyl, $-(C_0-C_4)$ alkylene-heterocyclyl, $-(C_0-C_4)$ alkylene-heteroaryl, or —CN. The alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, $-S(O)_q(C_1-C_3)$ alkyl, $-S(O)_qNR_{14}R_{15}$, $-NR_{14}R_{15}$, $-NR_{14}C(O)R_{15}$, halogen, —OH, or —CN.

In some embodiments of the Formulae above, $R_{11}$ is H, $(C_1-C_6)$ alkyl, $(C_2-C_6)$ alkenyl, $(C_2-C_6)$ alkynyl, $-(C_0-C_3)$ alkylene-aryl, $-(C_0-C_4)$ alkylene-$(C_3-C_8)$ cycloalkyl, $-(C_0-C_4)$ alkylene-heterocyclyl, $-(C_0-C_4)$ alkylene-heteroaryl, or —CN. The alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, $-S(O)_q(C_1-C_3)$ alkyl, $-S(O)_qNR_{14}R_{15}$, $-NR_{14}R_{15}$, $-NR_{14}C(O)R_{15}$, halogen, —OH, or —CN.

In some embodiments of the Formulae above, $R_{10}$ and $R_{11}$ together when on adjacent carbons can form a heterocyclyl ring optionally substituted with one or more substituents selected from oxo, $-C(O)(C_1-C_3)$ alkyl or $-NR_{14}NR_{15}$.

In some embodiments of the Formulae above, $R_{12}$ is selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, —O-aryl, —O-heteroaryl, —O-heterocyclyl, —O—$(C_3-C_8)$cycloalkyl, $-S(O)_qR_{10}$, $-(CH_2)_pC(O)OR_{10}$, $-C(O)NR_{14}R_{15}$, $-S(O)_qNR_{14}R_{15}$, $-NR_{14}R_{15}$, $-NR_{14}C(O)NR_{14}R_{15}$, $-NR_{14}C(O)OR_{10}$, $-NR_{14}SO_qR_{10}$, $-NR_{14}COR_{10}$, halogen, $-P(O)((C_1-C_6)alkyl)_2$, $-P(O)(aryl)_2$, $-SiMe_3$, $SF_5$ or —OH, wherein alkyl, aryl, heteroaryl, and cycloalkyl are optionally substituted with one or more $R_{13}$.

In one embodiment, $R_{13}$ is selected from D, $(C_1-C_6)$ alkyl, $(C_1-C_6)$ haloalkyl, $(C_1-C_6)$ alkoxy, halogen, $(C_1-C_6)$ haloalkoxy, $(C_1-C_6)$ hydroxyalkyl, heterocyclyl, heteroaryl, aryl, $-OR_{14}$, $C(O)R_{14}$, $-C(O)NR_{14}R_{15}$, $-NR_{14}R_{15}$, $-S(O)R_{14}$, $-NR_{14}S(O)_qR_{15}$, $-S(O)_qNR_{14}R_{15}$, $-NR_{14}C(O)NR_{14}R_{15}$, $-NR_{14}C(O)OR_{15}$, $-P(O)((C_1-C_6)alkyl)_2$, $-P(O)(aryl)_2$, $-SiMe_3$, $SF_5$ or $-CN$, wherein alkyl, cycloalkyl, aryl, heterocyclyl, and heteroaryl are substituted with one or more substituents independently selected from $(C_1-C_6)$ alkyl, $-NR_{14}C(O)R_{15}$, $-OH$, $-CN$, $-C(O)R_{14}$, or $-NR_{14}R_{15}$ In another embodiment, two $R_{13}$ together when on adjacent carbons form a heterocyclyl ring optionally substituted with one or more $R_{16}$. In yet another embodiment, two $R_{13}$ together when on adjacent carbons form a heteroaryl ring optionally substituted with one or more $R_{16}$. In another embodiment, two $R_{13}$ together with the carbon to which they are attached can form a spiroheterocyclyl optionally substituted with one or more $R_{16}$.

In one embodiment, $R_{14}$ is H, $(C_1-C_6)$ alkyl, $(C_2-C_6)$ alkenyl, $(C_2-C_6)$ alkynyl, $-(C_1-C_4)$ alkylene-$(C_3-C_8)$ cycloalkyl, $-(C_0-C_4)$ alkylene-heterocyclyl, $-(C_0-C_4)$ alkylene-aryl, $-(C_0-C_4)$ alkylene-heteroaryl, or $-CN$, where the alkyl, alkenyl, alkynyl, alkylene, cycloalkyl, heterocyclyl, aryl, and heteroaryl are optionally substituted with one or more $R_{16}$.

In some embodiments of the Formulae above, $R_{15}$ is H, $(C_1-C_6)$ alkyl, $(C_2-C_6)$ alkenyl, $(C_2-C_6)$ alkynyl, $-(C_1-C_4)$ alkylene-$(C_3-C_8)$ cycloalkyl, $-(C_0-C_4)$ alkylene-heterocyclyl, $-(C_0-C_4)$ alkylene-aryl, $-(C_0-C_4)$ alkylene-heteroaryl, or $-CN$, where the alkyl, alkenyl, alkynyl, alkylene, cycloalkyl, heterocyclyl, aryl, and heteroaryl are optionally substituted with one or more $R_{16}$.

In some embodiments of the Formulae above, $R_{14}$ and $R_{15}$ together can form a heterocyclyl ring optionally substituted with one or more $R_{16}$.

In some embodiments of the Formulae above, $R_{16}$ is D, $(C_1-C_6)$ alkyl, $(C_2-C_6)$ alkenyl, $(C_2-C_6)$ alkynyl, $(C_1-C_6)$ haloalkyl, $(C_1-C_6)$ alkoxy, $(C_1-C_6)$ haloalkoxy, $-C(O)(C_1-C_3)$ alkyl, $-NHC(O)(C_1-C_4)$ alkyl, $-CN$, $-CH_2CN$, $-CR_{10}R_{11}NR_{10}R_{11}$, oxo, $-NR_{10}R_{11}$, $-S(O)_q(C_1-C_6)$ alkyl, $-C(O)NR_{10}R_{11}$, $-S(O)_qNR_{10}R_{11}$, $-NR_{10}C(O)R_{10}R_{11}$, $-NR_{10}C(O)NR_{10}R_{11}$, or $-OH$. In another embodiment, two $R_{16}$ together when on adjacent carbons can form an aryl ring. In yet another embodiment, two $R_{16}$ together when on adjacent carbons can form a spiroheterocyclyl ring.

In some embodiments of the Formulae above, $R_{17}$ is H or $(C_1-C_6)$ alkyl. In another embodiment, $R_{17}$ is independently H or $(C_1-C_4)$ alkyl. In yet another embodiment, $R_{17}$ is independently H, methyl, ethyl, propyl, isopropyl, butyl, iso-butyl, or tert-butyl.

In some embodiments of the Formulae above, $R_{18}$ is H or $(C_1-C_6)$ alkyl. In another embodiment, $R_{18}$ is independently H, methyl, ethyl, propyl, isopropyl, butyl, iso-butyl, or tert-butyl.

In some embodiments of the Formulae above, $R_{18}$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, $-CN$, or $-NR_{17}R_{18}$.

In some embodiments of the Formulae above, m is 0, 1 or 2. In another embodiment, m is 0 or 1.

In some embodiments of the Formulae above, n is 0, 1, 2 or 3. In another embodiment, n is 0, 1, or 2. In another embodiment, n is 1.

In some embodiments of the Formulae above, p is 0. In another embodiment, p is 1. In yet another embodiment, p is 2.

In some embodiments of the Formulae above, q is 0. In another embodiment, q is 1. In yet another embodiment, q is 2.

In some embodiments of the Formulae above, $X_1$ is C. In another embodiment, $X_1$ is C and $X_2$ is N. In yet another embodiment, $X_1$ is C, $X_2$ is N and $R_1$ is OH. In another embodiment, $X_1$ is C, $X_2$ is N, $R_1$ is OH, and $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$. In another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, and $R_5$ is H. In yet another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, and $R_{5'}$ is H. In another embodiment, $X_1$ is C, $X_2$ is N, $R_1$ is OH, $R_2$ is $(C_1-C_5)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H and $R_6$ is H. In yet another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H, $R_6$ is H and $R_4$ is $(C_1-C_6)$ alkyl, aryl or heteroaryl optionally substituted with one or more $R_{12}$. In another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1-C_6)$ alkyl, aryl or heteroaryl optionally substituted with one or more $R_{12}$, and $R_{12}$ is $(C_1-C_6)$ alkyl, $(C_1-C_6)$ haloalkyl, halogen, $-O$-aryl, or $-O-$ heteroaryl optionally substituted with one or more $R_1$. In another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H, $R_6$ is H and $R_4$ is $(C_1-C_6)$ alkyl, aryl or heteroaryl optionally substituted with one or more $R_{12}$. In another embodiment, $X_1$ is C, $X_2$ is N, $R_1$ is OH, $R_2$ is $(C_1-C_8)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1-C_6)$ alkyl, aryl or heteroaryl optionally substituted with one or more $R_{12}$, $R_{12}$ is $(C_1-C_6)$ alkyl, $(C_1-C_6)$ haloalkyl, halogen, $-O$-aryl, or $-O$-heteroaryl optionally substituted with one or more $R_{13}$, and $R_{13}$ is $(C_1-C_6)$ alkyl, $(C_1-C_6)$ haloalkyl, $(C_1-C_6)$ alkoxy, halogen, $(C_1-C_6)$ haloalkoxy, heterocyclyl, heteroaryl, aryl, $-OR_{14}$, $-C(O)R_{14}$, $-C(O)NR_{14}R_{15}$, $-NR_{14}R_{15}$, $-S(O)_qR_{14}$, $-NR_{14}S(O)_qR_{15}$, $-S(O)_qNR_{14}R_{15}$, or $-CN$, wherein alkyl, cycloalkyl, aryl, heterocyclyl, and heteroaryl are substituted with one or more substituents independently selected from $(C_1-C_6)$ alkyl, $-NR_{14}C(O)R_{15}$, $-OH$, $-CN$, $-C(O)R_{14}$, or $-NR_{14}R_{15}$. In yet another embodiment, $X_1$ is C, $X_2$ is N, $R_1$ is OH, $R_2$ is $(C_1-C_5)$ alkyl, aryl, heteroaryl, $(C_3-C_8)$ cycloalkyl, heterocyclyl, $-NR_{10}R_{11}$, or $-OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1-C_6)$ alkyl, aryl or heteroaryl optionally substituted with one or more $R_{12}$, $R_{12}$ is $(C_1-C_6)$ alkyl, $(C_1-C_6)$ haloalkyl, halogen, $-O-$ aryl, or —O-heteroaryl optionally substituted with one or more $R_{13}$, and two $R_3$ together when on adjacent carbons form a heterocyclyl ring optionally substituted with one or more $R_{16}$, two $R_{13}$ together when on adjacent carbons form a heteroaryl ring optionally substituted with one or more $R_{16}$, or two $R_{13}$ together with the carbon to which they are attached can form a spiroheterocyclyl optionally substituted with one or more $R_{16}$.

In some embodiments of the Formulae above, $X_1$ is C. In another embodiment, $X_1$ is C and $X_2$ is CH. In yet another embodiment, $X_1$ is C, $X_2$ is CH and $R_1$ is OH. In another embodiment, $X_1$ is C, $X_2$ is CH, $R_1$ is OH, and $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$. In another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, and $R_5$ is H. In yet another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, and $R_{5'}$ is H. In another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H and $R_6$ is H. In yet another embodiment, $X_1$ is C, $X_2$ is CH, $R_1$ is OH, $R_2$ is $(C_1$-$C_5)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H, $R_6$ is H and $R_4$ is $(C_1$-$C_6)$ alkyl, aryl or heteroaryl optionally substituted with one or more $R_{12}$. In another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1$-$C_6)$ alkyl, aryl or heteroaryl optionally substituted with one or more $R_{12}$, and $R_{12}$ is $(C_1$-$C_6)$ alkyl, $(C_1$-$C_6)$ haloalkyl, halogen, —O-aryl, or —O-heteroaryl optionally substituted with one or more $R_1$. In another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H, $R_6$ is H and $R_4$ is $(C_1$-$C_6)$ alkyl, aryl or heteroaryl optionally substituted with one or more $R_{12}$. In another embodiment, $X_1$ is C, $X_2$ is CH, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1$-$C_6)$ alkyl, aryl or heteroaryl optionally substituted with one or more $R_{12}$, $R_{12}$ is $(C_1$-$C_6)$ alkyl, $(C_1$-$C_6)$ haloalkyl, halogen, —O-aryl, or —O-heteroaryl optionally substituted with one or more $R_{13}$, and $R_{13}$ is $(C_1$-$C_6)$ alkyl, $(C_1$-$C_6)$ haloalkyl, $(C_1$-$C_6)$ alkoxy, halogen, $(C_1$-$C_6)$ haloalkoxy, heterocyclyl, heteroaryl, aryl, —$OR_{14}$, —$C(O)R_{14}$, —$C(O)NR_{14}R_{15}$, —$NR_{14}R_{15}$, —$S(O)_qR_{14}$, —$NR_{14}S(O)_qR_{15}$, —$S(O)_qNR_{14}R_{15}$, or —CN, wherein alkyl, cycloalkyl, aryl, heterocyclyl, and heteroaryl are substituted with one or more substituents independently selected from $(C_1$-$C_6)$ alkyl, —$NR_{14}C(O)R_{15}$, —OH, —CN, —$C(O)R_1$a, or —$NR_{14}R_{15}$. In yet another embodiment, $X_1$ is C, $X_2$ is N, $R_1$ is OH, $R_2$ is $(C_1$-$C_8)$ alkyl, aryl, heteroaryl, $(C_3$-$C_8)$ cycloalkyl, heterocyclyl, —$NR_{10}R_{11}$, or —$OR_{10}$, wherein alkyl, aryl, cycloalkyl, and heterocyclyl are optionally substituted with one or more $R_8$, $R_5$ is H, $R_{5'}$ is H, $R_6$ is H, $R_4$ is $(C_1$-$C_6)$ alkyl, aryl or heteroaryl optionally substituted with one or more $R_{12}$, $R_{12}$ is $(C_1$-$C_6)$ alkyl, $(C_1$-$C_6)$ haloalkyl, halogen, —O-aryl, or —O-heteroaryl optionally substituted with one or more $R_{13}$, and two $R_{13}$ together when on adjacent carbons form a heterocyclyl ring optionally substituted with one or more $R_{16}$, two $R_{13}$ together when on adjacent carbons form a heteroaryl ring optionally substituted with one or more $R_{16}$, or two $R_{13}$ together with the carbon to which they are attached can form a spiroheterocyclyl optionally substituted with one or more $R_{16}$.

Non-limiting illustrative compounds of the invention include:

5-{[4-hydroxy-1-(3-phenylbutanoyl)piperidin-4-yl]methyl}-1-methyl-1H,4H,5H-pyrazolo[3,4-d]pyrimidin-4-one (1-1);

4-({4-[4-hydroxy-4-({1-methyl-4-oxo-1H,4H,5H-pyrazolo[3,4-d]pyrimidin-5-yl}methyl)piperidine-1-carbonyl]phenyl}methoxy)benzonitrile (I-10);

1-(4-fluorophenyl)-5-((4-hydroxy-1-(4-(5-methyl-5,6-dihydropyrrolo [3,4-c]pyrazol-1(4H)-yl)benzoyl)piperidin-4-yl)methyl)-1H-pyrazolo[3,4-d]pyrimidin-4(5H)-one (I-1000);

1-(4-fluorophenyl)-5-{[4-hydroxy-1-(4-{5-methyl-2H,4H,5H,6H-pyrrolo[3,4-c]pyrazol-2-yl}benzoyl)piperidin-4-yl]methyl}-1H,4H,5H-pyrazolo[3,4-d]pyrimidin-4-one (I-1001);

2-(4-(4-(4-((1-(4-fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetamide (I-1002);

5-((1-((2R,4S)-1-acryloyl-4-methylazetidine-2-carbonyl)-4-hydroxypiperidin-4-yl)methyl)-1-(4-fluorophenyl)-1H-pyrazolo[3,4-d]pyrimidin-4(5H)-one (I-1003);

5-{[1-(4-{2,5-diazabicyclo[2.2.1]heptan-2-yl}benzoyl)-4-hydroxypiperidin-4-yl]methyl}-1-(4-fluorophenyl)-1H,4H,5H-pyrazolo[3,4-d]pyrimidin-4-one trifluoroacetic acid salt (I-1005);

1-(4-fluorophenyl)-5-[(4-hydroxy-1-{4-[1-(2-hydroxyethyl)-1H-pyrazol-4-yl]benzoyl}piperidin-4-yl)methyl]-1H,4H,5H-pyrazolo[3,4-d]pyrimidin-4-one (I-1006);

5-((1-(4-fluorobenzoyl)-4-hydroxypiperidin-4-yl)methyl)-1-(4-(2-(1-methylpiperidin-2-yl)ethyl)phenyl)-1H-pyrazolo[3,4-d]pyrimidin-4(5H)-one (I-1007);

1-(3-(3-(dimethylamino)propyl)phenyl)-5-((1-(4-fluorobenzoyl)-4-hydroxypiperidin-4-yl)methyl)-1H-pyrazolo[3,4-d]pyrimidin-4(5H)-one (I-1008);

3-((1-(cyclopropanecarbonyl)-4-hydroxypiperidin-4-yl)methyl)-7-(3-(piperidin-1-ylmethyl)phenyl)-3H-pyrrolo[2,3-d]pyrimidin-4(7H)-one (I-1009);

3-[(1-cyclopropanecarbonyl-4-hydroxypiperidin-4-yl)methyl]-7-[4-fluoro-3-(piperidin-1-ylmethyl)phenyl]-3H,4H,7H-pyrrolo[2,3-d]pyrimidin-4-one (I-1010);

(S)-5-(1-(1-(4-Fluorobenzoyl)-4-hydroxypiperidin-4-yl)ethyl)-1-(4-fluorophenyl)-1H-pyrazolo[3,4-d]pyrimidin-4(5H)-one (I-1013);

6-{[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]oxy}pyridine-3-carbonitrile (I-1014);

1-(4-fluorophenyl)-5-({4-hydroxy-1-[(1r,4r)-4-[(6-methylpyrazin-2-yl)oxy]cyclohexanecarbonyl]piperidin-4-yl}methyl)-1H,4H,5H-pyrazolo[3,4-d]pyrimidin-4-one (I-1015);

1-(4-fluorophenyl)-5-({4-hydroxy-1-[(1r,4r)-4-[(2-methylpyrimidin-4-yl)oxy]cyclohexanecarbonyl]piperidin-4-yl}methyl)-1H,4H,5H-pyrazolo[3,4-d]pyrimidin-4-one (I-1016);

5-({4-hydroxy-1-[(1r,4r)-4-[(2-fluoropyridin-3-yl)oxy]cyclohexanecarbonyl]piperidin-4-yl}methyl)-1-phenyl-1H,4H,5H-pyrazolo[3,4-d]pyrimidin-4-one (I-1017);

1-(4-fluorophenyl)-5-({4-hydroxy-1-[(1r,4r)-4-{[6-(azetidin-1-yl)pyridin-2-yl]oxy}cyclohexanecarbonyl]piperidin-4-yl}methyl)-1H,4H,5H-pyrazolo[3,4-d]pyrimidin-4-one (I-1018);

1-(4-fluorophenyl)-5-({4-hydroxy-1-[(1r,4r)-4-[(5-methoxypyridin-2-yl)oxy]cyclohexanecarbonyl]piperidin-4-yl}methyl)-1H,4H,5H-pyrazolo[3,4-d]pyrimidin-4-one (I-1019);

5-({4-hydroxy-1-[(1r,4r)-4-[(5-methoxypyridin-2-yl)oxy]cyclohexanecarbonyl]piperidin-4-yl}methyl)-1-phenyl-1H,4H,5H-pyrazolo[3,4-d]pyrimidin-4-one (I-1020);

1-(4-fluorophenyl)-5-({4-hydroxy-1-[(1s,4s)-4-(pyrazin-2-yloxy)cyclohexanecarbonyl]piperidin-4-yl}methyl)-1H,4H,5H-pyrazolo[3,4-d]pyrimidin-4-one (I-1021);

1-(4-fluorophenyl)-5-({4-hydroxy-1-[(1r,4r)-4-[(2-methylpyrimidin-5-yl)oxy]cyclohexanecarbonyl]piperidin-4-yl}methyl)-1H,4H,5H-pyrazolo[3,4-d]pyrimidin-4-one (I-1022);

1-(4-fluorophenyl)-5-({4-hydroxy-1-[(1s,4s)-4-[(6-fluoropyridin-2-yl)amino]cyclohexanecarbonyl]piperidin-4-yl}methyl)-1H,4H,5H-pyrazolo[3,4-d]pyrimidin-4-one (I-1023);

1-(4-fluorophenyl)-5-({4-hydroxy-1-[(1r,4r)-4-[(6-fluoropyridin-2-yl)amino]cyclohexanecarbonyl]piperidin-4-yl}methyl)-1H,4H,5H-pyrazolo[3,4-d]pyrimidin-4-one (I-1024);

1-(4-fluorophenyl)-5-({4-hydroxy-1-[1-methyl-3-(1-phenylethyl)-1H-pyrazole-4-carbonyl]piperidin-4-yl}methyl)-1H,4H,5H-pyrazolo[3,4-d]pyrimidin-4-one (I-1025);

5-({1-[(3R)-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-1028);

5-({1-[(3S)-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-1029);

5-({4-hydroxy-1-[2-(1,2,3,4-tetrahydronaphthalen-1-yl)acetyl]piperidin-4-yl}methyl)-1-methyl-1H,4H,5H-pyrazolo[3,4-d]pyrimidin-4-one (I-103);

1-(4-fluorophenyl)-5-({4-hydroxy-1-[(1s,3s)-3-[(pyridin-3-yl)amino]cyclobutanecarbonyl]piperidin-4-yl}methyl)-1H,4H,5H-pyrazolo[3,4-d]pyrimidin-4-one (I-1030);

1-(4-fluorophenyl)-5-({4-hydroxy-1-[(1r,3r)-3-[(pyridin-3-yl)amino]cyclobutanecarbonyl]piperidin-4-yl}methyl)-1H,4H,5H-pyrazolo[3,4-d]pyrimidin-4-one (I-1031);

1-(4-fluorophenyl)-5-({4-hydroxy-1-[(1s,3s)-3-[(5-fluoropyridin-2-yl)amino]cyclobutanecarbonyl]piperidin-4-yl}methyl)-1H,4H,5H-pyrazolo[3,4-d]pyrimidin-4-one (I-1032);

1-(4-fluorophenyl)-5-({4-hydroxy-1-[(1r,3r)-3-[(5-fluoropyridin-2-yl)amino]cyclobutanecarbonyl]piperidin-4-yl}methyl)-1H,4H,5H-pyrazolo[3,4-d]pyrimidin-4-one (I-1033);

1-(4-fluorophenyl)-5-({4-hydroxy-1-[(1s,3s)-3-[(pyridin-2-yl)amino]cyclobutanecarbonyl]piperidin-4-yl}methyl)-1H,4H,5H-pyrazolo[3,4-d]pyrimidin-4-one (I-1034);

1-(4-fluorophenyl)-5-({4-hydroxy-1-[(1r,3r)-3-[(pyridin-2-yl)amino]cyclobutanecarbonyl]piperidin-4-yl}methyl)-1H,4H,5H-pyrazolo[3,4-d]pyrimidin-4-one (I-1035);

5-({1-[(3R)-4,4-difluoro-3-(3-fluoro-1H-pyrazol-1-yl)butanoyl]-4-hydroxypiperidin-4-yl}methyl)-1-[4-(trifluoromethyl)phenyl]-1H,4H,5H-pyrazolo[3,4-d]pyrimidin-4-one (I-1036), 5-({1-[(3S)-4,4-difluoro-3-(3-fluoro-1H-pyrazol-1-yl)butanoyl]-4-hydroxypiperidin-4-yl}methyl)-1-[4-(trifluoromethyl)phenyl]-1H,4H,5H-pyrazolo[3,4-d]pyrimidin-4-one (I-1037);

7-(4-fluorophenyl)-3-({4-hydroxy-1-[(1s,4s)-4-(pyridin-2-yloxy)cyclohexanecarbonyl]piperidin-4-yl}methyl)-3H,4H,7H-pyrrolo[2,3-d]pyrimidin-4-one (I-1038);

Syn-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer A (I-1039a);

Anti-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer B (I-1039b);

5-({4-hydroxy-1-[4-(phenoxymethyl)benzoyl]piperidin-4-yl}methyl)-1-methyl-1H,4H,5H-pyrazolo[3,4-d]pyrimidin-4-one (I-104);

7-(4-fluorophenyl)-3-({4-hydroxy-1-[(1s,4s)-4-[(1-methyl-1H-pyrazol-3-yl)amino]cyclohexanecarbonyl]piperidin-4-yl}methyl)-3H,4H,7H-pyrrolo[2,3-d]pyrimidin-4-one (I-1040);

7-(4-fluorophenyl)-3-({4-hydroxy-1-[(1r,4r)-4-[(1-methyl-1H-pyrazol-3-yl)amino]cyclohexanecarbonyl]piperidin-4-yl}methyl)-3H,4H,7H-pyrrolo[2,3-d]pyrimidin-4-one (I-1041);

1-[3-(3-fluoro-1H-pyrazol-1-yl)phenyl]-5-{[4-hydroxy-1-(1-methylcyclopropanecarbonyl)piperidin-4-yl]methyl}-1H,4H,5H-pyrazolo[3,4-d]pyrimidin-4-one (I-1042);

5-{[4-hydroxy-1-(1-methylcyclopropanecarbonyl)piperidin-4-yl]methyl}-1-{4-[4-(trifluoromethyl)-1H-pyrazol-1-yl]phenyl}-1H,4H,5H-pyrazolo[3,4-d]pyrimidin-4-one (I-1043);

1-[4-(4-chloro-1H-pyrazol-1-yl)phenyl]-5-{[4-hydroxy-1-(1-methylcyclopropanecarbonyl)piperidin-4-yl]methyl}-1H,4H,5H-pyrazolo[3,4-d]pyrimidin-4-one (I-1045);

1-(3-((3,3-difluorocyclobutyl)methoxy)phenyl)-5-((4-hydroxy-1-(1-methylcyclopropane-1-carbonyl)piperidin-4-yl)methyl)-1,5-dihydro-4H-pyrazolo[3,4-d]pyrimidin-4-one (I-1046);

1-{3-[(4,4-difluorocyclohexyl)oxy]phenyl}-5-{[4-hydroxy-1-(1-methylcyclopropanecarbonyl)piperidin-4-yl]methyl}-1H,4H,5H-pyrazolo[3,4-d]pyrimidin-4-one (I-1047), 5-({4-hydroxy-1-[3-(1H-pyrrol-1-yl)butanoyl]piperidin-4-yl}methyl)-1-methyl-1H,4H,5H-pyrazolo[3,4-d]pyrimidin-4-one (I-105);

5-({4-hydroxy-1-[(3S)-3-(1H-pyrazol-1-yl)butanoyl]piperidin-4-yl}methyl)-1-{4-[(3R)-3-hydroxy-3-methylpyrrolidin-1-yl]phenyl)-1H,4H,5H-pyrazolo[3,4-d]pyrimidin-4-one (I-1052);

5-({1-[4-(difluoromethoxy)benzoyl]-4-hydroxypiperidin-4-yl}methyl)-1-(4-methylphenyl)-1H,4H,5H-pyrazolo[3,4-d]pyrimidin-4-one (I-1058);

5-[(4-hydroxy-1-{4-[(1-methylpyrrolidin-3-yl)oxy]benzoyl}piperidin-4-yl)methyl]-1-(4-methylphenyl)-1H,4H,5H-pyrazolo[3,4-d]pyrimidin-4-one (I-1059);

4-[4-hydroxy-4-({1-methyl-4-oxo-1H,4H,5H-pyrazolo[3,4-d]pyrimidin-5-yl}methyl)piperidine-1-carbonyl]-N-phenylbenzene-1-sulfonamide (I-106);

5-({1-[(3R)-4,4-difluoro-3-(1H-pyrazol-1-yl)butanoyl]-4-hydroxypiperidin-4-yl}methyl)-1-(4-methylphenyl)-1H,4H,5H-pyrazolo[3,4-d]pyrimidin-4-one (I-1060);

5-({1-[(3S)-4,4-difluoro-3-(1H-pyrazol-1-yl)butanoyl]-4-hydroxypiperidin-4-yl}methyl)-1-(4-methylphenyl)-1H,4H,5H-pyrazolo[3,4-d]pyrimidin-4-one (I-1061);

5-[(4-hydroxy-1-{4-[(1-methylpiperidin-4-yl)oxy]benzoyl}piperidin-4-yl)methyl]-1-(4-methylphenyl)-1H,4H,5H-pyrazolo[3,4-d]pyrimidin-4-one (I-1062);

5-({4-hydroxy-1-[4-(pyrimidin-2-yloxy)benzoyl]piperidin-4-yl}methyl)-1-(4-methylphenyl)-1H,4H,5H-pyrazolo[3,4-d]pyrimidin-4-one (I-1063);

5-({4-hydroxy-1-[(1s,3s)-3-(pyridin-2-yloxy)cyclobutanecarbonyl]piperidin-4-yl}methyl)-1-(4-methylphenyl)-1H,4H,5H-pyrazolo[3,4-d]pyrimidin-4-one (I-1064);

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-cyclopropylurea (I-1065);

4-[(1-{5-[(cyclopropylmethyl)amino]pyridin-3-yl}-4-oxo-1H,4H,5H-pyrazolo[3,4-d]pyrimidin-5-yl)methyl]-4-hydroxy-N,N-dimethylpiperidine-1-carboxamide (I-1066);

7-(4-fluorophenyl)-3-({4-hydroxy-1-[(1r,4r)-4-[(1-methyl-1H-pyrazol-3-yl)oxy]cyclohexanecarbonyl]piperidin-4-yl}methyl)-3H,4H,7H-pyrrolo[2,3-d]pyrimidin-4-one (I-1067);

N-[(1r,4r)-4-[(4-[[1-(4-fluorophenyl)-4-oxo-1H,4H,5H-pyrazolo[3,4-d]pyrimidin-5-yl]methyl]-4-hydroxypiperidin-1-yl)carbonyl]cyclohexyl]acetamide (I-1068);

5-((4-hydroxy-1-((1r,4r)-4-(pyridin-2-yloxy)cyclohexanecarbonyl) piperidin-4-yl)methyl)-1-(4-(hydroxymethyl)phenyl)-1H-pyrazolo[3,4-d]pyrimidin-4(5H)-one (I-1069);

4-[4-hydroxy-4-({1-methyl-4-oxo-1H,4H,5H-pyrazolo[3,4-d]pyrimidin-5-yl}methyl)piperidine-1-carbonyl]-N-methyl 1-N-phenylbenzene-1-sulfonamide (I-107);

1-(4-bromophenyl)-5-{[1-(4-fluorobenzoyl)-4-hydroxypiperidin-4-yl]methyl}-1H,4H,5H-pyrazolo[3,4-d]pyrimidin-4-one (I-1070);

5-{[4-hydroxy-1-(6-methoxypyridine-3-carbonyl)piperidin-4-yl]methyl}-1-[4-(trifluoromethyl)phenyl]-1H,4H,5H-pyrazolo[3,4-d]pyrimidin-4-one (I-1071);

1-(4-fluorophenyl)-5-({4-hydroxy-1-[(1s,4s)-4-(cyclopropylamino)cyclohexanecarbonyl]piperidin-4-yl}methyl)-1H,4H,5H-pyrazolo[3,4-d]pyrimidin-4-one (I-1072);

1-(4-fluorophenyl)-5-({4-hydroxy-1-[(1r,4r)-4-[(cyclopropylmethyl)amino]cyclohexanecarbonyl]piperidin-4-yl}methyl)-1H,4H,5H-pyrazolo[3,4-d]pyrimidin-4-one (I-1073);

1-(4-fluorophenyl)-5-({4-hydroxy-1-[(1s,4s)-4-[(cyclopropylmethyl)amino]cyclohexanecarbonyl]piperidin-4-yl}methyl)-1H,4H,5H-pyrazolo[3,4-d]pyrimidin-4-one (I-1074);

N-[(1r,4r)-4-(4-{[1-(4-fluorophenyl)-4-oxo-1H,4H,5H-pyrazolo[3,4-d]pyrimidin-5-yl]methy1}-4-hydroxypiperidine-1-carbonyl)cyclohexyl]cyclopropanecarboxamide (I-1075);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-3-carboxamide (I-1076);

7-(4-fluorophenyl)-3-{[4-hydroxy-1-(2-methyl-1,3-oxazole-5-carbonyl)piperidin-4-yl]methyl}-3H,4H,7H-pyrrolo[2,3-d]pyrimidin-4-one (I-1077);

7-(4-fluorophenyl)-3-{[4-hydroxy-1-(1-methyl-1H-pyrazole-4-carbonyl)piperidin-4-yl]methyl}-3H,4H,7H-pyrrolo[2,3-d]pyrimidin-4-one (I-1078);

3-{[1-(1-cyclopropyl-1H-pyrazole-4-carbonyl)-4-hydroxypiperidin-4-yl]methyl}-7-(4-fluorophenyl)-3H,4H,7H-pyrrolo[2,3-d]pyrimidin-4-one (I-1079);

4-[4-hydroxy-4-({1-methyl-4-oxo-1H,4H,5H-pyrazolo[3,4-d]pyrimidin-5-yl}methyl)piperidine-1-carbonyl]-N-methyl-N-phenylbenzamide (I-108);

1-[3-(4-acetylpiperazin-1-yl)phenyl]-5-[(1-cyclopropanecarbonyl-4-hydroxypiperidin-4-yl)methyl]-1H,4H,5H-pyrazolo[3,4-d]pyrimidin-4-one (I-1080);

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1,6,4-thiomorpholine-1,1-dione (I-1081);

5-[(1-cyclopropanecarbonyl-4-hydroxypiperidin-4-yl)methyl]-1-[4-(1,2,3,4-tetrahydroquinolin-1-yl)phenyl]-1H,4H,5H-pyrazolo[3,4-d]pyrimidin-4-one (I-1082);

5-[(1-cyclopropanecarbonyl-4-hydroxypiperidin-4-yl)methyl]-1-[3-(1,2,3,4-tetrahydroquinolin-1-yl)phenyl]-1H,4H,5H-pyrazolo[3,4-d]pyrimidin-4-one (I-1083);

2-[1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)piperidin-3-yl]acetonitrile (I-1084);

1-(4-chlorophenyl)-5-({4-hydroxy-1-[2-(4-methylpiperazin-1-yl)-1,3-oxazole-5-carbonyl]piperidin-4-yl}methyl)-1H,4H,5H-pyrazolo[3,4-d]pyrimidin-4-one (I-1085);

1-(4-chlorophenyl)-5-({4-hydroxy-1-[2-(pyridin-2-yloxy)-1,3-oxazole-5-carbonyl]piperidin-4-yl}methyl)-1H,4H,5H-pyrazolo[3,4-d]pyrimidin-4-one (I-1086);

1-(4-chlorophenyl)-5-({4-hydroxy-1-[4-(1H-1,2,3,4-tetrazol-1-yl)benzoyl]piperidin-4-yl}methyl)-1H,4H,5H-pyrazolo[3,4-d]pyrimidin-4-one (I-1087);

1-(4-chlorophenyl)-5-({4-hydroxy-1-[4-(1H-imidazol-1-yl)benzoyl]piperidin-4-yl}methyl)-1H,4H,5H-pyrazolo[3,4-d]pyrimidin-4-one (I-1088);

1-(4-chlorophenyl)-5-({4-hydroxy-1-[4-(5-methyl-1H-1,2,3,4-tetrazol-1-yl)benzoyl]piperidin-4-yl}methyl)-1H,4H,5H-pyrazolo[3,4-d]pyrimidin-4-one (I-1089);

4-[4-hydroxy-4-({1-methyl-4-oxo-1H,4H,5H-pyrazolo[3,4-d]pyrimidin-5-yl}methyl)piperidine-1-carbonyl]-N-phenylbenzamide (I-109);

1-(4-chlorophenyl)-5-({4-hydroxy-1-[4-(1H-1,2,4-triazol-1-yl)benzoyl]piperidin-4-yl}methyl)-1H,4H,5H-pyrazolo[3,4-d]pyrimidin-4-one (I-1090);

1-(4-chlorophenyl)-5-{[1-(5-cyclopropyl-1,3,4-oxadiazole-2-carbonyl)-4-hydroxypiperidin-4-yl]methyl}-1H,4H,5H-pyrazolo[3,4-d]pyrimidin-4-one (I-1091);

1-(4-chlorophenyl)-5-{[1-(1-cyclopropyl-1H-imidazole-4-carbonyl)-4-hydroxypiperidin-4-yl]methyl}-1H,4H,5H-pyrazolo[3,4-d]pyrimidin-4-one (I-1092);

1-(4-chlorophenyl)-5-{[1-(1-cyclopropyl-1H-pyrazole-3-carbonyl)-4-hydroxypiperidin-4-yl]methyl}-1H,4H,5H-pyrazolo[3,4-d]pyrimidin-4-one (I-1093);

1-(4-chlorophenyl)-5-{[1-(1-cyclopropyl-1H-pyrazole-4-carbonyl)-4-hydroxypiperidin-4-yl]methyl}-1H,4H,5H-pyrazolo[3,4-d]pyrimidin-4-one (I-1095);

1-(4-chlorophenyl)-5-[(4-hydroxy-1-{4-[(1-methylpip-eridin-4-yl)oxy]benzoyl}piperidin-4-yl)methyl]-1H,4H,5H-pyrazolo[3,4-d]pyrimidin-4-one (I-1096), 1-(4-chlorophenyl)-5-[[1-([3-[2-(dimethylamino)ethoxy]phenyl]carbonyl)-4-hydroxypiperidin-4-yl]methyl]-1H,4H,5H-pyrazolo[3,4-d]pyrimidin-4-one (I-1097);

1-(4-chlorophenyl)-5-[(1-{3-[3-(dimethylamino)propoxy]benzoyl}-4-hydroxypiperidin-4-yl)methyl]-1H,4H,5H-pyrazolo[3,4-d]pyrimidin-4-one (I-1098);

1-(4-chlorophenyl)-5-[(1-[[4-(1,5-dimethyl-1H-imidazol-2-yl)phenyl]carbonyl]-4-hydroxypiperidin-4-yl)methyl]-1H,4H,5H-pyrazolo[3,4-d]pyrimidin-4-one (I-1099);

2-(3-{5-[(1-benzoyl-4-hydroxypiperidin-4-yl)methyl]-4-oxo-1H,4H,5H-pyrazolo[3,4-d]pyrimidin-1-yl}phenyl)acetic acid (I-11), N-{4-[4-hydroxy-4-({1-methyl-4-oxo-1H,4H,5H-pyrazolo[3,4-d]pyrimidin-5-yl}methyl)piperidine-1-carbonyl]phenyl}benzamide (I-110);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methylpyrazine-2-carboxamide (I-1100);

1-(4-chlorophenyl)-5-({1-[4-(1,2-dimethyl-1H-imidazol-5-yl)benzoyl]-4-hydroxypiperidin-4-yl}methyl)-1H,4H,5H-pyrazolo[3,4-d]pyrimidin-4-one (I-1101);

5-{[1-(4,4-di fluoro-3-phenylbutanoyl)-4-hydroxypiperidin-4-yl]methyl}-1-phenyl-1H,4H,5H-pyrazolo[3,4-d]pyrimidin-4-one (I-1102);

5-({1-[(3S)-4,4-difluoro-3-phenylbutanoyl]-4-hydroxypiperidin-4-yl}methyl)-1-phenyl-1H,4H,5H-pyrazolo[3,4-d]pyrimidin-4-one (I-1103);

5-({1-[(3R)-4,4-difluoro-3-phenylbutanoyl]-4-hydroxypiperidin-4-yl}methyl)-1-phenyl-1H,4H,5H-pyrazolo[3,4-d]pyrimidin-4-one (I-1104);

5-{[1-(4-benzyl-1,3-oxazole-5-carbonyl)-4-hydroxypiperidin-4-yl]methyl}-1-phenyl-1H,4H,5H-pyrazolo[3,4-d]pyrimidin-4-one (I-1108);

N-{4-[4-hydroxy-4-({1-methyl-4-oxo-1H,4H,5H-pyrazolo[3,4-d]pyrimidin-5-yl}methyl)piperidine-1-carbonyl]phenyl}benzenesulfonamide (I-111);

5-{[1-(3-benzyl-5-methyl-1,2-thiazole-4-carbonyl)-4-hydroxypiperidin-4-yl]methyl}-1-(4-fluorophenyl)-1H,4H,5H-pyrazolo[3,4-d]pyrimidin-4-one (I-1110);

1-(4-fluorophenyl)-5-({4-hydroxy-1-[(1r,4r)-4-(difluoromethoxy)cyclohexanecarbonyl]piperidin-4-yl}methyl)-1H,4H,5H-pyrazolo[3,4-d]pyrimidin-4-one (I-1112), 1-(4-fluorophenyl)-5-({4-hydroxy-1-[(1r,4r)-4-(pyrazin-2-yloxy)cyclohexanecarbonyl]piperidin-4-yl}methyl)-1H,4H,5H-pyrazolo[3,4-d]pyrimidin-4-one (I-1113);

1-(4-fluorophenyl)-5-({4-hydroxy-1-[(1r,4r)-4-[(1-methyl-1H-pyrazol-5-yl)oxy]cyclohexanecarbonyl]piperidin-4-yl}methyl)-1H,4H,5H-pyrazolo[3,4-d]pyrimidin-4-one (I-1114);

1-(4-fluorophenyl)-5-({4-hydroxy-1-[(1s,4s)-4-methoxycyclohexanecarbonyl]piperidin-4-yl}methyl)-1H,4H,5H-pyrazolo[3,4-d]pyrimidin-4-one (I-1115);

Syn-5-((4-Hydroxy-1-(1-methylcyclopropanecarbonyl)piperidin-4-yl)methyl)-1-(4-((4-methoxycyclohexyl)oxy)phenyl)-1H-pyrazolo[3,4-d]pyrimidin-4(5H)-one, isomer A (I-1116a);

Syn-5-((4-Hydroxy-1-(1-methylcyclopropanecarbonyl)piperidin-4-yl)methyl)-1-(4-((4-methoxycyclohexyl)oxy)phenyl)-1H-pyrazolo[3,4-d]pyrimidin-4(5H)-one, isomer b (I-1116b), 1-{4-[(4,4-difluorocyclohexyl)oxy]phenyl}-5-{[4-hydroxy-1-(1-methy 1 cyclopropanecarbonyl) piperidin-4-yl]methyl}-1H,4H,5H-pyrazolo[3,4-d]pyrimidin-4-one (I-1117);

5-{[4-hydroxy-1-(1-methylcyclopropanecarbonyl)piperidin-4-yl]methyl}-1-{4-[(3-methyloxetan-3-yl)methoxy]phenyl}-1H,4H,5H-pyrazolo[3,4-d]pyrimidin-4-one (I-1118);

1-{4-[(1-fluorocyclobutyl)methoxy]phenyl}-5-{[4-hydroxy-1-(1-methylcyclopropanecarbonyl) piperidin-4-yl]methyl}-1H,4H,5H-pyrazolo[3,4-d]pyrimidin-4-one (I-1119);

5-({4-hydroxy-1-[3-(1,3-thiazol-2-yl)butanoyl]piperidin-4-yl}methyl)-1-methyl-1H,4H,5H-pyrazolo[3,4-d]pyrimidin-4-one (I-112);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methylbenzamide (I-1120);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzamide (I-1121);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-fluorobenzamide (I-1122);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-fluorobenzamide (I-1123);

7-(4-fluorophenyl)-3-({4-hydroxy-1-[(1r,4r)-4-(pyridin-2-yloxy)cyclohexanecarbonyl]piperidin-4-yl}methyl)-3H,4H,7H-pyrrolo[2,3-d]pyrimidin-4-one (I-1124);

3-({1-[(3R)-4,4-difluoro-3-(3-fluoro-1H-pyrazol-1-yl)butanoyl]-4-hydroxypiperidin-4-yl}methyl)-7-(4-fluorophenyl)-3H,4H,7H-pyrrolo[2,3-d]pyrimidin-4-one (I-1125);

3-({1-[(3S)-4,4-difluoro-3-(3-fluoro-1H-pyrazol-1-yl)butanoyl]-4-hydroxypiperidin-4-yl}methyl)-7-(4-fluorophenyl)-3H,4H,7H-pyrrolo[2,3-d]pyrimidin-4-one (I-1126);

1-(4-chlorophenyl)-5-({4-hydroxy-1-[3-(pyrrolidin-1-ylmethyl)benzoyl]piperidin-4-yl}methyl)-1H,4H,5H-pyrazolo[3,4-d]pyrimidin-4-one (I-1127);

1-(4-chlorophenyl)-5-({4-hydroxy-1-[4-(1H-1,2,3-triazol-1-yl)benzoyl]piperidin-4-yl}methyl)-1H,4H,5H-pyrazolo[3,4-d]pyrimidin-4-one (I-1128);

1-(4-chlorophenyl)-5-({4-hydroxy-1-[4-(2H-1,2,3-triazol-2-yl)benzoyl]piperidin-4-yl}methyl)-1H,4H,5H-pyrazolo[3,4-d]pyrimidin-4-one (I-1129);

5-{[1-(2-chloro-4-phenoxybenzoyl)-4-hydroxypiperidin-4-yl]methyl}-1-methyl-1H,4H,5H-pyrazolo[3,4-d]pyrimidin-4-one (I-113);

1-(4-chlorophenyl)-5-{[1-(2-cyclopropyl-1,3-oxazole-5-carbonyl)-4-hydroxypiperidin-4-yl]methyl}-1H,4H,5H-pyrazolo[3,4-d]pyrimidin-4-one (I-1130);

1-(4-chlorophenyl)-5-({1-[(3R)-4,4-difluoro-3-(1H-pyrazol-1-yl)butanoyl]-4-hydroxypiperidin-4-yl}methyl)-1H,4H,5H-pyrazolo[3,4-d]pyrimidin-4-one (I-1131);

1-(4-chlorophenyl)-5-({1-[(3S)-4,4-difluoro-3-(1H-pyrazol-1-yl)butanoyl]-4-hydroxypiperidin-4-yl}methyl)-1H,4H,5H-pyrazolo[3,4-d]pyrimidin-4-one (I-1132);

1-{4-[(3,3-difluorocyclobutyl)methoxy]phenyl}-5-{[4-hydroxy-1-(1-methylcyclopropanecarbonyl)piperidin-4-yl]methyl}-1H,4H,5H-pyrazolo[3,4-d]pyrimidin-4-one (I-133);

1-{4-[(4,4-difluorocyclohexyl)oxy]phenyl}-5-{[4-hydroxy-1-(2-methyl-1,3-oxazole-5-carbonyl)piperidin-4-yl]methyl}-1H,4H,5H-pyrazolo[3,4-d]pyrimidin-4-one (I-1134);

1-{4-[(1-fluorocyclobutyl)methoxy]phenyl)-5-{[4-hydroxy-1-(2-methyl-1,3-oxazole-5-carbonyl)piperidin-4-yl]methyl)-1H,4H,5H-pyrazolo[3,4-d]pyrimidin-4-one (I-1135);

5-{[4-hydroxy-1-(1-methylcyclobutanecarbonyl)piperidin-4-yl]methyl}-1-{4-[(3-methyloxetan-3-yl)methoxy]phenyl)-1H,4H,5H-pyrazolo[3,4-d]pyrimidin-4-one (I-1136);

1-{4-[(1-fluorocyclobutyl)methoxy]phenyl)-5-{[4-hydroxy-1-(1-methylcyclobutanecarbonyl) piperidin-4-yl]methyl)-1H,4H,5H-pyrazolo[3,4-d]pyrimidin-4-one (I-1137), 4-hydroxy-4-[(1-{4-[(3R)-3-methoxypyrrolidin-1-yl]phenyl}-4-oxo-1H,4H,5H-pyrazolo[3,4-d]pyrimidin-5-yl)methyl]-N,N-dimethylpiperidine-1-carboxamide (I-1138), 5-({4-hydroxy-1-[(3S)-3-phenylbutanoyl]piperidin-4-yl}methyl)-1-(4-methylphenyl)-1H,4H,5H-pyrazolo[3,4-d]pyrimidin-4-one (I-1139);

5-{[1-(2-amino-4-chlorobenzoyl)-4-hydroxypiperidin-4-yl]methyl}-1-(4-methylphenyl)-1H,4H,5H-pyrazolo[3,4-d]pyrimidin-4-one (I-1140);

5-((4-Hydroxy-1-(4-(4-hydroxycyclohexyloxy)benzoyl)piperidin-4-yl)methyl)-1-p-tolyl-1H-pyrazolo[3,4-d]pyrimidin-4 (5H)-one (I-1141);

5-((4-hydroxy-1-(4-(1-methylazetidin-3-yloxy)benzoyl)piperidin-4-yl)methyl)-1-p-tolyl-1H-pyrazolo[3,4-d]pyrimidin-4 (5H)-one (I-1142);

5-((4-Hydroxy-1-(4-(oxetan-3-yloxy)benzoyl)piperidin-4-yl)methyl)-1-p-tolyl-1H-pyrazolo[3,4-d]pyrimidin-4 (5H)-one (I-1143);

5-({4-hydroxy-1-[4-(oxan-4-yloxy)benzoyl]piperidin-4-yl}methyl)-1-(4-methylphenyl)-1H,4H,5H-pyrazolo[3,4-d]pyrimidin-4-one (I-1144);

5-((4-hydroxy-1-(4-(piperidin-4-yloxy)benzoyl)piperidin-4-yl)methyl)-1-p-tolyl-1H-pyrazolo[3,4-d]pyrimidin-4 (5H)-one (I-1145);

5-[(1-cyclopropanecarbonyl-4-hydroxypiperidin-4-yl)methyl]-1-(4-{[2-(piperidin-1-yl)ethyl]amino}phenyl)-1H,4H,5H-pyrazolo[3,4-d]pyrimidin-4-one (I-1146);

5-[(1-cyclopropanecarbonyl-4-hydroxypiperidin-4-yl)methyl]-1-(4-{[2-(morpholin-4-yl)ethyl]amino}phenyl)-1H,4H,5H-pyrazolo[3,4-d]pyrimidin-4-one (I-1147);

5-[(1-cyclopropanecarbonyl-4-hydroxypiperidin-4-yl)methyl]-1-{4-[(2-ethylbutyl)amino]phenyl}-1H,4H,5H-pyrazolo[3,4-d]pyrimidin-4-one (I-1148);

5-[(1-cyclopropanecarbonyl-4-hydroxypiperidin-4-yl)methyl]-1-(4-{[2-(propan-2-yloxy)ethyl]amino}phenyl)-1H,4H,5H-pyrazolo[3,4-d]pyrimidin-4-one (I-1149);

5-{[4-hydroxy-1-(2-phenyl-1,2,3,4-tetrahydroisoquinoline-6-carbonyl)piperidin-4-yl]methyl}-1-methyl-1H,4H,5H-pyrazolo[3,4-d]pyrimidin-4-one (I-115);

5-[(1-cyclopropanecarbonyl-4-hydroxypiperidin-4-yl)methyl]-1-{4-[(cyclopropylmethyl)amino]phenyl}-1H,4H,5H-pyrazolo[3,4-d]pyrimidin-4-one (I-1150);

5-[(1-cyclopropanecarbonyl-4-hydroxypiperidin-4-yl)methyl]-1-(4-{[(1-methylpiperidin-3-yl)methyl]amino}phenyl)-1H,4H, 5H-pyrazolo[3,4-d]pyrimidin-4-one (I-1151);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzene-1-sulfonamide (I-1152);

5-[(1-cyclopropanecarbonyl-4-hydroxypiperidin-4-yl)methyl]-1-[3-(cyclopropylamino)phenyl]-1H,4H,5H-pyrazolo[3,4-d]pyrimidin-4-one (I-1153);

1-[3-(cyclohexylamino)phenyl]-5-[(1-cyclopropanecarbonyl-4-hydroxypiperidin-4-yl)methyl]-1H,4H,5H-pyrazolo[3,4-d]pyrimidin-4-one (I-1154);

1-[3-(benzylamino)phenyl]-5-[(1-cyclopropanecarbonyl-4-hydroxypiperidin-4-yl)methyl]-1H,4H,5H-pyrazolo[3,4-d]pyrimidin-4-one (I-1155);

5-[(1-cyclopropanecarbonyl-4-hydroxypiperidin-4-yl)methyl]-1-{3-[(2-phenylethyl)amino]phenyl}-1H,4H,5H-pyrazolo[3,4-d]pyrimidin-4-one (I-1156);

5-[(1-cyclopropanecarbonyl-4-hydroxypiperidin-4-yl)methyl]-1-{3-[(2,2-dimethylpropyl)amino]phenyl}-1H,4H,5H-pyrazolo[3,4-d]pyrimidin-4-one (I-1157);

5-[(1-cyclopropanecarbonyl-4-hydroxypiperidin-4-yl)methyl]-1-{3-[(pyridin-3-ylmethyl)amino]phenyl}-1H,4H,5H-pyrazolo[3,4-d]pyrimidin-4-one (I-1158);

5-({1-[(3R)-4,4-difluoro-3-(4-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-1159);

5-[(1-{3-[benzyl(methyl)amino]benzoyl}-4-hydroxypiperidin-4-yl)methyl]-1-methyl-1H,4H,5H-pyrazolo[3,4-d]pyrimidin-4-one (I-116);

5-{[4-hydroxy-1-(4-{[5-(2-hydroxyethoxy)pyridin-2-yl]oxy}benzoyl)piperidin-4-yl]methyl}-1-(4-methylphenyl)-1H,4H,5H-pyrazolo[3,4-d]pyrimidin-4-one (I-1160);

1-[4-(cyclohexylamino)phenyl]-5-[(1-cyclopropanecarbonyl-4-hydroxypiperidin-4-yl)methyl]-1H,4H,5H-pyrazolo[3,4-d]pyrimidin-4-one (I-1186);

5-[(1-cyclopropanecarbonyl-4-hydroxypiperidin-4-yl)methyl]-1-{4-[(2-phenylethyl)amino]phenyl}-1H,4H,5H-pyrazolo[3,4-d]pyrimidin-4-one (I-1187);

5-[(1-cyclopropanecarbonyl-4-hydroxypiperidin-4-yl)methyl]-1-{4-[(2,2-dimethylpropyl)amino]phenyl}-1H,4H,5H-pyrazolo[3,4-d]pyrimidin-4-one (I-1188);

5-[(1-cyclopropanecarbonyl-4-hydroxypiperidin-4-yl)methyl]-1-{4-[(pyridin-3-ylmethyl)amino]phenyl}-1H,4H,5H-pyrazolo[3,4-d]pyrimidin-4-one (I-1189);

5-[(1-{4-[benzyl(methyl)amino]benzoyl}-4-hydroxypiperidin-4-yl)methyl]-1-methyl-1H,4H,5H-pyrazolo[3,4-d]pyrimidin-4-one (I-119);

5-[(1-cyclopropanecarbonyl-4-hydroxypiperidin-4-yl)methyl]-1-{4-[(1H-pyrazol-3-yl)amino]phenyl}-1H,4H,5H-pyrazolo[3,4-d]pyrimidin-4-one (I-1190);

5-[(1-cyclopropanecarbonyl-4-hydroxypiperidin-4-yl)methyl]-1-{4-[(6-methoxypyridin-3-yl)amino]phenyl}-1H,4H,5H-pyrazolo[3,4-d]pyrimidin-4-one (I-1191), 5-[(1-cyclopropanecarbonyl-4-hydroxypiperidin-4-yl)methyl]-1-{4-[(2-methoxypyridin-3-yl)amino]phenyl}-1H,4H,5H-pyrazolo[3,4-d]pyrimidin-4-one (I-1192);

5-[(1-cyclopropanecarbonyl-4-hydroxypiperidin-4-yl)methyl]-1-{4-[(5-methyl-1,3,4-thiadiazol-2-yl)amino]phenyl}-1H,4H,5H-pyrazolo[3,4-d]pyrimidin-4-one (I-1193);

5-[(1-cyclopropanecarbonyl-4-hydroxypiperidin-4-yl)methyl]-1-(3-{[2-(morpholin-4-yl)ethyl]amino}phenyl)-1H,4H,5H-pyrazolo[3,4-d]pyrimidin-4-one (I-1194);

5-[(1-cyclopropanecarbonyl-4-hydroxypiperidin-4-yl)methyl]-1-{3-[(2-ethylbutyl)amino]phenyl}-1H,4H,5H-pyrazolo[3,4-d]pyrimidin-4-one (I-1195);

5-[(1-cyclopropanecarbonyl-4-hydroxypiperidin-4-yl)
methyl]-1-(3-{[2-(propan-2-yloxy)ethyl]
amino}phenyl)-1H,4H,5H-pyrazolo[3,4-d]pyrimidin-4-one (I-1196);

5-[(1-cyclopropanecarbonyl-4-hydroxypiperidin-4-yl)
methyl]-1-(3-{[(1-methylpiperidin-3-yl)methyl]
amino}phenyl)-1H,4H,5H-pyrazolo[3,4-d]pyrimidin-4-one (I-1197);

5-{[1-(3-benzyl-1-methy)-1H-pyrazole-4-carbonyl)-4-hydroxypiperidin-4-yl]methyl}-1-(4-fluorophenyl)-1H,4H, 5H-pyrazolo[3,4-d]pyrimidin-4-one (I-1161);

1-(4-fluorophenyl)-5-[(4-hydroxy-1-{1-methyl-3-[(1R)-1-phenyl ethyl]-1H-pyrazole-4-carbonyl}piperidin-4-yl)methyl]-1H,4H,5H-pyrazolo[3,4-d]pyrimidin-4-one (I-1162);

1-(4-fluorophenyl)-5-[(4-hydroxy-1-{1-methyl-3-[(1S)-1-phenyl ethyl]-1H-pyrazole-4-carbonyl}piperidin-4-yl)methyl]-1H,4H,5H-pyrazolo[3,4-d]pyrimidin-4-one (I-1163);

5-{[1-(3-benzyl-5-methyl-1,2-oxazole-4-carbonyl)-4-hydroxypiperidin-4-yl]methyl}-1-(4-fluorophenyl)-1H, 4H,5H-pyrazolo[3,4-d]pyrimidin-4-one (I-1164);

5-{[4-hydroxy-1-(1-methylcyclopropanecarbonyl)piperidin-4-yl]methyl}-1-{4-[4-(2-methoxyethyl)piperazin-1-yl]phenyl}-1H,4H,5H-pyrazolo[3,4-d]pyrimidin-4-one (I-1165);

1-(4-chlorophenyl)-5-({1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (I-1166);

1-(4-chlorophenyl)-5-({1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (I-1167);

5-{[1-(4-fluorobenzoyl)-4-hydroxypiperidin-4-yl]
methyl}-1-[4-(3-hydroxy-3-methylpyrrolidin-1-yl)
phenyl]-1H,4H,5H-pyrazolo[3,4-d]pyrimidin-4-one (I-1168);

5-[(1-cyclopropanecarbonyl-4-hydroxypiperidin-4-yl)
methyl]-1-(4-{5H,6H,7H,8H-imidazo[1,2-a]pyrimidin-8-yl}phenyl)-1H,4H,5H-pyrazolo[3,4-d]pyrimidin-4-one (I-1169);

5-({4-hydroxy-1-[3-(1,2,3,4-tetrahydroquinolin-1-yl)
benzoyl]piperidin-4-yl}methyl)-1-methyl-1H,4H,5H-pyrazolo[3,4-d]pyrimidin-4-one (I-117);

5{[1-(4-fluorobenzoyl)-4-hydroxypiperidin-4-yl]
methyl}-1-(4-{5H,6H,7H,8H-imidazo[1,2-a]pyrimidin-8-yl}phenyl)-1H,4H,5H-pyrazolo[3,4-d]pyrimidin-4-one (I-1170), 5-[(1-cyclopropanecarbonyl-4-hydroxypiperidin-4-yl)
methyl]-1-[4-(1,2,3,4-tetrahydroquinoxalin-1-yl)phenyl]-1H,4H,5H-pyrazolo[3,4-d]pyrimidin-4-one (I-1171);

5-{[1-(4-fluorobenzoyl)-4-hydroxypiperidin-4-yl]
methyl}-1-[4-(1,2,3,4-tetrahydroquinoxalin-1-yl)phenyl]-1H,4H,5H-pyrazolo[3,4-d]pyrimidin-4-one (I-1172);

5-[(1-cyclopropanecarbonyl-4-hydroxypiperidin-4-yl)
methyl]-1-(4-{4H,5H,6H,7H-[1,2,4]triazolo[1,5-a]pyrimidin-4-yl}phenyl)-1H,4H,5H-pyrazolo[3,4-d]pyrimidin-4-one (I-1173);

5-{[1-(4-fluorobenzoyl)-4-hydroxypiperidin-4-yl]
methyl}-1-(4-{4H,5H,6H,7H-[1,2,4]triazolo[1,5-a]pyrimidin-4-yl}phenyl)-1H,4H,5H-pyrazolo[3,4-d]pyrimidin-4-one (I-1174);

5-[(1-cyclopropanecarbonyl-4-hydroxypiperidin-4-yl)
methyl]-1-(4-{2-methyl-5H,6H,7H,8H-[1,2,4]triazolo[1,5-a]pyrazin-7-yl}phenyl)-1H,4H,5H-pyrazolo[3,4-d]pyrimidin-4-one (I-1175);

5-{[1-(4-fluorobenzoyl)-4-hydroxypiperidin-4-yl]
methyl}-1-(4-{2-methyl-5H,6H,7H,8H-[1,2,4]triazolo[1,5-a]pyrazin-7-yl}phenyl)-1H,4H,5H-pyrazolo[3,4-d]pyrimidin-4-one (I-1176);

5-[(1-cyclopropanecarbonyl-4-hydroxypiperidin-4-yl)
methyl]-1-(4-{5H,6H,7H,8H-[1,2,4]triazolo[1,5-a]pyrazin-7-yl}phenyl)-1H,4H,5H-pyrazolo[3,4-d]pyrimidin-4-one (I-1177), 5-{[1-(4-fluorobenzoyl)-4-hydroxypiperidin-4-yl]
methyl}-1-(4-{5H,6H,7H, 8H-[1,2,4]triazolo[1,5-a]pyrazin-7-yl}phenyl)-1H,4H,5H-pyrazolo[3,4-d]pyrimidin-4-one (I-1178);

5-{[1-(4-fluorobenzoyl)-4-hydroxypiperidin-4-yl]
methyl}-1-[4-(4-methyl-1,2,3,4-tetrahydroquinoxalin-1-yl)phenyl]-1H,4H,5H-pyrazolo[3,4-d]pyrimidin-4-one (I-1179);

5-{[1-(1-acetylpiperidine-4-carbonyl)-4-hydroxypiperidin-4-yl]methyl}-1-(4-fluorophenyl)-1H,4H,5H-pyrazolo[3,4-d]pyrimidin-4-one (I-1180), 5-[(1-{bicyclo[1.1.1]pentane-1-carbonyl}-4-hydroxypiperidin-4-yl)methyl]-1-(4-fluorophenyl)-1H,4H,5H-pyrazolo[3,4-d]pyrimidin-4-one (I-1181);

1-[4-(cyclopentylamino)phenyl]-5-[(1-cyclopropanecarbonyl-4-hydroxypiperidin-4-yl)methyl]-1H,4H,5H-pyrazolo[3,4-d]pyrimidin-4-one (I-1182);

5-[(1-cyclopropanecarbonyl-4-hydroxypiperidin-4-yl)
methyl]-1-[4-(morpholin-4-yl)phenyl]-1H,4H,5H-pyrazolo[3,4-d]pyrimidin-4-one (I-1183);

1-(4-fluorophenyl)-5-{[4-hydroxy-1-(5-methoxypyridine-2-carbonyl)piperidin-4-yl]methyl}-1H,4H,5H-pyrazolo[3,4-d]pyrimidin-4-one (I-1184);

5-[(1-{3-aminobicyclo[1,1,1]pentane-1-carbonyl}-4-hydroxypiperidin-4-yl)methyl]-1-(4-fluorophenyl)-1H, 4H,5H-pyrazolo[3,4-d]pyrimidin-4-one (I-1185);

5-[(1-cyclopropanecarbonyl-4-hydroxypiperidin-4-yl)
methyl]-1-{3-[(oxan-4-ylmethyl)amino]phenyl}-1H, 4H,5H-pyrazolo[3,4-d]pyrimidin-4-one (I-1198);

5-[(1-cyclopropanecarbonyl-4-hydroxypiperidin-4-yl)
methyl]-1-[4-(pyrrolidin-1-yl)phenyl]-1-1H,4H, 5H-pyrazolo[3,4-d]pyrimidin-4-one (I-1199);

5-({4-hydroxy-1-[4-(1,2,3,4-tetrahydroisoquinolin-2-yl)
benzoyl]piperidin-4-yl}methyl)-1-methy 1-1H,4H, 5H-pyrazolo[3,4-d]pyrimidin-4-one (I-12);

5-[(1-cyclopropanecarbonyl-4-hydroxypiperidin-4-yl)
methyl]-1-[3-(pyrrolidin-1-yl)phenyl]-1H,4H,5H-pyrazolo[3,4-d]pyrimidin-4-one (I-1200);

5-[(1-cyclopropanecarbonyl-4-hydroxypiperidin-4-yl)
methyl]-1-[4-(piperidin-1-yl)phenyl]-1H,4H,5H-pyrazolo[3,4-d]pyrimidin-4-one (I-1201);

5-[(1-cyclopropanecarbonyl-4-hydroxypiperidin-4-yl)
methyl]-1-[3-(piperidin-1-yl)phenyl]-1H,4H,5H-pyrazolol[3,4-d]pyrimidin-4-one (I-1202);

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)piperidine-4-carbonitrile (I-1203);

1-(4-[benzyl(methyl)amino]phenyl)-5-[(1-cyclopropanecarbonyl-4-hydroxypiperidin-4-yl)methyl]-1H,4H, 5H-pyrazolo[3,4-d]pyrimidin-4-one (I-1204);

5-[(1-cyclopropanecarbonyl-4-hydroxypiperidin-4-yl)
methyl]-1-[3-(4-phenylpiperidin-1-yl)phenyl]-1H,4H, 5H-pyrazolo[3,4-d]pyrimidin-4-one (I-1205);

5-[(1-cyclopropanecarbonyl-4-hydroxypiperidin-4-yl)
methyl]-1-{4-[(2-methoxyethyl)(methyl)amino]phenyl)-1H,4H,5H-pyrazolo[3,4-d]pyrimidin-4-one (I-1206);

5-[(1-cyclopropanecarbonyl-4-hydroxypiperidin-4-yl)
methyl]-1-{3-[(2-methoxyethyl)(methyl)amino]phe-
nyl)-1H,4H,5H-pyrazolo[3,4-d]pyrimidin-4-one
(I-1207);
N-[1-(4-{5-[(1-cyclopropanecarbonyl-4-hydroxypiperi-
din-4-yl)methyl]-4-oxo-1H,4H,5H-pyrazolo[3,4-d]py-
rimidin-1-yl}phenyl)piperidin-4-yl]acetamide
(I-1208);
5-[(1-cyclopropanecarbonyl-4-hydroxypiperidin-4-yl)
methyl]-1-{3-[4-(dimethylamino)piperidin-1-yl]phe-
nyl)-1H,4H,5H-pyrazolo[3,4-d]pyrimidin-4-one
(I-1209);
5-[(1-cyclopropanecarbonyl-4-hydroxypiperidin-4-yl)
methyl]-1-[3-(1,2,3,4-tetrahydroisoquinolin-2-yl)phe-
nyl]-1H,4H,5H-pyrazolo[3,4-d]pyrimidin-4-one
(I-1210);
1-[4-(4-acetylpiperazin-1-yl)phenyl]-5-[(1-cyclopropan-
ecarbonyl-4-hydroxypiperidin-4-yl)methyl]-1H,4H,
5H-pyrazolo[3,4-d]pyrimidin-4-one (I-1211);
1-(4-fluorophenyl)-5-({4-hydroxy-1-[(1r,4r)-4-
(pyridazin-3-yloxy)cyclohexanecarbonyl]piperidin-4-
yl}methyl)-1H,4H,5H-pyrazolo[3,4-d]pyrimidin-4-one
(I-1212);
5-[(1-cyclopropanecarbonyl-4-hydroxypiperidin-4-yl)
methyl]-1-[4-(2,4-dichlorophenyl)phenyl]-1H,4H,5H-
pyrazolo[3,4-d]pyrimidin-4-one (I-1213);
5-[(1-cyclopropanecarbonyl-4-hydroxypiperidin-4-yl)
methyl]-1-[4-(pyridin-2-yl)phenyl]-1H,4H,5H-pyra-
zolo[3,4-d]pyrimidin-4-one (I-1214);
5-[(1-cyclopropanecarbonyl-4-hydroxypiperidin-4-yl)
methyl]-1-[4-(1H-indazol-4-yl)phenyl]-1H,4H,5H-
pyrazolo[3,4-d]pyrimidin-4-one (I-1215);
5-[(1-cyclopropanecarbonyl-4-hydroxypiperidin-4-yl)
methyl]-1-(4-{8-oxa-2-azaspiro[4.5]decan-2-
yl}phenyl)-1H,4H,5H-pyrazolo[3,4-d]pyrimidin-4-one
(I-1216);
5-[(1-cyclopropanecarbonyl-4-hydroxypiperidin-4-yl)
methyl]-1-(3-{8-oxa-2-azaspiro[4.5]decan-2-
yl}phenyl)-1H,4H,5H-pyrazolo[3,4-d]pyrimidin-4-one
(I-1217);
5-{[1-(1-cyclopropylpiperidine-4-carbonyl)-4-hy-
droxypiperidin-4-yl]methyl}-1-(4-fluorophenyl)-1H,
4H,5H-pyrazolo[3,4-d]pyrimidin-4-one (I-1218);
1-(4-fluorophenyl)-5-[(4-hydroxy-1-{3-phenylbicyclo
[1.1.1]pentane-1-carbonyl}piperidin-4-yl)methyl]-1H,
4H,5H-pyrazolo[3,4-d]pyrimidin-4-one (I-1219);
5-[(1-{4-[(4aR,8aS)-decahydroisoquinolin-2-yl]ben-
zoyl}-4-hydroxypiperidin-4-yl)methyl]-1-methyl-1H,
4H,5H-pyrazolo[3,4-d]pyrimidin-4-one (I-122);
1-(4-fluorophenyl)-5-[(4-hydroxy-1-{pyrazolo[1,5-a]
pyridine-3-carbonyl}piperidin-4-yl)methyl]-1H,4H,
5H-pyrazolo[3,4-d]pyrimidin-4-one (I-1221);
5-({1-[5-(difluoromethoxy)pyridine-2-carbonyl]-4-hy-
droxypiperidin-4-yl}methyl)-1-(4-fluorophenyl)-1H,
4H,5H-pyrazolo[3,4-d]pyrimidin-4-one (I-1223);
5-[(1-{6-aminospiro[3.3]heptane-2-carbonyl}-4-hy-
droxypiperidin-4-yl)methyl]-1-(4-fluorophenyl)-1-1H,
4H, 5H-pyrazolo[3,4-d]pyrimidin-4-one (I-1224);
1-(4-fluorophenyl)-5-[(4-hydroxy-1-{2H,3H-pyrazolo[3,
2-b][1,3]oxazole-6-carbonyl}piperidin-4-yl)methyl]-
1H,4H,5H-pyrazolo[3,4-d]pyrimidin-4-one (I-1225);
1-(4-fluorophenyl)-5-({4-hydroxy-1-[(3S)-piperidine-3-
carbonyl]piperidin-4-yl}methyl)-1H,4H,5H-pyrazolo
[3,4-d]pyrimidin-4-one (I-1226);
1-(4-fluorophenyl)-5-({4-hydroxy-1-[(3S)-pyrrolidine-3-
carbonyl]piperidin-4-yl}methyl)-1H,4H,5H-pyrazolo
[3,4-d]pyrimidin-4-one (I-1227);
1-(4-fluorophenyl)-5-({4-hydroxy-1-[(3R)-piperidine-3-
carbonyl]piperidin-4-yl}methyl)-1H,4H,5H-pyrazolo
[3,4-d]pyrimidin-4-one (I-1228);
1-(4-fluorophenyl)-5-({4-hydroxy-1-[(3R)-pyrrolidine-3-
carbonyl]piperidin-4-yl}methyl)-1H,4H,5H-pyrazolo
[3,4-d]pyrimidin-4-one (I-1229);
5-({4-hydroxy-1-[4-(1,2,3,4-tetrahydroquinolin-1-yl)
benzoyl]piperidin-4-yl}methyl)-1-methyl-1H,4H,5H-
pyrazolo[3,4-d]pyrimidin-4-one (I-123);
5-[(1-cyclopropanecarbonyl-4-hydroxypiperidin-4-yl)
methyl]-1-[3-(phenylamino)phenyl]-1H,4H,5H-pyra-
zolo[3,4-d]pyrimidin-4-one (I-1230);
5-[(1-cyclopropanecarbonyl-4-hydroxypiperidin-4-yl)
methyl]-1-[4-(phenylamino)phenyl]-1H,4H,5H-pyra-
zolo[3,4-d]pyrimidin-4-one (I-1231);
5-[(1-cyclopropanecarbonyl-4-hydroxypiperidin-4-yl)
methyl]-1-{3-[(pyridin-4-yl)amino]phenyl)-1H,4H,
5H-pyrazolo[3,4-d]pyrimidin-4-one (I-1232);
5-[(1-cyclopropanecarbonyl-4-hydroxypiperidin-4-yl)
methyl]-1-{4-[(pyridin-2-yl)amino]phenyl)-1H,4H,
5H-pyrazolo[3,4-d]pyrimidin-4-one (I-1233);
5-[(1-cyclopropanecarbonyl-4-hydroxypiperidin-4-yl)
methyl]-1-(4-{[4-(morpholin-4-yl)phenyl]
amino}phenyl)-1H,4H,5H-pyrazolo[3,4-d]pyrimidin-
4-one (I-1234);
5-[(1-cyclopropanecarbonyl-4-hydroxypiperidin-4-yl)
methyl]-1-(4-{[1-(pyridin-3-ylmethyl)-1H-pyrazol-3-
yl]amino}phenyl)-1H,4H,5H-pyrazolo[3,4-d]pyrimi-
din-4-one (I-1235);
5-[(1-cyclopropanecarbonyl-4-hydroxypiperidin-4-yl)
methyl]-1-(4-{[1-(pyridin-2-ylmethyl)-1H-pyrazol-3-
yl]amino}phenyl)-1H,4H,5H-pyrazolo[3,4-d]pyrimi-
din-4-one (I-1236);
1-{4-[(2,1,3-benzoxadiazol-4-yl)amino]phenyl}-5-[(1-
cyclopropanecarbonyl-4-hydroxypiperidin-4-yl)
methyl]-1H,4H,5H-pyrazolo[3,4-d]pyrimidin-4-one
(I-1237);
5-[(1-cyclopropanecarbonyl-4-hydroxypiperidin-4-yl)
methyl]-1-{4-[(5-cyclopropyl-1,3,4-thiadiazol-2-yl)
amino]phenyl)-1H,4H,5H-pyrazolo[3,4-d]pyrimidin-
4-one (I-1238);
5-[(1-cyclopropanecarbonyl-4-hydroxypiperidin-4-yl)
methyl]-1-{4-[(3-phenyl-1,2,4-thiadiazol-5-yl)amino]
phenyl}-1H,4H,5H-pyrazolo[3,4-d]pyrimidin-4-one
(I-1239);
5-{[4-hydroxy-1-(4-{methyl[(2-methylphenyl)methyl]
amino}benzoyl)piperidin-4-yl]methyl}-1-methyl-1H,
4H,5H-pyrazolo[3,4-d]pyrimidin-4-one (I-124);
5-[(1-cyclopropanecarbonyl-4-hydroxypiperidin-4-yl)
methyl]-1-{4-[(1,3-thiazol-2-yl)amino]phenyl)-1H,4H,
5H-pyrazolo[3,4-d]pyrimidin-4-one (I-1240);
5-[(1-cyclopropanecarbonyl-4-hydroxypiperidin-4-yl)
methyl]-1-{4-[(5-methyl-1,2-oxazol-3-yl)amino]phe-
nyl)-1H,4H,5H-pyrazolo[3,4-d]pyrimidin-4-one
(I-1241);
1-{4-[(4-tert-butyl-1,3-thiazol-2-yl)amino]phenyl}-5-[(1-
cyclopropanecarbonyl-4-hydroxypiperidin-4-yl)
methyl]-1H,4H,5H-pyrazolo[3,4-d]pyrimidin-4-one
(I-1242);
1-{4-[(1,3-benzothiazol-6-yl)amino]phenyl}-5-[(1-cyclo-
propanecarbonyl-4-hydroxypiperidin-4-yl)methyl]-
1H,4H,5H-pyrazolo[3,4-d]pyrimidin-4-one (I-1243);
1-{4-[(5-tert-butyl-1H-pyrazol-3-yl)amino]phenyl}-5-
[(1-cyclopropanecarbonyl-4-hydroxypiperidin-4-yl)
methy 1]-1H,4H, 5H-pyrazolo[3,4-d]pyrimidin-4-one
(I-1244);

5-[(1-cyclopropanecarbonyl-4-hydroxypiperidin-4-yl)methyl]-1-(4-{[1-(4-fluorophenyl)-1H-pyrazol-3-yl]amino}phenyl)-1H,4H,5H-pyrazolo[3,4-d]pyrimidin-4-one (I-1245);

5-[(1-cyclopropanecarbonyl-4-hydroxypiperidin-4-yl)methyl]-1-{3-[(pyridin-2-yl)amino]phenyl}-1H,4H,5H-pyrazolo[3,4-d]pyrimidin-4-one (I-1246);

5-[(1-cyclopropanecarbonyl-4-hydroxypiperidin-4-yl)methyl]-1-(3-{[4-(morpholin-4-yl)phenyl]amino}phenyl)-1H,4H,5H-pyrazolo[3,4-d]pyrimidin-4-one (I-1247);

5-[(1-cyclopropanecarbonyl-4-hydroxypiperidin-4-yl)methyl]-1-{3-[(1H-pyrazol-3-yl)amino]phenyl}-1H,4H,5H-pyrazolo[3,4-d]pyrimidin-4-one (I-1248);

5-[(1-cyclopropanecarbonyl-4-hydroxypiperidin-4-yl)methyl]-1-{3-[(6-methoxypyridin-3-yl)amino]phenyl}-1H,4H,5H-pyrazolo[3,4-d]pyrimidin-4-one (I-1249);

5-({4-hydroxy-1-[4-(thiomorpholin-4-yl)benzoyl]piperidin-4-yl}methyl)-1-methyl-1H,4H,5H-pyrazolo[3,4-d]pyrimidin-4-one (I-125);

5-[(1-cyclopropanecarbonyl-4-hydroxypiperidin-4-yl)methyl]-1-{3-[(2-methoxypyridin-3-yl)amino]phenyl}-1H,4H,5H-pyrazolo[3,4-d]pyrimidin-4-one (I-1250);

5-[(1-cyclopropanecarbonyl-4-hydroxypiperidin-4-yl)methyl]-1-{3-[(5-methyl-1,3,4-thiadiazol-2-yl)amino]phenyl}-1H,4H,5H-pyrazolo[3,4-d]pyrimidin-4-one (I-1251);

5-[(1-cyclopropanecarbonyl-4-hydroxypiperidin-4-yl)methyl]-1-(3-{[3-(morpholin-4-yl)phenyl]amino}phenyl)-1H,4H,5H-pyrazolo[3,4-d]pyrimidin-4-one (I-1252);

5-[(1-cyclopropanecarbonyl-4-hydroxypiperidin-4-yl)methyl]-1-(3-{[2-(morpholin-4-yl)phenyl]amino}phenyl)-1H,4H,5H-pyrazolo[3,4-d]pyrimidin-4-one (I-1253);

6-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-3-carbonitrile (I-1254);

4-({1-[4-(cyanomethoxy)phenyl]-4-oxo-1H,4H,5H-pyrazolo[3,4-d]pyrimidin-5-yl}methyl)-4-hydroxy-N,N-dimethylpiperidine-1-carboxamide (I-1255);

4-hydroxy-4-({1-[4-(2-methoxyethoxy)phenyl]-4-oxo-1H,4H,5H-pyrazolo[3,4-d]pyrimidin-5-yl}methyl)-N,N-dimethylpiperidine-1-carboxamide (I-1256);

1-{3-[(1,3-benzothiazol-6-yl)amino]phenyl}-5-[(1-cyclopropanecarbonyl-4-hydroxypiperidin-4-yl)methyl]-1H,4H,5H-pyrazolo[3,4-d]pyrimidin-4-one (I-1257);

1-{3-[(5-tert-butyl-1H-pyrazol-3-yl)amino]phenyl}-5-[(1-cyclopropanecarbonyl-4-hydroxypiperidin-4-yl)methyl]-1H,4H,5H-pyrazolo[3,4-d]pyrimidin-4-one (I-1258);

5-[(1-cyclopropanecarbonyl-4-hydroxypiperidin-4-yl)methyl]-1-(3-{[1-(4-fluorophenyl)-1H-pyrazol-3-yl]amino}phenyl)-1H,4H,5H-pyrazolo[3,4-d]pyrimidin-4-one (I-1259);

5-({4-hydroxy-1-[4-(1-phenoxyethyl)benzoyl]piperidin-4-yl}methyl)-1-methyl-1H,4H,5H-pyrazolo[3,4-d]pyrimidin-4-one (I-126);

5-[(1-cyclopropanecarbonyl-4-hydroxypiperidin-4-yl)methyl]-1-{3-[4-(2-hydroxyethyl)piperazin-1-yl]phenyl}-1H,4H,5H-pyrazolo[3,4-d]pyrimidin-4-one (I-1260);

4-({1-[5-(cyclopentylamino)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1261);

4-hydroxy-N,N-dimethyl-4-[(4-oxo-1-{5-[(2-phenylethyl)amino]pyridin-3-yl}-1H,4H,5H-pyrazolo[3,4-d]pyrimidin-5-yl)methyl]piperidine-1-carboxamide (I-1262);

4-hydroxy-N,N-dimethyl-4-{[1-(5-{[2-(morpholin-4-yl)ethyl]amino}pyridin-3-yl)-4-oxo-1H,4H,5H-pyrazolo[3,4-d]pyrimidin-5-yl]methyl}piperidine-1-carboxamide (I-1263);

4-hydroxy-N,N-dimethyl-4-({1-[5-(morpholin-4-yl)pyridin-3-yl]-4-oxo-1H,4H,5H-pyrazolo[3,4-d]pyrimidin-5-yl}methyl)piperidine-1-carboxamide (I-1264);

4-({1-[5-(4-cyanopiperidin-1-yl)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1265);

4-hydroxy-N,N-dimethyl-4-[(1-{5-[4-(morpholin-4-yl)piperidin-1-yl]pyridin-3-yl}-4-oxo-1H,4H,5H-pyrazolo[3,4-d]pyrimidin-5-yl)methyl]piperidine-1-carboxamide (I-1266);

4-({1-[5-(1,1-dioxo-1,6,4-thiomorpholin-4-yl)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1267);

4-hydroxy-N,N-dimethyl-4-{[1-(5-{8-oxa-2-azaspiro[4.5]decan-2-yl}pyridin-3-yl)-4-oxo-1H,4H,5H-pyrazolo[3,4-d]pyrimidin-5-yl]methyl}piperidine-1-carboxamide (I-1268);

4-hydroxy-N,N-dimethyl-4-({4-oxo-1-[5-(piperazin-1-yl)pyridin-3-yl]-1H,4H,5H-pyrazolo[3,4-d]pyrimidin-5-yl}methyl)piperidine-1-carboxamide (I-1269);

5-[(1-{4-[1-(4-fluorophenoxy)ethyl]benzoyl}-4-hydroxypiperidin-4-yl)methyl]-1-methyl-1H,4H,5H-pyrazolo[3,4-d]pyrimidin-4-one (I-127);

4-({1-[5-(3-fluorophenyl)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1270);

4-({1-[5-(4-fluorophenyl)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1271);

4-[(1-{5-[4-(dimethylcarbamoyl)phenyl]pyridin-3-yl}-4-oxo-1H,4H,5H-pyrazolo[3,4-d]pyrimidin-5-yl)methyl]-4-hydroxy-N,N-dimethylpiperidine-1-carboxamide (I-1272);

4-hydroxy-N,N-dimethyl-4-[(4-oxo-1-{5-[4-(pyrrolidine-1-carbonyl)phenyl]pyridin-3-yl}-1H,4H,5H-pyrazolo[3,4-d]pyrimidin-5-yl)methyl]piperidine-1-carboxamide (I-1273);

4-({1-[5-(3,4-dimethoxyphenyl)pyridin-3-yl]-4-oxo-1H,4H,5H-pyrazolo[3,4-d]pyrimidin-5-yl}methyl)-4-hydroxy-N,N-dimethylpiperidine-1-carboxamide (I-1274);

4-hydroxy-N,N-dimethyl-4-({4-oxo-1-[5-(pyridin-3-yl)pyridin-3-yl]-1H,4H,5H-pyrazolo[3,4-d]pyrimidin-5-yl}methyl)piperidine-1-carboxamide (I-1275);

5-[(1-cyclopropanecarbonyl-4-hydroxypiperidin-4-yl)methyl]-1-(4-{[3-(morpholin-4-yl)phenyl]amino}phenyl)-1H,4H,5H-pyrazolo[3,4-d]pyrimidin-4-one (I-1276), 6-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-3-carbonitrile (I-1277);

5-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-2-carbonitrile (I-1278), 6-({4-[4-hydroxy-4-({1-methyl-4-oxo-1H,4H,5H-pyrazolo[3,4-d]pyrimidin-5-yl}methyl)piperidine-1-carbonyl]phenyl}methoxy)pyridine-2-carbonitrile (I-128);

4-[(1-{5-[3-(dimethylcarbamoyl)phenyl]pyridin-3-yl}-4-oxo-1H,4H,5H-pyrazolo[3,4-d]pyrimidin-5-yl)methyl]-4-hydroxy-N,N-dimethylpiperidine-1-carboxamide (I-1280);

4-hydroxy-N,N-dimethyl-4-[(1-{5-[3-(methylcarbamoyl)phenyl]pyridin-3-yl}-4-oxo-1H,4H,5H-pyrazolo[3,4-d]pyrimidin-5-yl)methyl]piperidine-1-carboxamide (I-1281);

4-hydroxy-4-{[1-(5-{3-[(2-hydroxyethyl)carbamoyl]phenyl}pyridin-3-yl)-4-oxo-1H,4H,5H-pyrazolo[3,4-d]pyrimidin-5-yl]methyl)-N,N-dimethylpiperidine-1-carboxamide (I-1282);

4-hydroxy-N,N-dimethyl-4-({1-[5-(1-methyl-1H-indazol-5-yl)pyridin-3-yl]-4-oxo-1H,4H,5H-pyrazolo[3,4-d]pyrimidin-5-yl}methyl)piperidine-1-carboxamide (I-1283), 1-[4-(benzyloxy)phenyl]-5-{[1-(4-fluorobenzoyl)-4-hydroxypiperidin-4-yl]methyl)-1H,4H,5H-pyrazolo[3,4-d]pyrimidin-4-one (I-1284);

1-[3-(benzyloxy)phenyl]-5-{[1-(4-fluorobenzoyl)-4-hydroxypiperidin-4-yl]methyl}-1H,4H,5H-pyrazolo[3,4-d]pyrimidin-4-one (I-1285);

4-({1-[4-(cyclopentyloxy)phenyl]-4-oxo-1H,4H,5H-pyrazolo[3,4-d]pyrimidin-5-yl}methyl)-4-hydroxy-N,N-dimethylpiperidine-1-carboxamide (I-1286);

1-[4-(cyclopentyloxy)phenyl]-5-{[1-(4-fluorobenzoyl)-4-hydroxypiperidin-4-yl]methyl}-1H,4H,5H-pyrazolo[3,4-d]pyrimidin-4-one (I-1287);

1-[3-(cyclopentyloxy)phenyl]-5-{[1-(4-fluorobenzoyl)-4-hydroxypiperidin-4-yl]methyl}-1H,4H,5H-pyrazolo[3,4-d]pyrimidin-4-one (I-1288);

4-({1-[4-(cyclopropylmethoxy)phenyl]-4-oxo-1H,4H,5H-pyrazolo[3,4-d]pyrimidin-5-yl}methyl)-4-hydroxy-N,N-dimethylpiperidine-1-carboxamide (I-1289);

6-({4-[4-hydroxy-4-({1-methy 1-4-oxo-1H,4H,5H-pyrazolo[3,4-d]pyrimidin-5-yl}methyl)piperidine-1-carbonyl]phenyl}methoxy)pyrazine-2-carbonitrile (I-129), 1-[4-(cyclopropylmethoxy)phenyl]-5-{[1-(4-fluorobenzoyl)-4-hydroxypiperidin-4-yl]methyl}-1H,4H,5H-pyrazolo[3,4-d]pyrimidin-4-one (I-1290);

1-[3-(cyclopropylmethoxy)phenyl]-5-{[1-(4-fluorobenzoyl)-4-hydroxypiperidin-4-yl]methyl}-1H,4H,5H-pyrazolo[3,4-d]pyrimidin-4-one (I-1291);

4-({1-[4-fluoro-3-(1-methyl-1H-pyrazol-4-yl)phenyl]-4-oxo-1H,4H,5H-pyrazolo[3,4-d]pyrimidin-5-yl}methyl)-4-hydroxy-N,N-dimethylpiperidine-1-carboxamide (I-1292);

4-hydroxy-4-[(1-{4-[2-(1H-imidazol-1-yl)ethoxy]phenyl}-4-oxo-1H,4H,5H-pyrazolo[3,4-d]pyrimidin-5-yl)methyl]-N,N-dimethylpiperidine-1-carboxamide (I-1293);

4-({1-[4-(carbamoylmethoxy)phenyl]-4-oxo-1H,4H,5H-pyrazolo[3,4-d]pyrimidin-5-yl}methyl)-4-hydroxy-N,N-dimethylpiperidine-1-carboxamide (I-1294);

4-({1-[4-(cyclobutylmethoxy)phenyl]-4-oxo-1H,4H,5H-pyrazolo[3,4-d]pyrimidin-5-yl}methyl)-4-hydroxy-N,N-dimethylpiperidine-1-carboxamide (I-1295);

4-hydroxy-N,N-dimethyl)-4-({1-[4-(3-methylbutoxy)phenyl]-4-oxo-1H,4H,5H-pyrazolo[3,4-d]pyrimidin-5-yl}methyl)piperidine-1-carboxamide (I-1296);

4-hydroxy-N,N-dimethyl-4-({4-oxo-1-[4-(2,2,2-trifluoroethoxy)phenyl]-1H,4H,5H-pyrazolo[3,4-d]pyrimidin-5-yl}methyl)piperidine-1-carboxamide (I-1297);

4-hydroxy-N,N-dimethyl-4-[(1-{4-[(1-methylpiperidin-2-yl)methoxy]phenyl}-4-oxo-1H,4H,5H-pyrazolo[3,4-d]pyrimidin-5-yl)methyl]piperidine-1-carboxamide (I-1298);

4-[(1-{4-[(4-cyanophenyl)methoxy]phenyl}-4-oxo-1H,4H,5H-pyrazolo[3,4-d]pyrimidin-5-yl)methyl]-4-hydroxy-N,N-dimethylpiperidine-1-carboxamide (I-1299);

5-({4-hydroxy-1-[4-(phenylamino)benzoyl]piperidin-4-yl}methyl)-1-methyl-1H,4H,5H-pyrazolo[3,4-d]pyrimidin-4-one (I-13);

4-[(1-{4-[(3-cyanophenyl)methoxy]phenyl}-4-oxo-1H, 4H, 5H-pyrazolo[3,4-d]pyrimidin-5-yl)methyl]-4-hydroxy-N,N-dimethylpiperidine-1-carboxamide (I-1300);

4-hydroxy-N,N-dimethyl-4-({4-oxo-1-[4-(pyridin-3-ylmethoxy)phenyl]-1H,4H,5H-pyrazolo[3,4-d]pyrimidin-5-yl}methyl)piperidine-1-carboxamide (I-1301);

4-hydroxy-N,N-dimethyl-4-({4-oxo-1-[4-(pyridin-2-ylmethoxy)phenyl]-1H,4H,5H-pyrazolo[3,4-d]pyrimidin-5-yl}methyl)piperidine-1-carboxamide (I-1302);

4-hydroxy-N,N-dimethyl-4-({1-[4-(oxan-4-ylmethoxy)phenyl]-4-oxo-1H,4H,5H-pyrazolo[3,4-d]pyrimidin-5-yl}methyl)piperidine-1-carboxamide (I-1303);

4-hydroxy-N,N-dimethyl-4-[(1-{4-[2-(morpholin-4-yl)-2-oxoethoxy]phenyl}-4-oxo-1H,4H,5H-pyrazolo[3,4-d]pyrimidin-5-yl)methyl]piperidine-1-carboxamide (I-1304);

5-{[1-(4-fluorobenzoyl)-4-hydroxypiperidin-4-yl]methyl}-1-{4-[2-(1H-imidazol-1-yl)ethoxy]phenyl)-1H,4H,5H-pyrazolo[3,4-d]pyrimidin-4-one (I-1305);

5-{[1-(4-fluorobenzoyl)-4-hydroxypiperidin-4-yl]methyl}-1-{3-[2-(1H-imidazol-1-yl)ethoxy]phenyl)-1H,4H,5H-pyrazolo[3,4-d]pyrimidin-4-one (I-1306);

2-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetamide (I-1307);

2-[3-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetamide (I-1308);

1-[4-(cyclobutylmethoxy)phenyl]-5-{[1-(4-fluorobenzoyl)-4-hydroxypiperidin-4-yl]methyl}-1H,4H,5H-pyrazolo[3,4-d]pyrimidin-4-one (I-1309);

5-[(1-{4-[4-(dimethylamino)piperidin-1-yl]benzoyl}-4-hydroxypiperidin-4-yl)methyl]-1-methyl-1H,4H,5H-pyrazolo[3,4-d]pyrimidin-4-one (I-131);

1-[3-(cyclobutylmethoxy)phenyl]-5-{[1-(4-fluorobenzoyl)-4-hydroxypiperidin-4-yl]methyl}-1H,4H,5H-pyrazolo[3,4-d]pyrimidin-4-one (I-1310);

5-{[1-(4-fluorobenzoyl)-4-hydroxypiperidin-4-yl]methyl}-1-[3-(3-methylbutoxy)phenyl]-1H,4H,5H-pyrazolo[3,4-d]pyrimidin-4-one (I-1311);

1-[3-(2,2-dimethylpropoxy)phenyl]-5-{[1-(4-fluorobenzoyl)-4-hydroxypiperidin-4-yl]methyl}-1H,4H,5H-pyrazolo[3,4-d]pyrimidin-4-one (I-1312);

5-{[1-(4-fluorobenzoyl)-4-hydroxypiperidin-4-yl]methyl}-1-{4-[(1-methylpiperidin-2-yl)methoxy]phenyl)-1H,4H,5H-pyrazolo[3,4-d]pyrimidin-4-one (I-1313);

5-{[1-(4-fluorobenzoyl)-4-hydroxypiperidin-4-yl]methyl}-1-{3-[(1-methylpiperidin-2-yl)methoxy]phenyl)-1H,4H,5H-pyrazolo[3,4-d]pyrimidin-4-one (I-1314);

4-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxymethyl]benzonitrile (I-1315);

4-[3-(5-{[1-(4-fluorobenzoyl)-4-hydroxypiperidin-4-yl] methyl)-4-oxo-1H,4H, 5H-pyrazolo[3,4-d]pyrimidin-1-yl)phenoxymethyl]benzonitrile (I-1316);

1-{3-[(4-chlorophenyl)methoxy]phenyl)-5-{[1-(4-fluorobenzoyl)-4-hydroxypiperidin-4-yl]methyl}-1H,4H, 5H-pyrazolo[3,4-d]pyrimidin-4-one (I-1317);

3-[4-(5-{[1-(4-fluorobenzoyl)-4-hydroxypiperidin-4-yl] methyl)-4-oxo-1H,4H,5H-pyrazolo[3,4-d]pyrimidin-1-yl)phenoxymethyl]benzonitrile (I-1318);

3-[3-(5-{[1-(4-fluorobenzoyl)-4-hydroxypiperidin-4-yl] methyl)-4-oxo-1H,4H,5H-pyrazolo[3,4-d]pyrimidin-1-yl}phenoxymethyl]benzonitrile (I-1319);

2-[4-(5-{[1-(4-fluorobenzoyl)-4-hydroxypiperidin-4-yl] methyl)-4-oxo-1H,4H,5H-pyrazolo[3,4-d]pyrimidin-1-yl)phenoxy]acetonitrile (I-1320);

2-[3-(5-{[1-(4-fluorobenzoyl)-4-hydroxypiperidin-4-yl] methyl)-4-oxo-1H,4H,5H-pyrazolo[3,4-d]pyrimidin-1-yl)phenoxy]acetonitrile (I-1321);

4-hydroxy-N,N-dimethyl-4-[(1-{5-[4-(methylcarbamoyl) phenyl]pyridin-3-yl}-4-oxo-1H,4H,5H-pyrazolo[3,4-d]pyrimidin-5-yl)methyl]piperidine-1-carboxamide (I-1322);

5-{[1-(4-fluorobenzoyl)-4-hydroxypiperidin-4-yl] methyl}-1-[4-(oxan-4-ylmethoxy)phenyl]-1H,4H,5H-pyrazolo[3,4-d]pyrimidin-4-one (I-1324);

5-{[1-(4-fluorobenzoyl)-4-hydroxypiperidin-4-yl] methyl}-1-[3-(oxan-4-ylmethoxy)phenyl]-1H,4H,5H-pyrazolo[3,4-d]pyrimidin-4-one (I-1325);

5-{[1-(4-fluorobenzoyl)-4-hydroxypiperidin-4-yl] methyl}-1-{4-[2-(morpholin-4-yl)-2-oxoethoxy]phenyl}-1H,4H,5H-pyrazolo[3,4-d]pyrimidin-4-one (I-1326);

5-{[1-(4-fluorobenzoyl)-4-hydroxypiperidin-4-yl] methyl}-1-{3-[2-(morpholin-4-yl)-2-oxoethoxy]phenyl}-1H,4H,5H-pyrazolo[3,4-d]pyrimidin-4-one (I-1327);

5-{[1-(4-fluorobenzoyl)-4-hydroxypiperidin-4-yl] methyl}-1-{3-[(2-phenyl-1,3-thiazol-4-yl)methoxy] phenyl}-1H,4H,5H-pyrazolo[3,4-d]pyrimidin-4-one (I-1328);

4-({1-[6-(3-cyanophenyl)pyridin-3-yl]-4-oxo-1H,4H,5H-pyrazolo[3,4-d]pyrimidin-5-yl}methyl)-4-hydroxy-N, N-dimethylpiperidine-1-carboxamide (I-1329);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzamide (I-1330);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-phenylacetamide (I-1331);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(3-methyl-1,2-oxazol-5-yl)acetamide (I-1332), N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzamide (I-1333);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-fluorobenzamide (I-1334);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxybenzamide (I-1335);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-4-carboxamide (I-1336);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methyl-1,3-thiazole-4-carboxamide (I-1337);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(oxan-4-yl)acetamide (I-1338);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxyacetamide (I-1339);

N-(3-{5-[(I-cyclopropanecarbonyl-4-hydroxypiperidin-4-yl)methyl]-4-oxo-1H,4H,5H-pyrazolo[3,4-d]pyrimidin-1-yl}phenyl)cyclopropanecarboxamide (I-1340);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1,3-dimethyl-1H-pyrazole-5-carboxamide (I-1341);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methyl-1,3-thiazole-5-carboxamide (I-1342), N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(dimethylamino)acetamide (I-1343);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-6-methylpyridine-3-carboxamide (I-1344);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-fluoropyridine-2-carboxamide (I-1345);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-2-carboxamide (I-1346);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methyl-1,2,3-thiadiazole-5-carboxamide (I-1347);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(methylamino)benzamide (I-1348);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-(methylamino)benzamide (I-1349);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxypyridine-3-carboxamide (I-1350);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1,3-dimethyl-1H-pyrazole-5-carboxamide (I-1351);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methyl-1,3-thiazole-5-carboxamide (I-1352); N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(dimethylamino)acetamide (I-1353);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-6-methylpyridine-3-carboxamide (I-1354);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-fluoropyridine-2-carboxamide (I-1355);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(1,1-dioxo-1,6,4-thiomorpholin-4-yl)acetamide (I-1356);

N-(3-{5-[(1-cyclopropanecarbonyl-4-hydroxypiperidin-4-yl)methyl]-4-oxo-1H,4H, 5H-pyrazolo[3,4-d]pyrimidin-1-yl}phenyl)-2-(morpholin-4-yl)acetamide (I-1357);

(2S)—N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpyrrolidine-2-carboxamide (I-1358);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpiperidine-2-carboxamide (I-1359);

5-({4-hydroxy-1-[(3R)-3-methoxy-3-phenylpropanoyl]piperidin-4-yl}methyl)-1-methyl-1H,4H,5H-pyrazolo[3,4-d]pyrimidin-4-one (I-136);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)oxane-4-carboxamide (I-1360);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(1H-pyrazol-1-yl)acetamide (I-1361);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,3-difluorocyclobutane-1-carboxamide (I-1362);

5-{[1-(4-fluorobenzoyl)-4-hydroxypiperidin-4-yl]methyl}-1-[4-(2-methoxyethoxy)phenyl]-1H,4H,5H-pyrazolo[3,4-d]pyrimidin-4-one (I-1363);

5-{[1-(4-fluorobenzoyl)-4-hydroxypiperidin-4-yl]methyl}-1-[3-(2-methoxyethoxy)phenyl]-1H,4H,5H-pyrazolo[3,4-d]pyrimidin-4-one (I-1364);

5-{[1-(4-fluorobenzoyl)-4-hydroxypiperidin-4-yl]methyl}-1-[3-(pyridin-3-ylmethoxy)phenyl]-1H,4H,5H-pyrazolo[3,4-d]pyrimidin-4-one (I-1365);

5-{[1-(4-fluorobenzoyl)-4-hydroxypiperidin-4-yl]methyl}-1-[3-(pyridin-4-ylmethoxy)phenyl]-1H,4H,5H-pyrazolo[3,4-d]pyrimidin-4-one (I-1366);

5-{[1-(4-fluorobenzoyl)-4-hydroxypiperidin-4-yl]methyl}-1-[4-(pyridin-2-ylmethoxy)phenyl]-1H,4H,5H-pyrazolo[3,4-d]pyrimidin-4-one (I-1367);

5-{[1-(4-fluorobenzoyl)-4-hydroxypiperidin-4-yl]methyl}-1-[3-(pyridin-2-ylmethoxy)phenyl]-1H,4H,5H-pyrazolo[3,4-d]pyrimidin-4-one (I-1368);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(3-methyl-1,2-oxazol-5-yl)acetamide (I-1369);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzamide (I-1370);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-fluorobenzamide (I-1371);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxybenzamide (I-1372);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-4-carboxamide (I-1373);

N-(4-{5-[(1-cyclopropanecarbonyl-4-hydroxypiperidin-4-yl)methyl]-4-oxo-1H,4H, 5H-pyrazolo[3,4-d]pyrimidin-1-yl}phenyl)-2-methyl-1,3-thiazole-4-carboxamide (I-1374);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(oxan-4-yl)acetamide (I-1375);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxyacetamide (I-1376);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanecarboxamide (I-1377);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methylbenzamide (I-1378);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzamide (I-1379);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-fluorobenzamide (I-1380);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-3-carboxamide (I-1381);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methylpyrazine-2-carboxamide (I-1382);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-2-carboxamide (I-1383);

N-(4-{5-[(1-cyclopropanecarbonyl-4-hydroxypiperidin-4-yl)methy l]-4-oxo-1H,4H, 5H-pyrazolo[3,4-d]pyrimidin-1-yl}phenyl)-2-(methylamino)benzamide (I-1384), N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-(methylamino)benzamide (I-1385);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxypyridine-3-carboxamide (I-1386);

5-[(1-cyclopropanecarbonyl-4-hydroxypiperidin-4-yl)methyl]-1-(3-{[1-(pyridin-3-ylmethyl)-1H-pyrazol-3-yl]amino}phenyl)-1H,4H,5H-pyrazolo[3,4-d]pyrimidin-4-one (I-1387);

5-[(1-cyclopropanecarbonyl-4-hydroxypiperidin-4-yl)methyl]-1-(3-{[1-(pyridin-2-ylmethyl)-1H-pyrazol-3-yl]amino}phenyl)-1H,4H,5H-pyrazolo[3,4-d]pyrimidin-4-one (I-1388);

5-[(1-cyclopropanecarbonyl-4-hydroxypiperidin-4-yl)methyl]-1-{3-[(1,3-thiazol-2-yl)amino]phenyl}-1H,4H,5H-pyrazolo[3,4-d]pyrimidin-4-one (I-1389);

5-{[1-(1-benzyl-1,2,3,4-tetrahydroquinoline-6-carbonyl)-4-hydroxypiperidin-4-yl]methyl}-1-methyl-1H,4H,5H-pyrazolo[3,4-d]pyrimidin-4-one (I-139), 5-[(1-cyclopropanecarbonyl-4-hydroxypiperidin-4-yl)methyl]-1-{3-[(5-methyl-1,2-oxazol-3-yl)amino]phenyl}-1H,4H,5H-pyrazolo[3,4-d]pyrimidin-4-one (I-1390);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(1,1-dioxo-1,6,4-thiomorpholin-4-yl)acetamide (I-1391), N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(morpholin-4-yl)acetamide (I-1392);

(2S)—N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpyrrolidine-2-carboxamide (I-1393);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpiperidine-2-carboxamide (I-1394);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)oxane-4-carboxamide (I-1395);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(1H-pyrazol-1-yl)acetamide (I-1396);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,3-difluorocyclobutane-1-carboxamide (I-1397);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-[methyl(phenyl)amino]acetamide (I-1398);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methyl-2-(morpholin-4-yl)propanamide (I-1399);

5-{[(3S,4R)-1-benzoyl-4-hydroxy-3-methoxypiperidin-4-yl]methyl}-1-phenyl-1H,4H,5H-pyrazolo[3,4-d]pyrimidin-4-one (I-14);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methyl-1,2-oxazole-4-sulfonamide (I-1400);

4-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1401);

5-[(1-cyclopropanecarbonyl-4-hydroxypiperidin-4-yl)methyl]-1-{4-[(oxan-4-ylmethyl)amino]phenyl}-1H,4H,5H-pyrazolo[3,4-d]pyrimidin-4-one (I-1402);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methylbenzene-1-sulfonamide (I-1403);

2-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1404);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzene-1-sulfonamide (I-1405);

3-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1406);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-fluorobenzene-1-sulfonamide (I-1407);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methylbenzene-1-sulfonamide (I-1408);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-[methyl(phenyl)amino]acetamide (I-1409);

5-({4-hydroxy-1-[(3R)-4,4,4-trifluoro-3-phenylbutanoyl]piperidin-4-yl}methyl)-1-phenyl-1H,4H,5H-pyrazolo[3,4-d]pyrimidin-4-one (I-141);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methyl-2-(morpholin-4-yl)propanamide (I-1410);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)acetamide (I-1411);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzamide (I-1412);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-phenylacetamide (I-1413);

3-{5-[(1-cyclopropanecarbonyl-4-hydroxypiperidin-4-yl)methyl]-4-oxo-1H,4H,5H-pyrazolol[3,4-d]pyrimidin-1-yl}-N-(oxetan-3-yl)benzamide (I-1414);

3-(5-[(1-cyclopropanecarbonyl-4-hydroxypiperidin-4-yl)methyl]-4-oxo-1H,4H,5H-pyrazolo[3,4-d]pyrimidin-1-yl)-N-phenylbenzamide (I-1415);

3-{5-[(1-cyclopropanecarbonyl-4-hydroxypiperidin-4-yl)methyl]-4-oxo-1H,4H,5H-pyrazolo[3,4-d]pyrimidin-1-yl}-N-(pyridin-3-yl)benzamide (I-1416);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methanesulfonamide (I-1417);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanesulfonamide (I-1418);

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)oxane-4-sulfonamide (I-1419);

5-({4-hydroxy-1-[(3S)-4,4,4-trifluoro-3-phenylbutanoyl]piperidin-4-yl}methyl)-1-phenyl-1H,4H,5H-pyrazolo[3,4-d]pyrimidin-4-one (I-142);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzenesulfonamide (I-1420);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,5-dimethyl-1,2-oxazole-4-sulfonamide (I-1421);

4-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1422);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzene-1-sulfonamide (I-1423);

N-(4-{5-[(1-cyclopropanecarbonyl-4-hydroxypiperidin-4-yl)methyl]-4-oxo-1H,4H, 5H-pyrazolo[3,4-d]pyrimidin-1-yl}phenyl)-4-methylbenzene-1-sulfonamide (I-1424);
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methylbenzene-1-sulfonamide (I-1425);
2-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1426);
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzene-1-sulfonamide (I-1427);
3-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide (I-1428);
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-fluorobenzene-1-sulfonamide (I-1429);
5-({4-hydroxy-1-[(3R)-4,4,4-trifluoro-3-phenylbutanoyl]piperidin-4-yl}methyl)-1-methyl-1H,4H,5H-pyrazolo[3,4-d]pyrimidin-4-one (I-143);
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methylbenzene-1-sulfonamide (I-1430),
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)methanesulfonamide (I-1431);
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanesulfonamide (I-1432),
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(4-fluorophenyl)methanesulfonamide (I-1433);
5-{[1-(4-fluorobenzoyl)-4-hydroxypiperidin-4-yl]methyl}-1-{4-[(3S)-3-hydroxypyrrolidin-1-yl]phenyl)-1H,4H,5H-pyrazolo[3,4-d]pyrimidin-4-one (I-1434);
3-cyclopentyl-1-(3-{5-[(1-cyclopropanecarbonyl-4-hydroxypiperidin-4-yl)methy 1]-4-oxo-1H,4H,5H-pyrazolo[3,4-d]pyrimidin-1-yl}phenyl)urea (I-1435);
5-{[1-(2-amino-4-fluorobenzoyl)-4-hydroxypiperidin-4-yl]methyl}-1-[4-(trifluoromethyl)phenyl]-1H,4H,5H-pyrazolo[3,4-d]pyrimidin-4-one (I-1436);
5-{[1-(2-cyclopropyl-1,3-oxazole-5-carbonyl)-4-hydroxypiperidin-4-yl]methy 1}-1-[4-(trifluoromethyl)phenyl]-1H,4H,5H-pyrazolo[3,4-d]pyrimidin-4-one (I-1437);
3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-phenylurea (I-1438);
3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-phenylurea (I-1439);
5-({4-hydroxy-1-[(3R)-4,4,4-trifluoro-3-phenylbutanoyl]piperidin-4-yl}methyl)-1-(4-methylphenyl)-1H,4H,5H-pyrazolo[3,4-d]pyrimidin-4-one (I-144);
3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(4-fluorophenyl)urea (I-1440);
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(4-methylphenyl)urea (I-1442);
1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(3-methoxypropyl)urea (I-1443);
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(3-methoxypropyl)urea (I-1444);
1-[4-(4-fluoropiperidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one (I-1445);
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-cyclopropylurea (I-1446);
3-(3-{5-[(1-cyclopropanecarbonyl-4-hydroxypiperidin-4-yl)methy 1]-4-oxo-1H,4H, 5H-pyrazolo[3,4-d]pyrimidin-1-yl}phenyl)-1-(pyridin-3-yl)urea (I-1447);
3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(pyridin-3-yl)urea (I-1448);
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(thiophen-3-yl)urea (I-1449);
5-({4-hydroxy-1-[(3S)-4,4,4-trifluoro-3-phenylbutanoyl]piperidin-4-yl}methyl)-1-(4-methylphenyl)-1H,4H, 5H-pyrazolo[3,4-d]pyrimidin-4-one (I-145),
5-[(1-cyclopropanecarbonyl-4-hydroxypiperidin-4-yl)methyl]-1-[3-(4-hydroxypiperidine-1-carbonyl)phenyl]-1H,4H,5H-pyrazolo[3,4-d]pyrimidin-4-one (I-1450);
5-[(1-cyclopropanecarbonyl-4-hydroxypiperidin-4-yl)methyl]-1-[3-(3-hydroxyazetidine-1-carbonyl)phenyl]-1H,4H,5H-pyrazolo[3,4-d]pyrimidin-4-one (I-1451);
3-{5-[(1-cyclopropanecarbonyl-4-hydroxypiperidin-4-yl)methyl]-4-oxo-1H,4H,5H-pyrazolo[3,4-d]pyrimidin-1-yl}-N-methylbenzamide (I-1452);
N-benzyl-3-{5-[(1-cyclopropanecarbonyl-4-hydroxypiperidin-4-yl)methyl]-4-oxo-1H,4H,5H-pyrazolo[3,4-d]pyrimidin-1-yl}benzamide (I-1453);
N-cyclobutyl-3-{5-[(1-cyclopropanecarbonyl-4-hydroxypiperidin-4-yl)methyl]-4-oxo-1H,4H,5H-pyrazolo[3,4-d]pyrimidin-1-yl}benzamide (I-1454);
3-{5-[(1-cyclopropanecarbonyl-4-hydroxypiperidin-4-yl)methyl]-4-oxo-1H,4H,5H-pyrazolo[3,4-d]pyrimidin-1-yl}-N-[(4-fluorophenyl)methyl]benzamide (I-1455);
3-{5-[(1-cyclopropanecarbonyl-4-hydroxypiperidin-4-yl)methyl]-4-oxo-1H,4H,5H-pyrazolo[3,4-d]pyrimidin-1-yl}-N-[2-(dimethylamino)ethyl]benzamide (I-1456);
3-{5-[(1-cyclopropanecarbonyl-4-hydroxypiperidin-4-yl)methyl]-4-oxo-1H,4H,5H-pyrazolo[3,4-d]pyrimidin-1-yl}-N-[(3-methyloxetan-3-yl)methyl]benzamide (I-1457);
4-({1-[4-fluoro-3-(3-fluoroazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide (I-1458);
4-({1-[4-fluoro-3-(3-hydroxyazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide (I-1459);
1-(4-fluorophenyl)-5-{[4-hydroxy-1-(1-methyl-1H-indazole-6-carbonyl)piperidin-4-yl]methyl}-1H,4H,5H-pyrazolo[3,4-d]pyrimidin-4-one (I-1460);

4-({1-[4-(4,4-difluoropiperidin-1-yl)phenyl]-4-oxo-1H,4H,5H-pyrazolo[3,4-d]pyrimidin-5-yl}methyl)-4-hydroxy-N,N-dimethylpiperidine-1-carboxamide (I-1461), 4-hydroxy-N,N-dimethyl-4-{[4-oxo-1-(4-{[2-(propan-2-yl oxy)ethyl]amino}phenyl)-1H,4H,5H-pyrazolo[3,4-d]pyrimidin-5-yl]methyl)piperidine-1-carboxamide (I-1462);

3-{5-[(1-cyclopropanecarbonyl-4-hydroxypiperidin-4-yl)methyl]-4-oxo-1H,4H,5H-pyrazolo[3,4-d]pyrimidin-1-yl}-N-(4-fluorophenyl)benzamide (I-1463);

3-{5-[(1-cyclopropanecarbonyl-4-hydroxypiperidin-4-yl)methyl]-4-oxo-1H,4H,5H-pyrazolo[3,4-d]pyrimidin-1-yl}-N-(1,3-thiazol-2-yl)benzamide (I-1464);

3-{5-[(1-cyclopropanecarbonyl-4-hydroxypiperidin-4-yl)methyl]-4-oxo-1H,4H,5H-pyrazolo[3,4-d]pyrimidin-1-yl}-N-(5-methyl-1,2-oxazol-3-yl)benzamide (I-1465);

5-[(1-cyclopropanecarbonyl-4-hydroxypiperidin-4-yl)methyl]-1-[3-(pyrrolidine-1-carbonyl)phenyl]-1H,4H,5H-pyrazolo[3,4-d]pyrimidin-4-one (I-1466);

5-[(1-cyclopropanecarbonyl-4-hydroxypiperidin-4-yl)methyl]-1-[3-(morpholine-4-carbonyl)phenyl]-1H,4H,5H-pyrazolo[3,4-d]pyrimidin-4-one (I-1467);

5-[(1-cyclopropanecarbonyl-4-hydroxypiperidin-4-yl)methyl]-1-{3-[4-(dimethylamino) piperidine-1-carbonyl]phenyl}-1H,4H,5H-pyrazolo[3,4-d]pyrimidin-4-one (I-1468);

5-[(1-cyclopropanecarbonyl-4-hydroxypiperidin-4-yl)methyl]-1-[3-(4-methylpiperazine-1-carbonyl)phenyl]-1H,4H,5H-pyrazolo[3,4-d]pyrimidin-4-one (I-1469);

5-{[1-(4,4-difluoro-3-phenylbutanoyl)-4-hydroxypiperidin-4-yl]methyl}-1-methyl-1H,4H,5H-pyrazolo[3,4-d]pyrimidin-4-one (I-147);

5-[(1-cyclopropanecarbonyl-4-hydroxypiperidin-4-yl)methyl]-1-[3-(3-fluoroazetidine-1-carbonyl)phenyl]-1H,4H,5H-pyrazolo[3,4-d]pyrimidin-4-one (I-1470);

1-(4-fluorophenyl)-5-[(4-hydroxy-1-{imidazo[1,2-a]pyrazine-2-carbonyl}piperidin-4-yl)methyl]-1H,4H,5H-pyrazolo[3,4-d]pyrimidin-4-one (I-1471);

1-(4-fluorophenyl)-5-{[4-hydroxy-1-(1H-indole-5-carbonyl)piperidin-4-yl]methyl)-1H,4H,5H-pyrazolo[3,4-d]pyrimidin-4-one (I-1472);

1-(4-fluorophenyl)-5-{[4-hydroxy-1-(1H-indole-2-carbonyl)piperidin-4-yl]methyl)-1H,4H,5H-pyrazolo[3,4-d]pyrimidin-4-one (I-1473);

1-(4-fluorophenyl)-5-{[4-hydroxy-1-(4,4,4-trifluorobutanoyl)piperidin-4-yl]methyl)-1H,4H,5H-pyrazolo[3,4-d]pyrimidin-4-one (I-1474);

5-{[1-(2,3-dihydro-1-benzofuran-5-carbonyl)-4-hydroxypiperidin-4-yl]methyl}-1-(4-fluorophenyl)-1H,4H,5H-pyrazolo[3,4-d]pyrimidin-4-one (I-1475);

5-{[1-(1H-1,2,3-benzotriazole-5-carbonyl)-4-hydroxypiperidin-4-yl]methyl}-1-(4-fluorophenyl)-1H,4H,5H-pyrazolo[3,4-d]pyrimidin-4-one (I-1476);

1-(4-fluorophenyl)-5-{[4-hydroxy-1-(1H-indole-6-carbonyl)piperidin-4-yl]methyl)-1H,4H,5H-pyrazolo[3,4-d]pyrimidin-4-one (I-1477);

5-{[1-(1,3-benzothiazole-6-carbonyl)-4-hydroxypiperidin-4-yl]methyl}-1-(4-fluorophenyl)-1H,4H,5H-pyrazolo[3,4-d]pyrimidin-4-one (I-1478);

N-tert-butyl-4-{[1-(4-fluorophenyl)-4-oxo-1H,4H,5H-pyrazolo[3,4-d]pyrimidin-5-yl]methyl}-4-hydroxypiperidine-1-carboxamide (I-1479);

3-cyclopentyl-1-(4-{5-[(I-cyclopropanecarbonyl-4-hydroxypiperidin-4-yl)methyl]-4-oxo-1H,4H,5H-pyrazolo[3,4-d]pyrimidin-1-yl}phenyl)urea (I-1480);

1-cyclohexyl-3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea (I-1481);

1-cyclohexyl-3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea (I-1482);

1-benzyl-3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea (I-1483);

1-benzyl-3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea (I-1484);

4-{5-[(1-cyclopropanecarbonyl-4-hydroxypiperidin-4-yl)methyl]-4-oxo-1H,4H,5H-pyrazolo[3,4-d]pyrimidin-1-yl}-N-methylbenzamide (I-1485), 4-{5-[(1-cyclopropanecarbonyl-4-hydroxypiperidin-4-yl)methyl]-4-oxo-1H,4H,5H-pyrazolo[3,4-d]pyrimidin-1-yl}-N-[(4-fluorophenyl)methyl]benzamide (I-1486);

4-{5-[(1-cyclopropanecarbonyl-4-hydroxypiperidin-4-yl)methyl]-4-oxo-1H,4H,5H-pyrazolo[3,4-d]pyrimidin-1-yl}-N-[2-(dimethylamino)ethyl]benzamide (I-1487);

4-{5-[(i-cyclopropanecarbonyl-4-hydroxypiperidin-4-yl)methyl]-4-oxo-1H,4H,5H-pyrazolo[3,4-d]pyrimidin-1-yl}-N-[(3-methyloxetan-3-yl)methyl]benzamide (I-1488);

4-{5-[(1-cyclopropanecarbonyl-4-hydroxypiperidin-4-yl)methyl]-4-oxo-1H,4H,5H-pyrazolo[3,4-d]pyrimidin-1-yl}-N-(oxetan-3-yl)benzamide (I-1489);

4-{5-[(1-cyclopropanecarbonyl-4-hydroxypiperidin-4-yl)methyl]-4-oxo-1H,4H,5H-pyrazolo[3,4-d]pyrimidin-1-yl}-N-phenylbenzamide (I-1490), 4-{5-[(1-cyclopropanecarbonyl-4-hydroxypiperidin-4-yl)methyl]-4-oxo-1H,4H,5H-pyrazolo[3,4-d]pyrimidin-1-yl}-N-(pyridin-3-yl)benzamide (I-1491);

4-{5-[(1-cyclopropanecarbonyl-4-hydroxypiperidin-4-yl)methyl]-4-oxo-1H,4H,5H-pyrazolo[3,4-d]pyrimidin-1-yl}-N-(4-fluorophenyl)benzamide (I-1492);

4-{5-[(1-cyclopropanecarbonyl-4-hydroxypiperidin-4-yl)methyl]-4-oxo-1H,4H,5H-pyrazolo[3,4-d]pyrimidin-1-yl}-N-(1,3-thiazol-2-yl)benzamide (I-1493);

4-{5-[(1-cyclopropanecarbonyl-4-hydroxypiperidin-4-yl)methyl]-4-oxo-1H,4H,5H-pyrazolo[3,4-d]pyrimidin-1-yl}-N-(5-methyl-1,2-oxazol-3-yl)benzamide (I-1494);

5-[(1-cyclopropanecarbonyl-4-hydroxypiperidin-4-yl)methyl]-1-[4-(morpholine-4-carbonyl)phenyl]-1H,4H,5H-pyrazolo[3,4-d]pyrimidin-4-one (I-1495);

5-[(1-cyclopropanecarbonyl-4-hydroxypiperidin-4-yl)methyl]-1-{4-[4-(dimethylamino) piperidine-1-carbonyl]phenyl}-1H,4H,5H-pyrazolo[3,4-d]pyrimidin-4-one (I-1496);

5-[(1-cyclopropanecarbonyl-4-hydroxypiperidin-4-yl)methyl]-1-[4-(4-methylpiperazine-1-carbonyl)phenyl]-1H,4H,5H-pyrazolo[3,4-d]pyrimidin-4-one (I-1497);

5-[(1-cyclopropanecarbonyl-4-hydroxypiperidin-4-yl)methyl]-1-[4-(3,3-difluoropyrrolidine-1-carbonyl)phenyl]-1H,4H,5H-pyrazolo[3,4-d]pyrimidin-4-one (I-1498);

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyrrolidine-1-carboxamide (I-1499);

5-{[1-(1-benzyl-1H-pyrrole-2-carbonyl)-4-hydroxypiperidin-4-yl]methyl}-1-phenyl-1H,4H,5H-pyrazolo[3,4-d]pyrimidin-4-one (I-150);

3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(oxan-4-yl)urea (I-1500);

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,3-dimethylurea (I-1501);

propan-2-yl N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)carbamate (I-1502);

4-[(1-{4-[(8aS)-octahydropyrrolo[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide (I-1503);

4-hydroxy-4-({1-[4-(4-hydroxy-4-methylpiperidin-1-yl)phenyl]-4-oxo-1H,4H,5H-pyrazolo[3,4-d]pyrimidin-5-yl}methyl)-N,N-dimethylpiperidine-1-carboxamide (I-1504);

5-{[1-(2,3-dihydro-1,4-benzodioxine-6-carbonyl)-4-hydroxypiperidin-4-yl]methyl}-1-(4-fluorophenyl)-1H,4H,5H-pyrazolo[3,4-d]pyrimidin-4-one (I-1505);

1-(4-fluorophenyl)-5-{[4-hydroxy-1-(5-methoxy-1-methyl-1H-pyrazole-3-carbonyl)piperidin-4-yl]methyl}-1H,4H,5H-pyrazolo[3,4-d]pyrimidin-4-one (I-1506);

5-{[1-(3,4-dihydro-2H-1-benzopyran-6-carbonyl)-4-hydroxypiperidin-4-yl]methyl}-1-(4-fluorophenyl)-1H,4H,5H-pyrazolo[3,4-d]pyrimidin-4-one (I-1507);

5-{[1-(2-cyclopropyl-1,3-oxazole-5-carbonyl)-4-hydroxypiperidin-4-yl]methyl}-1-{4-[(1-methylcyclobutyl)methoxy]phenyl}-1H,4H,5H-pyrazolo[3,4-d]pyrimidin-4-one (I-1508);

4-hydroxy-4-[(1-{4-[(3S)-3-methoxypyrrolidin-1-yl]phenyl}-4-oxo-1H,4H,5H-pyrazolo[3,4-d]pyrimidin-5-yl)methyl]-N,N-dimethylpiperidine-1-carboxamide (I-1509);

5-{[1-(4-fluoro-3-phenylbutanoyl)-4-hydroxypiperidin-4-yl]methyl}-1-methyl-1H,4H,5H-pyrazolo[3,4-d]pyrimidin-4-one (I-151);

5-({4-hydroxy-1-[4-(pyridin-2-yloxy)benzoyl]piperidin-4-yl}methyl)-1-(4-methylphenyl)-1H,4H,5H-pyrazolo[3,4-d]pyrimidin-4-one (I-1510);

5-{[4-hydroxy-1-(4,4,4-trifluorobutanoyl)piperidin-4-yl]methyl}-1-(4-methylphenyl)-1H,4H,5H-pyrazolo[3,4-d]pyrimidin-4-one (I-1511);

5-{[1-(2,3-dihydro-1-benzofuran-5-carbonyl)-4-hydroxypiperidin-4-yl]methyl}-1-(4-methylphenyl)-1H,4H,5H-pyrazolo[3,4-d]pyrimidin-4-one (I-1512);

5-{[4-hydroxy-1-(1,2,3-thiadiazole-4-carbonyl)piperidin-4-yl]methyl}-1-(4-methylphenyl)-1H,4H,5H-pyrazolo[3,4-d]pyrimidin-4-one (I-1513);

5-{[4-hydroxy-1-(2-methyl-1,3-oxazole-5-carbonyl)piperidin-4-yl]methyl}-1-(4-methylphenyl)-1H,4H,5H-pyrazolo[3,4-d]pyrimidin-4-one (I-1514);

5-[(4-hydroxy-1-{5H,6H,7H-pyrazolo[3,2-b][1,3]oxazine-2-carbonyl}piperidin-4-yl)methyl]-1-(4-methylphenyl)-1H,4H,5H-pyrazolo[3,4-d]pyrimidin-4-one (I-1516);

5-[(4-hydroxy-1-{2H,3H-pyrazolo[3,2-b][1,3]oxazole-6-carbonyl}piperidin-4-yl)methyl]-1-(4-methylphenyl)-1H,4H,5H-pyrazolo[3,4-d]pyrimidin-4-one (I-1517);

5-{[4-hydroxy-1-(5-methyl-1,2,3-thiadiazole-4-carbonyl)piperidin-4-yl]methyl}-1-(4-methylphenyl)-1H,4H,5H-pyrazolo[3,4-d]pyrimidin-4-one (I-1518);

1-(4-chlorophenyl)-5-({4-hydroxy-1-[4-(pyridin-2-yloxy)benzoyl]piperidin-4-yl}methyl)-1H,4H,5H-pyrazolo[3,4-d]pyrimidin-4-one (I-1519);

1-cyclopropyl-5-{[4-hydroxy-1-(4-phenoxybenzoyl)piperidin-4-yl]methyl}-1H,4H,5H-pyrazolo[3,4-d]pyrimidin-4-one (I-152);

1-(4-chlorophenyl)-5-{[4-hydroxy-1-(4,4,4-trifluorobutanoyl)piperidin-4-yl]methyl)-1H,4H,5H-pyrazolo[3,4-d]pyrimidin-4-one (I-1520);

1-(4-chlorophenyl)-5-{[1-(2,3-dihydro-1-benzofuran-5-carbonyl)-4-hydroxypiperidin-4-yl]methyl}-1H,4H,5H-pyrazolo[3,4-d]pyrimidin-4-one (I-1521);

1-(4-chlorophenyl)-5-{[4-hydroxy-1-(1,2,3-thiadiazole-4-carbonyl)piperidin-4-yl]methyl}-1H,4H,5H-pyrazolo[3,4-d]pyrimidin-4-one (I-1522);

1-(4-chlorophenyl)-5-{[1-(3-fluoro-4-methylbenzoyl)-4-hydroxypiperidin-4-yl]methyl}-1H,4H,5H-pyrazolo[3,4-d]pyrimidin-4-one (I-1523);

1-(4-chlorophenyl)-5-{[4-hydroxy-1-(2-methyl-1,3-oxazole-5-carbonyl)piperidin-4-yl]methyl}-1H,4H,5H-pyrazolo[3,4-d]pyrimidin-4-one (I-1524);

4-[(1-{4-[(9aS)-octahydro-1H-pyrido[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide (I-1525);

4-hydroxy-N,N-dimethyl-4-[(4-oxo-1-{4-[4-(trifluoromethyl)-1H-pyrazol-1-yl]phenyl}-1H,4H,5H-pyrazolo[3,4-d]pyrimidin-5-yl)methyl]piperidine-1-carboxamide (I-1526);

1-(4-chlorophenyl)-5-[(4-hydroxy-1-{2H,3H-pyrazolo[3,2-b][1,3]oxazole-6-carbonyl}piperidin-4-yl)methyl]-1H,4H,5H-pyrazolo[3,4-d]pyrimidin-4-one (I-1527), 1-(4-chlorophenyl)-5-({4-hydroxy-1-[4-(pyrimidin-2-yloxy)benzoyl]piperidin-4-yl}methyl)-1H,4H,5H-pyrazolo[3,4-d]pyrimidin-4-one (I-1528);

1-(4-chlorophenyl)-5-{[4-hydroxy-1-(5-methyl-1,2,3-thiadiazole-4-carbonyl)piperidin-4-yl]methyl}-1H,4H,5H-pyrazolo[3,4-d]pyrimidin-4-one (I-1529);

5-[(1-benzoyl-4-hydroxypiperidin-4-yl)methyl]-1-phenyl-1H,4H,5H-pyrazolo[3,4-d]pyrimidin-4-one (I-153);

1-(4-fluorophenyl)-5-{[4-hydroxy-1-(1,2,3-thiadiazole-4-carbonyl)piperidin-4-yl]methyl}-1H,4H,5H-pyrazolo[3,4-d]pyrimidin-4-one (I-1530), 5-{[1-(3-fluoro-4-methylbenzoyl)-4-hydroxypiperidin-4-yl]methyl}-1-(4-fluorophenyl)-1H,4H,5H-pyrazolo[3,4-d]pyrimidin-4-one (I-1531);

1-(4-fluorophenyl)-5-{[4-hydroxy-1-(4,4,4-trifluoro-3-methylbutanoyl)piperidin-4-yl]methyl}-1H,4H,5H-pyrazolo[3,4-d]pyrimidin-4-one (I-1532);

5-{[1-(4,4-difluorobutanoyl)-4-hydroxypiperidin-4-yl]methyl}-1-(4-fluorophenyl)-1H,4H,5H-pyrazolo[3,4-d]pyrimidin-4-one (I-1533);

2-[4-(4-{[1-(4-fluorophenyl)-4-oxo-1H,4H,5H-pyrazolo[3,4-d]pyrimidin-5-yl]methyl}-4-hydroxypiperidine-1-carbonyl)phenyl]-1,6,2-thiazolidine-1,1-dione (I-1534);

1-(4-fluorophenyl)-5-({4-hydroxy-1-[4-(1H-1,2,3-triazol-1-yl)benzoyl]piperidin-4-yl}methyl)-1H,4H,5H-pyrazolo[3,4-d]pyrimidin-4-one (I-1535);

1-(4-fluorophenyl)-5-({4-hydroxy-1-[4-(4-hydroxypiperidin-1-yl)benzoyl]piperidin-4-yl}methyl)-1H,4H,5H-pyrazolo[3,4-d]pyrimidin-4-one (I-1536);

5-({1-[2-(difluoromethoxy)acetyl]-4-hydroxypiperidin-4-yl}methyl)-1-(4-fluorophenyl)-1H,4H,5H-pyrazolo[3,4-d]pyrimidin-4-one (I-1537);

4-hydroxy-N,N-dimethyl-4-({4-oxo-1-[4-(1H-pyrazol-1-yl)phenyl]-1H,4H,5H-pyrazolo[3,4-d]pyrimidin-5-yl}methyl)piperidine-1-carboxamide (I-1538);

4-hydroxy-N,N-dimethyl-4-({1-[4-(4-methyl-1H-pyrazol-1-yl)phenyl]-4-oxo-1H,4H,5H-pyrazolo[3,4-d]pyrimidin-5-yl}methyl)piperidine-1-carboxamide (I-1539);

5-[(1-acetyl-4-hydroxypiperidin-4-yl)methyl]-1-phenyl-1H,4H,5H-pyrazolo[3,4-d]pyrimidin-4-one (I-154);

5-[(1-cyclopropanecarbonyl-4-hydroxypiperidin-4-yl)methyl]-1-[3-(4-methyl-1H-pyrazol-1-yl)phenyl]-1H,4H,5H-pyrazolo[3,4-d]pyrimidin-4-one (I-1540);

4-[(1-{4-[(9aR)-octahydro-1H-pyrido[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide (I-1541);

5-{[1-(2-cyclopropyl-1,3-oxazole-5-carbonyl)-4-hydroxypiperidin-4-yl]methyl}-1-(4-methylphenyl)-1H,4H,5H-pyrazolo[3,4-d]pyrimidin-4-one (I-1542);

4-hydroxy-N,N-dimethyl-4-{[4-oxo-1-(4-{[2-(piperidin-1-yl)ethyl]amino}phenyl)-1H,4H,5H-pyrazolo[3,4-d]pyrimidin-5-yl]methyl}piperidine-1-carboxamide (I-1543), 4-[(1-{4-[(3,3-dimethylcyclobutyl)amino]phenyl}-4-oxo-1H,4H,5H-pyrazolo[3,4-d]pyrimidin-5-yl)methyl]-4-hydroxy-N,N-dimethylpiperidine-1-carboxamide (I-1544);

1-(4-fluorophenyl)-5-{[4-hydroxy-1-(4,4,4-trifluoro-3-hydroxy-3-methylbutanoyl)piperidin-4-yl]methyl}-1H,4H,5H-pyrazolo[3,4-d]pyrimidin-4-one (I-1545);

4-[(1-{4-[(8aR)-octahydropyrrolo[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide (I-1546

5-{[4-hydroxy-1-(pyridine-4-carbonyl)piperidin-4-yl]methyl}-1-(4-phenylphenyl)-1H,4H,5H-pyrazolo[3,4-d]pyrimidin-4-one (I-1547);

4-hydroxy-N,N-dimethyl-4-[(4-oxo-1-{4-[4-(1H-pyrazol-1-yl)piperidin-1-yl]phenyl}-1H,4H,5H-pyrazolo[3,4-d]pyrimidin-5-yl)methyl]piperidine-1-carboxamide (I-1548

5-[(1-acetyl-4-hydroxypiperidin-4-yl)methyl]-1-[4-(trifluoromethyl)phenyl]-1H,4H,5H-pyrazolo[3,4-d]pyrimidin-4-one (I-1549);

5-{[4-hydroxy-1-(1-methyl-1H-imidazole-4-carbonyl)piperidin-4-yl]methyl}-1-phenyl-1H,4H,5H-pyrazolo[3,4-d]pyrimidin-4-one (I-155);

5-[(1-benzoyl-4-hydroxypiperidin-4-yl)methyl]-1-[4-(trifluoromethyl)phenyl]-1H,4H,5H-pyrazolo[3,4-d]pyrimidin-4-one (I-1550);

5-{[4-hydroxy-1-(4-methoxybenzoyl)piperidin-4-yl]methyl}-1-[4-(trifluoromethyl)phenyl]-1H,4H,5H-pyrazolo[3,4-d]pyrimidin-4-one (I-1551);

5-{[1-(4-fluorobenzoyl)-4-hydroxypiperidin-4-yl]methyl}-1-[4-(trifluoromethyl)phenyl]-1H,4H,5H-pyrazolo[3,4-d]pyrimidin-4-one (I-1552);

5-{[4-hydroxy-1-(pyridine-4-carbonyl)piperidin-4-yl]methyl}-1-[4-(trifluoromethyl)phenyl]-1H,4H,5H-pyrazolo[3,4-d]pyrimidin-4-one (I-1553);

5-({4-hydroxy-1-[2-(oxan-4-yl)acetyl]piperidin-4-yl}methyl)-1-[4-(trifluoromethyl)phenyl]-1H,4H,5H-pyrazolo[3,4-d]pyrimidin-4-one (I-1554);

5-({4-hydroxy-1-[4-(pyridin-2-yloxy)benzoyl]piperidin-4-yl}methyl)-1-[4-(trifluoromethyl)phenyl]-1H,4H,5H-pyrazolo[3,4-d]pyrimidin-4-one (I-1555);

5-{[1-(3-ethoxypropanoyl)-4-hydroxypiperidin-4-yl]methyl}-1-[4-(trifluoromethyl)phenyl]-1H,4H,5H-pyrazolo[3,4-d]pyrimidin-4-one (I-1556);

5-[(1-cyclobutanecarbonyl-4-hydroxypiperidin-4-yl)methyl]-1-[4-(trifluoromethyl)phenyl]-1H,4H,5H-pyrazolo[3,4-d]pyrimidin-4-one (I-1557);

5-{[1-(2,3-dihydro-1-benzofuran-5-carbonyl)-4-hydroxypiperidin-4-yl]methyl}-1-[4-(trifluoromethyl)phenyl]-1H,4H,5H-pyrazolo[3,4-d]pyrimidin-4-one (I-1558), 5-{[4-hydroxy-1-(pyridine-3-carbonyl)piperidin-4-yl]methyl}-1-[4-(trifluoromethyl)phenyl]-1H,4H,5H-pyrazolo[3,4-d]pyrimidin-4-one (I-1559);

5-{[1-(4-cyclopropylbenzoyl)-4-hydroxypiperidin-4-yl]methyl}-1-phenyl-1H,4H,5H-pyrazolo[3,4-d]pyrimidin-4-one (I-156);

5-{[1-(1,5-dimethyl-1H-pyrazole-3-carbonyl)-4-hydroxypiperidin-4-yl]methyl}-1-[4-(trifluoromethyl)phenyl]-1H,4H,5H-pyrazolo[3,4-d]pyrimidin-4-one (I-1560);

1-[3-(4-fluoropiperidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one (I-1561), 5-{[1-(2-aminobenzoyl)-4-hydroxypiperidin-4-yl]methy1}-1-[4-(trifluoromethyl)phenyl]-1H,4H,5H-pyrazolo[3,4-d]pyrimidin-4-one (I-1562);

5-{[4-hydroxy-1-(5-methyl-1,2-oxazole-3-carbonyl)piperidin-4-yl]methyl}-1-[4-(trifluoromethyl)phenyl]-1H,4H,5H-pyrazolo[3,4-d]pyrimidin-4-one (I-1563);

5-{[4-hydroxy-1-(1H-indole-6-carbonyl)piperidin-4-yl]methyl}-1-[4-(trifluoromethyl)phenyl]-1H,4H,5H-pyrazolo[3,4-d]pyrimidin-4-one (I-1564);

5-{[4-hydroxy-1-(1-methylpiperidine-4-carbonyl)piperidin-4-yl]methyl}-1-[4-(trifluoromethyl)phenyl]-1H,4H,5H-pyrazolo[3,4-d]pyrimidin-4-one (I-1565), 5-{[4-hydroxy-1-(oxane-4-carbonyl)piperidin-4-yl]methyl}-1-[4-(trifluoromethyl)phenyl]-1H,4H,5H-pyrazolo[3,4-d]pyrimidin-4-one (I-1566);

5-{[1-(4,4-difluorocyclohexanecarbonyl)-4-hydroxypiperidin-4-yl]methy 1}-1-[4-(trifluoromethyl)phenyl]-1H,4H,5H-pyrazolo[3,4-d]pyrimidin-4-one (I-1567);

5-{[1-(3,3-difluorocyclobutanecarbonyl)-4-hydroxypiperidin-4-yl]methyl}-1-[4-(trifluoromethyl)phenyl]-1H,4H,5H-pyrazolo[3,4-d]pyrimidin-4-one (I-1568);

1-(4-chlorophenyl)-5-[(4-hydroxy-1-{5H,6H,7H-pyrazolo[3,2-b][1,3]oxazine-2-carbonyl}piperidin-4-yl)methyl]-1H,4H,5H-pyrazolo[3,4-d]pyrimidin-4-one (I-1569);

5-{[4-hydroxy-1-(4-methoxybenzoyl)piperidin-4-yl]methyl}-1-phenyl-1H,4H,5H-pyrazolo[3,4-d]pyrimidin-4-one (I-157);

5-{[4-hydroxy-1-(1-methylcyclopropanecarbonyl)piperidin-4-yl]methyl}-1-{4-[3-(oxan-4-yl)azetidin-1-yl]phenyl)-1H,4H,5H-pyrazolo[3,4-d]pyrimidin-4-one (I-1570);

5-[(4-hydroxy-1-{5H,6H,7H-pyrazolo[3,2-b][1,3]oxazine-2-carbonyl}piperidin-4-yl)methyl]-1-[4-(trifluoromethyl)phenyl]-1H,4H,5H-pyrazolo[3,4-d]pyridin-4-one (I-1572);

5-[(4-hydroxy-1-{imidazo[1,5-a]pyridine-6-carbonyl}piperidin-4-yl)methyl]-1-[4-(trifluoromethyl)phenyl]-1H,4H,5H-pyrazolo[3,4-d]pyrimidin-4-one (I-1573);

5-[(4-hydroxy-1-{2H,3H-pyrazolo[3,2-b][1,3]oxazole-6-carbonyl}piperidin-4-yl)methyl]-1-[4-(trifluoromethyl)phenyl]-1H,4H,5H-pyrazolo[3,4-d]pyrimidin-4-one (I-1574);

5-({4-hydroxy-1-[4-(pyrimidin-2-yloxy)benzoyl]piperidin-4-yl}methyl)-1-[4-(trifluoromethyl)phenyl]-1H,4H,5H-pyrazolo[3,4-d]pyrimidin-4-one (I-1575), 1-[4-(5-{[1-(4-fluorobenzoyl)-4-hydroxypiperidin-4-yl]methyl)-4-oxo-1H,4H,5H-pyrazolo[3,4-d]pyrimidin-1-yl)phenyl]-3,3-dimethylurea (I-1576

5-[(1-cyclopropanecarbonyl-4-hydroxypiperidin-4-yl)methyl]-1-{3-[);4-(trifluoromethyl)-1H-pyrazol-1-yl]phenyl)-1H,4H,5H-pyrazolo[3,4-d]pyrimidin-4-one (I-1577);

5-[(1-cyclopropanecarbonyl-4-hydroxypiperidin-4-yl)methyl]-1-{4-[4-(trifluoromethyl)-1H-pyrazol-1-yl]phenyl)-1H,4H,5H-pyrazolo[3,4-d]pyrimidin-4-one (I-1578), 5-[(1-cyclopropanecarbonyl-4-hydroxypiperidin-4-yl)methyl]-1-(4-{[5-(trifluoromethyl)pyridin-2-yl]oxy}phenyl)-1H,4H,5H-pyrazolo[3,4-d]pyrimidin-4-one (I-1579);

5-[(1-cyclopropanecarbonyl-4-hydroxypiperidin-4-yl)methyl]-1-phenyl-1H,4H,5H-pyrazolo[3,4-d]pyrimidin-4-one (I-158);

5-[(1-cyclopropanecarbonyl-4-hydroxypiperidin-4-yl)methyl]-1-(4-{[4-(trifluoromethyl) pyrimidin-2-yl]oxy}phenyl)-1H,4H,5H-pyrazolo[3,4-d]pyrimidin-4-one (I-1580);

5-[(1-cyclopropanecarbonyl-4-hydroxypiperidin-4-yl)methyl]-1-{4-[4-(1H-pyrazol-1-yl)piperidin-1-yl]phenyl)-1H,4H,5H-pyrazolo[3,4-d]pyrimidin-4-one (I-1581);

5-[(1-cyclopropanecarbonyl-4-hydroxypiperidin-4-yl)methyl]-1-{4-[4-(1H-1,2,3-triazol-1-yl)piperidin-1-yl]phenyl)-1H,4H,5H-pyrazolo[3,4-d]pyrimidin-4-one (I-1582), 4-hydroxy-N,N-dimethyl-4-[(4-oxo-1-{4-[4-(1H-1,2,3-triazol-1-yl)piperidin-1-yl]phenyl}-1H,4H,5H-pyrazolo[3,4-d]pyrimidin-5-yl)methyl]piperidine-1-carboxamide (I-1583);

1-{4-[(9aR)-octahydro-1H-pyrido[1,2-a]piperazin-2-yl]phenyl)-5-[(1-cyclopropanecarbonyl-4-hydroxypiperidin-4-yl)methyl]-1H,4H,5H-pyrazolo[3,4-d]pyrimidin-4-one (I-1584);

1-(4-fluorophenyl)-5-({4-hydroxy-1-[4-(1H-1,2,3-triazol-1-yl)piperidine-1-carbonyl]piperidin-4-yl)methyl)-1H,4H,5H-pyrazolo[3,4-d]pyrimidin-4-one (I-1585);

1-[3-(4-chloro-1H-pyrazol-1-yl)phenyl]-5-[(1-cyclopropanecarbonyl-4-hydroxypiperidin-4-yl)methyl]-1H,4H,5H-pyrazolo[3,4-d]pyrimidin-4-one (I-1587);

1-[4-(4-chloro-1H-pyrazol-1-yl)phenyl]-5-[(1-cyclopropanecarbonyl-4-hydroxypiperidin-4-yl)methyl]-1H,4H,5H-pyrazolo[3,4-d]pyrimidin-4-one (I-1588), 5-[(1-cyclopropanecarbonyl-4-hydroxypiperidin-4-yl)methyl]-1-[4-(oxetan-3-yloxy)phenyl]-1H,4H,5H-pyrazolo[3,4-d]pyrimidin-4-one (I-1589);

5-{[4-hydroxy-1-(3-hydroxybenzoyl)piperidin-4-yl]methyl}-1-phenyl-1H,4H,5H-pyrazolo[3,4-d]pyrimidin-4-one (I-159);

5-[(1-cyclopropanecarbonyl-4-hydroxypiperidin-4-yl)methyl]-1-[4-(oxan-4-ylmethoxy)phenyl]-1H,4H,5H-pyrazolo[3,4-d]pyrimidin-4-one (I-1590);

5-[(1-acetyl-4-hydroxypiperidin-4-yl)methyl]-1-(4-phenyl phenyl)-1H,4H,5H-pyrazolo[3,4-d]pyrimidin-4-one (I-1591);

1-(4-chlorophenyl)-5-{[4-hydroxy-1-(1H-indole-6-carbonyl)piperidin-4-yl]methyl)-1H,4H,5H-pyrazolo[3,4-d]pyrimidin-4-one (I-1593);

1-(4-chlorophenyl)-5-({4-hydroxy-1-[3-(1H-1,2,3,4-tetrazol-1-yl)propanoyl]piperidin-4-yl}methyl)-1H,4H,5H-pyrazolo[3,4-d]pyrimidin-4-one (I-1594);

1-(4-chlorophenyl)-5-([4-hydroxy-1-(oxane-4-carbonyl)piperidin-4-yl]methyl)-1H,4H, 5H-pyrazolo[3,4-d]pyrimidin-4-one (I-1595);

1-(4-chlorophenyl)-5-[(4-hydroxy-1-{pyrazolo[1,5-a]pyridine-2-carbonyl}piperidin-4-yl)methyl]-1H,4H, 5H-pyrazolo[3,4-d]pyrimidin-4-one (I-1596);

1-(4-chlorophenyl)-5-{[1-(4,4-difluorocyclohexanecarbonyl)-4-hydroxypiperidin-4-yl]methyl}-1H,4H,5H-pyrazolo[3,4-d]pyrimidin-4-one (I-1597);

1-(4-chlorophenyl)-5-{[4-hydroxy-1-(3-methyloxetane-3-carbonyl)piperidin-4-yl]methyl}-1H,4H,5H-pyrazolo[3,4-d]pyrimidin-4-one (I-1598), 1-(4-chlorophenyl)-5-{[1-(3,3-difluorocyclobutanecarbonyl)-4-hydroxypiperidin-4-yl]methyl}-1H,4H,5H-pyrazolo[3,4-d]pyrimidin-4-one (I-1599);

5-[4-hydroxy-4-({4-oxo-1-phenyl-1H,4H,5H-pyrazolo[3,4-d]pyrimidin-5-yl}methyl)piperidine-1-carbonyl]-1,2-dihydropyridin-2-one (I-160);

1-(4-chlorophenyl)-5-{[4-hydroxy-1-(3-hydroxy-3-methylbutanoyl)piperidin-4-yl]methyl}-1H,4H,5H-pyrazolo[3,4-d]pyrindin-4-one (I-1600);

1-(4-chlorophenyl)-5-{[4-hydroxy-1-(4-methyl-1,3-oxazole-5-carbonyl)piperidin-4-yl]methyl}-1H,4H,5H-pyrazolo[3,4-d]pyrimidin-4-one (I-1601);

5-{[1-(3-ethoxypropanoyl)-4-hydroxypiperidin-4-yl]methyl}-1-(4-phenylphenyl)-1H,4H,5H-pyrazolo[3,4-d]pyrimidin-4-one (I-1602);

5-[(1-cyclobutanecarbonyl-4-hydroxypiperidin-4-yl)methyl]-1-(4-phenylphenyl)-1H,4H,5H-pyrazolo[3,4-d]pyrimidin-4-one (I-1603);

5-{[1-(2,3-dihydro-1-benzofuran-5-carbonyl)-4-hydroxypiperidin-4-yl]methyl}-1-(4-phenylphenyl)-1H,4H,5H-pyrazolo[3,4-d]pyrimidin-4-one (I-1604);

5-{[4-hydroxy-1-(pyridine-3-carbonyl)piperidin-4-yl]methyl}-1-(4-phenylphenyl)-1H,4H,5H-pyrazolo[3,4-d]pyrimidin-4-one (I-1605);

5-{[1-(1,5-dimethyl-1H-pyrazole-3-carbonyl)-4-hydroxypiperidin-4-yl]methyl}-1-(4-phenylphenyl)-1H,4H,5H-pyrazolo[3,4-d]pyrimidin-4-one (I-1606);

5-{[1-(dimethyl-1,3-thiazole-5-carbonyl)-4-hydroxypiperidin-4-yl]methyl}-1-(4-phenylphenyl)-1H,4H,5H-pyrazolo[3,4-d]pyrimidin-4-one (I-1607);

5-{[1-(2-aminobenzoyl)-4-hydroxypiperidin-4-yl]methyl}-1-(4-phenylphenyl)-1H,4H,5H-pyrazolo[3,4-d]pyrimidin-4-one (I-1608);

5-{[4-hydroxy-1-(1H-indole-6-carbonyl)piperidin-4-yl]methyl}-1-(4-phenylphenyl)-1H,4H,5H-pyrazolo[3,4-d]pyrimidin-4-one (I-1609);

5-{[4-hydroxy-1-(1H-indazole-3-carbonyl)piperidin-4-yl]methyl}-1-phenyl-1H,4H,5H-pyrazolo[3,4-d]pyrimidin-4-one (I-161);

5-{[4-hydroxy-1-(oxane-4-carbonyl)piperidin-4-yl]methyl}-1-(4-phenylphenyl)-1H,4H,5H-pyrazolo[3,4-d]pyrimidin-4-one (I-1610);

5-{[1-(3,3-difluorocyclobutanecarbonyl)-4-hydroxypiperidin-4-yl]methyl}-1-(4-phenylphenyl)-1H,4H,5H-pyrazolo[3,4-d]pyrimidin-4-one (I-1611);

5-{[1-(2-amino-4-fluorobenzoyl)-4-hydroxypiperidin-4-yl]methyl}-1-(4-phenylphenyl)-1H,4H,5H-pyrazolo[3,4-d]pyrimidin-4-one (I-1612);

5-{[4-hydroxy-1-(2-methyl-1,3-oxazole-5-carbonyl)piperidin-4-yl]methyl}-1-(4-phenylphenyl)-1H,4H,5H-pyrazolo[3,4-d]pyrimidin-4-one (I-1613);

5-{[1-(4-fluorobenzoyl)-4-hydroxypiperidin-4-yl]methyl}-1-{4-[1-(oxan-4-yl)-1H-pyrazol-4-yl]phenyl)-1H,4H,5H-pyrazolo[3,4-d]pyrimidin-4-one (I-1614);

5-{[1-(4-fluorobenzoyl)-4-hydroxypiperidin-4-yl] methyl}-1-{4-[1-(oxetan-3-yl)-1H-pyrazol-4-yl]phenyl}-1H,4H,5H-pyrazolo[3,4-d]pyrimidin-4-one (I-1615);

5-{[1-(4-fluorobenzoyl)-4-hydroxypiperidin-4-yl] methyl}-1-{4-[1-(1-hydroxy-2-methylpropan-2-yl]-1H-pyrazol-4-yl]phenyl}-1H,4H,5H-pyrazolo[3,4-d] pyrimidin-4-one (I-1616);

5-{[1-(4-fluorobenzoyl)-4-hydroxypiperidin-4-yl] methyl}-1-{4-[1-(2-hydroxy-2-methylpropyl)-1H-pyrazol-4-yl]phenyl}-1H,4H,5H-pyrazolo[3,4-d]pyrimidin-4-one (I-1617), 1-(4-{7-azaspiro[3.5]nonan-7-yl}phenyl)-5-[(1-cyclopropanecarbonyl-4-hydroxypiperidin-4-yl)methyl]-1H,4H,5H-pyrazolo[3,4-d]pyrimidin-4-one (I-1618);

1-(4-{3-azaspiro[5.5]undecan-3-yl}phenyl)-5-{[1-(4-fluorobenzoyl)-4-hydroxypiperidin-4-yl]methyl}-1H,4H,5H-pyrazolo[3,4-d]pyrimidin-4-one (I-1619);

5-{[1-(3-aminobenzoyl)-4-hydroxypiperidin-4-yl] methyl}-1-phenyl-1H,4H,5H-pyrazolo[3,4-d]pyrimidin-4-one (I-162);

1-(4-{3-azaspiro[5.5]undecan-3-yl}phenyl)-5-[(1-cyclopropanecarbonyl-4-hydroxypiperidin-4-yl)methyl]-1H,4H,5H-pyrazolo[3,4-d]pyrimidin-4-one (I-1620);

5-{[1-(4-fluorobenzoyl)-4-hydroxypiperidin-4-yl] methyl}-1-(4-{9-methyl-3,9-diazaspiro[5.5]undecan-3-yl}phenyl)-1H,4H,5H-pyrazolo[3,4-d]pyrimidin-4-one (I-1621);

5-[(1-cyclopropanecarbonyl-4-hydroxypiperidin-4-yl) methyl]-1-(4-{9-methyl-3,9-diazaspiro[5.5]undecan-3-yl}phenyl)-1H,4H,5H-pyrazolo[3,4-d]pyrimidin-4-one (I-1622);

5-{[1-(4-fluorobenzoyl)-4-hydroxypiperidin-4-yl] methyl}-1-[4-(4-methyl-1H-pyrazol-1-yl)phenyl]-1H,4H,5H-pyrazolo[3,4-d]pyrimidin-4-one (I-1623);

5-{[1-(4-fluorobenzoyl)-4-hydroxypiperidin-4-yl] methyl}-1-{4-[4-(trifluoromethyl)-1H-pyrazol-1-yl] phenyl}-1H,4H,5H-pyrazolo[3,4-d]pyrimidin-4-one (I-1624);

5-[(1-acetyl-4-hydroxypiperidin-4-yl)methyl]-1-(4-chlorophenyl)-1H,4H,5H-pyrazolo[3,4-d]pyrimidin-4-one (I-1625);

1-(4-chlorophenyl)-5-{[4-hydroxy-1-(1H-pyrazole-3-carbonyl)piperidin-4-yl]methyl}-1H,4H,5H-pyrazolo[3,4-d]pyrimidin-4-one (I-1626);

1-(4-chlorophenyl)-5-{[1-(5-cyclopropyl-1H-pyrazole-3-carbonyl)-4-hydroxypiperidin-4-yl]methyl}-1H,4H,5H-pyrazolol[3,4-d]pyrimidin-4-one (I-1628);

1-(4-chlorophenyl)-5-{[4-hydroxy-1-(3-methyl-1,2-oxazole-5-carbonyl)piperidin-4-yl]methyl}-1H,4H,5H-pyrazolo[3,4-d]pyrimidin-4-one (I-1629);

1-(4-chlorophenyl)-5-[(4-hydroxy-1-{imidazo[1,2-a] pyridine-6-carbonyl}piperidin-4-yl)methyl]-1H,4H,5H-pyrazolo[3,4-d]pyrimidin-4-one (I-1630);

1-(4-chlorophenyl)-5-[(1-cyclobutanecarbonyl-4-hydroxypiperidin-4-yl)methyl]-1H,4H,5H-pyrazolo[3,4-d]pyrimidin-4-one (I-1631);

1-(4-chlorophenyl)-5-{[4-hydroxy-1-(1-methylcyclopropanecarbonyl)piperidin-4-yl]methyl}-1H,4H,5H-pyrazolo[3,4-d]pyrimidin-4-one (I-1632);

1-(4-chlorophenyl)-5-{[4-hydroxy-1-(5-methyl-1,2-oxazole-3-carbonyl)piperidin-4-yl]methyl}-1H,4H,5H-pyrazolo[3,4-d]pyrimidin-4-one (I-1633);

1-(4-chlorophenyl)-5-{[4-hydroxy-1-(5-methyl-1H-pyrazole-3-carbonyl)piperidin-4-yl]methyl}-1H,4H,5H-pyrazolo[3,4-d]pyrimidin-4-one (I-1634);

1-(4-chlorophenyl)-5-{[1-(1,3-dimethyl-1H-pyrazole-5-carbonyl)-4-hydroxypiperidin-4-yl]methyl}-1H,4H,5H-pyrazolo[3,4-d]pyrimidin-4-one (I-1635);

5-{[4-hydroxy-1-(1-methylcyclopropanecarbonyl)piperidin-4-yl]methyl}-1-{4-[3-(morpholin-4-yl)azetidin-1-yl]phenyl)-1H,4H,5H-pyrazolo[3,4-d]pyrimidin-4-one (I-1636);

5-{[4-hydroxy-1-(1-methylcyclopropanecarbonyl)piperidin-4-yl]methyl}-1-{3-[3-(morpholin-4-yl)azetidin-1-yl]phenyl)-1H,4H,5H-pyrazolo[3,4-d]pyrimidin-4-one (I-1637);

rel-5-{[4-hydroxy-1-(1-methylcyclopropanecarbonyl)piperidin-4-yl]methyl}-1-{4-[(3R,5S)-3,4,5-trimethylpiperazin-1-yl]phenyl)-1H,4H,5H-pyrazolo[3,4-d] pyrimidin-4-one (I-1638);

1-{4-[(3S)-3,4-dimethylpiperazin-1-yl]phenyl}-5-{[4-hydroxy-1-(1-methylcyclopropanecarbonyl)piperidin-4-yl]methyl}-1H,4H,5H-pyrazolo[3,4-d]pyrimidin-4-one (I-1639);

N-{4-[4-hydroxy-4-({4-oxo-1-phenyl-1H,4H,5H-pyrazolo[3,4-d]pyrimidin-5-yl}methyl)piperidine-1-carbonyl]phenyl}methanesulfonamide (I-164);

1-{4-[(3R)-3,4-dimethylpiperazin-1-yl]phenyl}-5-{[4-hydroxy-1-(1-methylcyclopropanecarbonyl)piperidin-4-yl]methyl}-1H,4H,5H-pyrazolo[3,4-d]pyrimidin-4-one (I-1640);

5-{[4-hydroxy-1-(1-methylcyclopropanecarbonyl)piperidin-4-yl]methyl}-1-[4-(4-methylpiperazin-1-yl)phenyl]-1H,4H,5H-pyrazolo[3,4-d]pyrimidin-4-one (I-1641);

5-{[4-hydroxy-1-(1-methylcyclopropanecarbonyl)piperidin-4-yl]methyl}-1-{4-[4-(oxetan-3-yl)piperidin-1-yl] phenyl)-1H,4H,5H-pyrazolo[3,4-d]pyrimidin-4-one (I-1642);

5-{[4-hydroxy-1-(1-methylcyclopropanecarbonyl)piperidin-4-yl]methyl}-1-(4-{6-oxa-3-azabicyclo[3.1.1]heptan-3-yl}phenyl)-1H,4H,5H-pyrazolo[3,4-d]pyrimidin-4-one (I-1643);

5-{[4-hydroxy-1-(1-methylcyclopropanecarbonyl)piperidin-4-yl]methyl}-1-(3-{8-methyl-3,8-diazabicyclo[3.2.1]octan-3-yl}phenyl)-1H,4H,5H-pyrazolo[3,4-d] pyrimidin-4-one (I-1644

5-{[4-hydroxy-1-(1-methylcyclopropanecarbonyl)piperidin-4-yl]methyl}-1-[3-(3,4,5-trimethylpiperazin-1-yl) phenyl]-1H,4H,5H-pyrazolo[3,4-d]pyrimidin-4-one (I-1645);

1-{3-[(3S)-3,4-dimethylpiperazin-1-yl]phenyl}-5-{[4-hydroxy-1-(1-methylcyclopropanecarbonyl)piperidin-4-yl]methyl}-1H,4H,5H-pyrazolo[3,4-d]pyrimidin-4-one (I-1646);

1-(4-chlorophenyl)-5-{[4-hydroxy-1-(6-methoxypyridine-3-carbonyl)piperidin-4-yl]methyl}-1H,4H,5H-pyrazolo[3,4-d]pyrimidin-4-one (I-1647);

1-(4-chlorophenyl)-5-{[1-(6-fluoropyridine-3-carbonyl)-4-hydroxypiperidin-4-yl]methyl}-1H,4H,5H-pyrazolo[3,4-d]pyrimidin-4-one (I-1648);

1-(4-chlorophenyl)-5-[(4-hydroxy-1-{imidazo[1,5-a] pyridine-6-carbonyl}piperidin-4-yl)methyl]-1H,4H,5H-pyrazolo[3,4-d]pyrimidin-4-one (I-1649);

1-(4-chlorophenyl)-5-({4-hydroxy-1-[4-(4-hydroxypiperidin-1-yl)benzoyl]piperidin-4-yl}methyl)-1H,4H,5H-pyrazolo[3,4-d]pyrimidin-4-one (I-1650);

1-(4-chlorophenyl)-5-{[4-hydroxy-1-(4,4,4-trifluoro-3-hydroxy-3-methylbutanoyl)piperidin-4-yl]methyl}-1H,4H,5H-pyrazolo[3,4-d]pyrimidin-4-one (I-1651);

5-{[1-(2-amino-4-fluorobenzoyl)-4-hydroxypiperidin-4-yl]methyl}-1-(4-chlorophenyl)-1H,4H,5H-pyrazolo[3,4-d]pyrimidin-4-one (I-1652);

5-[(1-cyclopropanecarbonyl-4-hydroxypiperidin-4-yl)methyl]-1-(4-{4H,5H,6H,7H-pyrazolo[1,5-a]pyrimidin-4-yl}phenyl)-1H,4H,5H-pyrazolo[3,4-d]pyrimidin-4-one (I-1653);

5-{[1-(4-fluorobenzoyl)-4-hydroxypiperidin-4-yl]methyl}-1-(4-{4H,5H,6H,7H-pyrazolo[1,5-a]pyrimidin-4-yl}phenyl)-1H,4H,5H-pyrazolo[3,4-d]pyrimidin-4-one (I-1654);

5-[(1-cyclopropanecarbonyl-4-hydroxypiperidin-4-yl)methyl]-1-{4-[(3S)-3-hydroxypyrrolidin-1-yl]phenyl)-1H,4H,5H-pyrazolo[3,4-d]pyrimidin-4-one (I-1655);

1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(propan-2-yl)urea (I-1656);

5-[(1-cyclopropanecarbonyl-4-hydroxypiperidin-4-yl)methyl]-1-[4-(3-hydroxy-3-methylpyrrolidin-1-yl)phenyl]1H,4H,5H-pyrazolo[3,4-d]pyrimidin-4-one (I-1657);

5-{[4-hydroxy-1-(4-methyl-1,3-oxazole-5-carbonyl)piperidin-4-yl]methyl}-1-(4-phenylphenyl)-1H,4H,5H-pyrazolo[3,4-d]pyrimidin-4-one (I-1658);

5-{[1-(2-cyclopropyl-1,3-oxazole-5-carbonyl)-4-hydroxypiperidin-4-yl]methyl}-1-(4-phenylphenyl)-1H,4H,5H-pyrazolo[3,4-d]pyrimidin-4-one (I-1659);

5-({4-hydroxy-1-[3-(hydroxymethyl)benzoyl]piperidin-4-yl}methyl)-1-phenyl-1H,4H, 5H-pyrazolo[3,4-d]pyrimidin-4-one (I-166);

5-{[4-hydroxy-1-(5-methoxypyridine-2-carbonyl)piperidin-4-yl]methyl}-1-(4-phenylphenyl)-1H,4H,5H-pyrazolo[3,4-d]pyrimidin-4-one (I-1660);

5-{[4-hydroxy-1-(6-methoxypyridine-3-carbonyl)piperidin-4-yl]methyl}-1-(4-phenylphenyl)-1H,4H,5H-pyrazolo[3,4-d]pyrimidin-4-one (I-1661);

5-{[1-(6-fluoropyridine-3-carbonyl)-4-hydroxypiperidin-4-yl]methyl}-1-(4-phenylphenyl)-1H,4H,5H-pyrazolo[3,4-d]pyrimidin-4-one (I-1662);

5-[(4-hydroxy-1-{5H,6H,7H-pyrazolo[3,2-b][1,3]oxazine-2-carbonyl}piperidin-4-yl)methyl]-1-(4-phenylphenyl)-1H,4H,5H-pyrazolo[3,4-d]pyrimidin-4-one (I-1663);

5-[(4-hydroxy-1-{imidazo[1,5-a]pyridine-6-carbonyl}piperidin-4-yl)methyl]-1-(4-phenylphenyl)-1H,4H,5H-pyrazolo[3,4-d]pyrimidin-4-one (I-1664);

5-({4-hydroxy-1-[4-(1H-1,2,3-triazol-1-yl)benzoyl]piperidin-4-yl}methyl)-1-(4-phenylphenyl)-1H,4H,5H-pyrazolo[3,4-d]pyrimidin-4-one (I-1665);

4-({1-[3-(4-chloro-1H-pyrazol-1-yl)phenyl]-4-oxo-1H,4H,5H-pyrazolo[3,4-d]pyrimidin-5-yl}methyl)-4-hydroxy-N,N-dimethylpiperidine-1-carboxamide (I-1666);

5-[(1-cyclopropanecarbonyl-4-hydroxypiperidin-4-yl)methyl]-1-[4-(oxan-4-yloxy)phenyl]-1H,4H,5H-pyrazolo[3,4-d]pyrimidin-4-one (I-1667), 5-{[1-(4-fluorobenzoyl)-4-hydroxypiperidin-4-yl]methyl}-1-[4-(1H-pyrazol-1-yl)phenyl]-1H,4H,5H-pyrazolo[3,4-d]pyrimidin-4-one (I-1668);

5-[(1-cyclopropanecarbonyl-4-hydroxypiperidin-4-yl)methyl]-1-{4-[3-(trifluoromethyl)-5H,6H,7H,8H-[1,2,4]triazolo[4,3-a]pyrimidin-8-yl]phenyl}-1H,4H,5H-pyrazolo[3,4-d]pyrimidin-4-one (I-1669);

5-{[4-hydroxy-1-(2-hydroxybenzoyl)piperidin-4-yl]methy 1}-1-phenyl-1H,4H, 5H-pyrazolo[3,4-d]pyrimidin-4-one (I-167);

5-{[1-(4-fluorobenzoyl)-4-hydroxypiperidin-4-yl]methyl}-1-[4-(pyridin-3-yl)phenyl]-1H,4H,5H-pyrazolo[3,4-d]pyrimidin-4-one (I-1670);

5-{[1-(4-fluorobenzoyl)-4-hydroxypiperidin-4-yl]methyl}-1-[4-(pyrimidin-5-yl)phenyl]-1H,4H,5H-pyrazolo[3,4-d]pyrimidin-4-one (I-1671);

5-{[1-(4-fluorobenzoyl)-4-hydroxypiperidin-4-yl]methyl}-1-[4-(1-methyl-1H-pyrazol-4-yl)phenyl]-1H,4H,5H-pyrazolo[3,4-d]pyrimidin-4-one (I-1672);

5-[(1-cyclopropanecarbonyl-4-hydroxypiperidin-4-yl)methyl]-1-(4-{4H,6H,7H-pyrazolo[3,2-c][1,4]oxazin-3-yl}phenyl)-1H,4H,5H-pyrazolo[3,4-d]pyrimidin-4-one (I-1673), 5-{[4-hydroxy-1-(1-methylcyclopropanecarbonyl)piperidin-4-yl]methyl}-1-{4-[3-(2-hydroxypropan-2-yl)azetidin-1-yl]phenyl}-1H,4H,5H-pyrazolo[3,4-d]pyrimidin-4-one (I-1674);

1-[3-(4,4-difluoropiperidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one (I-1675), 5-{[4-hydroxy-1-(1-methylcyclopropanecarbonyl)piperidin-4-yl]methyl}-1-{3-[3-(2-hydroxypropan-2-yl)azetidin-1-yl]phenyl}-1H,4H,5H-pyrazolo[3,4-d]pyrimidin-4-one (I-1676);

5-{[4-hydroxy-1-(1-methylcyclopropanecarbonyl)piperidin-4-yl]methyl}-1-[4-(3-hydroxyazetidin-1-yl)phenyl]-1H,4H,5H-pyrazolo[3,4-d]pyrimidin-4-one (I-1677);

5-{[4-hydroxy-1-(1-methylcyclopropanecarbonyl)piperidin-4-yl]methyl}-1-[3-(3-hydroxyazetidin-1-yl)phenyl]-1H,4H,5H-pyrazolo[3,4-d]pyrimidin-4-one (I-1678);

1-[4-(3-fluoroazetidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one (I-1679);

5-{[4-hydroxy-1-(1H-pyrazole-3-carbonyl)piperidin-4-yl]methyl}-1-phenyl-1H,4H,5H-pyrazolo[3,4-d]pyrimidin-4-one (I-168);

1-[3-(3-fluoroazetidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one (I-1680);

1-(4-fluorophenyl)-5-{[4-hydroxy-1-(4-{3-methyl-3,8-diazabicyclo[3.2.1]octan-8-yl}benzoyl)piperidin-4-yl]methyl)-1H,4H,5H-pyrazolo[3,4-d]pyrimidin-4-one (I-1681);

5-{[ 1-(4-{1,4-diazabicyclo[3.2.2]nonan-4-yl}benzoyl)4-hydroxypiperidin-4-yl]methyl}-1-(4-fluorophenyl)-1H,4H,5H-pyrazolo[3,4-d]pyrimidin-4-one (I-1682);

5-[(1-{4-[(9aS)-octahydro-1H-pyrrolo[1,2-a][1,4]diazepin-2-yl]benzoyl}-4-hydroxypiperidin-4-yl)methyl]-1-fluorophenyl)-1-1H,4H, 5H-pyrazolo[3,4-d]pyrimidin-4-one (I-1683);

5-{[1-(2-cyclopropyl-1,3-oxazole-5-carbonyl)-4-hydroxypiperidin-4-yl]methyl}-1-{4-[4-(hydroxymethyl)-1H-pyrazol-1-yl]phenyl)-1H,4H,5H-pyrazolo[3,4-d]pyrimidin-4-one (I-1684);

5-{[1-(2-cyclopropyl-1,3-oxazole-5-carbonyl)-4-hydroxypiperidin-4-yl]methyl}-1-{4-[4-(trifluoromethyl)-1H-pyrazol-1-yl]phenyl)-1H,4H,5H-pyrazolo[3,4-d]pyrimidin-4-one (I-1685);

1-[4-(4-chloro-1H-pyrazol-1-yl)phenyl]-5-{[1-(2-cyclopropyl-1,3-oxazole-5-carbonyl)-4-hydroxypiperidin-4-yl]methyl)-1H,4H,5H-pyrazolo[3,4-d]pyrimidin-4-one (I-1686);

5-{[4-hydroxy-1-(2-methyl-1,3-oxazole-5-carbonyl)piperidin-4-yl]methyl}-1-{4-[4-(hydroxymethyl)-1H-pyrazol-1-yl]phenyl)-1H,4H,5H-pyrazolo[3,4-d]pyrimidin-4-one (I-1687);

5-{[4-hydroxy-1-(2-methyl-1,3-oxazole-5-carbonyl)piperidin-4-yl]methyl}-1-{4-[4-(trifluoromethyl)-1H-pyrazol-1-yl]phenyl)-1H,4H,5H-pyrazolo[3,4-d]pyrimidin-4-one (I-1688);

1-{3-[(3R)-3,4-dimethylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1689);

5-{[4-hydroxy-1-(1 H-indazole-6-carbonyl)piperidin-4-yl]methyl}-1-phenyl-1H,4H,5H-pyrazolo[3,4-d]pyrimidin-4-one (I-169);

5-{[4-hydroxy-1-(1-methylcyclopropanecarbonyl)piperidin-4-yl]methyl}-1-[3-(4-methylpiperazin-1-yl)phenyl]-1H,4H,5H-pyrazolo[3,4-d]pyrimidin-4-one (I-1690);

5-{[4-hydroxy-1-(1-methylcyclopropanecarbonyl)piperidin-4-yl]methyl}-1-{3-[4-(oxetan-3-yl)piperidin-1-yl]phenyl)-1H,4H,5H-pyrazolo[3,4-d]pyrimidin-4-one (I-1691);

5-{[4-hydroxy-1-(1-methylcyclopropanecarbonyl)piperidin-4-yl]methyl}-1-(3-{6-oxa-3-azabicyclo[3.1.1]heptan-3-yl}phenyl)-1H,4H,5H-pyrazolo[3,4-d]pyrimidin-4-one (I-1692);

1-{4-[3-(difluoromethyl)-4-methylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1693);

1-{3-[3-(difluoromethyl)-4-methylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1694);

rel-3-({1-[(3R)-4,4-difluoro-3-(3-fluoro-1H-pyrazol-1-yl)butanoyl]-4-hydroxypiperidin-4-yl}methyl)-7-methyl-3H,4H,7H-pyrrolo[2,3-d]pyrimidin-4-one (I-1695);

rel-3-({1-[(3R)-4,4-difluoro-3-(3-fluoro-1H-pyrazol-1-yl)butanoyl]-4-hydroxypiperidin-4-yl}methyl)-7-methyl-3H,4H,7H-pyrrolo[2,3-d]pyrimidin-4-one (I-1696);

rel-5-({1-[(3R)-4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one (I-1697);

rel-5-({1-[(3R)-4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one (I-1698);

1-{3-[4-(2,2-difluoroethyl)piperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1699);

5-{[1-(2-aminobenzoyl)-4-hydroxypiperidin-4-yl]methyl}-1-phenyl-1H,4H,5H-pyrazolo[3,4-d]pyrimidin-4-one (I-17);

N-[(2R)-2-benzyl-3-[4-hydroxy-4-({1-methyl-4-oxo-1H,4H,5H-pyrazolo[3,4-d]pyrimidin-5-yl}methyl)piperidin-1-yl]-3-oxopropyl]ethene-1-sulfonamide (I-170

5-{[4-hydroxy-1-(1-methylcyclopropanecarbonyl)piperidin-4-yl]methyl}-1-{3-[4-(oxetan-3-yl)piperazin-1-yl]phenyl)-1H,4H,5H-pyrazolo[3,4-d]pyrimidin-4-one (I-1700);

5-{[4-hydroxy-1-(1-methylcyclopropanecarbonyl)piperidin-4-yl]methyl}-1-{4-[4-(oxetan-3-yl)piperazin-1-yl]phenyl)-1H,4H,5H-pyrazolo[3,4-d]pyrimidin-4-one (I-1701);

1-{3-[(1S,4S)-5-acetyl-2,5-diazabicyclo[2.2.1]heptan-2-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1702);

4-{[1-(4-fluorophenyl)-4-oxo-1H,4H,5H-pyrazolo[3,4-d]pyrimidin-5-yl]methyl}-N-[(4-fluorophenyl)methyl]-4-hydroxypiperidine-1-carboxamide (I-1703);

4-{[1-(4-fluorophenyl)-4-oxo-1H,4H,5H-pyrazolo[3,4-d]pyrimidin-5-yl]methyl)-4-hydroxy-N-phenylpiperidine-1-carboxamide (I-1704);

N-(4-fluorophenyl)-4-{[1-(4-fluorophenyl)-4-oxo-1H,4H,5H-pyrazolo[3,4-d]pyrimidin-5-yl]methyl)-4-hydroxypiperidine-1-carboxamide (I-1705);

4-{[1-(4-fluorophenyl)-4-oxo-1H,4H,5H-pyrazolo[3,4-d]pyrimidin-5-yl]methyl)-4-hydroxy-N-(3-methoxypropyl)piperidine-1-carboxamide (I-1706);

N-cyclopropyl-4-{[1-(4-fluorophenyl)-4-oxo-1H,4H,5H-pyrazolo[3,4-d]pyrimidin-5-yl]methyl}-4-hydroxypiperidine-1-carboxamide (I-1707), 4-{[1-(4-fluorophenyl)-4-oxo-1H,4H,5H-pyrazolo[3,4-d]pyrimidin-5-yl]methyl)-4-hydroxy-N-(pyridin-3-yl)piperidine-1-carboxamide (I-1708);

5-[(1-cyclopropanecarbonyl-4-hydroxypiperidin-4-yl)methyl]-1-[4-(3-hydroxyazetidine-1-carbonyl)phenyl]-1H,4H,5H-pyrazolo[3,4-d]pyrimidin-4-one (I-1709);

N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]ethene-1-sulfonamide (I-171);

5-{[4-hydroxy-1-(1-methylcyclopropanecarbonyl)piperidin-4-yl]methyl}-1-[4-(3-methyl-1H-pyrazol-1-yl)phenyl]-1H,4H,5H-pyrazolo[3,4-d]pyrimidin-4-one (I-1710);

5-{[4-hydroxy-1-(3-methyloxetane-3-carbonyl)piperidin-4-yl]methyl}-1-[4-(3-methyl-1H-pyrazol-1-yl)phenyl]-1H,4H,5H-pyrazolo[3,4-d]pyrimidin-4-one (I-1711);

1-{4-[4-(2,2-difluoroethyl)piperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one (I-1712

5-{[4-hydroxy-1-(3-methy 1 oxetane-3-carbonyl)piperidin-4-yl]methy 1}-1-[4-(1H-pyrazol-1-yl)phenyl]-1H,4H,5H-pyrazolo[3,4-d]pyrimidin-4-one (I-1713);

5-{[4-hydroxy-1-(1-methyl cyclopropanecarbonyl)piperidin-4-yl]methyl}-1-(4-{3-oxa-9-azaspiro[5.5]undecan-9-yl}phenyl)-1H,4H,5H-pyrazolo[3,4-d]pyrimidin-4-one (I-1714);

5-{[4-hydroxy-1-(1-methylcyclopropanecarbonyl)piperidin-4-yl]methyl}-1-(4-{l-oxa-8-azaspiro[4.5]decan-8-yl}phenyl)-1H,4H,5H-pyrazolo[3,4-d]pyrimidin-4-one (I-1715);

5-{[4-hydroxy-1-(1-methyl cyclopropanecarbonyl)piperidin-4-yl]methy 1}-1-(4-{2-oxa-7-azaspiro[3.5]nonan-7-yl}phenyl)-1H,4H,5H-pyrazolo[3,4-d]pyrimidin-4-one (I-1716);

5-{[4-hydroxy-1-(1-methylcyclobutanecarbonyl)piperidin-4-yl]methy 1}-1-{4-[4-(trifluoromethyl)-1H-pyrazol-1-yl]phenyl}-1H,4H,5H-pyrazolo[3,4-d]pyrimidin-4-one (I-1717);

1-(4-{2,2-difluoro-7-azaspiro[3.5]nonan-7-yl}phenyl)-5-{[4-hydroxy-1-(1-methylcyclobutanecarbonyl)piperidin-4-yl]methyl)-1H,4H,5H-pyrazolo[3,4-d]pyrimidin-4-one (I-1718);

5-{[4-hydroxy-1-(1-methylcyclobutanecarbonyl)piperidin-4-yl]methyl}-1-{4-[1-(oxan-4-yl)-1H-pyrazol-4-yl]phenyl)-1H,4H,5H-pyrazolo[3,4-d]pyrimidin-4-one (I-1719);

3-[4-hydroxy-4-({4-oxo-1-phenyl-1H,4H,5H-pyrazolo[3,4-d]pyrimidin-5-yl}methyl)piperidine-1-carbonyl]benzamide (I-172);

1-[4-(1-cyclopropyl-1H-pyrazol-4-yl)phenyl]-5-{[4-hydroxy-1-(1-methylcyclobutanecarbonyl) piperidin-4-yl]methyl}-1H,4H,5H-pyrazolo[3,4-d]pyrimidin-4-one (I-1720);

1-{4-[1-(difluoromethyl)-1H-pyrazol-4-yl]phenyl}-5-{[4-hydroxy-1-(1-methylcyclobutanecarbonyl)piperidin-4-yl]methyl}-1H,4H,5H-pyrazolo[3,4-d]pyrimidin-4-one (I-1721);

5-{[4-hydroxy-1-(1-methylcyclopropanecarbonyl)piperidin-4-yl]methyl}-1-{4-[1-(oxan-4-yl)-1H-pyrazol-4-yl]phenyl)-1H,4H,5H-pyrazolo[3,4-d]pyrimidin-4-one (I-1722);

1-[4-(1-cyclopropyl-1H-pyrazol-4-yl)phenyl]-5-{[4-hydroxy-1-(1-methylcyclopropanecarbonyl)piperidin-4-yl]methyl}-1H,4H,5H-pyrazolo[3,4-d]pyrimidin-4-one (I-1723);

1-(4-fluorophenyl)-5-{[4-hydroxy-1-(4-{l-methyl-octahydro-1H-pyrrolo[3,4-b]pyridin-6-yl}benzoyl)piperidin-4-yl]methyl}-1H,4H,5H-pyrazolo[3,4-d]pyrimidin-4-one (I-1724);

5-[(1-cyclopropanecarbonyl-4-hydroxypiperidin-4-yl)methyl]-1-[4-(4-methylpyridin-2-yl)phenyl]-1H,4H,5H-pyrazolo[3,4-d]pyrimidin-4-one (I-1725);

5-[(1-cyclopropanecarbonyl-4-hydroxypiperidin-4-yl)methyl]-1-[4-(5-methylpyridin-2-yl)phenyl]-1H,4H,5H-pyrazolo[3,4-d]pyrimidin-4-one (I-1726);

5-[(1-cyclopropanecarbonyl-4-hydroxypiperidin-4-yl)methyl]-1-[4-(1,2,3,4-tetrahydro-1,5-naphthyridin-1-yl)phenyl]-1H,4H,5H-pyrazolo[3,4-d]pyrimidin-4-one (I-1727);

1-[4-(4,4-difluoropiperidin-1-yl)phenyl]-5-{[4-hydroxy-1-(1-methylcyclopropanecarbonyl)piperidin-4-yl]methyl}-1H,4H,5H-pyrazolo[3,4-d]pyrimidin-4-one (I-1728);

5-{[1-(4-fluorobenzoyl)-4-hydroxypiperidin-4-yl]methyl}-1-[4-(1,2,3,4-tetrahydro-1,6-naphthyridin-1-yl)phenyl]-1H,4H,5H-pyrazolo[3,4-d]pyrimidin-4-one (I-1729);

N-{4-[4-hydroxy-4-({4-oxo-1-phenyl-1H,4H,5H-pyrazolo[3,4-d]pyrimidin-5-yl}methyl)piperidine-1-carbonyl]phenyl}ethene-1-sulfonamide (I-173);

5-{[1-(4-fluorobenzoyl)-4-hydroxypiperidin-4-yl]methyl}-1-[4-(1,2,3,4-tetrahydro-1,5-naphthyridin-1-yl)phenyl]-1H,4H,5H-pyrazolo[3,4-d]pyrimidin-4-one (I-1730);

5-{[4-hydroxy-1-(1-methylcyclopropanecarbonyl)piperidin-4-yl]methyl}-1-{3-[3-(oxan-4-yl)azetidin-1-yl]phenyl)-1H,4H,5H-pyrazolo[3,4-d]pyrimidin-4-one (I-1732);

1-[4-(4-chloro-1H-pyrazol-1-yl)phenyl]-5-{[4-hydroxy-1-(2-methyl-1,3-oxazole-5-carbonyl)piperidin-4-yl]methyl}-1H,4H,5H-pyrazolo[3,4-d]pyrimidin-4-one (I-1733);

5-{[1-(4-fluorobenzoyl)-4-hydroxypiperidin-4-yl]methyl}-1-{4-[4-(hydroxymethyl)-1H-pyrazol-1-yl]phenyl)-1H,4H,5H-pyrazolo[3,4-d]pyrimidin-4-one (I-1734);

5-[(1-{4-[(8aS)-octahydropyrrolo[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one (I-1735);

5-[(1-cyclopropanecarbonyl-4-hydroxypiperidin-4-yl)methyl]-1-(4-{pyrazolo[1,5-a]pyridin-3-yl}phenyl)-1H,4H,5H-pyrazolo[3,4-d]pyrimidin-4-one (I-1736);

5-[(1-cyclopropanecarbonyl-4-hydroxypiperidin-4-yl)methyl]-1-{4-[5-(trifluoromethyl)pyridin-3-yl]phenyl)-1H,4H,5H-pyrazolo[3,4-d]pyrimidin-4-one (I-1737);

1-[4-(1,2-benzoxazol-4-yl)phenyl]-5-[(1-cyclopropanecarbonyl-4-hydroxypiperidin-4-yl)methyl]-1H,4H,5H-pyrazolo[3,4-d]pyrimidin-4-one (I-1738);

5-[(1-cyclopropanecarbonyl-4-hydroxypiperidin-4-yl)methyl]-1-(4-{2-hydroxy-7-azaspiro[3.5]nonan-7-yl}phenyl)-1H,4H,5H-pyrazolo[3,4-d]pyrimidin-4-one (I-1739);

5-{[1-(4-fluorobenzoyl)-4-hydroxypiperidin-4-yl]methyl}-1-{4-[2-(hydroxymethyl)-7-azaspiro[3.5]nonan-7-yl]phenyl)-1H,4H,5H-pyrazolo[3,4-d]pyrimidin-4-one (I-1740);

5-[(1-cyclopropanecarbonyl-4-hydroxypiperidin-4-yl)methyl]-1-{4-[2-(hydroxymethyl)-7-azaspiro[3.5]nonan-7-yl]phenyl)-1H,4H,5H-pyrazolo[3,4-d]pyrimidin-4-one (I-1741);

5-[(1-cyclopropanecarbonyl-4-hydroxypiperidin-4-yl)methyl]-1-(4-{2,2-difluoro-7-azaspiro[3.5]nonan-7-yl}phenyl)-1H,4H,5H-pyrazolo[3,4-d]pyrimidin-4-one (I-1742);

1-{4-[1-(difluoromethyl)-1H-pyrazol-4-yl]phenyl}-5-{[1-(4-fluorobenzoyl)-4-hydroxypiperidin-4-yl]methyl}-1H,4H,5H-pyrazolo[3,4-d]pyrimidin-4-one (I-1743);

4-{4-[4-(5-{[1-(4-fluorobenzoyl)-4-hydroxypiperidin-4-yl]methyl}-4-oxo-1H,4H,5H-pyrazolo[3,4-d]pyrimidin-1-yl)phenyl]-1H-pyrazol-1-yl}-1,6-thiane-1,1-dione (I-1744), 3-{4-[4-(5-{[1-(4-fluorobenzoyl)-4-hydroxypiperidin-4-yl]methyl}-4-oxo-1H,4H,5H-pyrazolo[3,4-d]pyrimidin-1-yl)phenyl]-1H-pyrazol-1-yl}-1,6-thietane-1,1-dione (I-1745);

1-[4-(1-cyclopropyl-1H-pyrazol-4-yl)phenyl]-5-{[1-(4-fluorobenzoyl)-4-hydroxypiperidin-4-yl]methyl}-1H,4H,5H-pyrazolo[3,4-d]pyrimidin-4-one (I-1746);

1-{4-[(1S,4S)-5-acetyl-2,5-diazabicyclo[2.2.1]heptan-2-yl]phenyl)-5-{[4-hydroxy-1-(1-methylcyclopropanecarbonyl)piperidin-4-yl]methyl}-1H,4H,5H-pyrazolo[3,4-d]pyrimidin-4-one (I-1747);

1-{3-[(1R,4R)-5-acetyl-2,5-diazabicyclo[2.2.1]heptan-2-yl]phenyl)-5-{[4-hydroxy-1-(1-methylcyclopropanecarbonyl)piperidin-4-yl]methyl}-1H,4H,5H-pyrazolo[3,4-d]pyrimidin-4-one (I-1748);

1-{4-[(1R,4R)-5-acetyl-2,5-diazabicyclo[2.2.1]heptan-2-yl]phenyl)-5-{[4-hydroxy-1-(1-methylcyclopropanecarbonyl)piperidin-4-yl]methyl}-1H,4H,5H-pyrazolo[3,4-d]pyrimidin-4-one (I-1749);

5-({4-hydroxy-1-[(3R)-3-(1H-pyrazol-1-yl)butanoyl]piperidin-4-yl}methyl)-1-phenyl-1H,4H,5H-pyrazolo[3,4-d]pyrimidin-4-one (I-175);

5-{[4-hydroxy-1-(1-methylcyclopropanecarbonyl)piperidin-4-yl]methyl}-1-(3-[4-(2-methoxyethyl)piperazin-1-yl]phenyl)-1H,4H,5H-pyrazolo[3,4-d]pyrimidin-4-one (I-1750);

1-[3-(5-{[4-hydroxy-1-(1-methylcyclopropanecarbonyl) piperidin-4-yl]methyl)-4-oxo-1H,4H,5H-pyrazolo[3,4-d]pyrimidin-1-yl)phenyl]piperidine-4-carbonitrile (I-1751);

1-[4-(5-{[4-hydroxy-1-(1-methylcyclopropanecarbonyl) piperidin-4-yl]methyl)-4-oxo-1H,4H,5H-pyrazolo[3,4-d]pyrimidin-1-yl)phenyl]piperidine-4-carbonitrile (I-1752);

5-({1-[4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one (I-1753);

1-[4-(3-fluoro-1H-pyrazol-1-yl)phenyl]-5-{[4-hydroxy-1-(1-methylcyclopropanecarbonyl) piperidin-4-yl]methyl)-1H,4H,5H-pyrazolo[3,4-d]pyrimidin-4-one (I-1754);

1-(4-{6-azaspiro[2.5]octan-6-yl}phenyl)-5-[(1-cyclopropanecarbonyl-4-hydroxypiperidin-4-yl)methyl]-1H,4H,5H-pyrazolo[3,4-d]pyrimidin-4-one (I-1755);

5-{[1-(4-fluorobenzoyl)-4-hydroxypiperidin-4-yl]methyl}-1-{4-[(3-methyloxetan-3-yl)methoxy]phenyl}1H,4H,5H-pyrazolo[3,4-d]pyrimidin-4-one (I-1756);

2-[2-(dimethylamino)ethoxy]ethyl 4-{[1-(4-fluorophenyl)-4-oxo-1H,4H,5H-pyrazolo[3,4-d]pyrimidin-5-yl]methyl}-4-hydroxypiperidine-1-carboxylate (I-1757);

2-(1H-imidazol-1-yl)ethyl 4-{[1-(4-fluorophenyl)-4-oxo-1H,4H,5H-pyrazolo[3,4-d]pyrimidin-5-yl]methyl}-4-hydroxypiperidine-1-carboxylate (I-1759);

5-({4-hydroxy-1-[(3S)-3-(1H-pyrazol-1-yl)butanoyl]piperidin-4-yl}methyl)-1-phenyl-1H,4H,5H-pyrazolo[3,4-d]pyrimidin-4-one (I-176);

1-methylpiperidin-4-yl 4-{[1-(4-fluorophenyl)-4-oxo-1H,4H,5H-pyrazolo[3,4-d]pyrimidin-5-yl]methyl}-4-hydroxypiperidine-1-carboxylate (I-1762);

5-[(1-cyclopropanecarbonyl-4-hydroxypiperidin-4-yl) methyl]-1-[4-(3-methyl-1,2-benzoxazol-5-yl)phenyl]-1H,4H,5H-pyrazolo[3,4-d]pyrimidin-4-one (I-1763);

5-[(1-cyclopropanecarbonyl-4-hydroxypiperidin-4-yl) methyl]-1-[4-(1-methyl-1H-indazol-6-yl)phenyl]-1H,4H,5H-pyrazolo[3,4-d]pyrimidin-4-one (I-1764);

5-[(1-cyclopropanecarbonyl-4-hydroxypiperidin-4-yl) methyl]-1-[4-(3-methyl-1H-indazol-7-yl)phenyl]-1H,4H,5H-pyrazolo[3,4-d]pyrimidin-4-one (I-1765);

1-[4-(1,2-benzoxazol-5-yl)phenyl]-5-[(1-cyclopropanecarbonyl-4-hydroxypiperidin-4-yl)methyl]-1H,4H,5H-pyrazolo[3,4-d]pyrimidin-4-one (I-1766);

5-[(1-cyclopropanecarbonyl-4-hydroxypiperidin-4-yl) methyl]-1-(4-{5H,6H,7H,8H-[1,2,4]triazolo[4,3-a]pyridin-3-yl}phenyl)-1H,4H,5H-pyrazolo[3,4-d]pyrimidin-4-one (I-1767), 5-[(1-cyclopropanecarbonyl-4-hydroxypiperidin-4-yl) methyl]-1-(4-{1H-pyrrolo[3,2-b]pyridin-5-yl}phenyl)-1H,4H,5H-pyrazolo[3,4-d]pyrimidin-4-one (I-1768);

5-[(1-cyclopropanecarbonyl-4-hydroxypiperidin-4-yl) methyl]-1-{4-[2-(trifluoromethyl)pyrimidin-4-yl]phenyl}-1H,4H,5H-pyrazolo[3,4-d]pyrimidin-4-one (I-1769);

(S)-3-((1-(4,4-difluoro-3-(3-fluoro-1H-pyrazol-1-yl)butanoyl)-4-hydroxypiperidin-4-yl)methyl)-7-(4-fluorophenyl)-6-methyl-3,7-dihydro-4H-pyrrolo[2,3-d]pyrimidin-4-one (I-1770);

(R)-3-((1-(4,4-difluoro-3-(3-fluoro-1H-pyrazol-1-yl)butanoyl)-4-hydroxypiperidin-4-yl)methyl)-7-(4-fluorophenyl)-6-methyl-3,7-dihydro-4H-pyrrolo[2,3-d]pyrimidin-4-one (I-1771);

7-(4-fluorophenyl)-3-((4-hydroxy-1-((1r,4r)-4-({1-methyl-1H-pyrazol-3-yl)oxy)cyclohexane-1-carbonyl) piperidin-4-yl)methyl)-6-methyl-3,7-dihydro-4H-pyrrolo[2,3-d]pyrimidin-4-one (I-1772);

7-(4-fluorophenyl)-3-((4-hydroxy-1-((1s,4s)-4-({1-methyl-1H-pyrazol-3-yl)oxy)cyclohexane-1-carbonyl) piperidin-4-yl)methyl)-6-methyl-3,7-dihydro-4H-pyrrolo[2,3-d]pyrimidin-4-one (I-1773);

(S)-3-((1-(4,4-difluoro-3-(3-fluoro-1H-pyrazol-1-yl)butanoyl)-4-hydroxypiperidin-4-yl)methyl)-7-(4-morpholinophenyl)-3,7-dihydro-4H-pyrrolo[2,3-d]pyrimidin-4-one (I-1774);

(S)-3-((1-(4,4-difluoro-3-(3-fluoro-1H-pyrazol-1-yl)butanoyl)-4-hydroxypiperidin-4-yl)methyl)-7-(3-morpholinophenyl)-3,7-dihydro-4H-pyrrolo[2,3-d]pyrimidin-4-one (I-1775);

(R)-3-((1-(4,4-difluoro-3-(3-fluoro-1H-pyrazol-1-yl)butanoyl)-4-hydroxypiperidin-4-yl)methyl)-7-(4-morpholinophenyl)-3,7-dihydro-4H-pyrrolo[2,3-d]pyrimidin-4-one (I-1776);

(R)-3-((1-(4,4-difluoro-3-(3-fluoro-1H-pyrazol-1-yl)butanoyl)-4-hydroxypiperidin-4-yl)methyl)-7-(3-morpholinophenyl)-3,7-dihydro-4H-pyrrolo[2,3-d]pyrimidin-4-one (I-1777);

1-(4-((3,3-difluoro-1-methylcyclobutyl)methoxy)phenyl)-5-((4-hydroxy-1-(1-methylcyclopropane-1-carbonyl)piperidin-4-yl)methyl)-1,5-dihydro-4H-pyrazolo[3,4-d]pyrimidin-4-one (I-1778);

(S)—N-(2-benzyl-3-(4-hydroxy-4-((4-oxo-1-phenyl-1,4-dihydro-5H-pyrazolo[3,4-d]pyrimidin-5-yl)methyl)piperidin-1-yl)-3-oxopropyl)ethenesulfonamide (I-1779);

1-(4-(1-(difluoromethyl)-1H-pyrazol-4-yl)phenyl)-5-((4-hydroxy-1-(1-methylcyclopropane-1-carbonyl)piperidin-4-yl)methyl)-1,5-dihydro-4H-pyrazolo[3,4-d]pyrimidin-4-one (I-1800);

1-(4-(3,3-difluorocyclobutoxy)phenyl)-5-((4-hydroxy-1-(J-methylcyclopropane-1-carbonyl)piperidin-4-yl) methyl)-1,5-dihydro-4H-pyrazolo[3,4-d]pyrimidin-4-one (I-1801);

5-({4-hydroxy-1-[(3R)-3-(1H-pyrrol-1-yl)butanoyl]piperidin-4-yl}methyl)-1-phenyl-1H,4H,5H-pyrazolo[3,4-d]pyrimidin-4-one (I-177);

5-({4-hydroxy-1-[(3S)-3-(1H-pyrrol-1-yl)butanoyl]piperidin-4-yl}methyl)-1-phenyl-1H,4H,5H-pyrazolo[3,4-d]pyrimidin-4-one (I-178);

4-[4-hydroxy-4-({4-oxo-1-phenyl-1H,4H,5H-pyrazolo[3,4-d]pyrimidin-5-yl}methyl)piperidine-1-carbonyl]benzamide (I-179);

5-[(1-benzoyl-4-hydroxypiperidin-4-yl)methyl]-1-(2-hydroxyphenyl)-1H,4H,5H-pyrazolo[3,4-d]pyrimidin-4-one (I-18);

5-({4-hydroxy-1-[4-(methoxymethyl)benzoyl]piperidin-4-yl}methyl)-1-phenyl-1H,4H,5H-pyrazolo[3,4-d]pyrimidin-4-one (I-180);

N-{3-[4-hydroxy-4-({4-oxo-1-phenyl-1H,4H,5H-pyrazolo[3,4-d]pyrimidin-5-yl}methyl)piperidine-1-carbonyl]phenyl}acetamide (I-181);

4-[4-hydroxy-4-({4-oxo-1-phenyl-1H,4H,5H-pyrazolo[3,4-d]pyrimidin-5-yl}methyl)piperidine-1-carbonyl]-N-methylbenzene-1-sulfonamide (I-182);

4-[4-hydroxy-4-({4-oxo-1-phenyl-1H,4H,5H-pyrazolo[3,4-d]pyrimidin-5-yl}methyl)piperidine-1-carbonyl]-N-methylbenzamide (I-184);

5-[(1-cyclohexanecarbonyl-4-hydroxypiperidin-4-yl) methyl]-1-phenyl-1H,4H,5H-pyrazolo[3,4-d]pyrimidin-4-one (I-189);

5-[(1-benzoyl-4-hydroxypiperidin-4-yl)methyl]-1-(3-hydroxyphenyl)-1H,4H,5H-pyrazolo[3,4-d]pyrimidin-4-one (I-19);

5-{[1-(4-fluorobenzoyl)-4-hydroxypiperidin-4-yl]methyl}-1-phenyl-1H,4H,5H-pyrazolo[3,4-d]pyrimidin-4-one (I-190);

5-{[4-hydroxy-1-(pyridine-4-carbonyl)piperidin-4-yl]methyl}-1-phenyl-1H,4H,5H-pyrazolo[3,4-d]pyrimidin-4-one (I-191);

5-{[4-hydroxy-1-(4,4,4-trifluorobutanoyl)piperidin-4-yl]methyl}-1-phenyl-1H,4H,5H-pyrazolo[3,4-d]pyrimidin-4-one (I-192);

5-{[1-(3-ethoxypropanoyl)-4-hydroxypiperidin-4-yl]methyl}-1-phenyl-1H,4H,5H-pyrazolo[3,4-d]pyrimidin-4-one (I-193);

5-[(1-cyclobutanecarbonyl-4-hydroxypiperidin-4-yl)methyl]-1-phenyl-1H,4H, 5H-pyrazolo[3,4-d]pyrimidin-4-one (I-194);

5-[(1-cyclopentanecarbonyl-4-hydroxypiperidin-4-yl)methyl]-1-phenyl-1H,4H,5H-pyrazolo[3,4-d]pyrimidin-4-one (I-195);

5-{[1-(2,2-dimethylpropanoyl)-4-hydroxypiperidin-4-yl]methyl}-1-phenyl-1H,4H,5H-pyrazolo[3,4-d]pyrimidin-4-one (I-196);

5-{[1-(3,5-dimethylbenzoyl)-4-hydroxypiperidin-4-yl]methyl}-1-phenyl-1H,4H, 5H-pyrazolo[3,4-d]pyrimidin-4-one (I-197);

5-{[4-hydroxy-1-(3-methylbenzoyl)piperidin-4-yl]methyl}-1-phenyl-1H,4H,5H-pyrazolo[3,4-d]pyrimidin-4-one (I-198);

5-{[4-hydroxy-1-(4-methylbenzoyl)piperidin-4-yl]methyl}-1-phenyl-1H,4H,5H-pyrazolo[3,4-d]pyrimidin-4-one (I-199);

5'{[1-(2-fluoro-4-phenylbenzoyl)-4-hydroxypiperidin-4-yl]methyl}-1-methyl-1H,4H,5H-pyrazolo[3,4-d]pyrimidin-4-one (I-2);

5-({1-[3-(aminomethyl)benzoyl]-4-hydroxypiperidin-4-yl}methyl)-1-phenyl-1H,4H,5H-pyrazolo[3,4-d]pyrimidin-4-one (I-20);

5-{[1-(3,4-dimethylbenzoyl)-4-hydroxypiperidin-4-yl]methyl}-1-phenyl-1H,4H,5H-pyrazolo[3,4-d]pyrimidin-4-one (I-200);

5-{[1-(3-fluoro-4-methoxybenzoyl)-4-hydroxypiperidin-4-yl]methyl}-1-phenyl-1H,4H,5H-pyrazolo[3,4-d]pyrimidin-4-one (I-201);

5-{[1¹-(2,3-dihydro-1-benzofuran-5-carbonyl)-4-hydroxypiperidin-4-yl]methyl}-1-phenyl-1H,4H,5H-pyrazolo[3,4-d]pyrimidin-4-one (I-202);

5-{[1-(3,5-dimethoxybenzoyl)-4-hydroxypiperidin-4-yl]methyl}-1-phenyl-1H,4H,5H-pyrazolo[3,4-d]pyrimidin-4-one (I-203);

5-{[1-(3-fluorobenzoyl)-4-hydroxypiperidin-4-yl]methyl}-1-phenyl-1H,4H,5H-pyrazolo[3,4-d]pyrimidin-4-one (I-204);

5-{[1-(2-fluorobenzoyl)-4-hydroxypiperidin-4-yl]methyl}-1-phenyl-1H,4H,5H-pyrazolo[3,4-d]pyrimidin-4-one (I-205);

5-{[1-(2-fluoro-3-methylbenzoyl)-4-hydroxypiperidin-4-yl]methyl}-1-phenyl-1H,4H,5H-pyrazolo[3,4-d]pyrimidin-4-one (I-206);

5-{[1-(3,4-difluorobenzoyl)-4-hydroxypiperidin-4-yl]methyl}-1-phenyl-1H,4H,5H-pyrazolo[3,4-d]pyrimidin-4-one (I-207);

5-{[1-(2,5-difluorobenzoyl)-4-hydroxypiperidin-4-yl]methyl}-1-phenyl-1H,4H,5H-pyrazolo[3,4-d]pyrimidin-4-one (I-208);

5-{[1-(2,4-difluorobenzoyl)-4-hydroxypiperidin-4-yl]methyl}-1-phenyl-1H,4H,5H-pyrazolo[3,4-d]pyrimidin-4-one (I-209);

5-{[1-(3-chloro-4-fluorobenzoyl)-4-hydroxypiperidin-4-yl]methyl}-1-phenyl-1H,4H,5H-pyrazolo[3,4-d]pyrimidin-4-one (I-210);

5-{[1-(3-chloro-4-methylbenzoyl)-4-hydroxypiperidin-4-yl]methyl}-1-phenyl-1H,4H,5H-pyrazolo[3,4-d]pyrimidin-4-one (I-211);

5-{[1-(4-chloro-3-methylbenzoyl)-4-hydroxypiperidin-4-yl]methyl}-1-phenyl-1H,4H,5H-pyrazolo[3,4-d]pyrimidin-4-one (I-212);

5-{[1-(3,4-dichlorobenzoyl)-4-hydroxypiperidin-4-yl]methyl}-1-phenyl-1H,4H,5H-pyrazolo[3,4-d]pyrimidin-4-one (I-213);

5-{[1-(3-chloro-4-methoxybenzoyl)-4-hydroxypiperidin-4-yl]methyl}-1-phenyl-1H,4H,5H-pyrazolo[3,4-d]pyrimidin-4-one (I-214), 5-{[4-hydroxy-1-(2-methylbenzoyl)piperidin-4-yl]methyl}-1-phenyl-1H,4H,5H-pyrazolo[3,4-d]pyrimidin-4-one (I-215);

5-{[1-(2,5-dimethylbenzoyl)-4-hydroxypiperidin-4-yl]methyl}-1-phenyl-1H,4H,5H-pyrazolo[3,4-d]pyrimidin-4-one (I-216);

5-{[1-(2,4-dimethylbenzoyl)-4-hydroxypiperidin-4-yl]methyl}-1-phenyl-1H,4H,5H-pyrazolo[3,4-d]pyrimidin-4-one (I-217);

5-{[1-(5-chloro-2-methoxybenzoyl)-4-hydroxypiperidin-4-yl]methyl}-1-phenyl-1H,4H,5H-pyrazolo[3,4-d]pyrimidin-4-one (I-218);

5-{[1-(4-chloro-2-methoxybenzoyl)-4-hydroxypiperidin-4-yl]methyl}-1-phenyl-1H,4H,5H-pyrazolo[3,4-d]pyrimidin-4-one (I-219);

3-{5-[(1-benzoyl-4-hydroxypiperidin-4-yl)methyl]-4-oxo-1H,4H,5H-pyrazolo[3,4-d]pyrimidin-1-yl}benzoic acid (I-22);

5-{[1-(2,3-dimethoxybenzoyl)-4-hydroxypiperidin-4-yl]methy1}-1-phenyl-1H,4H,5H-pyrazolo[3,4-d]pyrimidin-4-one (I-220);

5-{[1-(2,5-dimethoxybenzoyl)-4-hydroxypiperidin-4-yl]methyl}-1-phenyl-1H,4H,5H-pyrazolo[3,4-d]pyrimidin-4-one (I-221);

5-{[1-(2,4-dimethoxybenzoyl)-4-hydroxypiperidin-4-yl]methyl}-1-phenyl-1H,4H,5H-pyrazolo[3,4-d]pyrimidin-4-one (I-222);

5-{[1-(2,5-dichlorobenzoyl)-4-hydroxypiperidin-4-yl]methyl}-1-phenyl-1H,4H,5H-pyrazolo[3,4-d]pyrimidin-4-one (I-223);

5-{[1-(2,4-dichlorobenzoyl)-4-hydroxypiperidin-4-yl]methyl}-1-phenyl-1H,4H,5H-pyrazolo[3,4-d]pyrimidin-4-one (I-224);

5-{[4-hydroxy-1-(pyridine-3-carbonyl)piperidin-4-yl]methyl}-1-phenyl-1H,4H,5H-pyrazolo[3,4-d]pyrimidin-4-one (I-225);

5-{[1-(4-chloro-3-methoxybenzoyl)-4-hydroxypiperidin-4-yl]methyl}-1-phenyl-1H,4H,5H-pyrazolo[3,4-d]pyrimidin-4-one (I-226), 5-{[4-hydroxy-1-(5-methylpyrazine-2-carbonyl)piperidin-4-yl]methyl}-1-phenyl-1H,4H,5H-pyrazolo[3,4-d]pyrimidin-4-one (I-227);

5-{[4-hydroxy-1-(pyridine-2-carbonyl)piperidin-4-yl]methyl}-1-phenyl-1H,4H,5H-pyrazolo[3,4-d]pyrimidin-4-one (I-228);

5-{[1-(1,5-dimethyl-1H-pyrazole-3-carbonyl)-4-hydroxypiperidin-4-yl]methyl}-1-phenyl-1H,4H,5H-pyrazolo[3,4-d]pyrimidin-4-one (I-229);

5-({1-[4-(cyclopropylamino)benzoyl]-4-hydroxypiperidin-4-yl}methyl)-1-phenyl-1H,4H,5H-pyrazolo[3,4-d]pyrimidin-4-one (I-23);

5-{[1-(dimethyl-1,3-thiazole-5-carbonyl)-4-hydroxypiperidin-4-yl]methyl}-1-phenyl-1H,4H,5H-pyrazolo[3,4-d]pyrimidin-4-one (I-230);

5-{[4-hydroxy-1-(1,2,3-thiadiazole-4-carbonyl)piperidin-4-yl]methyl}-1-phenyl-1H,4H,5H-pyrazolo[3,4-d]pyrimidin-4-one (I-231);

5-{[1-(2-amino-4-chlorobenzoyl)-4-hydroxypiperidin-4-yl]methyl}-1-phenyl-1H,4H,5H-pyrazolo[3,4-d]pyrimidin-4-one (I-232);

5-{[1-(2-amino-5-chlorobenzoyl)-4-hydroxypiperidin-4-yl]methyl}-1-phenyl-1H,4H,5H-pyrazolo[3,4-d]pyrimidin-4-one (I-233);

5-{[1-(2-amino-3-methylbenzoyl)-4-hydroxypiperidin-4-yl]methyl}-1-phenyl-1H,4H,5H-pyrazolo[3,4-d]pyrimidin-4-one (I-234);

5-{[4-hydroxy-1-(5-methyl-1,2-oxazole-3-carbonyl)piperidin-4-yl]methyl}-1-phenyl-1H,4H,5H-pyrazolo[3,4-d]pyrimidin-4-one (I-235);

5-{[4-hydroxy-1-(5-methyl-1H-pyrazole-3-carbonyl)piperidin-4-yl]methyl}-1-phenyl-1H,4H,5H-pyrazolo[3,4-d]pyrimidin-4-one (I-236);

5-{[4-hydroxy-1-(4-methyl-1,3-thiazole-5-carbonyl)piperidin-4-yl]methyl}-1-phenyl-1H,4H,5H-pyrazolo[3,4-d]pyrimidin-4-one (I-237);

5-{[4-hydroxy-1-(6-methylpyridine-3-carbonyl)piperidin-4-yl]methyl}-1-phenyl-1H,4H,5H-pyrazolo[3,4-d]pyrimidin-4-one (I-238);

5-({4-hydroxy-1-[2-(trifluoromethyl)pyrimidine-5-carbonyl]piperidin-4-yl}methyl)-1-phenyl-1H,4H,5H-pyrazolo[3,4-d]pyrimidin-4-one (I-239);

5-{[1-(5-fluoropyridine-2-carbonyl)-4-hydroxypiperidin-4-yl]methyl}-1-phenyl-1H,4H,5H-pyrazolo[3,4-d]pyrimidin-4-one (I-240);

5-{[1-(5-ethyl-1,3-oxazole-4-carbonyl)-4-hydroxypiperidin-4-yl]methyl}-1-phenyl-1H,4H,5H-pyrazolo[3,4-d]pyrimidin-4-one (I-241);

5-{[1-(3-fluoro-4-methylbenzoyl)-4-hydroxypiperidin-4-yl]methyl}-1-phenyl-1H,4H,5H-pyrazolo[3,4-d]pyrimidin-4-one (I-242);

5-{[1-(3-fluoro-2-methylbenzoyl)-4-hydroxypiperidin-4-yl]methyl}-1-phenyl-1H,4H,5H-pyrazolo[3,4-d]pyrimidin-4-one (I-243);

5-{[1-(5-fluoro-2-methylbenzoyl)-4-hydroxypiperidin-4-yl]methyl}-1-phenyl-1H,4H,5H-pyrazolo[3,4-d]pyrimidin-4-one (I-244);

5-{[1-(dimethyl-1,2-oxazole-4-carbonyl)-4-hydroxypiperidin-4-yl]methyl}-1-phenyl-1H,4H,5H-pyrazolo[3,4-d]pyrimidin-4-one (I-245);

5-{[1-(2,3-difluorobenzoyl)-4-hydroxypiperidin-4-yl]methyl}-1-phenyl-1H,4H,5H-pyrazolo[3,4-d]pyrimidin-4-one (I-246);

5-{[4-hydroxy-1-(1H-indole-4-carbonyl)piperidin-4-yl]methyl}-1-phenyl-1H,4H,5H-pyrazolo[3,4-d]pyrimidin-4-one (I-247);

5-{[1-(4,4-dimethylpentanoyl)-4-hydroxypiperidin-4-yl]methyl}-1-phenyl-1H,4H,5H-pyrazolo[3,4-d]pyrimidin-4-one (I-248), 5-{[4-hydroxy-1-(oxane-4-carbonyl)piperidin-4-yl]methyl}-1-phenyl-1H,4H, 5H-pyrazolo[3,4-d]pyrimidin-4-one (I-249);

1-(4-tert-butylphenyl)-5-[(1-cyclopropanecarbonyl-4-hydroxypiperidin-4-yl)methyl]-1H,4H,5H-pyrazolo[3,4-d]pyrimidin-4-one (I-25);

5-{[4-hydroxy-1-(1-methyl-1H-pyrrole-2-carbonyl)piperidin-4-yl]methyl}-1-phenyl-1H,4H,5H-pyrazolo[3,4-d]pyrimidin-4-one (I-250);

5-{[1-(3,3-difluorocyclobutanecarbonyl)-4-hydroxypiperidin-4-yl]methyl}-1-phenyl-1H,4H,5H-pyrazolo[3,4-d]pyrimidin-4-one (I-251);

5-{[4-hydroxy-1-(2-phenyl-1,3-oxazole-5-carbonyl)piperidin-4-yl]methyl}-1-phenyl-1H,4H,5H-pyrazolo[3,4-d]pyrimidin-4-one (I-252);

N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]prop-2-ynamide (I-259);

5-[(1-cyclopropanecarbonyl-4-hydroxypiperidin-4-yl)methyl]-1-(2,4,6-trimethylphenyl)-1H,4H,5H-pyrazolo[3,4-d]pyrimidin-4-one (I-26);

5-[(1-cyclopropanecarbonyl-4-hydroxypiperidin-4-yl)methyl]-1-(2,4-dichlorophenyl)-1H,4H,5H-pyrazolo[3,4-d]pyrimidin-4-one (I-264);

5-[(1-benzoyl-4-hydroxypiperidin-4-yl)methyl]-1-(4-fluorophenyl)-1H,4H,5H-pyrazolo[3,4-d]pyrimidin-4-one (I-266);

1-(4-fluorophenyl)-5-{[4-hydroxy-1-(4-methoxybenzoyl)piperidin-4-yl]methyl}-1H,4H,5H-pyrazolo[3,4-d]pyrimidin-4-one (I-267);

5-{[1-(4-fluorobenzoyl)-4-hydroxypiperidin-4-yl]methyl}-1-(4-fluorophenyl)-1H,4H,5H-pyrazolo[3,4-d]pyrimidin-4-one (I-268);

5-[(1-cyclopropanecarbonyl-4-hydroxypiperidin-4-yl)methyl]-1-[4-(propan-2-yl)phenyl]-1H,4H,5H-pyrazolo[3,4-d]pyrimidin-4-one (I-27);

5-{[4-hydroxy-1-(1-methylcyclopropanecarbonyl)piperidin-4-yl]methyl}-1-phenyl-1H,4H,5H-pyrazolo[3,4-d]pyrimidin-4-one (I-271);

4-[4-hydroxy-4-({4-oxo-1-phenyl-1H,4H,5H-pyrazolo[3,4-d]pyrimidin-5-yl}methyl)piperidine-1-carbonyl]benzoic acid (I-272);

5-({4-hydroxy-1-[4-(trifluoromethoxy)benzoyl]piperidin-4-yl}methyl)-1-phenyl-1H,4H,5H-pyrazolo[3,4-d]pyrimidin-4-one (I-273);

5-({1-[4-(difluoromethoxy)benzoyl]-4-hydroxypiperidin-4-yl}methyl)-1-phenyl-1H,4H,5H-pyrazolo[3,4-d]pyrimidin-4-one (I-274);

5-[(1-cyclopropanecarbonyl-4-hydroxypiperidin-4-yl)methyl]-1-(4-phenylphenyl)-1H,4H,5H-pyrazolo[3,4-d]pyrimidin-4-one (I-276);

5-({4-hydroxy-1-[1-(trifluoromethyl)cyclopropanecarbonyl]piperidin-4-yl}methyl)-1-phenyl-1H,4H,5H-pyrazolo[3,4-d]pyrimidin-4-one (I-277);

4-{[1-(4-fluorophenyl)-4-oxo-1H,4H,5H-pyrazolo[3,4-d]pyrimidin-5-yl]methyl)-4-hydroxy-N,N-dimethylpiperidine-1-carboxamide (I-279);

5-[(1-cyclopropanecarbonyl-4-hydroxypiperidin-4-yl)methyl]-1-[4-(trifluoromethyl)phenyl]-1H,4H,5H-pyrazolo[3,4-d]pyrimidin-4-one (I-28);

5-{[1-(4-chlorobenzoyl)-4-hydroxypiperidin-4-yl]methyl}-1-phenyl-1H,4H,5H-pyrazolo[3,4-d]pyrimidin-4-one (I-280);

5-[(1-benzoyl-4-hydroxypiperidin-4-yl)methyl]-1-[3-(hydroxymethyl)phenyl]-1H,4H,5H-pyrazolo[3,4-d]pyrimidin-4-one (I-281);

5-{[1-(4-chloroquinoline-7-carbonyl)-4-hydroxypiperidin-4-yl]methyl}-1-phenyl-1H,4H,5H-pyrazolo[3,4-d]pyrimidin-4-one (I-282);

5-{[1-(4-cyclopropoxybenzoyl)-4-hydroxypiperidin-4-yl]methyl}-1-(4-fluorophenyl)-1H,4H,5H-pyrazolo[3,4-d]pyrimidin-4-one (I-283), 4-{[1-(4-fluorophenyl)-4-oxo-1H,4H,5H-pyrazolo[3,4-d]pyrimidin-5-yl]methyl}-4-hydroxy-N-methylpiperidine-1-carboxamide (I-284);

5-{[1-(2-chloropyridine-4-carbonyl)-4-hydroxypiperidin-4-yl]methy1}-1-phenyl-1H,4H,5H-pyrazolo[3,4-d]pyrimidin-4-one (I-287);

5-{[1-(2,5-dichloropyridine-4-carbonyl)-4-hydroxypiperidin-4-yl]methyl}-1-phenyl-1H,4H,5H-pyrazolo[3,4-d]pyrimidin-4-one (I-288);

5-[(1-{bicyclo[1.1.1]pentane-1-carbonyl}-4-hydroxypiperidin-4-yl)methyl]-1-phenyl-1H,4H,5H-pyrazolo[3,4-d]pyrimidin-4-one (I-289);

1-cyclohexyl-5-[(1-cyclopropanecarbonyl-4-hydroxypiperidin-4-yl)methyl]-1H,4H,5H-pyrazolo[3,4-d]pyrimidin-4-one (I-29);

5-({4-hydroxy-1-[3-(trifluoromethyl)bicyclo[1.1.1]pentane-1-carbonyl]piperidin-4-yl}methyl)-1-phenyl-1H,4H,5H-pyrazolo[3,4-d]pyrimidin-4-one (I-290);

5-({4-hydroxy-1-[4-(1,1,1-trifluoro-2-hydroxypropan-2-yl)benzoyl]piperidin-4-yl}methyl)-1-phenyl-1H,4H,5H-pyrazolo[3,4-d]pyrimidin-4-one (I-291);

2-cyano-N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]acetamide (I-292);

5-({1-[4-(1,1-difluoroethyl)benzoyl]-4-hydroxypiperidin-4-yl}methyl)-1-phenyl-1H,4H,5H-pyrazolo[3,4-d]pyrimidin-4-one (I-294);

5-[(1-cyclopropanecarbonyl-4-hydroxypiperidin-4-yl)methyl]-1-(4-phenoxyphenyl)-1H,4H,5H-pyrazolo[3,4-d]pyrimidin-4-one (I-296);

5-({4-hydroxy-1-[4-(4-methylphenoxy)benzoyl]piperidin-4-yl}methyl)-1-methyl-1H,4H,5H-pyrazolo[3,4-d]pyrimidin-4-one (I-3);

5-[(1-cyclopropanecarbonyl-4-hydroxypiperidin-4-yl)methyl]-1-(pyridin-3-yl)-1H,4H,5H-pyrazolo[3,4-d]pyrimidin-4-one (I-30);

5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one, Enantiomer A (I-301a), 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one, Enantiomer B (I-301b);

5-{[1-(4-chlorobenzoyl)-4-hydroxypiperidin-4-yl]methyl}-1-(4-fluorophenyl)-1H,4H,5H-pyrazolo[3,4-d]pyrimidin-4-one (I-302);

5-{[1-(3-chlorobenzoyl)-4-hydroxypiperidin-4-yl]methyl}-1-(4-fluorophenyl)-1H,4H,5H-pyrazolo[3,4-d]pyrimidin-4-one (I-303);

5-{[1-(4-cyclopropylbenzoyl)-4-hydroxypiperidin-4-yl]methyl}-1-(4-fluorophenyl)-1H, 5H-pyrazolo[3,4-d]pyrimidin-4-one (I-304);

5-{[1-(3-chloro-1-methyl-1H-pyrazole-4-carbonyl)-4-hydroxypiperidin-4-yl]methyl}-1-phenyl-1H,4H,5H-pyrazolo[3,4-d]pyrimidin-4-one (I-305);

5-({1-[4-(difluoromethoxy)benzoyl]-4-hydroxypiperidin-4-yl}methyl)-1-(4-fluorophenyl)-1H,4H,5H-pyrazolo[3,4-d]pyrimidin-4-one (I-306);

1-(4-fluorophenyl)-5-{[4-hydroxy-1-(4-methylbenzoyl)piperidin-4-yl]methyl)-1H,4H,5H-pyrazolo[3,4-d]pyrimidin-4-one (I-307);

5-{[1-(3-fluoro-4-methoxybenzoyl)-4-hydroxypiperidin-4-yl]methyl}-1-(4-fluorophenyl)-1H,4H,5H-pyrazolo[3,4-d]pyrimidin-4-one (I-308);

5-{[1-(3,4-difluorobenzoyl)-4-hydroxypiperidin-4-yl]methyl}-1-(4-fluorophenyl)-1H,4H,5H-pyrazolo[3,4-d]pyrimidin-4-one (I-309);

5-[(1-cyclopropanecarbonyl-4-hydroxypiperidin-4-yl)methyl]-1-(4-methanesulfonylphenyl)-1H,4H,5H-pyrazolo[3,4-d]pyrimidin-4-one (I-31);

5-{[1-(2,4-difluorobenzoyl)-4-hydroxypiperidin-4-yl]methyl}-1-(4-fluorophenyl)-1H,4H,5H-pyrazolo[3,4-d]pyrimidin-4-one (I-310);

5-{[1-(3-chloro-4-methoxybenzoyl)-4-hydroxypiperidin-4-yl]methyl}-1-(4-fluorophenyl)-1H,4H,5H-pyrazolo[3,4-d]pyrimidin-4-one (I-311);

1-(4-fluorophenyl)-5-{[4-hydroxy-1-(4-methyl-1,3-oxazole-5-carbonyl)piperidin-4-yl]methyl}-1H,4H,5H-pyrazolo[3,4-d]pyrimidin-4-one (I-312);

5-{[1-(dimethyl-1,3-oxazole-5-carbonyl)-4-hydroxypiperidin-4-yl]methyl}-1-(4-fluorophenyl)-1H,4H,5H-pyrazolo[3,4-d]pyrimidin-4-one (I-313);

5-{[1-(2-cyclopropyl-1,3-oxazole-5-carbonyl)-4-hydroxypiperidin-4-yl]methyl}-1-(4-fluorophenyl)-1H,4H,5H-pyrazolo[3,4-d]pyrimidin-4-one (I-314);

5-({1-[2-(dimethylamino)-1,3-oxazole-5-carbonyl]-4-hydroxypiperidin-4-yl}methyl)-1-(4-fluorophenyl)-1H,4H,5H-pyrazolo[3,4-d]pyrimidin-4-one (I-315);

5-[(1-benzoyl-4-hydroxypiperidin-4-yl)methyl]-1-(4-phenoxyphenyl)-1H,4H,5H-pyrazolo[3,4-d]pyrimidin-4-one (I-316);

5-{[1-(2,4-dichlorobenzoyl)-4-hydroxypiperidin-4-yl]methyl}-1-(4-fluorophenyl)-1H,4H,5H-pyrazolo[3,4-d]pyrimidin-4-one (I-317);

5-[(1-cyclopropanecarbonyl-4-hydroxypiperidin-4-yl)methyl]-1-(pyridin-4-yl)-1H,4H,5H-pyrazolo[3,4-d]pyrimidin-4-one (I-32);

5-[(1-cyclopropanecarbonyl-4-hydroxypiperidin-4-yl)methyl]-1-(3,4-dichlorophenyl)-1H,4H,5H-pyrazolo[3,4-d]pyrimidin-4-one (I-33);

5-[(1-cyclopropanecarbonyl-4-hydroxypiperidin-4-yl)methyl]-1-[4-(3-fluorophenyl)phenyl]-1H,4H,5H-pyrazolo[3,4-d]pyrimidin-4-one (I-330);

4-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzamide (I-332);

5-[(1-cyclopropanecarbonyl-4-hydroxypiperidin-4-yl)methyl]-1-{4-[4-(pyrrolidine-1-carbonyl)phenyl]phenyl}-1H,4H,5H-pyrazolo[3,4-d]pyrimidin-4-one (I-333);

5-[(1-cyclopropanecarbonyl-4-hydroxypiperidin-4-yl)methyl]-1-[4-(3,4-dimethoxyphenyl)phenyl]-1H,4H,5H-pyrazolo[3,4-d]pyrimidin-4-one (I-334);

5-[(1-cyclopropanecarbonyl-4-hydroxypiperidin-4-yl)methyl]-1-[4-(2,4-difluorophenyl)phenyl]-1H,4H,5H-pyrazolo[3,4-d]pyrimidin-4-one (I-335);

5-[(1-cyclopropanecarbonyl-4-hydroxypiperidin-4-yl)methyl]-1-[4-(3,5-difluorophenyl)phenyl]-1H,4H,5H-pyrazolo[3,4-d]pyrimidin-4-one (I-337);

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile (I-339);

5-[(1-cyclopropanecarbonyl-4-hydroxypiperidin-4-yl)methyl]-1-[3-(trifluoromethyl)phenyl]-1H,4H,5H-pyrazolo[3,4-d]pyrimidin-4-one (I-34);

4-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile (I-340);

5-[(1-cyclopropanecarbonyl-4-hydroxypiperidin-4-yl)methyl]-1-[3-(4-methoxyphenyl)phenyl]-1H,4H,5H-pyrazolo[3,4-d]pyrimidin-4-one (I-342);

5-[(1-cyclopropanecarbonyl-4-hydroxypiperidin-4-yl)methyl]-1-[3-(3-phenylphenyl)phenyl]-1H,4H,5H-pyrazolo[3,4-d]pyrimidin-4-one (I-344);

1-[3-(2-chlorophenyl)phenyl]-5-[(1-cyclopropanecarbonyl-4-hydroxypiperidin-4-yl)methyl]-1H,4H,5H-pyrazolol[3,4-d]pyrimidin-4-one (I-345);

5-[(1-cyclopropanecarbonyl-4-hydroxypiperidin-4-yl)methyl]-1-[3-(3-fluorophenyl)phenyl]-1H,4H,5H-pyrazolo[3,4-d]pyrimidin-4-one (I-346);

1-[3-(3-chlorophenyl)phenyl]-5-[(1-cyclopropanecarbonyl-4-hydroxypiperidin-4-yl)methyl]-1H,4H,5H-pyrazolo[3,4-d]pyrimidin-4-one (I-347);

5-[(1-cyclopropanecarbonyl-4-hydroxypiperidin-4-yl)methyl]-1-[3-(4-fluorophenyl)phenyl]-1H,4H,5H-pyrazolo[3,4-d]pyrimidin-4-one (I-348);

5-[(1-cyclopropanecarbonyl-4-hydroxypiperidin-4-yl)methyl]-1-[3-(4-methanesulfonylphenyl)phenyl]-1H,4H,5H-pyrazolo[3,4-d]pyrimidin-4-one (I-349), 1-(4-chlorophenyl)-5-[(1-cyclopropanecarbonyl-4-hydroxypiperidin-4-yl)methyl]-1H,4H,5H-pyrazolo[3,4-d]pyrimidin-4-one (I-35);

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzamide (I-350);

5-[(1-cyclopropanecarbonyl-4-hydroxypiperidin-4-yl)methyl]-1-{3-[4-(pyrrolidine-1-carbonyl)phenyl]phenyl)-1H,4H,5H-pyrazolo[3,4-d]pyrimidin-4-one (I-351);

5-[(1-cyclopropanecarbonyl-4-hydroxypiperidin-4-yl)methyl]-1-[3-(3,4-dimethoxyphenyl)phenyl]-1H,4H,5H-pyrazolo[3,4-d]pyrimidin-4-one (I-352);

5-[(1-cyclopropanecarbonyl-4-hydroxypiperidin-4-yl)methyl]-1-[3-(2,4-difluorophenyl)phenyl]-1H,4H,5H-pyrazolo[3,4-d]pyrimidin-4-one (I-354);

5-[(1-cyclopropanecarbonyl-4-hydroxypiperidin-4-yl)methyl]-1-[3-(3,4-difluorophenyl)phenyl]-1H,4H,5H-pyrazolo[3,4-d]pyrimidin-4-one (I-355);

5-[(1-cyclopropanecarbonyl-4-hydroxypiperidin-4-yl)methyl]-1-[3-(3,5-difluorophenyl)phenyl]-1H,4H,5H-pyrazolo[3,4-d]pyrimidin-4-one (I-357);

3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile (I-359);

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile (I-360);

5-[(1-cyclopropanecarbonyl-4-hydroxypiperidin-4-yl)methyl]-1-{4-[3-(dimethylamino)phenyl]phenyl)-1H,4H,5H-pyrazolo[3,4-d]pyrimidin-4-one (I-361);

5-[(1-cyclopropanecarbonyl-4-hydroxypiperidin-4-yl)methyl]-1-{4-[2-methyl-4-(1H-pyrazol-1-yl)phenyl]phenyl)-1H,4H,5H-pyrazolo[3,4-d]pyrimidin-4-one (I-363), 5-[(1-cyclopropanecarbonyl-4-hydroxypiperidin-4-yl)methyl]-1-[4-(dimethyl-1,2-oxazol-4-yl)phenyl]-1H,4H,5H-pyrazolo[3,4-d]pyrimidin-4-one (I-364);

5-[(1-cyclopropanecarbonyl-4-hydroxypiperidin-4-yl)methyl]-1-[4-(pyridin-3-yl)phenyl]-1H,4H,5H-pyrazolo[3,4-d]pyrimidin-4-one (I-365);

5-[(1-cyclopropanecarbonyl-4-hydroxypiperidin-4-yl)methyl]-1-[4-(pyrimidin-5-yl)phenyl]-1H,4H,5H-pyrazolo[3,4-d]pyrimidin-4-one (I-366);

5-[(1-cyclopropanecarbonyl-4-hydroxypiperidin-4-yl)methyl]-1-[4-(1-methyl-1H-pyrazol-4-yl)phenyl]-1H,4H,5H-pyrazolo[3,4-d]pyrimidin-4-one (I-367);

5-[(1-cyclopropanecarbonyl-4-hydroxypiperidin-4-yl)methyl]-1-(4-{4-[2-(morpholin-4-yl)ethoxy]phenyl}phenyl)-1H,4H,5H-pyrazolo[3,4-d]pyrimidin-4-one (I-368);

5-[(1-cyclopropanecarbonyl-4-hydroxypiperidin-4-yl)methyl]-1-(4-{4-[2-(dimethylamino)ethoxy]phenyl}phenyl)-1H,4H,5H-pyrazolo[3,4-d]pyrimidin-4-one (I-369);

N-[2-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)phenyl]methanesulfonamide (I-370);

5-[(1-cyclopropanecarbonyl-4-hydroxypiperidin-4-yl)methyl]-1-[4-(2-methanesulfonylphenyl)phenyl]-1H,4H,5H-pyrazolo[3,4-d]pyrimidin-4-one (I-371);

5-[(1-cyclopropanecarbonyl-4-hydroxypiperidin-4-yl)methyl]-1-[4-(3-hydroxyphenyl)phenyl]-1H,4H,5H-pyrazolo[3,4-d]pyrimidin-4-one (I-372);

5-[(1-cyclopropanecarbonyl-4-hydroxypiperidin-4-yl)methyl]-1-[4-(5-fluoropyridin-3-yl)phenyl]-1H,4H,5H-pyrazolo[3,4-d]pyrimidin-4-one (I-373);

5-[(1-cyclopropanecarbonyl-4-hydroxypiperidin-4-yl)methyl]-1-(3-[3-(dimethylamino)phenyl]phenyl)-1H,4H,5H-pyrazolo[3,4-d]pyrimidin-4-one (I-374);

5-[(1-cyclopropanecarbonyl-4-hydroxypiperidin-4-yl)methyl]-1-{3-[4-(dimethylamino)phenyl]phenyl)-1H,4H,5H-pyrazolo[3,4-d]pyrimidin-4-one (I-375);

5-[(1-cyclopropanecarbonyl-4-hydroxypiperidin-4-yl)methyl]-1-[3-(dimethyl-1,2-oxazol-4-yl)phenyl]-1H,4H,5H-pyrazolo[3,4-d]pyrimidin-4-one (I-377);

5-[(1-cyclopropanecarbonyl-4-hydroxypiperidin-4-yl)methyl]-1-[3-(pyridin-3-yl)phenyl]-1H,4H,5H-pyrazolo[3,4-d]pyrimidin-4-one (I-378);

5-[(1-cyclopropanecarbonyl-4-hydroxypiperidin-4-yl)methyl]-1-[3-(pyrimidin-5-yl)phenyl]-1H,4H,5H-pyrazolo[3,4-d]pyrimidin-4-one (I-379);

5-[(1-cyclopropanecarbonyl-4-hydroxypiperidin-4-yl)methyl]-1-(4-fluorophenyl)-1H,4H,5H-pyrazolo[3,4-d]pyrimidin-4-one (I-38);

5-[(1-cyclopropanecarbonyl-4-hydroxypiperidin-4-yl)methyl]-1-[3-(1-methyl-1H-pyrazol-4-yl)phenyl]-1H,4H,5H-pyrazolo[3,4-d]pyrimidin-4-one (I-380);

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N-methylbenzamide (I-381);

5-[(1-cyclopropanecarbonyl-4-hydroxypiperidin-4-yl)methyl]-1-{3-[5-hydroxy-2-(trifluoromethoxy)phenyl]phenyl)-1H,4H,5H-pyrazolo[3,4-d]pyrimidin-4-one (I-382);

N-[2-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)phenyl]methanesulfonamide (I-383);

5-[(1-cyclopropanecarbonyl-4-hydroxypiperidin-4-yl)methyl]-1-[3-(2-methanesulfonylphenyl)phenyl]-1H,4H,5H-pyrazolo[3,4-d]pyrimidin-4-one (I-384);

5-[(1-cyclopropanecarbonyl-4-hydroxypiperidin-4-yl)methyl]-1-[3-(3-hydroxyphenyl)phenyl]-1H,4H,5H-pyrazolo[3,4-d]pyrimidin-4-one (I-385);

5-[(1-cyclopropanecarbonyl-4-hydroxypiperidin-4-yl)methyl]-1-{3-[6-(dimethylamino)pyridin-3-yl]phenyl)-1H,4H,5H-pyrazolo[3,4-d]pyrimidin-4-one (I-386

5-[(1-cyclopropanecarbonyl-4-hydroxypiperidin-4-yl)methyl]-1-[3-(5-fluoropyridin-3-yl)phenyl]-1H,4H,5H-pyrazolo[3,4-d]pyrimidin-4-one (I-387);

5-[(1-cyclopropanecarbonyl-4-hydroxypiperidin-4-yl)methyl]-1-{4-[3-(morpholine-4-carbonyl)phenyl]phenyl)-1H,4H,5H-pyrazolo[3,4-d]pyrimidin-4-one (I-388);

5-[(1-cyclopropanecarbonyl-4-hydroxypiperidin-4-yl)
methyl]-1-[4-(3,5-dimethyl-1H-pyrazol-4-yl)phenyl]-
1H,4H,5H-pyrazolo[3,4-d]pyrimidin-4-one (I-389), 5-[(1-cyclopropanecarbonyl-4-hydroxypiperidin-4-yl)
methyl]-1-{4-[5-fluoro-2-(hydroxymethyl)phenyl]phe-
nyl)-1H,4H,5H-pyrazolo[3,4-d]pyrimidin-4-one
(I-390);

5-[(1-cyclopropanecarbonyl-4-hydroxypiperidin-4-yl)
methyl]-1-[4-(3-fluoro-5-methoxyphenyl)phenyl]-1H,
4H,5H-pyrazolo[3,4-d]pyrimidin-4-one (I-391);

3-(4-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzamide-1-sulfona-
mide (I-392);

3-(4-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzamide (I-394);

3-(4-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N-(2-hydroxyethyl)benzamide
(I-395);

5-[(1-cyclopropanecarbonyl-4-hydroxypiperidin-4-yl)
methyl]-1-[4-(1-methyl-1H-indazol-5-yl)phenyl]-1H,
4H,5H-pyrazolo[3,4-d]pyrimidin-4-one (I-396);

5-[(1-cyclopropanecarbonyl-4-hydroxypiperidin-4-yl)
methyl]-1-{4-[3-(cyclopropylmethoxy)phenyl]phe-
nyl)-1H,4H,5H-pyrazolo[3,4-d]pyrimidin-4-one
(I-397);

5-[(1-cyclopropanecarbonyl-4-hydroxypiperidin-4-yl)
methyl]-1-{4-[3-(pyrolidin-1-yl)phenyl]phenyl)-1H,
4H,5H-pyrazolo[3,4-d]pyrimidin-4-one (I-399);

4-hydroxy-N-methyl-4-({1-methyl-4-oxo-1H,4H,5H-
pyrazolo[3,4-d]pyrimidin-5-yl}methyl)-N-(4-phe-
nylphenyl)piperidine-1-carboxamide (I-4);

N-[(1r,3r)-3-[4-hydroxy-4-({4-oxo-1-phenyl-1H,4H,5H-
pyrazolo[3,4-d]pyrimidin-5-yl}methyl)piperidine-1-
carbonyl]cyclobutyl]ethane-1-sulfonamide (I-40);

5-[(1-cyclopropanecarbonyl-4-hydroxypiperidin-4-yl)
methyl]-1-{3-[2-(dimethylamino)pyrimidin-5-yl]phe-
nyl)-1H,4H,5H-pyrazolo[3,4-d]pyrimidin-4-one
(I-400);

5-[(1-cyclopropanecarbonyl-4-hydroxypiperidin-4-yl)
methyl]-1-{3-[2-(morpholin-4-yl)pyrimidin-5-yl]phe-
nyl)-1H,4H,5H-pyrazolo[3,4-d]pyrimidin-4-one
(I-401);

1-[3-(5-chloropyridin-3-yl)phenyl]-5-[(1-cyclopropan-
ecarbonyl-4-hydroxypiperidin-4-yl)methyl]-1H,4H,
5H-pyrazolo[3,4-d]pyrimidin-4-one (I-401);

5-[(1-cyclopropanecarbonyl-4-hydroxypiperidin-4-yl)
methyl]-1-{3-[3-(morpholine-4-carbonyl)phenyl]phe-
nyl)-1H,4H,5H-pyrazolo[3,4-d]pyrimidin-4-one
(I-402);

5-[(1-cyclopropanecarbonyl-4-hydroxypiperidin-4-yl)
methyl]-1-{3-[5-fluoro-2-(hydroxymethyl)phenyl]phe-
nyl)-1H,4H,5H-pyrazolo[3,4-d]pyrimidin-4-one
(I-403);

5-[(1-cyclopropanecarbonyl-4-hydroxypiperidin-4-yl)
methyl]-1-[3-(3-fluoro-5-methoxyphenyl)phenyl]-1H,
4H,5H-pyrazolo[3,4-d]pyrimidin-4-one (I-404);

3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzene-1-sulfona-
mide (I-405);

5-[(1-cyclopropanecarbonyl-4-hydroxypiperidin-4-yl)
methyl]-1-[3-(1H-indol-4-yl)phenyl]-1H,4H,5H-pyra-
zolo[3,4-d]pyrimidin-4-one (I-406);

3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzamide (I-407);

3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N-methylbenzamide (I-408);

3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N-(2-hydroxyethyl)benzamide
(I-409);

5-[(1-cyclopropanecarbonyl-4-hydroxypiperidin-4-yl)
methyl]-1-[3-(1-methyl-1H-indazol-5-yl)phenyl]-1H,
4H,5H-pyrazolo[3,4-d]pyrimidin-4-one (I-410);

5-[(1-cyclopropanecarbonyl-4-hydroxypiperidin-4-yl)
methyl]-1-{3-[3-(cyclopropylmethoxy)phenyl]phe-
nyl)-1H,4H,5H-pyrazolo[3,4-d]pyrimidin-4-one
(I-411);

5-[(1-cyclopropanecarbonyl-4-hydroxypiperidin-4-yl)
methyl]-1-{3-[3-(pyrrolidin-1-yl)phenyl]phenyl)-1H,
4H,5H-pyrazolo[3,4-d]pyrimidin-4-one (I-413);

5-[(1-cyclopropanecarbonyl-4-hydroxypiperidin-4-yl)
methyl]-1-[3-(morpholin-4-ylmethyl)phenyl]-1H,4H,
5H-pyrazolo[3,4-d]pyrimidin-4-one (I-415);

1-(4-{[cyclohexyl(ethyl)amino]methyl}phenyl)-5-[(1-cy-
clopropanecarbonyl-4-hydroxypiperidin-4-yl)methyl]-
1H,4H,5H-pyrazolo[3,4-d]pyrimidin-4-one (I-416);

5-[(1-cyclopropanecarbonyl-4-hydroxypiperidin-4-yl)
methyl]-1-[4-(morpholin-4-ylmethyl)phenyl]-1H,4H,
5H-pyrazolo[3,4-d]pyrimidin-4-one (I-417);

1-(4-fluorophenyl)-5-{[4-hydroxy-1-(pyridine-4-carbo-
nyl)piperidin-4-yl]methyl}-1H,4H,5H-pyrazolo[3,4-d]
pyrimidin-4-one (I-418);

1-(4-fluorophenyl)-5-({4-hydroxy-1-[6-(morpholin-4-yl)
pyridine-3-carbonyl]piperidin-4-yl}methyl)-1H,4H,
5H-pyrazolo[3,4-d]pyrimidin-4-one (I-419);

1-(4-fluorophenyl)-5-({4-hydroxy-1-[6-(2,2,2-
trifluoroethoxy}pyridine-3-carbonyl]piperidin-4-
yl}methyl)-1H,4H,5H-pyrazolo[3,4-d]pyrimidin-4-one
(I-420);

1-(4-fluorophenyl)-5-{[4-hydroxy-1-(pyri dine-3-carbo-
nyl)piperidin-4-yl]methyl}-1H,4H,5H-pyrazolo[3,4-d]
pyrimidin-4-one (I-421);

1-(4-fluorophenyl)-5-({4-hydroxy-1-[6-(trifluoromethyl)
pyridine-3-carbonyl]piperidin-4-yl}methyl)-1H,4H,
5H-pyrazolo[3,4-d]pyrimidin-4-one (I-422);

1-(4-fluorophenyl)-5-({4-hydroxy-1-[3-(trifluoromethyl)
bicyclo[1.1.1]pentane-1-carbonyl]piperidin-4-
yl}methyl)-1-1H,4H, 5H-pyrazolo[3,4-d]pyrimidin-4-
one (I-423);

4-hydroxy-N-methyl-4-{[4-oxo-1-(4-phenylphenyl)-1H,
4H,5H-pyrazolo[3,4-d]pyrimidin-5-yl]methyl)piperi-
dine-1-carboxamide (I-425);

5-{[(3S,4S)-1-benzoyl-3-fluoro-4-hydroxypiperidin-4-yl]
methyl}-1-phenyl-1H,4H,5H-pyrazolo[3,4-d]pyrimi-
din-4-one (I-426);

5-[(1-cyclopropanecarbonyl-4-hydroxypiperidin-4-yl)
methyl]-1-[4-({[2-(dimethylamino)ethyl](methyl)
amino}methyl)phenyl]-1H,4H,5H-pyrazolo[3,4-d]py-
rimidin-4-one (I-427);

N-{1-[(4-{5-[(1-cyclopropanecarbonyl-4-hydroxypiperi-
din-4-yl)methyl]-4-oxo-1H,4H,5H-pyrazolo[3,4-d]py-
rimidin-1-yl}phenyl)methyl]piperidin-4-yl}acetamide
(I-428);

5-[(1-cyclopropanecarbonyl-4-hydroxypiperidin-4-yl)
methyl]-1-[4-(pyrrolidin-1-ylmethyl)phenyl]-1H,4H,
5H-pyrazolo[3,4-d]pyrimidin-4-one (I-430);

5-[(1-cyclopropanecarbonyl-4-hydroxypiperidin-4-yl)methyl]-1-[4-(piperidin-1-ylmethyl)phenyl]-1H,4H,5H-pyrazolo[3,4-d]pyrimidin-4-one (I-431);

1-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]piperidine-4-carbonitrile (I-432);

1-(4-{[benzyl(methyl)amino]methyl}phenyl)-5-[(1-cyclopropanecarbonyl-4-hydroxypiperidin-4-yl)methyl]-1H,4H,5H-pyrazolo[3,4-d]pyrimidin-4-one (I-433), 5-[(1-cyclopropanecarbonyl-4-hydroxypiperidin-4-yl)methyl]-1-(4-{([(2-methoxyethyl)(methyl)amino]methyl}phenyl)-1H,4H,5H-pyrazolo[3,4-d]pyrimidin-4-one (I-434);

5-[(1-cyclopropanecarbonyl-4-hydroxypiperidin-4-yl)methyl]-1-(4-{[4-(dimethylamino)piperidin-1-yl]methyl}phenyl)-1H,4H,5H-pyrazolo[3,4-d]pyrimidin-4-one (I-435);

5-[(1-cyclopropanecarbonyl-4-hydroxypiperidin-4-yl)methyl]-1-(4-{[methyl(2-methylpropyl)amino]methyl}phenyl)-1H,4H,5H-pyrazolo[3,4-d]pyrimidin-4-one (I-436);

5-[(1-cyclopropanecarbonyl-4-hydroxypiperidin-4-yl)methyl]-1-[4-(1,2,3,4-tetrahydroisoquinolin-2-ylmethyl)phenyl]-1H,4H,5H-pyrazolo[3,4-d]pyrimidin-4-one (I-437);

1-{4-[(4-acetylpiperazin-1-yl)methyl]phenyl)-5-[(1-cyclopropanecarbonyl-4-hydroxypiperidin-4-yl)methyl]-1H,4H,5H-pyrazolo[3,4-d]pyrimidin-4-one (I-438);

4-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]-1$\lambda^6$,4-thiomorpholine-1,1-dione (I-439);

5-[(1R)-1-[1-(4-fluorobenzoyl)-4-hydroxypiperidin-4-yl]ethyl]-1-(4-fluorophenyl)-1H,4H,5H-pyrazolo[3,4-d]pyrimidin-4-one (I-44);

5-[(1-cyclopropanecarbonyl-4-hydroxypiperidin-4-yl)methyl]-1-[4-({[(6-ethylpyridin-3-yl)methyl](methyl)amino}methyl)phenyl]-1H,4H,5H-pyrazolo[3,4-d]pyrimidin-4-one (I-440);

2-{1-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]piperidin-3-yl}acetonitrile (I-441);

5-[(1-cyclopropanecarbonyl-4-hydroxypiperidin-4-yl)methyl]-1-(4-{[cyclopropyl(oxan-4-yl)amino]methyl}phenyl)-1H,4H,5H-pyrazolo[3,4-d]pyrimidin-4-one (I-442);

5-[(1-cyclopropanecarbonyl-4-hydroxypiperidin-4-yl)methyl]-1-(4-{8-oxa-2-azaspiro[4.5]decan-2-ylmethyl}phenyl)-1H,4H,5H-pyrazolo[3,4-d]pyrimidin-4-one (I-443);

5-[(1-cyclopropanecarbonyl-4-hydroxypiperidin-4-yl)methyl]-1-[3-(pyrrolidin-1-ylmethyl)phenyl]-1H,4H,5H-pyrazolo[3,4-d]pyrimidin-4-one (I-444);

5-[(1-cyclopropanecarbonyl-4-hydroxypiperidin-4-yl)methyl]-1-[3-(piperidin-1-ylmethyl)phenyl]-1H,4H,5H-pyrazolo[3,4-d]pyrimidin-4-one (I-445);

1-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]piperidine-4-carbonitrile (I-446);

1-(3-{[benzyl(methyl)amino]methyl}phenyl)-5-[(1-cyclopropanecarbonyl-4-hydroxypiperidin-4-yl)methyl]-1H,4H,5H-pyrazolo[3,4-d]pyrimidin-4-one (I-447);

5-[(1-cyclopropanecarbonyl-4-hydroxypiperidin-4-yl)methyl]-1-[3-({[2-(dimethylamino)ethyl](methyl)amino}methyl)phenyl]-1H,4H,5H-pyrazolo[3,4-d]pyrimidin-4-one (I-448);

5-[(1-cyclopropanecarbonyl-4-hydroxypiperidin-4-yl)methyl]-1-(3-{[(2-methoxyethyl)(methyl)amino]methyl}phenyl)-1H,4H,5H-pyrazolo[3,4-d]pyrimidin-4-one (I-449);

N-(2-{4-[4-hydroxy-4-({1-methyl-4-oxo-1H,4H,5H-pyrazolo[3,4-d]pyrimidin-5-yl}methyl)piperidine-1-carbonyl]phenyl}phenyl)ethene-1-sulfonamide (I-45);

N-{1-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]piperidin-4-yl}acetamide (I-450);

5-[(1-cyclopropanecarbonyl-4-hydroxypiperidin-4-yl)methyl]-1-(3-{[4-(dimethylamino)piperidin-1-yl]methyl}phenyl)-1H,4H,5H-pyrazolo[3,4-d]pyrimidin-4-one (I-451);

5-[(1-cyclopropanecarbonyl-4-hydroxypiperidin-4-yl)methyl]-1-(3-{[methyl(2-methylpropyl)amino]methyl}phenyl)-1H,4H, 5H-pyrazolo[3,4-d]pyrimidin-4-one (I-452);

5-[(1-cyclopropanecarbonyl-4-hydroxypiperidin-4-yl)methyl]-1-[3-(1,2,3,4-tetrahydroisoquinolin-2-ylmethyl)phenyl]-1H,4H,5H-pyrazolo[3,4-d]pyrimidin-4-one (I-453);

1-{3-[(4-acetylpiperazin-1-yl)methyl]phenyl}-5-[(1-cyclopropanecarbonyl-4-hydroxypiperidin-4-yl)methyl]-1H,4H,5H-pyrazolo[3,4-d]pyrimidin-4-one (I-454);

4-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]-1$\lambda^6$,4-thiomorpholine-1,1-dione (I-455);

2-{1-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methyl]piperidin-3-yl}acetonitrile (I-456);

5-[(1-cyclopropanecarbonyl-4-hydroxypiperidin-4-yl)methyl]-1-(3-{8-oxa-2-azaspiro[4.5]decan-2-ylmethyl}phenyl)-1H,4H,5H-pyrazolo[3,4-d]pyrimidin-4-one (I-457);

1-(4-fluorophenyl)-5-({4-hydroxy-1-[2-(oxan-4-yl)acetyl]piperidin-4-yl}methyl)-1H,4H,5H-pyrazolo[3,4-d]pyrimidin-4-one (I-458);

1-(4-fluorophenyl)-5-{[4-hydroxy-1-(2-methoxyacetyl)piperidin-4-yl]methyl}-1H,4H,5H-pyrazolo[3,4-d]pyrimidin-4-one (I-459);

N-[(2R)-1-[4-hydroxy-4-({1-methyl-4-oxo-1H,4H,5H-pyrazolo[3,4-d]pyrimidin-5-yl}methyl)piperidin-1-yl]-1-oxo-3-phenylpropan-2-yl]ethene-1-sulfonamide (I-46);

3-[1-(4-{[1-(4-fluorophenyl)-4-oxo-1H,4H,5H-pyrazolo[3,4-d]pyrimidin-5-yl]methyl}-4-hydroxypiperidin-1-yl}-1-oxopropan-2-yl]-1,3-oxazolidin-2-one (I-461);

5-{[1-(4,4-difluorocyclohexanecarbonyl)-4-hydroxypiperidin-4-yl]methyl}-1-(4-fluorophenyl)-1H,4H,5H-pyrazolo[3,4-d]pyrimidin-4-one (I-462);

5-{([1-(2-cyclopropylacetyl)-4-hydroxypiperidin-4-yl]methyl}-1-(4-fluorophenyl)-1H,4H, 5H-pyrazolo[3,4-d]pyrimidin-4-one (I-463);

1-(4-fluorophenyl)-5-{[4-hydroxy-1-(1-methylcyclobutanecarbonyl)piperidin-4-yl]methyl}-1H,4H,5H-pyrazolo[3,4-d]pyrimidin-4-one (I-464);

1-(4-fluorophenyl)-5-{[4-hydroxy-1-(6-methoxypyridine-3-carbonyl)piperidin-4-yl]methyl}-1H,4H,5H-pyrazolo[3,4-d]pyrimidin-4-one (I-465);

1-(4-fluorophenyl)-5-{[1-(6-fluoropyridine-3-carbonyl)-4-hydroxypiperidin-4-yl]methyl}-1H,4H,5H-pyrazolo[3,4-d]pyrimidin-4-one (I-466);

5-({4-hydroxy-1-[4-((1-hydroxycyclopropyl)benzoyl]piperidin-4-yl}methyl)-1-phenyl-1H,4H,5H-pyrazolo[3,4-d]pyrimidin-4-one (I-467);

1-(4-fluorophenyl)-5-({4-hydroxy-1-[4-(1-hydroxycyclopropyl)benzoyl]piperidin-4-yl}methyl)-1H,4H,5H-pyrazolo[3,4-d]pyrimidin-4-one (I-468);

5-{[(3R,4S)-1-benzoyl-3-fluoro-4-hydroxypiperidin-4-yl]methyl}-1-phenyl-1H,4H,5H-pyrazolo[3,4-d]pyrimidin-4-one (I-469);

5-{[1-(3-chloro-1H-pyrazole-4-carbonyl)-4-hydroxypiperidin-4-yl]methyl}-1-phenyl-1H,4H,5H-pyrazolo[3,4-d]pyrimidin-4-one (I-47);

4-hydroxy-N-methyl-4-{[4-oxo-1-(6-phenylpyridin-3-yl}-1H,4H,5H-pyrazolo[3,4-d]pyrimidin-5-yl]methyl)piperidine-1-carboxamide (I-470);

1-[3-(Cyclopentylamino)phenyl]-5-[(1-cyclopropanecarbonyl-4-hydroxypiperidin-4-yl)methyl]-1H,4H,5H-pyrazolo[3,4-d]pyrimidin-4-one (I-471);

5-[(1-Cyclopropanecarbonyl-4-hydroxypiperidin-4-yl)methyl]-1-[3-(morpholin-4-yl)phenyl]-1H,4H,5H-pyrazolo[3,4-d]pyrimidin-4-one (I-472);

1-(4-Fluorophenyl)-5-[(4-hydroxy-1-{8-oxabicyclo[3.2.1]octane-3-carbonyl}piperidin-4-yl)methyl]-1H,4H,5H-pyrazolo[3,4-d]pyrimidin-4-one (I-473), 4-({1-[4-(Benzyloxy)phenyl]-4-oxo-1H,4H,5H-pyrazolo[3,4-d]pyrimidin-5-yl}methyl)-4-hydroxy-N,N-dimethylpiperidine-1-carboxamide (I-474);

4-((1-(4',6-Difluoro-[1,1'-biphenyl]-3-yl)-4-oxo-1,4-dihydro-5H-pyrazolo[3,4-d]pyrimidin-5-yl)methyl)-4-hydroxy-N,N-dimethylpiperidine-1-carboxamide (I-475);

N-(3-(5-((1-(cyclopropanecarbonyl)-4-hydroxypiperidin-4-yl)methyl)-4-oxo-4,5-dihydro-1H-pyrazolo[3,4-d]pyrimidin-1-yl)phenyl)acetamide (I-476);

N-(3-(5-((1-(Cyclopropanecarbonyl)-4-hydroxypiperidin-4-yl)methyl)-4-oxo-4,5-dihydro-1H-pyrazolo[3,4-d]pyrimidin-1-yl)phenyl)-3,5-dimethylisoxazole-4-sulfonamide (I-477);

1-(3-(5-((1-(Cyclopropanecarbonyl)-4-hydroxypiperidin-4-yl)methyl)-4-oxo-4,5-dihydro-1H-pyrazolo[3,4-d]pyrimidin-1-yl)phenyl)-3-isopropylurea (I-478);

5-((1-(Cyclopropanecarbonyl)-4-hydroxypiperidin-4-yl)methyl)-1-(3-(3,3-difluoropyrrolidine-1-carbonyl)phenyl)-1,5-dihydro-4H-pyrazolo[3,4-d]pyrimidin-4-one (I-479);

3-[(1-benzoyl-4-hydroxypiperidin-4-yl)methyl]-7-(4-fluorophenyl)-3H,4H,7H-pyrrolo[2,3-d]pyrimidin-4-one (I-48), 1-(4-Fluorophenyl)-5-((4-hydroxy-1-(1H-pyrrolo[3,2-c]pyridine-2-carbonyl)piperidin-4-yl)methyl)-1,5-dihydro-4H-pyrazolo[3,4-d]pyrimidin-4-one (I-480);

4-{[1-(4-Fluorophenyl)-4-oxo-1H,4H,5H-pyrazolo[3,4-d]pyrimidin-5-yl]methyl}-4-hydroxy-N-(propan-2-yl)piperidine-1-carboxamide (I-481);

N-(3,3-Dimethylcyclobutyl)-4-((1-(4-fluorophenyl)-4-oxo-1,4-dihydro-5H-pyrazolo[3,4-d]pyrimidin-5-yl)methyl)-4-hydroxypiperidine-1-carboxamide (I-482);

1-(4-Chlorophenyl)-5-{[4-hydroxy-1-(1H-indole-2-carbonyl)piperidin-4-yl]methyl}-1H,4H,5H-pyrazolo[3,4-d]pyrimidin-4-one (I-483);

(R)-5-((1-(4-fluorobenzoyl)-4-hydroxypiperidin-4-yl)methyl)-1-(octahydro-2H-pyrido[1,2-a]pyrazin-2-yl)phenyl)-1,5-dihydro-4H-pyrazolo[3,4-d]pyrimidin-4-one (I-484);

5-[(1-Cyclopropanecarbonyl-4-hydroxypiperidin-4-yl)methyl]-1-(4-{imidazo[1,2-a]pyridin-8-yl}phenyl)-1H,4H,5H-pyrazolo[3,4-d]pyrimidin-4-one (I-485);

3-(Pyrrolidin-1-yl)propyl 4-((1-(4-fluorophenyl)-4-oxo-1,4-dihydro-5H-pyrazolo[3,4-d]pyrimidin-5-yl)methyl)-4-hydroxypiperidine-1-carboxylate (I-486);

5-[(1-{4-[(8aR)-octahydropyrrolo[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one (I-487);

5-{[4-Hydroxy-1-(2-methyl-1,3-oxazole-5-carbonyl)piperidin-4-yl]methyl}-1-[4-(4-methyl-1H-pyrazol-1-yl)phenyl]-1H,4H, 5H-pyrazolo[3,4-d]pyrimidin-4-one (I-488);

1-{4-[1-(Difluoromethyl)-1H-pyrazol-4-yl]phenyl)-5-{[4-hydroxy-1-(1-methylcyclopropanecarbonyl)piperidin-4-yl]methyl}-1H,4H,5H-pyrazolo[3,4-d]pyrimidin-4-one (I-489);

3-[(1-benzoyl-4-hydroxypiperidin-4-yl)methyl]-7-(4-fluorophenyl)-6-methyl-3H,4H,7H-pyrrolo[2,3-d]pyrimidin-4-one (I-49);

1-(4-{2,2-Difluoro-7-azaspiro[3.5]nonan-7-yl}phenyl)-5-{[4-hydroxy-1-(1-methylcyclopropanecarbonyl)piperidin-4-yl]methyl}-1H,4H,5H-pyrazolo[3,4-d]pyrimidin-4-one (I-490);

1-{4-[(5-Chloropyridin-2-yl)oxy]phenyl}-5-[(1-cyclopropanecarbonyl-4-hydroxypiperidin-4-yl)methyl]-1H, 4H,5H-pyrazolo[3,4-d]pyrimidin-4-one (I-491);

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3,3-dimethylurea (I-492);

Propan-2-yl N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)carbamate (I-493);

3-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-1-(oxan-4-yl)urea (I-494);

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-(oxetan-3-yl)urea (I-495);

4-({1-[4-(3,3-dimethylazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide (I-496), 5-[(1-Cyclopropanecarbonyl-4-hydroxypiperidin-4-yl)methyl]-1-[3-(1H-pyrazol-1-yl)phenyl]-1H,4H,5H-pyrazolo[3,4-d]pyrimidin-4-one (I-497);

5-[(1-Cyclopropanecarbonyl-4-hydroxypiperidin-4-yl)methyl]-1-[3-(piperazin-1-yl)phenyl]-1H,4H,5H-pyrazolo[3,4-d]pyrimidin-4-one (I-498);

5-[(1-Cyclopropanecarbonyl-4-hydroxypiperidin-4-yl)methyl]-1-[4-(piperazin-1-yl)phenyl]-1H,4H,5H-pyrazolo[3,4-d]pyrimidin-4-one (I-499);

1-(3-{[cyclohexyl(ethyl)amino]methyl}phenyl)-5-[(1-cyclopropanecarbonyl-4-hydroxypiperidin-4-yl)methyl]-1H,4H,5H-pyrazolo[3,4-d]pyrimidin-4-one (I-5);

4-Hydroxy-N,N-dimethyl-4-{[4-oxo-1-(4-phenoxyphenyl)-1H,4H,5H-pyrazolo[3,4-d]pyrimidin-5-yl]methyl)piperidine-1-carboxamide (I-500);

4-{[1-(4-Fluorophenyl)-4-oxo-1H,4H,5H-pyrazolo[3,4-d]pyrimidin-5-yl]methyl}-4-hydroxy-N-(oxan-4-yl)piperidine-1-carboxamide (I-501);

(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)urea (I-502);

(3-{5-[(1-Cyclopropanecarbonyl-4-hydroxypiperidin-4-yl)methyl]-4-oxo-1H,4H,5H-pyrazolo[3,4-d]pyrimidin-1-yl}phenyl)urea (I-503);

5-[(1-Cyclopropanecarbonyl-4-hydroxypiperidin-4-yl) methyl]-1-{4-[(methylsulfamoyl)amino]phenyl)-1H, 4H,5H-pyrazolo[3,4-d]pyrimidin-4-one (I-504);

5-[(1-Cyclopropanecarbonyl-4-hydroxypiperidin-4-yl) methyl]-1-{4-[(dimethylsulfamoyl)amino]phenyl}-1H, 4H,5H-pyrazolo[3,4-d]pyrimidin-4-one (I-505);

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-methylurea (I-506), 1-(3-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-methylurea (I-507);

4-{[1-(4-{3,9-Diazaspiro[5.5]undecan-3-yl}phenyl)-4-oxo-1H,4H,5H-pyrazolo[3,4-d]pyrimidin-5-1]methyl)-4-hydroxy-N,N-dimethylpiperidine-1-carboxamide (I-508);

1-(4-Fluorophenyl)-5-[(4-hydroxy-1-{4-[(3S)-3-hydroxypyrrolidin-1-yl]benzoyl}piperidin-4-yl)methyl]-1H,4H,5H-pyrazolo[3,4-d]pyrimidin-4-one (I-509);

7-[3-(aminomethyl)phenyl]-3-{[1-(4-fluorobenzoyl)-4-hydroxypiperidin-4-yl]methyl}-3H,4H,7H-pyrrolo[2,3-d]pyrimidin-4-one (I-51);

1-(4-fluorophenyl)-5-({4-hydroxy-1-[3-(pyrrolidin-1-ylmethyl)benzoyl]piperidin-4-yl}methyl)-1H,4H,5H-pyrazolo[3,4-d]pyrimidin-4-one (I-510);

1-(4-fluorophenyl)-5-({4-hydroxy-1-[3-(1H-pyrazol-1-yl)butanoyl]piperidin-4-yl}methyl)-1H,4H,5H-pyrazolo[3,4-d]pyrimidin-4-one (I-513);

1-(4-fluorophenyl)-5-({4-hydroxy-1-[(3S)-3-(1H-pyrazol-1-yl)butanoyl]piperidin-4-yl}methyl)-1H,4H,5H-pyrazolo[3,4-d]pyrimidin-4-one (I-514);

1-(4-fluorophenyl)-5-({4-hydroxy-1-[(3R)-3-(1H-pyrazol-1-yl)butanoyl]piperidin-4-yl}methyl)-1H,4H,5H-pyrazolo[3,4-d]pyrimidin-4-one (I-515);

5-({1-[3-(difluoromethoxy)cyclobutanecarbonyl]-4-hydroxypiperidin-4-yl}methyl)-1-(4-fluorophenyl)-1H,4H,5H-pyrazolo[3,4-d]pyrimidin-4-one (I-516);

5-({1-[(3R)-4,4-difluoro-3-(1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-517);

5-({1-[(3S)-4,4-difluoro-3-(1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-518);

5-({1-[(3S)-3-{2H,4H,5H,6H-cyclopenta[c]pyrazol-2-yl}butanoyl]-4-hydroxypiperidin-4-yl}methyl)-1-(4-fluorophenyl)-1H,4H,5H-pyrazolo[3,4-d]pyrimidin-4-one (I-519);

3-{[1-(4-fluorobenzoyl)-4-hydroxypiperidin-4-yl]methyl}-7-(5-fluoropyridin-2-yl)-3H,4H,7H-pyrrolo[2,3-d]pyrimidin-4-one (I-52);

5-({1-[(3R)-3-{2H,4H,5H,6H-cyclopenta[c]pyrazol-2-yl}butanoyl]-4-hydroxypiperidin-4-yl}methyl)-1-(4-fluorophenyl)-1H,4H,5H-pyrazolo[3,4-d]pyrimidin-4-one (I-520);

5-({1-[(3S)-3-{1H,4H,5H,6H-cyclopenta[c]pyrazol-1-yl}butanoyl]-4-hydroxypiperidin-4-yl}methyl)-1-(4-fluorophenyl)-1H,4H,5H-pyrazolo[3,4-d]pyrimidin-4-one (I-521), 5-({1-[(3R)-3-{1H,4H,5H,6H-cyclopenta[c]pyrazol-1-yl}butanoyl]-4-hydroxypiperidin-4-yl}methyl)-1-(4-fluorophenyl)-1H,4H,5H-pyrazolo[3,4-d]pyrimidin-4-one (I-522);

1-(4-fluorophenyl)-5-{[4-hydroxy-1-(3-{octahydrocyclopenta[c]pyrrol-2-yl}butanoyl)piperidin-4-yl]methyl}-1H,4H,5H-pyrazolo[3,4-d]pyrimidin-4-one (I-523);

1-(4-fluorophenyl)-5-({4-hydroxy-1-[(3S)-3-{octahydrocyclopenta[c]pyrrol-2-yl}butanoyl]piperidin-4-yl}methyl)-1H,4H,5H-pyrazolo[3,4-d]pyrimidin-4-one (I-524);

1-(4-fluorophenyl)-5-({4-hydroxy-1-[(3R)-3-{octahydrocyclopenta[c]pyrrol-2-yl}butanoyl]piperidin-4-yl}methyl)-1H,4H,5H-pyrazolo[3,4-d]pyrimidin-4-one (I-525);

1-(4-fluorophenyl)-5-({4-hydroxy-1-[4-(1,1,1-trifluoro-2-hydroxypropan-2-yl)benzoyl]piperidin-4-yl}methyl)-1H,4H,5H-pyrazolo[3,4-d]pyrimidin-4-one (I-526);

1-(4-fluorophenyl)-5-[(4-hydroxy-1-{4-[(2R)-1,1,1-trifluoro-2-hydroxy propan-2-yl]benzoyl}piperidin-4-yl)methyl]-1H,4H,5H-pyrazolo[3,4-d]pyrimidin-4-one (I-527), 1-(4-fluorophenyl)-5-[(4-hydroxy-1-{4-[(2S)-1,1,1-trifluoro-2-hydroxy propan-2-yl]benzoyl}piperidin-4-yl)methyl]-1H,4H,5H-pyrazolo[3,4-d]pyrimidin-4-one (I-528);

1-(4-fluorophenyl)-5-({4-hydroxy-1-[4-(pyrrolidin-1-ylmethyl)benzoyl]piperidin-4-yl}methyl)-1H,4H,5H-pyrazolo[3,4-d]pyrimidin-4-one (I-529);

1-(4-fluorophenyl)-5-({4-hydroxy-1-[4-(morpholin-4-ylmethyl)benzoyl]piperidin-4-yl}methyl)-1H,4H,5H-pyrazolo[3,4-d]pyrimidin-4-one (I-530);

1-(4-fluorophenyl)-5-{[4-hydroxy-1-(2-methyl-1,3-oxazole-5-carbonyl)piperidin-4-yl]methyl}-1H,4H,5H-pyrazolo[3,4-d]pyrimidin-4-one (I-531);

1-(4-fluorophenyl)-5-[(4-hydroxy-1-{5H,6H,7H-pyrazolo[3,2-b][1,3]oxazine-2-carbonyl}piperidin-4-yl) methyl]-1H,4H,5H-pyrazolo[3,4-d]pyrimidin-4-one (I-532);

1-(4-fluorophenyl)-5-[(4-hydroxy-1-{4-[(1-methylpiperidin-4-yl)oxy]benzoyl}piperidin-4-yl)methyl]-1H,4H,5H-pyrazolo[3,4-d]pyrimidin-4-one (I-533);

1-(4-fluorophenyl)-5-({4-hydroxy-1-[5-(piperidin-1-yl)-1,3,4-oxadiazole-2-carbonyl]piperidin-4-yl}methyl)-1H,4H,5H-pyrazolo[3,4-d]pyrimidin-4-one (I-534);

1-(4-fluorophenyl)-5-({4-hydroxy-1-[4-(1H-pyrazol-1-yl)benzoyl]piperidin-4-yl}methyl)-1H,4H,5H-pyrazolo[3,4-d]pyrimidin-4-one (I-535);

1-(4-fluorophenyl)-5-({4-hydroxy-1-[2-(piperidin-1-yl)-1,3-oxazole-5-carbonyl]piperidin-4-yl}methyl)-1H, 4H,5H-pyrazolo[3,4-d]pyrimidin-4-one (I-536);

5-({1-[3-fluoro-4-(4-methylpiperazin-1-yl)benzoyl]-4-hydroxypiperidin-4-yl}methyl)-1-(4-fluorophenyl)-1H,4H,5H-pyrazolo[3,4-d]pyrimidin-4-one (I-537);

1-(4-fluorophenyl)-5-({4-hydroxy-1-[4-(pyridin-2-yloxy) benzoyl]piperidin-4-yl}methyl)-1H,4H,5H-pyrazolo [3,4-d]pyrimidin-4-one (I-538);

1-(4-fluorophenyl)-5-({4-hydroxy-1-[4-(pyrimidin-2-yloxy)benzoyl]piperidin-4-yl}methyl)-1H,4H,5H-pyrazolo[3,4-d]pyrimidin-4-one (I-539);

4-{3-chloro-4-[4-hydroxy-4-({1-methyl-4-oxo-1H,4H,5H-pyrazolo[3,4-d]pyrimidin-5-yl}methyl)piperidine-1-carbonyl]phenyl}-N,N-dimethylbenzamide (I-54);

5-{[1-(1-benzyl-1H-indole-2-carbonyl)-4-hydroxypiperidin-4-yl]methyl}-1-(4-fluorophenyl)-1H,4H,5H-pyrazolo[3,4-d]pyrimidin-4-one (I-540);

5-{[1-(1-benzyl-1H-pyrazole-5-carbonyl)-4-hydroxypiperidin-4-yl]methyl}-1-(4-fluorophenyl)-1H,4H,5H-pyrazolo[3,4-d]pyrimidin-4-one (I-541);

5-({1-[(3S)-4,4-difluoro-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-542);

5-({1-[(3R)-4,4-difluoro-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-543);

1-(4-fluorophenyl)-5-({4-hydroxy-1-[4-(pyridin-2-yloxy)cyclohexanecarbonyl]piperidin-4-yl}methyl)-1H,4H,5H-pyrazolo[3,4-d]pyrimidin-4-one (I-544), 1-(4-fluorophenyl)-5-({4-hydroxy-1-[(1s,4s)-4-(pyridin-2-yloxy)cyclohexanecarbonyl]piperidin-4-yl}methyl)-1H,4H,5H-pyrazolo[3,4-d]pyrimidin-4-one (I-545);

1-(4-fluorophenyl)-5-({4-hydroxy-1-[(1r,4r)-4-(pyridin-2-yloxy)cyclohexanecarbonyl]piperidin-4-yl}methyl)-1H,4H,5H-pyrazolo[3,4-d]pyrimidin-4-one (I-546);

1-(4-fluorophenyl)-5-({4-hydroxy-1-[5-(pyridin-2-yloxy}pyridine-2-carbonyl]piperidin-4-yl)methyl)-1H,4H,5H-pyrazolo[3,4-d]pyrimidin-4-one (I-547);

1-(4-fluorophenyl)-5-({4-hydroxy-1-[(1r,4r)-4-(1H-pyrazol-1-yl)cyclohexanecarbonyl]piperidin-4-yl}methyl)-1H,4H,5H-pyrazolo[3,4-d]pyrimidin-4-one (I-548);

1-(4-fluorophenyl)-5-({4-hydroxy-1-[(1s,4s)-4-(1H-pyrazol-1-yl)cyclohexanecarbonyl]piperidin-4-yl}methyl)-1H,4H,5H-pyrazolo[3,4-d]pyrimidin-4-one (I-549);

5-[(1-{2-chloro-4-[4-(piperidine-1-carbonyl)phenyl]benzoyl}-4-hydroxypiperidin-4-yl)methyl]-1-methyl-1H,4H,5H-pyrazolo[3,4-d]pyrimidin-4-one (I-55);

1-(4-fluorophenyl)-5-{[4-hydroxy-1-(4-{2H,3H-pyrazolo[3,2-b][1,3]oxazol-7-yl}benzoyl)piperidin-4-yl]methyl}-1H,4H,5H-pyrazolo[3,4-d]pyrimidin-4-one (I-550);

1-(4-fluorophenyl)-5-{[4-hydroxy-1-(4-{5H,6H,7H-pyrazolo[3,2-b][1,3]oxazin-3-yl}benzoyl)piperidin-4-yl]methyl}-1H,4H,5H-pyrazolo[3,4-d]pyrimidin-4-one (I-551);

1-(4-fluorophenyl)-5-{[4-hydroxy-1-(4-{4H,5H,6H,7H-pyrazolo[1,5-a]pyrimidin-3-yl}benzoyl)piperidin-4-yl]methyl}-1H,4H,5H-pyrazolo[3,4-d]pyrimidin-4-one (I-552);

1-(4-fluorophenyl)-5-{[4-hydroxy-1-(4-{4-methyl-4H,5H,6H,7H-pyrazolo[1,5-a]pyrimidin-3-yl}benzoyl)piperidin-4-yl]methyl}-1H,4H,5H-pyrazolo[3,4-d]pyrimidin-4-one (I-553);

5-{[1-(2-amino-4-chlorobenzoyl)-4-hydroxypiperidin-4-yl]methyl}-1-(4-fluorophenyl)-1H,4H,5H-pyrazolo[3,4-d]pyrimidin-4-one (I-554);

1-(4-fluorophenyl)-5-({4-hydroxy-1-[2-(morpholin-4-yl)-1,3-oxazole-5-carbonyl]piperidin-4-yl}methyl)-1H,4H,5H-pyrazolo[3,4-d]pyrimidin-4-one (I-555);

5-{[1-(5-cyclopropyl-1,3,4-oxadiazole-2-carbonyl)-4-hydroxypiperidin-4-yl]methyl}-1-(4-fluorophenyl)-1H,4H,5H-pyrazolo[3,4-d]pyrimidin-4-one (I-556);

5-{[1-(5-benzyl-1,3-oxazole-4-carbonyl)-4-hydroxypiperidin-4-yl]methyl}-1-(4-fluorophenyl)-1H,4H,5H-pyrazolo[3,4-d]pyrimidin-4-one (I-557);

1-(4-fluorophenyl)-5-[(1-{1-[(4-fluorophenyl)methyl]-1H-pyrrole-2-carbonyl}-4-hydroxypiperidin-4-yl)methyl]-1H,4H,5H-pyrazolo[3,4-d]pyrimidin-4-one (I-558);

5-[(1-{1-[(2,6-difluorophenyl)methyl]-1H-pyrrole-2-carbonyl}-4-hydroxypiperidin-4-yl)methyl]-1-(4-fluorophenyl)-1H,4H,5H-pyrazolo[3,4-d]pyrimidin-4-one (I-559);

5-{[4-hydroxy-1-(4-phenoxybenzoyl)piperidin-4-yl]methyl}-1-methyl-1H,4H,5H-pyrazolo[3,4-d]pyrimidin-4-one (I-56);

1-(4-fluorophenyl)-5-[(1-{1-[(3-fluorophenyl)methyl]-1H-pyrrole-2-carbonyl}-4-hydroxypiperidin-4-yl) methyl]-1H,4H,5H-pyrazolo[3,4-d]pyrimidin-4-one (I-560);

1-(4-fluorophenyl)-5-[(1-{1-[(2-fluorophenyl)methyl]-1H-pyrrole-2-carbonyl}-4-hydroxypiperidin-4-yl)methyl]-1H,4H,5H-pyrazolo[3,4-d]pyrimidin-4-one (I-561);

1-(4-fluorophenyl)-5-[(4-hydroxy-1-{4-[(1-methyl-1H-pyrazol-4-yl)oxy]benzoyl}piperidin-4-yl)methyl]-1H,4H,5H-pyrazolo[3,4-d]pyrimidin-4-one (I-562), 1-(4-fluorophenyl)-5-[(4-hydroxy-1-{4-[(5-methyl-1,2-oxazol-3-yl)oxy]benzoyl}piperidin-4-yl)methyl]-1H,4H,5H-pyrazolo[3,4-d]pyrimidin-4-one (I-563), 1-[4-(4-fluorophenyl)phenyl]-5-{[4-hydroxy-1-(piperazine-1-carbonyl)piperidin-4-yl]methyl}-1H,4H,5H-pyrazolo[3,4-d]pyrimidin-4-one (I-564);

N-[(1s,3s)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-enamide (I-568);

N-[(1S,3R)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclopentyl]prop-2-enamide (I-569);

5-({4-hydroxy-1-[(3R)-3-phenylbutanoyl]piperidin-4-yl}methyl)-1-methyl-1H,4H,5H-pyrazolo[3,4-d]pyrimidin-4-one (I-57);

N-[(1R,3S)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclopentyl]prop-2-enamide (I-570);

1-(4-fluorophenyl)-5-({4-hydroxy-1-[(2R)-1-(prop-2-enoyl)azetidine-2-carbonyl]piperidin-4-yl}methyl)-1H,4H,5H-pyrazolo[3,4-d]pyrimidin-4-one (I-574);

N-[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]prop-2-enamide (I-575);

N-[(1s,4s)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]prop-2-enamide (I-576);

N-[(1s,3s)-3-[2-(4-{[1-(4-fluorophenyl)-4-oxo-1H,4H,5H-pyrazolo[3,4-d]pyrimidin-5-yl]methyl}-4-hydroxypiperidin-1-yl)-2-oxoethyl]cyclobutyl]prop-2-ynamide (I-578);

1-(4-fluorophenyl)-5-({4-hydroxy-1-[(2S)-2-methyl-1-(prop-2-enoyl)azetidine-2-carbonyl]piperidin-4-yl}methyl)-1H,4H,5H-pyrazolo[3,4-d]pyrimidin-4-one (I-579);

1-benzyl-5-({4-hydroxy-1-[(3R)-3-phenylbutanoyl]piperidin-4-yl}methyl)-1H,4H,5H-pyrazolo[3,4-d]pyrimidin-4-one (I-58);

1-(4-fluorophenyl)-5-({4-hydroxy-1-[(2R)-2-methyl-1-(prop-2-enoyl)azetidine-2-carbonyl]piperidin-4-yl}methyl)-1H,4H,5H-pyrazolo[3,4-d]pyrimidin-4-one (I-580);

N-[(1r,3r)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]acetamide (I-582);

5-((1-(3-(aminomethyl)benzoyl)-4-hydroxypiperidin-4-yl) methyl)-1-(4-fluorophenyl)-1H-pyrazolo[3,4-d]pyrimidin-4(5H)-one (I-585);

5-((1-(4-(1-(aminomethyl)cyclopropyl)benzoyl)-4-hydroxypiperidin-4-yl)methyl)-1-(4-fluorophenyl)-1H-pyrazolo[3,4-d]pyrimidin-4 (5H)-one hydrochloride (I-586);

N-((1-(4-(4-((1-(4-fluorophenyl)-4-oxo-1H-pyrazolo[3, 4-d]pyrimidin-5 (4H)-yl)methyl)-4-hydroxypiperidine-1-carbonyl)phenyl)cyclopropyl)methyl)acetamide (I-587);

N-methyl-N-[(1r,3r)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-ynamide (I-589);

1-tert-butyl-5-({4-hydroxy-1-[(3R)-3-phenylbutanoyl]piperidin-4-yl}methyl)-1H,4H,5H-pyrazolo[3,4-d]pyrimidin-4-one (I-59);

1-tert-butyl-5-{[4-hydroxy-1-(4-phenoxybenzoyl)piperidin-4-yl]methyl)-1H,4H,5H-pyrazolo[3,4-d]pyrimidin-4-one (I-60);

N-methyl-N-[(1s,3s)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-ynamide (I-600);

1-(4-fluorophenyl)-5-((4-hydroxy-1-(3-((3-hydroxy-3-methyl-pyrrolidin-1-yl)methyl)benzoyl)piperidin-4-yl) methyl)-1H-pyrazolo[3,4-d]pyrimidin-4 (5H)-one (I-601);

1-(4-fluorophenyl)-5-[(4-hydroxy-1-{3-[1-(pyrrolidin-1-yl)ethyl]benzoyl}piperidin-4-yl)methyl]-1H,4H,5H-pyrazolo[3,4-d]pyrimidin-4-one (I-602);

5-([1-[(5-benzyl-1H-pyrazol-4-yl)carbonyl]-4-hydroxypiperidin-4-yl]methyl}-1-(4-fluorophenyl)-1H, 4H,5H-pyrazolo[3,4-d]pyrimidin-4-one (I-603);

1-(4-fluorophenyl)-5-{[4-hydroxy-1-(4-{5-methyl-2,5-diazabicyclo[2.2.1]heptan-2-yl}benzoyl)piperidin-4-yl]methyl}-1H,4H,5H-pyrazolo[3,4-d]pyrimidin-4-one (I-604);

1-(4-fluorophenyl)-5-((4-hydroxy-1-(4-(1-methylpiperidin-4-yl) benzoyl)piperidin-4-yl)methyl)-1H-pyrazolo[3,4-d]pyrimidin-4 (5H)-one (I-605), 1-(4-fluorophenyl)-5-[(4-hydroxy-1-[[4-(4-methylpiperazin-1-yl) phenyl]carbonyl]piperidin-4-yl)methyl]-1H, 4H,5H-pyrazolo[3,4-d]pyrimidin-4-one (I-606);

1-(4-fluorophenyl)-5-{[4-hydroxy-1-(4-{octahydro-1H-pyrido[1,2-a]piperazin-2-yl}benzoyl)piperidin-4-yl] methyl}-1H,4H,5H-pyrazolo[3,4-d]pyrimidin-4-one (I-607);

5-[(1-{4-[(9aR)-octahydro-1H-pyrido[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one (I-608);

5-[(1-{4-[(9aS)-octahydro-1H-pyrido[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one (I-609);

5-({4-hydroxy-1-[(3R)-3-phenylbutanoyl]piperidin-4-yl}methyl)-1-(propan-2-yl}-1H,4H,5H-pyrazolo[3,4-d]pyrimidin-4-one (I-61);

1-(4-fluorophenyl)-5-[(4-hydroxy-1-[[4-(pyridin-2-yloxy)piperidin-1-yl]carbonyl]piperidin-4-yl)methyl]-1H,4H,5H-pyrazolo[3,4-d]pyrimidin-4-one (I-610);

5-((1-(4-(5,6-dihydropyrrolo[3,4-c]pyrazol-1 (4H)-yl) benzoyl)-4-hydroxypiperidin-4-yl)methyl)-1-(4-fluorophenyl)-1H-pyrazolo[3,4-d]pyrimidin-4 (5H)-one (I-611);

1-(4-fluorophenyl)-5-[(4-hydroxy-1-{4-[4-(hydroxymethyl)-1H-pyrazol-1-yl]benzoyl}piperidin-4-yl) methyl]-1H,4H,5H-pyrazolo[3,4-d]pyrimidin-4-one (I-612);

5-((1-(4-(4-(aminomethyl)-1H-pyrazol-1-yl)benzoyl)-4-hydroxypiperidin-4-yl)methyl)-1-(4-fluorophenyl)-1H-pyrazolo[3,4-d]pyrimidin-4 (5H)-one (I-613);

1-(4-fluorophenyl)-5-(1-[4-hydroxy-1-[(4-methoxyphenyl)carbonyl]piperidin-4-yl]ethyl)-1H,4H,5H-pyrazolo[3,4-d]pyrimidin-4-one (I-614);

1-(4-fluorophenyl)-5-(1-[4-hydroxy-1-[(4-methoxyphenyl)carbonyl]piperidin-4-yl]ethyl)-1H,4H,5H-pyrazolo[3,4-d]pyrimidin-4-one (I-615);

5-(1-(1-(3-(aminomethyl)benzoyl)-4-hydroxypiperidin-4-yl)ethyl)-1-(4-fluorophenyl)-1H-pyrazolo[3,4-d]pyrimidin-4 (5H)-one hydrochloride (I-616);

5-[(4-hydroxypiperidin-4-yl)methyl]-1-(4-methoxyphenyl)-1H,4H,5H-pyrazolo[3,4-d]pyrimidin-4-one (I-617);

4-Hydroxy-4-[[1-(4-methoxyphenyl)-4-oxo-1H,4H,5H-pyrazolo[3,4-d]pyrimidin-5-yl]methyl]-N,N-dimethylpiperidine-1-carboxamide (I-618);

4-Hydroxy-4-[[1-(4-hydroxyphenyl)-4-oxo-1H,4H,5H-pyrazolo [3,4-d]pyrimidin-5-yl]methyl]-N,N-dimethylpiperidine-1-carboxamide (I-619);

5-{[4-hydroxy-1-(4-phenoxybenzoyl)piperidin-4-yl] methyl}-1-(propan-2-yl)-1H,4H,5H-pyrazolo[3,4-d] pyrimidin-4-one (I-62), 5-{[1-(4-fluorobenzoyl)-4-hydroxypiperidin-4-yl] methyl}-1-(4-methoxyphenyl)-1H,4H,5H-pyrazolo[3, 4-d]pyrimidin-4-one (I-620);

5-{[1-(4-fluorobenzoyl)-4-hydroxypiperidin-4-yl] methyl}-1-(3-methoxyphenyl)-1H,4H, 5H-pyrazolo[3, 4-d]pyrimidin-4-one (I-621);

5-{[1-(4-fluorobenzoyl)-4-hydroxypiperidin-4-yl] methyl}-1-(4-hydroxyphenyl)-1H,4H,5H-pyrazolo[3, 4-d]pyrimidin-4-one (I-622);

5-{[1-(4-fluorobenzoyl)-4-hydroxypiperidin-4-yl] methyl}-1-(3-hydroxyphenyl)-1H,4H,5H-pyrazolo[3, 4-d]pyrimidin-4-one (I-623);

5-(1-(1-(4-fluorobenzoyl)-4-hydroxypiperidin-4-yl) ethyl)-1-(4-methoxyphenyl)-1H-pyrazolo[3,4-d]pyrimidin-4 (5H)-one (I-624);

5-{l-[4-hydroxy-1-(4-methoxybenzoyl)piperidin-4-yl] ethyl}-1-(4-methoxyphenyl)-1H,4H,5H-pyrazolo[3,4-d]pyrimidin-4-one (I-625);

1-(3-bromo-4-fluorophenyl)-5-{[1-(4-fluorobenzoyl)-4-hydroxypiperidin-4-yl]methyl}-1H,4H,5H-pyrazolo[3, 4-d]pyrimidin-4-one (I-626);

1-(4-fluoro-3-methoxyphenyl)-5-{[1-(4-fluorobenzoyl)-4-hydroxypiperidin-4-yl]methyl}-1H,4H,5H-pyrazolo [3,4-d]pyrimidin-4-one (I-627

5-{[1-(4-fluorobenzoyl)-4-hydroxypiperidin-4-yl] methyl}-1-(6-fluoropyridin-3-yl)-1H,4H,5H-pyrazolo [3,4-d]pyrimidin-4-one (I-628);

5-{[1-(2-cyclopropyl-1,3-oxazole-5-carbonyl)-4-hydroxypiperidin-4-yl]methyl}-1-(4-cyclopropylphenyl)-1H,4H,5H-pyrazolo[3,4-d]pyrimidin-4-one (I-629);

5-({4-hydroxy-1-[(3R)-3-phenylbutanoyl]piperidin-4-yl}methyl)-3-methyl-1-phenyl-1H,4H,5H-pyrazolo[3, 4-d]pyrimidin-4-one (I-63);

1-(4-bromophenyl)-5-[(1-cyclopropanecarbonyl-4-hydroxypiperidin-4-yl)methyl]-1H,4H,5H-pyrazolo[3,4-d]pyrimidin-4-one (I-630);

1-(3-bromo-4-chlorophenyl)-5-[(1-cyclopropanecarbonyl-4-hydroxypiperidin-4-yl)methyl]-1H,4H,5H-pyrazolo[3,4-d]pyrimidin-4-one (I-631);

1-(4-fluoro-3-hydroxyphenyl)-5-([1-[(4-fluorophenyl)carbonyl]-4-hydroxypiperidin-4-yl]methyl)-1H,4H,5H-pyrazolo[3,4-d]pyrimidin-4-one (I-632);

5-[(1-cyclopropanecarbonyl-4-hydroxypiperidin-4-yl)methyl]-1-[4-fluoro-3-(3-methoxy-3-methylpyrrolidin-1-yl)phenyl]-1H,4H,5H-pyrazolo[3,4-d]pyrimidin-4-one (I-633);

5-((1-benzoyl-4-hydroxypiperidin-4-yl)methyl)-1-(4-fluoro-3-(4-methylpiperazin-1-yl)phenyl)-1H-pyrazolo[3,4-d]pyrimidin-4 (5H)-one (I-634);

1-(3-Amino-4-fluorophenyl)-5-([1-[(4-fluorophenyl)carbonyl]-4-hydroxypiperidin-4-yl]methyl)-1H,4H,5H-pyrazolo[3,4-d]pyrimidin-4-one (I-635);

5-[(1-cyclopropanecarbonyl-4-hydroxypiperidin-4-yl)methyl]-1-[4-fluoro-3-(3-hydroxy-3-methylpyrrolidin-1-yl)phenyl]-1H,4H,5H-pyrazolo[3,4-d]pyrimidin-4-one (I-636);

5-[(1-cyclopropanecarbonyl-4-hydroxypiperidin-4-yl)methyl]-1-{4-fluoro-3-[(3S)-3-hydroxy-3-methylpyrrolidin-1-yl]phenyl)-1H,4H,5H-pyrazolo[3,4-d]pyrimidin-4-one (I-637);

5-[(1-cyclopropanecarbonyl-4-hydroxypiperidin-4-yl)methyl]-1-{4-fluoro-3-[(3R)-3-hydroxy-3-methylpyrrolidin-1-yl]phenyl)-1H,4H, 5H-pyrazolo[3,4-d]pyrimidin-4-one (I-638);

1-[4-fluoro-3-(morpholin-4-yl)phenyl]-5-{[1-(4-fluorobenzoyl)-4-hydroxypiperidin-4-yl]methyl}-1H,4H,5H-pyrazolo[3,4-d]pyrimidin-4-one (I-639);

5-{[4-hydroxy-1-(4-phenoxybenzoyl)piperidin-4-yl]methyl}-3-methyl-1-phenyl-1H,4H,5H-pyrazolo[3,4-d]pyrimidin-4-one (I-64);

1-(4-fluoro-3-(hydroxymethyl)phenyl)-5-((1-(4-fluorobenzoyl)-4-hydroxypiperidin-4-yl)methyl)-1H-pyrazolo[3,4-d]pyrimidin-4 (5H)-one (I-640);

5-({1-[4-(difluoromethoxy)benzoyl]-4-hydroxypiperidin-4-yl}methyl)-1-[4-fluoro-3-(hydroxymethyl)phenyl]-1H,4H,5H-pyrazolo[3,4-d]pyrimidin-4-one (I-641);

1-[4-fluoro-3-(hydroxymethyl)phenyl]-5-({4-hydroxy-1-[4-(pyridin-2-yloxy)benzoyl]piperidin-4-yl}methyl)-1H,4H,5H-pyrazolo[3,4-d]pyrimidin-4-one (I-642);

1-(Biphenyl-4-yl)-5-((4-hydroxy-1-(2-morpholinooxazole-5-carbonyl) piperidin-4-yl)methyl)-1H-pyrazolo[3,4-d]pyrimidin-4 (5H)-one (I-643);

5-({1-[4,4-di fluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one (I-644);

5-({1-[(3R)-4,4-difluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one (I-645);

5-({1-[(3S)-4,4-difluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one (I-646);

5-({4-hydroxy-1-[3-(1H-pyrazol-1-yl)butanoyl]piperidin-4-yl}methyl)-1-(4-phenylphenyl)-1H,4H,5H-pyrazolo[3,4-d]pyrimidin-4-one (I-648), 5-({4-hydroxy-1-[(3S)-3-(1H-pyrazol-1-yl)butanoyl]piperidin-4-yl}methyl)-1-(4-phenylphenyl)-1H,4H,5H-pyrazolo[3,4-d]pyrimidin-4-one (I-649);

1-(4-fluorophenyl)-5-({4-hydroxy-1-[(3R)-3-phenylbutanoyl]piperidin-4-yl}methyl)-1H,4H,5H-pyrazolo[3,4-d]pyrimidin-4-one (I-65);

5-({4-hydroxy-1-[(3R)-3-(1H-pyrazol-1-yl)butanoyl]piperidin-4-yl}methyl)-1-(4-phenylphenyl)-1H,4H,5H-pyrazolo[3,4-d]pyrimidin-4-one (I-650);

1-[4-(4-fluorophenyl)phenyl]-5-({4-hydroxy-1-[3-(1H-pyrazol-1-yl)butanoyl]piperidin-4-yl}methyl)-1H,4H,5H-pyrazolo[3,4-d]pyrimidin-4-one (I-652);

1-[4-(4-fluorophenyl)phenyl]-5-({4-hydroxy-1-[(3R)-3-(1H-pyrazol-1-yl)butanoyl]piperidin-4-yl}methyl)-1H,4H,5H-pyrazolo[3,4-d]pyrimidin-4-one (I-653);

1-[4-(4-fluorophenyl)phenyl]-5-({4-hydroxy-1-[(3S)-3-(1H-pyrazol-1-yl)butanoyl]piperidin-4-yl}methyl)-1H,4H,5H-pyrazolo[3,4-d]pyrimidin-4-one (I-654);

4-([1-[4-(4-fluorophenyl)phenyl]-4-oxo-1H,4H,5H-pyrazolo[3,4-d]pyrimidin-5-yl]methyl)-4-hydroxy-N-methylpiperidine-1-carboxamide (I-655);

5-((1-(1-acryloylazetidine-2-carbonyl)-4-hydroxypiperidin-4-yl) methyl)-1-(biphenyl-4-yl)-1H-pyrazolo[3,4-d]pyrimidin-4 (5H)-one (I-657);

N-[(1r,3r)-3-(4-hydroxy-4-{[4-oxo-1-(4-phenylphenyl)-1H,4H,5H-pyrazolo[3,4-d]pyrimidin-5-yl]methyl)piperidine-1-carbonyl)cyclobutyl]prop-2-ynamide (I-658);

5-({4-hydroxy-1-[(2S)-2-methyl-1-(prop-2-enoyl)azetidine-2-carbonyl]piperidin-4-yl}methyl)-1-(4-phenylphenyl)-1H,4H,5H-pyrazolo[3,4-d]pyrimidin-4-one (I-659);

1-(4-fluorophenyl)-5-{[4-hydroxy-1-(4-phenoxybenzoyl)piperidin-4-yl]methyl}-1H,4H,5H-pyrazolo[3,4-d]pyrimidin-4-one (I-66);

5-({4-hydroxy-1-[(2R)-2-methyl-1-(prop-2-enoyl)azetidine-2-carbonyl]piperidin-4-yl}methyl)-1-(4-phenylphenyl)-1H,4H,5H-pyrazolo[3,4-d]pyrimidin-4-one (I-660);

pyrrolidin-3-ylmethyl 4-hydroxy-4-{[4-oxo-1-(4-phenylphenyl)-1H,4H,5H-pyrazolo[3,4-d]pyrimidin-5-yl]methyl)piperidine-1-carboxylate (I-661);

N-(4-fluoropyrrolidin-3-yl)-4-hydroxy-4-{[4-oxo-1-(4-phenylphenyl)-1H,4H,5H-pyrazolo[3,4-d]pyrimidin-5-yl]methyl)piperidine-1-carboxamide (I-662);

N-[(3R)-4-fluoropyrrolidin-3-yl]-4-hydroxy-4-{[4-oxo-1-(4-phenylphenyl)-1H,4H,5H-pyrazolo[3,4-d]pyrimidin-5-yl]methyl)piperidine-1-carboxamide (I-663);

N-[(3S)-4-fluoropyrrolidin-3-yl]-4-hydroxy-4-{[4-oxo-1-(4-phenylphenyl)-1H,4H,5H-pyrazolo[3,4-d]pyrimidin-5-yl]methyl)piperidine-1-carboxamide (I-664);

5-((1-benzoyl-4-hydroxypiperidin-4-yl)methyl)-1-(2-(hydroxymethyl)biphenyl-4-yl)-1H-pyrazolo[3,4-d]pyrimidin-4 (5H)-one (I-665);

5-[(1-cyclopropanecarbonyl-4-hydroxypiperidin-4-yl)methyl]-1-[3-(hydroxymethyl)-4-phenylphenyl]-1H,4H,5H-pyrazolo[3,4-d]pyrimidin-4-one (I-666);

5-([4-hydroxy-1-[(morpholin-4-yl)carbonyl]piperidin-4-yl]methyl}-1-[3-(hydroxymethyl)-4-phenylphenyl]-1H,4H,5H-pyrazolo[3,4-d]pyrimidin-4-one (I-667);

1-[3-(Aminomethyl)-4-phenylphenyl]-5-[(1-cyclopropanecarbonyl-4-hydroxypiperidin-4-yl)methyl]-1H,4H,5H-pyrazolo[3,4-d]pyrimidin-4-one (I-668), 5-[(1-cyclopropanecarbonyl-4-hydroxypiperidin-4-yl)methyl]-1-{3-[(dimethylamino)methyl]-4-phenylphenyl}-1H,4H,5H-pyrazolo[3,4-d]pyrimidin-4-one (I-669);

5-({4-hydroxy-1-[(3R)-3-phenylbutanoyl]piperidin-4-yl}methyl)-1-[3-(trifluoromethyl)phenyl]-1H,4H,5H-pyrazolo[3,4-d]pyrimidin-4-one (I-67);

5-([1-[(4-fluorophenyl)carbonyl]-4-hydroxypiperidin-4-yl]methyl}-1-(4-[[2-(propan-2-yloxy)ethyl]amino]phenyl)-1H,4H,5H-pyrazolo[3,4-d]pyrimidin-4-one (I-670);

5-[(1-benzoyl-4-hydroxypiperidin-4-yl)methyl]-1-(4-{[2-(propan-2-yloxy)ethyl]amino}phenyl)-1H,4H,5H-pyrazolo[3,4-d]pyrimidin-4-one (I-671);

5-([4-hydroxy-1-[(4-methylphenyl)carbonyl]piperidin-4-yl]methyl)-1-[4-[4-(2-hydroxyethoxy)-1H-pyrazol-1-yl]phenyl]-1H,4H,5H-pyrazolo[3,4-d]pyrimidin-4-one (I-672);

5-{[1-(4-fluorobenzoyl)-4-hydroxypiperidin-4-yl]methyl}-1-[4-(3-methyl-1H-1,2,4-triazol-1-yl)phenyl]-1H,4H,5H-pyrazolo[3,4-d]pyrimidin-4-one (I-673);

5-((1-(cyclopropanecarbonyl)-4-hydroxypiperidin-4-yl)methyl)-1-(2'-(2-(dimethylamino)ethylamino)biphenyl-4-yl)-1H-pyrazolo[3,4-d]pyrimidin-4 (5H)-one (I-674);

5-[(1-cyclopropanecarbonyl-4-hydroxypiperidin-4-yl)methyl]-1-[4-[4-(pyrrolidin-3-yloxy)phenyl]phenyl]-1H,4H,5H-pyrazolo[3,4-d]pyrimidin-4-one (I-675);

5-[(1-cyclopropanecarbonyl-4-hydroxypiperidin-4-yl)methyl]-1-(4-{4-[2-(dimethylamino)ethoxy]-3-fluorophenyl}phenyl)-1H,4H,5H-pyrazolo[3,4-d]pyrimidin-4-one (I-676);

5-[(1-cyclopropanecarbonyl-4-hydroxypiperidin-4-yl)methyl]-1-(4-{2-[2-(dimethylamino)ethoxy]phenyl}phenyl)-1H,4H,5H-pyrazolo[3,4-d]pyrimidin-4-one (I-677);

5-[(1-cyclopropanecarbonyl-4-hydroxypiperidin-4-yl)methyl]-1-(4-[4-[(1-methylpyrrolidin-3-yl)oxy]phenyl]phenyl)-1H,4H,5H-pyrazolo[3,4-d]pyrimidin-4-one (I-678);

5-[(1-cyclopropanecarbonyl-4-hydroxypiperidin-4-yl)methyl]-1-[4-(4-{[(3R)-1-methylpyrrolidin-3-yl]oxy}phenyl)phenyl]-1H,4H,5H-pyrazolo[3,4-d]pyrimidin-4-one (I-679);

5-({4-hydroxy-1-[(3R)-3-phenylbutanoyl]piperidin-4-yl}methyl)-1-(4-methylphenyl)-1H,4H,5H-pyrazolo[3,4-d]pyrimidin-4-one (I-68);

5-[(1-cyclopropanecarbonyl-4-hydroxypiperidin-4-yl)methyl]-1-[4-(4-{[(3S)-1-methylpyrrolidin-3-yl]oxy}phenyl)phenyl]-1H,4H,5H-pyrazolo[3,4-d]pyrimidin-4-one (I-680);

5-((1-(cyclopropanecarbonyl)-4-hydroxypiperidin-4-yl)methyl)-1-(4-(1-(2,2-difluoroethyl)piperidin-4-yl)phenyl)-1H-pyrazolo[3,4-d]pyrimidin-4 (5H)-one (I-681);

4-hydroxy-N,N-dimethyl-4-({1-[4-(oxan-4-yl)phenyl]-4-oxo-1H,4H,5H-pyrazolo[3,4-d]pyrimidin-5-yl}methyl)piperidine-1-carboxamide (I-682);

4-[(1-{4-[1-(2,2-difluoroethyl)piperidin-4-yl]phenyl}-4-oxo-1H,4H,5H-pyrazolo[3,4-d]pyrimidin-5-yl)methyl]-4-hydroxy-N,N-dimethylpiperidine-1-carboxamide (I-683);

5-[(1-cyclopropanecarbonyl-4-hydroxypiperidin-4-yl)methyl]-1-(4-{6-[(3S)-3-(methylamino)pyrrolidin-1-yl]pyridin-3-yl}phenyl)-1H,4H,5H-pyrazolo[3,4-d]pyrimidin-4-one (I-684);

5-((1-(cyclopropanecarbonyl)-4-hydroxypiperidin-4-yl)methyl)-1-(4-(6-(3-(methylamino)pyrrolidin-1-yl)pyridin-3-yl)phenyl)-1H-pyrazolo[3,4-d]pyrimidin-4 (5H)-one (I-685);

5-[(1-cyclopropanecarbonyl-4-hydroxypiperidin-4-yl)methyl]-1-(4-{6-[(3S)-3-hydroxypyrrolidin-1-yl]pyridin-3-yl}phenyl)-1H,4H,5H-pyrazolo[3,4-d]pyrimidin-4-one (I-686);

5-[(1-cyclopropanecarbonyl-4-hydroxypiperidin-4-yl)methyl]-1-(4-{6-[(3R)-3-hydroxypyrrolidin-1-yl]pyridin-3-yl}phenyl)-1H,4H,5H-pyrazolo[3,4-d]pyrimidin-4-one (I-687);

5-[(1-cyclopropanecarbonyl-4-hydroxypiperidin-4-yl)methyl]-1-(4-{4-[3-(methylamino)pyrrolidin-1-yl]phenyl}phenyl)-1H,4H,5H-pyrazolo[3,4-d]pyrimidin-4-one (I-688);

5-[(1-cyclopropanecarbonyl-4-hydroxypiperidin-4-yl)methyl]-1-(4-{4-[(3S)-3-(methylamino)pyrrolidin-1-yl]phenyl}phenyl)-1H,4H,5H-pyrazolo[3,4-d]pyrimidin-4-one (I-689);

5-{[4-hydroxy-1-(4-phenoxybenzoyl)piperidin-4-yl]methyl}-1-(4-methylphenyl)-1H,4H,5H-pyrazolo[3,4-d]pyrimidin-4-one (I-69);

5-[(1-cyclopropanecarbonyl-4-hydroxypiperidin-4-yl)methyl]-1-(4-{4-[(3R)-3-(methylamino) pyrrolidin-1-yl]phenyl}phenyl)-1H,4H,5H-pyrazolo[3,4-d]pyrimidin-4-one (I-690);

1-[4-[3-(3-aminooxetan-3-yl)phenyl]phenyl]-5-[(1-cyclopropanecarbonyl-4-hydroxypiperidin-4-yl)methyl]-1H,4H,5H-pyrazolo[3,4-d]pyrimidin-4-one (I-691), 5-([1-[(4-fluorophenyl)carbonyl]-4-hydroxypiperidin-4-yl]methyl)-1-[4-[(1-methylazetidin-3-yl)oxy]phenyl]-1H,4H,5H-pyrazolo[3,4-d]pyrimidin-4-one (I-692);

5-{[1-(4-fluorobenzoyl)-4-hydroxypiperidin-4-yl]methyl}-1-{4-[(4-fluorooxan-4-yl)methoxy]phenyl)-1H,4H,5H-pyrazolo[3,4-d]pyrimidin-4-one (I-693), 1-{4-[(4,4-difluorocyclohexyl)oxy]phenyl)-5-{[1-(4-fluorobenzoyl)-4-hydroxypiperidin-4-yl]methyl}-1H,4H,5H-pyrazolo[3,4-d]pyrimidin-4-one (I-694);

5-[(1-cyclopropanecarbonyl-4-hydroxypiperidin-4-yl)methyl]-1-{4-[(4,4-difluorocyclohexyl)oxy]phenyl)-1H,4H,5H-pyrazolo[3,4-d]pyrimidin-4-one (I-695);

5-{[1-(4-fluorobenzoyl)-4-hydroxypiperidin-4-yl]methyl}-1-{4-[(1-fluorocyclobutyl)methoxy]phenyl)-1H,4H,5H-pyrazolo[3,4-d]pyrimidin-4-one (I-696);

1-(4-(4,4-difluorocyclohexyloxy)phenyl)-5-((4-hydroxy-1-(4-methylpiperazine-1-carbonyl)piperidin-4-yl)methyl)-1H-pyrazolo[3,4-d]pyrimidin-4 (5H)-one (I-697);

5-((1-(cyclopropanecarbonyl)-4-hydroxypiperidin-4-yl)methyl)-1-(2-(piperazin-1-yl)biphenyl-4-yl}-1H-pyrazolo[3,4-d]pyrimidin-4 (5H)-one (I-698);

5-{[1-(2-cyclopropyl-1,3-oxazole-5-carbonyl)-4-hydroxypiperidin-4-yl]methyl}-1-[4-(4,4-difluoropiperidin-1-yl)phenyl]-1H,4H,5H-pyrazolo[3,4-d]pyrimidin-4-one (I-699);

5-({4-hydroxy-1-[(3R)-3-phenylbutanoyl]piperidin-4-yl}methyl)-1-(pyridin-2-yl)-1H,4H,5H-pyrazolo[3,4-d]pyrimidin-4-one (I-70);

1-[4-(4,4-difluoropiperidin-1-yl)phenyl]-5-{[4-hydroxy-1-(4-methylbenzoyl)piperidin-4-yl]methyl}-1H,4H,5H-pyrazolo[3,4-d]pyrimidin-4-one (I-700);

1-[3-chloro-4-(4-methylpiperazin-1-yl)phenyl]-5-[(1-cyclopropanecarbonyl-4-hydroxypiperidin-4-yl)methyl]-1H,4H,5H-pyrazolo[3,4-d]pyrimidin-4-one (I-701);

5-[(1-cyclopropanecarbonyl-4-hydroxypiperidin-4-yl)methyl]-1-[3-(morpholin-4-yl)-4-phenylphenyl]-1H,4H,5H-pyrazolo[3,4-d]pyrimidin-4-one (I-702);

5-([1-[(4-fluorophenyl)carbonyl]-4-hydroxypiperidin-4-yl]methyl}-1-(1-methyl-1H-pyrazol-4-yl)-1H,4H,5H-pyrazolo[3,4-d]pyrimidin-4-one (I-703);

5-{[1-(4-fluorobenzoyl)-4-hydroxypiperidin-4-yl]methyl}-1-(1-phenyl-1H-pyrazol-4-yl)-1H,4H,5H-pyrazolo[3,4-d]pyrimidin-4-one (I-704);

1-(1-cyclopropyl-1H-pyrazol-4-yl)-5-({1-[4-(difluoromethoxy)benzoyl]-4-hydroxypiperidin-4-yl}methyl)-1H,4H,5H-pyrazolo[3,4-d]pyrimidin-4-one (I-705), 4-((7-(4-fluorophenyl)-4-oxo-6-phenyl-4H-pyrrolo[2,3-d]pyrimidin-3 (7H)-yl)methyl)-4-hydroxy-N,N-dimethylpiperidine-1-carboxamide (I-706);

1-[4-(dimethylamino)phenyl]-5-([1-[(4-fluorophenyl)car-bonyl]-4-hydroxypiperidin-4-yl]methyl)-1H,4H,5H-pyrazolo[3,4-d]pyrimidin-4-one (I-707);

5-{[4-hydroxy-1-(4-phenoxybenzoyl)piperidin-4-yl]methyl}-1-(pyridin-2-yl)-1H,4H,5H-pyrazolo[3,4-d]pyrimidin-4-one (I-71);

1-(4-(1H-1,2,3-triazol-1-yl)phenyl)-5-((1-(4-fluoroben-zoyl)-4-hydroxypiperidin-4-yl)methyl)-1H-pyrazolo[3,4-d]pyrimidin-4(5H)-one (I-711);

5-{[1-(4-fluorobenzoyl)-4-hydroxypiperidin-4-yl]methyl}-1-[4-(5-methyl-1,3,4-oxadiazol-2-yl)phenyl]-1H,4H,5H-pyrazolo[3,4-d]pyrimidin-4-one (I-712);

5-([1-[(4-Fluorophenyl)carbonyl]-4-hydroxypiperidin-4-yl]methyl)-1-[4-(1-hydroxycyclopropyl)phenyl]-1H,4H,5H-pyrazolo[3,4-d]pyrimidin-4-one (I-713);

5-{[(3R,4R)-1-benzoyl-3-fluoro-4-hydroxypiperidin-4-yl]methyl}-1-phenyl-1H,4H,5H-pyrazolo[3,4-d]pyrimidin-4-one (I-716);

5-{[(3S,4R)-1-benzoyl-3-fluoro-4-hydroxypiperidin-4-yl]methyl}-1-phenyl-1H,4H,5H-pyrazolo[3,4-d]pyrimidin-4-one (I-717);

1-(4-fluorophenyl)-5-((4-hydroxy-1-(4-({1-methyl-1H-pyrazol-3-yl)oxy)benzoyl)piperidin-4-yl)methyl)-1H-pyrazolo[3,4-d]pyrimidin-4(5H)-one (I-719);

5-({4-hydroxy-1-[(3R)-3-phenylbutanoyl]piperidin-4-yl}methyl)-1-phenyl-1H,4H,5H-pyrazolo[3,4-d]pyrimidin-4-one (I-72);

5-(1-(1-(4-fluorobenzoyl)-4-hydroxypiperidin-4-yl)-2-hydroxyethyl)-1-(4-fluorophenyl)-1H-pyrazolo[3,4-d]pyrimidin-4(5H)-one (I-720);

8-((1-(4-fluorophenyl)-4-oxo-1,4-dihydro-5H-pyrazolo[3,4-d]pyrimidin-5-yl)methyl)-8-hydroxyoctahydro-4H-quinolizin-4-one (I-721);

1-(4-fluorophenyl)-5-({4-hydroxy-1-[(1r,4r)-4-methoxycyclohexanecarbonyl]piperidin-4-yl}methyl)-1H,4H,5H-pyrazolo[3,4-d]pyrimidin-4-one (I-722);

4-(4-{[1-(4-fluorophenyl)-4-oxo-1H,4H,5H-pyrazolo[3,4-d]pyrimidin-5-yl]methyl}-4-hydroxypiperidine-1-carbonyl)-1Ωω-thiane-1,1-dione (I-723);

1-(4-fluorophenyl)-5-{[4-hydroxy-1-(4,5,6,7-tetrahydro-1H-indazole-6-carbonyl)piperidin-4-yl]methyl]-1H,4H,5H-pyrazolo[3,4-d]pyrimidin-4-one (I-724);

1-(4-fluorophenyl)-5-{[4-hydroxy-1-(1-methyl-4,5,6,7-tetrahydro-1H-indazole-6-carbonyl)piperidin-4-yl]methyl)-1H,4H,5H-pyrazolo[3,4-d]pyrimidin-4-one (I-725);

5-{[1-(1-cyclopropyl-1H-pyrazole-4-carbonyl)-4-hydroxypiperidin-4-yl]methyl}-1-(4-fluorophenyl)-1H,4H,5H-pyrazolo[3,4-d]pyrimidin-4-one (I-726), 1-(4-fluorophenyl)-5-({4-hydroxy-1-[(1r,4r)-4-(1-methyl-1H-pyrazol-4-yl)cyclohexanecarbonyl]piperidin-4-yl}methyl)-1H,4H,5H-pyrazolo[3,4-d]pyrimidin-4-one (I-727);

1-(4-fluorophenyl)-5-({4-hydroxy-1-[(1s,4s)-4-(1-methyl-1H-pyrazol-4-yl)cyclohexanecarbonyl]piperidin-4-yl}methyl)-1H,4H,5H-pyrazolo[3,4-d]pyrimidin-4-one (I-728);

5-{[4-hydroxy-1-(4-phenoxybenzoyl)piperidin-4-yl]methyl}-1-phenyl-1H,4H, 5H-pyrazolo[3,4-d]pyrimidin-4-one (I-73);

5-({1-[(3R)-3-(3-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one (I-731);

5-({1-[(3S)-3-(3-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one (I-732);

5-({1-[(3R)-3-(4-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one (I-733);

5-({1-[(3S)-3-(4-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one (I-734);

5-({1-[(3R)-4,4-difluoro-3-(4-methyl-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-735);

5-({1-[(3S)-4,4-difluoro-3-(4-methyl-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-736);

1-(4-fluorophenyl)-5-[(4-hydroxy-1-[[(1r,4r)-4-[(5-fluoropyridin-2-yl)oxy]cyclohexyl]carbonyl]piperidin-4-yl)methyl]-1H,4H,5H-pyrazolo[3,4-d]pyrimidin-4-one (I-737);

1-(4-fluorophenyl)-5-[(4-hydroxy-1-[[(1s,4s)-4-[(5-fluoropyridin-2-yl) oxy]cyclohexyl]carbonyl]piperidin-4-yl)methyl]-1H,4H,5H-pyrazolo[3,4-d]pyrimidin-4-one (I-738);

1-(4-fluorophenyl)-5-({4-hydroxy-1-[(1r,4r)-4-[(6-fluoropyridin-2-yl)oxy]cyclohexanecarbonyl]piperidin-4-yl}methyl)-1H,4H,5H-pyrazolo[3,4-d]pyrimidin-4-one (I-739);

5-({4-hydroxy-1-[4-(1H-imidazol-1-ylmethyl)benzoyl]piperidin-4-yl}methyl)-1-methyl-1H,4H,5H-pyrazolo[3,4-d]pyrimidin-4-one (I-74);

1-(4-fluorophenyl)-5-({4-hydroxy-1-[(1s,4s)-4-[(6-fluoropyridin-2-yl)oxy]cyclohexanecarbonyl]piperidin-4-yl}methyl)-1H,4H,5H-pyrazolo[3,4-d]pyrimidin-4-one (I-740);

5-({4-hydroxy-1-[(1r,4r)-4-[(6-fluoropyridin-2-yl)oxy]cyclohexanecarbonyl]piperidin-4-yl}methyl)-1-phenyl-1H,4H,5H-pyrazolo[3,4-d]pyrimidin-4-one (I-741);

5-({4-hydroxy-1-[(1s,4s)-4-[(6-fluoropyridin-2-yl)oxy]cyclohexanecarbonyl]piperidin-4-yl}methyl)-1-phenyl-1H,4H,5H-pyrazolo[3,4-d]pyrimidin-4-one (I-742);

5-({4-hydroxy-1-[(1r,4r)-4-[(5-fluoropyridin-2-yl)oxy]cyclohexanecarbonyl]piperidin-4-yl}methyl)-1-phenyl-1H,4H,5H-pyrazolo[3,4-d]pyrimidin-4-one (I-743);

5-({4-hydroxy-1-[(1s,4s)-4-[(5-fluoropyridin-2-yl)oxy]cyclohexanecarbonyl]piperidin-4-yl}methyl)-1-phenyl-1H,4H,5H-pyrazolo[3,4-d]pyrimidin-4-one (I-744);

1-(4-fluorophenyl)-5-({4-hydroxy-1-[(1s,4s)-1-methyl-4-(pyridin-2-yloxy)cyclohexanecarbonyl]piperidin-4-yl}methyl)-1H,4H,5H-pyrazolo[3,4-d]pyrimidin-4-one (I-745);

1-(4-fluorophenyl)-5-({4-hydroxy-1-[(1r,4r)-1-methyl-4-(pyridin-2-yloxy)cyclohexanecarbonyl]piperidin-4-yl}methyl)-1H,4H,5H-pyrazolo[3,4-d]pyrimidin-4-one (I-746);

1-(4-fluorophenyl)-5-({4-hydroxy-1-[(1s,4s)-4-(pyrimidin-2-yloxy)cyclohexanecarbonyl]piperidin-4-yl}methyl)-1H,4H,5H-pyrazolo[3,4-d]pyrimidin-4-one (I-747);

1-(4-fluorophenyl)-5-({4-hydroxy-1-[(1r,4r)-4-(pyrimidin-2-yloxy)cyclohexanecarbonyl]piperidin-4-yl}methyl)-1H,4H,5H-pyrazolo[3,4-d]pyrimidin-4-one (I-748);

1-(4-fluorophenyl)-5-({4-hydroxy-1-[(1s,4s)-4-(pyridin-3-yloxy)cyclohexanecarbonyl]piperidin-4-yl}methyl)-1H,4H,5H-pyrazolo[3,4-d]pyrimidin-4-one (I-749);

5-({4-hydroxy-1-[4-(1H-1,2,3,4-tetrazol-1-ylmethyl)benzoyl]piperidin-4-yl}methyl)-1-methyl-1H,4H,5H-pyrazolo[3,4-d]pyrimidin-4-one (I-75);

1-(4-fluorophenyl)-5-({4-hydroxy-1-[(1r,4r)-4-(pyridin-3-yloxy)cyclohexanecarbonyl]piperidin-4-yl}methyl)-1H,4H,5H-pyrazolo[3,4-d]pyrimidin-4-one (I-750);

1-(4-fluorophenyl)-5-({4-hydroxy-1-[(1s,4s)-4-(pyridin-4-yloxy)cyclohexanecarbonyl]piperidin-4-yl}methyl)-1H,4H,5H-pyrazolo[3,4-d]pyrimidin-4-one (I-751);

1-(4-fluorophenyl)-5-({4-hydroxy-1-[(1r,4r)-4-(pyridin-4-yloxy)cyclohexanecarbonyl]piperidin-4-yl}methyl)-1H,4H,5H-pyrazolo[3,4-d]pyrimidin-4-one (I-752);

1-(4-fluorophenyl)-5-({4-hydroxy-1-[(1s,4s)-4-[(1-methyl-1H-pyrazol-3-yl)oxy]cyclohexanecarbonyl]piperidin-4-yl}methyl)-1H,4H,5H-pyrazolo[3,4-d]pyrimidin-4-one (I-753);

1-(4-fluorophenyl)-5-({4-hydroxy-1-[(1r,4r)-4-[(1-methyl-1H-pyrazol-3-yl)oxy]cyclohexanecarbonyl]piperidin-4-yl}methyl)-1H,4H,5H-pyrazolo[3,4-d]pyrimidin-4-one (I-754);

1-(4-fluorophenyl)-5-({4-hydroxy-1-[(1s,4s)-4-[(5-methyl-1,2-oxazol-3-yl)oxy]cyclohexanecarbonyl]piperidin-4-yl}methyl)-1H,4H,5H-pyrazolo[3,4-d]pyrimidin-4-one (I-755);

1-(4-fluorophenyl)-5-({4-hydroxy-1-[(1r,4r)-4-[(5-methyl-1,2-oxazol-3-yl)oxy]cyclohexanecarbonyl]piperidin-4-yl}methyl)-1H,4H,5H-pyrazolo[3,4-d]pyrimidin-4-one (I-756);

1-(4-fluorophenyl)-5-({4-hydroxy-1-[(1s,4s)-4-[(1-methyl-1H-pyrazol-4-yl)oxy]cyclohexanecarbonyl]piperidin-4-yl}methyl)-1H,4H,5H-pyrazolo[3,4-d]pyrimidin-4-one (I-757), 1-(4-fluorophenyl)-5-({4-hydroxy-1-[(1r,4r)-4-[(1-methyl-1H-pyrazol-4-yl)oxy]cyclohexanecarbonyl]piperidin-4-yl}methyl)-1H,4H,5H-pyrazolo[3,4-d]pyrimidin-4-one (I-758);

5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one (I-759);

5-{[1-(2-benzylbenzoyl)-4-hydroxypiperidin-4-yl]methyl}-1-methyl-1H,4H,5H-pyrazolo[3,4-d]pyrimidin-4-one (I-76);

5-({1-[(2R)-2-benzylazetidine-1-carbonyl]-4-hydroxypiperidin-4-yl}methyl)-1-(4-fluorophenyl)-1H,4H,5H-pyrazolo[3,4-d]pyrimidin-4-one (I-760);

1-(4-fluorophenyl)-5-[(4-hydroxy-1-{1H,4H,5H,6H,7H-pyrazolo[3,4-c]pyridine-6-carbonyl}piperidin-4-yl)methyl]-1H,4H,5H-pyrazolo[3,4-d]pyrimidin-4-one (I-761);

1-(4-fluorophenyl)-5-[(4-hydroxy-1-{1-methyl-1H,4H,5H,6H,7H-pyrazolo[3,4-c]pyridine-6-carbonyl}piperidin-4-yl)methyl]-1H,4H,5H-pyrazolo[3,4-d]pyrimidin-4-one (I-762), 1-(4-fluorophenyl)-5-({4-hydroxy-1-[(1s,4s)-4-[(1-methyl-1H-pyrazol-5-yl)amino]cyclohexanecarbonyl]piperidin-4-yl}methyl)-1H,4H,5H-pyrazolo[3,4-d]pyrimidin-4-one (I-763);

1-(4-fluorophenyl)-5-({4-hydroxy-1-[(1r,4r)-4-[(1-methyl-1H-pyrazol-5-yl)amino]cyclohexanecarbonyl]piperidin-4-yl}methyl)-1H,4H,5H-pyrazolo[3,4-d]pyrimidin-4-one (I-764);

1-(4-fluorophenyl)-5-({4-hydroxy-1-[(1s,4s)-4-[(1-methyl-1H-pyrazol-3-yl)amino]cyclohexanecarbonyl]piperidin-4-yl}methyl)-1H,4H,5H-pyrazolo[3,4-d]pyrimidin-4-one (I-765);

1-(4-fluorophenyl)-5-({4-hydroxy-1-[(1r,4r)-4-[(1-methyl-1H-pyrazol-3-yl)amino]cyclohexanecarbonyl]piperidin-4-yl}methyl)-1H,4H,5H-pyrazolo[3,4-d]pyrimidin-4-one (I-766);

1-(4-fluorophenyl)-5-({4-hydroxy-1-[(1s,4s)-4-(phenylamino)cyclohexanecarbonyl]piperidin-4-yl}methyl)-1H,4H,5H-pyrazolo[3,4-d]pyrimidin-4-one (I-767), 1-(4-fluorophenyl)-5-({4-hydroxy-1-[(1r,4r)-4-(phenylamino)cyclohexanecarbonyl]piperidin-4-yl}methyl)-1H,4H,5H-pyrazolo[3,4-d]pyrimidin-4-one (I-768), 1-(4-fluorophenyl)-5-({4-hydroxy-1-[(1r,4r)-4-(cyclopropylamino)cyclohexanecarbonyl]piperidin-4-yl}methyl)-1H,4H,5H-pyrazolo[3,4-d]pyrimidin-4-one (I-769);

5-({1-[3-(3-fluorophenyl)butanoyl]-4-hydroxypiperidin-4-yl}methyl)-1-methyl-1H,4H,5H-pyrazolo[3,4-d]pyrimidin-4-one (I-77);

5-{[1-(2-cyclopropyl-1,3-oxazole-5-carbonyl)-4-hydroxypiperidin-4-yl]methyl}-1-{4-[(3,3-difluorocyclobutyl)methoxy]phenyl}-1H,4H,5H-pyrazolo[3,4-d]pyrimidin-4-one (I-770);

1-(4-chlorophenyl)-5-[(1-[[2-(cyclopropylamino)-1,3-oxazol-5-yl]carbonyl]-4-hydroxypiperidin-4-yl)methyl]-1H,4H,5H-pyrazolo[3,4-d]pyrimidin-4-one (I-771);

1-(4-chlorophenyl)-5-{[4-hydroxy-1-(1-methyl-1H-pyrazole-4-carbonyl)piperidin-4-yl]methyl}-1H,4H,5H-pyrazolo[3,4-d]pyrimidin-4-one (I-772

5-((1-(3-(3-aminopropoxy)benzoyl)-4-hydroxypiperidin-4-yl)methyl)-1-(4-chlorophenyl)-1H-pyrazolo[3,4-d]pyrimidin-4(5H)-one (I-774);

5-((4-hydroxy-1-(1-methyl cyclopropanecarbonyl)piperidin-4-yl) methyl)-1-(4-(1-methyl-1H-pyrazol-4-yl)phenyl)-1H-pyrazolo[3,4-d]pyrimidin-4(5H)-one (I-775);

5-([1-[(2-Cyclopropyl-1,3-oxazol-5-yl)carbonyl]-4-hydroxypiperidin-4-yl]methyl)-1-[4-(1-methyl-1H-pyrazol-4-yl)phenyl]-1H,4H,5H-pyrazolo[3,4-d]pyrimidin-4-one (I-776);

(S)-1-(4-(hexahydro-1H-pyrido[1,2-a]pyrazin-2(6H)-yl)phenyl)-5-((4-hydroxy-1-(1-methylcyclopropanecarbonyl)piperidin-4-yl) methyl)-1H-pyrazolo[3,4-d]pyrimidin-4(5H)-one (I-777);

(R)-1-(4-(hexahydro-1H-pyrido[1,2-a]pyrazin-2(6H)-yl)phenyl)-5-((4-hydroxy-1-(1-methylcyclopropanecarbonyl)piperidin-4-yl)methyl)-1H-pyrazolo[3,4-d]pyrimidin-4(5H)-one (I-778);

5-([1-[(2-cyclopropyl-1,3-oxazol-5-yl)carbonyl]-4-hydroxypiperidin-4-yl]methyl)-1-[4-(4-methyl-1H-pyrazol-1-yl)phenyl]-1H,4H,5H-pyrazolo[3,4-d]pyrimidin-4-one (I-779);

5-({1-[3-(4-fluorophenyl)butanoyl]-4-hydroxypiperidin-4-yl}methyl)-1-methyl-1H,4H,5H-pyrazolo[3,4-d]pyrimidin-4-one (I-78);

5-{[1-(2-cyclopropyl-1,3-oxazole-5-carbonyl)-4-hydroxypiperidin-4-yl]methyl}-1-[4-(1H-pyrazol-1-yl)phenyl]-1H,4H,5H-pyrazolo[3,4-d]pyrimidin-4-one (I-780);

5-{[4-hydroxy-1-(1-methylcyclopropanecarbonyl)piperidin-4-yl]methyl}-1-[4-(1H-pyrazol-1-yl)phenyl]-1H,4H,5H-pyrazolo[3,4-d]pyrimidin-4-one (I-781);

5-{[4-hydroxy-1-(1-methylcyclobutanecarbonyl)piperidin-4-yl]methyl}-1-[4-(1H-pyrazol-1-yl)phenyl]-1H,4H,5H-pyrazolo[3,4-d]pyrimidin-4-one (I-782);

(R)-5-((1-(cyclohexanecarbonyl)-4-hydroxypiperidin-4-yl)methyl)-1-(4-(3-hydroxy-3-methylpyrrolidin-1-yl)phenyl)-1H-pyrazolo[3,4-d]pyrimidin-4(5H)-one (I-783);

1-(4-{3-azabicyclo[3.1.0]hexan-3-yl}phenyl)-5-({1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (I-784);

1-(4-{3-azabicyclo[3.1.0]hexan-3-yl}phenyl)-5-({1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (I-785);

1-(4-(4,4-Difluorocyclohexylamino)phenyl)-5-((4-hydroxy-1-(1-methylcyclopropanecarbonyl) piperidin-4-yl)methyl)-1H-pyrazolo[3,4-d]pyrimidin-4(5H)-one (I-786);

N-(4'-(4-((1-(4-ethynylphenyl)-4-oxo-1H-pyrazolo[3,4-d]pyrimidin-5(4H)-yl)methyl)-4-hydroxypiperidine-1-carbonyl)biphenyl-2-yl)ethenesulfonamide (I-787);

5-([1-[(3R)-4,4-difluoro-3-(3-fluoro-1H-pyrazol-1-yl)butanoyl]-4-hydroxypiperidin-4-yl]methyl)-1-[3-(morpholin-4-yl)phenyl]-1H,4H,5H-pyrazolo[3,4-d]pyrimidin-4-one (I-788);

5-([1-[(3S)-4,4-difluoro-3-(3-fluoro-1H-pyrazol-1-yl)butanoyl]-4-hydroxypiperidin-4-yl]methyl)-1-[3-(morpholin-4-yl)phenyl]-1H,4H,5H-pyrazolo[3,4-d]pyrimidin-4-one (I-789);

5-{[4-hydroxy-1-(2-methyl-4-phenylbutanoyl)piperidin-4-yl]methy 1}-1-methyl-1H,4H, 5H-pyrazolo[3,4-d]pyrimidin-4-one (I-79);

1-(3-{3-azabicyclo[3.1.0]hexan-3-yl}phenyl)-5-({1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (T-790);

1-(3-{3-azabicyclo[3.1.0]hexan-3-yl}phenyl)-5-({1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one (I-791);

(R)-3-((1-(4,4-difluoro-3-(1H-pyrazol-1-yl)butanoyl)-4-hydroxypiperidin-4-yl)methyl)-7-(3-(4-methylpiperazin-1-yl)phenyl)-3H-pyrrolo[2,3-d]pyrimidin-4(7H)-one (I-792);

(S)-3-((1-(4,4-difluoro-3-(1H-pyrazol-1-yl)butanoyl)-4-hydroxypiperidin-4-yl)methyl)-7-(3-(4-methylpiperazin-1-yl)phenyl)-3H-pyrrolo[2,3-d]pyrimidin-4(7H)-one (I-793);

7-(4-fluorophenyl)-3-((4-hydroxy-1-(trans-4-({1-methyl-1H-pyrazol-5-yl}oxy) cyclohexanecarbonyl)piperidin-4-yl)methyl)-3H-pyrrolo[2,3-d]pyrimidin-4(7H)-one (I-794);

1-(4-ethylphenyl)-5-((4-hydroxy-1-(4-(1-methylpiperidin-4-yloxy)benzoyl)piperidin-4-yl)methyl)-1H-pyrazolo[3,4-d]pyrimidin-4(5H)-one (I-795);

(R)-5-((1-(4,4-difluoro-3-(3-fluoro-1H-pyrazol-1-yl)butanoyl)-4-hydroxypiperidin-4-yl)methyl)-1-p-tolyl-1H-pyrazolo[3,4-d]pyrimidin-4(5H)-one (I-796);

(S)-5-((1-(4,4-difluoro-3-(3-fluoro-1H-pyrazol-1-yl)butanoyl)-4-hydroxypiperidin-4-yl)methyl)-1-p-tolyl-1H-pyrazolo[3,4-d]pyrimidin-4(5H)-one (I-797);

5-([1-[(1-cyclopropyl-1H-pyrazol-4-yl)carbonyl]-4-hydroxypiperidin-4-yl]methyl)-1-(4-cyclopropylphenyl)-1H,4H,5H-pyrazolo[3,4-d]pyrimidin-4-one (I-798);

1-(4-cyclopropylphenyl)-5-((4-hydroxy-1-(2-methyloxazole-5-carbonyl)piperidin-4-yl)methyl)-1H-pyrazolo[3,4-d]pyrimidin-4(5H)-one (I-799), 5-{[1-(2-benzylcyclopropanecarbonyl)-4-hydroxypiperidin-4-yl]methyl}-1-methyl-1H,4H,5H-pyrazolo[3,4-d]pyrimidin-4-one (I-80), 1-(4-fluorophenyl)-5-({4-hydroxy-1-[(2S)-1-(prop-2-ynoyl)azetidine-2-carbonyl]piperidin-4-yl}methyl)-1H,4H,5H-pyrazolo[3,4-d]pyrimidin-4-one (I-803);

1-(4-Fluorophenyl)-5-((4-hydroxy-1-(trans-4-(5-methylisoxazol-3-ylamino) cyclohexanecarbonyl)piperidin-4-yl)methyl)-1H-pyrazolo[3,4-d]pyrimidin-4(5H)-one (I-806);

1-(4-Fluorophenyl)-5-((4-hydroxy-1-(cis-4-(5-methylisoxazol-3-ylamino)cyclohexanecarbonyl) piperidin-4-yl)methyl)-1H-pyrazolo[3,4-d]pyrimidin-4(5H)-one (I-807);

5-{[4-hydroxy-1-(2-methoxy-3-phenylpropanoyl)piperidin-4-yl]methyl}-1-methyl-1H,4H,5H-pyrazolo[3,4-d]pyrimidin-4-one (I-81);

4-{[1-(3-bromo-4-fluorophenyl)-4-oxo-1H,4H, 5H-pyrazolo[3,4-d]pyrimidin-5-yl]methyl}-4-hydroxy-N,N-dimethylpiperidine-1-carboxamide (I-810);

4-{[1-(3-bromophenyl)-4-oxo-1H,4H,5H-pyrazolo[3,4-d]pyrimidin-5-yl]methyl}-4-hydroxy-N,N-dimethylpiperidine-1-carboxamide (I-811);

4-(5-((1-(cyclopropanecarbonyl)-4-hydroxypiperidin-4-yl)methyl)-4-oxo-4,5-dihydropyrazolo[3,4-d]pyrimidin-1-yl)benzoic acid (I-812);

N-[(2R)-1-[4-hydroxy-4-({4-oxo-1-phenyl-1H,4H,5H-pyrazolo[3,4-d]pyrimidin-5-yl}methyl)piperidin-1-yl]-1-oxo-3-phenylpropan-2-yl]ethene-1-sulfonamide (I-814);

Anti-5-((4-Hydroxy-1-(1-methylcyclopropanecarbonyl) piperidin-4-yl)methyl)-1-(4-((4-methoxycyclohexyl)oxy)phenyl)-1H-pyrazolo[3,4-d]pyrimidin-4(5H)-one, isomer A (I-815a);

Syn-5-((4-Hydroxy-1-(1-methylcyclopropanecarbonyl) piperidin-4-yl)methyl)-1-(4-((4-methoxycyclohexyl)oxy)phenyl)-1H-pyrazolo[3,4-d]pyrimidin-4(5H)-one, isomer B (I-815b);

5-((1-(4-fluorobenzoyl)-4-hydroxypiperidin-4-yl)methyl)-1-(4-((3-hydroxy-1-methylazetidin-3-yl)methoxy)phenyl)-1H-pyrazolo[3,4-d]pyrimidin-4(5H)-one (I-816);

5-{[1-(2-cyclopropyl-1,3-oxazole-5-carbonyl)-4-hydroxypiperidin-4-yl]methyl}-1-{4-[(4,4-difluorocyclohexyl)oxy]phenyl}-1H,4H,5H-pyrazolo[3,4-d]pyrimidin-4-one (I-817);

5-[(1-cyclopropanecarbonyl-4-hydroxypiperidin-4-yl)methyl]-1-{4-[3-(4-methylpiperazin-1-yl)-1H-pyrazol-1-yl]phenyl}-1H,4H,5H-pyrazolo[3,4-d]pyrimidin-4-one (I-818);

5-[(1-cyclopropanecarbonyl-4-hydroxypiperidin-4-yl)methyl]-1-{4-[4-(morpholin-4-yl)-1H-pyrazol-1-yl]phenyl}-1H,4H,5H-pyrazolo[3,4-d]pyrimidin-4-one (I-819);

5-{[4-hydroxy-1-(4,4,4-trifluoro-3-phenylbutanoyl)piperidin-4-yl]methyl}-1-methyl-1H,4H,5H-pyrazolo[3,4-d]pyrimidin-4-one (I-82);

5-{[1-(4-fluorobenzoyl)-4-hydroxypiperidin-4-yl]
methyl}-1-(4-{1H,4H,6H,7H-pyrano[4,3-c]pyrazol-1-
yl}phenyl)-1H,4H,5H-pyrazolo[3,4-d]pyrimidin-4-one
(I-820);

5-([1-[(3R)-4,4-difluoro-3-(1H-pyrazol-1-yl)butanoyl]-4-
hydroxypiperidin-4-yl]methyl)-1-[4-(piperidin-1-yl)
phenyl]-1H,4H,5H-pyrazolo[3,4-d]pyrimidin-4-one
(I-821);

5-([1-[(3S)-4,4-difluoro-3-(1H-pyrazol-1-yl)butanoyl]-4-
hydroxypiperidin-4-yl]methyl)-1-[4-(piperidin-1-yl)
phenyl]-1H,4H,5H-pyrazolo[3,4-d]pyrimidin-4-one
(I-822);

1-(3-{[2-(dimethylamino)ethyl](methyl)amino}phenyl)-
5-{[1-(4-fluorobenzoyl)-4-hydroxypiperidin-4-yl]
methyl}-1H,4H,5H-pyrazolo[3,4-d]pyrimidin-4-one
(I-823);

1-[4-fluoro-3-(piperazin-1-yl)phenyl]-5-{[1-(4-fluo-
robenzoyl)-4-hydroxypiperidin-4-yl]methyl}-1H,4H,
5H-pyrazolo[3,4-d]pyrimidin-4-one (I-824);

5-({1-[4,4-difluoro-3-(1H-pyrazol-1-yl)butanoyl]-4-hy-
droxypiperidin-4-yl}methyl)-1-[4-(4-methylpiperazin-
1-yl)phenyl]-1H,4H,5H-pyrazolo[3,4-d]pyrimidin-4-
one (I-825);

5-({1-[(3R)-4,4-difluoro-3-(1H-pyrazol-1-yl)butanoyl]-
4-hydroxypiperidin-4-yl}methyl)-1-[4-(4-methylpiper-
azin-1-yl)phenyl]-1H,4H,5H-pyrazolo[3,4-d]pyrimi-
din-4-one (I-826);

5-({1-[(3S)-4,4-difluoro-3-(1H-pyrazol-1-yl)butanoyl]-4-
hydroxypiperidin-4-yl}methyl)-1-[4-(4-methylpiper-
azin-1-yl)phenyl]-1H,4H,5H-pyrazolo[3,4-d]pyrimi-
din-4-one (I-827);

5-({1-[4,4-difluoro-3-(1H-pyrazol-1-yl)butanoyl]-4-hy-
droxypiperidin-4-yl}methyl)-1-[3-(4-methylpiperazin-
1-yl)phenyl]-1H,4H,5H-pyrazolo[3,4-d]pyrimidin-4-
one (I-828);

5-({1-[(3R)-4,4-difluoro-3-(1H-pyrazol-1-yl)butanoyl]-
4-hydroxypiperidin-4-yl}methyl)-1-[3-(4-methylpiper-
azin-1-yl)phenyl]-1H,4H,5H-pyrazolo[3,4-d]pyrimi-
din-4-one (I-829);

2-(2-{4-[4-hydroxy-4-({1-methyl-4-oxo-1H,4H,5H-
pyrazolo[3,4-d]pyrimidin-5-yl}methyl)piperidine-1-
carbonyl]phenyl}phenyl)acetonitrile (I-83);

5-({1-[(3S)-4,4-difluoro-3-(1H-pyrazol-1-yl)butanoyl]-4-
hydroxypiperidin-4-yl}methyl)-1-[3-(4-methylpiper-
azin-1-yl)phenyl]-1H,4H,5H-pyrazolo[3,4-d]pyrimi-
din-4-one (I-830);

5-({4-hydroxy-1-[1-(prop-2-enoyl)azetidine-2-carbonyl]
piperidin-4-yl}methyl)-1-[3-(4-methylpiperazin-1-yl)
phenyl]-1H,4H,5H-pyrazolo[3,4-d]pyrimidin-4-one
(I-831);

5-({4-hydroxy-1-[1-(prop-2-enoyl)azetidine-2-carbonyl]
piperidin-4-yl}methyl)-1-[4-(4-methylpiperazin-1-yl)
phenyl]-1H,4H,5H-pyrazolo[3,4-d]pyrimidin-4-one
(I-832);

5-({1-[(3R)-4,4-difluoro-3-(1H-pyrazol-1-yl)butanoyl]-
4-hydroxypiperidin-4-yl}methyl)-1-{4-[(3S)-3-hy-
droxy-3-methylpyrrolidin-1-yl]phenyl}-1H,4H,5H-
pyrazolo[3,4-d]pyrimidin-4-one (I-833), 5-({1-[(3R)-4,4-difluoro-3-(1H-pyrazol-1-yl)butanoyl]-
4-hydroxypiperidin-4-yl}methyl)-1-{4-[(3R)-3-hy-
droxy-3-methylpyrrolidin-1-yl]phenyl}-1H,4H,5H-
pyrazolo[3,4-d]pyrimidin-4-one (I-834);

5-({1-[(3S)-4,4-difluoro-3-(1H-pyrazol-1-yl)butanoyl]-4-
hydroxypiperidin-4-yl}methyl)-1-{4-[(3S)-3-hydroxy-
3-methylpyrrolidin-1-yl]phenyl)-1H,4H,5H-pyrazolo
[3,4-d]pyrimidin-4-one (I-835);

5-({1-[(3S)-4,4-difluoro-3-(1H-pyrazol-1-yl)butanoyl]-4-
hydroxypiperidin-4-yl}methyl)-1-{4-[(3R)-3-hydroxy-
3-methylpyrrolidin-1-yl]phenyl)-1H,4H,5H-pyrazolo
[3,4-d]pyrimidin-4-one (I-836);

5-({4-hydroxy-1-[(3S)-3-(1H-pyrazol-1-yl)butanoyl]pip-
eridin-4-yl}methyl)-1-{4-[(3S)-3-hydroxy-3-meth-
ylpyrrolidin-1-yl]phenyl)-1H,4H,5H-pyrazolo[3,4-d]
pyrimidin-4-one (I-837);

5-({4-hydroxy-1-[(3S)-3-(1H-pyrazol-1-yl)butanoyl]pip-
eridin-4-yl}methyl)-1-{4-[(3R)-3-hydroxy-3-meth-
ylpyrrolidin-1-yl]phenyl)-1H,4H,5H-pyrazolo[3,4-d]
pyrimidin-4-one (I-838);

5-({4-hydroxy-1-[(3R)-3-(1H-pyrazol-1-yl)butanoyl]pip-
eridin-4-yl}methyl)-1-{4-[(3S)-3-hydroxy-3-meth-
ylpyrrolidin-1-yl]phenyl)-1H,4H,5H-pyrazolo[3,4-d]
pyrimidin-4-one (I-839);

1-(2-{4-[4-hydroxy-4-({1-methyl-4-oxo-1H,4H,5H-
pyrazolo[3,4-d]pyrimidin-5-yl}methyl)piperidine-1-
carbonyl]phenyl}phenyl)cyclopropane-1-carbonitrile
(I-84);

5-({4-hydroxy-1-[(3R)-3-(1H-pyrazol-1-yl)butanoyl]pip-
eridin-4-yl}methyl)-1-{4-[(3R)-3-hydroxy-3-meth-
ylpyrrolidin-1-yl]phenyl)-1H,4H,5H-pyrazolo[3,4-d]
pyrimidin-4-one (I-840);

5-[(1-cyclopropanecarbonyl-4-hydroxypiperidin-4-yl)
methyl]-1-(4-[4-[(3S)-pyrrolidin-3-yloxy]phenyl]phe-
nyl)-1H,4H,5H-pyrazolo[3,4-d]pyrimidin-4-one
(I-841);

5-[(1-cyclopropanecarbonyl-4-hydroxypiperidin-4-yl)
methyl]-1-(4-[4-[(3R)-pyrrolidin-3-yloxy]phenyl]phe-
nyl)-1H,4H,5H-pyrazolo[3,4-d]pyrimidin-4-one
(I-842);

5-((1-(cyclopropanecarbonyl)-4-hydroxypiperidin-4-yl)
methyl)-1-(4-(piperidin-4-yl)phenyl)-1H-pyrazolo[3,
4-d]pyrimidin-4(5H)-one (I-843);

5-[(1-cyclopropanecarbonyl-4-hydroxypiperidin-4-yl)
methyl]-1-{4-[4-(4-methylpiperazin-1-yl)phenyl]phe-
nyl)-1H,4H,5H-pyrazolo[3,4-d]pyrimidin-4-one
(I-844);

5-[(1-cyclopropanecarbonyl-4-hydroxypiperidin-4-yl)
methyl]-1-(4-{6-[3-(methylamino) pyrrolidin-1-yl]
pyridin-3-yl}phenyl)-1H,4H,5H-pyrazolo[3,4-d]py-
rimidin-4-one (I-845);

1-(4-cyclobutylphenyl)-5-{[4-hydroxy-1-(2-methyl-1,3-
oxazole-5-carbonyl)piperidin-4-yl]methyl}-1H,4H,5H-
pyrazolo[3,4-d]pyrimidin-4-one (I-846);

1-(4-cyclobutylphenyl)-5-{[1-(2-cyclopropyl-1,3-oxa-
zole-5-carbonyl)-4-hydroxypiperidin-4-yl]methyl)-1H,
4H,5H-pyrazolo[3,4-d]pyrimidin-4-one (I-847);

3-{[1-(2-cyclopropyl-1,3-oxazole-5-carbonyl)-4-hy-
droxypiperidin-4-yl]methyl}-7-(4-fluorophenyl)-3H,
4H,7H-pyrrolo[2,3-d]pyrimidin-4-one (I-849);

5-({1-[4-(4-chlorophenoxy)benzoyl]-4-hydroxypiperi-
din-4-yl}methyl)-1-methyl-1H,4H,5H-pyrazolo[3,4-d]
pyrimidin-4-one (I-85);

3-{[1-(2-cyclopropyl-1,3-oxazole-5-carbonyl)-4-hy-
droxypiperidin-4-yl]methyl}-7-(4-fluorophenyl)-6-
methyl-3H,4H,7H-pyrrolo[2,3-d]pyrimidin-4-one
(I-850);

5-({1-[4-(difluoromethoxy)benzoyl]-4-hydroxypiperidin-
4-yl}methyl)-1-[4-(hydroxymethyl)phenyl]-1H,4H,
5H-pyrazolo[3,4-d]pyrimidin-4-one (I-851);

5-({4-hydroxy-1-[(1r,4r)-4-(pyridin-2-yloxy)cyclohexan-
ecarbonyl]piperidin-4-yl}methyl)-1-[4-(hydroxym-
ethyl)phenyl]-1H,4H,5H-pyrazolo[3,4-d]pyrimidin-4-
one (I-852);

5-({4-hydroxy-1-[(1s,4s)-4-(pyridin-2-yloxy)cyclohexanecarbonyl]piperidin-4-yl}methyl)-1-[4-(hydroxymethyl)phenyl]-1H,4H,5H-pyrazolo[3,4-d]pyrimidin-4-one (I-853);

1-[4-(azetidin-1-ylmethyl)phenyl]-5-([1-[(3S)-4,4-difluoro-3-(1H-pyrazol-1-yl)butanoyl]-4-hydroxypiperidin-4-yl]methyl)-1H,4H,5H-pyrazolo[3,4-d]pyrimidin-4-one (I-854);

1-[4-(azetidin-1-ylmethyl)phenyl]-5-([1-[(3R)-4,4-difluoro-3-(1H-pyrazol-1-yl)butanoyl]-4-hydroxypiperidin-4-yl]methyl)-1H,4H,5H-pyrazolo[3,4-d]pyrimidin-4-one (I-855);

5-[(1-cyclopropanecarbonyl-4-hydroxypiperidin-4-yl)methyl]-1-[3-[2-(dimethylamino)ethoxy]-4-phenylphenyl]-1H,4H,5H-pyrazolo[3,4-d]pyrimidin-4-one (I-856);

5-({1-[4-(4-fluorophenoxy)benzoyl]-4-hydroxypiperidin-4-yl}methyl)-1-methyl-1H,4H,5H-pyrazolo[3,4-d]pyrimidin-4-one (I-86);

5-({4-hydroxy-1-[(3S)-4,4,4-trifluoro-3-phenylbutanoyl]piperidin-4-yl}methyl)-1-methyl-1H,4H,5H-pyrazolo[3,4-d]pyrimidin-4-one (I-861);

5-({1-[4-(4-bromophenoxy)benzoyl]-4-hydroxypiperidin-4-yl}methyl)-1-methyl-1H,4H,5H-pyrazolo[3,4-d]pyrimidin-4-one (I-87);

5-({4-hydroxy-1-[4-(4-hydroxyphenoxy)benzoyl]piperidin-4-yl}methyl)-1-methyl-1H,4H,5H-pyrazolo[3,4-d]pyrimidin-4-one (I-88);

5-({4-hydroxy-1-[4-(3-hydroxyphenoxy)benzoyl]piperidin-4-yl}methyl)-1-methyl-1H,4H,5H-pyrazolo[3,4-d]pyrimidin-4-one (I-89);

5-[(4-hydroxy-1-{4-[(pyrimidin-2-yloxy)methyl]benzoyl}piperidin-4-yl)methyl]-1-methyl-1H,4H,5H-pyrazolo[3,4-d]pyrimidin-4-one (I-9);

5-({1-[4-(3-chlorophenoxy)benzoyl]-4-hydroxypiperidin-4-yl}methyl)-1-methyl-1H,4H,5H-pyrazolo[3,4-d]pyrimidin-4-one (I-90);

5-({1-[4-(3-bromophenoxy)benzoyl]-4-hydroxypiperidin-4-yl}methyl)-1-methyl-1H,4H,5H-pyrazolo[3,4-d]pyrimidin-4-one (I-91);

1-(1-cyclopropyl-1H-pyrazol-4-yl)-5-{[1-(4-fluorobenzoyl)-4-hydroxypiperidin-4-yl]methyl}-1H,4H,5H-pyrazolo[3,4-d]pyrimidin-4-one (I-910);

1-(4-fluorophenyl)-5-({4-hydroxy-1-[4-(5-methyl-1,3,4-oxadiazol-2-yl)benzoyl]piperidin-4-yl}methyl)-1H,4H,5H-pyrazolo[3,4-d]pyrimidin-4-one (I-911);

1-(4-fluorophenyl)-5-({4-hydroxy-1-[(3S)-4,4,4-trifluoro-3-(1H-pyrazol-1-yl)butanoyl]piperidin-4-yl}methyl)-1H,4H,5H-pyrazolo[3,4-d]pyrimidin-4-one (I-912);

1-(4-fluorophenyl)-5-({4-hydroxy-1-[(3R)-4,4,4-trifluoro-3-(1H-pyrazol-1-yl)butanoyl]piperidin-4-yl}methyl)-1H,4H,5H-pyrazolo[3,4-d]pyrimidin-4-one (I-913);

1-(4-fluorophenyl)-5-({4-hydroxy-1-[2-(4-hydroxypiperidin-1-yl)-1,3-oxazole-5-carbonyl]piperidin-4-yl}methyl)-1H,4H,5H-pyrazolo[3,4-d]pyrimidin-4-one (I-915);

5-({4-hydroxy-1-[2-(4-hydroxypiperidin-1-yl)-1,3-oxazole-5-carbonyl]piperidin-4-yl}methyl)-1-(4-phenylphenyl)-1H,4H,5H-pyrazolo[3,4-d]pyrimidin-4-one (I-916);

5-({4-hydroxy-1-[(1r,3r)-3-(pyridin-2-yloxy)cyclobutanecarbonyl]piperidin-4-yl}methyl)-1-(4-methyl phenyl)-1H,4H, 5H-pyrazolo[3,4-d]pyrimidin-4-one (I-917);

5-({1-[(3S)-4,4-difluoro-3-(4-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one (I-918);

1-(4-chlorophenyl)-5-({4-hydroxy-1-[4-(4H-1,2,4-triazol-4-yl)benzoyl]piperidin-4-yl}methyl)-1H,4H,5H-pyrazolo[3,4-d]pyrimidin-4-one (I-919);

5-{[4-hydroxy-1-(4-{[5-(trifluoromethyl)pyridin-2-yl]oxy}benzoyl)piperidin-4-yl]methyl}-1-methyl-1H,4H,5H-pyrazolo[3,4-d]pyrimidin-4-one (I-92);

1-(4-chlorophenyl)-5-[(4-hydroxy-1-{6-[(1-methylpyrrolidin-3-yl)oxy]pyridine-3-carbonyl}piperidin-4-yl)methyl]-1H,4H,5H-pyrazolo[3,4-d]pyrimidin-4-one (I-920);

1-(4-fluorophenyl)-5-({4-hydroxy-1-[1-methyl-3-(1H-pyrazol-1-ylmethyl)-1H-pyrazole-4-carbonyl]piperidin-4-yl}methyl)-1H,4H,5H-pyrazolo[3,4-d]pyrimidin-4-one (I-921);

1-(4-fluorophenyl)-5-[(4-hydroxy-1-{4-[(5-methyl-1,2-oxazol-3-yl)oxy]piperidine-1-carbonyl}piperidin-4-yl)methyl]-1H,4H,5H-pyrazolo[3,4-d]pyrimidin-4-one (I-922);

1-(4-fluorophenyl)-5-[(4-hydroxy-1-{4-[(1-methyl-1H-pyrazol-4-yl)oxy]piperidine-1-carbonyl}piperidin-4-yl)methyl]-1H,4H,5H-pyrazolo[3,4-d]pyrimidin-4-one (I-923);

N-[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]acetamide (I-924), 1-(4-fluorophenyl)-5-({4-hydroxy-1-[(1s,4s)-4-(oxan-4-yloxy)cyclohexanecarbonyl]piperidin-4-yl}methyl)-1H,4H,5H-pyrazolo[3,4-d]pyrimidin-4-one (I-925);

1-(4-fluorophenyl)-5-({4-hydroxy-1-[(1r,4r)-4-(oxan-4-yloxy)cyclohexanecarbonyl]piperidin-4-yl}methyl)-1H,4H,5H-pyrazolo[3,4-d]pyrimidin-4-one (I-926);

4-{[1-(4-bromophenyl)-4-oxo-1H,4H,5H-pyrazolo[3,4-d]pyrimidin-5-yl]methyl}-4-hydroxy-N,N-dimethylpiperidine-1-carboxamide (I-928);

5-({4-hydroxy-1-[4-(pyridin-3-yloxy)benzoyl]piperidin-4-yl}methyl)-1-methyl-1H,4H,5H-pyrazolo[3,4-d]pyrimidin-4-one (I-93);

5-({4-hydroxy-1-[4-(4-methoxyphenoxy)benzoyl]piperidin-4-yl}methyl)-1-methyl-1H,4H,5H-pyrazolo[3,4-d]pyrimidin-4-one (I-94);

5-({4-hydroxy-1-[4-(3-methylphenoxy)benzoyl]piperidin-4-yl}methyl)-1-methyl-1H,4H,5H-pyrazolo[3,4-d]pyrimidin-4-one (I-95);

N-[(1r,3r)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-ynamide (I-950);

N-[(1R,2S)-2-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-ynamide (I-952), N-[(1r,3r)-3-[2-(4-{[1-(4-fluorophenyl)-4-oxo-1H,4H,5H-pyrazolo[3,4-d]pyrimidin-5-yl]methyl}-4-hydroxypiperidin-1-yl)-2-oxoethyl]cyclobutyl]prop-2-ynamide (I-958);

4-{4-[4-hydroxy-4-({1-methyl-4-oxo-1H,4H,5H-pyrazolo[3,4-d]pyrimidin-5-yl}methyl)piperidine-1-carbonyl]phenoxy}benzonitrile (I-96);

1-(3-aminophenyl)-5-((1-(cyclopropanecarbonyl)-4-hydroxypiperidin-4-yl)methyl)-1H-pyrazolo[3,4-d]pyrimidin-4(5H)-one (I-964);

1-(4-aminophenyl)-5-[(1-cyclopropanecarbonyl-4-hydroxypiperidin-4-yl)methyl]-1H,4H,5H-pyrazolo[3,4-d]pyrimidin-4-one (I-965);

4-((1-(4-fluoro-3-(piperazin-1-yl)phenyl)-4-oxo-1H-pyrazolo[3,4-d]pyrimidin-5(4H)-yl)methyl)-4-hydroxy-N,N-dimethylpiperidine-1-carboxamide (I-966);

4-hydroxy-N,N-dimethyl-4-({4-oxo-1-[4-(piperazin-1-yl)phenyl]-1H,4H,5H-pyrazolo[3,4-d]pyrimidin-5-yl}methyl)piperidine-1-carboxamide (I-967);

4-[(1-{4-[(3R,4R)-3-fluoro-4-hydroxypyrrolidin-1-yl]phenyl}-4-oxo-1H,4H,5H-pyrazolo[3,4-d]pyrimidin-5-yl)methyl]-4-hydroxy-N,N-dimethylpiperidine-1-carboxamide (I-968);

1-[4-chloro-3-(morpholin-4-yl)phenyl]-5-{[1-(4-fluorobenzoyl)-4-hydroxypiperidin-4-yl]methyl]-1H,4H,5H-pyrazolo[3,4-d]pyrimidin-4-one (I-969);

5-({1-[4-(3,4-dimethylphenoxy)benzoyl]-4-hydroxypiperidin-4-yl}methyl)-1-methyl-1H,4H,5H-pyrazolo[3,4-d]pyrimidin-4-one (I-97);

5-[(1-benzoyl-4-hydroxypiperidin-4-yl)methyl]-1-[3-fluoro-4-(4-methylpiperazin-1-yl)phenyl]-1H,4H,5H-pyrazolo[3,4-d]pyrimidin-4-one (I-970);

5-[(1-cyclopropanecarbonyl-4-hydroxypiperidin-4-yl)methyl]-1-{4-fluoro-3-[(3S)-3-methoxy-3-methylpyrrolidin-1-yl]phenyl}-1H,4H,5H-pyrazolo[3,4-d]pyrimidin-4-one (I-971);

5-[(1-cyclopropanecarbonyl-4-hydroxypiperidin-4-yl)methyl]-1-{4-fluoro-3-[(3R)-3-methoxy-3-methylpyrrolidin-1-yl]phenyl)-1H,4H,5H-pyrazolo[3,4-d]pyrimidin-4-one (I-972);

5-{5-[(1-cyclopropanecarbonyl-4-hydroxypiperidin-4-yl)methyl]-4-oxo-1H,4H,5H-pyrazolo[3,4-d]pyrimidin-1-yl}-2-(4-methylpiperazin-1-yl)benzonitrile (I-973);

4-((1-(3-((3R,4R)-3-fluoro-4-hydroxypyrrolidin-1-yl)phenyl)-4-oxo-1H-pyrazolo[3,4-d]pyrimidin-5(4H)-yl)methyl)-4-hydroxy-N,N-dimethylpiperidine-1-carboxamide (I-974);

5-[(1-cyclopropanecarbonyl-4-hydroxypiperidin-4-yl)methyl]-1-{4-[4-(4-methylpiperazin-1-yl)-1H-pyrazol-1-yl]phenyl}-1H,4H,5H-pyrazolo[3,4-d]pyrimidin-4-one (I-975);

5-{[1-(4-fluorobenzoyl)-4-hydroxypiperidin-4-yl]methyl}-1-(4-{2H,4H,6H,7H-pyrano[4,3-c]pyrazol-2-yl}phenyl)-1H,4H,5H-pyrazolo[3,4-d]pyrimidin-4-one (I-976);

5-[(1-cyclopropanecarbonyl-4-hydroxypiperidin-4-yl)methyl]-1-{4-[4-(2-hydroxy ethoxy)-1H-pyrazol-]-yl-1-phenyl)-1H,4H,5H-pyrazolo[3,4-d]pyrimidin-4-one (I-977);

5-[(1-cyclopropanecarbonyl-4-hydroxypiperidin-4-yl)methyl]-1-{4-[3-(morpholin-4-yl}-1H-pyrazol-1-yl]phenyl)-1H,4H,5H-pyrazolo[3,4-d]pyrimidin-4-one (I-978);

5-[(1-cyclopropanecarbonyl-4-hydroxypiperidin-4-yl)methyl]-1-(4-hydroxyphenyl)-1H,4H,5H-pyrazolo[3,4-d]pyrimidin-4-one (I-980);

5-{[1-(2-cyclopropyl-1,3-oxazole-5-carbonyl)-4-hydroxypiperidin-4-yl]methyl}-1-{4-[(1-fluorocyclobutyl)methoxy]phenyl)-1H,4H,5H-pyrazolo[3,4-d]pyrimidin-4-one (I-981);

5-((1-(4-fluorobenzoyl)-4-hydroxypiperidin-4-yl)methyl)-1-(4-(((1-hydroxycyclobutyl)methoxy)phenyl)-1H-pyrazolo[3,4-d]pyrimidin-4(5H)-one (I-982);

5-((1-(4-fluorobenzoyl)-4-hydroxypiperidin-4-yl)methyl)-1-(4-(2-methyl-1H-imidazol-4-yl)phenyl)-1H-pyrazolo[3,4-d]pyrimidin-4(5H)-one (I-983);

1-[4-(1,5-dimethyl-1H-imidazol-2-yl)phenyl]-5-([1-[(4-fluorophenyl)carbonyl]-4-hydroxypiperidin-4-yl]methyl)-1H,4H,5H-pyrazolo[3,4-d]pyrimidin-4-one (I-984);

5-((1-(2-Cyclopropyloxazole-5-carbonyl)-4-hydroxypiperidin-4-yl) methyl)-1-(4-(pyridin-3-yl)phenyl)-1H-pyrazolo[3,4-d]pyrimidin-4(5H)-one (I-985);

5-([1-[(4-fluorophenyl)carbonyl]-4-hydroxypiperidin-4-yl]methyl)-1-[4-(4-methyl-1H-imidazol-1-yl)phenyl]-1H-pyrazolo[3,4-d]pyrimidin-4(5H)-one (I-987);

5-{[1-(4-fluorobenzoyl)-4-hydroxypiperidin-4-yl]methyl}-1-[4-(2-methyl-1H-imidazol-1-yl)phenyl]-1H,4H,5H-pyrazolo[3,4-d]pyrimidin-4-one (I-988), 5-((1-(4-(difluoromethoxy)benzoyl)-4-hydroxypiperidin-4-yl)methyl)-1-(3-(hydroxymethyl)phenyl)-1H-pyrazolo[3,4-d]pyrimidin-4(5H)-one (I-989);

5-{[1-(3-cyclopropyl-3-phenylpropanoyl)-4-hydroxypiperidin-4-yl]methyl}-1-methyl-1H,4H,5H-pyrazolo[3,4-d]pyrimidin-4-one (I-99);

1-(4-fluoro-3-(hydroxymethyl)phenyl)-5-((4-hydroxy-1-(4-(pyrimidin-2-yloxy)benzoyl)piperidin-4-yl)methyl)-1H-pyrazolo[3,4-d]pyrimidin-4(5H)-one (I-990);

4-hydroxy-4-((1-(4-(1-isopropylpiperidin-4-yl)phenyl)-4-oxo-1H-pyrazolo[3,4-d]pyrimidin-5(4H)-yl)methyl)-N,N-dimethylpiperidine-1-carboxamide (I-992);

5-{[1-(4-fluorobenzoyl)-4-hydroxypiperidin-4-yl]methyl}-1-[3-(piperidin-4-yl)phenyl]-1H,4H,5H-pyrazolo[3,4-d]pyrimidin-4-one (I-993);

4-hydroxy-N,N-dimethyl-4-({4-oxo-1-[4-(piperidin-4-yl)phenyl]-1H,4H,5H-pyrazolo[3,4-d]pyrimidin-5-yl}methyl)piperidine-1-carboxamide (I-994), (R)-5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one, enantiomer A (I-995);

(S)-5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one, enantiomer B (I-996);

5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one (I-996a);

(S)-5-((1-(4-fluorobenzoyl)-4-hydroxypiperidin-4-yl)methyl)-1-(4-(S-methylsulfonimidoyl) phenyl)-1,5-dihydro-4H-pyrazolo[3,4-d]pyrimidin-4-one, enantiomer A (I-997);

(R)-5-((1-(4-fluorobenzoyl)-4-hydroxypiperidin-4-yl)methyl)-1-(4-(S-methylsulfonimidoyl) phenyl)-1,5-dihydro-4H-pyrazolo[3,4-d]pyrimidin-4-one, enantiomer B (I-998);

5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one (I-998a); and 1-[4-[(4-[[1-(4-fluorophenyl)-4-oxo-1H,4H,5H-pyrazolo[3,4-d]pyrimidin-5-yl]methyl]-4-hydroxypiperidin-1-yl)carbonyl]phenyl]-1H-pyrazole-4-carboxylic acid (I-999).

In another embodiment of the invention, the compounds of Formula (I) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of USP7. In one embodiment, the compounds of the present invention are inhibitors of USP7.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula (I).

Those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention can be synthesized by following the steps outlined in General Schemes 1, 2, 3, and 4 which comprise different sequences of assembling intermediates IIa, IIb, IIIa, IIIb, IIIx, IVa, IVb, IVx, Va, Vb, Vx, VIIx, and VIIIx. Starting materials are either commercially available or made by known procedures in the reported literature or as illustrated.

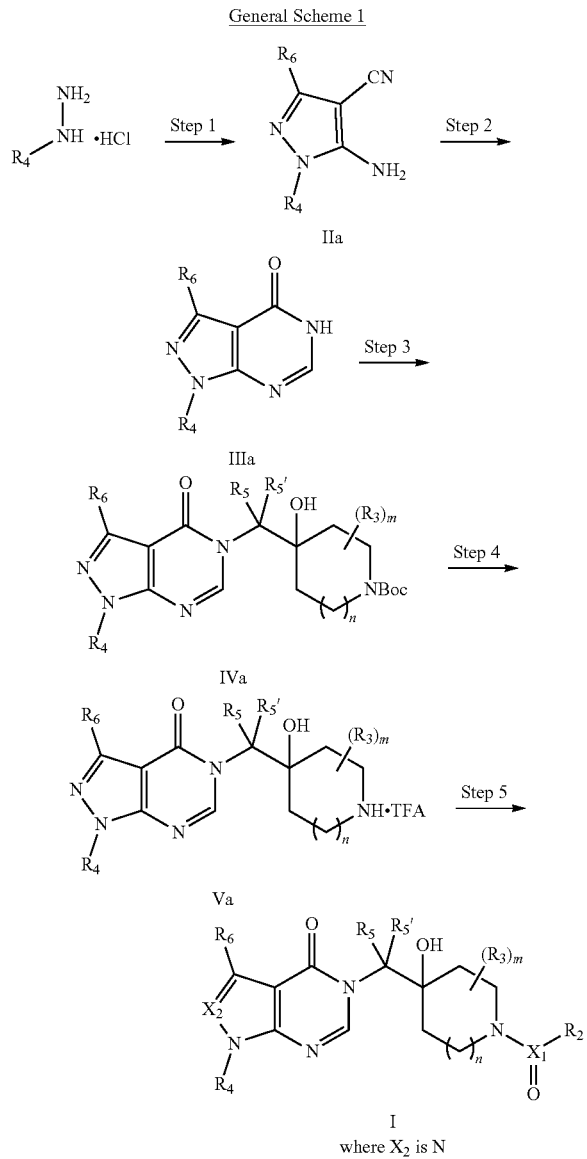

wherein $R_2$-$R_6$, $X_1$, m, and n are defined as in Formula (I).

The general way of preparing target molecules of Formula (I) by using intermediates IIa, IIIa, IVa, and Va is outlined in General Scheme 1. Cyclization of a hydrazine hydrochloride (or the hydrazine) with a 2-(ethoxymethylidene)propanedinitrile optionally using a base, i.e., triethylamine or N,N-diisopropylethylamine (DIPEA), in solvent, i.e., ethanol, at elevated temperatures provides intermediate IIa. Intermediate IIIa is then prepared by cyclization of nitrile IIa and formic acid in the presence of a catalytic amount of water at an elevated temperature Alternatively, intermediate IIa can be obtained by treating IIa with a strong acid, i.e., sulfuric acid, to obtain an amide intermediate which is then cyclized to the pyrazolo pyrimidine IIIa with triethyl orthoformate and acetic anhydride at an elevated temperature. Nucleophilic addition of IIIa to a tert-butyl-1,6-[3]-dioxa-8-azaspiro[2.7]decan-7-one intermediate in a solvent, i.e., dimethylformamide (DMF) at elevated temperature provides IVa. Deprotection of intermediate IVa using a strong acid such as trifluoroacetic acid (TFA) in a solvent, i.e., dichloromethane (DCM) yields Va. Acylation of intermediate Va to produce a compound of Formula (I) where $X_1$ is C, can be accomplished by coupling of an acid under standard coupling conditions using a coupling reagent, i.e., [bis(dimethylamino)methylene]-1H-1,2,3-triazolo[4,5-b]pyridinium 3-oxide hexafluorophosphate (HATU), or O-benzotriazole-N,N,N',N'-tetramethyl-uronium-hexafluorophosphate (HBTU), and a base, i.e., triethylamine or N,N-diisopropylethylamine (DIPEA), in a solvent, e.g., dichloromethane or DMF to provide compounds of Formula (I). Alternatively, intermediate Va can be acylated with an acid chloride or carbamoyl chloride using a base, i.e., triethylamine or DIPEA, and optionally in solvent to produce a compound of Formula (I) where $X_1$ is C. For synthesis of a compound of Formula (I) where $X_1$ is S or S(O), intermediate Va is treated with a sulfonyl chloride or a sulfinic chloride and a base, i.e., triethylamine or N,N-diisopropylethylamine (DIPEA), in a solvent, i.e., dichloromethane, DMF to provide the desired product of Formula (I).

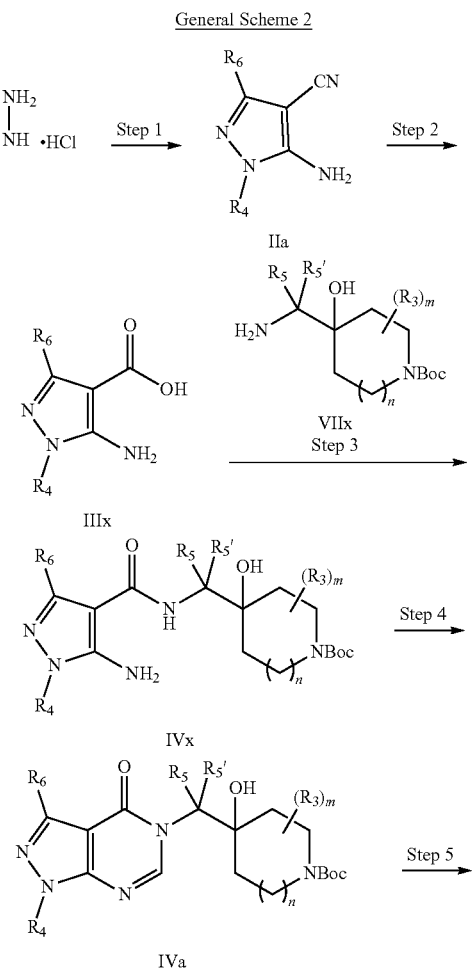

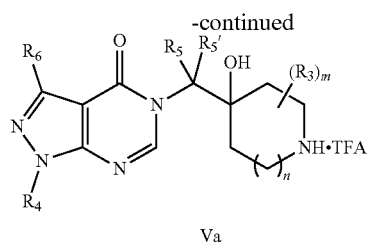

Va

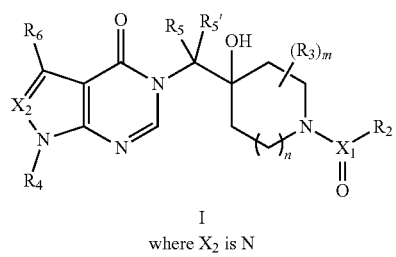

I
where X₂ is N wherein R₂-R₆, X₁, m, and n are defined as in Formula (I).

Alternatively, molecules of Formula (I) can be prepared using intermediates IIa, IIIx, IVx, IVa, and Va as outlined in General Scheme 2. Cyclization of a hydrazine hydrochloride (or the hydrazine) with a 2-(ethoxymethylidene)propanedinitrile optionally using a base, i.e., triethylamine or N,N-diisopropylethylamine (DIPEA), in solvent, i.e., ethanol, at elevated temperatures provides intermediate IIa. Hydrolysis of IIa using an acid (i.e., dilute hydrochloric acid) or a base (i.e., sodium hydroxide solution) in a solvent (i.e., water) provides carboxylic acid IIIx. Coupling of the acid IIIx with amine VIIx under standard coupling conditions using a coupling reagent, i.e., 1-[bis(dimethylamino)methylene]-1H-1,2,3-triazolo[4,5-b]pyridinium3-oxid hexafluoro-phosphate (HATU), or O-benzotriazole-N,N,N',N'-tetramethyl-uronium-hexafluoro-phosphate (HBTU), and a base, i.e., triethylamine or N,N-diisopropylethylamine (DIPEA), in a solvent, e.g., dichloromethane or DMF provides IVx. Intermediate IVa is then prepared by cyclization of IVx and formic acid in the presence of a catalytic amount of water at an elevated temperature. Deprotection of intermediate IVa using a strong acid such as trifluoroacetic acid (TFA) in a solvent, i.e., dichloromethane (DCM) yields Va. Acylation of intermediate Va to produce a compound of Formula (I) where X₁ is C, can be accomplished by coupling of an acid under standard coupling conditions using a coupling reagent, i.e., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, i.e., triethylamine or N,N-diisopropylethylamine (DTPEA), in a solvent, e.g., dichloromethane or DMF to provide compounds of Formula (I). Alternatively, intermediate Va can be acylated with an acid chloride or carbamoyl chloride using a base, i.e., triethylamine or DIPEA, and optionally in solvent to produce a compound of Formula (I) where X₁ is C. For synthesis of a compound of Formula (I) where X₁ is S or S(O), intermediate Va is treated with a sulfonyl chloride or a sulfinic chloride and a base, i.e., triethylamine or N,N-diisopropylethylamine (DIPEA), in a solvent, i.e., dichloromethane, DMF to provide the desired product of Formula (I).

General Scheme 3

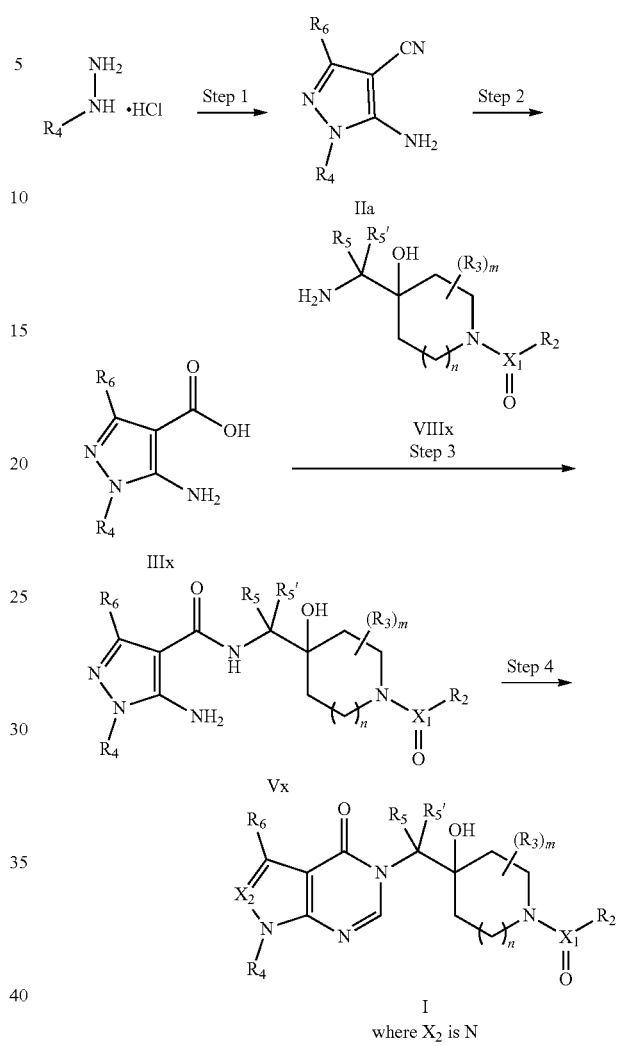

wherein R₂-R₆, X₁, m, and n are defined as in Formula (I).

Molecules of Formula (I) can also be prepared using intermediates IIa, IIIx, and Vx as outlined above in General Scheme 3. Cyclization of a hydrazine hydrochloride (or the hydrazine) with a 2-(ethoxymethylidene)propanedinitrile optionally using a base, i.e., triethylamine or N,N-diisopropylethylamine (DIPEA), in solvent, i.e., ethanol, at elevated temperatures provides intermediate IIa. Hydrolysis of IIa using an acid (i.e., dilute hydrochloric acid) or a base (i.e., sodium hydroxide solution) in a solvent (i.e., water) provides carboxylic acid IIIx Coupling of the acid IIIx with amine VIIIx under standard coupling conditions using a coupling reagent, i.e., [bis(dimethylamino)methylene]-1H-1,2,3-triazolo[4,5-b]pyridinium 3-oxide hexafluoro-phosphate (HATU), or O-benzotriazole-N,N,N',N'-tetramethyl-uronium-hexafluoro-phosphate (HBTU), and a base, i.e., triethylamine or N,N-diisopropylethylamine (DIPEA), in a solvent, e.g., dichloromethane or DMF provides Vx. Cyclization of Vx and formic acid in the presence of a catalytic amount of water at an elevated temperature provides compounds of Formula (I). Alternatively, of compounds of Formula (I) can be obtained by treating Vx with a strong acid, i.e., sulfuric acid, to obtain an amide intermediate which is then cyclized to the pyrrolo pyrimidine of Formula (I) with triethyl orthoformate and acetic anhydride at an elevated temperature.

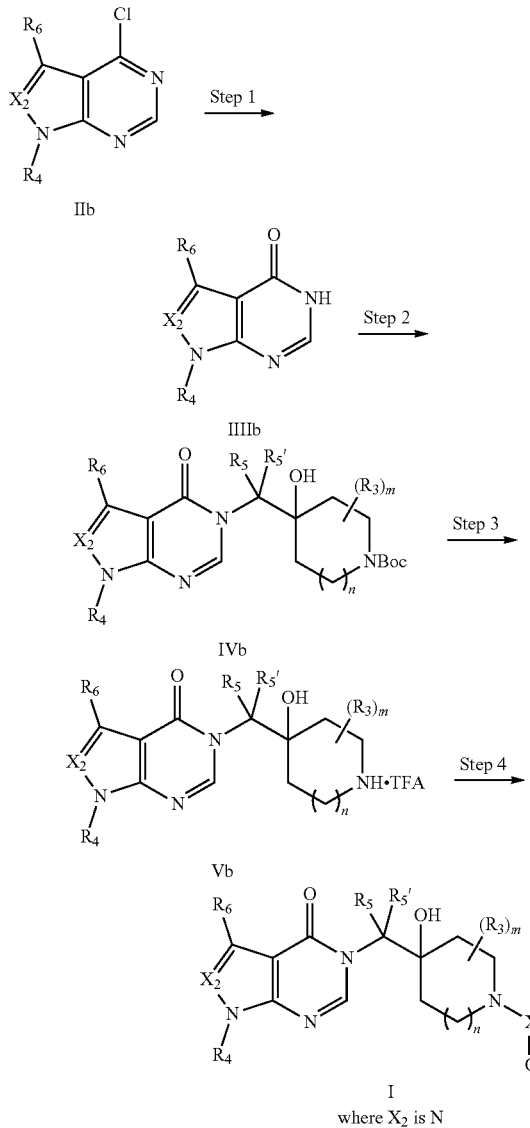

General Scheme 4 wherein $R_2$-$R_6$, $X_1$, m, and n are defined as in Formula (I).

The general way of preparing target molecules of Formula (I) by using intermediates IIb, IIIb, IVb, and Vb is outlined in General Scheme 4. Treatment of Intermediate IIb with 1,4-diazabicyclo[2.2.2]octane (DABCO), a solvent, i.e., dioxane and/or water, and a base, i.e., potassium carbonate or cesium carbonate, etc., at an elevated temperature provides intermediate IIIb. Nucleophilic addition of IIIb to a tert-butyl-1,6-[3]-dioxa-8-azaspiro[2.7]decan-7-one intermediate using a base, i.e., potassium carbonate or cesium carbonate, etc., in a solvent, i.e., dimethylformamide (DMF) at elevated temperature provides IVb. Deprotection of intermediate IVb using a strong acid such as trifluoroacetic acid (TFA) in a solvent, i.e., dichloromethane (DCM) yields Vb. Acylation of intermediate Vb to produce a compound of Formula (I) where $X_1$ is $CR_7$, can be accomplished by coupling of an acid under standard coupling conditions using a coupling reagent, i.e., [bis(dimethylamino)methylene]-1H-1,2,3-triazolo[4,5-b]pyridinium 3-oxide hexafluorophosphate (HATU), or O-benzotriazole-N,N,N',N'-tetramethyl-uronium-hexafluoro-phosphate (HBTU), and a base, i.e., triethylamine or N,N-diisopropylethylamine (DIPEA), in a solvent, e.g., dichloromethane or DMF. Alternatively, intermediate Vb can be acylated with an acid chloride or carbamoyl chloride using a base, i.e., triethylamine or DIPEA, and in a solvent, i.e., dichloromethane to produce a compound of Formula (I) where $X_1$ is C. For synthesis of compounds of Formula (I) where $X_1$ is S or S(O), Vb is treated with a sulfonyl chloride or a sulfinic chloride and a base, i.e., triethylamine or N,N-diisopropylethylamine (DIPEA), in a solvent, i.e., dichloromethane, DMF to provide the desired product of Formula (I).

A mixture of enantiomers, diastereomers, cis/trans isomers resulting from the process described above can be separated into their single components by chiral salt technique, chromatography using normal phase, reverse phase or chiral column, depending on the nature of the separation.

It should be understood that in the description and formula shown above, the various groups $R_2$-$R_5$, $R_5'$, $R_6$, $X_1$, $X_2$, m, n, and other variables are as defined above, except where otherwise indicated. Furthermore, for synthetic purposes, the compounds of General Schemes 1, 2, 3, and 4 are mere representative with elected radicals to illustrate the general synthetic methodology of the compounds of Formula (I) as defined herein.

Methods of Using the Disclosed Compounds

Another aspect of the invention relates to a method of treating a disease or disorder associated with modulation of USP7. The method comprises administering to a patient in need of a treatment for diseases or disorders associated with modulation of USP7 an effective amount the compositions and compounds of Formula (I).

In another aspect, the present invention is directed to a method of inhibiting USP7. The method involves administering to a patient in need thereof an effective amount of a compound of Formula (I).

Another aspect of the present invention relates to a method of treating, preventing, inhibiting or eliminating a disease or disorder in a patient associated with the inhibition of USP7, the method comprising administering to a patient in need thereof an effective amount of a compound of Formula (I). In one embodiment, the disease or disorder is selected from the group consisting of cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The present invention also relates to the use of an inhibitor of USP7 for the preparation of a medicament used in the treatment, prevention, inhibition or elimination of a disease or condition mediated by USP7, wherein the medicament comprises a compound of Formula (I).

In another aspect, the present invention relates to a method for the manufacture of a medicament for treating, preventing, inhibiting, or eliminating a disease or condition mediated by USP7, wherein the medicament comprises a compound of Formula (I).

Another aspect of the present invention relates to a compound of Formula (I) for use in the manufacture of a medicament for treating a disease associated with inhibiting USP7.

In another aspect, the present invention relates to the use of a compound of Formula (I) in the treatment of a disease associated with inhibiting USP7.

Another aspect of the invention relates to a method of treating cancer. The method comprises administering to a patient in need thereof an effective amount of a compound of Formula (I).

In another aspect, the present invention relates to a method of treating a neurodegenerative disease. The method comprises administering to a patient in need thereof an effective amount of a compound of Formula (I).

Another aspect of the invention relates to a method of treating a viral infection and disease. The method comprises administering to a patient in need thereof an effective amount of a compound of Formula (I).

In another aspect, the present invention relates to a method of treating an inflammatory disease or condition. The method comprises administering to a patient in need thereof an effective amount of a compound of Formula (I).

Another aspect of the invention relates to a method of inducing cell cycle arrest, apoptosis in tumor cells, and/or enhanced tumor-specific T cell immunity. The method comprises contacting the cells with an effective amount of a compound of Formula (I).

In one embodiment, the present invention relates to the use of an inhibitor of USP7 for the preparation of a medicament used in treatment, prevention, inhibition or elimination of a disease or disorder associated with associated with cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

In another embodiment, the present invention relates to a compound of Formula (I) or a pharmaceutical composition comprising a compound of the present invention and a pharmaceutically acceptable carrier used for the treatment of cancers including, but not limited to, liposarcoma, neuroblastoma, glioblastoma, bladder cancer, adrenocortical cancer, multiple myeloma, colorectal cancer, non-small cell lung cancer, Human Papilloma Virus-associated cervical, oropharyngeal, penis, anal, thyroid or vaginal cancer or Epstein-Barr Virus-associated nasopharyngeal carcinoma, gastric cancer, rectal cancer, thyroid cancer, Hodgkin lymphoma or diffuse large B-cell lymphoma.

In some embodiments, the patient is selected for treatment based on gene amplification and/or elevated tumor expression of USP7, MDM2 or MDM4 relative to tissue-matched expression. In other embodiments, the patient is selected for the treatment based on tumor expression of wild type TP53 or based on the tumor immune cell composition, specifically elevated regulatory T lymphocytes, CD4+CD25+FoxP3+ T cells.

In some embodiments, administration of a compound of Formula (I) or a pharmaceutical composition comprising a compound of the present invention and a pharmaceutically acceptable carrier induces a change in the cell cycle or cell viability.

For example, the change in the cell cycle or cell viability may be indicated by decreased tumor levels of MDM2 protein and/or increased levels of TP53, CDKNIA (p21, Cip1), PUMA or BAX or by increased expression of one or more p53 target genes. In one embodiment, the p53 target genes include, but are not limited to, CDKNIA (p21, Cip1), BBC3 (PUMA), BAX or MDM2.

In another embodiment, the present invention relates to a compound of Formula (I) or a pharmaceutical composition comprising a compound of the present invention and a pharmaceutically acceptable carrier used for the treatment of neurodegenerative diseases including, but not limited to, Alzheimer's disease, multiple sclerosis, Huntington's disease, infectious meningitis, encephalomyelitis, Parkinson's disease, amyotrophic lateral sclerosis, or encephalitis.

Another embodiment of the present invention relates to a compound of Formula (I) or a pharmaceutical composition comprising a compound of the present invention and a pharmaceutically acceptable carrier used for the treatment of viral infections and diseases including but not limited to, herpes simplex-1 or-2 viral infections, hepatitis A, hepatitis C, SARS coronavirus infection and disease, Epstein-Barr virus, rhinoviral infections and diseases, adenoviral infections and diseases, or poliomyelitis.

In another embodiment, the present invention relates to a compound of Formula (I) or a pharmaceutical composition comprising a compound of the present invention and a pharmaceutically acceptable carrier used for the treatment of inflammatory diseases or conditions is associated with metabolic disorders including, but not limited to, Type II diabetes, insulin resistance cardiovascular disease, arrhythmia, atherosclerosis, coronary artery disease, hypertriglyceridemia, dyslipidemia, retinopathy, nephropathy, neuropathy, or macular edema.

In another embodiment, the present invention relates to a compound of Formula (I) or a pharmaceutical composition comprising a compound of the present invention and a pharmaceutically acceptable carrier used for the treatment of inflammatory diseases or conditions is associated with inflammatory bowel diseases including, but not limited to, ileitis, ulcerative colitis, Barrett's syndrome, or Crohn's disease Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of USP7 including, cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases, comprising administering to a patient suffering from at least one of said diseases or disorder a compound of Formula (I).

One therapeutic use of the compounds or compositions of the present invention which inhibit USP7 is to provide treatment to patients or subjects suffering from cancer and metastasis, neurodegenerative diseases, immunological disorders, diabetes, bone and joint diseases, osteoporosis, arthritis inflammatory disorders, cardiovascular diseases, ischemic diseases, viral infections and diseases, viral infectivity and/or latency, and bacterial infections and diseases.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Analytical Methods, Materials, and Instrumentation

Unless otherwise noted, reagents and solvents were used as received from commercial suppliers. Proton nuclear magnetic resonance (NMR) spectra were obtained on either Bruker or Varian spectrometers at 300 or 400 MHz. Spectra are given in ppm (δ) and coupling constants, J, are reported in Hertz. Tetramethylsilane (TMS) was used as an internal standard. Mass spectra were collected using a Waters ZQ Single Quad Mass Spectrometer (ion trap electrospray ionization (ESI)). Purity and low resolution mass spectral data were measured using Waters Acquity i-class ultra-performance liquid chromatography (UPLC) system with Acquity Photo Diode Array Detector, Acquity Evaporative Light Scattering Detector (ELSD) and Waters ZQ Mass Spectrometer. Data was acquired using Waters MassLynx 4.1 software and purity characterized by UV wavelength 220 nm, evaporative light scattering detection (ELSD) and electrospray positive ion (ESI). (Column: Acquity UPLC BEH C18 1.7 µm 2.1×50 mm; Flow rate 0.6 mL/min; Solvent A (95/5/0.1%: 10 mM Ammonium Formate/Acetonitrile/Formic Acid), Solvent B (95/5/0.09%: Acetonitrile/Water/Formic Acid); gradient: 5-100% B from 0 to 2 mins, hold 100% B to 2.2 mins and 5% B at 2.21 mins. Preparatory HPLC purifications were conducted on a Waters SunFire C18 OBD Prep Column, 100 Å, 5 µm, 19 mm×50 mm, Waters XBridge BEH C18 OBD Prep Column, 130 Å, 5 µm, 19 mm×50 mm with UV detection (Waters 2489 UV/998 PDA), Waters SunFire C18 OBD Prep Column, 100 Å, 5 µm, 19 mm×150 mm, Waters XBridge BEH Shield RP18 OBD Prep Column, 130 Å, 5 µm, 19 mm×150 mm, or Waters XSelect CSH C18 OBD Prep Column, 130 Å, 5 µm, 19 mm×150 mm at 254 nm or 220 nm using a standard solvent gradient program (i.e., HPLC Methods 1-8 or as designated below). The absolute configuration of the separated enantiomers of the compounds in the examples described herein were not determined. As such, the configuration of the resolved materials were arbitrarily assigned as R or S in each case.

Preparative HPLC Method 1 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid/Mobile phase B acetonitrile with 0.1% formic acid
Column: Waters SunFire C18 OBD Prep Column, 100 Å, 5 µm, 19 mm×50 mm
Column temperature: Ambient
LC gradient: Hold 0% B for 0.9 min, then 0% to 5% in 0.01 min; then 5% to 35% in 3.84 min; then 35% to 100% in 0.01 min; hold at 100% for 0.74 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+

Preparative HPLC Method 2 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide/Mobile phase B acetonitrile with 0.1% ammonium hydroxide
Column: Waters XBridge BEH C18 OBD Prep Column, 130 Å, 5 µm, 19 mm×50 mm Column temperature: Ambient
LC gradient: Hold 0% B for 0.9 min, then 0% to 5% in 0.01 min; then 5% to 35% in 3.84 min; then 35% to 100% in 0.01 min; hold at 100% for 0.74 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+

Preparative HPLC Method 3 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid/Mobile phase B acetonitrile with 0.1% formic acid
Column: Waters SunFire C18 OBD Prep Column, 100 Å, 5 µm, 19 mm×50 mm Column temperature: Ambient
LC gradient: 15% for 0.9 min, then 15% to 25% in 0.01 min, then 25% to 65% in 3.84 min; and 65% to 100% in 0.01 min; hold at 100% for 0.74 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+

Preparative HPLC Method 4 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide/Mobile phase B acetonitrile with 0.1% ammonium hydroxide
Column: Waters XBridge BEH C18 OBD Prep Column, 130 Å, 5 µm, 19 mm×50 mm
Column temperature: Ambient
LC gradient: Hold 15% B for 0.9 min, then 15% to 25% in 0.01 min; then 25% to 65% in 3.84 min; then 65 to 100% to 100% in 0.01 min; hold at 100% for 0.74 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+

Preparative HPLC Method 5 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid/Mobile phase B acetonitrile with 0.1% formic acid
Column: Waters SunFire C18 OBD Prep Column, 100 Å, 5 µm, 19 mm×50 mm
Column temperature: Ambient
LC gradient: Hold 35% B for 0.9 min, then 35% to 45% in 0.01 min; then 45% to 85% in 3.84 min; then 85 to 100% to 100% in 0.01 min; hold at 100% for 0.74 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+

Preparative HPLC Method 6 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide/Mobile phase B acetonitrile with 0.1% ammonium hydroxide
Column: Waters XBridge BEH C18 OBD Prep Column, 130 Å, 5 µm, 19 mm×50 mm
Column temperature: Ambient
LC gradient: Hold 35% B for 0.9 min, then 35% to 45% in 0.01 min; then 45% to 85% in 3.84 min; then 85 to 100% to 100% in 0.01 min; hold at 100% for 0.74 min.
LC Flow rate: 23 mL/min binary pump, 2 mL/min acetonitrile at column dilution
UV wavelength: 220 nm and 254 nm Ionization Mode: Electrospray Ionization; positive/negative; ESI+
Preparative HPLC Method 7 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% formic acid/Mobile phase B acetonitrile with 0.1% formic acid
Column: Waters SunFire C18 OBD Prep Column, 100 Å, 5 µm, 19 mm×50 mm
Column temperature: Ambient
LC gradient: Hold 50% B for 0.9 min, then 50% to 60% in 0.01 min; then 60% to 100% in 3.84 min; then hold at 100% for 0.75 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+
Preparative HPLC Method 8 (ESI, 5.5 min Method):
Instruments: HPLC: Waters 2545 Binary Gradient Module. MS: Waters 3100/ZQ Mass Detector. UV: Waters 2489 UV/998 PDA.
Conditions: Mobile phase A: water with 0.1% ammonium hydroxide/Mobile phase B acetonitrile with 0.1% ammonium hydroxide
Column: Waters XBridge BEH C18 OBD Prep Column, 130 Å, 5 µm, 19 mm×50 mm
Column temperature: Ambient
LC gradient: Hold 50% B for 0.9 min, then 50% to 60% in 0.01 min; then 60% to 100% in 3.84 min; then hold at 100% for 0.75 min.
LC Flow rate: 23 mL/min binary pump, 2 mL/min acetonitrile at column dilution
UV wavelength: 220 nm and 254 nm
Ionization Mode: Electrospray Ionization; positive/negative; ESI+
Abbreviations used in the following examples and elsewhere herein are:
  atm atmosphere
  br broad
  BINAP (2,2'-bis(diphenylphosphino)-1,1'-binaphthyl)
  DABCO 1,4-diazabicyclo[2.2.2]octane
  DBU 2,3,4,6,7,8,9,10-octahydropyrimido[1,2-a]azepine
  DIPEA N,N-diisopropylethylamine
  DMA N,N-dimethylacetamide
  DMF N,N-dimethylformamide
  DMSO dimethyl sulfoxide
  dppf 1,1'-bis(diphenylphosphino)ferrocene
  EDC N-(3-Dimethylaminopropyl)-N'-ethylcarbodiimide hydrochloride
  ESI electrospray ionization
  h hour(s)
  HATU [bis(dimethylamino)methylene]-1H-1,2,3-triazolo[4,5-b]pyridinium 3-oxide hexafluorophosphate
  HPLC high-performance liquid chromatography
  LCMS liquid chromatography-mass spectrometry
  m multiplet
  MHz megahertz
  min minutes
  MPLC Medium pressure liquid chromatography
  MS molecular sieves
  MTBE 2-methoxy-2-methylpropane
  MW microwave
  NMR nuclear magnetic resonance
  ppm parts per million
  RuPhos 2-dicyclohexylphosphino-2',6'-diisopropoxybiphenyl
  TBDMS tertbutyldimethylsilyl
  TFA Trifluoroacetic acid
  TLC thin layer chromatography
  X-Phos 2-Dicyclohexylphosphino-2',4',6'-triisopropylbiphenyl Example 1: Intermediate 2-1. tert-Butyl 4-hydroxy-4-({1-methyl-4-oxo-1,4-dihydro-5H-pyrazolo[3,4-d]pyrimidin-5-yl}methyl)piperidine-1-carboxylate

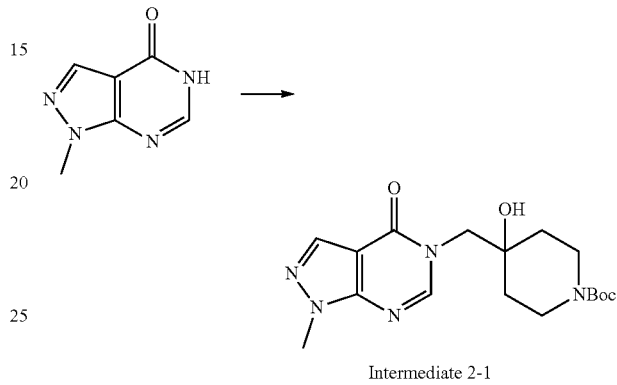

Intermediate 2-1

The title compound (16.7 g, 77%). was prepared according to the procedure described for Example 21, Intermediate 2-29, Step 4, utilizing 1-methyl-1H-pyrazolo[3,4-d]pyrimidin-4(5H)-one (9.0 g, 59.9 mmol) as staring material $^1$H NMR (400 MHz, CDCl$_3$) δ 8.08 (s, 1H), 7.99 (s, 1H), 4.24-3.98 (m, 2H), 4.00 (s, 3H), 3.97-3.78 (m, 2H), 3.21-3.09 (m, 2H), 2.96 (s, 1H), 1.66-1.56 (m, 2H), 1.56-1.48 (m, 2H), 1.45 (s, 9H) ppm. LCMS: (ESI) m/z 386 [M+Na].

Example 2: Intermediate 2-2. 5-((4-Hydroxypiperidin-4-yl)methyl)-1-methyl-1H-pyrazolo[3,4-d]pyrimidin-4(5H)-one trifluoroacetic acid salt

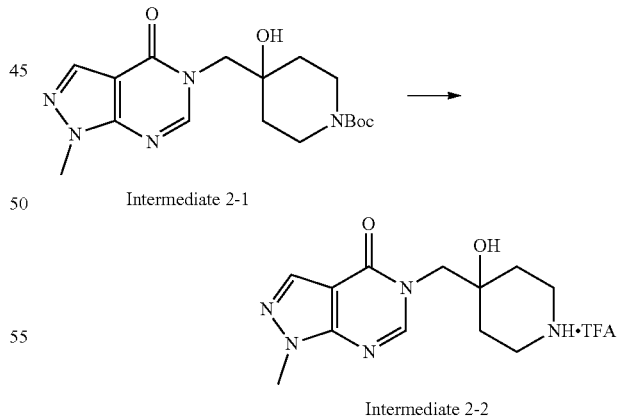

Intermediate 2-2

The title compound was prepared according to the procedure described for Example 21 described herein below, Intermediate 2-28, Step 5, utilizing tert-butyl 4-hydroxy-4-((1-methyl-4-oxo-1H-pyrazolo[3,4-d]pyrimidin-5(4H)-yl)methyl)piperidine-1-carboxylate from Intermediate 2-1 (7.80 g, 21.5 mmol) as starting material which was used without any further purification. LCMS: (ESI) m/z 264 [M+H].

Example 2a: Intermediate 2-2a. 5-((4-Hydroxypiperidin-4-yl)methyl)-1-methyl-1,5-dihydro-4H-pyrazolo[3,4-d]pyrimidin-4-one, hydrochloric acid salt Intermediate 2-2a

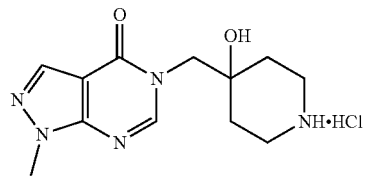

In a ½ dram reaction vial, tert-butyl 4-hydroxy-4-({1-methyl-4-oxo-1,4-dihydro-5H-pyrazolo[4,3-c]pyridin-5-yl)methyl)piperidine-1-carboxylate (Intermediate 2-1, 0.2 M 1,4-dioxane, 0.15 mL, 0.030 mmol) and hydrochloric acid (4.0 M 1,4-dioxane, 0.075 mL, 0.3 mmol) were combined. The vial was capped and agitated at 50° C. for 3 hours. The reaction was cooled and dried under a stream of nitrogen to provide 5-((4-hydroxypiperidin-4-yl)methyl)-1-methyl-1,5-dihydro-4H-pyrazolo[3,4-d]pyrimidin-4-one, hydrochloric acid salt without any further purification. LCMS: (ESI) m/z 264 [M+H].

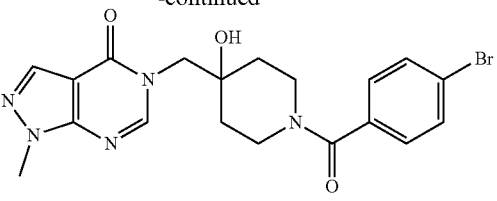

Intermediate 2-3

A 100-mL round-bottom flask was charged with 5-((4-hydroxypiperidin-4-yl)methyl)-1-methyl-1H-pyrazolo[3,4-d]pyrimidin-4(5H)-one trifluoroacetic acid salt (Intermediate 2-2, 2.70 g, 7.15 mmol), 4-bromobenzoic acid (1.51 g, 7.51 mmol), and 1,2-dichloroethane (38 mL). Hydroxybenzotriazole hydrate (547 mg, 3.58 mmol), triethylamine (4.98 mL, 35.8 mmol), and EDC (1.44 g, 7.51 mmol) were then added to the slurry. The reaction mixture was stirred at 50° C. for 3 h. The resulting suspension was cooled in an ice bath

TABLE 1

The Intermediates in Table 1 were synthesized according to the procedure described in Example 2a above.

| Intermediate No.: | Precursor Used | LCMS: (ESI) m/z [M + H] |
|---|---|---|
| Intermediate 2-2b. 1-(4-chlorophenyl)-5-((4-hydroxypiperidin-4-yl)methyl)-1,5-dihydro-4H-pyrazolo[3,4-d]pyrimidin-4-one hydrochloric acid salt | Intermediate 2-28 | 360, 362 |
| Intermediate 2-86. 1-(4-fluorophenyl)-5-((4-hydroxypiperidin-4-yl)methyl)-1,5-dihydro-4H-pyrazolo[3,4-d]pyrimidin-4-one hydrochloric acid salt | Intermediate 2-29 | 344 |

Example 3: Intermediate 2-3. 5-((1-(4-Bromobenzoyl)-4-hydroxypiperidin-4-yl)methyl)-1-methyl-1,5-dihydro-4H-pyrazolo[3,4-d]pyrimidin-4-one

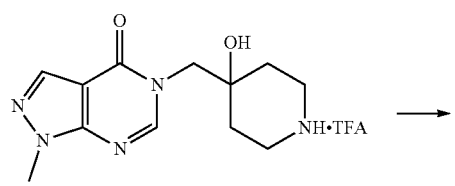

Intermediate 2-2 and stirred for 30 min. The solids were filtered and washed with 9:1 hexanes-ethyl acetate (25 mL) to afford 5-((1-(4-bromobenzoyl)-4-hydroxypiperidin-4-yl)methyl)-1-methyl-1,5-dihydro-4H-pyrazolo[3,4-d]pyrimidin-4-one (Intermediate 2-3, 2.58 g, 81%). $^1$H NMR (400 MHz, CDCl$_3$) δ 8.08 (s, 1H), 7.96 (s, 1H), 7.54 (d, 2H), 7.28 (d, 2H), 4.55-4.36 (m, 1H), 4.27-4.12 (m, 1H), 4.09-3.93 (m, 1H), 4.00 (s, 3H), 3.69-3.51 (m, 1H), 3.50-3.34 (m, 1H), 3.32 (s, 1H), 1.80-1.62 (m, 2H), 1.62-1.44 (m, 2H) ppm. LCMS: (ESI) m/z 446, 448 [M+H].

The Intermediate in Table 2 was synthesized according to the procedure outlined in Example 3 above.

TABLE 2

| Intermediate No.: | Precursor Used | LCMS: (ESI) m/z [M + H] |
|---|---|---|
| Intermediate 2-4. 5-((1-(3-Bromobenzoyl)-4-hydroxypiperidin-4-yl)methyl)-1-methyl-1,5-dihydro-4H-pyrazolo[3,4-d]pyrimidin-4-one | 2-2 and 3-bromo-benzoic acid | 446, 448 |

Example 4: Intermediate 2-5. 2'-(Cyanomethyl)-[1,1'-biphenyl]-4-carboxylic acid

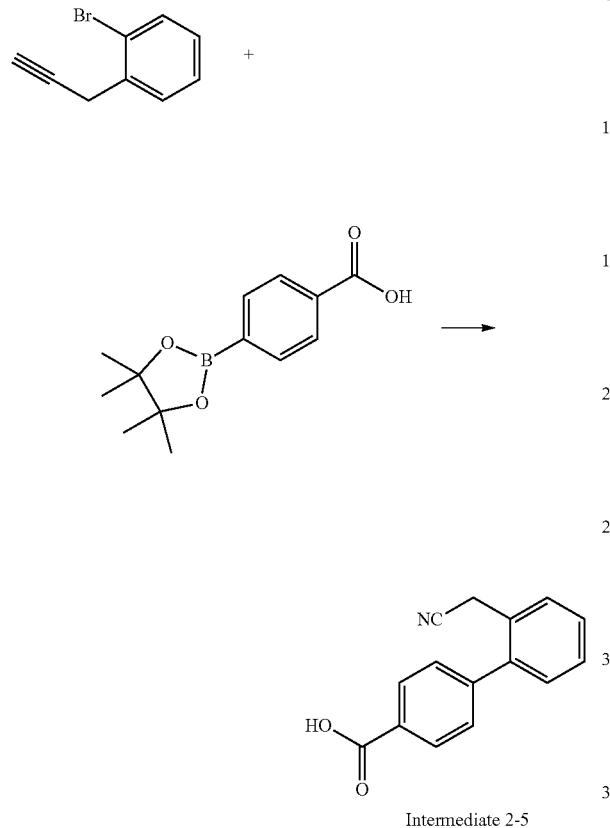

Intermediate 2-5

2-(2-Bromophenyl)acetonitrile (500 mg, 2.55 mmol), 4-(4,4,5,5-tetramethyl-1,3,2-dioxaborolan-2-yl)benzoic acid (633 mg, 2.55 mmol), tetrakis[triphenylphosphine]palladium(0) (147 mg, 0.13 mmol), tribasic potassium phosphate (1.62 g, 7.64 mmol), 1,4-dioxane (30 mL) and water (3 mL) were added to a 100-mL round-bottom flask fitted with a nitrogen inlet, magnetic stir bar and condenser. The resulting solution was stirred for 16 h at 100° C. The solids were removed by filtration and the filtrate was concentrated under vacuum. The residue was purified by preparative TLC with ethyl acetate/petroleum ether (1:5 v/v) to provide 2'-(cyanomethyl)-[1,1'-biphenyl]-4-carboxylic acid (Intermediate 2-5, 500 mg, 83%). LCMS: (ESI) m/z 236 [M−H].

The Intermediates in Table 3 were synthesized according to the procedure outlined in Example 4 above.

Example 5: Intermediate 2-229a. 4-(5-(tert-butoxycarbonyl)-2,5-diaza-bicyclo[2.2.1]heptan-2-yl)benzoic acid

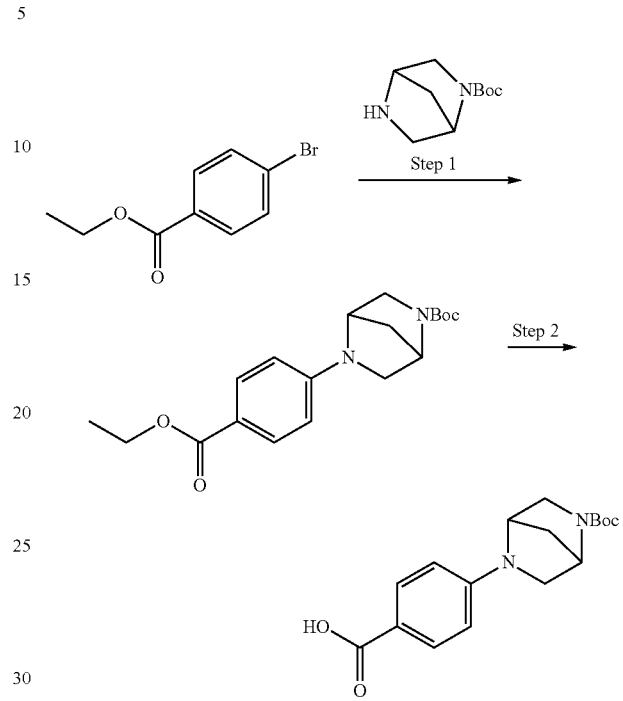

Step 1. tert-butyl 5-(4-(ethoxycarbonyl)phenyl)-2,5-diaza-bicyclo[2.2.1]heptane-2-carboxylate A 100-mL round-bottom flask was charged with ethyl 4-bromobenzoate (500 mg, 2.18 mmol), tris(dibenzylideneacetone)dipalladium-chloroform adduct (226 mg, 0.22 mmol), 2,2'-bis(diphenylphosphino)-1,1'-binaphthyl (261 mg, 0.44 mmol), cesium carbonate (2.14 g, 6.57 mmol), toluene (20 mL) and tert-butyl 2,5-diazabicyclo[2.2.1]heptane-2-carboxylate (521 mg, 2.61 mmol). The resulting solution was stirred for 24 h at 110° C. The reaction was cooled to room temperature and quenched by the addition of water (20 mL). The resulting solution was extracted with of dichloromethane (4×20 mL). The combined organic layers were dried over anhydrous sodium sulfate, filtered and concentrated under vacuum. The residue was purified by preparative thin layer chromatography eluting with ethyl acetate/petroleum ether (1:10 to 1:1, v/v). The collected fractions were combined and concentrated under vacuum to

TABLE 3

| Intermediate No.: | Precursor Used | LCMS: (ESI) m/z [M + H] |
|---|---|---|
| Intermediate 2-134 2'-aminobiphenyl-4-carboxylic acid | 2-bromoaniline and 4-(tetramethyl-1,3,2-dioxaborolan-2-yl)benzoic acid, utilizing 1,1'-bis(diphenylphosphino)ferrocene palladium(II) chloride complex with dichloromethane as the catalyst | 214 |
| Intermediate 2-25 2'-(1-cyanocyclopropyl)-[1,1'-biphenyl]-4-carboxylic acid | 1-(2-Bromophenyl)cyclopropane-1-carbonitrile and 4-(4,4,5,5-tetramethyl-1,3,2-dioxaborolan-2-yl)benzoic acid | 262 (M − H) | afford tert-butyl 5-(4-(ethoxycarbonyl)phenyl)-2,5-diaza-bicyclo[2.2.1]heptane-2-carboxylate as a yellow oil (700 mg, 92%). LCMS: (ESI) m/z 347 [M+H].

Step 2. 4-(5-(tert-butoxycarbonyl)-2,5-diaza-bicyclo [2.2.1]heptan-2-yl)benzoic acid (2-229a)

The title compound was prepared according to the procedure outlined in Example 10, Step 2 utilizing tert-butyl 5-(4-(ethoxycarbonyl)phenyl)-2,5-diaza-bicyclo[2.2.1]heptane-2-carboxylate (600 mg, 1.73 mmol) as starting material (370 mg, 67%). LCMS: (ESI) m/z 319 [M+H].

Example 6: Intermediate 2-7. 5-((4-Hydroxy-1-(4-(hydroxymethyl)benzoyl)piperidin-4-yl)methyl)-1-methyl-1,5-dihydro-4H-pyrazolo[3,4-d]pyrimidin-4-one

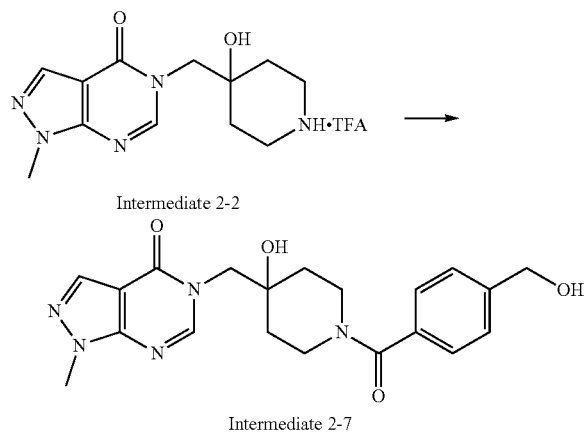

In a 20 mL vial was added 5-((4-hydroxypiperidin-4-yl)methyl)-1-methyl-1H-pyrazolo[3,4-d]pyrimidin-4(5H)-one trifluoroacetic acid salt (Intermediate 2-2) (0.643 g, 1.71 mmol), 4-(hydroxymethyl)benzoic acid (0.310 g, 2.04 mmol) and HATU (775 mg, 2.04 mmol) in DMF (6.8 mL) followed by triethylamine (2.13 mL, 15.3 mmol) to give a tan solution. The reaction was stirred for 24 h, diluted with ethyl acetate (50 mL) and poured into a separatory funnel. The organic layer was washed successively with saturated aqueous ammonium chloride (25 mL), saturated aqueous sodium bicarbonate (25 mL), and saturated aqueous sodium chloride (25 mL). The organic layer was separated, dried with anhydrous magnesium sulfate, filtered and concentrated under reduced pressure to give a residue which was purified by column chromatography (Biotage, 50 g silica gel column, eluting with ethyl acetate/hexanes gradient) to give 5-((4-hydroxy-1-(4-(hydroxymethyl)benzoyl)piperidin-4-yl)methyl)-1-methyl-1,5-dihydro-4H-pyrazolo[3,4-c]pyrimidin-4-one (Intermediate 2-7, 300 mg, 37%). H NMR (300 MHz, DMSO-$d_6$) δ 8.23 (s, 1H), 8.06 (s, 1H), 7.37-7.30 (m, 4H), 4.96, (s, 1H), 4.50 (s, 2H), 4.2-4.0 (m, 3H), 3.89 (s, 3H), 3.5-3.2 (m, 4H), 1.7-1.2 (m, 4H) ppm. LCMS: (ESI) m/z 397.95 [M+H].

The Intermediates in Table 4 were synthesized according to the procedure described for Example 6 above.

TABLE 4

| Intermediate No.: | Precursor Used | LCMS: (ESI) m/z [M + H] |
|---|---|---|
| Intermediate 2-38. 5-((1-(2'-amino-[1,1'-biphenyl]-4-carbonyl)-4-hydroxypiperidin-4-yl)methyl)-1-methyl-1,5-dihydro-4H-pyrazolo[3,4-d]pyrimidin-4-one | 2-2 and 4-(2-aminophenyl)benzoic acid | 459 |
| Intermediate 2-30. 1-(4-Bromophenyl)-5-((1-(cyclopropanecarbonyl)-4-hydroxypiperidin-4-yl)methyl)-1,5-dihydro-4H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and cyclopropanoic acid | 472, 474 |
| Intermediate 2-31. 1-(3-bromophenyl)-5-((1-(cyclopropanecarbonyl)-4-hydroxypiperidin-4-yl)methyl)-1,5-dihydro-4H-pyrazolo[3,4-d]pyrimidin-4-one | 1-(3-bromophenyl)-5-((4-hydroxypiperidin-4-yl)methyl)-1,5-dihydro-4H-pyrazolo[3,4-d]pyrimidin-4-one and cyclopropanoic acid | 472, 474 |
| Intermediate 2-870. 5-([1-[(4-bromophenyl)carbonyl]-4-hydroxypiperidin-4-yl]methyl)-1-(4-fluorophenyl)-1H,4H,5H-pyrazolo[3,4-d]pyrimidin-4-one | 1-(4-fluorophenyl)-5-((4-hydroxypiperidin-4-yl)methyl)-1,5-dihydro-4H-pyrazolo[3,4-d]pyrimidin-4-one and 4-bromobenzoic acid | 526, 528 |
| Intermediate 2-871. 3-(5-((1-(cyclopropanecarbonyl)-4-hydroxypiperidin-4-yl)methyl)-4-oxo-4,5-dihydro-1H-pyrazolo[3,4-d]pyrimidin-1-yl)benzoic acid | I-20 and cyclopropanoic acid | 437 |
| Intermediate 2-872. 1-(4-bromophenyl)-5-((4-hydroxy-1-(1-methylcyclopropane-1-carbonyl)piperidin-4-yl)methyl)-1,5-dihydro-4H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and 1-methylcyclopropane-1-carboxylic acid | 487 |

TABLE 4-continued

| Intermediate No.: | Precursor Used | LCMS: (ESI) m/z [M + H] |
|---|---|---|
| Intermediate 2-873. 1-(3-bromophenyl)-5-((4-hydroxy-1-(1-methylcyclopropane-1-carbonyl)piperidin-4-yl)methyl)-1,5-dihydro-4H-pyrazolo[3,4-d]pyrimidin-4-one | 1-(3-bromophenyl)-5-((4-hydroxypiperidin-4-yl)methyl)-1,5-dihydro-4H-pyrazolo[3,4-d]pyrimidin-4-one and 1-methylcyclopropane-1-carboxylic acid | 486, 488 |
| Intermediate 2-874. 1-(3-bromophenyl)-5-((1-(4-fluorobenzoyl)-4-hydroxypiperidin-4-yl)methyl)-1,5-dihydro-4H-pyrazolo[3,4-d]pyrimidin-4-one | 1-(3-bromophenyl)-5-((4-hydroxypiperidin-4-yl)methyl)-1,5-dihydro-4H-pyrazolo[3,4-d]pyrimidin-4-one and 4-fluorobenzoic acid | 526, 528 |
| Intermediate 2-875. 1-(4-bromophenyl)-5-((1-(4-fluorobenzoyl)-4-hydroxypiperidin-4-yl)methyl)-1,5-dihydro-4H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and 4-fluorobenzoic acid | 526, 528 |
| Intermediate 2-876. 1-(4-bromophenyl)-5-((4-hydroxy-1-(2-methyloxazole-5-carbonyl)piperidin-4-yl)methyl)-1,5-dihydro-4H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and 2-methyloxazole-5-carboxylic acid | 514 |
| Intermediate 2-844a. 1-(4-bromophenyl)-5-([1-[(2-cyclopropyl-1,3-oxazol-5-yl)carbonyl]-4-hydroxypiperidin-4-yl]methyl)-1H,4H,5H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and 2-cyclopropyloxazole-5-carboxylic acid | 538, 540 |
| Intermediate 2-859a: 5-((1-(4-fluorobenzoyl)-4-hydroxypiperidin-4-yl)methyl)-1-(4-(methylthio)phenyl)-1H-pyrazolo[3,4-d]pyrimidin-4(5H)-one | 5-((4-hydroxypiperidin-4-yl)methyl)-1-(4-(methylthio)phenyl)-1,5-dihydro-4H-pyrazolo[3,4-d]pyrimidin-4-one and 4-fluorobenzoic acid | 494 |
| Intermediate 2-320a: 4-(2-chloro-5-[5-[(1-cyclopropanecarbonyl-4-hydroxypiperidin-4-yl) methyl]-4-oxo-1H,4H,5H-pyrazolo[3,4-d]pyrimidin-1-yl]phenyl)piperazine-1-carboxylate | 1-(3-bromo-4-chlorophenyl)-5-((4-hydroxypiperidin-4-yl)methyl)-1,5-dihydro-4H-pyrazolo[3,4-d]pyrimidin-4-one and cyclopropanoic acid | 554 |
| Intermediate 2-31. 1-(4-bromophenyl)-5-([4-hydroxy-1-[(4-methylphenyl)carbonyl]piperidin-4-yl]methyl)-1H,4H,5H-pyrazolo[3,4-d]pyrimidin-4-one | 1-(4-bromophenyl)-5-((4-hydroxypiperidin-4-yl)methyl)-1,5-dihydro-4H-pyrazolo[3,4-d]pyrimidin-4-one and 4-methylbenzoic acid | 522, 524 |
| Intermediate 2-31a. 5-((1-(cyclopropanecarbonyl)-4-hydroxypiperidin-4-yl)methyl)-1-(4-methoxyphenyl)-1,5-dihydro-4H-pyrazolo[3,4-d]pyrimidin-4-one | 5-((4-hydroxypiperidin-4-yl)methyl)-1-(4-methoxyphenyl)-1,5-dihydro-4H-pyrazolo[3,4-d]pyrimidin-4-one and cyclopropanoic acid | 424 |
| Intermediate 2-31b. 1-(3-bromo-4-fluorophenyl)-5-((1-(cyclopropanecarbonyl)-4-hydroxypiperidin-4-yl)methyl)-1,5-dihydro-4H-pyrazolo[3,4-d]pyrimidin-4-one | 1-(3-bromo-4-fluorophenyl)-5-((4-hydroxypiperidin-4-yl)methyl)-1,5-dihydro-4H-pyrazolo[3,4-d]pyrimidin-4-one, TFA salt and cyclopropanoic acid | 490, 492 |

Example 7: Intermediate 2-7b.
1-(5-bromopyridin-2-yl)pyrrolidin-3-ol

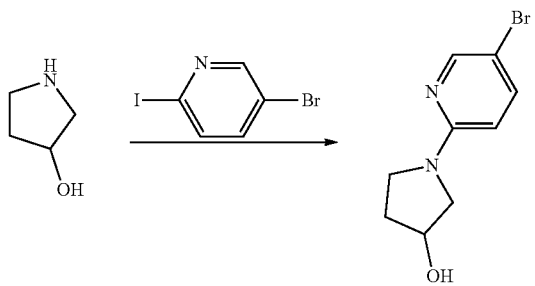 [SMILES: OC1CCNC1 ; Brc1ccc(I)nc1 ; OC1CCN(c2ccc(Br)cn2)C1]

A 250-mL round-bottom flask fitted with a nitrogen balloon, magnetic stir bar, condenser and thermometer was charged with pyrrolidin-3-ol (350 mg, 4.02 mmol), 5-bromo-2-iodopyridine (1 g, 3.52 mmol), toluene (60 mL), tris(dibenzylideneacetone)dipalladium (80 mg, 0.09 mmol), (+/−)-2,2'-bis(diphenylphosphino)-1,1'-binaphthyl (110 mg, 0.18 mmol) and sodium tert-butoxide (1.02 g, 10.6 mmol). The reaction mixture was stirred for 14 h at 70° C. in an oil bath. After cooling to 23° C., the reaction was quenched with water (60 mL). The product was extracted with ethyl acetate (4×60 mL). The combined organic layers were dried over anhydrous sodium sulfate, filtered and concentrated under vacuum. The residue was purified by column chromatography eluting with dichloromethane/methanol (10:1 v/v) to afford 1-(5-bromopyridin-2-yl)pyrrolidin-3-ol as a red solid (300 mg, 35%). LCMS: (ES) m/z 243, 245 [M+H].

Example 8: Intermediate 2-8. 2-Phenyl-1,2,3,4-tetrahydroisoquinoline-6-carboxylic acid

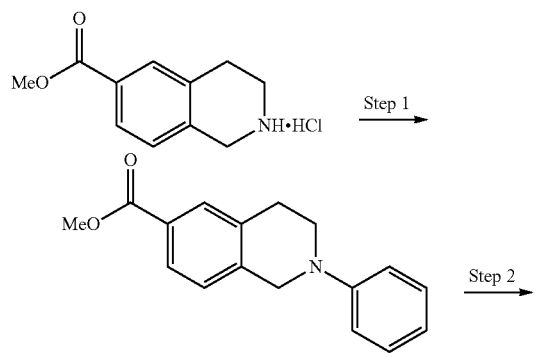

Step 1. Methyl 2-phenyl-1,2,3,4-tetrahydroisoquinoline-6-carboxylate

A mixture of methyl 1,2,3,4-tetrahydroisoquinoline-6-carboxylate hydrochloride (230 mg, 1.01 mmol), bromobenzene (230 mg, 1.47 mmol), and cesium carbonate (0.66 g, 2.02 mmol) in 1,4-dioxane (10 mL) was purged with nitrogen. RuPhos precatalyst (15 mg, 0.020 mmol) was added and the reaction mixture was heated at 80° C. for 30 min, then 120° C. for 16 h. The solvent was removed under vacuum. The residue was diluted with water (30 mL), poured into a separatory funnel, and washed with ethyl acetate (3×50 mL). The combined organic layers were dried over sodium sulfate and the solvent was removed under vacuum and the crude mixture was purified on silica gel using a gradient of 0-100% ethyl acetate/hexanes, to give methyl 2-phenyl-1,2,3,4-tetrahydroisoquinoline-6-carboxylate (200 mg, 74%). $^1$H NMR (400 MHz, CDCl$_3$) δ 8.00-7.76 (m, 2H), 7.30-7.12 (m, 3H), 6.75 (d, 2H), 6.75 (t, 1H), 4.35 (s, 2H), 3.84 (s, 3H), 3.39 (t, 2H), 2.94 (t, 2H) ppm. LCMS: (ESI) m/z 268 [M+H].

Step 2. 2-Phenyl-1,2,3,4-tetrahydroisoquinoline-6-carboxylic acid

Sodium hydroxide (1.0 M aqueous, 2.24 mL, 2.24 mmol) was stirred with methyl 2-phenyl-1,2,3,4-tetrahydroisoquinoline-6-carboxylate (Step 1, 200 mg, 0.75 mmol) in tetrahydrofuran (5 mL) at 50° C. for 48 h. Hydrochloric acid (1.0 M solution in water) was added to the reaction until the pH was 4. The mixture was poured into a separatory funnel and washed with ethyl acetate (3×50 mL). The combined organic layers were dried over sodium sulfate to afford 2-phenyl-1,2,3,4-tetrahydroisoquinoline-6-carboxylic acid (Intermediate 2-8, 150 mg, 79%), which was used without any further purification. LCMS: (ESI) m/z 254 [M+H]

The Intermediates in Table 5 were synthesized according to the procedure described in Example 8.

TABLE 5

| Intermediate No.: | Precursor Used | LCMS: (ESI) m/z [M + H] |
|---|---|---|
| Intermediate 2-63. 3-fluoro-4-(4-methylpiperazin-1-yl)benzoic acid | Methyl 4-bromo-3-fluorobenzoate and 1-methylpiperazine | 239 |
| Intermediate 2-868a. 4-(5-(Tert-butoxycarbonyl)-2,5-diaza-bicyclo[2.2.1]heptan-2-yl)benzoic acid | Methyl 4-bromo-3-benzoate and tert-butyl 2,5-diazabicyclo[2.2.1]heptane-2-carboxylate | 319 |

-continued

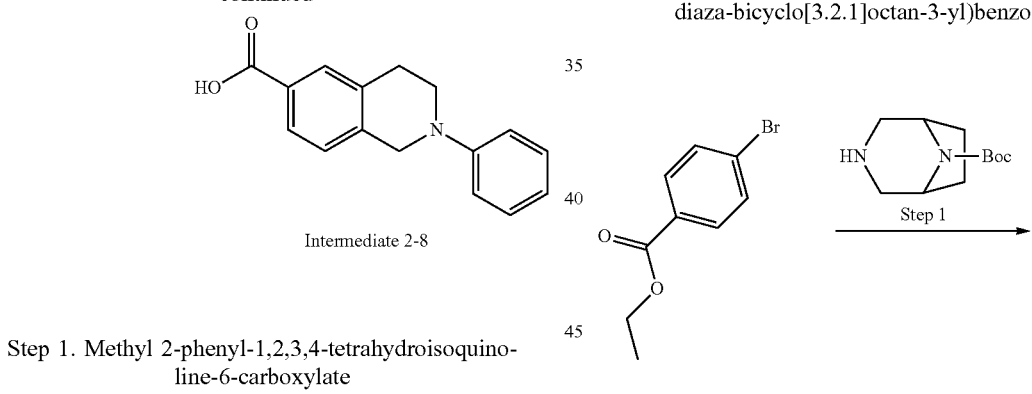

Intermediate 2-8

Example 9: Intermediate 2-65. 4-(8-Methyl-3,8-diaza-bicyclo[3.2.1]octan-3-yl)benzoic acid

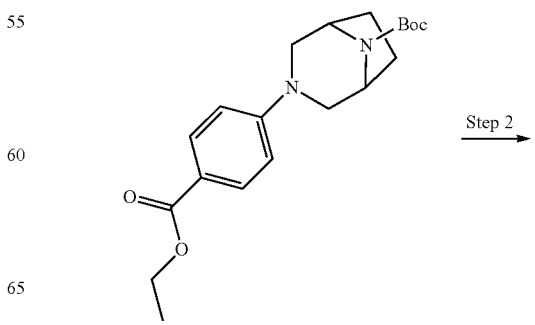

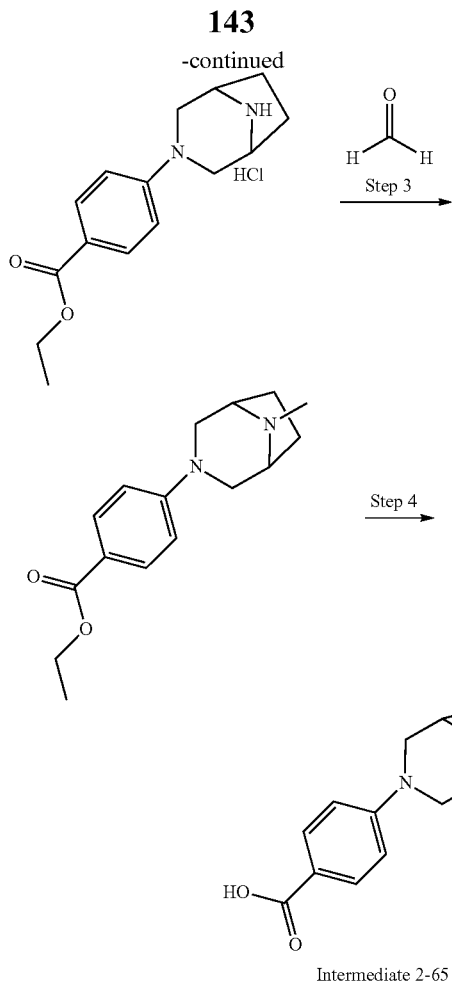

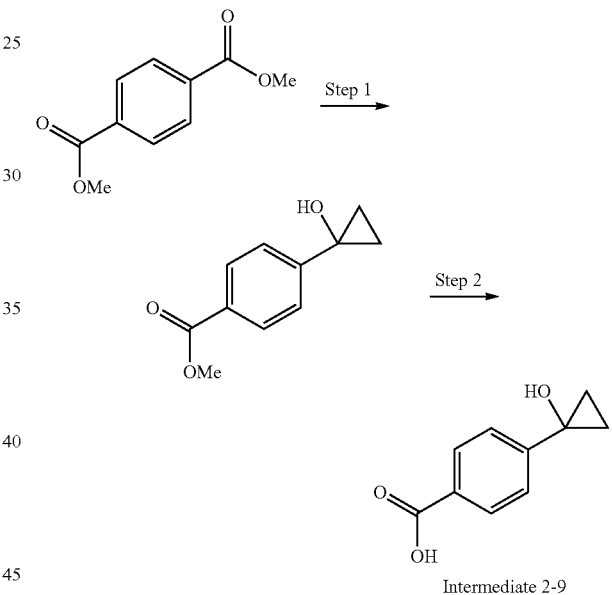

Intermediate 2-9

Step 1. Ethyl-4-(3,8-diaza-bicyclo[3.2.1]octan-8-carboxylicacid,1,1-dimethylethylester-3-yl)benzoate Title compound (300 mg, 38%) was prepared according to procedure described in Example 8, Step 1, utilizing 4-bromobenzoate (500 mg, 2.18 mmol) and tert-butyl 3,8-diazabicyclo[3.2.1]octane-8-carboxylate (930 mg, 4.38 mmol) as starting materials. LCMS: (ESI) m/z 361 [M+H].

Step 2. Ethyl 4-(3,8-diaza-bicyclo[3.2.1]octan-3-yl)benzoate hydrochloride

Title compound was prepared according to the procedure outlined in Example 2a, utilizing ethyl-4-(3,8-diaza-bicyclo[3.2.1]octan-8-carboxylicacid,1,1-dimethylethylester-3-yl)benzoate (Step 1, 300 mg, 0.83 mmol) as starting material which was used directly for next step without further purification (200 mg, 92%). LCMS: (ESI) m/z 261 [M+H].

Step 3. Ethyl 4-(8-methyl-3,8-diaza-bicyclo[3.2.1]octan-3-yl)benzoate

A 100-mL round-bottom flask was charged with ethyl 4-(3,8-diaza-bicyclo[3.2.1]octan-3-yl)benzoate hydrochloride (Step 2, 200 mg, 0.67 mmol), methanol (10 mL), formaldehyde (10 mL) and sodium triacetoxyborohydride (450 mg, 2.12 mmol). The resulting mixture was stirred for 4 h at 23° C. The reaction was then quenched by the addition of water (30 mL). The resulting solution was extracted with ethyl acetate (3×40 mL) and washed with brine (40 mL). The organic layer was dried over anhydrous sodium sulfate, filtered and concentrated under vacuum. The residue was purified by column chromatography eluting with ethyl acetate/petroleum ether (1:5 v/v) to afford to afford ethyl 4-(8-methyl-3,8-diaza-bicyclo[3.2.1]octan-3-yl)benzoate as a colorless oil (170 mg, 92%). LCMS (ESI) m/z 275 [M+H].

Step 4. 4-(8-Methyl-3,8-diaza-bicyclo[3.2.1]octan-3-yl)benzoic acid

The title compound was prepared according to the procedure outlined in Example 10, Step 2 utilizing ethyl 4-(8-methyl-3,8-diaza-bicyclo[3.2.1]octan-3-yl)benzoate (Step 3, 170 mg, 0.62 mmol) as starting material (130 mg, 85%) as a colorless oil which was used directly in the next step without further purification. LCMS: (ES) m/z 247 [M+H].

Example 10: Intermediate 2-9. 4-(1-Hydroxycyclopropyl)benzoic acid

Step 1. Methyl 4-(1-hydroxycyclopropyl)benzoate

Ether (30 mL), titanium(IV) isopropoxide (0.5 mL, 1.69 mmol) and dimethyl terephthalate (1.00 g, 5.15 mmol) were added to a 100-mL 3-necked round-bottom flask fitted with a nitrogen inlet, magnetic stir bar and condenser. This was followed by the addition of ethylmagnesium bromide (3.0 M in ether, 2.6 mL, 7.80 mmol) dropwise with stirring at 10° C. The resulting solution was stirred for 2 h at room temperature and then quenched by the addition of sulfuric acid (15% wt, 50 mL). The resulting solution was extracted with ethyl acetate (4×30 mL). The organic layers were combined and washed with saturated aqueous sodium carbonate (50 mL) and brine (50 mL). The mixture was dried over anhydrous sodium sulfate, filtered and concentrated under vacuum. The residue was purified by preparative TLC plate with petroleum ether/ethyl acetate (15:1 v/v) to afford methyl 4-(1-hydroxycyclopropyl)benzoate (250 mg, 25%). LCMS: (ESI) m/z 193 [M+H].

Step 2. 4-(1-Hydroxycyclopropyl)benzoic acid

Methanol (20 mL), methyl 4-(1-hydroxycyclopropyl)benzoate (Step 1, 200 mg, 1.04 mmol), and lithium hydroxide (10% aqueous, 5 mL) were added to a 100-mL round-bottom flask fitted with a nitrogen inlet, magnetic stir bar and condenser. The resulting solution was stirred for 1 h at room temperature. The pH value of the solution was adjusted to 4 with hydrogen chloride (1.0 M aqueous). The resulting solution was extracted with dichloromethane (4×20 mL) and the organic layers were combined, dried over anhydrous sodium sulfate and concentrated under vacuum to afford 4-(1-hydroxycyclopropyl)benzoic acid (Intermediate 2-9) which was used without further purification. LCMS: (ESI) m/z 177 [M−H].

Example 11: Intermediate 2-11. 5-((4-Hydroxypiperidin-4-yl)methyl)-1-(6-phenylpyridin-3-yl)-1,5-dihydro-4H-pyrazolo[3,4-d]pyrimidin-4-one trifluoroacetic acid salt

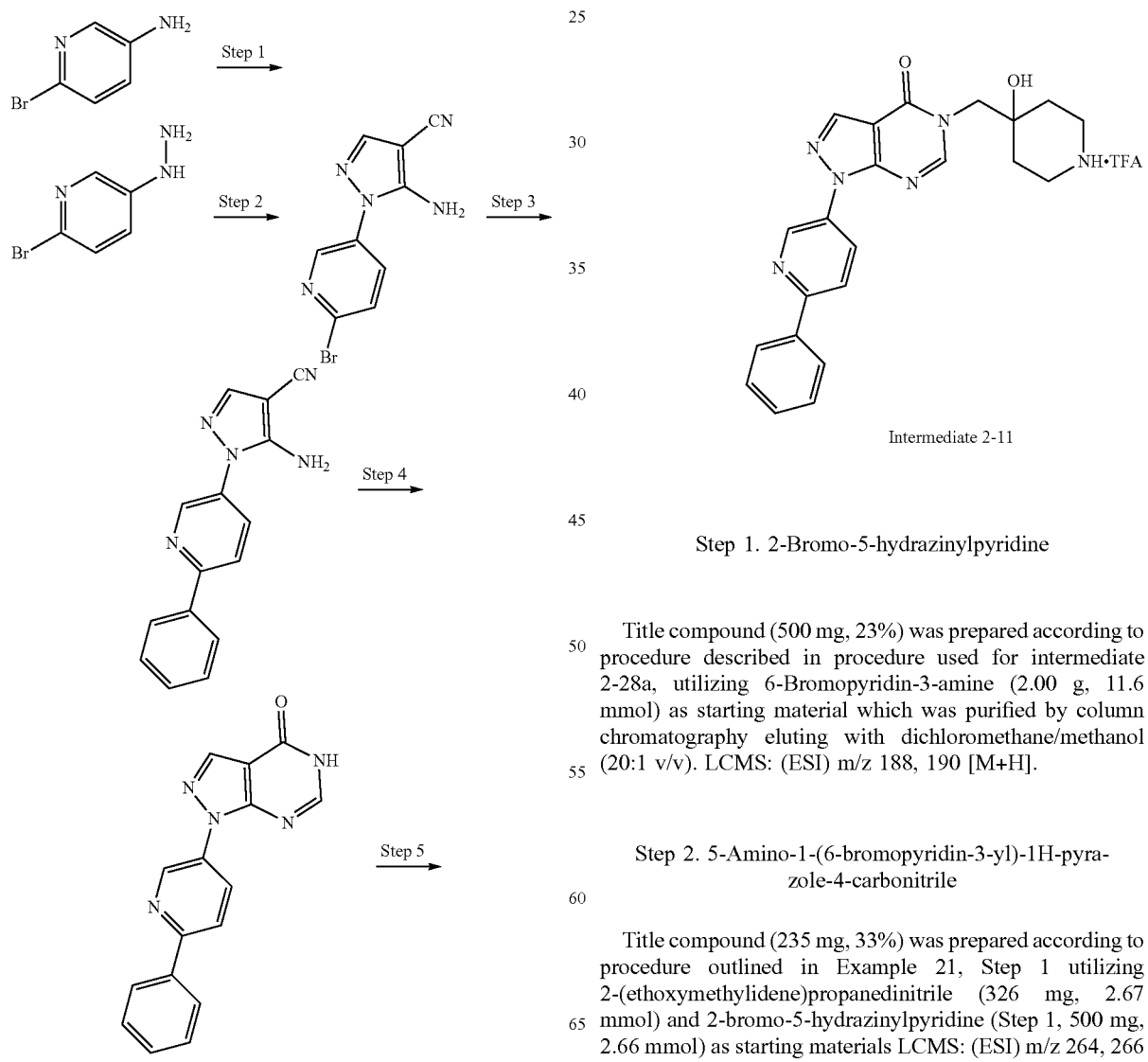

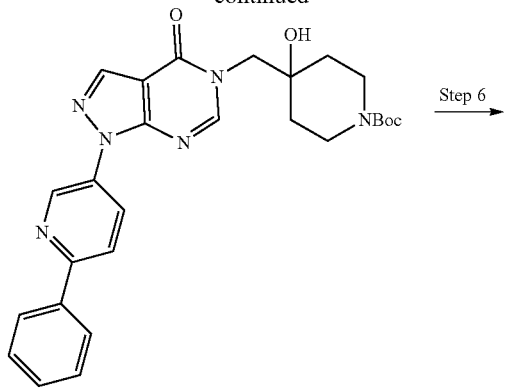

Intermediate 2-11

Step 1. 2-Bromo-5-hydrazinylpyridine

Title compound (500 mg, 23%) was prepared according to procedure described in procedure used for intermediate 2-28a, utilizing 6-Bromopyridin-3-amine (2.00 g, 11.6 mmol) as starting material which was purified by column chromatography eluting with dichloromethane/methanol (20:1 v/v). LCMS: (ESI) m/z 188, 190 [M+H].

Step 2. 5-Amino-1-(6-bromopyridin-3-yl)-1H-pyrazole-4-carbonitrile

Title compound (235 mg, 33%) was prepared according to procedure outlined in Example 21, Step 1 utilizing 2-(ethoxymethylidene)propanedinitrile (326 mg, 2.67 mmol) and 2-bromo-5-hydrazinylpyridine (Step 1, 500 mg, 2.66 mmol) as starting materials LCMS: (ESI) m/z 264, 266 [M+H].

Step 3. 5-Amino-1-(6-phenylpyridin-3-yl)-1H-pyrazole-4-carbonitrile Buchwald dppf, phosphate tribasic Title compound (180 mg, 93%) was prepared according to procedure outlined in Example 5 utilizing 5-Amino-1-(6-bromopyridin-3-yl)-1H-pyrazole-4-carbonitrile (Step 2, 195 mg, 0.74 mmol), phenylboronic acid (136 mg, 1.11 mmol), 1,4-dioxane (15 mL), and [1,1'-bis(diphenylphosphino)ferrocene]dichloropalladium (II), complex with dichloromethane (48 mg) followed by column chromatography purification using ethyl acetate/petroleum ether (1:1 v/v) LCMS: (ESI) m/z 262 [M+H].

Step 4. 1-(6-phenylpyridin-3-yl)-1,5-dihydro-4H-pyrazolo[3,4-d]pyrimidin-4-one

5-Amino-1-(6-phenylpyridin-3-yl)-1H-pyrazole-4-carbonitrile (Step 3, 170 mg, 0.65 mmol, 1.00 equiv) and formic acid (18 mL) were added to a 100-mL round-bottom flask fitted with a magnetic stir bar and condenser. The resulting solution was heated at reflux for 16 h, then cooled to room temperature and concentrated under vacuum. The solids were washed with ethyl acetate (3×20 mL) and dried to give 1-(6-phenylpyridin-3-yl)-1,5-dihydro-4H-pyrazolo[3,4-d]pyrimidin-4-one (170 mg, 90%). LCMS: (ESI) m/z 290 [M+H].

Step 5. tert-Butyl 4-hydroxy-4-((4-oxo-1-(6-phenylpyridin-3-yl)-1,4-dihydro-5H-pyrazolo [3,4-d]pyrimidin-5-yl)methyl)piperidine-1-carboxylate Title compound (235 mg, 33%) was prepared according to procedure outlined in Example 21, Step 4 utilizing 1-(6-phenylpyridin-3-yl)-1,5-dihydro-4H-pyrazolo[3,4-d]pyrimidin-4-one (Step 4, 160 mg, 0.55 mmol) as starting material followed by column chromatography purification using ethyl acetate/petroleum ether (1:3 v/v) (210 mg, 76%). LCMS: (ESI) m/z 503 [M+H].

Step 6. 5-((4-Hydroxypiperidin-4-yl)methyl)-1-(6-phenylpyridin-3-yl)-1,5-dihydro-4H-pyrazolo[3,4-d]pyrimidin-4-one trifluoroacetic acid salt Title compound (235 mg, 33%) was prepared according to procedure outlined in Example 21, Step 5 utilizing tert-Butyl 4-hydroxy-4-((4-oxo-1-(6-phenylpyridin-3-yl)-1,4-dihydro-5H-pyrazolo [3,4-d]pyrimidin-5-yl)methyl)piperidine-1-carboxylate (Step 5, 210 mg, 0.42 mmol), as starting material which was used without further purification. LCMS: (ESI) m/z 402 [M+H].

The Intermediates in Table 6 were synthesized according to the procedure described for Example 11, Steps 2, 3 and Step 6.

TABLE 6

| Intermediate No.: | Precursor Used | LCMS: (ESI) m/z [M + H] |
|---|---|---|
| Intermediate 2-32. 5-[(4-hydroxypiperidin-4-yl) methyl]-1-(4-phenylphenyl)-1H,4H,5H-pyrazolo [3,4-d] pyrimidin-4-one, trifluoroacetic acid salt | 1-(4-Bromophenyl)-1,5-dihydro-4H-pyrazolo[3,4-d]pyrimidin-4-one and phenylboronic acid | 402 |
| Intermediate 2-877. 1-(4'-fluoro-[1,1'-biphenyl]-4-yl)-5-((4-hydroxypiperidin-4-yl)methyl)-1,5-dihydro-4H-pyrazolo[3,4-d]pyrimidin-4-one, trifluoroacetic acid salt | 1-(4-Bromophenyl)-1,5-dihydro-4H-pyrazolo[3,4-d]pyrimidin-4-one and 4-fluorophenylboronic acid | 420 |
| Intermediate 2-879. 5-((4-hydroxypiperidin-4-yl)methyl)-1-(3'-(trifluoromethyl)biphenyl-4-yl)-1H-pyrazolo[3,4-d]pyrimidin-4 (5H)-one, trifluoroacetic acid salt | 1-(4-Bromophenyl)-1,5-dihydro-4H-pyrazolo[3,4-d]pyrimidin-4-one and 3-trifluorophenylboronic acid | 470 |

Example 12: Intermediate 2-13.
2-Chloro-4-phenoxybenzoic acid

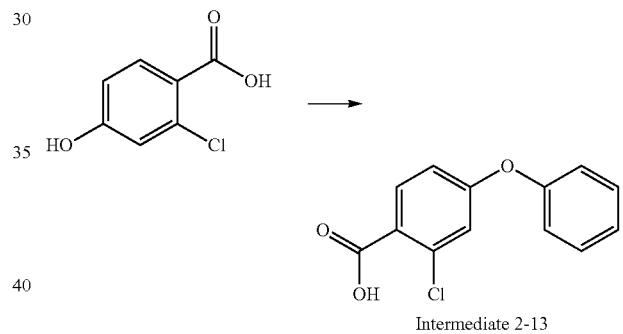

Intermediate 2-13

2-Chloro-4-hydroxybenzoic acid (3.00 g, 17.4 mmol), dichloromethane (100 mL), phenylboronic acid (4.24 g, 34.8 mmol), copper (II) acetate (7.87 g, 43.3 mmol), triethylamine (5.27 g, 52.1 mmol) and 4 Å molecular sieves (MS) (3.00 g) were added to a 250-mL round-bottom flask fitted with a nitrogen inlet and magnetic stir bar. The reaction mixture was stirred for 16 h at room temperature. The solids were filtered and the filtrate was concentrated under vacuum. The residue was purified on a silica gel column with dichloromethane/methanol (10:1 v/v) to afford 2-chloro-4-phenoxybenzoic acid (Intermediate 2-13, 790 mg, 18%). LCMS: (ESI) m/z 247 [M−H].

Example 13: Intermediate 2-26.
2-Phenyloxazole-5-carboxylic acid

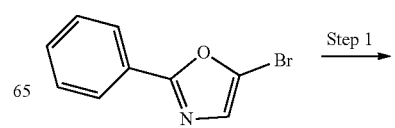

Step 1

-continued

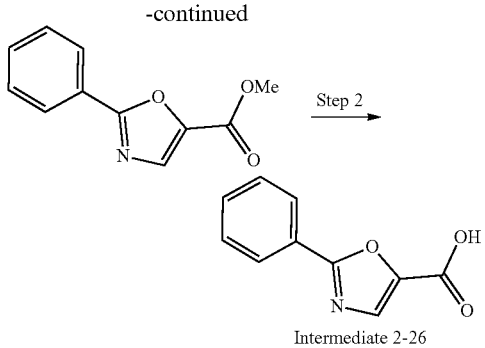

Intermediate 2-26

Step 1. Methyl 2-phenyloxazole-5-carboxylate

5-Bromo-2-phenyl-1,3-oxazole (500 mg, 2.23 mmol), [1,1'-bis(diphenylphosphino) ferrocene]dichloropalladium (II), complex with dichloromethane (96 mg, 0.12 mmol), triethylamine (1.00 mL, 7.17 mmol) and methanol (20 mL) were added to a 50-mL pressure tank reactor (3 atm) fitted with a magnetic stir bar and thermometer. The reactor was evacuated and flushed three times with nitrogen. Carbon monoxide was bubbled into the reactor and the resulting mixture was stirred for 16 h at 120° C. The reaction was then quenched by the addition water (50 mL) and extracted with dichloromethane (3×50 mL). The organic layers were combined, dried over anhydrous sodium sulfate, filtered and concentrated under vacuum. The residue was purified by silica gel column chromatography eluting with ethyl acetate/petroleum ether (1:2 v/v) to afford methyl 2-phenyloxazole-5-carboxylate (350 mg, 77%). LCMS: (ESI) m/z 204 [M+H].

Step 2. 2-Phenyloxazole-5-carboxylic acid

Title compound was prepared according to procedure outlined in Example 10, Step 2, utilizing methyl 2-phenyloxazole-5-carboxylate (Step 1, 350 mg, 1.72 mmol) as starting material, and was used without further purification. LCMS: (ESI) m/z 188 [M−H].

Example 14: Intermediate 2-17. 1-Benzyl-1H-pyrrole-2-carboxylic acid

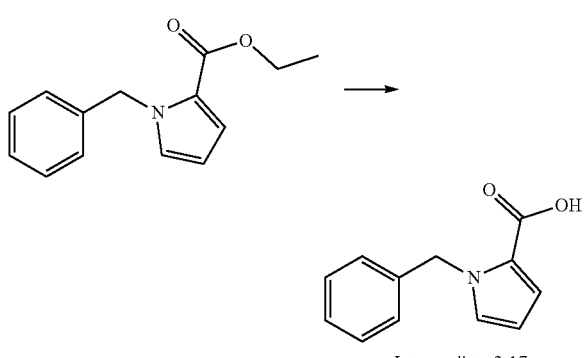

Intermediate 2-17

Ethyl 1-benzyl-1H-pyrrole-2-carboxylate (458 mg, 2.00 mmol), potassium hydroxide (1.12 g, 20.0 mmol), water (10 mL) and methanol (50 mL) were added to a 100-mL round-bottom flask fitted with a magnetic stir bar, thermometer and condenser. The resulting solution was stirred for 16 h at 70° C. The pH of the solution was adjusted to 2 with hydrochloric acid (6.0 M aqueous) and the resulting solution was extracted with ethyl acetate (3×30 mL). The organic layers were combined, dried over anhydrous sodium sulfate, filtered and concentrated under vacuum to give 1-benzyl-1H-pyrrole-2-carboxylic acid (Intermediate 2-17), which was used in the next step without purification. LCMS: (ESI) m/z 200 [M−H]

Example 15: Intermediate 2-21. 3-(1H-Pyrazol-1-yl)butanoic acid

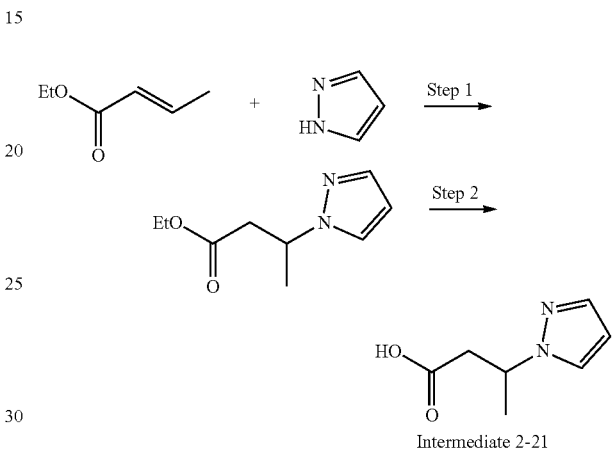

Intermediate 2-21

Step 1. Ethyl 3-(1H-pyrazol-1-yl)butanoate 1H-pyrazole (1.00 g, 14.7 mmol), ethyl (E)-but-2-enoate (2.50 g, 21.9 mmol), acetonitrile (30 mL) and DBU (1.20 g, 7.88 mmol) were added to a 100-mL round-bottom flask fitted with a magnetic stir bar. The resulting solution was stirred for 16 h at room temperature. The reaction was then quenched by the addition of water (50 mL) and extracted with dichloromethane (3×40 mL). The organic layers were combined, dried over anhydrous sodium sulfate, filtered and concentrated under vacuum to give ethyl 3-(1H-pyrazol-1-yl)butanoate which was used in the next step without any further purification. LCMS: (ESI) m/z 183 [M+H].

Step 2. 3-(1H-Pyrazol-1-yl)butanoic acid

Title compound was prepared according to a similar procedure outlined for Example 10, Step 2 utilizing ethyl 3-(1H-pyrazol-1-yl)butanoate (Step 1, 2.0 g, 11.0 mmol) as starting material which was used without further purification.

Example 16: Intermediate 2-51. 4,4-difluoro-3-(1H-pyrazol-1-yl)butanoic acid

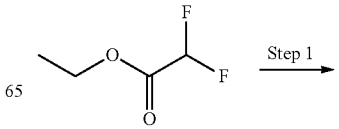

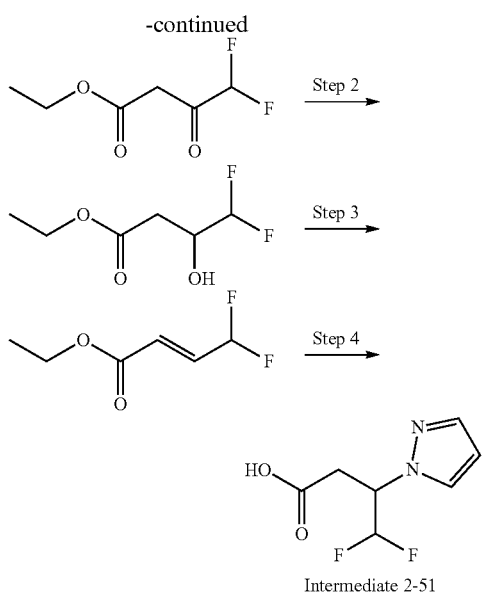

Intermediate 2-51

Step 1. Ethyl 4,4-difluoro-3-oxobutanoate

A 500-mL round-bottom flask was charged with sodium ethoxide (28.3 g, 416 mmol) and ethanol (80 mL) followed by the addition of a solution of ethyl 2,2-difluoroacetate (43 g, 347 mmol) in ethyl acetate (170 mL) added slowly with stirring at 23° C. The resulting solution was stirred for 2 h at 60° C. Upon cooling to 23° C., the reaction was quenched by the addition of hydrochloric acid (6M, 150 mL) and the pH of the solution was adjusted to 4-5. The resulting solution was extracted with ethyl acetate (3×200 mL) and the organic layers were combined and dried over anhydrous sodium sulfate and concentrated under vacuum to afford ethyl 4,4-difluoro-3-oxobutanoate as a colorless oil which was used without further purification (29 g, 42%). GCMS m/z 166.

Step 2. Ethyl 4,4-difluoro-3-hydroxybutanoate

A 500-mL round-bottom flask was charged with ethyl 4,4-difluoro-3-oxobutanoate (8 g, 48.16 mmol), toluene (250 mL) and sodium borohydride (2.38 g, 64.63 mmol). The resulting solution was stirred for 2 h at 65° C. The reaction was then quenched by the addition of water (100 mL) The resulting solution was extracted with ethyl acetate (3×50 mL) and the organic layers were combined, washed with brine, dried over anhydrous sodium sulfate and concentrated under vacuum. The residue was purified by column chromatography eluting with ethyl acetate/petroleum ether (1:5 to 1:2 v/v) to afford ethyl 4,4-difluoro-3-hydroxybutanoate (6.81 g, 84%). GCMS m/z 168.

Step 3. (E)-ethyl 4,4-difluorobut-2-enoate

A 25-mL round-bottom flask was charged with ethyl 4,4-difluoro-3-hydroxybutanoate (5 g, 48.16 mmol) and phosphorus pentoxide (3.4 g, 23.62 mmol). The resulting solution was stirred for 2 h at 70° C. in an oil bath. The crude product was purified by distillation under reduced pressure (1 mm Hg) and the fraction was collected at 100° C. to give (E)-ethyl 4,4-difluorobut-2-enoate as a colorless oil (1.8 g, 25%). GCMS m/z 150.

Step 4. 4,4-difluoro-3-(1H-pyrazol-1-yl)butanoic acid

A 100-mL round-bottom flask was charged with 1H-pyrazole (102 mg, 1.50 mmol) and tetrahydrofuran (20 mL) followed by the addition of sodium hydride (52 mg, 2.17 mmol) at 0° C. The resulting solution was stirred 30 min at 0° C. before adding (E)-ethyl 4,4-difluorobut-2-enoate (150 mg, 1.00 mmol). The resulting solution was stirred 16 h at 23° C. The reaction was quenched by the addition of 10 mL of water and extracted with ethyl acetate (30 mL). The pH of the aqueous layer was adjusted to 4-5 with hydrochloride (6 M) and extracted with dichloromethane (2×30 mL). The organic layers were combined, dried over anhydrous sodium sulfate and concentrated under vacuum to give 4,4-difluoro-3-(1H-pyrazol-1-yl)butanoic acid (90 mg) as a yellow oil which was used without further purification. LCMS: (ESI) r/z 191 [M+H].

The Intermediates below were synthesized according to the procedures outlined in Example 16 above.

TABLE 7

| Intermediate No.: | Precursor Used | MS (ESI, m/z) [M + H] |
|---|---|---|
| Intermediate 2-52. 4,4-difluoro-3-(5-fluoro-1H-pyrazol-1-yl)butanoic acid | 3-fluoro-1H-pyrazole | 209 |
| Intermediate 2-53. 4,4-difluoro-3-(4-fluoro-1H-pyrazol-1-yl)butanoic acid | 4-fluoro-1H-pyrazole | 209 |
| Intermediate 2-99. 3-(4-chloro-1H-pyrazol-1-yl)-4,4-difluorobutanoic acid | 4-chloro-1H-pyrazole | 225, 227 |
| Intermediate 2-100. 3-(3-chloro-1H-pyrazol-1-yl)-4,4-difluorobutanoic acid | 3-chloro-1H-pyrazole | 225, 227 |
| Intermediate 2-101. 4,4-difluoro-3-(4-methyl-1H-pyrazol-1-yl)butanoic acid | 3-methyl-1H-pyrazole | 205 |
| Intermediate 2-98. 3-(difluoromethoxy)cyclobutanecarboxylic acid | ethyl 3-oxobutanoate (Step 2) and 3-fluoro-1H-pyrazole | 173 |
| Intermediate 2-163. 4,4,4-Trifluoro-3-(1H-pyrazol-1-yl)butanoic acid | 2,2,2-trifluoroacetate (Step 1) and 1H-pyrazole | 209 |
| Intermediate 2-163A. 4,4,4-trifluoro-3-(3-fluoro-1H-pyrazol-1-yl)butanoic acid | 2,2,2-trifluoroacetate (Step 1) and 3-fluoro-1H-pyrazole | 227 |

Example 17: Intermediate 2-43.
4-Fluoro-3-phenylbutanoic acid

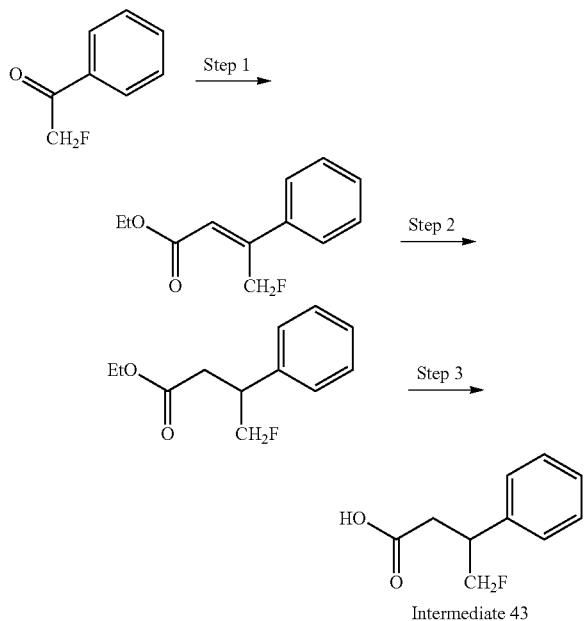

Intermediate 43

Step 1. Ethyl (Z)-4-fluoro-3-phenylbut-2-enoate

Sodium hydride (188 mg, 7.83 mmol) and tetrahydrofuran (10 mL) were added to a 3-necked 100-mL round-bottom flask fitted with a nitrogen inlet, magnetic stir bar, and thermometer. Ethyl 2-(diethoxyphosphoryl)acetate (1.05 g, 4.68 mmol) was added dropwise with stirring at 0° C. and the resulting solution was stirred for 1 h at 0° C. A solution of 2-fluoro-1-phenylethan-1-one (500 mg, 3.62 mmol) in tetrahydrofuran (10 mL) was added at 0° C. and the resulting solution was stirred for 30 min at 0° C. and then for 16 h at room temperature. The reaction was quenched by the addition of saturated aqueous ammonium chloride (30 mL) and extracted with ether (4×30 mL). The organic layers were combined, dried over anhydrous sodium sulfate, filtered and concentrated under vacuum. The residue was purified by column chromatography using ethyl acetate/petroleum ether (1:30 v/v) to afford ethyl (Z)-4-fluoro-3-phenylbut-2-enoate (630 mg, 84%). LCMS: (ESI) m/z 209 [M+H].

Step 2. Ethyl 4-fluoro-3-phenylbutanoate

Ethyl (Z)-4-fluoro-3-phenylbut-2-enoate (Step 1, 200 mg, 0.96 mmol), palladium on carbon (10% wt, 30 mg) and ethyl acetate (30 mL) were added to a 100-mL round-bottom flask fitted with a magnetic stir bar. The reaction mixture was purged and pressurized with hydrogen (2 atm) and then stirred for 40 min at room temperature. The reaction mixture was then filtered and concentrated under reduced pressure to afford ethyl 4-fluoro-3-phenylbutanoate which was used in next step without further purification. GCMS: m/z 210 [M+].

Step 3. 4-Fluoro-3-phenylbutanoic acid

Ethyl 4-fluoro-3-phenylbutanoate (200 mg, 0.96 mmol), lithium hydroxide (202 mg, 4.80 mmol), water (5 mL) and methanol (20 mL) were added to a 100-mL round-bottom flask fitted with a magnetic stir bar. The resulting solution was stirred for 2 h at room temperature. The pH was adjusted to 5 with hydrogen chloride (6.0 M aqueous) and the mixture was extracted with dichloromethane (5×20 mL). The organic layers were combined, dried over anhydrous sodium sulfate, filtered and concentrated under vacuum. The crude product was purified by preparative HPLC (Waters SunFire C18 OBD Prep Column, 100 Å, 5 μm, 19 mm×150 mm; Mobile phase A: 0.05% aqueous trifluoroacetic acid, Mobile phase B: acetonitrile; Gradient: 20% B to 60% B over 12 min; Detector: 220 and 254 nm) to give 4-fluoro-3-phenylbutanoic acid (Intermediate 2-43, 89 mg, 51%). LCMS: (ESI) m/z 181 [M−H]. $^1$H NMR (300 MHz, CDCl$_3$) δ 10.29-8.78 (m, 1H), 7.36-6.99 (m, 5H), 4.69-4.38 (m, 2H), 3.58-3.43 (m, 1H), 2.98-2.70 (m, 2H) ppm.

The Intermediates below were synthesized according to the procedures outlined in Example 17.

TABLE 8

| Intermediate No.: | Precursor Used | MS (ESI, m/z)[M − H] |
|---|---|---|
| Intermediate 2-12. 3-(Thiazol-2-yl)butanoic acid | 1-(1,3-thiazol-2-yl)ethan-1-one | 170 |

Example 18: Intermediate 2-22.
3-(1H-Pyrrol-1-yl)butanoic acid

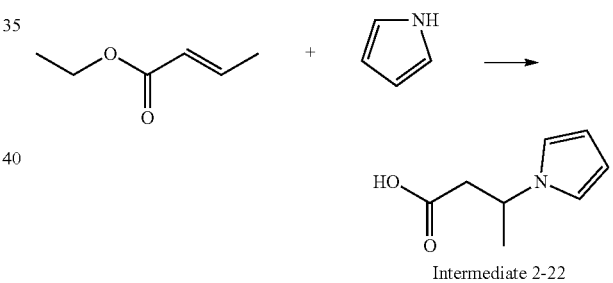

Intermediate 2-22

1H-Pyrrole (1.00 g, 14.9 mmol), ethyl (2E)-but-2-enoate (1.70 g, 14.9 mmol) and DMF (20 mL) were added to a 100-mL round-bottom flask fitted with a nitrogen inlet, magnetic stir bar and thermometer. This was followed by the addition of sodium hydride (60% in mineral oil, 180 mg, 4.50 mmol) at −10° C. The resulting solution was allowed to warm to room temperature and stirred for 16 h. The reaction was then quenched by the addition of water (20 mL). The resulting solution was stirred for 2 h at room temperature. The pH was adjusted to ~6 with hydrochloric acid (1.0 M aqueous). The resulting solution was extracted with dichloromethane (4×50 mL) and the organic layers were combined, dried over anhydrous sodium sulfate, filtered and concentrated under vacuum to give 3-(1H-pyrrol-1-yl)butanoic acid (Intermediate 2-22) which was used without further purification. LCMS: (ESI) m/z 152 [M−H]

The Intermediates below were synthesized according to the procedures described in Example 18. For 2-54 and 2-55, hydrolysis was facilitated by the addition of a solution of lithium hydroxide (2.5 mmol) in water (20 mL).

TABLE 9

| Intermediate No.: | Precursor Used | MS (ESI, m/z) [M + H] |
|---|---|---|
| Intermediate 2-54. 3-(hexahydro-cyclopenta[c]pyrrol-2-(1H)-yl)butanoic acid | octahydro-cyclopenta[c]pyrrole | 198 |
| Intermediate 2-55. 3-(5,6-dihydro-cyclopenta[c]pyrazol-2(4H)-yl)butanoic acid | 2,4,5,6-tetrahydro-cyclopenta[c]pyrazole | 195 |

Example 19: Intermediate 2-931a. 1-[4-(3-hydroxy-3-methylpyrrolidin-1-yl)phenyl]-5-[(4-hydroxypiperidin-4-yl)methyl]-1H,4H,5H-pyrazolo[3,4-d]pyrimidin-4-one, TFA salt

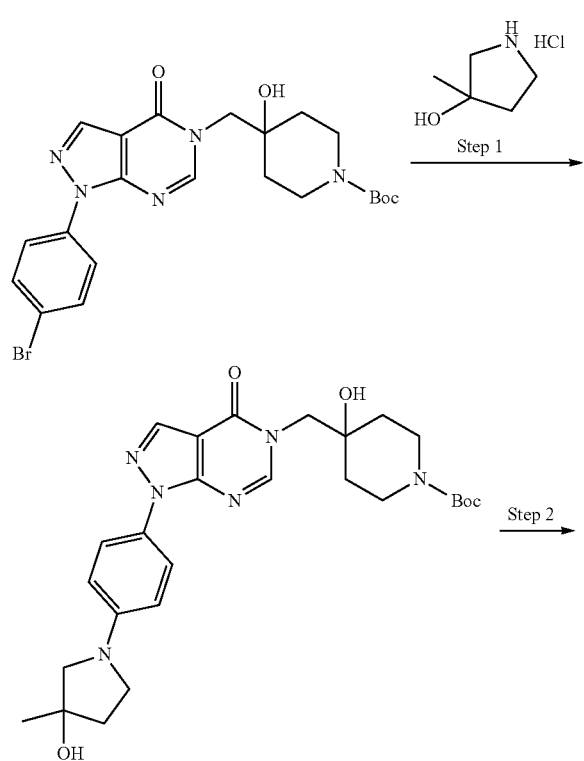

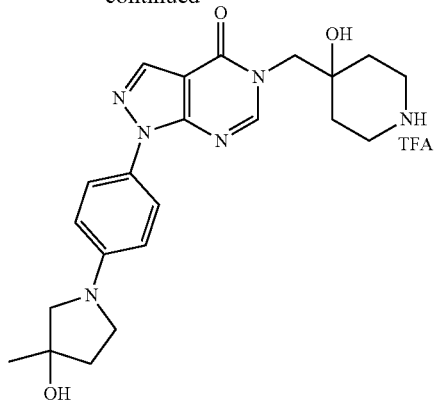

Step 1. Tert-butyl 4-hydroxy-4-([1-[4-(3-hydroxy-3-methylpyrrolidin-1-yl)phenyl]-4-oxo-1H,4H,5H-pyrazolo[3,4-d]pyrimidin-5-yl]methyl)piperidine-1-carboxylate A 100-mL round-bottom flask fitted with a nitrogen balloon, magnetic stir bar, condenser and thermometer was charged with tert-butyl 4-[[1-(4-bromophenyl)-4-oxo-1H,4H,5H-pyrazolo[3,4-d]pyrimidin-5-yl]methyl]-4-hydroxypiperidine-1-carboxylate (900 mg, 1.78 mmol), 3-methylpyrrolidin-3-ol hydrochloride (990 mg, 7.19 mmol), cesium carbonate (3.82 g, 11.7 mmol), 1,4-dioxane (30 mL), tetra(dibenzylideneacetone)dipalladium (207 mg, 0.18 mmol) and Xphos (171 mg, 0.36 mmol). The resulting solution was stirred for 16 h at 100° C. After cooling to 23° C., the reaction was quenched by the addition of water (30 mL). The resulting mixture was extracted with dichloromethane (4×30 mL). The combined organic layers were dried over anhydrous sodium sulfate, filtered and concentrated under vacuum. The residue was purified by column chromatography eluting with dichloromethane/methanol (50:1-20:1, v/v) to give tert-butyl 4-hydroxy-4-([1-[4-(3-hydroxy-3-methylpyrrolidin-1-yl)phenyl]-4-oxo-1H, 4H, 5H-pyrazolo[3,4-d]pyrimidin-5-yl]methyl)piperidine-1-carboxylate as a yellow solid (700 mg, 75%). LCMS: (ES) m/z 525 [M+H].

Step 2. 1-[4-(3-hydroxy-3-methylpyrrolidin-1-yl)phenyl]-5-[(4-hydroxypiperidin-4-yl)methyl]-1H,4H,5H-pyrazolo[3,4-d]pyrimidin-4-one, TFA salt The title compound was prepared according to procedure outlined in Example 2 utilizing tert-butyl 4-hydroxy-4-([I-[4-(3-hydroxy-3-methylpyrrolidin-1-yl)phenyl]-4-oxo-1H,4H,5H-pyrazolo[3,4-d]pyrimidin-5-yl]methyl)piperidine-1-carboxylate (200 mg, 0.38 mmol) as starting material (210 mg, >95%). LCMS: (ES) m/z 425 [M+H].

Table 10: The Intermediates below were synthesized according to the procedures described in Example 19.

TABLE 10

| Intermediate No.: | Precursor Used | MS (ESI, m/z) [M + H] |
|---|---|---|
| Intermediate 2-410. 1-(3-(3-azabicyclo[3.1.0]hexan-3-yl)phenyl)-5-((4-hydroxypiperidin-4-yl)methyl)-1,5-dihydro-4H-pyrazolo[3,4-d]pyrimidin-4-one | tert-butyl 4-[[1-(3-bromophenyl)-4-oxo-1H,4H,5H-pyrazolo[3,4-d]pyrimidin-5-yl]methyl]-4-hydroxypiperidine-1-carboxylate and 3-azabicyclo[3.1.0]hexane | 407, 408 |
| Intermediate 2-1100. 5-((4-hydroxypiperidin-4-yl)methyl)-1-(3-morpholinophenyl)-1,5-dihydro-4H- | tert-butyl 4-[[1-(3-bromophenyl)-4-oxo-1H,4H,5H-pyrazolo[3,4-d]pyrimidin-5-yl]methyl]-4- | 411 |

TABLE 10-continued

| Intermediate No.: | Precursor Used | MS (ESI, m/z) [M + H] |
|---|---|---|
| pyrazolo[3,4-d]pyrimidin-4-one, TFA salt | hydroxypiperidine-1-carboxylate and morpholine | |
| Intermediate 2-1111. 5-((4-hydroxypiperidin-4-yl)methyl)-1-(3-(4-methylpiperazin-1-yl)phenyl)-1,5-dihydro-4H-pyrazolo[3,4-d]pyrimidin-4-one, TFA salt | tert-butyl 4-[[1-(3-bromophenyl)-4-oxo-1H,4H,5H-pyrazolo[3,4-d]pyrimidin-5-yl]methyl]-4-hydroxypiperidine-1-carboxylate and 1-methylpiperazine | 424 |
| Intermediate 2-1112. 5-((4-hydroxypiperidin-4-yl)methyl)-1-(4-(4-methylpiperazin-1-yl)phenyl)-1,5-dihydro-4H-pyrazolo[3,4-d]pyrimidin-4-one, TFA salt | tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate and 1-methylpiperazine | 424 |
| Intermediate 2-1113. 5-((4-hydroxypiperidin-4-yl)methyl)-1-(4-morpholinophenyl)-1,5-dihydro-4H-pyrazolo[3,4-d]pyrimidin-4-one, TFA salt | tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate and morpholine | 411 |
| Intermediate 2-1114. 5-((4-hydroxypiperidin-4-yl)methyl)-1-(4-(piperidin-1-yl)phenyl)-1,5-dihydro-4H-pyrazolo[3,4-d]pyrimidin-4-one, TFA salt | tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate and piperidine | 409 |
| Intermediate 2-1115. 1-(4-(3-azabicyclo[3.1.0]hexan-3-yl)phenyl)-5-((4-hydroxypiperidin-4-yl)methyl)-1,5-dihydro-4H-pyrazolo[3,4-d]pyrimidin-4-one, TFA salt | tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate 3-azabicyclo[3.1.0]hexane | 407 |

Example 20: N-[(2R)-2-benzyl-3-[4-hydroxy-4-({4-oxo-1-phenyl-1H,4H,5H-pyrazolo[3,4-d]pyrimidin-5-yl}methyl)piperidin-1-yl]-3-oxopropyl]prop-2-ynamide

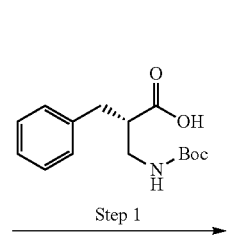

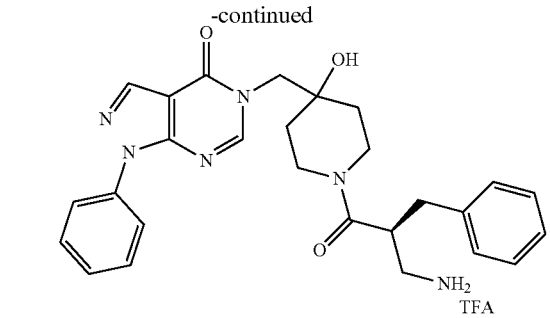

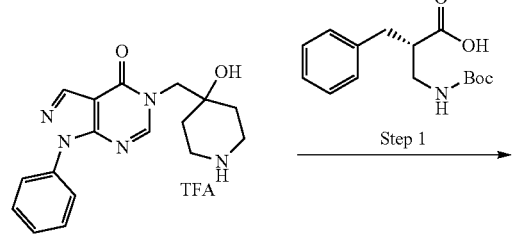

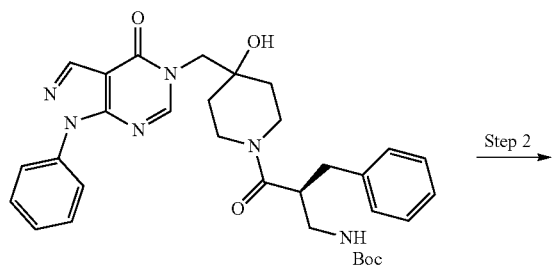

Step 1. Tert-butyl-N-[(2S)-2-benzyl-3-[4-hydroxy-4-([4-oxo-1-phenyl-1H,4H,5H-pyrazolo[3,4-d]pyrimidin-5-yl]methyl)piperidin-1-yl]-3-oxopropyl]carbamate The title compound was prepared according to the procedure outlined in Example 3 utilizing 5-[(4-hydroxypiperidin-4-yl)methyl]-1-phenyl-1H,4H,5H-pyrazolo[3,4-d]pyrimidin-4-one TFA salt (0.20 g, 0.46 mmol) and (2R)-2-benzyl-3-[[(tert-butoxy)carbonyl]amino]propanoic acid as starting materials followed by column chromatography purification eluting with ethyl acetate/petroleum ether (1:1 v/v) (0.190 g, 57%) LCMS: (ESI) m/z 587 [M+H].

Step 2. 5-([1-[(2S)-3-amino-2-benzylpropanoyl]-4-hydroxypiperidin-4-yl]methyl)-1-phenyl-1H,4H,5H-pyrazolo[3,4-d]pyrimidin-4-one, TFA salt The title compound was prepared according to the procedure outlined in Example 2 utilizing tert-butyl N-[(2S)-2-benzyl-3-[4-hydroxy-4-([4-oxo-1-phenyl-1H,4H,5H-pyrazolo[3,4-d]pyrimidin-5-yl]methyl)piperidin-1-yl]-3-oxopropyl]carbamate (0.190 g, 0.32 mmol) as starting material which was used without further purification. LCMS: (ESI) nm/z 487 [M+H].

TABLE 11

The Intermediates below were synthesized according to the procedures outlined in Example 20.

| Intermediate No.: | Precursor Used | MS (ESI, m/z) [M + H] |
|---|---|---|
| Intermediate 2-487. (R)-5-((1-(2-amino-3-phenylpropanoyl)-4-hydroxypiperidin-4-yl)methyl)-1-phenyl-1H-pyrazolo[3,4-d]pyrimidin-4 (5H)-one, TFA salt | 5-[(4-hydroxypiperidin-4-yl)methyl]-1-phenyl-1H,4H,5H-pyrazolo[3,4-d]pyrimidin-4-one TFA salt and (R)-2-(tert-butoxycarbonylamino)-3-phenylpropanoic acid | 473 |
| Intermediate 2-934a. (R)-5-((1-(azetidine-2-carbonyl)-4-hydroxypiperidin-4-yl) methyl)-1-(4-fluorophenyl)-1H-pyrazolo[3,4-d]pyrimidin-4(5H)-one, TFA salt | 1-(4-fluorophenyl)-5-[(4-hydroxypiperidin-4-yl)methyl]-1H,4H,5H-pyrazolo[3,4-d]pyrimidin-4-one TFA salt (Intermediate 2-28) and 1-tert-butyl-2-oxo-1-[3],3-oxazocane-7-carboxylic acid | 427 |
| Intermediate 2-935a. 1-(4-fluorophenyl)-5-((4-hydroxy-1-(piperidine-3-carbonyl)piperidin-4-yl)methyl)-1,5-dihydro-4H-pyrazolo[3,4-d]pyrimidin-4-one, TFA salt | 1-(4-fluorophenyl)-5-[(4-hydroxypiperidin-4-yl)methyl]-1H,4H,5H-pyrazolo[3,4-d]pyrimidin-4-one TFA salt (Intermediate 2-28) and 1-(tert-butoxycarbonyl)piperidine-3-carboxylic acid | 455 |
| Intermediate 2-111. 1-(4-fluorophenyl)-5-[(4-hydroxy-1-[[(1r,4r)-4-amino-cyclohexyl]carbonyl]piperidin-4-yl)methyl]-1H,4H,5H-pyrazolo[3,4-d]pyrimidin-4-one, TFA salt | 1-(4-fluorophenyl)-5-[(4-hydroxypiperidin-4-yl)methyl]-1H,4H,5H-pyrazolo[3,4-d]pyrimidin-4-one TFA salt (Intermediate 2-28) and trans-4-[(tert-butoxy)carbonyl]aminocyclohexane-1-carboxylic acid | 469 |

Example 21: Intermediates 2-28 and 2-29

1-(4-Fluorophenyl)-5-((4-hydroxypiperidin-4-yl)methyl)-1,5-dihydro-4H-pyrazolo[3,4-d]pyrimidin-4-one trifluoroacetic acid salt (Intermediate 2-28) and tert-Butyl 4-((1-(4-fluorophenyl)-4-oxo-1,4-dihydro-5H-pyrazolo[3,4-d]pyrimidin-5-yl) methyl-4-hydroxypiperidine-1-carboxylate (Intermediate 2-29)

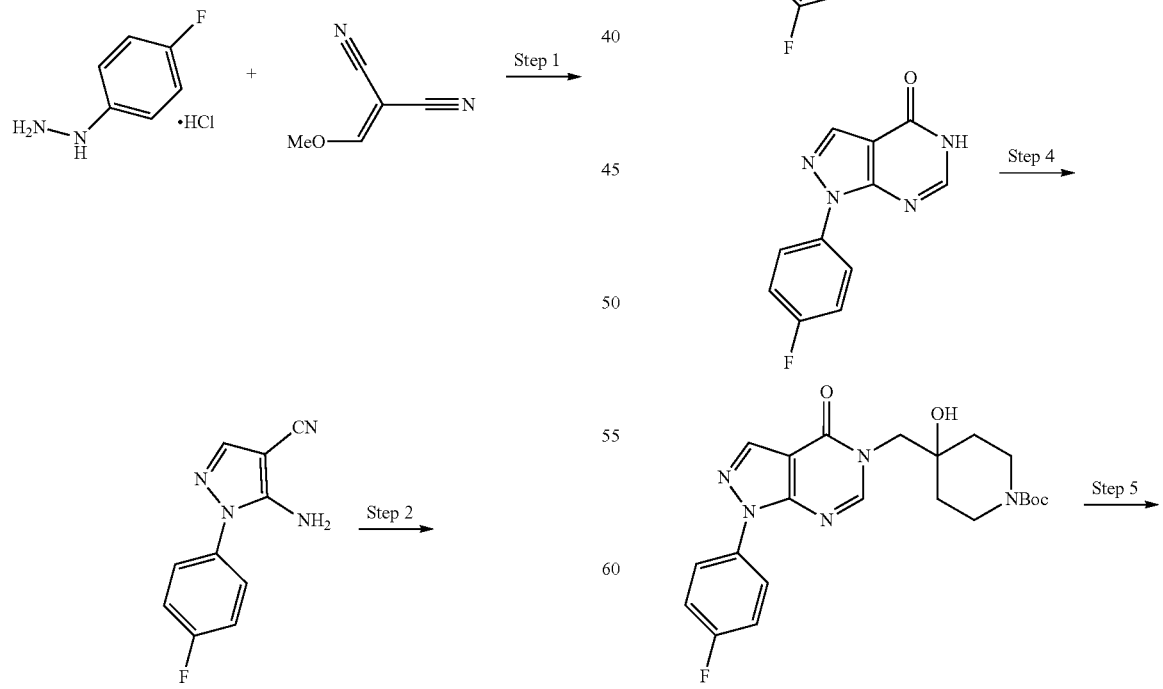

Intermediate 2-29

-continued

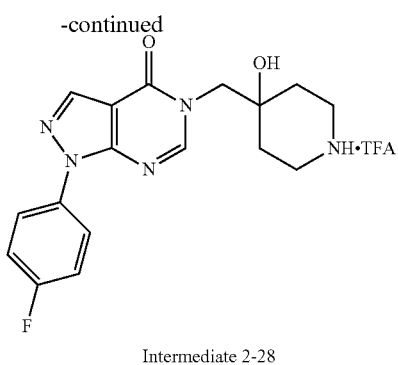

Intermediate 2-28

Step 1. 5-Amino-1-(4-fluorophenyl)-1H-pyrazole-4-carbonitrile 2-(Methoxymethylene)malononitrile (1.00 g, 8.19 mmol), (4-fluorophenyl) hydrazine hydrochloride (1.40 g, 8.61 mmol), triethylamine (1.66 g, 16.4 mmol) and ethanol (50 mL) were added to a 100-mL round-bottom flask fitted with a magnetic stir bar and condenser. The resulting solution was heated at reflux for 16 h. The resulting mixture was concentrated under vacuum. The residue was purified by column chromatography eluting with dichloromethane/methanol (10:1 v/v) to give 5-amino-1-(4-fluorophenyl)-1H-pyrazole-4-carbonitrile (1.00 g, 60%). LCMS: (ESI) m/z 203 [M+H].

Step 2. 5-Amino-1-(4-fluorophenyl)-1H-pyrazole-4-carboxamide

5-Amino-1-(4-fluorophenyl)-1H-pyrazole-4-carboxamide (Step 1, 900 mg, 4.45 mmol) was added dropwise to sulfuric acid (10 mL) at 0° C. The resulting solution was stirred for 2 h at 25° C. The pH of the solution was adjusted to 8 by the addition of sodium carbonate (10% aqueous). The resulting mixture was extracted with dichloromethane (4×50 mL) and the organic layers were combined, dried over anhydrous sodium sulfate, filtered and concentrated under vacuum to provide 5-amino-1-(4-fluorophenyl)-1H-pyrazole-4-carboxamide which was used in Step 3 without further purification. LCMS: (ESI) m/z 221 [M+H].

Step 3. 1-(4-Fluorophenyl)-1,5-dihydro-4H-pyrazolo[3,4-d]pyrimidin-4-one

5-Amino-1-(4-fluorophenyl)-1H-pyrazole-4-carboxamide (Step 2, 1.00 g, 4.54 mmol), triethyl orthoformate (20 mL) and acetic anhydride (20 mL) were added to a 100-mL round-bottom flask fitted with a magnetic stir bar and condenser. The resulting solution was heated at reflux for 1 h and then concentrated under vacuum. The solids were collected and washed with hexane (3×20 mL) to afford 1-(4-fluorophenyl)-1,5-dihydro-4H-pyrazolo[3,4-d]pyrimidin-4-one which was used in the next step without further purification. LCMS: (ESI) m/z 231 [M+H].

Step 4. tert-Butyl 4-((1-(4-fluorophenyl)-4-oxo-1,4-dihydro-5H-pyrazolo[3,4-d]pyrimidin-5-yl)methyl)-4-hydroxypiperidine-1-carboxylate 1-(4-Fluorophenyl)-1,5-dihydro-4H-pyrazolo[3,4-d]pyrimidin-4-one (Step 3, 1.00 g, 4.34 mmol), tert-butyl 1-oxa-6-azaspiro[2.5]octane-6-carboxylate (926 mg, 4.34 mmol), cesium carbonate (4.30 g, 13.2 mmol) and DMF (50 mL) were added to a 100-mL round-bottom flask fitted with a magnetic stir bar and thermometer. The resulting solution was stirred for 5 h at 80° C. The resulting solution was diluted with water (50 mL). The mixture was extracted with MTBE (5×20 mL) and the organic layers were combined, dried over anhydrous sodium sulfate, filtered and concentrated under vacuum. The residue was purified by column chromatography eluting with dichloromethane/methanol (50:1 v/v) to give tert-butyl 4-((1-(4-fluorophenyl)-4-oxo-1,4-dihydro-5H-pyrazolo[3,4-d]pyrimidin-5-yl)methyl)-4-hydroxypiperidine-1-carboxylate (Intermediate 2-29, 500 mg, 26%), LCMS: (ESI) m/z 444 [M+H]

Step 5. 1-(4-Fluorophenyl)-5-((4-hydroxypiperidin-4-yl)methyl)-1,5-dihydro-4H-pyrazolo[3,4-d]pyrimidin-4-one trifluoroacetic acid salt tert-Butyl 4-((1-(4-fluorophenyl)-4-oxo-1,4-dihydro-5H-pyrazolo[3,4-d]pyrimidin-5-yl)methyl)-4-hydroxypiperidine-1-carboxylate (Step 4, 500 mg, 1.13 mmol), dichloromethane (30 mL) and trifluoroacetic acid (3 mL) were added to a 50-mL round-bottom flask fitted with a magnetic stir bar and condenser. The resulting solution was stirred for 2 h at 25° C. The resulting mixture was concentrated under vacuum to give 1-(4-fluorophenyl)-5-((4-hydroxypiperidin-4-yl)methyl)-1,5-dihydro-4H-pyrazolo[3,4-d]pyrimidin-4-one trifluoroacetic acid salt (Intermediate 2-28) which was used without further purification. LCMS: (ESI) m/z 344 [M+H].

Table 12: The intermediates in Table 12 were synthesized according to procedure described Example 21. All intermediates prepared according to Intermediate 2-28 were isolated as TFA salts, unless otherwise specified. Some hydrazines were prepared according to general procedure described below.

A 250-mL 3-necked round-bottom flask fitted with a magnetic stir bar and thermometer was charged with corresponding aniline or amine (89.20 mmol), hydrochloric acid (100 mL, 6N) followed by the addition of a solution of sodium nitrite (107.25 mmol) in water (20 mL) slowly added with stirring for 1 h at −20 to −10° C. To the reaction was slowly added a solution of $SnCl_2$ (269.2 mmol) in hydrochloric acid (50 mL, 12N) and stirring continued for 1 h. The reaction was warmed to 23° C. and the pH was adjusted to 8 with potassium hydroxide (6 N). The solids were removed by filtration. The combined organic layers were dried over anhydrous sodium sulfate, filtered and concentrated under vacuum to afford the desired hydrazine.

TABLE 12

| Intermediate No.: | Procedure used in accordance with intermediate | Precursor Used | LCMS: (ESI) m/z [M + H] |
|---|---|---|---|
| Intermediate 2-a. 1-(4-bromophenyl)-5-((4-hydroxypiperidin-4-yl)methyl)-1,5-dihydro-4H-pyrazolo[3,4-d]pyrimidin-4-one | 2-28 | (4-bromophenyl)hydrazine hydrochloride salt | 404, 406 |
| Intermediate 29-xa. tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate | 2-29 | (4-bromophenyl)hydrazine hydrochloride salt | 504, 506 |
| Intermediate 2-16. 5-((4-hydroxypiperidin-4-yl)methyl)-1-(p-tolyl)-1,5-dihydro-4H-pyrazolo[3,4-d]pyrimidin-4-one | 2-28 | | 340 |
| Intermediate 2-18. 5-((4-hydroxypiperidin-4-yl)methyl)-1-phenyl-1,5-dihydro-4H-pyrazolo[3,4-d]pyrimidin-4-one | 2-28 | | 326 |
| Intermediate 2-19. 1-cyclopropyl-5-((4-hydroxypiperidin-4-yl)methyl)-1,5-dihydro-4H-pyrazolo[3,4-d]pyrimidin-4-one | 2-28 | | 290 |
| Intermediate 2-20. Methyl 3-(5-((4-hydroxypiperidin-4-yl)methyl)-4-oxo-4,5-dihydro-1H-pyrazolo[3,4-d]pyrimidin-1-yl)benzoate | 2-28 | | 384 |
| Intermediate 2-30. 1-(3-bromophenyl)-5-((4-hydroxypiperidin-4-yl)methyl)-1,5-dihydro-4H-pyrazolo[3,4-d]pyrimidin-4-one | 2-28 | (3-bromophenyl)hydrazine hydrochloride salt | 404, 406 |
| Intermediate 30a tert-butyl 4-[[1-(3-bromophenyl)-4-oxo-1H,4H,5H-pyrazolo[3,4-d]pyrimidin-5-yl]methyl]-4-hydroxypiperidine-1-carboxylate | 2.29 | (3-bromophenyl)hydrazine hydrochloride salt | 504, 506 |
| Intermediate 2-36. 5-((4-hydroxypiperidin-4-yl)methyl)-1-(4-phenoxyphenyl)-1,5-dihydro-4H-pyrazolo[3,4-d]pyrimidin-4-one | 2-28 | | 418 |
| Intermediate 2-28a. 1-(4-(tert-butyl)phenyl)-5-((4-hydroxypiperidin-4-yl)methyl)-1,5-dihydro-4H-pyrazolo[3,4-d]pyrimidin-4-one | 2-28 | | 382 |
| Intermediate 2-28b. 5-((4-hydroxypiperidin-4-yl)methyl)-1-mesityl-1,5-dihydro-4H-pyrazolo[3,4-d]pyrimidin-4-one | 2-28 | | 368 |
| Intermediate 2-28c. 5-((4-hydroxypiperidin-4-yl)methyl)-1-(4-isopropylphenyl)-1,5-dihydro-4H-pyrazolo[3,4-d]pyrimidin-4-one | 2-28 | | 368 |
| Intermediate 2-28d. 5-((4-hydroxypiperidin-4-yl)methyl)-1-(4-(trifluoromethyl)phenyl)-1,5-dihydro-4H-pyrazolo[3,4-d]pyrimidin-4-one | 2-28 | | 394 |
| Intermediate 2-28f. 1-cyclohexyl-5-((4-hydroxypiperidin-4-yl)methyl)-1,5-dihydro-4H-pyrazolo[3,4-d]pyrimidin-4-one | 2-28 | | 332 |
| Intermediate 2-28g. 5-((4-hydroxypiperidin-4-yl)methyl)-1-(pyridin-3-yl)-1,5-dihydro-4H-pyrazolo[3,4-d]pyrimidin-4-one | 2-28 | | 327 |
| Intermediate 2-28h. 5-((4-hydroxypiperidin-4-yl)methyl)-1-(4-(methylsulfonyl)phenyl)-1,5-dihydro-4H-pyrazolo[3,4-d]pyrimidin-4-one | 2-28 | | 404 |
| Intermediate 2-28i. 5-((4-hydroxypiperidin-4-yl)methyl)-1-(pyridin-4-yl)-1,5-dihydro-4H-pyrazolo[3,4-d]pyrimidin-4-one | 2-28 | | 327 |
| Intermediate 2-28j. 1-(3,4-dichlorophenyl)-5-((4-hydroxypiperidin-4-yl)methyl)-1,5-dihydro-4H-pyrazolo[3,4-d]pyrimidin-4-one | 2-28 | | 394, 396 |
| Intermediate 2-28k. 5-((4-hydroxypiperidin-4-yl)methyl)-1-(3-(trifluoromethyl)phenyl)-1,5-dihydro-4H-pyrazolo[3,4-d]pyrimidin-4-one | 2-28 | | 394 |
| Intermediate 2-119a. 1-(4-chlorophenyl)-5-((4-hydroxypiperidin-4-yl)methyl)-1,5-dihydro-4H-pyrazolo[3,4-d]pyrimidin-4-one | 2-28 | | 360 |
| Intermediate 2-94. 5-[(4-hydroxypiperidin-4-yl)methyl]-1-(4-methoxyphenyl)-1H,4H,5H-pyrazolo[3,4-d]pyrimidin-4-one | 2-28 | | 356 |
| Intermediate 926aa. 5-((4-Hydroxypiperidin-4-yl)methyl)-1-(3- | 2-28 | (3-methoxyphenyl)hydrazine | 356 |

TABLE 12-continued

| Intermediate No.: | Procedure used in accordance with intermediate | Precursor Used | LCMS: (ESI) m/z [M + H] |
|---|---|---|---|
| methoxyphenyl)-1H-pyrazolo[3,4-d]pyrimidin-4(5H)-one, TFA salt | | hydrochloride salt | |
| Intermediate 2-93. 1-(3-bromo-4-fluorophenyl)-5-((4-hydroxypiperidin-4-yl)methyl)-1,5-dihydro-4H-pyrazolo[3,4-d]pyrimidin-4-one | 2-28 | Hydrazine was prepared according to the general procedure above | 422 |
| Intermediate 2-150. tert-butyl 4-hydroxy-4-([4-oxo-1-[4-(trifluoromethyl) phenyl]-1H,4H,5H-pyrazolo[3,4-d]pyrimidin-5-yl]methyl)piperidine-1-carboxylate | 2-29 | (4-(trifluoromethyl)phenyl)hydrazine | 494 |
| Intermediate 2-2c. tert-butyl 4-((1-(4-chlorophenyl)-4-oxo-1,4-dihydro-5H-pyrazolo[3,4-d]pyrimidin-5-yl)methyl)-4-hydroxypiperidine-1-carboxylate | 2-29 | 4-chlorophenyl hydrazine | 460 |
| Intermediate 2-181aa. 5-((4-Hydroxypiperidin-4-yl)methyl)-1-(2-methoxyphenyl)-1,5-dihydro-4H-pyrazolo[3,4-d]pyrimidin-4-one | 2-28 | (2-Methoxyphenyl)hydrazine hydrochloride | 356 |
| Intermediate 2-925aa. 1-(4-(4-chloro-1H-pyrazol-1-yl)phenyl)-5-((4-hydroxypiperidin-4-yl)methyl)-1H-pyrazolo[3,4-d]pyrimidin-4(5H)-one | 2-28 | 4-chloro-1-(4-hydrazinylphenyl)-1H-pyrazole | 426, 428 |
| Intermediate 2-859aa. 5-((4-hydroxypiperidin-4-yl)methyl)-1-(4-(methylthio)phenyl)-1,5-dihydro-4H-pyrazolo[3,4-d]pyrimidin-4-one | 2-28 | (4-(methylthio)phenyl) hydrazine hydrochloride, prepared according to procedure used for intermediate 2-28 utilizing (4-(methylthio)phenyl)aniline as starting material | 371 |
| Intermediate 2-815a. 5-((4-hydroxypiperidin-4-yl)methyl)-1-(3-nitrophenyl)-1H-pyrazolo[3,4-d]pyrimidin-4(5H)-one | 2-28 | 3-nitrophenyl hydrazine hydrochloride | 370 |
| Intermediate 2-817a. 5-((4-hydroxypiperidin-4-yl)methyl)-1-(4-nitrophenyl)-1H-pyrazolo[3,4-d]pyrimidin-4(5H)-one | 2-28 | 4-nitrophenyl hydrazine hydrochloride | 370 |
| Intermediate 2-678a. 1-(4-Bromo-3-methoxyphenyl)-5-[(4-hydroxypiperidin-4-yl) methyl]-1H,4H,5H-pyrazolo[3,4-d]pyrimidin-4-one | 2-28 | (4-bromo-3-methoxyphenyl)hydrazine prepared from 4-bromo-3-methoxyaniline | 434, 436 |
| Intermediate 2-533a. 1-(4-ethylphenyl)-5-((4-hydroxypiperidin-4-yl)methyl)-1H-pyrazolo [3,4-d]pyrimidin-4(5H)-one | 2-28 | (4-ethylphenyl)hydrazine hydrochloride prepared from 4-ethylaniline | 353 |
| Intermediate 2-535a. 1-(4-cyclopropylphenyl)-5-[(4-hydroxypiperidin-4-yl)methyl]-1H,4H,5H-pyrazolo[3,4-d]pyrimidin-4-one | 2-28 | (4-cyclopropylphenyl)hydrazine hydrochloride prepared from 4-cyclopropylaniline | 365 |
| Intermediate 2-329a. 5-[(4-hydroxypiperidin-4-yl)methyl]-1-(1-methyl-1H-pyrazol-4-yl)-1H,5H-pyrazolo[3,4-d]pyrimidin-4-one | 228 | 4-hydrazinyl-1-methyl-1H-pyrazole | 329 |
| Intermediate 2-331a. 1-(1-cyclopropyl-1H-pyrazol-4-yl)-5-((4-hydroxypiperidin-4-yl)methyl)-1,5-dihydro-4H-pyrazolo[3,4-d]pyrimidin-4-one | 2-28 | 1-cyclopropyl-4-hydrazinyl-1H-pyrazole | 355 |
| Intermediate 2-330a. 5-((4-hydroxypiperidin-4-yl)methyl)-1-(1-phenyl-1H-pyrazol-4-yl)-1,5-dihydro-4H-pyrazolo[3,4-d]pyrimidin-4-one | 2-28 | 4-hydrazinyl-1-phenyl-1H-pyrazole | 391 |
| Intermediate 2-320aa. 1-(3-bromo-4-chlorophenyl)-5-((4-hydroxypiperidin-4-yl)methyl)-1,5-dihydro-4H-pyrazolo[3,4-d]pyrimidin-4-one | 2-28 | (3-bromo-4-chlorophenyl)hydrazine HCl | 437, 439 |
| Intermediate 2-258ba. 1-(3-bromo-4-fluorophenyl)-5-((4-hydroxypiperidin-4- | 2-28 | 3-bromo-4-fluorophenylhydrazine | 422, 424 |

TABLE 12-continued

| Intermediate No.: | Procedure used in accordance with intermediate | Precursor Used | LCMS: (ESI) m/z [M + H] |
|---|---|---|---|
| yl)methyl)-1,5-dihydro-4H-pyrazolo[3,4-d]pyrimidin-4-one | | HCl | |
| Intermediate 2-256. 1-(4-fluoro-3-methoxyphenyl)-5-((4-hydroxypiperidin-4-yl)methyl)-1,5-dihydro-4H-pyrazolo[3,4-d]pyrimidin-4-one | 2-28 | 3-methoxy-4-fluorophenylhydrazine HCl | 373 |
| Intermediate 2-252A. 1-(6-fluoropyridin-3-yl)-5-((4-hydroxypiperidin-4-yl)methyl)-1,5-dihydro-4H-pyrazolo[3,4-d]pyrimidin-4-one | 2-28 | 2-fluoro-5-hydrazinylpyridine HCl | 344 |

Example 22: Intermediate 2-922a. 1-[3-(3-fluoro-1H-pyrazol-1-yl)phenyl]-5-[(4-hydroxypiperidin-4-yl)methyl]-1H,4H,5H-pyrazolo[3,4-d]pyrimidin-4-one, TFA salt

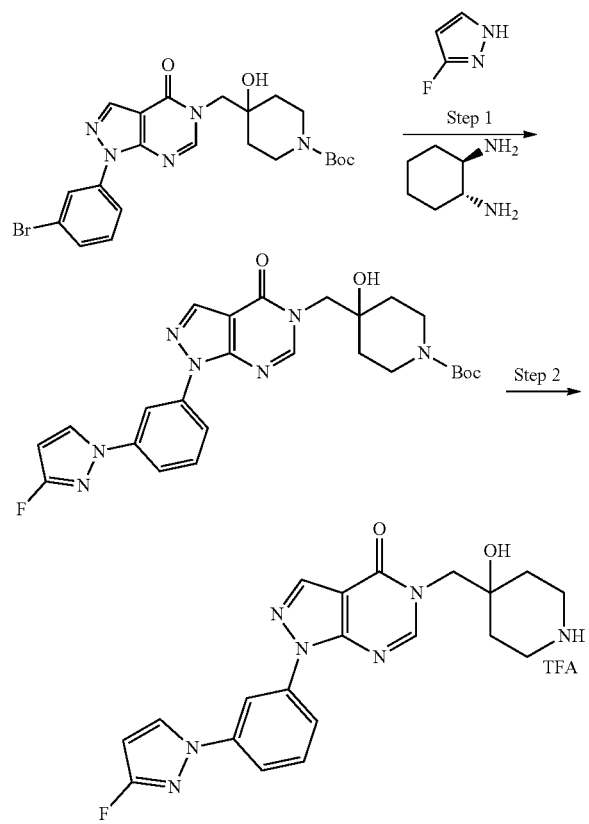

Step 1. Tert-butyl 4-([1-[3-(3-fluoro-1H-pyrazol-1-yl)phenyl]-4-oxo-1H,4H,5H-pyrazolo[3,4-d]pyrimidin-5-yl]methyl)-4-hydroxypiperidine-1-carboxylate A 50-mL 3-necked round-bottom fitted with a nitrogen balloon, magnetic stir bar condenser and thermometer was charged with tert-butyl 4-[[1-(3-bromophenyl)-4-oxo-1H,4H,5H-pyrazolo[3,4-d]pyrimidin-5-yl]methyl]-4-hydroxypiperidine-1-carboxylate (Intermediate 30a, 294 mg, 0.58 mmol), 1,4-dioxane (10 mL), 3-fluoro-1H-pyrazole (100 mg, 1.16 mmol), CuI (5.7 mg, 0.03 mmol), potassium carbonate (248 mg, 1.79 mmol) and (1R,2R)-cyclohexane-1,2-diamine (17 mg, 0.15 mmol) The resulting mixture was stirred for 16 h at 100° C. under nitrogen. After cooling to 25° C., the reaction was quenched with water (10 mL). The product was extracted with ethyl acetate (3×20 mL). The combined organic layers were dried over anhydrous sodium sulfate, filtered and concentrated under vacuum. The residue was purified by column chromatography eluting with dichloromethane/ethyl acetate (5:1-2:1, v/v) to give tert-butyl 4-([1-[3-(3-fluoro-1H-pyrazol-1-yl)phenyl]-4-oxo-1H,4H,5H-pyrazolo[3,4-d]pyrimidin-5-yl]methyl)-4-hydroxypiperidine-1-carboxylate (100 mg, 34%). LCMS: (ES) m/z 510 [M+H]

Step 2. 1-[3-(3-fluoro-1H-pyrazol-1-yl)phenyl]-5-[(4-hydroxypiperidin-4-yl)methyl]-1H,4H,5H-pyrazolo[3,4-d]pyrimidin-4-one, TFA salt The title compound was prepared according to procedure outlined in Example 2, utilizing tert-butyl-4-([1-[3-(3-fluoro-1H-pyrazol-1-yl)phenyl]-4-oxo-1H,4H,5H-pyrazolo[3,4-d]pyrimidin-5-yl]methyl)-4-hydroxypiperidine-1-carboxylate (Step 1, 100 mg, 0.20 mmol), as starting material (110 mg, >95%). LCMS: (ES) m/z 410 [M+H].

The Intermediate below was synthesized according to the general procedure outlined above in Example 22.

TABLE 13

| Intermediate No.: | Precursor Used | LCMS: (ESI, m/z) [M + H]+ |
|---|---|---|
| Intermediate 923a. 5-((4-hydroxypiperidin-4-yl)methyl)-1-(4-(4-(trifluoromethyl)-1H-pyrazol-1-yl)phenyl)-1,5-dihydro-4H-pyrazolo[3,4-d]pyrimidin-4-one | Intermediate 29-xa tert-butyl 4-((1-(4-bromophenyl)-4-oxo-1,4-dihydro-5H-pyrazolo[3,4-d]pyrimidin-5-yl)methyl)-4-hydroxypiperidine-1-carboxylate and 4-(trifluoromethyl)-1H-pyrazole | 557 |

Example 23: Intermediate 926a. 5-((4-Hydroxy-1-(1-methylcyclopropanecarbonyl) piperidin-4-yl)methyl)-1-(3-hydroxyphenyl)-1H-pyrazolo[3,4-d]pyrimidin-4(5H)-one

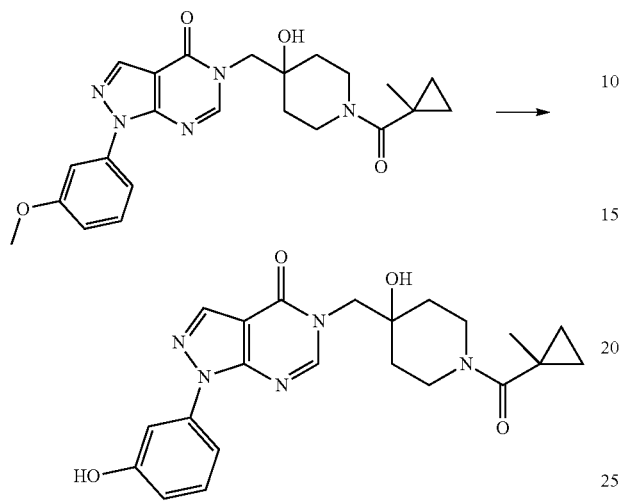

A 50-mL 3-necked round-bottom fitted with a nitrogen balloon, magnetic stir bar and thermometer was charged with 5-([4-hydroxy-1-[(1-methylcyclopropyl)carbonyl]piperidin-4-yl]methyl)-1-(3-methoxyphenyl)-1H,4H,5H-pyrazolo[3,4-d]pyrimidin-4-one (prepared according to procedure outlined in Example 6, utilizing 5-[(4-hydroxypiperidin-4-yl)methyl]-1-(3-methoxyphenyl)-1H, 4H,5H-pyrazolo[3,4-d]pyrimidin-4-one Intermediate 926aa, and 1-methylcyclopropane-1-carboxylic acid)(800 mg, 1.74 mmol) and dichloromethane (5 mL). To the reaction was added boron tribromide in dichloromethane (8.69 mL, 8.69 mmol, 1 M) dropwise with stirring at −50° C. After addition, the resulting solution was stirred for 16 h at 25° C. The reaction was quenched with water (20 mL). The product was extracted with dichloromethane (3×30 mL) and the organic layers were combined, dried over anhydrous sodium sulfate and concentrated under vacuum to afford 5-([4-hydroxy-1-[(1-methylcyclopropyl)carbonyl]piperidin-4-yl]methyl)-1-(3-hydroxyphenyl)-1H,4H,5H-pyrazolo[3,4-d]pyrimidin-4-one as a light yellow solid (620 mg, 84%). LCMS: (ESI) m/z 424[M+H].

Example 24: Intermediate 2-33. 1-(3-(Hydroxymethyl)phenyl)-5-((4-hydroxypiperidin-4-yl)methyl)-1,5-dihydro-4H-pyrazolo[3,4-d]pyrimidin-4-one trifluoroacetic acid salt

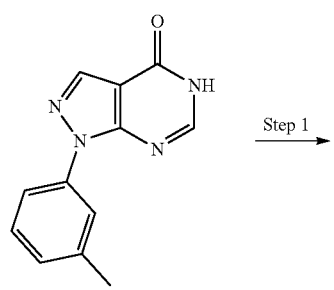

Step 1

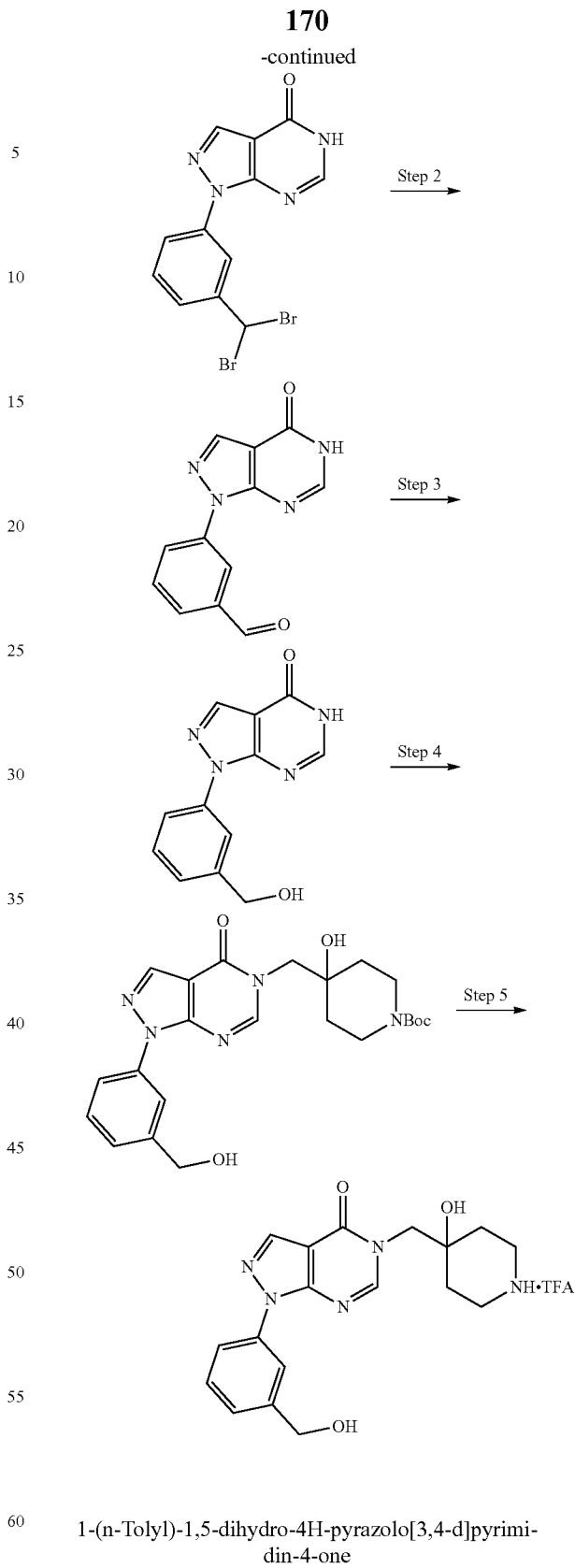

1-(n-Tolyl)-1,5-dihydro-4H-pyrazolo[3,4-d]pyrimidin-4-one

The title compound was prepared according to the procedure outlined in Example 21, Step 1 to Step 3, utilizing (3-methylphenyl)hydrazine hydrogen chloride as starting material (7.27 g, 64%). LCMS: (ESI) m/z 227 [M+H].

Step 1. 1-(3-(Dibromomethyl)phenyl)-1,5-dihydro-4H-pyrazolo[3,4-d]pyrimidin-4-one 1-(m-Tolyl)-1,5-dihydro-4H-pyrazolo[3,4-d]pyrimidin-4-one (500 mg, 2.21 mmol), benzoyl peroxide (268 mg, 1.05 mmol), N-bromosuccinimide (473 mg, 2.66 mmol) and carbon tetrachloride (50 mL) were added to a 100-mL round-bottom flask fitted with a nitrogen inlet, magnetic stir bar and condenser. The resulting solution was stirred for 16 h at 100° C. The resulting mixture was concentrated under vacuum to give 1-(3-(dibromomethyl)phenyl)-1,5-dihydro-4H-pyrazolo[3,4-d]pyrimidin-4-one which was used in next step without further purification. LCMS: (ESI) nm/383, 385, 387 [M+H].

Step 2. 3-(4-Oxo-4,5-dihydro-1H-pyrazolo[3,4-d]pyrimidin-1-yl)benzaldehyde 1-(3-(Dibromomethyl)phenyl)-1,5-dihydro-4H-pyrazolo[3,4-d]pyrimidin-4-one (Step 1, 800 mg, 2.08 mmol), calcium carbonate (10.0 g), 1,4-dioxane (50 mL) and water (50 mL) were added to a 250-mL round-bottom flask fitted with a nitrogen inlet, magnetic stir bar and condenser. The resulting solution was heated to reflux for 2 h. The solids were filtered and the filtrate was concentrated under vacuum to give 3-(4-oxo-4,5-dihydro-1H-pyrazolo[3,4-d]pyrimidin-1-yl)benzaldehyde which was used in next step without further purification. LCMS: (ESI) m/z 241 [M+H].

Step 3. 1-(3-(Hydroxymethyl)phenyl)-1,5-dihydro-4H-pyrazolo[3,4-d]pyrimidin-4-one 3-(4-Oxo-4,5-dihydro-1H-pyrazolo[3,4-d]pyrimidin-1-yl)benzaldehyde (Step 2, 500 mg, 2.08 mmol), methanol (30 mL) and sodium borohydride (70 mg, 1.85 mmol, 0.89 equiv) were added to a 100-mL round-bottom flask fitted with a nitrogen inlet, magnetic stir bar and condenser. The resulting solution was stirred for 2 h at room temperature and then concentrated under vacuum. The residue was purified by preparative TLC with dichloromethane/methanol (5:1 v/v) to provide 1-(3-(hydroxymethyl)phenyl)-1,5-dihydro-4H-pyrazolo[3,4-d]pyrimidin-4-one (120 mg, 24%), LCMS: (ESI) m/z 243 [M+H]

Step 4. tert-Butyl 4-hydroxy-4-((1-(3-(hydroxymethyl)phenyl)-4-oxo-1,4-dihydro-5H-pyrazolo[3,4-d]pyrimidin-5-yl)methyl)piperidine-1-carboxylate The title compound was prepared according to the procedure described in Example 21, Step 4, utilizing 1-(3-(hydroxymethyl)phenyl)-1,5-dihydro-4H-pyrazolo[3,4-d]pyrimidin-4-one (Step 3, 300 mg, 1.24 mmol) as starting material followed by purification by preparative TLC with dichloromethane/methanol (20:1 v/v) (80 mg, 14%). LCMS: (ESI) m/z 456 [M+H].

Step 5. 1-(3-(Hydroxymethyl)phenyl)-5-((4-hydroxypiperidin-4-yl)methyl)-1,5-dihydro-4H-pyrazolo[3,4-d]pyrimidin-4-one trifluoroacetic acid salt The title compound was prepared according to the procedure described in Example 21, Step 4, utilizing tert-Butyl 4-hydroxy-4-((1-(3-(hydroxymethyl)phenyl)-4-oxo-1,4-dihydro-5H-pyrazolo[3,4-d]pyrimidin-5-yl)methyl)piperidine-1-carboxylate as starting material (Step 4, 80 mg, 0.18 mmol and was used without further purification. LCMS: (ESI) m/z 356 [M+H]

Example 25: Intermediate 925a. 4-chloro-1-(4-hydrazinylphenyl)-1H-pyrazole, HCl salt

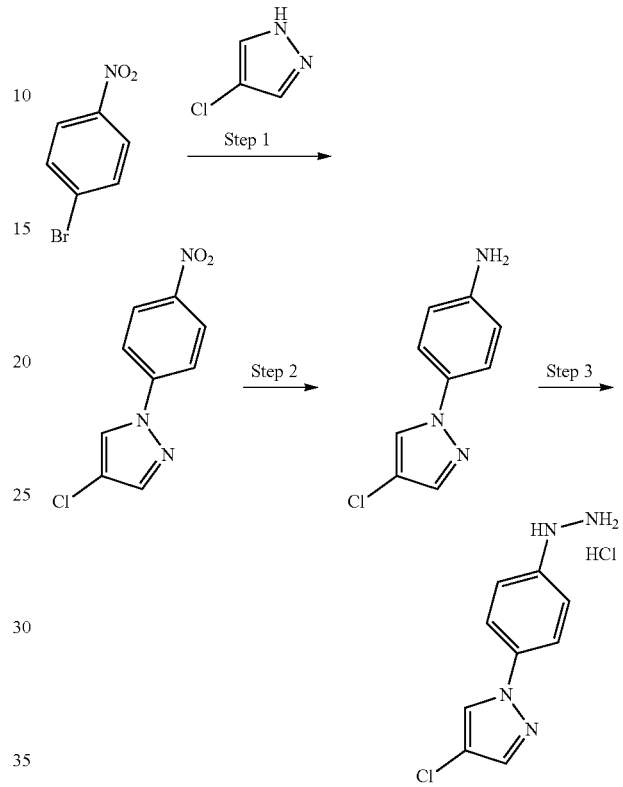

Step 1. 4-Chloro-1-(4-nitrophenyl)-1H-pyrazole

A 250-mL 3-necked round-bottom fitted with a magnetic stir bar condenser and thermometer was charged with 4-chloro-1H-pyrazole (3 g, 29 mmol), N,N-dimethylformamide (80 mL), 1-fluoro-4-nitrobenzene (4 g, 28.4 mmol) and cesium carbonate (27.8 g, 85.3 mmol). The resulting mixture was stirred for 1 h at 110° C. After cooling to 23° C., the reaction was quenched with water (150 mL). The solids were collected by filtration, washed with water (50 mL) and dried in an oven to afford 4-chloro-1-(4-nitrophenyl)-1H-pyrazole as a light yellow solid (6.2 g, 96%). LCMS: (ESI) m/z 224, 226 [M+H].

Step 2. 4-(4-chloro-1H-pyrazol-1-yl)benzenamine

A 100-mL 3-necked round-bottom fitted with a magnetic stir bar condenser and thermometer was charged with 4-chloro-1-(4-nitrophenyl)-1H-pyrazole (Step 1, 3 g, 13.4 mmol), ethanol (10 mL), water (10 mL), iron (2.5 g, 44.8 mmol), ammonium chloride (2.1 g, 39.3 mmol) and tetrahydrofuran (10 mL). The resulting mixture was stirred for 1 h at 80° C. After cooling to 23° C., the solids were removed by filtration and the filtrate was concentrated under vacuum. The residue was diluted with water (100 mL) and the resulting mixture was extracted with ethyl acetate (3×100 mL). The combined organic layers were washed with brine (100 mL), dried over anhydrous sodium sulfate, filtered and concentrated under vacuum to afford 4-chloro-1-(4-nitrophenyl)-1H-pyrazole as a light yellow solid (2.0 g, 77%). LCMS: (ESI) m/z 194, 196 [M+H].

Step 3.
4-chloro-1-(4-hydrazinylphenyl)-1H-pyrazole, hydrochloride salt

A 100-mL 3-necked round-bottom fitted with a magnetic stir bar and thermometer was charged with 4-(4-chloro-1H-pyrazol-1-yl)aniline (Step 2, 2.0 g, 10.33 mmol), hydrochloric acid (12 N, 20 mL) and ethanol (10 mL). The resulting solution was cooled to −20° C. followed by sodium nitrite (1.06 g, 15.4 mmol) in water (5 mL) added dropwise with stirring at −20° C. After the mixture was stirred for 0.5 h at −10° C., tin(II) chloride (4.6 g, 20.4 mmol) was added in portions at −10° C. The resulting solution was then stirred for additional 0.5 h at −10° C. The solids were collected by filtration and dried in an oven to afford the HCl salt of 4-chloro-1-(4-hydrazinylphenyl)-1H-pyrazole (800 mg crude, 32%). LCMS: (ESI) m/z 209, 211 [M+H].

The Intermediates in Table 14 were prepared according to the procedures outlined in Example 25.

TABLE 14

| Intermediate No.: | Precursor Used (Step 2 and Step 3 for the synthesis) | LCMS: (ESI, m/z) [M + H]+ |
|---|---|---|
| Intermediate 2-1329. 4-hydrazinyl-1-methyl-1H-pyrazole, HCl salt | 1-methyl-4-nitro-1H-pyrazole | 113 |
| Intermediate 2-330a 4-hydrazinyl-1-phenyl-1H-pyrazole, HCl salt | 1-phenyl-4-nitro-1H-pyrazole | 175 |
| Intermediate 2-331a. 1-cyclopropyl-4-hydrazinyl-1H-pyrazole, HCl salt | 1-cyclopropyl-4-nitro-1H-pyrazole | 139 |

Example 26. Intermediate 2-35.
4-(1,1,1-Trifluoro-2-hydroxypropan-2-yl)benzoic acid

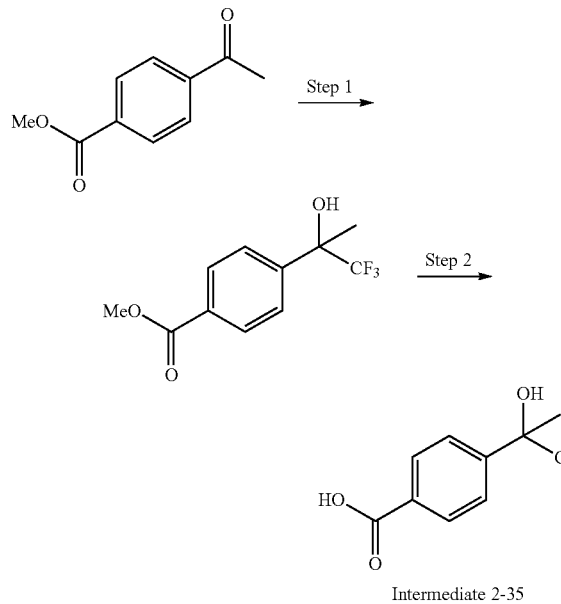

Intermediate 2-35

Step 1. Methyl 4-(1,1,1-trifluoro-2-hydroxypropan-2-yl)benzoate

Methyl 4-acetylbenzoate (1.00 g, 5.61 mmol), tetrahydrofuran (50 mL), tetrabutylammonium fluoride (1.0 M in tetrahydrofuran, 33 mL), and trimethyl(trifluoromethyl)silane (2.40 g, 16.9 mmol) were added to a 250-mL round-bottom flask at 0° C. The resulting solution was stirred for 16 h at room temperature. Brine (10 mL) was added and the mixture was extracted with ethyl acetate (3×20 mL). The organic layers were combined, dried over anhydrous sodium sulfate, filtered and concentrated under vacuum. The residue was purified by column chromatography eluting with ethyl acetate/petroleum ether (15:85 v/v) to give methyl 4-(1,1,1-trifluoro-2-hydroxypropan-2-yl)benzoate (850 mg, 53%). LCMS: (ESI) m/z 249 [M+H].

Step 2.
4-(1,1,1-Trifluoro-2-hydroxypropan-2-yl)benzoic acid

Methyl 4-(1,1,1-trifluoro-2-hydroxypropan-2-yl)benzoate (Step 1, 450 mg, 1.81 mmol), methanol (30 mL), lithium hydroxide (228 mg, 5.43 mmol) and water (10 mL) were added to a 100-mL round-bottom flask. The resulting solution was stirred for 2 h at 60° C. and then concentrated under vacuum. The pH value of the solution was adjusted to 4 with hydrogen chloride (1.0 M aqueous). The solution was then extracted with dichloromethane (3×10 mL) and the organic layers were combined, dried over anhydrous sodium sulfate, filtered and concentrated under vacuum to give 4-(1,1,1-trifluoro-2-hydroxypropan-2-yl)benzoic acid (Intermediate 2-35) which was used without further purification. LCMS: (ESI) m/z 233 [M−H].

Example 27: Intermediate 2-36. Phenyl(1-oxa-6-azaspiro[2.5]octan-6-yl)methanone

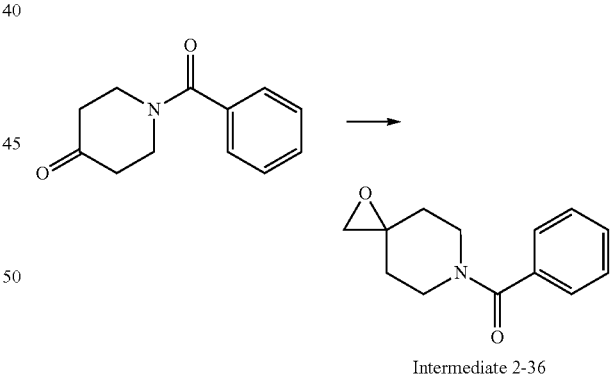

Intermediate 2-36

Trimethylsulfoxonium iodide (11.2 g, 51.0 mmol), dimethyl sulfoxide (15 mL) and sodium hydride (60% in mineral oil, 157 mg, 6.54 mmol) were added to a 50-mL round-bottom flask fitted with a magnetic stir. The resulting mixture was stirred for 30 min at room temperature. 1-benzoylpiperidin-4-one (500 mg, 2.18 mmol) was added and the resulting solution was stirred at room temperature for 4 h The reaction was quenched by the addition of water (30 mL) and extracted with dichloromethane (3×30 mL). The organic layers were combined, dried over anhydrous sodium sulfate, filtered and concentrated under vacuum. The residue was purified by column chromatography using ethyl acetate to afford phenyl(1-oxa-6-azaspiro[2.5]octan-6-yl)methanone (Intermediate 2-36, 2.00 g, 54%). LCMS: (ESI) m/z 218 [M+H].

The Intermediates in Table 15 were prepared according to a procedure similar to that outlined in Example 27.

TABLE 15

| Intermediate No.: | Precursor Used | LCMS: (ESI) m/z [M + H] |
| --- | --- | --- |
| Intermediate 2-46. (4-Fluorophenyl)(1-oxa-6-azaspiro[2.5]octan-6-yl)methanone | 1-(4-Fluorobenzoyl)piperidin-4-one | 236 |
| Intermediate 2-619a. 6-cyclopropanecarbonyl-1-oxa-6-azaspiro[2.5]octane | 1-(cyclopropanecarbonyl)piperidin-4-one | 181 |

Example 28: Intermediate 2-40. 3-(3-((1-(4-Fluorobenzoyl)-4-hydroxypiperidin-4-yl)methyl)-4-oxo-3,4-dihydro-7H-pyrrolo[2,3-d]pyrimidin-7-yl)benzonitrile

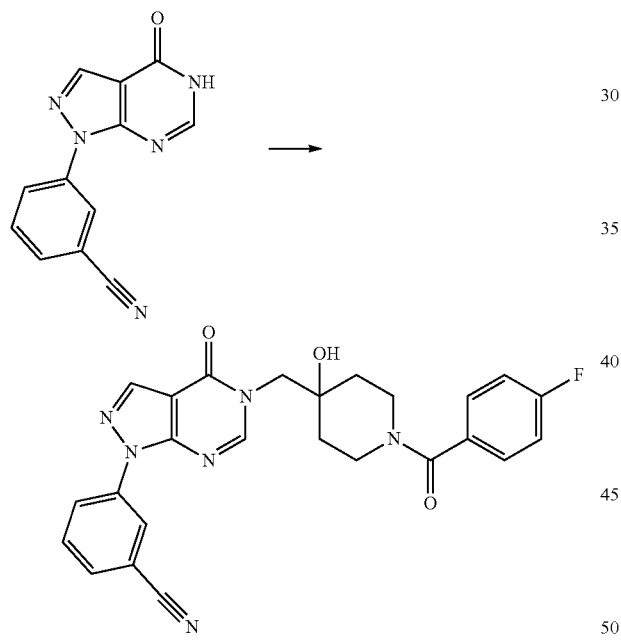

3-(4-Oxo-3,4-dihydro-7-pyrrolo[2,3-d]pyrimidin-7-yl) benzonitrile (prepared from pyrrolo[2,3-d]pyrimidine and 3-cyanophenylboronic acid) (180 mg, 0.76 mmol), (4-fluorophenyl)(1-oxa-6-azaspiro[2.5]octan-6-yl)methanone (Intermediate 2-46, 180 mg, 0.77 mmol), cesium carbonate (745 mg, 2.29 mmol) and DMF (10 mL) were added to a 100-mL round-bottom flask fitted with a magnetic stir bar and condenser. The resulting solution was stirred for 90 min at 80° C. and then quenched by the addition of water (30 mL). The resulting solution was extracted with ethyl acetate (4×40 mL) and the organic layers were combined, dried over anhydrous sodium sulfate, filtered and concentrated under reduced pressure to afford the title compound which was used without further purification. LCMS: (ESI) m/z 472 [M+H].

Example 29: Intermediate 2-112. 1-(4-fluorophenyl)-5-((4-hydroxypiperidin-4-yl)methyl)-1H-pyrazolo[3,4-d]pyrimidin-4(5H)-one Trifluoroacetic acid salt

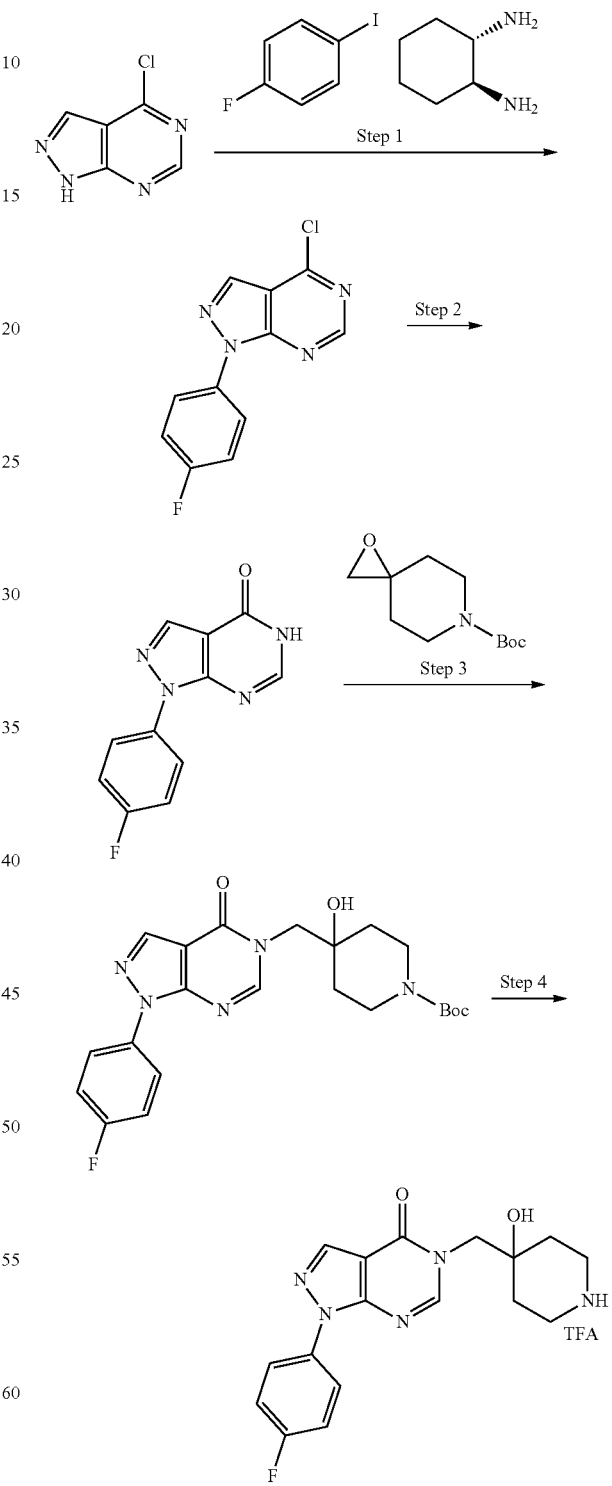

Intermediate 2-112

Step 1. 4-Chloro-7-(4-fluorophenyl)-7H-pyrrolo[2,3-d]pyrimidine

A 100-mL 3-necked round-bottom flask fitted with a nitrogen inlet, magnetic stir bar, condenser and thermometer was charged with 4-chloro-7H-pyrrolo[2,3-d]pyrimidine (2 g, 13.0 mmol), 1-fluoro-4-iodobenzene (3.3 g, 14.9 mmol), potassium carbonate (3.58 g, 25.9 mmol), 1,4-dioxane (40 mL), (1R,2R)-cyclohexane-1,2-diamine (300 mg, 2.63 mmol) and cuprous iodide (493 mg, 2.59 mmol). The resulting solution was stirred 16 h at 110° C. in an oil bath under nitrogen. After cooling to 25° C., the solids were removed by filtration and the filtrate was concentrated under vacuum. The residue was purified by column chromatography eluting with ethyl acetate/petroleum ether (1:2, v/v) to afford 4-chloro-7-(4-fluorophenyl)-7H-pyrrolo[2,3-d]pyrimidine as a light yellow solid (1.0 g, 31%). LCMS: (ESI) m/z 248, 250 [M+H].

Step 2. 7-(4-Fluorophenyl)-3H-pyrrolo[2,3-d]pyrimidin-4(7H)-one

A 100-mL 3-necked round-bottom flask fitted with a magnetic stir bar, condenser and thermometer was charged with 4-chloro-7-(4-fluorophenyl)-7H-pyrrolo[2,3-d]pyrimidine (Step 1, 800 mg, 3.23 mmol), 1,4-dioxane (10 mL, 118.0 mmol), water (50 mL), potassium carbonate (4.2 g, 30.4 mmol) and 1,4-diazabicyclo[2.2.2]octane (727 mg, 6.48 mmol). The resulting solution was stirred for 3 h at 80° C. in an oil bath. After cooling to 25° C., the reaction was quenched with water (70 mL). The product was extracted with ethyl acetate (3×50 mL) The combined organic layers were dried over anhydrous sodium sulfate, filtered and concentrated under vacuum to afford 7-(4-fluorophenyl)-3H,4H,7H-pyrrolo[2,3-d]pyrimidin-4-one as a white solid (700 mg, 94%). LCMS: (ESI) m/z 230 [M+H].

Step 3. tert-butyl 4-((7-(4-fluorophenyl)-4-oxo-4H-pyrrolo[2,3-d]pyrimidin-3(7H)-yl)methyl)-4-hydroxypiperidine-1-carboxylate Title compound (500 mg, 43%). was prepared according to the procedure outline in Example 21, Step 4, utilizing 7-(4-fluorophenyl)-3H,4H,7H-pyrrolo[2,3-d]pyrimidin-4-one (Step 2, 600 mg, 2.62 mmol) as starting material followed by column chromatography purification eluting with methanol/dichloromethane (1:20, v/v) LCMS: (ESI) m/z 443 [M+H].

Step 4. 7-(4-fluorophenyl)-3-((4-hydroxypiperidin-4-yl)methyl)-3H-pyrrolo[2,3-d]pyrimidin-4(7H)-one Trifluoroacetic acid salt Title compound (470 mg, 95%) was prepared according to the procedure outline in Example 21, Step 5, utilizing tert-butyl 4-[[7-(4-fluorophenyl)-4-oxo-3H,4H,7H-pyrrolo[2,3-d]pyrimidin-3-yl] methyl]-4-hydroxypiperidine-1-carboxylate (Step 3, 500 mg, 1.13 mmol) as starting material LCMS: (ESI) m/z 343 [M+H].

The Intermediate in Table 16 was prepared using a procedure similar to that outlined for Example 30.

TABLE 16

| Intermediate No.: | Precursor Used | LCMS: (ESI) m/z [M + H] |
|---|---|---|
| Intermediate 2-2100. 7-(5-fluoropyridin-2-yl)-3-((4-hydroxypiperidin-4-yl)methyl)-3,7-dihydro-4H-pyrrolo[2,3-d]pyrimidin-4-one | 4-chloro-7H-pyrrolo[2,3-d]pyrimidine and 2-bromo-5-fluoropyridine | 344 |

Example 31: Intermediate 2-2101. 3-((4-hydroxypiperidin-4-yl)methyl)-7-(3-(4-methylpiperazin-1-yl)phenyl)-3H-pyrrolo[2,3-d]pyrimidin-4(7H)-one, Trifluoroacetic acid salt

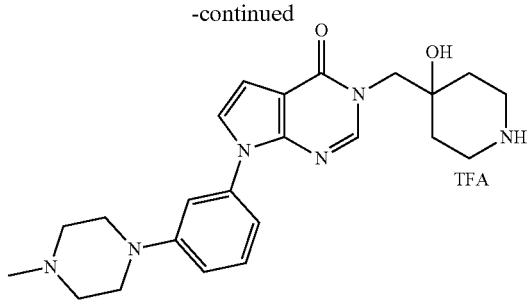

Step 1. 7-(3-Bromophenyl)-4-chloro-7H-pyrrolo[2,3-d]pyrimidine

A 250-mL round-bottom flask fitted with a magnetic stir bar was charged with 4-chloro-7H-pyrrolo[2,3-d]pyrimidine (2.0 g, 13.0 mmol), (3-bromophenyl)boronic acid (3.12 g, 15.5 mmol), cupric acetate (708 mg, 3.90 mmol), dichloromethane (60 mL) and pyridine (3.08 g, 38.94 mmol). The resulting solution was stirred for 5 h at 25° C. The solids were removed by filtration and the filtrate was concentrated under vacuum. The residue was diluted with water (50 mL) and the product was extracted with dichloromethane (5×40 mL). The combined organic layers were washed with hydrochloric acid (40 mL, 6N), dried over anhydrous sodium sulfate, filtered and concentrated under vacuum. The residue was purified by column chromatography eluting with ethyl acetate/petroleum ether (1:2, v/v) to give 7-(3-bromophenyl)-4-chloro-7H-pyrrolo[2,3-d]pyrimidine (2.0 g, 50%). LCMS: (ESI) m/z 308, 310, 312[M+H].

Step 2. 7-(3-Bromophenyl)-3H-pyrrolo[2,3-d]pyrimidin-4(7H)-one

A 250-mL 3-necked round-bottom flask fitted with a magnetic stir bar, condenser and thermometer was charged with 7-(3-bromophenyl)-4-chloro-7H-pyrrolo[2,3-d]pyrimidine (Step 1, 800 mg, 2.59 mmol), 1,4-diazabicyclo[2.2.2]octane (581 mg, 5.18 mmol), potassium carbonate (3.37 g, 24.4 mmol), 1,4-dioxane (20 mL) and water (40 mL). The resulting solution was stirred 16 h at 100° C. in an oil bath. After cooling to 25° C., the reaction was diluted with water (50 mL). The product was extracted with ethyl acetate (3×50 mL). The combined organic layers were dried over anhydrous sodium sulfate and concentrated under vacuum. The residue was purified by column chromatography eluting with ethyl acetate/petroleum ether (9:1, v/v) to give 7-(3-bromophenyl)-3H,4H,7H-pyrrolo[2,3-d]pyrimidin-4-one (600 mg, 80%). LCMS: (ESI) m/z 290, 292[M+H].

Step 3. Tert-butyl 4-((7-(3-bromophenyl)-4-oxo-4H-pyrrolo[2,3-d]pyrimidin-3(7H)-yl)methyl)-4-hydroxypiperidine-1-carboxylate A 100-mL 3-necked round-bottom flask fitted with a magnetic stir bar, condenser and thermometer was charged with 7-(3-bromophenyl)-3H,4H,7H-pyrrolo[2,3-d]pyrimidin-4-one (300 mg, 1.03 mmol), tert-butyl 1-oxa-6-azaspiro[2.5]octane-6-carboxylate (264 mg, 1.24 mmol), cesium carbonate (Step 2, 1.01 g, 3.10 mmol) and N,N-dimethylformamide (20 mL). The solution was stirred for 2 h at 80° C. in an oil bath. After cooling to 25° C., the reaction was quenched with water (50 mL). The product was extracted with ethyl acetate (5×30 mL). The combined organic layers were dried over anhydrous sodium sulfate, filtered and concentrated under vacuum to afford tert-butyl 4-[[7-(3-bromophenyl)-4-oxo-3H,4H,7H-pyrrolo[2,3-d]pyrimidin-3-yl]methyl]-4-hydroxypiperidine-1-carboxylate (230 mg). LCMS: (ESI) m/z 503, 505[M+H].

Step 4. Tert-butyl 4-hydroxy-4-((7-(3-(4-methylpiperazin-1-yl)phenyl)-4-oxo-4H-pyrrolo[2,3-d]pyrimidin-3(7H)-yl)methyl)piperidine-1-carboxylate A 100-mL 3-necked round-bottom flask fitted with a nitrogen balloon, magnetic stir bar, condenser and thermometer was charged with tert-butyl 4-[[7-(3-bromophenyl)-4-oxo-3H,4H,7H-pyrrolo[2,3-d]pyrimidin-3-yl]methyl]-4-hydroxypiperidine-1-carboxylate (Step 3, 170 mg, 0.34 mmol), 1-methylpiperazine (44.3 mg, 0.44 mmol), cesium carbonate (332.5 mg, 1.02 mmol), 1,4-dioxane (20 mL), tris(dibenzylideneacetone)dipalladium-chloroform adduct (35.2 mg, 0.03 mmol) and (+/−)-2,2'-bis(diphenylphosphino)-1,1'-binaphthyl (21 mg, 0.03 mmol). The resulting solution was stirred for 16 h at 110° C. in an oil bath under nitrogen. After cooling to 25° C., the solids were removed by filtration and the filtrate was diluted with water (100 mL). The product was extracted with ethyl acetate (3×30 mL). The organic layers were combined, dried over anhydrous sodium sulfate and concentrated under vacuum. The residue was purified by column chromatography eluting with dichloromethane/methanol (10:1, v/v) to give tert-butyl 4-hydroxy-4-([7-[3-(4-methylpiperazin-1-yl)phenyl]-4-oxo-3H,4H,7H-pyrrolo[2,3-d]pyrimidin-3-yl]methyl)piperidine-1-carboxylate (100 mg, 57%). LCMS: (ESI) m/z 523[M+H].

Step 5. 3-((4-hydroxypiperidin-4-yl)methyl)-7-(3-(4-methylpiperazin-1-yl)phenyl)-3H-pyrrolo[2,3-d]pyrimidin-4(7H)-one, TFA salt A 50-mL round-bottom flask fitted with a magnetic stir bar was charged with tert-butyl 4-hydroxy-4-([7-[3-(4-methylpiperazin-1-yl)phenyl]-4-oxo-3H,4H,7H-pyrrolo[2,3-d]pyrimidin-3-yl]methyl)piperidine-1-carboxylate (Step 4, 100 mg, 0.19 mmol), dichloromethane (10 mL) and trifluoroacetic acid (1 mL). The resulting solution was stirred for 3 h at 25° C. The resulting mixture was concentrated under vacuum to give the TFA salt of 3-[(4-hydroxypiperidin-4-yl)methyl]-7-[3-(4-methylpiperazin-1-yl)phenyl]-3H,4H,7H-pyrrolo[2,3-d]pyrimidin-4-one (130 mg, >95%). LCMS: (ESI) m/z 423[M+H].

The Intermediates in Table 17 were prepared using a procedure similar to that outlined for Example 31 and isolated as TFA salts.

TABLE 17

| Intermediate No.: | Precursor Used | LCMS: (ESI) m/z [M + H] |
|---|---|---|
| Intermediate 2-2102: 7-(4-fluorophenyl)-3-((4-hydroxypiperidin-4-yl)methyl)-6-methyl- | 4-chloro-6-methyl-7H-pyrrolo[2,3-d]pyrimidine and (4- | 357 |

TABLE 17-continued

| Intermediate No.: | Precursor Used | LCMS: (ESI) m/z [M + H] |
|---|---|---|
| 3,7-dihydro-4H-pyrrolo[2,3-d]pyrimidin-4-one | Fluorophenyl)boronic acid. Synthesis does not include step 4 | |
| Intermediate 2-2103: 3-((4-hydroxypiperidin-4-yl)methyl)-7-(3-morpholinophenyl)-3,7-dihydro-4H-pyrrolo[2,3-d]pyrimidin-4-one | 4-chloro-7H-pyrrolo[2,3-d]pyrimidine, 3-bromoboronic acid and morpholine | 410 |
| Intermediate 2-2105: 3-((4-hydroxypiperidin-4-yl)methyl)-7-(4-morpholinophenyl)-3,7-dihydro-4H-pyrrolo[2,3-d]pyrimidin-4-one | 4-chloro-7H-pyrrolo[2,3-d]pyrimidine, 4-bromoboronic acid and morpholine | 410 |
| Intermediate 872a. 3-((4-hydroxypiperidin-4-yl)methyl)-7-(3-(piperidin-1-ylmethyl)phenyl)-3H-pyrrolo[2,3-d]pyrimidin-4(7H)-one | 4-chloro-7H-pyrrolo[2,3-d]pyrimidine and (3-formylphenyl)boronic acid.* | 422 |
| Intermediate 2-2105: 7-(4-fluoro-3-(piperidin-1-ylmethyl)phenyl)-3-((4-hydroxypiperidin-4-yl)methyl)-3,7-dihydro-4H-pyrrolo[2,3-d]pyrimidin-4-one | 4-chloro-7H-pyrrolo[2,3-d]pyrimidine and (3-formyl-4-fluorophenyl)boronic acid.* | 440 |

*Introduction of piperidine was achieved under reductive amination conditions when a solution of 3-(4-chloro-7H-pyrrolo[2,3-d]pyrimidin-7-yl)benzaldehyde Intermediate (600 mg, 2.33 mmol), piperidine (198 mg, 2.33 mmol), dichloromethane (50 mL), and glacial acetic acid (0.2 mL) was treated with sodium cyanoborohydride (294 mg, 4.68 mmol) at 0° C.

Example 32: Intermediate 2-47. 3-((1-(4-Fluorobenzoyl)-4-hydroxypiperidin-4-yl)methyl)-7-(piperidin-4-yl)-3,7-dihydro-4H-pyrrolo[2,3-d]pyrimidin-4-one trifluoroacetic acid salt

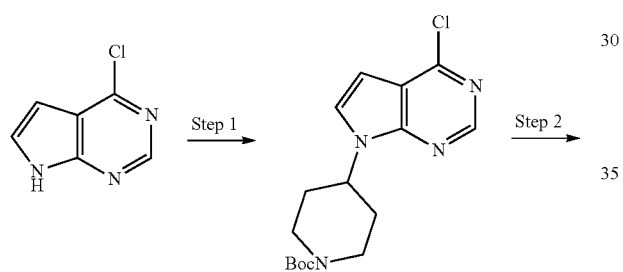

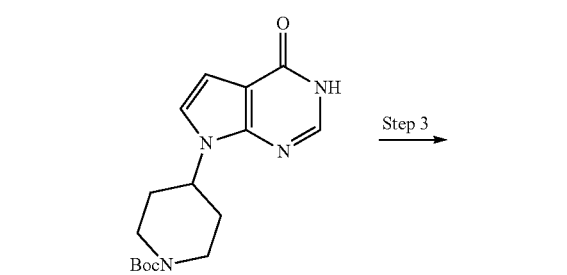

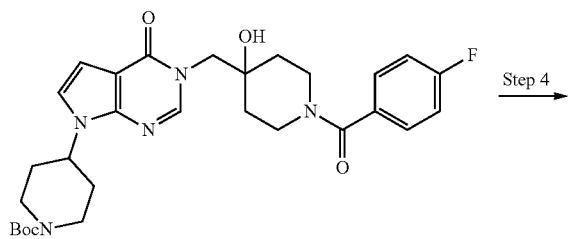

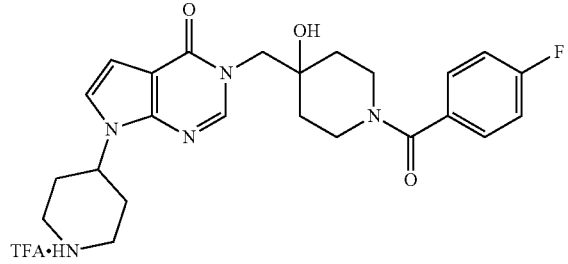

Intermediate 2-47

Step 1. tert-Butyl 4-(4-chloro-7H-pyrrolo[2,3-d]pyrimidin-7-yl)piperidine-1-carboxylate 4-Chloro-7H-pyrrolo[2,3-d]pyrimidine (2.00 g, 13.0 mmol), tert-butyl 4-hydroxypiperidine-1-carboxylate (7.80 g, 38.8 mmol), triphenylphosphine (4.52 g, 17.2 mmol) and tetrahydrofuran (120 mL) were added to a 500-mL 3-necked round-bottom flask fitted with a nitrogen inlet and magnetic stir bar. A solution of diethyl azodicarboxylate (6.80 g, 39.1 mmol) in toluene (30 mL) was then added dropwise with stirring at room temperature. The resulting solution was stirred for 4 h at room temperature, quenched by the addition of water (100 mL) and extracted with dichloromethane (3×100 mL). The organic layers were combined, dried over anhydrous sodium sulfate, filtered and concentrated under reduced pressure. The residue was purified by column chromatography using ethyl acetate/petroleum ether (1:1 v/v) to afford tert-butyl 4-(4-chloro-7H-pyrrolo[2,3-d]pyrimidin-7-yl)piperidine-1-carboxylate (2.50 g, 57%). LCMS: (ESI) m/z 337 [M+H].

Step 2. tert-Butyl 4-(4-oxo-3,4-dihydro-7H-pyrrolo[2,3-d]pyrimidin-7-yl)piperidine-1-carboxylate tert-Butyl 4-(4-chloro-7H-pyrrolo[2,3-d]pyrimidin-7-yl)piperidine-1-carboxylate (Step 1, 2.50 g, 7.42 mmol), DABCO (1.70 g, 15.2 mmol), potassium carbonate (10.2 g, 73.8 mmol), 1,4-dioxane (80 mL) and water (40 mL) were added to a 250-mL round-bottom flask fitted with a magnetic stir bar and condenser. The resulting solution was stirred for 4 h at 60° C., diluted with water (50 mL) and extracted with ethyl acetate (5×50 mL). The organic layers were combined, washed with brine (100 mL), dried over anhydrous sodium sulfate, filtered and concentrated under vacuum. The residue was purified by column chromatography using dichloromethane/methanol (10/1 v/v) to afford tert-butyl 4-(4-oxo-3,4-dihydro-7H-pyrrolo[2,3-d]pyrimidin-7-yl)piperidine-1-carboxylate (1.30 g, 55%). LCMS: (ESI) m/z 319 [M+H]

Step 3. tert-Butyl 4-(3-((1-(4-fluorobenzoyl)-4-hydroxypiperidin-4-yl)methyl)-4-oxo-3,4-dihydro-7H-pyrrolo[2,3-d]pyrimidin-7-yl)piperidine-1-carboxylate tert-butyl 4-(4-oxo-3,4-dihydro-7H-pyrrolo[2,3-d]pyrimidin-7-yl)piperidine-1-carboxylate (Step 2, 600 mg, 1.88 mmol), (4-fluorophenyl)(1-oxa-6-azaspiro[2.5]octan-6-yl)methanone (Intermediate 2-46, 300 mg, 1.28 mmol), cesium carbonate (1.25 g, 3.83 mmol) and DMF (50 mL) were added to a 100-mL round-bottom flask fitted with a magnetic stir bar and condenser. The resulting solution was stirred for 2 h at 80° C. and then quenched by the addition of water (30 mL). The resulting solution was extracted with ethyl acetate (4×50 mL) and the organic layers were combined, washed with brine (100 mL), dried over anhydrous sodium sulfate, filtered and concentrated under reduced pressure. The residue was purified by preparative TLC with methanol/dichloromethane (1:20 v/v) to afford tert-butyl 4-(3-((1-(4-fluorobenzoyl)-4-hydroxypiperidin-4-yl)methyl)-4-oxo-3,4-dihydro-7H-pyrrolo[2,3-d]pyrimidin-7-yl)piperidine-1-carboxylate (600 mg, 58%). LCMS: (ESI) m/z 554 [M+H].

Step 4. 3-((1-(4-Fluorobenzoyl)-4-hydroxypiperidin-4-yl)methyl)-7-(piperidin-4-yl)-3,7-dihydro-4H-pyrrolo[2,3-d]pyrimidin-4-one trifluoroacetic acid salt tert-Butyl 4-(3-((1-(4-fluorobenzoyl)-4-hydroxypiperidin-4-yl)methyl)-4-oxo-3,4-dihydro-7H-pyrrolo[2,3-d]pyrimidin-7-yl)piperidine-1-carboxylate (Step 3, 600 mg, 1.08 mmol), dichloromethane (30 mL) and trifluoroacetic acid (6 mL) were added to a 100-mL round-bottom flask fitted with a magnetic stir bar. The resulting solution was stirred for 2 h at room temperature and then concentrated under reduced pressure to give 3-((1-(4-fluorobenzoyl)-4-hydroxypiperidin-4-yl)methyl)-7-(piperidin-4-yl)-3,7-dihydro-4H-pyrrolo[2,3-d]pyrimidin-4-one trifluoroacetic acid salt (Intermediate 2-47) which was used in next step without further purification. LCMS: (ESI) m/z 454 [M+H].

Example 33: Intermediate 2-57. 4-(pyrrolidin-1-ylmethyl)benzoic acid

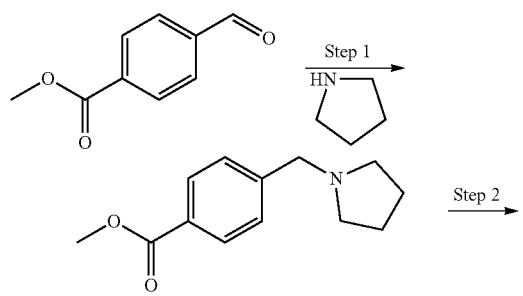

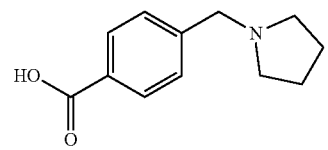

Intermediate 2-57

Step 1. Methyl 4-(pyrrolidin-1-ylmethyl)benzoate

A 250-mL round-bottom flask was charged with methyl 3-formylbenzoate (1 g, 6.09 mmol) pyrrolidine (433 mg, 6.09 mmol) and chloroform (100 mL). The resulting solution was stirred at 0° C. for 1 h. Sodium borohydride (70 mg, 1.85 mmol) and acetic acid (5 mL) were added to the mixture at 0° C. The resulting solution was stirred 16 h at 23° C. The pH of the solution was adjusted to 8 with saturated sodium bicarbonate solution (30 mL) and extracted with dichloromethane (3×100 mL). The organic layers were combined, dried over anhydrous sodium sulfate, filtered and concentrated under vacuum. The residue was purified by column chromatography eluting with ethyl acetate/petroleum ether (1:4 v/v) to afford methyl 4-(pyrrolidin-1-ylmethyl)benzoate (500 mg, 37%) as a colorless oil. LCMS: (ESI) m/z 220 [M+H].

Step 2. 3-(Pyrrolidin-1-ylmethyl)benzoic acid

A 100-mL round-bottom flask was charged with methyl 3-(pyrrolidin-1-ylmethyl) benzoate (500 mg, 2.28 mmol), methanol (20 mL), lithium hydroxide (274 mg, 11.44 mmol) and water (5 mL). The resulting solution was stirred for 1 h at 40° C. The pH of the solution was adjusted to 6 with hydrochloric acid (6.0 M). The solids were collected by filtration, washed with ethyl acetate (3×20 mL) and dried in an oven to afford 4-(pyrrolidin-1-ylmethyl)benzoic acid as a white solid which was used without further purification (Intermediate 2-57, 650 mg, >95%). LCMS (ESI) m/z 206 [M+H].

The Intermediates in Table 18 were synthesized according to the procedures above.

TABLE 18

| Intermediate No.: | Precursor Used | MS (ESI, m/z) [M + H]. |
|---|---|---|
| Intermediate 2-58. 4-(morpholinomethyl)benzoic acid | methyl 3-formylbenzoate and morpholine | 222 |
| Intermediate 2-176. 4-[(6-fluoropyridin-2-yl)amino]cyclohexane-1-carboxylic acid | ethyl 4-oxocyclohexane-1-carboxylate and 6-fluoropyridin-2-amine | 239 |

Example 34: Intermediate 2-59.
5-(Piperidin-1-yl)-1,3,4-oxadiazole-2-carboxylic acid

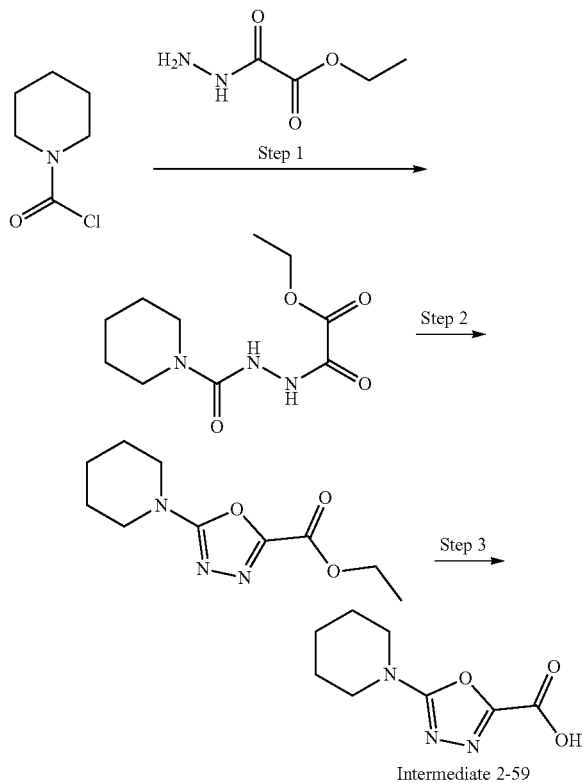

Intermediate 2-59

Step 1. Ethyl 2-oxo-2-(2-(piperidine-1-carbonyl)hydrazinyl)acetate

A 25-mL round-bottom flask was charged with piperidine-1-carbonyl chloride (178 mg, 1.21 mmol), ethyl (hydrazinecarbonyl)formate (132 mg, 1.00 mmol), triethylamine (152 mg, 1.50 mmol) and tetrahydrofuran (10 mL). The resulting solution was stirred 16 h at 60° C. The reaction was then quenched by the addition of 20 mL of water and extracted with dichloromethane (2×10 mL). The organic layers were combined and washed with water (10 mL) and brine (10 mL), dried over anhydrous sodium sulfate, filtered and concentrated under vacuum. The residue was purified by column chromatography eluting with ethyl acetate/petroleum ether (5:1 to 20:1 v/v) to afford ethyl 2-oxo-2-(2-(piperidine-1-carbonyl hydrazinyl)acetate (200 mg, 82%) as a white solid. LCMS (ESI) m/z 244 [M+H].

Step 2. Ethyl 5-(piperidin-1-yl)-1,3,4-oxadiazole-2-carboxylate

A 25-mL round-bottom flask was charged with 2-oxo-2-(2-(piperidine-1-carbonyl hydrazinyl)acetate (Step 1, 100 mg, 0.41 mmol), 4-methylbenzene-1-sulfonyl chloride (78 mg, 0.41 mmol), triethylamine (50 mg, 0.49 mmol) and dichloromethane (15 mL). The resulting solution was stirred 16 h at 23° C. The reaction was then quenched by the addition of water (10 mL) and the resulting mixture was extracted with dichloromethane (3×10 mL). The organic layers were combined and washed with water (10 mL) and brine (10 mL), dried over anhydrous sodium sulfate, filtered and concentrated under vacuum. The residue was purified by column chromatography eluting with ethyl acetate/petroleum ether (2:1 to 10:1 v/v) to afford ethyl 5-(piperidin-1-yl)-1,3,4-oxadiazole-2-carboxylate as an off-white solid (80 mg, 87%). LCMS: (ESI) r/z 226 [M+H].

Step 3. 5-(Piperidin-1-yl)-1,3,4-oxadiazole-2-carboxylic acid

A 25-mL round-bottom flask was charged with ethyl 5-(piperidin-1-yl)-1,3,4-oxadiazole-2-carboxylate (Step 2, 80 mg, 0.35 mmol), lithium hydroxide (17 mg, 0.70 mmol), water (5 mL) and tetrahydrofuran (5 mL). The resulting solution was stirred for 3 h at 23° C. The pH of the solution was adjusted to 5-6 with hydrochloric acid (6.0 M). The resulting solution was extracted with dichloromethane (2×30 mL) and the organic layers were combined, dried over anhydrous sodium sulfate, filtered and concentrated under vacuum to afford 5-(piperidin-1-yl)-1,3,4-oxadiazole-2-carboxylic acid (Intermediate 2-59, 60 mg, 87%) as an off-white solid which was used directly in the next step without further purification. LCMS (ESI) m/z 198 [M+H].

The Intermediate in Table 19 below was synthesized according to the procedures above, starting with the chloride described in Table 19.

TABLE 19

| Intermediate No.: | Precursor Used | MS (ESI, m/z) [M + H]. |
|---|---|---|
| Intermediate 2-76. 5-cyclopropyl-1,3,4-oxadiazole-2-carboxylic acid | cyclopropanecarbonyl chloride | 155 |

Example 35: Intermediate 2-60.
4-(1H-pyrazol-1-yl)benzoic acid

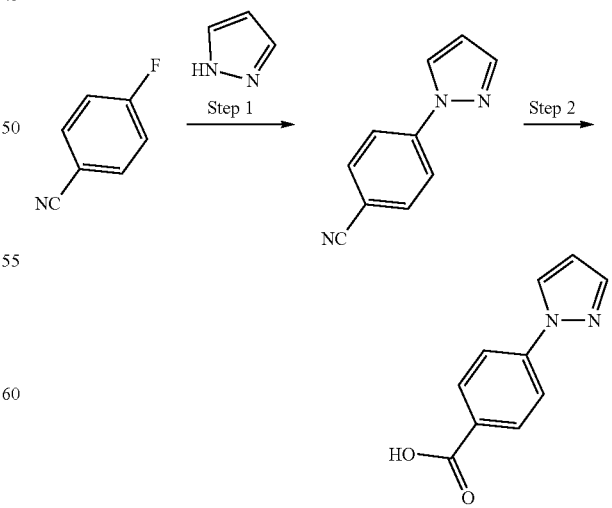

Intermediate 2-60

Step 1. 4-(1H-pyrazol-1-yl)benzonitrile

A 100-mL round-bottom flask was charged with 4-fluorobenzonitrile (2 g, 16.51 mmol), cesium carbonate (16 g, 49.11 mmol), N,N-dimethylformamide (20 mL) and 1H-pyrazole (2.24 g, 32.90 mmol). The resulting solution was refluxed for 2 h. The solids were removed by filtration and the filtrate was concentrated under vacuum. The residue was purified by column chromatography eluting with ethyl acetate/petroleum ether (1:10 to 1:4 v/v) to afford 4-(1H-pyrazol-1-yl)benzonitrile as a yellow oil (1.3 g, 47%). LCMS: (ESI) nm/z 170 [M+H].

Step 2. 4-(1H-pyrazol-1-yl)benzoic acid

A 250-mL round-bottom flask was charged with 4-(1H-pyrazol-1-yl)benzonitrile (Step 1, 2 g, 11.82 mmol), ethanol (40 mL), water (40 mL) and sodium hydroxide (705 mg, 17.63 mmol). The resulting solution was stirred at 105° C. 16 h and then concentrated under vacuum. The residue was diluted with water (30 mL) and extracted with ethyl acetate (50 mL). The pH of the aqueous phase was adjusted to 5 with hydrochloric acid (6.0 M). The solids were collected by filtration, washed with water (10 mL) and dried in an oven to afford 4-(1H-pyrazol-1-yl)benzoic acid as a light yellow solid (Intermediate 2-60, 1 g, 45%). LCMS: (ESI) m/z 189 [M+H].

The Intermediates in Table 20 were prepared according to the procedure outlined in Example 35.

TABLE 20

| Intermediate No.: | Precursor Used | MS (ESI, m/z) [M + H]. |
|---|---|---|
| Intermediates 862a and 862b. Tert-butyl2-(4-(methoxycarbonyl)phenyl)pyrrolo[3,4-c]pyrazole-5(2H,4H,6H)-carboxylate and tert-butyl 1-(4-(methoxycarbonyl)phenyl)pyrrolo[3,4-c]pyrazole-5(1H,4H,6H)-carboxylate | Methyl 4-fluorobenzoate and tert-butyl-1H,4H,5H,6H-pyrrolo[3,4-c]pyrazole-5-carboxylate | 344 |
| Intermediates 2-238a. 4-(4-cyano-1H-pyrazol-1-yl)benzoic acid | ethyl 4-bromobenzoate and 1H-pyrazole-4-carbonitrile | 214 |
| Intermediates 2-880. (S)-4-(3-Hydroxypyrrolidin-1-yl)benzoic acid | Ethyl 4-fluorobenzoate and (S)-pyrrolidin-3-ol | 208 |
| Intermediates 2-60a and 2-60b. 4-(2H-1,2,3-triazol-2-yl)benzoic acid and 4-(1H-1,2,3-triazol-1-yl)benzoic acid | 4-fluorobenzonitrile and 1,2,3-triazole | 188 [M − H] |

Example 36: Intermediate 2-336aa. 4-(1H-1,2,3-triazol-1-yl)benzenamine and 4-(1H-1,2,3-triazol-2-yl)benzenamine

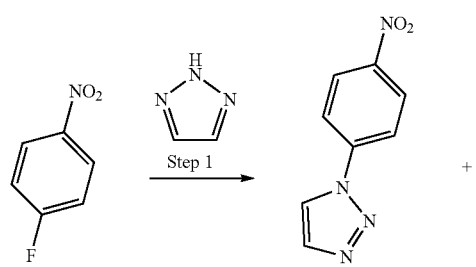

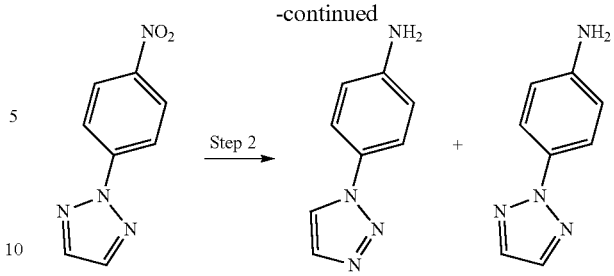

Step 1. 1-(4-nitrophenyl)-1H-1,2,3-triazole and 2-(4-nitrophenyl)-2H-1,2,3-triazole A 250-mL 3-necked round-bottom flask was charged with 2H-1,2,3-triazole (1.061 g, 15.4 mmol), N,N-dimethylformamide (60 mL), 1-fluoro-4-nitrobenzene (2 g, 14.2 mmol) and K$_2$CO$_3$ (5.87 g, 42.2 mmol). The resulting solution was stirred for 16 h at 110° C. in an oil bath and cooled to 25° C. The reaction was diluted with water (50 mL). The product was extracted with ethyl acetate (5×30 mL) The combined organic layers were concentrated under vacuum. The residue was purified by preparative HPLC* to afford the mixture of 1-(4-nitrophenyl)-1H-1,2,3-triazole and 2-(4-nitrophenyl)-2H-1,2,3-triazole (1:3) (1.6 g, 59%) as a yellow solid. LCMS: (ESI) m/z 191 [M+H]. *Column: silica gel. Mobile phase A: ethyl acetate/Mobile phase B: petroleum ether. Gradient: 10% B to 50% B over 35 min. Detector: 254 nm.

Step 2. 4-(1H-1,2,3-triazol-1-yl)benzenamine and 4-(1H-1,2,3-triazol-2-yl)benzenamine A 250-mL 3-necked round-bottom flask fitted with a magnetic stir bar, condenser and thermometer was charged with the mixture of 1-(4-nitrophenyl)-1H-1,2,3-triazole and 2-(4-nitrophenyl)-2H-1,2,3-triazole (Step 1, 1 g, 5.26 mmol), ethanol (30 mL), water (30 mL), Fe (1.5 g, 26.8 mmol), ammonium chloride (832 mg, 15.6 mmol). The resulting solution was stirred for 3 h at 80° C. in an oil bath. The reaction was cooled to 23° C. and the solids were removed by filtration. The filtrate was concentrated under vacuum and the residue was diluted with water (30 mL). The product was extracted with ethyl acetate (5×30 mL). The combined organic layers were concentrated under vacuum to afford a mixture of 4-(1H-1,2,3-triazol-1-yl)benzenamine and 4-(1H-1,2,3-triazol-2-yl)benzenamine (800 mg, 94%) as a yellow solid. LCMS: (ESI) m/z 161 [M+H].

Example 37: Intermediate 2-61.
2-(piperidin-1-yl)-1,3-oxazole-5-carboxylic acid

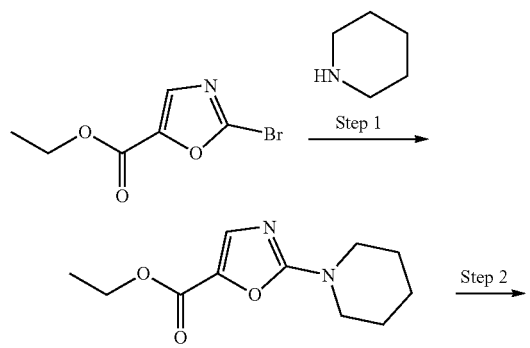

Step 1. Ethyl 2-(piperidin-1-yl)-1,3-oxazole-5-carboxylate

A 5-ml, microwave tube was charged with ethyl 2-bromo-1,3-oxazole-5-carboxylate (500 mg, 2.27 mmol), piperidine (219 mg, 2.57 mmol) and (trifluoromethyl)benzene (2 mL). The final reaction mixture was irradiated with microwave radiation for 30 min at 150° C. The resulting solution was cooled to 23° C. and concentrated under vacuum. The residue was purified by column chromatography eluting with ethyl acetate/petroleum ether (1:1 v/v) to afford ethyl 2-(piperidin-1-yl)-1,3-oxazole-5-carboxylate as a white solid (400 mg, 78%). LCMS: (ESI) m/z 225 [M+H].

Step 2. 2-(piperidin-1-yl)-1,3-oxazole-5-carboxylic acid

A 100-ml round-bottom flask was charged with ethyl 2-(piperidin-1-yl)-1,3-oxazole-5-carboxylate (Step 1, 400 mg, 1.78 mmol), lithium hydroxide (129 mg, 5.39 mmol), methanol (15 mL) and water (2 mL). The resulting solution was stirred for 3 h at 55° C. The resulting solution was diluted with 30 mL of water and the pH was adjusted to 5-6 with hydrochloric acid (6.0 M). The mixture was extracted with ethyl acetate (3×50 mL). The organic layers were combined, dried over anhydrous sodium sulfate, filtered and concentrated under vacuum to afford 2-(piperidin-1-yl)-1,3-oxazole-5-carboxylic acid (Intermediate 2-61, 350 mg, 99%) as a light yellow oil which was used directly in the next step without further purification. LCMS: (ESI) m/z 197 [M+H].

The Intermediates in Table 21 below were synthesized according to the procedures outlined above.

TABLE 21

| Intermediate No.: | Precursor Used | MS (ESI, m/z) [M + H]. |
|---|---|---|
| Intermediate 2-62. 4-(morpholinomethyl)benzoic acid | methyl 2-bromo-1,3-oxazole-5-carboxylate and morpholine | 199 |
| Intermediate 2-165. 2-(4-Hydroxypiperidin-1-yl)oxazole-5-carboxylic acid | methyl 2-bromo-1,3-oxazole-5-carboxylate and 4-hydroxypiperidine | 213 |
| Intermediate 2-117. 2-(4-Methylpiperazin-1-yl)oxazole-5-carboxylic acid | methyl 2-bromo-1,3-oxazole-5-carboxylate and 1-methylpiperazine | 212 |
| Intermediate 2-881. 2-(Cyclopropylamino)-1,3-oxazole-5-carboxylate and | methyl 2-bromo-1,3-oxazole-5-carboxylic acid cyclopropylamine | 167 |

-continued

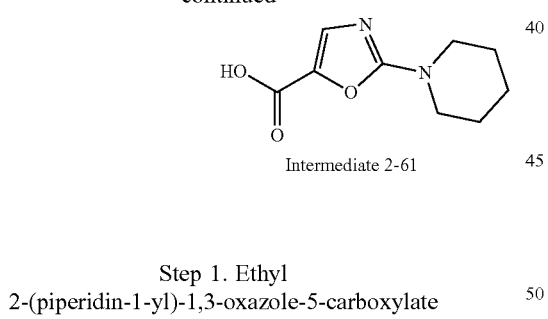

Intermediate 2-61

Example 37a: Intermediate 2-64.
1-benzyl-1H-pyrazole-5-carboxylic acid

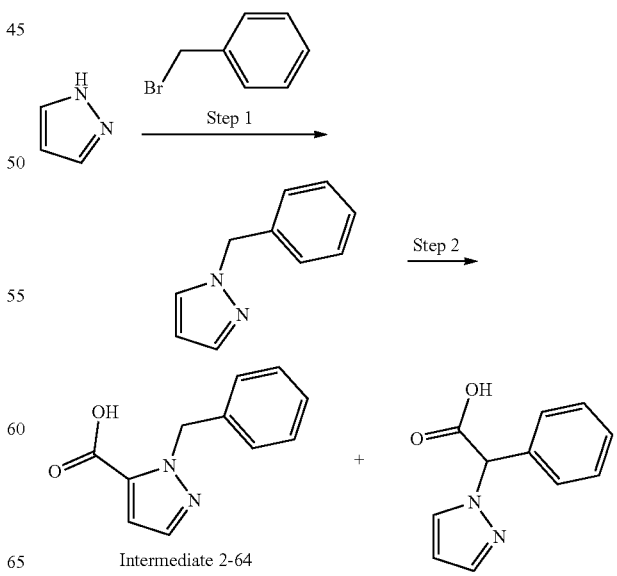

Intermediate 2-64

Step 1. 1-benzyl-1H-pyrazole

A 250-mL, round-bottom flask was charged with 1H-pyrazole (1 g, 14.69 mmol), potassium hydroxide (1.2 g, 21.39 mmol), potassium carbonate (3 g, 21.71 mmol), tetrabutylammonium bromide (7 g, 21.71 mmol), xylene (50 mL) and (bromomethyl)benzene (2.5 g, 14.62 mmol). The resulting mixture was stirred 16 h at 23° C. The reaction was then quenched by the addition of 150 mL of water. The resulting mixture was extracted with ethyl acetate (3×80 mL) and washed with 200 mL of water. The organic layers were combined, dried over anhydrous sodium sulfate, filtered and concentrated under vacuum. The residue was purified by column chromatography eluting with ethyl acetate/petroleum ether (1:3 v/v) to afford 1-benzyl-1H-pyrazole as a light yellow solid (1.3 g, 56%). LCMS: (ESI) m/z 159 [M+H].

Step 2. 1-benzyl-1H-pyrazole-5-carboxylic acid

A 100-mL 3-necked round-bottom flask equipped with a nitrogen balloon and thermometer was charged with 1-benzyl-1H-pyrazole (Step 1, 400 mg, 2.53 mmol) and tetrahydrofuran (25 mL). To the reaction was added n-butyl lithium (2.5 mL, 1.0 mmol) at −78° C. The resulting mixture was stirred for 1 hour at −78° C. in a dry ice bath before carbon dioxide was bubbled into the mixture. The resulting solution was stirred for additional 1 hour at −78° C. in a dry ice bath and then quenched by the addition of 30 mL of water and extracted with ethyl acetate (3×40 mL). The organic layers were combined, dried over anhydrous sodium sulfate, filtered and concentrated under vacuum to afford 1-benzyl-1H-pyrazole-5-carboxylic acid (including by product: 2-phenyl-2-(1H-pyrazol-1-yl)acetic acid) as a white oil which was used directly in the next step without further purification (Intermediate 2-64, 150 mg, 29%). LCMS: (ESI) m/z 203 [M+H].

Example 38: Intermediate 2-71. 4-(1H-pyrazol-1-yl)cyclohexanecarboxylic acid yl)cyclohexanecarboxylic acid

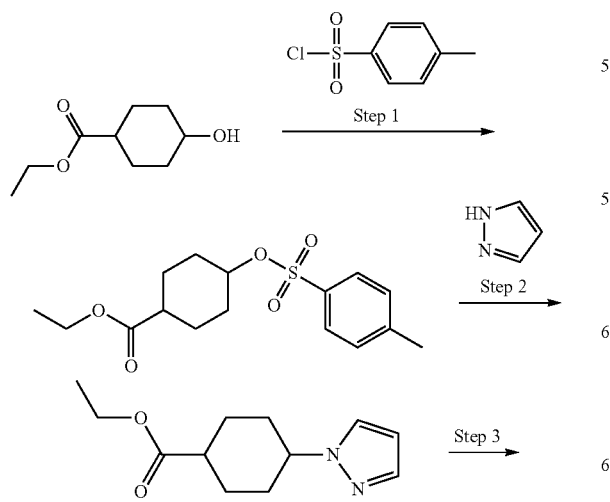

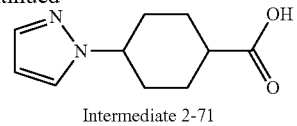

Intermediate 2-71

Step 1. ethyl 4-(tosyloxy)cyclohexanecarboxylate

A 250-mL round-bottom flask was charged with ethyl 4-hydroxycyclohexane-1-carboxylate (3 g, 17.42 mmol), 4-methylbenzene-1-sulfonyl chloride (5 g, 26.23 mmol), dichloromethane (50 mL) and triethylamine (5.28 g, 52.18 mmol). The resulting solution was stirred for 4 h at 23° C. The reaction was then quenched with water (50 mL). The mixture was extracted with dichloromethane (2×50 mL) and the organic layers were combined, dried over anhydrous sodium sulfate, filtered and concentrated under vacuum. The residue was purified by column chromatography eluting with ethyl acetate/petroleum ether (1:10 v/v) to afford ethyl 4-(tosyloxy)cyclohexanecarboxylate as a yellow solid (2.7 g, 47%). LCMS: (ESI) m/z 327 [M+H].

Step 2. ethyl 4-(1H-pyrazol-1-yl)cyclohexanecarboxylate

A 100-mL round-bottom flask was charged with ethyl 4-(tosyloxy) cyclohexanecarboxylate (Step 1, 2 g, 6.13 mmol), 1H-pyrazole (626 mg, 9.20 mmol), N,N-dimethylformamide (60 mL) and cesium carbonate (6 g, 18.42 mmol). The resulting solution was stirred 16 h at 80° C. After cooling to room temperature, the reaction was then quenched by the addition of water (60 mL) and extracted with ethyl acetate (3×60 mL). The organic layers were combined, dried over anhydrous sodium sulfate, filtered and concentrated under vacuum. The residue was purified by column chromatography eluting with ethyl acetate/petroleum ether (1:1 v/v) to afford ethyl 4-(1H-pyrazol-1-yl) cyclohexanecarboxylate as a yellow solid (400 mg, 29%). LCMS: (ESI) m/z 223 [M+H].

Step 3. 4-(1H-pyrazol-1-yl)cyclohexanecarboxylic acid

The title compound was prepared according to procedure outlined in Example 8, Step 2, utilizing ethyl 4-(1H-pyrazol-1-yl) cyclohexanecarboxylate (100 mg, 0.45 mmol) as starting material (Intermediate 2-71, 40 mg, 46%) which was used without further purification. LCMS: (ESI) m/z 195 [M+H].

Example 39: Intermediate 2-72. 4-(3,4-Dihydro-2H-pyrrolo[2,1-b][1,3]oxazin-8-yl)benzoic acid

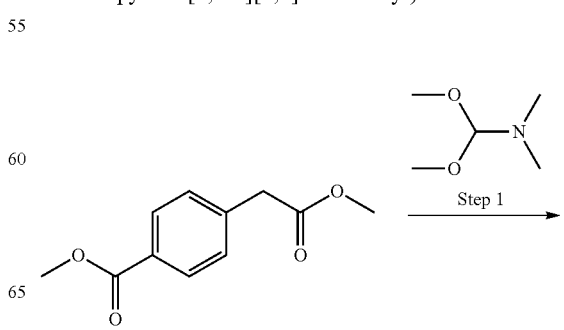

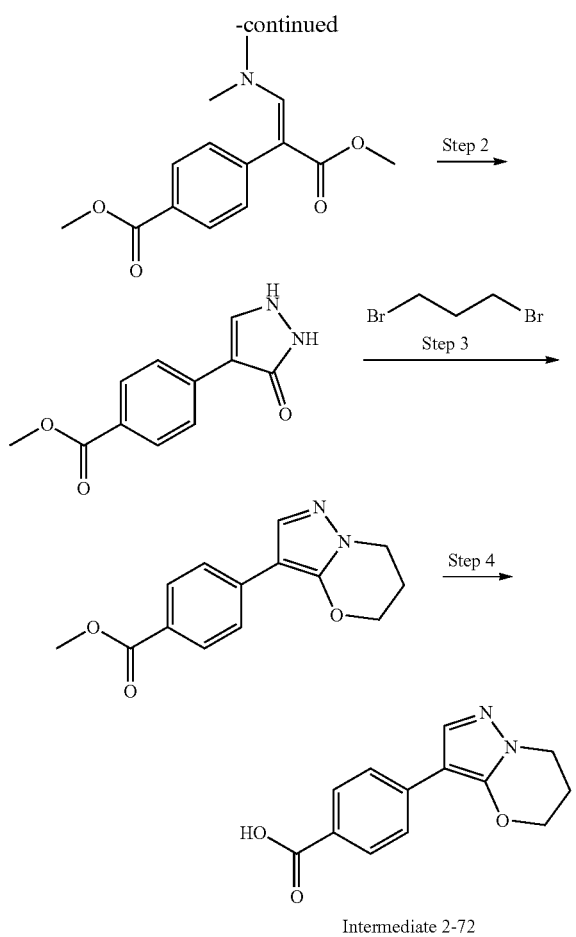

Intermediate 2-72

Step 1. Methyl 4-(1-(dimethylamino)-3-methoxy-3-oxoprop-1-en-2-yl)benzoate

A 50-mL round-bottom flask was charged with methyl 4-(2-methoxy-2-oxoethyl) benzoate (1 g, 4.80 mmol), (dimethoxymethyl)dimethylamine (571 mg, 4.79 mmol) and N,N-dimethylformamide (15 mL). The resulting solution was stirred for 4 h at 60° C. After cooling to 23° C., the reaction was quenched with water (30 mL) and the product was extracted with ethyl acetate (3×30 mL). The organic layers were combined, dried over anhydrous sodium sulfate, filtered and concentrated under vacuum. The residue was purified by column chromatography eluting with ethyl acetate/petroleum ether (1:1 v/v) to afford methyl 4-(1-(dimethylamino)-3-methoxy-3-oxoprop-1-en-2-yl)benzoate as a yellow solid (800 mg, 63%). LCMS: (ESI) m/z 264 [M+H].

Step 2. Methyl 4-(5-oxo-2,5-dihydro-1H-pyrazol-4-yl)benzoate

A 50-mL round-bottom flask was charged with methyl 4-(1-(dimethylamino)-3-methoxy-3-oxoprop-1-en-2-yl) benzoate (Step 1, 800 mg, 3.04 mmol), hydrazine hydrochloride (310 mg, 4.56 mmol), triethylamine (921 mg, 9.10 mmol) and ethanol (20 mL). The resulting solution was stirred for 2 h at 90° C. and cooled to 23° C. before concentrating the solution under vacuum. The residue was purified by preparative thin layer chromatography eluting with dichloromethane/methanol (10:1 v/v) to afford methyl 4-(5-oxo-2,5-dihydro-1H-pyrazol-4-yl)benzoate as a yellow solid (520 mg, 78%). LCMS: (ESI) m/z 219 [M+H].

Step 3. Methyl 4-(6,7-dihydro-5H-pyrazolo[5,1-b][1,3]oxazin-3-yl)benzoate

A 50-mL round-bottom flask was charged with methyl 4-(5-oxo-2,5-dihydro-1H-pyrazol-4-yl)benzoate (Step 2, 250 mg, 1.15 mmol), 1,3-dibromopropane (232 mg, 1.15 mmol), cesium carbonate (1.12 g, 3.44 mmol) and DMF (15 mL). The resulting solution was stirred 16 h at 80° C. The mixture was allowed to cool to 23° C. and then quenched with water (15 mL) and extracted with ethyl acetate (3×20 mL). The organic layers were combined, dried over anhydrous sodium sulfate, filtered and concentrated under vacuum. The residue was purified by preparative thin layer chromatography eluting with dichloromethane/methanol (20:1 v/v) to afford methyl 4-(6,7-dihydro-5H-pyrazolo[5,1-b][1,3]oxazin-3-yl)benzoate as a yellow solid (100 mg, 34%). LCMS: (ESI) m/z 259 [M+H].

Step 4. 4-(3,4-Dihydro-2H-pyrrolo[2,1-b][1,3]oxazin-8-yl)benzoic acid

The title compound was prepared according to procedure outlined in Example 8, Step 2, utilizing methyl 4-(6,7-dihydro-5H-pyrazolo[5,1-b][1,3]oxazin-3-yl)benzoate (Step 3, 100 mg, 0.39 mmol) as starting material (Intermediate 2-72, 80 mg, 85%). LCMS: (ESI) m/z 245 [M+H].

The Intermediate in Table 22 below was synthesized according to the procedures outlined above.

TABLE 22

| Intermediate No.: | Precursor Used | MS (ESI, m/z) [M + H]. |
|---|---|---|
| Intermediate 2-73. 4-(2,3-Dihydropyrazolo[5,1-b]oxazol-7-yl)benzoic acid | methyl 4-(2-methoxy-2-oxoethyl) benzoate | 231 |

Example 40: Intermediate 2-74. 4-(4,5,6,7-Tetrahydropyrazolo[1,5-a]pyrimidin-3-yl)benzoic acid

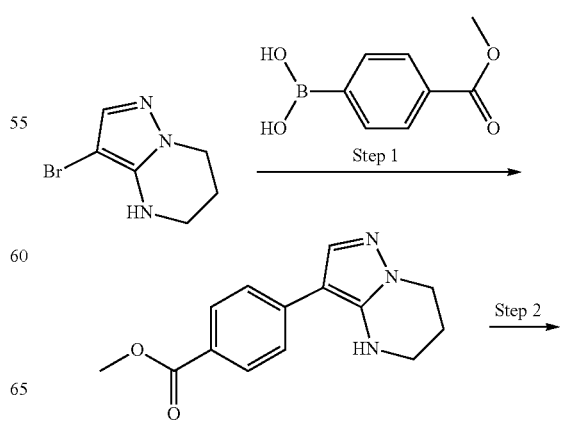

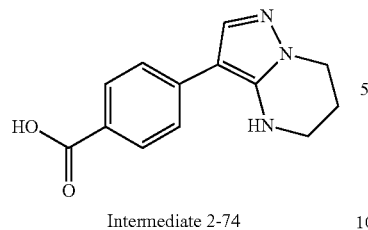

Intermediate 2-74

Step 1. Methyl 4-(4,5,6,7-tetrahydropyrazolo[1,5-a]pyrimidin-3-yl)benzoate

A 100-mL round-bottom flask equipped with a nitrogen balloon was charged with [4-(methoxycarbonyl)phenyl]boronic acid (400 mg, 2.22 mmol), 3-bromo-4H,5H,6H,7H-pyrazolo[1,5-a]pyrimidine (300 mg, 1.48 mmol), potassium carbonate (946.7 mg, 4.46 mmol), toluene (20 mL), tris(dibenzylideneacetone)dipalladium-chloroform adduct (136 mg, 0.15 mmol), dicyclohexyl(2',6'-dimethoxybiphenyl-2-yl) phosphine (61 mg, 0.15 mmol) and cesium fluoride (22.6 mg, 0.15 mmol) The resulting solution was stirred 16 h at 120° C. in an oil bath. The reaction mixture was allowed to cool to 23° C. and the solids were filtered. The filtrate was concentrated under vacuum and the residue was purified by column chromatography eluting with ethyl acetate/petroleum ether (3:2 v/v) to afford methyl 4-(4,5,6,7-tetrahydropyrazolo[1,5-a]pyrimidin-3-yl)benzoate as a yellow solid (160 mg, 42%). LCMS: (ESI) m/z 258 [M+H].

Step 2. 4-(4,5,6,7-Tetrahydropyrazolo[1,5-a]pyrimidin-3-yl)benzoic acid

The title compound was prepared according to procedure outlined in Example 10, Step 2, utilizing methyl 4-(4,5,6,7-tetrahydropyrazolo[1,5-a]pyrimidin-3-yl)benzoate (Step 1, 120 mg, 0.47 mmol), as starting material purified by column chromatography eluting with dichloromethane/methanol (20:1 v/v) (Intermediate 2-74.80 mg, 71%). LCMS: (ESI) m/z 244 [M+H].

The Intermediate in Table 23 below was synthesized according to the procedures outlined above. 3-bromo-4H,5H,6H,7H-pyrazolo[1,5-a]pyrimidine (40 mg, 0.20 mmol) was alkylated prior to following the procedures above with iodomethane (28 mg, 0.20 mmol) in DMF (10 mL) in the presence of NaH (9 mg, 0.23 mmol).

TABLE 23

| Intermediate No.: | Precursor Used | MS (ESI, m/z) [M + H]. |
|---|---|---|
| Intermediate 2-75. 4-(4-Methyl-4,5,6,7-tetrahydropyrazolo[1,5-a]pyrimidin-3-yl)benzoic acid | 3-bromo-4H,5H,6H,7H-pyrazolo[1,5-a]pyrimidine and [4-(methoxycarbonyl)phenyl]boronic acid | 231 |

Example 41: Intermediate 2-77. 5-benzyloxazole-4-carboxylic acid

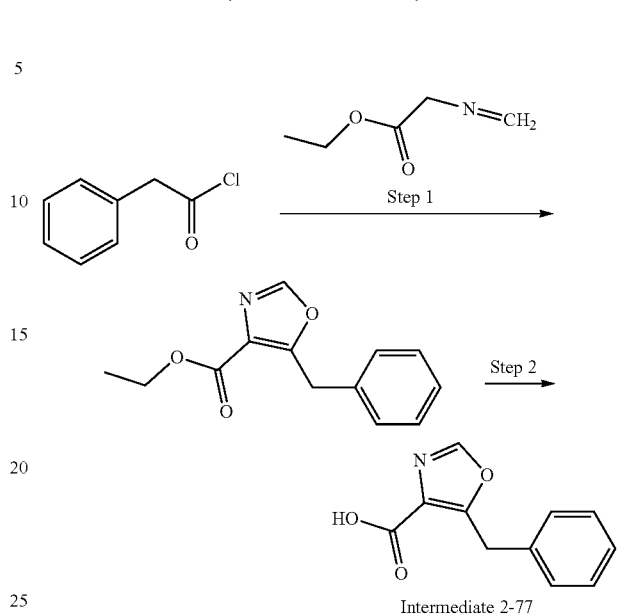

Intermediate 2-77

Step 1. Ethyl 5-benzyloxazole-4-carboxylate

A 100-mL round-bottom flask was charged with 2-phenylacetyl chloride (0.500 g, 3.23 mmol), ethyl 2-(methylideneamino)acetate (0.366 g, 3.18 mmol), 1,8-Diazabicyclo[5.4.0]undec-7-ene (0.492 g, 3.23 mmol), tetrahydrofuran (30 mL). The resulting solution was stirred for 16 h at 23° C. and then diluted with water (30 mL). The product was extracted with of ethyl acetate (3×20 mL). The combined organic layers were dried over anhydrous sodium sulfate, filtrated and concentrated under vacuum to afford ethyl 5-benzyloxazole-4-carboxylate (0.070 g, 9%) as a white solid which was directly used in the next step without purification. LCMS: (ESI) m/z 232 [M+H].

Step 2. 5-benzyloxazole-4-carboxylic acid

The title compound was prepared according to procedure outlined in Example 10, Step 2, utilizing 5-benzyloxazole-4-carboxylate (Step 1, 0.070 g, 0.30 mmol) as starting material which was directly used in the next step without purification (Intermediate 2-77, 0.060 g, 49%). LCMS: (ESI) m/z 204 [M+H].

Example 42: Intermediate 2-78. 1-[(4-fluorophenyl)methyl]-1H-pyrrole-2-carboxylic acid

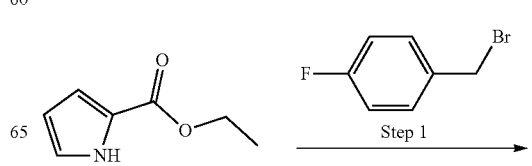

197

-continued

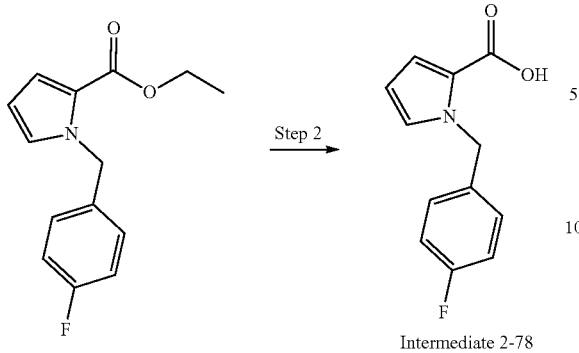

Intermediate 2-78

Step 1. Ethyl 1-[(4-fluorophenyl)methyl]-1H-pyrrole-2-carboxylate

A 100-mL round-bottom flask was charged with ethyl-1H-pyrrole-2-carboxylate (617 mg, 4.43 mmol), 1-(bromomethyl)-4-fluorobenzene (1.0 g, 5.29 mmol), cesium carbonate (4.3 g, 13.20 mmol) and N,N-dimethylformamide (20 mL). The resulting solution was stirred for 16 h at 60° C. in an oil bath. After cooling to 23° C., the reaction was quenched with water (30 mL). The resulting solution was extracted with ethyl acetate (3×30 mL). The combined organic layers were dried over anhydrous sodium sulfate, filtrated and concentrated under vacuum. The residue was purified by column chromatography eluting with ethyl acetate/petroleum ether (1:10 v/v) to afford ethyl 1-[(4-fluorophenyl)methyl]-1H-pyrrole-2-carboxylate (1.04 g, 95%). LCMS: (ESI) m/z 248 [M+H].

Step 2. 1-[(4-fluorophenyl)methyl]-1H-pyrrole-2-carboxylic acid

The title compound was prepared according to procedure outlined in Example 8, Step 2, utilizing ethyl 1-[(4-fluorophenyl)methyl]-1H-pyrrole-2-carboxylate (Step 1, 1.04 g, 4.21 mmol) as starting material (Intermediate 2-78, 300 mg, 33%) which was used without further purification. LCMS (ESI) m/z 220 [M+H].

Table 23a: The Intermediates in Table 23a below were also synthesized according to the procedures outlined above.

198

Example 43: Intermediate 2-85. tert-butyl 4-hydroxy-4-[(1S)-1-[1-(4-methoxyphenyl)-4-oxo-1H,4H,5H-pyrazolo[3,4-d]pyrimidin-5-yl]ethyl]piperidine-1-carboxylate

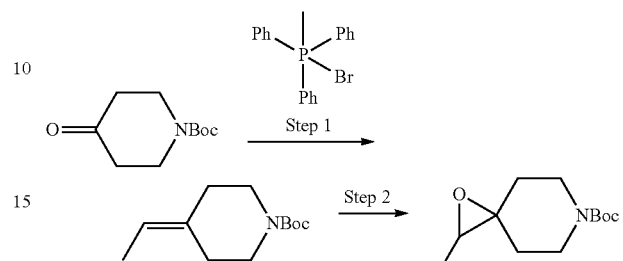

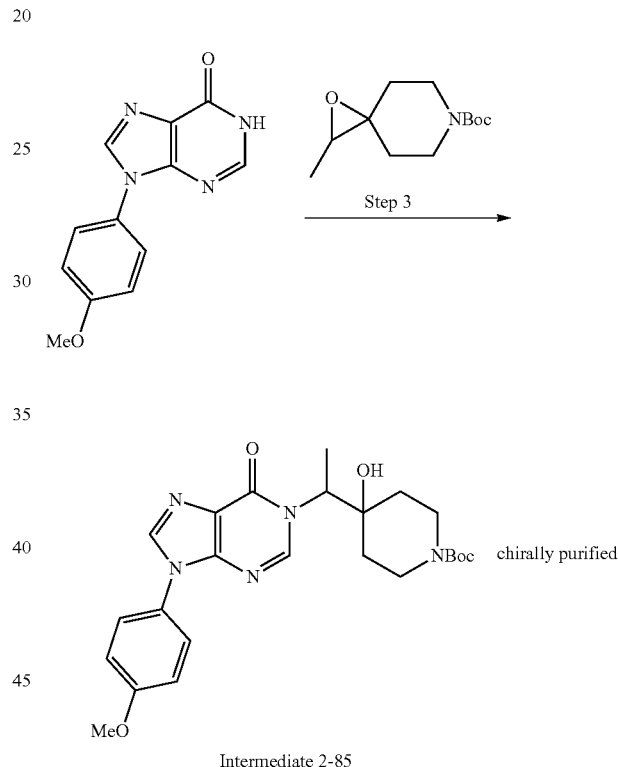

Intermediate 2-85

TABLE 23a

| Intermediate No.: | Precursor Used | MS (ESI, m/z) [M + H]. |
|---|---|---|
| Intermediate 2-79. 1-(2,6-Difluorobenzyl)-1H-pyrrole-2-carboxylic acid | ethyl-1H-pyrrole-2-carboxylate and 1-(bromomethyl)-2,6-difluorobenzene | 238 |
| Intermediate 2-80. 1-[(3-fluorophenyl)methyl]-1H-pyrrole-2-carboxylic acid | ethyl-1H-pyrrole-2-carboxylate and 1-(bromomethyl)-3-fluorobenzene | 220 |
| Intermediate 2-81. 1-(2-fluorobenzyl)-1H-pyrrole-2-carboxylic acid | ethyl-1H-pyrrole-2-carboxylate and 1-(bromomethyl)-2-fluorobenzene | 220 |
| Intermediate 2-143. 1-(2-fluorobenzyl)-1H-pyrrole-2-carboxylic acid | ethyl 1H-pyrrole-2-carboxylate and 1-(bromomethyl)-2-fluorobenzene | 220 |

Step 1. Tert-butyl 4-ethylidenepiperidine-1-carboxylate

A 250-mL 3-necked round-bottom flask equipped with a balloon filled with nitrogen was charged with bromo(ethyl) triphenyl-5-phosphane (9.3 g, 25.05 mmol), and tetrahydrofuran (100 mL). To the reaction was added n-butyl lithium (2.5M in hexane, 11 mL, 27.5 mmol) dropwise with stirring at −78° C. for 1 h before adding tert-butyl 4-oxopiperidine-1-carboxylate (5 g, 25.09 mmol) as a solution in tetrahydrofuran (20 mL) at −20° C. Stirring was continued for 1 h at −20° C. before quenching with water (30 mL). The product was extracted with ethyl acetate (5×50 mL). The combined organic layers were combined, dried over anhydrous sodium sulfate, filtered and concentrated under vacuum. The residue was purified by column chromatography eluting with ethyl acetate/petroleum ether (1:9 v/v) to afford tert-butyl 4-ethylidenepiperidine-1-carboxylate (4.2 g, 79%) as a light yellow solid. LCMS (ESI) m/z 212 [M+H].

Step 2. tert-butyl-2-methyl-1-oxa-6-azaspiro[2.5]octane-6-carboxylate

A 250-mL, round-bottom flask was charged with tert-butyl 4-ethylidenepiperidine-1-carboxylate (Step 1, 4.2 g, 19.88 mmol), 3-chloroperoxybenzoic acid (5.16 g, 29.9 mmol) and dichloromethane (100 mL). The resulting solution was stirred for 3 h at room temperature and quenched with aqueous saturated sodium sulfite solution (10 mL). The pH was adjusted to 7 with sodium bicarbonate (6 M) and the product was extracted with dichloromethane (3×100 mL). The combined organic layers were dried over anhydrous sodium sulfate, filtered and concentrated under vacuum. The residue was purified by column chromatography eluting with ethyl acetate/petroleum ether (1:10 to 1:5 v/v) to afford tert-butyl 2-methyl-1-oxa-6-azaspiro[2.5]octane-6-carboxylate (3.8 g, 84%) b as a colorless liquid. LCMS (ESI) m/z 228 [M+H].

Step 3. tert-butyl 4-hydroxy-4-(1-(1-(4-methoxyphenyl)-4-oxo-1H-pyrazolo[3,4-d]pyrimidin-5 (4H)-yl)ethyl)piperidine-1-carboxylate The title compound was prepared according to the procedure outlines in Example 28 utilizing 1-(4-methoxyphenyl)-1H,4H,5H-pyrazolo[3,4-d]pyrimidin-4-one (prepared according to the procedure outline in Example 21, Step 3, using p-methoxy hydrazine hydrochloride as the starting material, 2.3 g, 9.49 mmol) and tert-butyl 2-methyl-1-oxa-6-azaspiro[2.5]octane-6-carboxylate (Step 2, 2.6 g, 11.44 mmol), followed by column chromatography purification eluting with ethyl acetate/petroleum ether (1:1 v/v) (3.8 g, 81%) LCMS (ESI) m/z 470 [M+H]. The racemic product (tert-butyl 4-hydroxy-4-(1-(1-(4-methoxyphenyl)-4-oxo-1H-pyrazolo[3,4-d]pyrimidin-5 (4H)-yl)ethyl)piperidine-1-carboxylate) (2.25 g) was further purified by prep-SFC* to afford 1-tert-butyl 4-hydroxy-4-[(1S)-1-[1-(4-methoxyphenyl)-4-oxo-1H,4H,5H-pyrazolo[3,4-d]pyrimidin-5-yl]ethyl] piperidine-1-carboxylate (Intermediate 2-85, 629.1 mg, retention time: 2.02 min, 14.3%, stereochemistry unconfirmed) as a white solid. 1H NMR (300 MHz, DMSO-$d_6$) δ 0.95-1.19 (m, 1H), 1.20-1.44 (m, 13H), 1.45-1.71 (m, 2H), 2.79-3.15 (m, 2H), 3.50-3.81 (m, 2H), 3.83 (s, 3H), 4.85-5.10 (d, J=7.5 Hz, 1H), 5.11 (s, 1H), 7.00-7.18 (m, 2H), 7.81-8.00 (m, 2H), 8.32 (s, 1H), 8.39 (s, 1H). LCMS (ESI) m/z 470 [M+H].

1-tert-butyl-4-hydroxy-4-[(1S)-1-[1-(4-methoxyphenyl)-4-oxo-1H,4H,5H-pyrazolo[3,4-d]pyrimidin-5-yl]ethyl]-1[3],3-oxazocan-2-one (Intermediate 2-85, 614 mg, 14%) as a white solid, Retention time: 1.46 min, stereochemistry unconfirmed). $^1$H NMR (300 MHz, DMSO-$d_6$) δ 0.92-1.11 (m, 1H), 1.17-1.44 (m, 13H), 150-1.75 (m, 2H), 2.80-3.18 (m, 2H), 3.45-3.80 (m, 2H), 3.82 (s, 3H), 4.85-5.02 (m, 1H), 5.11 (brs, 1H), 6.92-7.22 (m, 2H), 7.75-8.05 (m, 2H), 8.32 (s, 1H), 8.39 (s, 1H). MS (ESI, m/z) 470 [M+H]+. *SFC column: CHIRALCEL OJ-3, 4.6×50 mm, 3 um. Mobile Phase A 0.1% aqueous DEA/Mobile phase B: methanol, Flow rate: 4 ml/min. Detector: 220 and 254 nm.

The Intermediate in Table 24 below was synthesized according to the procedures outlined in Example 43.

TABLE 24

| Intermediate No.: | Precursor Used | MS (ESI, m/z) [M + H]. |
|---|---|---|
| Intermediate 2-87, 1-(4-fluorophenyl)-5-(1-(4-hydroxypiperidin-4-yl)ethyl)-1H-pyrazolo[3,4-d]pyrimidin-4 (5H)-one, TFA salt | 1-(4-fluorophenyl)-1H,4H,5H-pyrazolo[3,4-d]pyrimidin-4-one and tert-butyl 2-methyl-1-oxa-6-azaspiro[2.5]octane-6-carboxylate | 358 |

Example 44: Intermediate 2-878a. 6-[(4-Fluorophenyl)carbonyl]-2-methyl-1-oxa-6-azaspiro[2.5]octane

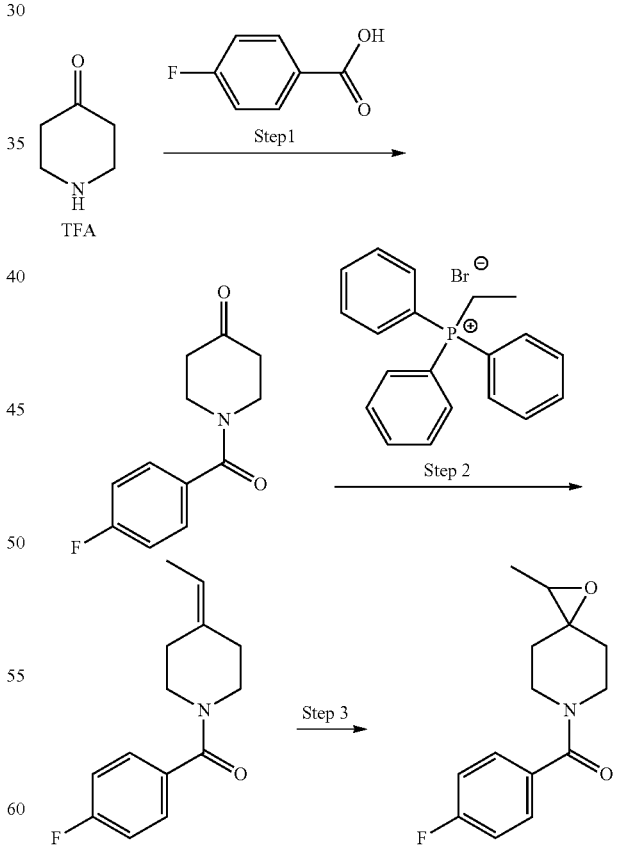

Step 1. 1-(4-Fluorobenzoyl)piperidin-4-one

The title compound was prepared according to procedure described in Example 7 utilizing the piperidin-4-one, TFA salt (1 g, 4.69 mmol) and 4-fluorobenzoic acid (1.44 g, 10.3 mmol followed by purification by column chromatography eluting with ethyl acetate/petroleum ether (1:1, v/v) (800 mg, 77%). LCMS: (ESI) m/z 222 [M+H].

Step 2. (4-Ethylidenepiperidin-1-yl)(4-fluorophenyl)methanone

The title compound was prepared according to the procedure outlined in Example 43, Step 1, utilizing 1-(4-fluorobenzoyl)piperidin-4-one (Step 1, 800 mg, 3.62 mmol) as starting material which was purified by column chromatography eluting with ethyl acetate/petroleum ether (1:3, v/v) (250 mg, 30%). LCMS: (ESI) m/z 234 [M+H].

Step 3. 6-[(4-Fluorophenyl)carbonyl]-2-methyl-1-oxa-6-azaspiro[2.5]octane

The title compound was prepared according to the procedure outlined in Example 43, Step 2, utilizing (4-ethylidenepiperidin-1-yl)(4-fluorophenyl)methanone (Step 2, 250 mg, 1.07 mmol) as starting material (250 mg, 93%). LCMS: (ESI) m/z 250 [M+H].

Example 45. Intermediate 2-88. 4-((1-(4-Fluorophenyl)-4-oxo-1,4-dihydro-5H-pyrazolo [3,4-d]pyrimidin-5-yl)methyl)-4-hydroxypiperidine-1-carbonyl chloride

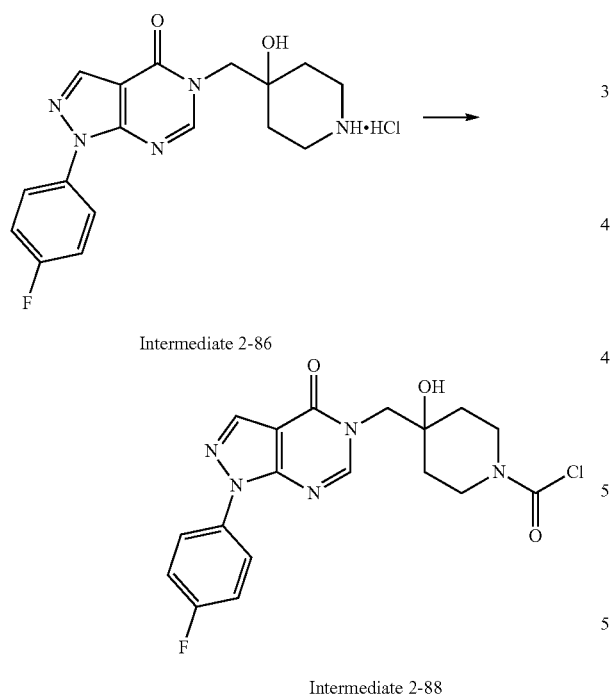

Triphosgene (0.078 g, 0.263 mmol), triethylamine (0.092 mL, 0.658 mmol), and THF (1.0 mL) were added to a 10-mL round bottom flask fitted with a nitrogen inlet and magnetic stir bar. The mixture was cooled to −45° C., and a solution of 1-(4-fluorophenyl)-5-((4-hydroxypiperidin-4-yl)methyl)-1,5-dihydro-4H-pyrazolo[3,4-d]pyrimidin-4-one hydrochloride (Intermediate 2-86, 0.05 g, 0.132 mmol) in THF (1.0 mL) was added slowly while maintaining the temperature below −35° C. The mixture was stirred for 1 h cold, warmed to room temperature, and then concentrated under reduced pressure to dryness. The residue was purified by column chromatography using dichloromethane-ethyl acetate (1:1 v/v) to give 4-((1-(4-fluorophenyl)-4-oxo-1,4-dihydro-5H-pyrazolo[3,4-d]pyrimidin-5-yl)methyl)-4-hydroxypiperidine-1-carbonyl chloride (Intermediate 2-88, 40 mg, 75%). LCMS: (ESI) m/z 406.09 [M+H].

Example 46: Intermediate 91.
1-methyl-4-nitro-1H-pyrazole

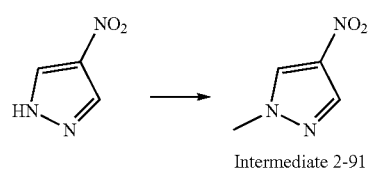

Intermediate 2-91

A 250-mL round-bottom flask fitted with a nitrogen inlet, magnetic stir bar and thermometer was charged with 4-nitro-1H-pyrazole (5 g, 44.22 mmol) and acetonitrile (120 mL) and sodium hydride (2.1 g, 87.50 mmol, 60% wt) at −5° C. To the reaction was added iodomethane (7.5 g, 52.8 mmol). The product was stirred for 16 h at 23° C. and quenched with water (20 mL). The product was extracted with ethyl acetate (5×40 mL). The combined organic layers were dried over anhydrous sodium sulfate, filtered and concentrated under vacuum. The residue was purified by column chromatography eluting with ethyl acetate/petroleum ether (1:5 v/v) to afford 1-methyl-4-nitro-1H-pyrazole (Intermediate 2-91, 5.2 g, 93%). LCMS: (ESI) m/z 128 [M 1H].

Example 47: Intermediate 2-92.
1-phenyl-4-nitro-1H-pyrazole

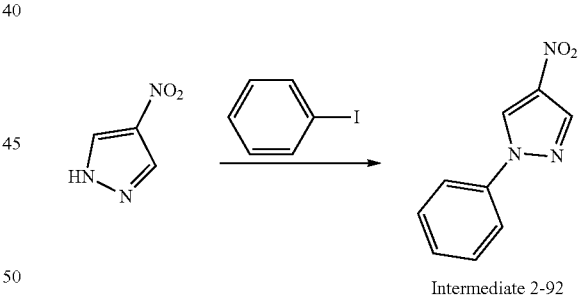

Intermediate 2-92

A 250-mL 3-necked round-bottom flask fitted with a nitrogen inlet, magnetic stir bar and thermometer was charged with 4-nitro-1H-pyrazole (4 g, 35.37 mmol), iodobenzene (8 g, 39.2 mmol), copper (I) iodide (2.44 g, 12.8 mmol), potassium carbonate (9.66 g, 69.9 mmol) and N,N-dimethylformamide (100 mL). The resulting solution was stirred for 12 h at 110° C. and cooled to 23° C. The reaction was quenched with water (80 mL). The product was extracted with ethyl acetate (3×100 mL). The combined organic layers were dried over anhydrous sodium sulfate and concentrated under vacuum. The residue was purified by column chromatography eluting with ethyl acetate/petroleum ether (2:3 v/v) to afford of 4-nitro-1-phenyl-1H-pyrazole (Intermediate 2-92, 2.2 g, 33%). LCMS: (ESI) m/z 190 [M+H].

The Intermediate in Table 25 below was synthesized according to the procedures outlined in Example 47.

TABLE 25

| Intermediate No.: | Precursor Used | MS (ESI, m/z) [M + H]. |
|---|---|---|
| Intermediate 2-331a. 1-cyclopropyl-4-nitro-1H-pyrazole | 4-nitro-1H-pyrazole | 358 |

Example 46. Intermediate 2-96. 1-methyl-4,5,6,7-tetrahydro-1H-indazole-6-carboxylic acid

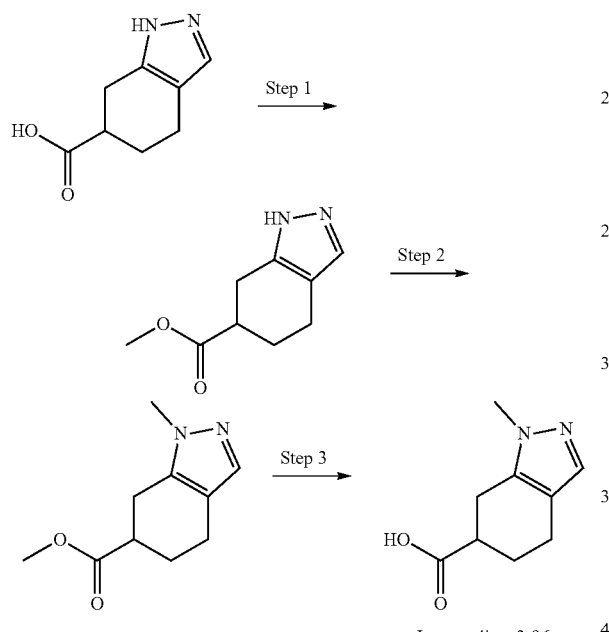

Intermediate 2-96

Step 1. Methyl 4,5,6,7-tetrahydro-11H-indazole-6-carboxylate

A 50-mL round-bottom flask fitted with a magnetic stir bar was charged with 4,5,6,7-tetrahydro-1H-indazole-6-carboxylic acid (640 mg, 3.96 mmol), methanol (10 mL) and thionyl chloride (1.43 g, 12.0 mmol). The resulting solution was stirred for 2 h at 23° C. The reaction mixture was concentrated under vacuum to afford methyl 4,5,6,7-tetrahydro-1H-indazole-6-carboxylate as a yellow oil (645 mg, 90%). LCMS: (ESI) m/z 181 [M+H].

Step 2. Methyl 1-methyl-4,5,6,7-tetrahydro-1H-indazole-6-carboxylate

A 50-mL round-bottom flask fitted with a magnetic stir bar was charged with methyl 4,5,6,7-tetrahydro-1H-indazole-6-carboxylate (Step 1, 360 mg, 2.00 mmol) and tetrahydrofuran (5 mL, 61.7 mmol). Sodium hydride (120 mg, 3.00 mmol, 60% wt) was added in one portion. The reaction mixture was stirred for 2 h at 23° C. before adding iodomethane (340 mg, 2.40 mmol) dropwise. The resulting solution was stirred for 2 h at 23° C. and quenched with water (20 mL). The product was extracted with ethyl acetate (3×30 mL). The organic layers were combined, dried over anhydrous sodium sulfate and concentrated under vacuum. The residue was purified by column chromatography eluting with ethyl acetate/petroleum ether (1:10, v/v) to afford methyl 1-methyl-4,5,6,7-tetrahydro-1H-indazole-6-carboxylate as a yellow oil (340 mg, 88%). LCMS: (ESI) m/z 195 [M+H].

Step 3. 1-methyl-4,5,6,7-tetrahydro-1H-indazole-6-carboxylic acid

The title compound was prepared according to the procedure outline in Example 10, Step 2 utilizing methyl 1-methyl-4,5,6,7-tetrahydro-1H-indazole-6-carboxylate (Step 2, 194 mg, 1.00 mmol), as starting material (Intermediate 2-96, 180 mg, >95%). LCMS: (ESI) m/z 181 [M+H].

Example 47: Intermediate 2-97. 4-(1-methyl-1H-pyrazol-4-yl)cyclohexane-1-carboxylic acid

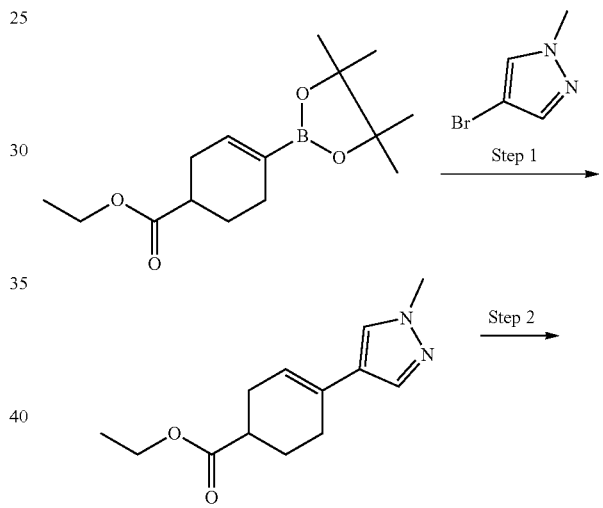

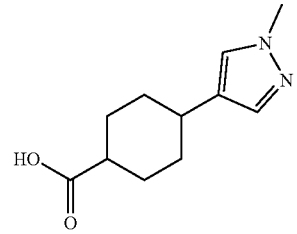

Intermediate 2-97

Step 1. Ethyl 4-(1-methyl-1H-pyrazol-4-yl)cyclohex-3-ene-1-carboxylate

A 100-mL 3-necked round-bottom flask fitted with a nitrogen inlet, magnetic stir bar, condenser and thermometer was charged with ethyl 4-(tetramethyl-1,3,2-dioxaborolan-2-yl)cyclohex-3-ene-1-carboxylate (500 mg, 1.78 mmol), Pd(PPh₃)₄(206 mg, 0.18 mmol), potassium phosphate (1.13 g, 5.34 mmol), water (4 mL), 4-bromo-1-methyl-1H-pyrazole (431 mg, 2.68 mmol) and 1.4-dioxane (40 mL). The solution was stirred 12 h at 100° C. under nitrogen. The reaction mixture was cooled to 25° C. and diluted with water (40 mL). The product was extracted with dichloromethane (3×20 mL). The combined organic layers were dried over anhydrous sodium sulfate, filtered and concentrated under vacuum. The residue was purified by column chromatography eluting with ethyl acetate/petroleum ether (1:10, v/v) to afford ethyl 4-(1-methyl-1H-pyrazol-4-yl)cyclohex-3-ene-1-carboxylate (0.35 g, 84%). LCMS: (ESI) m/z 235 [M+H].

Step 2. Methyl 4-(1-methyl-1H-pyrazol-4-yl)cyclohexane-1-carboxylate

A 100-mL round-bottom flask fitted with a hydrogen balloon, magnetic stir bar was charged with methyl 4-(1-methyl-1H-pyrazol-4-yl)cyclohex-3-ene-1-carboxylate (Step 1, 300 mg, 1.36 mmol), palladium on carbon (50 mg, 10% wt) and methanol (20 mL). The mixture was stirred 12 h at 25° C. under hydrogen. The solids were removed by filtration and the filtrate was concentrated under vacuum to afford methyl 4-(1-methyl-1H-pyrazol-4-yl)cyclohexane-1-carboxylate (0.21 g, 74%). LCMS: (EST) m/z 237 [M+H].

Step 3. 4-(1-methyl-1H-pyrazol-4-yl)cyclohexane-1-carboxylic acid

The title compound was prepared according to the procedure outlined in Example 10, Step 2, utilizing methyl 4-(1-methyl-1H-pyrazol-4-yl)cyclohexane-1-carboxylate (Step 2, 200 mg, 0.90 mmol) as starting material (Intermediate 2-97, 150 mg, 80%). LCMS: (ESI) m/z 209 [M+H].

Example 48: Intermediate 2-114. 1-(4-Fluorophenyl)-5-((4-hydroxy-1-(4-oxocyclohexanecarbonyl)piperidin-4-yl)methyl)-1H-pyrazolo[3,4-d]pyrimidin-4(5H)-one

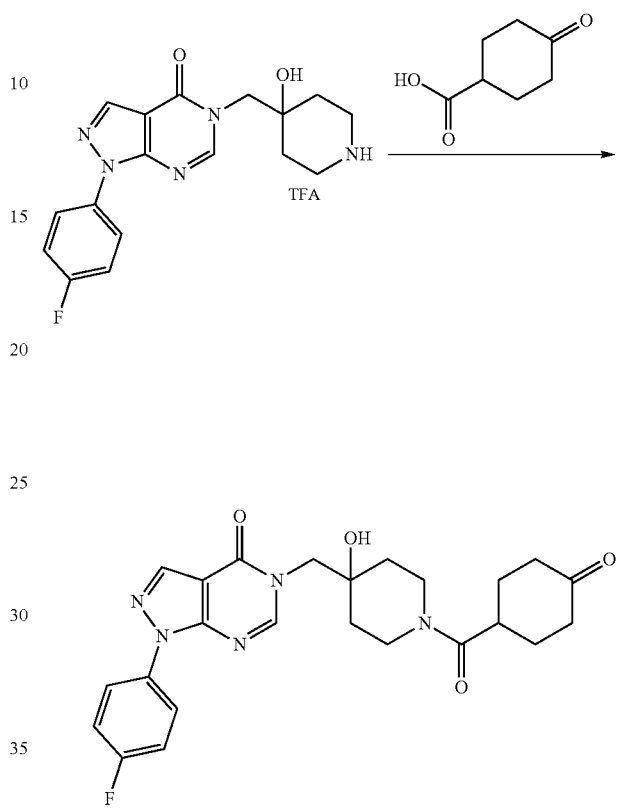

Intermediate 2-114

The title compound was prepared according to procedure outlined in Example 6 utilizing 1-(4-fluorophenyl)-5-[(4-hydroxypiperidin-4-yl)methyl]-1H,4H,5H-pyrazolo[3,4-d]pyrimidin-4-one TFA salt (Intermediate 2-28, 1.0 g, 2.19 mmol) and 4-oxocyclohexane-1-carboxylic acid (prepared according to procedure outline in Example 8, Step 2, utilizing ethyl 4-oxocyclohexane-1-carboxylate as starting material, 625 mg, 4.40 mmol), 1.0 g, 49%). LCMS: (ESI) m/z 468 [M+H].

The Intermediates in Table 26 were synthesized according to the procedure for Example 48 above.

TABLE 26

| Intermediate No.: | Precursor Used | LCMS: (ES) m/z [M + H] |
|---|---|---|
| Intermediate 2-917aa. 5-((4-hydroxy-1-(4-oxocyclohexanecarbonyl)piperidin-4-yl)methyl)-1-phenyl-1H-pyrazolo[3,4-d]pyrimidin-4(5H)-one | 5-((4-hydroxypiperidin-4-yl)methyl)-1-phenyl-1,5-dihydro-4H-pyrazolo[3,4-d]pyrimidin-4-one, TFA salt and 4-oxocyclohexane-1-carboxylic acid | 450 |
| Intermediate 2-920aa. 7-(4-fluorophenyl)-3-((4-hydroxy-1-(4-oxocyclohexane-1-carbonyl)piperidin-4-yl)methyl)-3,7-dihydro-4H-pyrrolo[2,3-d]pyrimidin-4-one | 7-(4-fluorophenyl)-3-((4-hydroxypiperidin-4-yl)methyl)-3,7-dihydro-4H-pyrrolo[2,3-d]pyrimidin-4-one TFA salt and 4-oxocyclohexane-1-carboxylic acid | 467 |

Example 49: Intermediate 2-116.
2-cyclopropyl-1,3-oxazole-5-carboxylic acid

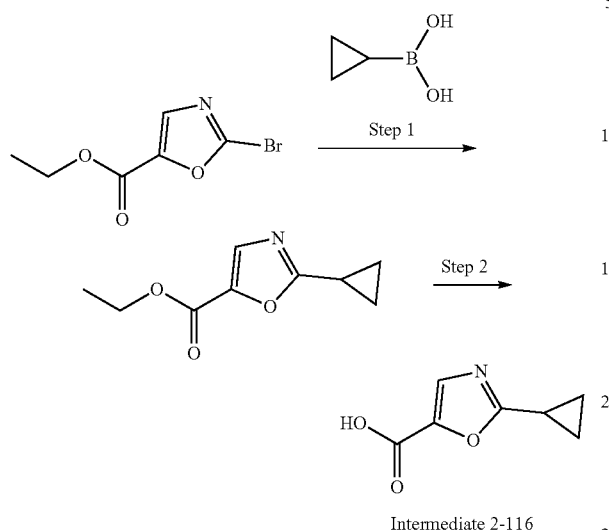

Intermediate 2-116

Step 1. ethyl 2-cyclopropyl-1,3-oxazole-5-carboxylate

A 100-mL round-bottom flask purged and maintained with an inert atmosphere of nitrogen was charged with ethyl 2-bromo-1,3-oxazole-5-carboxylate (600 mg, 2.73 mmol), cyclopropylboronic acid (377 mg, 4.39 mmol), toluene (30 mL, 282 mmol), potassium phosphate (1.59 g, 7.49 mmol) in water (4 mL) and 1,1'-(diphenyl phosphine) ferrocene methylene chloride palladium dichloride (12 mg, 0.06 mmol). The solution was stirred for 16 h at 120° C. in an oil bath. The reaction quenched with water (10 mL) and the product was extracted with ethyl acetate (3×20 mL). The combined organic layers were dried over anhydrous sodium sulfate, filtrated and concentrated under vacuum. The residue was purified by column chromatography eluting with ethyl acetate/petroleum ether (1:20 to 1:5 v/v) to give ethyl 2-cyclopropyl-1,3-oxazole-5-carboxylate (70 mg, 61%). LCMS (ES) m/z 182 [M+H].

Step 2. 2-cyclopropyl-1,3-oxazole-5-carboxylic acid

Title compound (400 mg, 86%) was prepared according to the procedure described in Example 10, Step 2, utilizing ethyl 2-cyclopropyl-1,3-oxazole-5-carboxylate (Step 1, 550 mg, 3.04 mmol) as starting material (400 mg, 86%). LCMS: (ES) m/z 154 [M+H].

Example 50: Intermediate 2-119.
1-Cyclopropyl-1H-imidazole-4-carboxylic acid

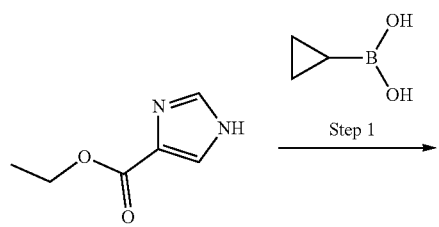

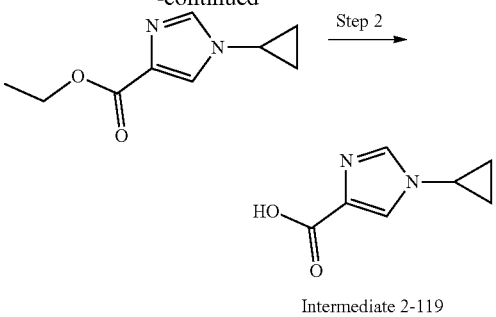

Intermediate 2-119

Step 1. Ethyl 1-cyclopropyl-1H-imidazole-4-carboxylate

A 250-mL round-bottom flask was charged with ethyl 1H-imidazole-4-carboxylate (500 mg, 3.57 mmol), cyclopropylboronic acid (614.7 mg, 7.16 mmol), sodium carbonate (757 mg, 7.14 mmol), 1,2-dichloroethane (30 mL), 4,4'-bipyridine (558 mg, 3.58 mmol) and cupric acetate (646 mg, 3.56 mmol). The resulting mixture was stirred for 16 h at 70° C. and cooled to 23° C. The solids were removed by filtration and the filtrate was concentrated under vacuum. The residue was purified by column chromatography eluting with ethyl acetate/petroleum ether (1:1 v/v) to afford ethyl 1-cyclopropyl-1H-imidazole-4-carboxylate (300 mg, 47%). LCMS: (ESI) m/z 181 [M+H].

Step 2. 1-Cyclopropyl-1H-imidazole-4-carboxylic acid

Title compound (60 mg, 89%) was prepared according to the procedure described in Example 37, Step 2, utilizing ethyl 1-cyclopropyl-1H-imidazole-4-carboxylate (Step 1, 80 mg, 0.44 mmol) as starting material and used next without further purification. LCMS (ESI) m/z 153 [M+H].

The Intermediate in Table 27 below was also synthesized according to the procedures outlined for Example 50.

TABLE 27

| Intermediate No.: | Precursor Used | MS (ESI, m/z) [M + H]. |
|---|---|---|
| Intermediate 2-120A & 2-120B. 1-cyclopropyl-1H-pyrazole-3-carboxylic acid and 1-cyclopropyl-1H-pyrazole-5-carboxylic acid | methyl 1H-pyrazole-3-carboxylate and cyclopropylboronic acid | 153 |
| Intermediate 2-121. 1-Cyclopropyl-1H-pyrazole-4-carboxylic acid | methyl 1H-pyrazole-4-carboxylate and cyclopropylboronic acid | 153 |

Example 51: Intermediate 2-124.
4-Benzyloxazole-5-carboxylic acid

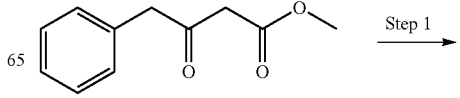

209

-continued

210

Example 52: Intermediate 2-125.
4-(1-methylpyrrolidin-3-yloxy)benzoic acid

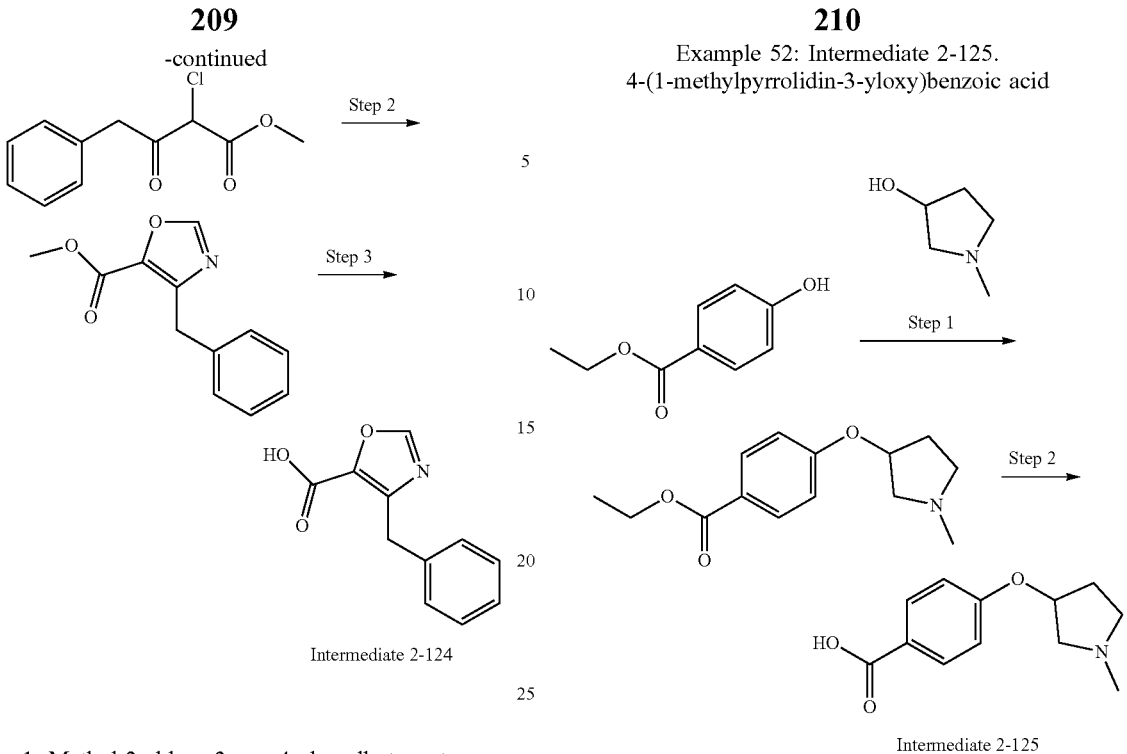

Intermediate 2-124

Intermediate 2-125

Step 1. Methyl 2-chloro-3-oxo-4-phenylbutanoate

A 250-mL round-bottom flask was charged with methyl 3-oxo-4-phenylbutanoate (1.92 g, 9.99 mmol), sulfuryl dichloride (1.62 g, 12.0 mmol) and dichloromethane (50 mL). The resulting solution was stirred for 1 h at 23° C. and then quenched with water (50 mL). The product was extracted with dichloromethane (2×100 mL). The combined organic layers were washed with brine (50 mL), dried over anhydrous sodium sulfate, filtered and concentrated under vacuum. The residue was purified by column chromatography eluting with ethyl acetate/petroleum ether (1:100 to 1:30 v/v) to afford methyl 2-chloro-3-oxo-4-phenylbutanoate (1.65 g, 73%) as a yellow solid. LCMS: (ESI) m/z 227 [M+H].

Step 2. Methyl 4-benzyloxazole-5-carboxylate

A 250-mL round-bottom flask was charged with methyl 2-chloro-3-oxo-4-phenylbutanoate (Step 1, 2.26 g, 9.97 mmol), formic acid (30 mL) and ammonium formate (2.31 g, 30.00 mmol). The resulting solution was stirred for 3 h at 100° C. The reaction was cooled to 23° C. and quenched with saturated sodium bicarbonate (50 mL). The product was extracted with ethyl acetate (3×50 mL). The combined organic layers were washed with brine (50 mL), dried over anhydrous sodium sulfate, filtered and concentrated under vacuum. The residue was purified by column chromatography eluting with ethyl acetate/petroleum ether (1:50 to 1:8 v/v) to afford methyl 4-benzyloxazole-5-carboxylate (300 mg, 14%) as a yellow solid. LCMS: (ESI) m/z 218 [M+H].

Step 3. 4-Benzyloxazole-5-carboxylic acid

The title compound was prepared according to the procedure outlined in Example 8, Step 2, utilizing methyl 4-benzyloxazole-5-carboxylate (Step 2, 300 mg, 1.38 mmol) as starting material (Intermediate 2-124, 245 mg, 87%). LCMS: (ESI) m/z 204 [M+H].

Step 1. ethyl 4-(1-methylpyrrolidin-3-yloxy)benzoate

A 100-mL round-bottom flask with a nitrogen ball was charged with piperidin-4-ol (1 g, 9.89 mmol), triphenylphosphine (3.5 g, 13.34 mmol), ethyl 4-hydroxybenzoate (2.25 g, 13.5 mmol), tetrahydrofuran (50 mL) and diethyl azodicarboxylate (3.45 g, 19.8 mmol). The resulting solution was stirred 16 h at 23° C. and concentrated under vacuum. The residue was purified by column chromatography eluting with ethyl acetate/petroleum ether (1:1 v/v) to afford ethyl 4-(1-methylpyrrolidin-3-yloxy)benzoate (0.5 g, 20%). LCMS: (ESI) m/z 250 [M+H].

Step 2. 4-(1-methylpyrrolidin-3-yloxy)benzoic acid

The title compound was prepared according to the procedure outlined in Example 10, Step 2, utilizing ethyl 4-(1-methylpyrrolidin-3-yloxy)benzoate (Step 1, 200 mg, 0.80 mmol) as starting material (Intermediate 2-125, 0.15 g, 84%) as a yellow oil used without further purification. LCMS: (ESI) m/z 222 [M+H].

The Intermediates in Table 28 below were synthesized according to the procedures outlined for Example 52.

TABLE 28

| Intermediate No.: | Precursor Used | MS (ESI, m/z) [M + H]. |
|---|---|---|
| Intermediate 2-477a. 4-(1-(tert-butoxycarbonyl)piperidin-4-yloxy)benzoic acid | tert-butyl 4-hydroxypiperidine-1-carboxylate and ethyl 4-hydroxybenzoate | 322 |
| Intermediate 2-126. 4-(1-methylpiperidin-4-yloxy)benzoic acid | 1-methylpiperidin-4-ol and ethyl 4-hydroxybenzoate | 153 |

Example 53: Intermediate 2-136. 4-(N-methylsulfamoyl)benzoic acid

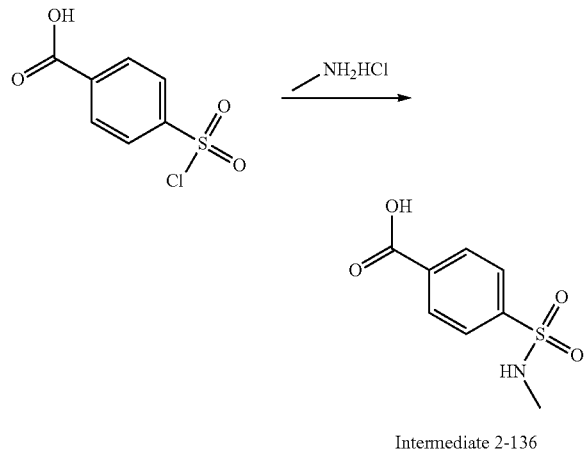

Intermediate 2-136

A 100-mL round-bottom flask fitted with a magnetic stir bar was charged with triethylamine (1 mL), dichloromethane (10 mL) and methanamine hydrochloride (362 mg, 5.40 mmol) and 4-(chlorosulfonyl)benzoic acid (400 mg, 1.81 mmol) in dichloromethane (5 mL) added in portions at 25° C. The resulting solution was stirred for 4 h at 25° C. The reaction mixture was quenched with water (20 mL). The product was extracted with ethyl acetate (3×30 mL). The combined organic layers were dried over anhydrous sodium sulfate, filtered and concentrated under vacuum. The residue was purified by preparative thin layer chromatography eluting with dichloromethane/methanol (20:1, v/v) to afford 4-(methylsulfamoyl)benzoic acid as a light yellow solid (Intermediate 2-136, 214 mg, 55%). LCMS: (ESI) m/z 216 [M+H].

Example 54: Intermediate 2-140. 3-benzyl-1-methyl-1H-pyrazole-4-carboxylic acid

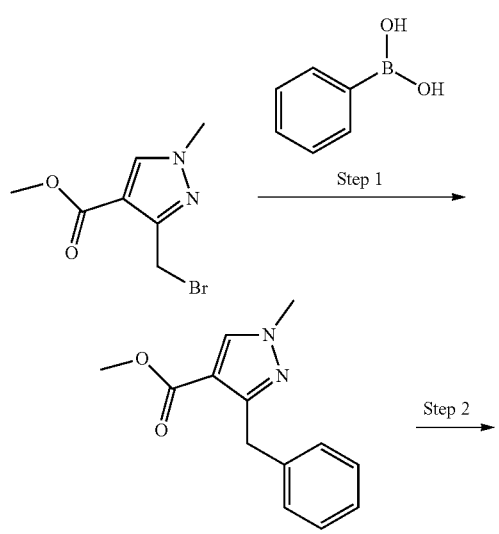

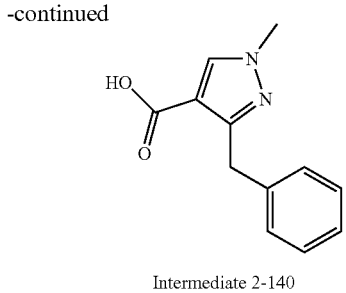

Intermediate 2-140

Step 1. Methyl 3-benzyl-1-methyl-11H-pyrazole-4-carboxylate

A 100-mL round-bottom flask flushed with nitrogen was charged with methyl 3-(bromomethyl)-1-methyl-1H-pyrazole-4-carboxylate (600 mg, 2.60 mmol), Pd(dppf)$_2$Cl$_2$CH$_2$Cl$_2$ (200 mg, 0.27 mmol), potassium carbonate (674 mg, 4.88 mmol), 1,4-dioxane (40 mL), water (4 mL) and phenylboronic acid (600 mg, 4.88 mmol). The resulting solution was stirred for 16 h at 100° C. under nitrogen. After cooling to 25° C., the reaction was quenched with water (20 mL) and the product was extracted with ethyl acetate (3×30 mL). The combined organic layers were washed with brine (3×20 mL), dried over anhydrous sodium sulfate, filtered and concentrated under vacuum. The residue was purified by column chromatography eluting with ethyl acetate/petroleum ether (1:1, v/v) to afford methyl 3-benzyl-1-methyl-1H-pyrazole-4-carboxylate (150 mg, 26%). LCMS: (ES) m/z 231 [M+H].

Step 2. 3-Benzyl-1-methyl-1H-pyrazole-4-carboxylic acid

The title compound was prepared according to the procedure outlined in Example 10, Step 2, utilizing—methyl 3-benzyl-1-methyl-1H-pyrazole-4-carboxylate (Step 1, 150 mg, 0.65 mmol),—as starting material (Intermediate 2-140, 160 mg, >95%). LCMS: (ES) m/z 217 [M+H].

Example 55: Intermediate 2-141. 1-Methyl-3-(1-phenylethyl)-1H-pyrazole-4-carboxylic acid

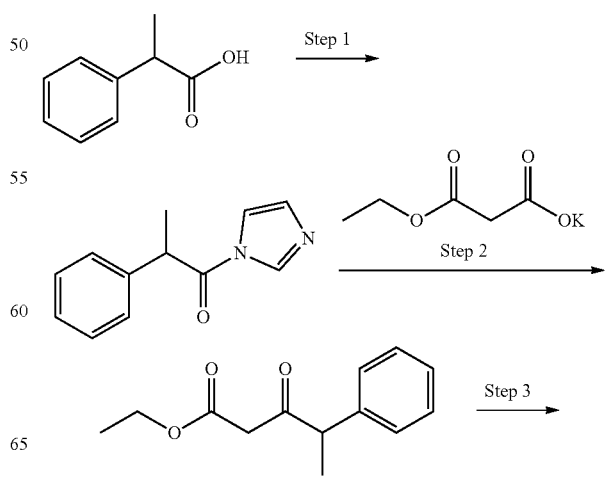

213

-continued

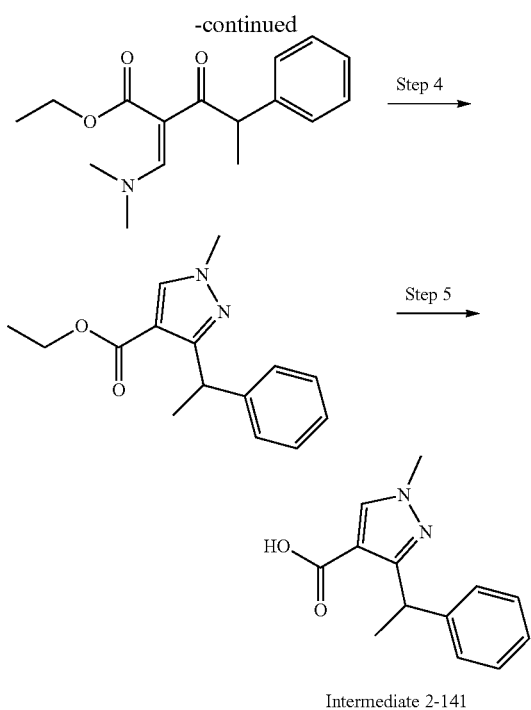

Intermediate 2-141

Step 1. 1-(1H-imidazol-1-yl)-2-phenylpropan-1-one

A 500-mL round-bottom flask fitted with a magnetic stir bar was charged with 2-phenylpropanoic acid (15 g, 100 mmol), acetonitrile (200 mL) and 1-[(1H-imidazol-1-yl) carbonyl]-1H-imidazole (16.2 g, 99.9 mmol). The resulting solution was stirred for 2 h at 25° C. The mixture was concentrated under vacuum and the residue was diluted with water (50 mL). The product was extracted with dichloromethane (3×100 mL). The combined organic layers were washed with brine (50 mL), dried over anhydrous sodium sulfate, filtered and concentrated under vacuum to give 1-(1H-imidazol-1-yl)-2-phenylpropan-1-one (28 g, >95%). LCMS: (ES) m-z 201 [M+H].

Step 2. Ethyl 3-oxo-4-phenylpentanoate

A 1-L round-bottom flask fitted with a magnetic stir bar was charged with 1-ethyl 3-potassium propanedioate (35 g, 206 mmol), acetonitrile (500 mL), triethylamine (31 g, 306 mmol), magnesium chloride (24 g, 252 mmol) and 1-(1H-imidazol-1-yl)-2-phenylpropan-1-one (Step 1, 20 g, 100 mmol). The resulting solution was stirred for 10 h at 25° C. The mixture was concentrated under vacuum. The residue was diluted with water (100 mL) and the product was extracted with dichloromethane (3×100 mL). The combined organic layers were dried over anhydrous sodium sulfate, filtered and concentrated under vacuum. The residue was purified by column chromatography eluting with ethyl acetate/petroleum ether (1:1, v/v) to give ethyl 3-oxo-4-phenylpentanoate (20 g, 91%). LCMS: (ES) m/z 221 [M+H].

Step 3. Ethyl-2-[(dimethylamino)methylidene]-3-oxo-4-phenylpentanoate

A 50-mL 3-necked round-bottom flask fitted with a magnetic stir bar, condenser and thermometer was charged with

214 ethyl 3-oxo-4-phenylpentanoate (Step 2, 1 g, 4.54 mmol) and N,N-dimethylformamide dimethyl acetal (30 mL). The resulting solution was stirred for 1 h at 110° C. After cooling to 25° C., the mixture was concentrated under vacuum to give ethyl-2-[(dimethylamino)methylidene]-3-oxo-4-phenylpentanoate as a yellow oil (1 g, 80%). LCMS: (ES) m/z 276 [M+H].

Step 4. Ethyl 1-methyl-3-(1-phenylethyl)-1H-pyrazole-4-carboxylate

A 100-mL round-bottom flask fitted with a magnetic stir bar was charged with ethyl-2-[(dimethylamino)methylidene]-3-oxo-4-phenylpentanoate (Step 3, 550 mg, 2.00 mmol), ethanol (20 mL), a solution of methylhydrazine in water (10 mL, 40%) and triethylamine (606 mg, 5.99 mmol). The resulting solution was stirred for 3 h at 25° C. The solvent was removed under vacuum and the residue was diluted with water (20 mL). The product was extracted with ethyl acetate (3×30 mL). The combined organic layers were dried over anhydrous sodium sulfate, filtered and concentrated under vacuum. The residue was purified by column chromatography eluting with ethyl acetate/petroleum ether (1:1, v/v) to give ethyl 1-methyl-3-(1-phenylethyl)-1H-pyrazole-4-carboxylate (340 mg, 66%). LCMS: (ES) m/z 259 [M+H].

Step 5. 1-Methyl-3-(1-phenylethyl)-1H-pyrazole-4-carboxylic acid

The title compound was prepared according to the procedure outline din Example 10, Step 2, utilizing ethyl 1-methyl-3-(1-phenylethyl)-1H-pyrazole-4-carboxylate (Step 4, 340 mg, 1.32 mmol) as starting material (Intermediate 2-141, 300 mg, >95%). LCMS: (ES) m/z 231 [M+H].

Example 56: Intermediate 2-144.
3-benzyl-5-methyl-1,2-oxazole-4-carboxylic acid

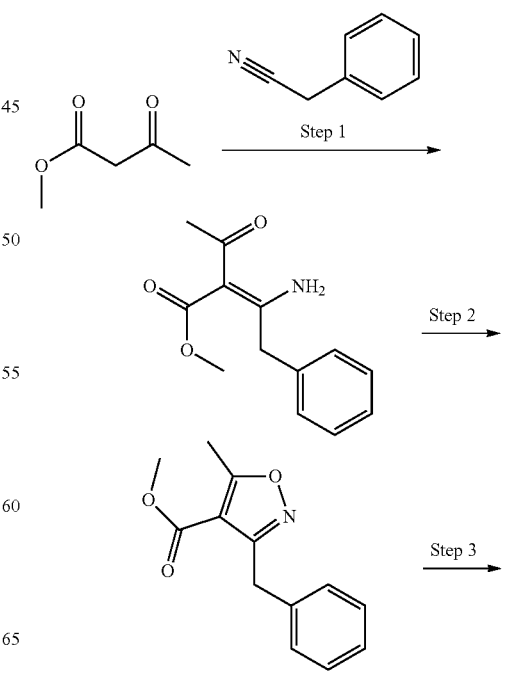

215
-continued

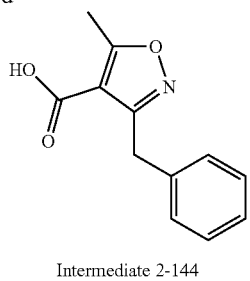

Intermediate 2-144

Step 1. Methyl (2E)-2-acetyl-3-amino-4-phenylbut-2-enoate

A 100-mL 3-necked round-bottom flask fitted with a magnetic stir bar, condenser and thermometer was charged with methyl 3-oxobutanoate (3.24 mL, 27.9 mmol), SnCl$_4$ in dichloromethane (3.5 mL, 3.50 mmol, 1 M), toluene (40 mL) and 2-phenylacetonitrile (3.46 mL). The resulting solution was stirred for 2 h at 110° C. After cooling to 25° C., the solids were removed by filtration. The filtrate was diluted with water (20 mL). The resulting mixture was extracted with dichloromethane (3×20 mL). The combined organic layers were washed with saturated ammonium bicarbonate (20 mL), dried over anhydrous sodium sulfate, filtered and concentrated under vacuum. The residue was purified by column chromatography eluting with ethyl acetate/petroleum ether (1:10, v/v) to afford methyl (2E)-2-acetyl-3-amino-4-phenylbut-2-enoate as a yellow oil (3.2 g, 49%). LCMS: (ES) m/z 234 [M+H].

Step 2. Methyl 3-benzyl-5-methyl-1,2-oxazole-4-carboxylate

A 100-mL 3-necked round-bottom flask fitted with a magnetic stir bar, condenser and thermometer was charged with triethylamine (0.75 mL), ethanol (15 mL) and hydroxylamine (375 mg, 11.35 mmol). The mixture was stirred for 1 h at 25° C. before adding methyl (2E)-2-acetyl-3-amino-4-phenylbut-2-enoate (Step 1, 1.05 g, 4.50 mmol). The reaction was heated to 100° C. and stirred for 5 h. After cooling to 25° C., the resulting mixture was concentrated under vacuum. The residue was purified by column chromatography eluting with ethyl acetate/petroleum ether (1:5, v/v) to afford methyl 3-benzyl-5-methyl-1,2-oxazole-4-carboxylate as a yellow oil (800 mg, 77%). LCMS: (ES) m/z 232 [M+H].

Step 3. 3-benzyl-5-methyl-1,2-oxazole-4-carboxylic acid

The title compound was prepared according to the procedure outlined in Example 14, utilizing methyl 3-benzyl-5-methyl-1,2-oxazole-4-carboxylate (Step 2, 300 mg, 1.30 mmol) as starting material, (Intermediate 2-144, 0.15 g, 53%). LCMS: (ES) m/z 218 [M+H].

216

Example 57: Intermediate 2-147. 1-methyl-4-(1H-pyrazol-4-yl)piperazine Hydrochloride salt

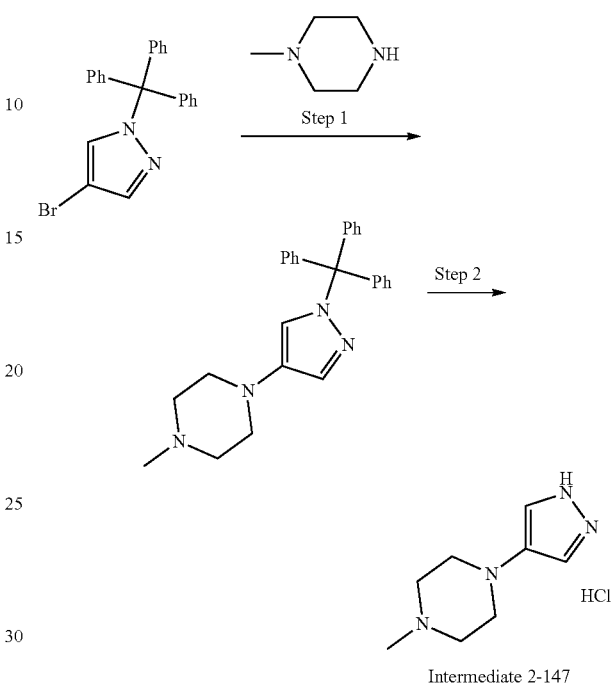

Intermediate 2-147

Step 1. 1-Methyl-4-(1-trityl-1H-pyrazol-4-yl)piperazine

A 100-mL 3-necked round-bottom flask fitted with a nitrogen balloon, magnetic stir bar, condenser and thermometer was charged with 4-bromo-1-(triphenylmethyl)-1H-pyrazole (1 g, 2.57 mmol), 1-methylpiperazine (516 mg, 5.15 mmol), sodium tert-butoxide (743 mg, 7.73 mmol), toluene (30 mL), tris(dibenzylideneacetone)dipalladium-chloroform adduct (207 mg, 0.20 mmol) and X-Phos (123 mg, 0.26 mmol). The solution was stirred for 16 h at 120° C. in an oil bath. After cooling to 25° C., the reaction was quenched with water (30 mL). The product was extracted with ethyl acetate (3×30 mL). The combined organic layers were dried over anhydrous sodium sulfate, filtered and concentrated under vacuum. The residue was purified by column chromatography eluting with dichloromethane/methanol (10:1, v/v) to afford 1-methyl-4-[1-(triphenylmethyl)-1H-pyrazol-4-yl]piperazine as a brown solid (200 mg, 19%). LCMS: (ESI) m/z 409 [M+H].

Step 2. 1-methyl-4-(1H-pyrazol-4-yl)piperazine Hydrochloride salt

A 100-mL round-bottom flask fitted with a magnetic stir bar was charged with 1-methyl-4-[1-(triphenylmethyl)-1H-pyrazol-4-yl]piperazine (Step 1, 200 mg, 0.49 mmol) and hydrogen chloride in 1,4-dioxane (15 mL, 3M). The solution was stirred for 2 h at 25° C. and concentrated under vacuum. The residue was diluted with ethyl acetate (20 mL). The solids were collected by filtration, washed with ethyl acetate (10 mL) and dried in an oven to afford the 1-methyl-4-(1H- pyrazol-4-yl)piperazine, HCl salt (Intermediate 2-147, 250 mg). LCMS: (ESI) m/z 167[M+H]

Example 58: Intermediate 2-148. 2H,4H,6H,7H-pyrano[4,3-c]pyrazole

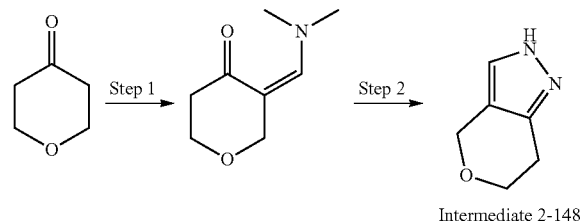

Intermediate 2-148

Step 1. (Z)-3-((dimethylamino)methylene)-tetrahydropyran-4-one

A 100-mL 3-necked round-bottom flask fitted with a magnetic stir bar, condenser and thermometer was charged with oxan-4-one (1 g, 9.99 mmol), DMF-DMA (30 mL). The solution was stirred for 3 h at 110° C. The reaction mixture was cooled to 25° C. and concentrated under vacuum to afford (Z)-3-((dimethylamino)methylene)tetrahydro-4H-pyran-4-one (600 mg, 39%). LCMS: (ESI) m/z 156 [M+H].

Step 2. 2H,4H,6H,7H-pyrano[4,3-c]pyrazole

A 50-mL 3-necked round-bottom flask fitted with a magnetic stir bar, condenser and thermometer was charged with (Z)-3-((dimethylamino)methylene)tetrahydro-4H-pyran-4-one (Step 1, 600 mg, 3.87 mmol), hydrazine (1 mL) and ethanol (20 mL). The solution was stirred for 5 h at 90° C. and cooled to 25° C. The solution was concentrated under vacuum and purified by column chromatography eluting with dichloromethane/methanol (30:1, v/v) to afford 2H,4H,6H,7H-pyrano[4,3-c]pyrazole as a white solid (Intermediate 2-148, 300 mg, 63%). LCMS: (ESI) m/z 125 [M+H].

Example 59: Intermediate 2-149. 5-((1-(cyclopropanecarbonyl)-4-hydroxypiperidin-4-yl)methyl)-1-(4-(4,4,5,5-tetramethyl-1,3,2-dioxaborolan-2-yl)phenyl)-1H-pyrazolo[3,4-d]pyrimidin-4(5H)-one

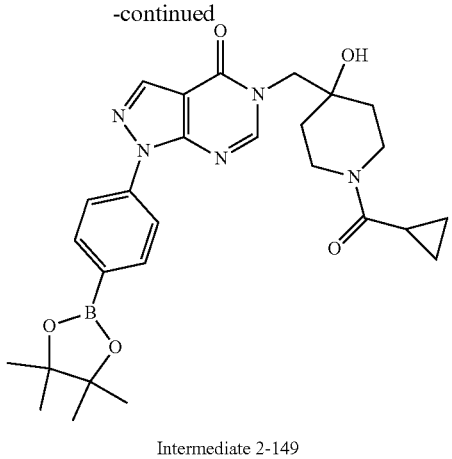

Intermediate 2-149

A 250-mL 3-necked round-bottom flask was fitted with a nitrogen balloon, magnetic stir bar, condenser and thermometer was charged with 1-(4-bromophenyl)-5-((1-(cyclopropane-carbonyl)-4-hydroxypiperidin-4-yl)methyl)-1H-pyrazolo[3,4-d]pyrimidin-4(5H)-one (2.5 g, 5.29 mmol), 4,4,5,5-tetramethyl-2-(tetramethyl-1,3,2-dioxaborolan-2-yl)-1,3,2-dioxaborolane (2 g, 7.88 mmol), 1,1'-bis(diphenylphosphino) ferrocenepalladium(II)dichloride dichloromethane complex (217 mg, 0.27 mmol), potassium acetate (1.56 g, 15.90 mmol) and N,N-dimethylformamide (50 mL). The resulting solution was stirred for 5 h at 90° C. under nitrogen. After cooling to 23° C., the reaction was with water (200 mL). The product was extracted with ethyl acetate (4×200 mL). The combined organic layers were dried over anhydrous sodium sulfate, filtered and concentrated under vacuum. The solids were collected by filtration, washed with methanol (100 mL) and dried in an oven to afford 5-((1-(cyclopropanecarbonyl)-4-hydroxypiperidin-4-yl)methyl)-1-(4-(4,4,5,5-tetramethyl-1,3,2-dioxaborolan-2-yl)phenyl)-1H-pyrazolo[3,4-d]pyrimidin-4(5H)-one (Intermediate 2-149, 1.80 g, 65%). $^1$H-NMR (400 MHz, DMSO-$d_6$) δ 0.65-0.75 (m, 4H), 1.32 (s, 12H), 1.35-1.65 (m, 4H), 1.92-2.00 (m, 1H), 2.92-3.01 (m, 1H), 3.34-3.45 (m, 1H), 3.95-4.15 (m, 4H), 4.97 (s, 1H), 7.86 (d, J=8.4 Hz, 2H), 8.17 (d, J=8.4 Hz, 2H), 8.39 (s, 1H), 8.40 (s, 1H). LCMS: (ESI) m/z 520 [M+H].

Example 60: Intermediate 2-152. 4-((1-(3-bromophenyl)-4-oxo-1H-pyrazolo[3,4-d]pyrimidin-5(4H)-yl) methyl)-4-hydroxy-N,N-dimethylpiperidine-1-carboxamide

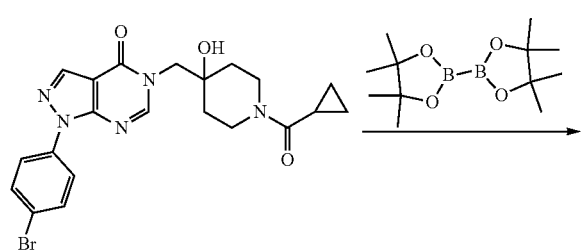

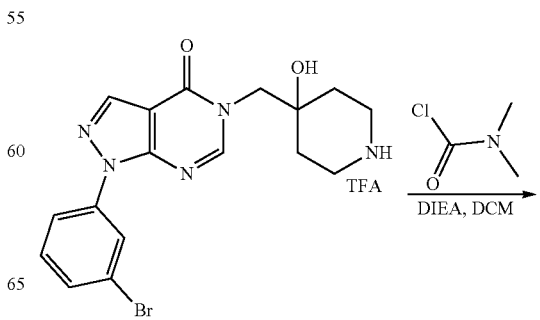

219

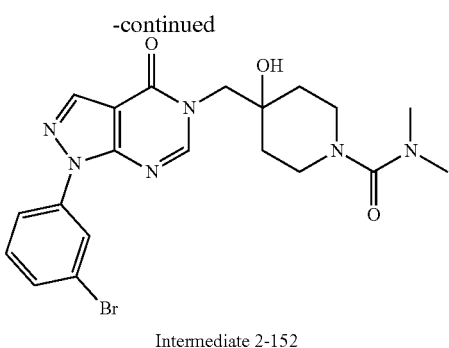

Intermediate 2-152

A 250-mL round-bottom flask was charged with the TFA salt of 1-(3-bromophenyl)-5-((4-hydroxypiperidin-4-yl)methyl)-1H-pyrazolo[3,4-d]pyrimidin-4(5H)-one (4.40 g, 9.98 mmol), dichloromethane (100 mL) and DIPEA (3.87 g, 29.94 mmol). This was followed by the addition of a solution of N,N-dimethylcarbamoyl chloride (1.28 g, 11.90 mmol) in dichloromethane (30 mL) at 0° C. After addition, the resulting solution was stirred for 1 h at 0° C. The reaction was then quenched by the addition of 50 mL of water. The resulting mixture was extracted with dichloromethane (3×100 mL) and the organic layers combined, washed with brine (100 mL), dried over anhydrous sodium sulfate, filtered and concentrated under vacuum. The residue was purified by column chromatography eluting with dichloromethane/methanol (20:1, v/v) to afford 4-((1-(3-bromophenyl)-4-oxo-1H-pyrazolo[3,4-d]pyrimidin-5(4H)-yl)methyl)-4-hydroxy-N,N-dimethylpiperidine-1-carboxamide (Intermediate 2-152, 3.28 g, 69%). $^1$H-NMR (400 MHz, DMSO-$d_6$) δ 1.36-1.39 (m, 2H), 1.54-1.61 (m, 2H), 2.72 (s, 6H), 2.95-3.01 (m, 2H), 3.27-3.32 (m, 2H), 4.04 (s, 2H), 4.88 (brs, 1H), 7.53-7.57 (m, 1H), 7.60-7.63 (m, 1H), 8.12-8.15 (m, 1H), 8.34 (t, J=2.4 Hz, 1H), 8.40 (s, 1H), 8.41 (s, 1H). LCMS: (ESI) m/z 475, 477 [M+H].

Table 29: The Intermediates in Table 29 were prepared according to the procedure outlined in Example 60.

TABLE 29

| Intermediate No.: | Precursor Used | MS (ESI, m/z) [M + H]. |
|---|---|---|
| Intermediate 2-828a. 4-[[1-(3-bromo-4-fluorophenyl)-4-oxo-1H,4H,5H-pyrazolo[3,4-d]pyrimidin-5-yl]methyl]-4-hydroxy-N,N-dimethylpiperidine-1-carboxamide | 1-(3-bromo-4-fluorophenyl)-5-((4-hydroxypiperidin-4-yl)methyl)-1,5-dihydro-4H-pyrazolo[3,4-d]pyrimidin-4-one, TFA salt | 493 |

Example 61: Intermediate 2-103a. Methyl 4-hydroxy-1-methylcyclohexanecarboxylate

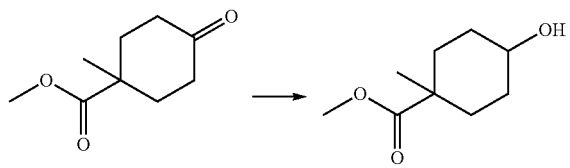

220

Step 1. Methyl 4-hydroxy-1-methylcyclohexanecarboxylate

A 100-mL 3-necked round-bottom flask fitted with a magnetic stir bar and thermometer was charged with methyl 1-methyl-4-oxocyclohexane-1-carboxylate (552 mg, 3.24 mmol) and methanol (20 mL). Then sodium borohydride (226 mg, 5.97 mmol) was added at 0° C. The resulting solution was stirred for 3 h at 0° C. and concentrated under vacuum. The solids were filtered and washed with ethyl acetate (3×50 mL). The filtrate was concentrated under vacuum to afford methyl 4-hydroxy-1-methylcyclohexane-1-carboxylate (400 mg, 68%). LCMS: (ESI) m/z 173 [M+H].

Example 62: Intermediate 2-67. 5-(Pyridin-2-yloxy)picolinic acid

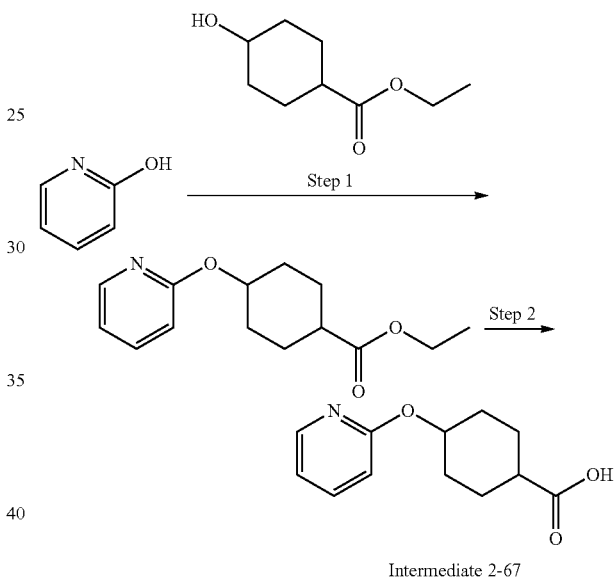

Intermediate 2-67

Step 1. Ethyl 4-(pyridin-2-yloxy)cyclohexane-1-carboxylate

A 100-mL 3-necked round-bottom flask equipped with a nitrogen balloon was charged with ethyl 4-hydroxycyclohexane-1-carboxylate (1.81 g, 10.51 mmol), pyridin-2-ol (500 mg, 5.26 mmol), triphenylphosphine (2.76 g, 10.52 mmol) and tetrahydrofuran (20 mL). A solution of diethyl azodicarboxylate (1.83 g, 10.51 mmol) in tetrahydrofuran (5 mL) was added at 0° C. The resulting solution was stirred 16 h at 23° C. and then concentrated under vacuum. The residue was purified by column chromatography eluting with ethyl acetate/petroleum ether (1:30 to 1:10 v/v) to afford ethyl 4-(pyridin-2-yloxy)cyclohexane-1-carboxylate (600 mg, 46%). LCMS: (ESI) m/z 250 [M+H].

Step 2. 4-(Pyridin-2-yloxy)cyclohexane-1-carboxylic acid

The title compound was prepared according to the procedure outlined in Example 10, Step 2, utilizing ethyl 4-(pyridin-2-yloxy)cyclohexane-1-carboxylate (Step 1, 600 mg, 2.41 mmol), as starting material (Intermediate 2-67, 450 mg, 85%). LCMS (ESI) m/z 222 [M+H].

The Intermediates in Table 30 below were synthesized according to the procedures outlined above.

TABLE 30

| Intermediate No.: | Precursor Used | MS (ESI, m/z) [M + H] |
|---|---|---|
| Intermediate 2-103. 1-methyl-4-(pyridin-2-yloxy) cyclohexanecarboxylic acid | pyridin-2-ol and methyl 4-hydroxy-1-methylcyclohexane-1-carboxylate (Intermediate 2-103a) | 236 |
| Intermediate 2-104. 4-[(5-fluoropyridin-2-yl)oxy]cyclohexane-1-carboxylic acid | 5-fluoropyridin-2-ol and ethyl 4-hydroxycyclohexane-1-carboxylate | 240 |
| Intermediate 2-105. 4-(6-fluoropyridin-2-yloxy) cyclohexanecarboxylic acid | 6-fluoropyridin-2-ol ethyl 4-hydroxycyclohexane-1-carboxylate | 240 |
| Intermediate 2-106. 4-(pyridin-3-yloxy) cyclohexanecarboxylic acid | 3-hydroxypyridine and ethyl 4-hydroxycyclohexane-1-carboxylate | 222 |
| Intermediate 2-113. (1r,4r)-4-(Pyridin-2-yloxy) cyclohexanecarboxylic acid | cis-4-hydroxycyclohexane-1-carboxylate and pyridin-2-ol | 222 |
| Intermediate 2-128. (1s,3s)-3-(pyridin-2-yloxy)cyclobutane-1-carboxylic acid | methyl (1r,3r)-3-hydroxycyclobutane-1-carboxylate and pyridin-2-ol | 194 |
| Intermediate 2-4000. (1r,4r)-4-((2-methylpyrimidin-5-yl)oxy)cyclohexane-1-carboxylic acid | cis-4-hydroxycyclohexane-1-carboxylate and 2-methyl-4-hydroxypyrimidine | 237 |

Example 63: Intermediate 2-68.
5-(Pyridin-2-yloxy)picolinic acid

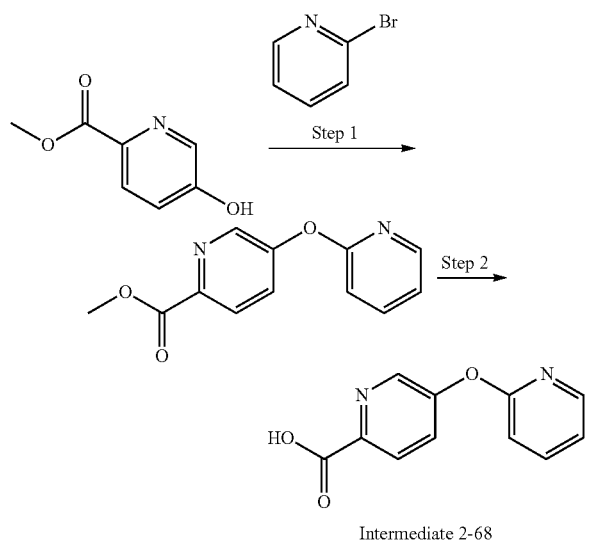

Intermediate 2-68

Step 1. Methyl 5-(pyridin-2-yloxy)picolinate

A 50-mL round-bottom flask was charged with methyl 5-hydroxypyridine-2-carboxylate (306 mg, 2.00 mmol), potassium carbonate (552 mg, 3.99 mmol) and 2-bromopyridine (632 mg, 4.00 mmol) in DMF (10 mL). The resulting solution was stirred for 3 h at 150° C. and cooled to 23° C. The reaction was quenched with water (20 mL) and the product was extracted with dichloromethane (3×10 mL). The organic layers were combined, dried over anhydrous sodium sulfate, filtered and concentrated under vacuum. The residue was purified by preparative thin layer chromatography eluting with 1/30-1/4 ethyl acetate/petroleum ether (1:30 to 1:4 v/v) to afford methyl 5-(pyridin-2-yloxy)picolinate (320 mg, 70%). LCMS: (ESI) m/z 231 [M+H].

Step 2. 5-(Pyridin-2-yloxy)picolinic acid

The title compound was prepared according to the procedure outlined in Example 8, Step 2, utilizing methyl 5-(pyridin-2-yloxy)picolinate (Step 1, 230 mg, 1.00 mmol) as starting material (Intermediate 2-68, 180 mg, 83%). LCMS: (ESI) m/z 217 [M+H].

The compounds below were also synthesized according to the procedures outlined above.

TABLE 31

| Intermediate No.: | Precursor Used | MS (ESI, m/z) [M + H] |
|---|---|---|
| Intermediate 2-69. 4-(Pyridin-2-yloxy)benzoic acid | 4-hydroxybenzoic acid and 2-chloropyridine | 216 |
| Intermediate 2-70. 4-(pyrimidin-2-yloxy)benzoic acid | 4-hydroxybenzoic acid and 2-bromopyrimidine | 217 |
| Intermediate 2-169. (1r,4r)-4-((5-cyanopyridin-2-yl)oxy)cyclohexane-1-carboxylic acid | cis-4-hydroxycyclohexane-1-carboxylate and 6-chloronicotinonitrile | 247 |

TABLE 31-continued

| Intermediate No.: | Precursor Used | MS (ESI, m/z) [M + H] |
|---|---|---|
| Intermediate 2-170. (1r,4r)-4-((6-methylpyrazin-2-yl)oxy)cyclohexane-1-carboxylic acid | cis-4-hydroxycyclohexane-1-carboxylate and 2-chloro-6-methylpyrazine | 237 |
| Intermediate 2-171. (1r,4r)-4-((2-methylpyrimidin-4-yl)oxy)cyclohexane-1-carboxylic acid | cis-4-hydroxycyclohexane-1-carboxylate and 4-chloro-2-methylpyrimidine | 237 |
| Intermediate 2-82. 4-(1-methyl-1H-pyrazol-4-yloxy)benzoic acid | 4-hydroxybenzoic acid and 4-chloro-1-methyl-1H-pyrazole | 219 |
| Intermediate 2-118. 2-(Pyridin-2-yloxy)oxazole-5-carboxylic acid | 2-chloro-1,3-oxazole-5-carboxylate and pyridin-2-ol | 207 |

Example 64: Intermediate 2-102. 4-(Pyrimidin-2-yloxy)cyclohexanecarboxylate acid

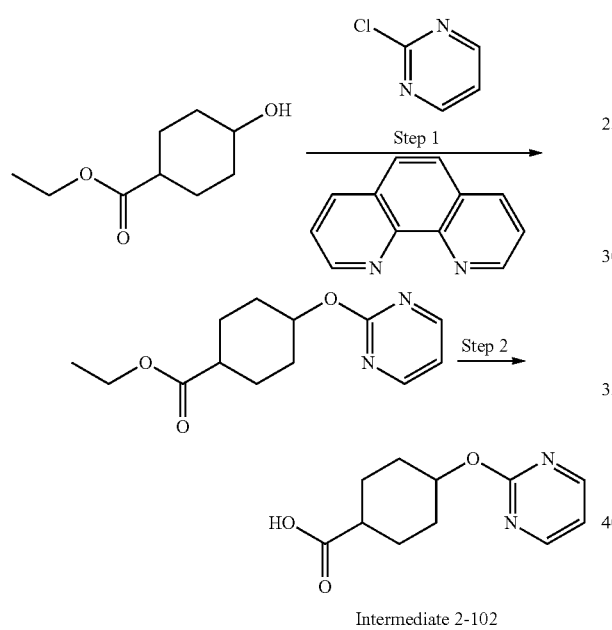

Intermediate 2-102

Step 1. Ethyl 4-(pyrimidin-2-yloxy)cyclohexanecarboxylate

A 100-mL 3-necked round-bottom flask fitted with a nitrogen balloon, magnetic stir bar, condenser and thermometer was charged with ethyl 4-hydroxycyclohexane-1-carboxylate (1 g, 5.81 mmol), CuI (111 mg, 0.58 mmol), Cs$_2$CO$_3$ (3.79 g, 11.6 mmol), toluene (25 mL), 2-chloropyrimidine (665 mg, 5.81 mmol), 1,10-phenanthroline (209 mg, 1.16 mmol). The resulting solution was stirred for 24 h at 120° C. in an oil bath. The resulting solution was cooled to 20° C. and quenched with water (50 mL). The product was extracted with ethyl acetate (5×50 mL). The combined organic layers were dried over anhydrous sodium sulfate, filtered and concentrated under vacuum. The residue was purified by column chromatography eluting with ethyl acetate/hexane (1:4, v/v) to afford ethyl 4-(pyrimidin-2-yloxy)cyclohexane-1-carboxylate (0.356 g, 24%). LCMS: (ESI) m/z 251 [M+H].

Step 2. 4-(Pyrimidin-2-yloxy)cyclohexanecarboxylic acid

The title compound was prepared according to procedure outlined in Example 10, Step 2, utilizing ethyl 4-(pyrimidin-2-yloxy)cyclohexane-1-carboxylate (Step 1, 356 mg, 1.42 mmol) as starting material (Intermediate 2-102, (222 mg 70%) LCMS: (ESI) m/z 223 [M+H].

Example 65: Intermediate 2-145. 4-(5-(2-Hydroxyethoxy)pyridin-2-yloxy)benzoic acid

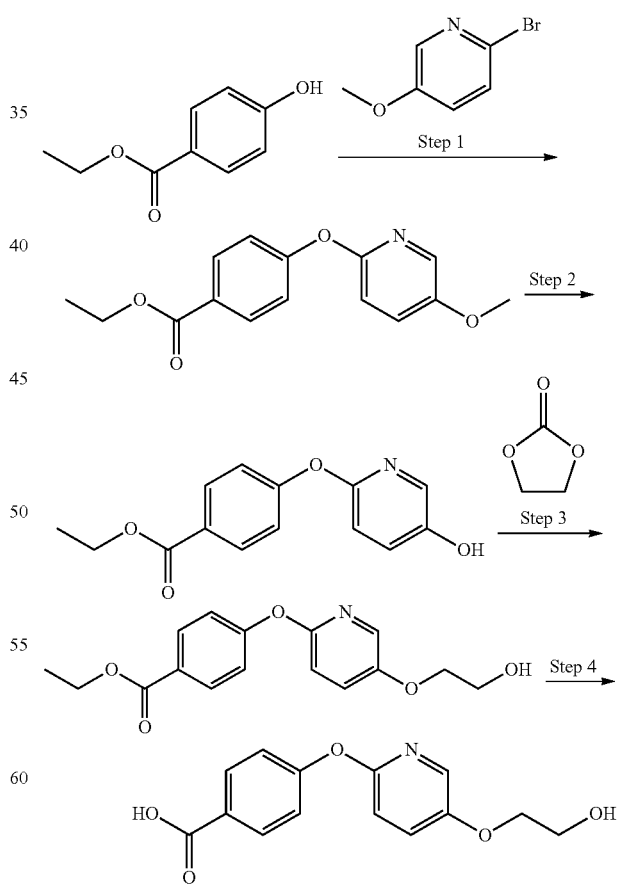

Intermediate 2-145

Step 1. Ethyl 4-(5-methoxypyridin-2-yloxy)benzoate

A 50-mL 3-necked round-bottom flask fitted with a nitrogen balloon, magnetic stir bar, condenser and thermometer was charged with ethyl 4-hydroxybenzoate (1.66 g, 9.99 mmol), DMSO (20 mL), CuI (95 mg, 0.50 mmol), picolinic acid (123 mg, 1.00 mmol), $K_3PO_4$ (4.24 g, 19.97 mmol) and 2-bromo-5-methoxypyridine (1.88 g, 10.0 mmol). The resulting solution was stirred for 16 h at 90° C. After cooling to 25° C., the reaction was quenched with water (50 mL). The product was extracted with ethyl acetate (3×50 mL). The combined organic layers were washed with brine (50 mL), dried over anhydrous sodium sulfate, filtered and concentrated under vacuum. The residue was purified by column chromatography eluting with dichloromethane/methanol (10:1, v/v) to afford ethyl 4-(5-methoxypyridin-2-yloxy)benzoate as a yellow solid (1.20 g, 44%). LCMS: (ESI) m/z 274 [M+H].

Step 2. Ethyl 4-(5-hydroxypyridin-2-yloxy)benzoate

A 25-mL round-bottom flask fitted with a magnetic stir bar was charged with ethyl 4-(5-methoxypyridin-2-yloxy)benzoate (Step 1, 320 mg, 1.17 mmol), dichloromethane (10 mL) and a solution of $BBr_3$ in dichloromethane (1.5 mL, 1.5 mmol, 1M). The resulting solution was stirred for 16 h at 25° C. The pH was adjusted to 7-8 with saturated sodium bicarbonate. The resulting mixture was extracted with dichloromethane (3×30 mL). The combined organic layers were washed brine (30 mL), dried over anhydrous sodium sulfate, filtered and concentrated under vacuum. The residue was purified by preparative thin layer chromatography eluting with ethyl acetate/petroleum ether (2:1, v/v) to afford ethyl 4-(5-hydroxypyridin-2-yloxy)benzoate (130 mg, 43%). LCMS: (ESI) m/z 260 [M+H]

Step 3. Ethyl 4-(5-(2-hydroxyethoxy)pyridin-2-yloxy)benzoate

A 50-mL 3-necked round-bottom flask fitted with a magnetic stir bar, condenser and thermometer was charged with ethyl 4-(5-hydroxypyridin-2-yloxy)benzoate (Step 2, 259 mg, 1.00 mmol), N,N-dimethylformamide (15 mL), cesium carbonate (652 mg, 2.00 mmol) and 1,3-dioxolan-2-one (132 mg, 1.50 mmol). The resulting solution was stirred for 3 h at 80° C. The reaction mixture was cooled to 27° C. The reaction was quenched with water (25 mL). The product was extracted with dichloromethane (3×25 mL). The combined organic layers were dried over anhydrous sodium sulfate, filtered and concentrated under vacuum. The residue was purified by preparative thin layer chromatography eluting with ethyl acetate/petroleum ether (5:1, v/v) to afford ethyl 4-(5-(2-hydroxyethoxy)pyridin-2-yloxy)benzoate as a yellow solid (242 mg, 80%). LCMS: (ESI) m/z 304 [M+H].

Step 4. 4-(5-(2-Hydroxyethoxy)pyridin-2-yloxy)benzoic acid

The title compound was prepared according to the procedure outlined in Example 8, Step 2, utilizing ethyl 4-(5-(2-hydroxyethoxy)pyridin-2-yloxy)benzoate (Step 3, 242 mg, 0.80 mmol) as starting material (Intermediate 2-145, 180 mg, 82%). LCMS: (ESI) m/z 276 [M+H].

Example 66: Intermediate 2-146. trans-4-(Pyridazin-3-yloxy) cyclohexanecarboxylic acid

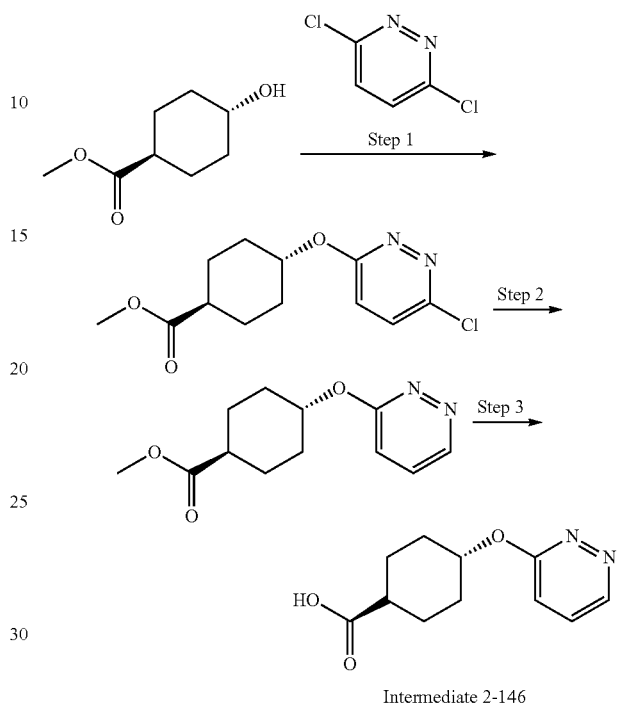

Intermediate 2-146

Step 1. Trans-methyl 4-(6-chloropyridazin-3-yloxy)cyclohexanecarboxylate

A 5-mL microwave tube fitted with a magnetic stir bar was charged with methyl trans-4-hydroxycyclohexane-1-carboxylate (200 mg, 1.26 mmol), 3,6-dichloropyridazine (188 mg, 1.26 mmol) and N,N-dimethylformamide (2.5 mL) followed by sodium hydride (65.6 mg, 1.64 mmol, 60%) added in portions. The microwave tube was sealed until the bubbling ceased and the reaction mixture was irradiated with microwave for 30 min at 100° C. After cooling to 25° C., the resulting mixture was poured into water (10 mL) The mixture was extracted with ethyl acetate (3×30 mL) and the combined organic layers were dried over anhydrous sodium sulfate, filtered and concentrated under vacuum. The residue was purified by preparative thin layer chromatography eluting with ethyl acetate/petroleum (1:3, v/v) to afford methyl trans-4-[(6-chloropyridazin-3-yl)oxy]cyclohexane-1-carboxylate as an off-white solid (80 mg, 23%). LCMS: (ESI) m/z 271, 273[M+H].

Step 2. Trans-methyl 4-(pyridazin-3-yloxy)cyclohexanecarboxylate

A 100-mL round-bottom flask fitted with a hydrogen balloon, magnetic stir bar was charged with methyl trans-4-[(6-chloropyridazin-3-yl)oxy]cyclohexane-1-carboxylate (Step 1, 80 mg, 0.30 mmol), methanol (15 mL), triethanolamine (59.8 mg, 0.59 mmol) and palladium on carbon (30 mg, 0.03 mmol, 10%). The solution was stirred for 2 h at 25° C. under hydrogen. The solids were removed by filtration. The filtrate was concentrated under vacuum to afford methyl trans-4-(pyridazin-3-yloxy)cyclohexane-1-carboxylate as a colorless oil (60 mg). LCMS: (ESI) m/z 237[M+H].

Step 3.
Trans-4-(pyridazin-3-yloxy)cyclohexanecarboxylic acid

The title compound was prepared according to the procedure outlined in Example 8, Step 2, utilizing methyl trans-4-(pyridazin-3-yloxy)cyclohexane-1-carboxylate (Step 2, 60 mg, 0.25 mmol) as starting material (Intermediate 2-146, 45 mg). LCMS: (ESI) m/z 223 [M+H].

Example 67: Intermediate 172. trans-4-[[6-(azetidin-1-yl)pyridin-2-yl]oxy]cyclohexane-1-carboxylic acid

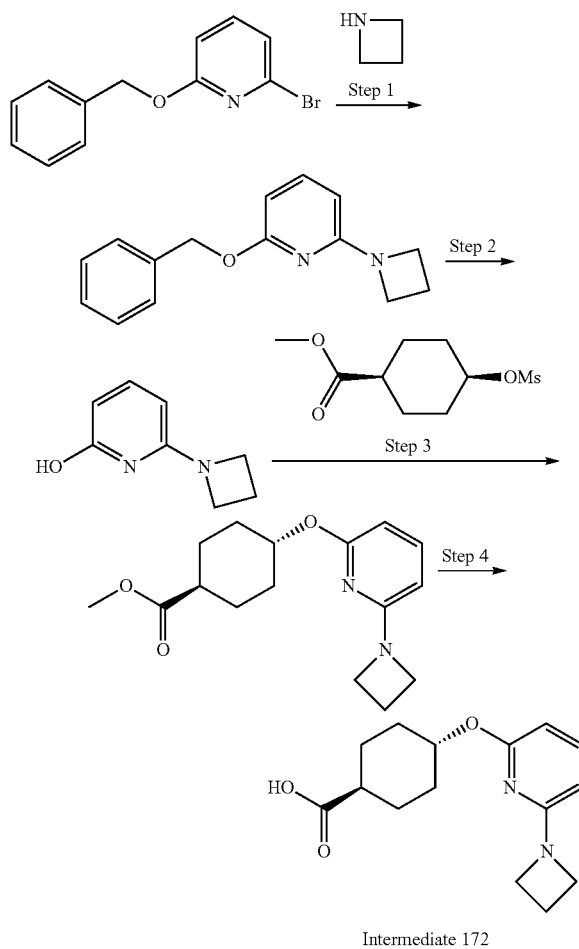

Intermediate 172

Step 1. 2-(azetidin-1-yl)-6-(benzyloxy)pyridine

A 250-mL 3-necked round-bottom flask fitted with a nitrogen balloon, magnetic stir bar and thermometer was charged with 2-(benzyloxy)-6-bromopyridine (1 g, 3.79 mmol), Pd$_2$(dba)$_3$·CHCl$_3$ (400 mg, 0.39 mmol), BiNAP (480 mg, 0.77 mmol), potassium tert-butoxide (732 mg, 6.52 mmol), toluene (20 mL) and azetidine (440 mg, 7.71 mmol). The resulting solution was stirred for 6 h at 80° C. After cooling to 25° C., the reaction was quenched with water (20 mL). The product was extracted with ethyl acetate (4×30 mL) and the organic layers were combined. The solution was dried over anhydrous sodium sulfate, filtered and concentrated under vacuum. The residue was purified by column chromatography eluting with ethyl acetate/petroleum ether (1:5, v/v) to afford 2-(azetidin-1-yl)-6-(benzyloxy)pyridine as light yellow oil (0.6 g, 66%). LCMS: (ESI) m/z 241 [M+H].

Step 2. 6-(azetidin-1-yl)pyridin-2-ol

The title compound was prepared according to the procedure outlined in Example 180 utilizing 2-(azetidin-1-yl)-6-(benzyloxy)pyridine (Step 1, 500 mg, 2.08 mmol), as starting material (0.35 g, >95%). LCMS: (ESI) m/z 151[M+H].

Step 3. Trans-methyl-4-[[6-(azetidin-1-yl)pyridin-2-yl]oxy]cyclohexane-1-carboxylate The title compound was prepared according to the procedure outlined in Example 66, Step 1, utilizing 6-(azetidin-1-yl)pyridin-2-ol (Step 2, 127 mg, 0.85 mmol) and cis-methyl-4-(methanesulfonyloxy)cyclohexane-1-carboxylate (200 mg, 0.85 mmol) as starting materials. The title compound was purified by preparative TLC eluting with ethyl acetate/petroleum ether (1:3, v/v) (60 mg, 24%). LCMS: (ESI) m/z 291 [M+H].

Step 4. Trans-4-[[6-(azetidin-1-yl)pyridin-2-yl]oxy]cyclohexane-1-carboxylic acid The title compound was prepared according to the procedure outlined in Example 10, Step 2, utilizing trans-methyl-4-[[6-(azetidin-1-yl)pyridin-2-yl]oxy]cyclohexane-1-carboxylate (Step 3, 60 mg, 0.21 mmol) as starting material (34 mg, 59%). LCMS: (ESI) r/z 277 [M+H].

Example 68: Intermediate 175. cis-4-(pyrazin-2-yloxy)cyclohexanecarboxylic acid

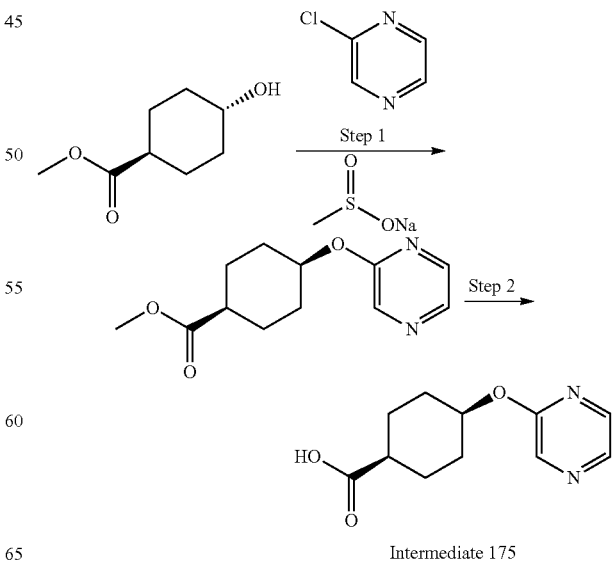

Intermediate 175

Step 1. Cis-methyl 4-(pyrazin-2-yloxy)cyclohexanecarboxylate

A 100-mL 3-necked round-bottom flask fitted with a magnetic stir bar, condenser and thermometer was charged with methyl trans-4-hydroxycyclohexane-1-carboxylate (400 mg, 2.53 mmol), N,N-dimethylformamide (15 mL), 2-chloropyrazine (348 mg, 3.03 mmol), potassium carbonate (1.05 g, 7.60 mmol) and sodium methanesulfinate (387 mg, 3.79 mmol). The resulting mixture was stirred for 16 h at 120° C. in an oil bath. After cooling to 25° C., the reaction was quenched with water (30 mL). The product was extracted with ethyl acetate (3×30 mL) and the combined organic layers dried over anhydrous sodium sulfate, filtered and concentrated under vacuum. The residue was purified by preparative thin layer chromatography eluting with ethyl acetate/petroleum (1:4, v/v) to afford methyl cis-4-(pyrazin-2-yloxy)cyclohexane-1-carboxylate (80 mg, 13%). LCMS: (ESI) m/z 237[M+H].

Step 2. Cis-4-(pyrazin-2-yloxy)cyclohexanecarboxylic acid

The title compound was prepared according to the procedure outline in Example 8, Step 2, utilizing methyl cis-4-(pyrazin-2-yloxy)cyclohexane-1-carboxylate (Step 1, 80 mg, 0.34 mmol) as starting material (65 mg, 86%). LCMS: (ESI) m/z 223[M+H].

The Intermediates in Table 32 below were synthesized according to the procedures outlined above.

TABLE 32

| Intermediate No.: | Precursor Used | MS (ESI, m/z) [M + H] |
|---|---|---|
| Intermediate 2-132. trans-4-(pyrazin-2-yloxy)cyclohexanecarboxylic acid | methyl cis-4-hydroxycyclohexane-1-carboxylate and 2-chloropyrazine | 223 |

Example 69: Intermediate 2-107. 4-[(1-methyl-1H-pyrazol-4-yl)oxy]cyclohexane-1-carboxylic

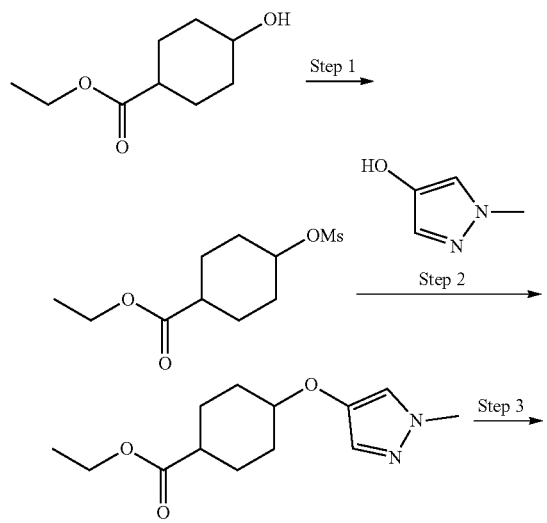

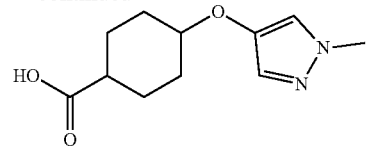

Intermediate 2-107

Step 1. Ethyl 4-(methanesulfonyloxy)cyclohexane-1-carboxylate

A 250-mL 3-necked round-bottom flask fitted with a magnetic stir bar and thermometer was charged with ethyl 4-hydroxycyclohexane-1-carboxylate (1.5 g, 8.71 mmol), triethylamine (2.64 g, 26.09 mmol) and dichloromethane (50 mL). To the reaction was added methanesulfonyl chloride (1.49 g, 13.01 mmol) added dropwise with stirring at 0° C. The resulting solution was stirred for 2 h at 25° C. The resulting solution was diluted with water (20 mL) and the product was extracted with dichloromethane (3×20 mL). The combined organic layers were dried over anhydrous sodium sulfate, filtered and concentrated under vacuum. The residue was purified by column chromatography eluting with ethyl acetate/petroleum ether (1:5, v/v) to afford ethyl 4-(methanesulfonyloxy) cyclohexane-1-carboxylate as a light yellow oil (1.2 g, 55%). LCMS: (ESI) m/z 251 [M+H], 155 [M-OMs].

Step 2. Ethyl 4-[(1-methyl-1H-pyrazol-4-yl)oxy]cyclohexane-1-carboxylate

A 100-mL 3-necked round-bottom flask fitted with a magnetic stir bar, condenser and thermometer was charged with ethyl 4-(methanesulfonyloxy)cyclohexane-1-carboxylate (Step 1, 600 mg, 2.40 mmol), potassium carbonate (993 mg, 7.18 mmol), N,N-dimethylformamide (10 mL) and 1-methyl-1H-pyrazol-4-ol (353 mg, 3.60 mmol). The resulting solution was stirred 7 h at 60° C. and cooled to 25° C. The product was diluted with water (40 mL) and extracted with dichloromethane (3×50 mL). The combined organic layers were dried over sodium sulfate, filtered and concentrated under vacuum. The residue was purified by a preparative TLC plate eluting with ethyl acetate/petroleum ether (1:1, v/v) to afford ethyl 4-[(1-methyl-1H-pyrazol-4-yl)oxy] cyclohexane-1-carboxylate as a yellow oil (0.42 g, 69%). LCMS: (ESI) m/z 253 [M+H].

Step 3. 4-[(1-methyl-1H-pyrazol-4-yl)oxy]cyclohexane-1-carboxylic

The title compound was prepared according to the procedure outline in Example 8, Step 2, utilizing ethyl 4-[(1-methyl-1H-pyrazol-4-yl)oxy]cyclohexane-1-carboxylate (Step 2, 300 mg, 1.19 mmol) as starting material (Intermediate 2-107, 0.16 g, 60%). LCMS: (ESI) m/z 225 [M+H].

The Intermediates in Table 33 were synthesized according to the procedure above for Example 69.

TABLE 33

| Intermediate No.: | Precursor Used | LCMS: (ES) m/z [M + H] |
|---|---|---|
| Intermediate 2-108. 4-(pyridin-4-yloxy)cyclohexane-1-carboxylic acid | ethyl 4-(methanesulfonyloxy)cyclohexane-1-carboxylate and 4-hydroxypyridine | 222 |
| Intermediate 2-109. 4-[(1-methyl-1H-pyrazol-3-yl)oxy]cyclohexane-1-carboxylic acid | ethyl 4-(methanesulfonyloxy)cyclohexane-1-carboxylate and 1-methyl-1H-pyrazol-3-ol | 225 |
| Intermediate 2-110. 4-[(5-methyl-1,2-oxazol-3-yl)oxy]cyclohexane-1-carboxylic acid | ethyl 4-(methanesulfonyloxy)cyclohexane-1-carboxylate and 5-methylisoxazol-3-ol | 226 |
| Intermediate 2-174. (1r,4r)-4-((2-fluoropyridin-3-yl)oxy)cyclohexane-1-carboxylic acid | (1s,4s)-4-((methylsulfonyl)oxy)cyclohexane-1-carboxylic acid and 2-fluoropyridin-3-ol | 240 |
| Intermediate 2-173. 4-[(5-methoxypyridin-2-yl)oxy]cyclohexane-1-carboxylic acid | ethyl 4-(methanesulfonyloxy)cyclohexane-1-carboxylate and 5-methoxypyridin-2-ol | 252 |
| Intermediate 2-130. (1r,4r)-4-(1-methyl-1H-pyrazol-5-yloxy)cyclohexane-carboxylic acid | (1s,4s)-4-((methylsulfonyl)oxy)cyclohexane-1-carboxylic acid and 1-methyl-1H-pyrazol-5-ol | 225 |

Example 70: Intermediate 2-228a.
1,5-dibenzyl-1H-pyrazole-4-carboxylic acid

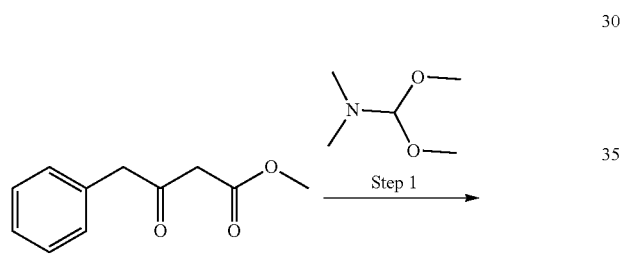

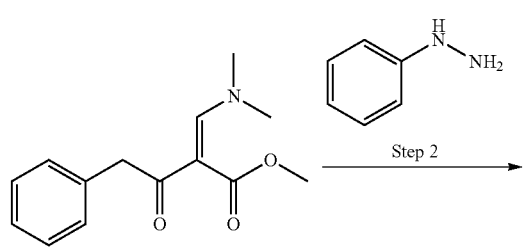

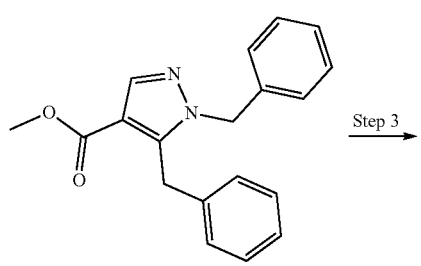

-continued

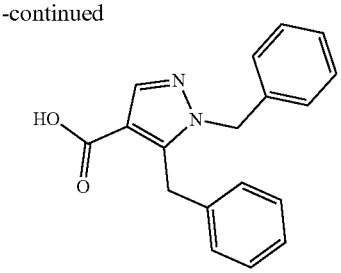

Step 1. Methyl 2-((dimethylamino)methylene)-3-oxo-4-phenylbutanoate

A 50-mL round-bottom flask was charged with methyl 3-oxo-4-phenylbutanoate (1.92 g, 9.99 mmol) and (dimethoxymethyl)dimethylamine (1.43 g, 12.0 mmol). The resulting solution was stirred for 1 h at 23° C. The resulting mixture was concentrated under vacuum. The residue was purified by column chromatography eluting with ethyl acetate/petroleum ether (1:3, v/v) to afford methyl 2-((dimethylamino)methylene)-3-oxo-4-phenylbutanoate (2.30 g, 93%). LCMS: (ESI) m/z 248 [M+H].

Step 2. Methyl 1,5-dibenzyl-1H-pyrazole-4-carboxylate

A 50-mL round-bottom flask was charged with methyl 2-((dimethylamino)methylene)-3-oxo-4-phenylbutanoate (Step 1, 850 mg, 3.44 mmol), phenylhydrazine (557 mg, 5.15 mmol) and ethanol (25 mL). The resulting solution was refluxed for 3 h. The resulting mixture was concentrated under vacuum. The residue was diluted with water (30 mL) and the product was extracted with ethyl acetate (5×30 mL). The organic layers were combined, washed with brine (30 mL), dried over anhydrous sodium sulfate, filtered and concentrated under vacuum. The residue was purified by column chromatography eluting with ethyl acetate/petroleum ether (1:3, v/v) to afford methyl 1,5-dibenzyl-1H- pyrazole-4-carboxylate as a yellow solid (620 mg, 59%). LCMS: (ESI) m/z 307 [M+H].

Step 3. 1,5-dibenzyl-1H-pyrazole-4-carboxylic acid

The title compound was prepared according to the procedure outlined in Example 14 utilizing methyl 1,5-dibenzyl-1H-pyrazole-4-carboxylate (Step 2, 620 mg, 2.02 mmol as starting material (472 mg, 80%). LCMS: (ESI) m/z 293 [M+H].

Example 71: Intermediate 2-160.
4-(1,1-difluoroethyl)benzoic acid

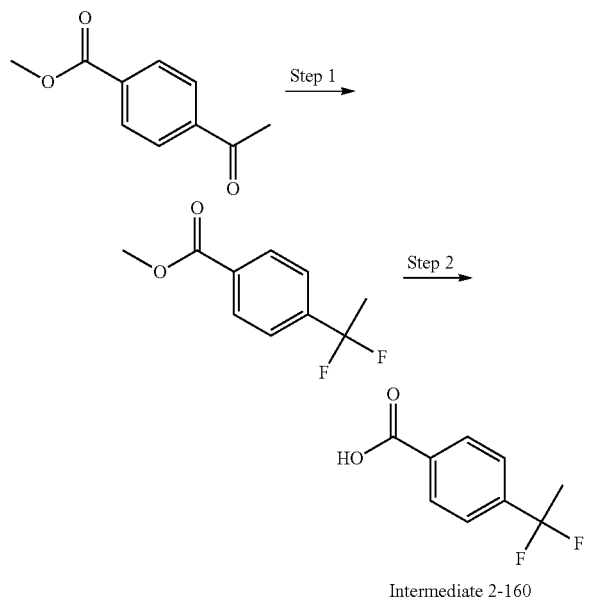

Intermediate 2-160

Step 1. Methyl 4-(1,1-difluoroethyl)benzoate

A 100-mL high pressure reaction tube fitted with a magnetic stir bar, condenser and thermometer was charged with methyl 4-acetylbenzoate (300 mg, 1.68 mmol), ethanol (0.02 mL), diethyl(trifluoro-4-sulfanyl)amine (814 mg, 5.05 mmol) and chloroform (20 mL). The resulting solution was sealed and stirred for 10 h at 80° C. After cooling to 23° C., the reaction mixture was poured into a saturated aqueous sodium bicarbonate (30 mL). The product was extracted with dichloromethane (3×30 mL). The combined organic layers were dried over anhydrous sodium sulfate, filtered and concentrated under vacuum. The residue was purified by column chromatography eluting with ethyl acetate/petroleum ether (4:1 v/v)) to afford methyl 4-(1,1-difluoroethyl) benzoate as a yellow solid (200 mg, 59%). LCMS (ESI) m/z 201 [MI-H].

Step 2. 4-(1,1-Difluoroethyl)benzoic acid

The title compound was prepared according to the procedure outline in Example 10, Step 2, utilizing methyl 4-(1,1-difluoroethyl)benzoate (Step 1, 150 mg, 0.75 mmol) as starting material (Intermediate 2-160, 150 mg). LCMS (ESI, m/z 185 [M−H].

Example 72: Intermediate 2-166.
4-(oxan-4-yloxy)cyclohexane-1-carboxylic acid

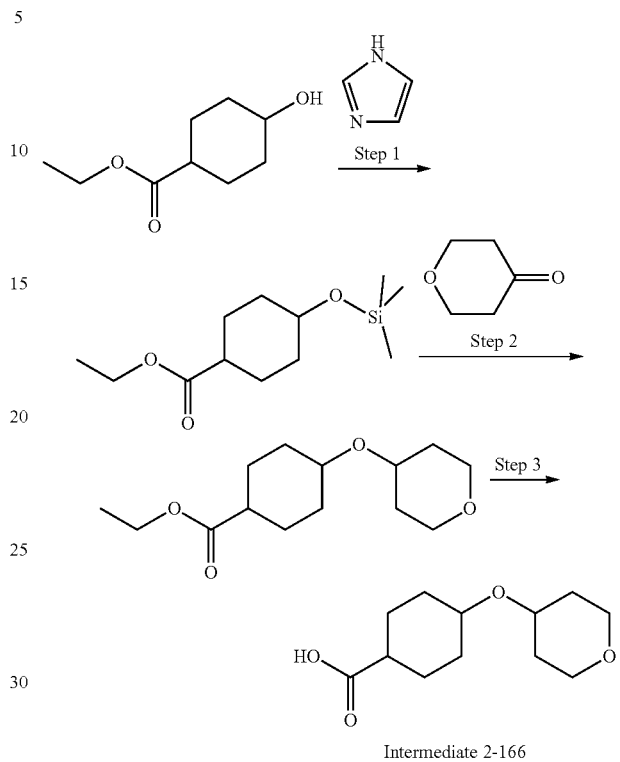

Intermediate 2-166

Step 2. Ethyl 4-[(trimethylsilyl)oxy]cyclohexane-1-carboxylate

A 50-mL 3-necked round-bottom flask fitted with a nitrogen balloon, magnetic stir bar and thermometer was charged with ethyl 4-[(trimethylsilyl)oxy]cyclohexane-1-carboxylate (Step 1, 200 mg, 0.82 mmol), dichloromethane (8 mL) and oxan-4-one (70 mg, 0.70 mmol) followed by trimethylsilyl trifluoromethanesulfonate (18 mg, 0.08 mmol) added dropwise with stirring at −78° C. over 5 min. Stirring continued for 1 h before adding triethylsilane (93 mg, 0.80 mmol) in dichloromethane (1 mL) in portions. Following the addition, the reaction was warmed to 23° C. and stirred for 16 h. The reaction was quenched with saturated sodium bicarbonate (10 mL). The product was extracted with ethyl acetate (3×20 mL). The combined organic layers were washed with brine (2×20 mL), dried over anhydrous sodium sulfate, filtered and concentrated under vacuum. The residue was purified by column chromatography eluting with petroleum ether/ethyl acetate (10:1, v/v) to afford ethyl 4-(oxan-4-yloxy)cyclohexane-1-carboxylate as light yellow oil (120 mg, 57%). GCMS: m/z 256.

Step 3. 4-(Oxan-4-yloxy)cyclohexane-1-carboxylic acid

The title compound was prepared according to the procedure outline in Example 10, Step 2, utilizing ethyl 4-(oxan-4-yloxy)cyclohexane-1-carboxylate (Step 2, 100 mg, 0.39 mmol) as starting material (Intermediate 2-166, 50 mg, 56%). LCMS: (ESI) m/z 227 [M−H].

235

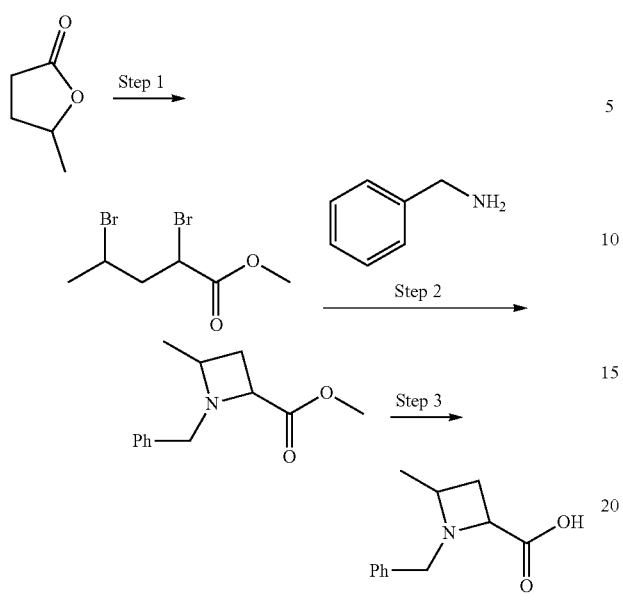

Step 1. Methyl 2,4-dibromopentanoate

A 500-mL 3-necked round-bottom with fitted with a magnetic stir bar, condenser and thermometer was charged with 5-methyloxolan-2-one (10 g, 100 mmol), methanol (100 mL), hydrochloric acid (20 mL, 12N) and phosphorus tribromide (4.5 mL). Bromine (6 mL) was added in portions at 25° C. After addition, the resulting solution was stirred for 30 min at 110° C. in an oil bath and cooled to 25° C., the solution was diluted with methanol (100 mL) and hydrochloric acid (20 mL, 12 N). The resulting solution was stirred for 16 h at 25° C. and then concentrated under vacuum. The residue was diluted with water (100 mL) and the product was extracted with ethyl acetate (3×30 mL). The combined organic layers were dried over anhydrous sodium sulfate and concentrated under vacuum to afford methyl 2,4-dibromopentanoate as a colorless oil (6 g).

Step 2. Methyl 1-benzyl-4-methylazetidine-2-carboxylate

A 500-mL 3-necked round-bottom flask fitted with a magnetic stir bar, condenser and thermometer was charged with methyl 2,4-dibromopentanoate (Step 1, 4 g, 14.6 mmol), acetonitrile (100 mL) and phenylmethanamine (1.72 g, 16.1 mmol) The resulting solution was stirred for 6 h at 65° C. in an oil bath and cooled to 25° C., the resulting mixture was concentrated under vacuum. The residue was purified by column chromatography eluting with ethyl acetate/petroleum ether (1:1, v/v) to afford methyl 1-benzyl-4-methylazetidine-2-carboxylate as a light brown oil (2 g, 62%). LCMS: (ESI) m/z 220 [M+H].

Step 3. 1-Benzyl-4-methylazetidine-2-carboxylic acid

A 250-mL 3-necked round-bottom flask fitted with a magnetic stir bar, condenser and thermometer was charged with methyl 1-benzyl-4-methylazetidine-2-carboxylate (Step 2, 2 g, 9.12 mmol), water (30 mL) and barium hydroxide (3.13 g, 18.3 mmol). The resulting solution was

236 stirred for 2 h at 90° C. in an oil bath and cooled to 25° C., the pH was adjusted to 6 with hydrochloric acid (3 N). The product was extracted with ethyl acetate (3×60 mL). The combined organic layers were dried over anhydrous sodium sulfate, filtered and concentrated under vacuum to afford 1-benzyl-4-methylazetidine-2-carboxylic acid as a colorless oil (1.8 g, 96%). LCMS: (ESI) m/z 206 [M+H].

Example 74: Intermediate 2-176a. tert-Butyl 4-methoxy-1-oxa-6-azaspiro[2.5]octane-6-carboxylate

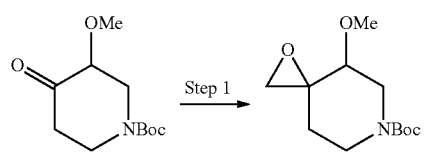 [SMILES: COC1CN(C(=O)OC(C)(C)C)CCC1=O ; COC1CN(C(=O)OC(C)(C)C)CCC12CO2]

Step 1. tert-Butyl 4-methoxy-1-oxa-6-azaspiro[2.5]octane-6-carboxylate

Trimethylsulfoxonium iodide (1.45 g, 6.55 mmol), dimethyl sulfoxide (20 mL) and sodium hydride (157 mg, 6.54 mmol) were added to a 50-mL round-bottom flask fitted with a magnetic stir bar under an inert atmosphere. The resulting solution was stirred for 1 h at 0° C. tert-Butyl 3-methoxy-4-oxopiperidine-1-carboxylate (500 mg, 2.18 mmol) was added and the resulting solution was stirred at room temperature for 5 h. The reaction mixture was quenched by the addition of water (20 mL) and extracted with ether (3×30 mL). The organic layers were combined, dried over anhydrous sodium sulfate, filtered and concentrated under vacuum to give tert-butyl 4-methoxy-1-oxa-6-azaspiro[2.5]octane-6-carboxylate (500 mg, 94%). LCMS: (ESI) m/z 244 [M+H].

Example 75: Intermediate 2-198a. (4-Fluorophenyl)(2-methyl-1-oxa-6-azaspiro[2.5]octan-6-yl)methanone

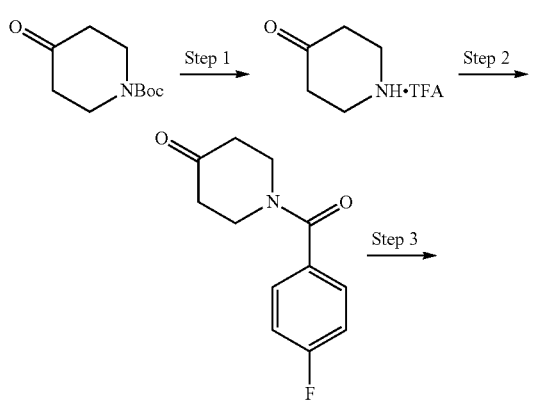

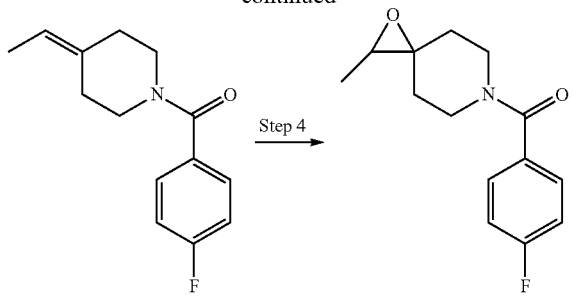

Step 1. Piperidin-4-one trifluoroacetic acid salt tert-Butyl 4-oxopiperidine-1-carboxylate (3 g, 15.0 mmol), dichloromethane (15 mL), and trifluoroacetic acid (3 mL) was added to a 100-mL round-bottom flask with magnetic stir bar. The resulting solution was stirred for 3 h at room temperature. The resulting mixture was concentrated under vacuum to give piperidin-4-one trifluoroacetic acid salt which was used in next step without further purification.

Step 2. 1-(4-Fluorobenzoyl)piperidin-4-one

The title compound was prepared according to the procedure outline in Example 7 utilizing piperidin-4-one trifluoroacetic acid salt (Step 1, 4.69 mmol) and 4-fluorobenzoic acid (1.44 g, 10.3 mmol) as starting materials followed by purification by column chromatography eluting with ethyl acetate/petroleum ether (1:1 v/v). (800 mg, 77%). LCMS: (ESI) m/z 222 [M+H].

Step 3. (4-Ethylidenepiperidin-1-yl)(4-fluorophenyl)methanone

Tetrahydrofuran (10 mL) and potassium tert-butoxide (814 mg, 7.27 mmol) were added to a 100-mL 3-necked round-bottom flask equipped with a magnetic stir bar. A solution of ethyltriphenylphosphonium bromide (4.00 g, 10.8 mmol) in tetrahydrofuran (10 mL) was added dropwise at room temperature over 10 min. To this mixture was added a solution of 1-(4-fluorobenzoyl)piperidin-4-one (Step 2, 800 mg, 3.62 mmol) in tetrahydrofuran (10 mL) dropwise with stirring at room temperature over 2 min. The resulting solution was stirred for 3 h at 40° C. and then cooled to room temperature The resulting solution was diluted with n-hexane (50 mL), filtered, dried over anhydrous sodium sulfate and concentrated under vacuum. The residue was purified by column chromatography eluting with ethyl acetate/petroleum ether (1:3 v/v) to give (4-ethylidenepiperidin-1-yl)(4-fluorophenyl)methanone (250 mg, 30%). LCMS: (ESI) m/z 234 [M+H].

Step 4. (4-Fluorophenyl)(2-methyl-1-oxa-6-azaspiro[2.5]octan-6-yl)methanone (4-Ethylidenepiperidin-1-yl)(4-fluorophenyl)methanone (Step 3, 250 mg, 1.07 mmol), 3-chloroperbenzoic acid (239 mg, 1.38 mmol) and chloroform (20 mL) were added to a 100-mL round-bottom flask with a magnetic stir bar. The resulting solution was stirred for 16 h at room temperature and then washed with saturated aqueous sodium thiosulfate (30 mL) and saturated aqueous sodium bicarbonate (10 mL). The mixture was extracted with dichloromethane (5×20 mL). The organic layers were combined, dried over anhydrous sodium sulfate and concentrated under vacuum. The residue was purified by column chromatography using ethyl acetate/petroleum ether (1:4 v/v) to give (4-fluorophenyl)(2-methyl-1-oxa-6-azaspiro[2.5]octan-6-yl)methanone. LCMS: (ESI) m/z 250 [M+H].

Example 76: Intermediate 2-313a: N-[3-(3-chlorophenyl)oxetan-3-yl]-2-methylpropane-2-sulfinamide

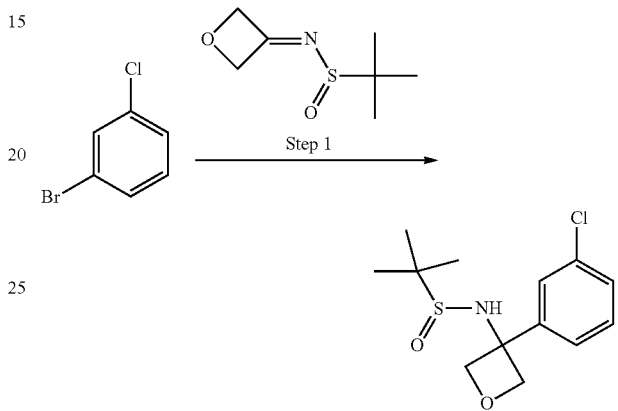

A 100-mL 3-necked round-bottom flask fitted with a nitrogen inlet, magnetic stir bar and thermometer was charged with 1-bromo-3-chlorobenzene (1 g, 5.22 mmol) and tetrahydrofuran (20 mL) followed n-BuLi (1.5 mL, 2.5 M in hexane) added dropwise at −78° C. To the reaction was added 2-methyl-N-(oxetan-3-ylidene)propane-2-sulfinamide (1.11 g, 6.33 mmol) in tetrahydrofuran (5 mL) at −78° C. and stirred for 5 h at −78° C. in a dry ice bath under nitrogen. The reaction was quenched with water (30 mL). The product was extracted with dichloromethane (3×50 mL). The combined organic layers were dried over anhydrous sodium sulfate, filtered and concentrated under vacuum. The residue was purified by column chromatography eluting with ethyl acetate/petroleum ether (1:50 to 1:10 v/v) to afford N-[3-(3-chlorophenyl)oxetan-3-yl]-2-methylpropane-2-sulfinamide (800 mg, 53%) as a white solid. LCMS: (ESI) m/z 288, 290 [M+H].

Example 77: Intermediate 2-235a 4-(pyridin-2-yloxy)piperidine-1-carboxylate chloride

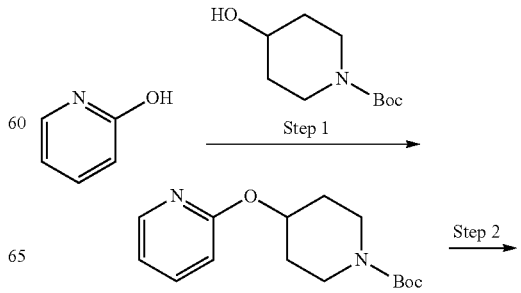

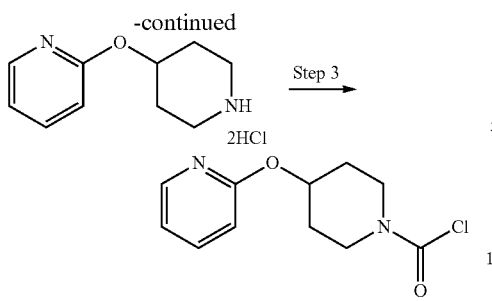

Step 1. Tert-butyl 4-(pyridin-2-yloxy)piperidine-1-carboxylate

A 100-mL 3-necked round-bottom flask equipped with a nitrogen balloon was charged with pyridin-2-ol (500 mg, 5.26 mmol), tert-butyl 4-hydroxypiperidine-1-carboxylate (3.17 g, 15.75 mmol), triphenylphosphine (4.14 g, 15.78 mmol), tetrahydrofuran (20 mL). A solution of diethyl azodicarboxylate (2.75 g, 15.79 mmol) in tetrahydrofuran (5 mL) was added at 0° C. After addition, the solution was stirred for 5 h at 23° C. The mixture was concentrated under vacuum. The residue was purified by column chromatography eluting with ethyl acetate/petroleum ether (7:100 v/v) to afford tert-butyl 4-(pyridin-2-yloxy)piperidine-1-carboxylate as a white solid (600 mg, 41%). LCMS: (ESI) m/z 279 [M+H].

Step 2. 2-(piperidin-4-yloxy)pyridine dihydrochloride

A 100-mL round-bottom flask was charged with tert-butyl 4-(pyridin-2-yloxy)piperidine-1-carboxylate (Step 1, 600 mg, 2.16 mmol) and dioxane (10 mL) followed by the addition of hydrochloric acid in dioxane (3 M, 20 mL). The resulting solution was stirred for 3 h at 23° C. The resulting mixture was concentrated under vacuum to afford 2-(piperidin-4-yloxy)pyridine dihydrochloride as a white solid which was used without further purification (500 mg, >95%). LCMS: (ESI) mii 179 [M+H].

Step 3. 4-(pyridin-2-yloxy)piperidine-1-carbonyl chloride

A 100-mL round-bottom flask was charged with triphosgene (107 mg, 0.36 mmol) and dichloromethane (10 mL). 2-(piperidin-4-yloxy)pyridine dihydrochloride (Step 2, 150 mg, 0.60 mmol) and N,N-diisopropylethylamine (181.8 mg, 1.41 mmol) were added dropwise at 0° C. The resulting solution was stirred for 3 h at 0° C. The mixture was concentrated under vacuum to afford 4-(pyridin-2-yloxy)piperidine-1-carbonyl chloride as a yellow solid which was used without further purification (150 mg, >95%). LCMS: (ESI) m/z 241, 243 [M+H].

The Intermediates in Table 34 were synthesized according to the procedure above.

TABLE 34

| Intermediate No.: | Precursor Used | LCMS: (ES) m/z [M + H] |
|---|---|---|
| Intermediate 2-108X. 4-((5-methylisoxazol-3-yl)oxy)piperidine-1-carbonyl chloride | tert-butyl 4-hydroxypiperidine-1-carboxylate and 5-methylisoxazol-3-ol | 245, 247 |

TABLE 34-continued

| Intermediate No.: | Precursor Used | LCMS: (ES) m/z [M + H] |
|---|---|---|
| Intermediate 2-109Y. 4-((1-methyl-1H-pyrazol-4-yl)oxy)piperidine-1-carbonyl chloride | tert-butyl 4-hydroxypiperidine-1-carboxylate and 1-methyl-1H-pyrazol-4-ol | 244, 246 |

Example 78: Intermediate 2-339a. 5-[(3-fluoro-4-hydroxypiperidin-4-yl)methyl]-1-phenyl-1H,4H,5H-pyrazolo[3,4-d]pyrimidin-4-one

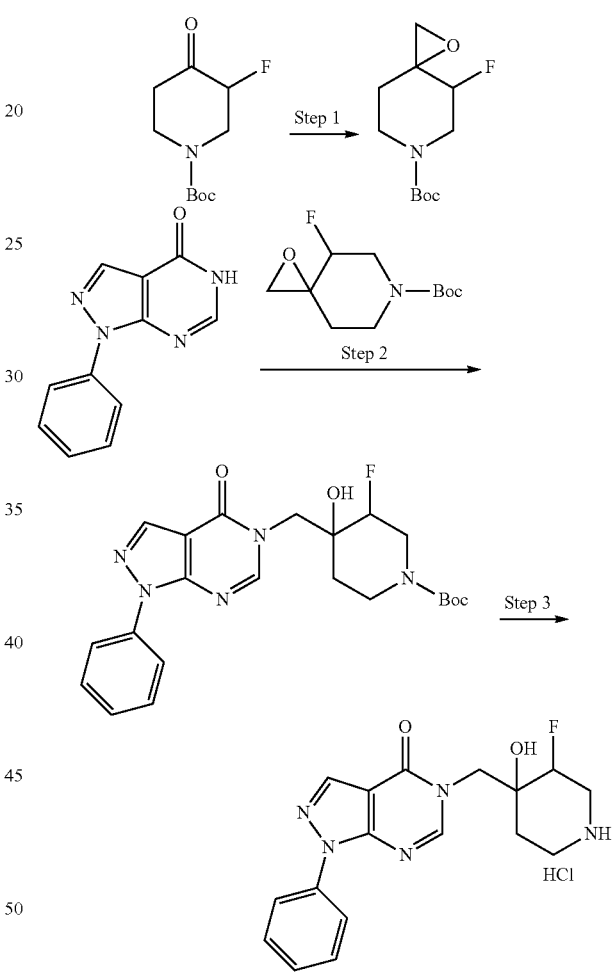

Step 1. tert-butyl 4-fluoro-1-oxa-6-azaspiro[2.5]octane-6-carboxylate

A 100-mL round-bottom flask fitted with a nitrogen inlet, magnetic stir bar and thermometer was charged with a solution of dimethylmethanesulfinyl iodide (13.8 g, 62.5 mmol) in dimethyl sulphoxide (30 mL) followed by sodium hydride (1.5 g, 62.5 mmol, 60% wt) at 0-5° C. After 20 min of vigorous stirring tert-butyl 3-fluoro-4-oxopiperidine-1-carboxylate (10.4 g, 47.9 mmol) in dimethyl sulphoxide (10 mL) was added dropwise at 10° C. over 10 min. The resulting solution was stirred for 16 h at 23° C. under nitrogen. The reaction was quenched with water (30 mL). The product was extracted with ethyl acetate (3×30 mL). The combined organic extracts were washed with brine (20 mL), dried over anhydrous sodium sulfate and concentrated under vacuum to afford tert-butyl 4-fluoro-1-oxa-6-azspiro [2.5]octane-6-carboxylate (2.45 g, 17%) as a yellow oil which was used in next step without further purification. LCMS: (ESI) m/z 232 [M+H].

Step 2. tert-butyl-4-hydroxy-4-([4-oxo-1-phenyl-1H, 4H,5H-pyrazolo[3,4-d]pyrimidin-5-yl]methyl)piperidine-1-carboxylate The title compound was prepared according to the [procedure outlined in Example 877 utilizing tert-butyl 4-fluoro-1-oxa-6-azaspiro[2.5]octane-6-carboxylate (Step 1, 2.45 g, 7.08 mmol) and 1-phenyl-1H,4H,5H-pyrazolo[3,4-d]pyrimidin-4-one (1.5 g, 10.6 mmol) followed purification by column chromatography eluting with ethyl acetate/petroleum ether (1:2 v/v) (800 mg, 17%). LCMS: (ESI) m/z 444 [M+H].

Step 3. 5-[(3-fluoro-4-hydroxypiperidin-4-yl) methyl]-1-phenyl-1H,4H,5H-pyrazolo[3,4-d]pyrimidin-4-one The title compound was prepared according to procedure outlined in Example 2a utilizing tert-butyl 3-fluoro-4-hydroxy-4-([4-oxo-1-phenyl-1H,4H,5H-pyrazolo[3,4-d]pyrimidin-5-yl]methyl)piperidine-1-carboxylate (Step 2, 760 mg, 1.72 mmol) (650 mg, >95%). LCMS: (ESI) m/z 344 [M+H].

Example 79: Intermediate 2-345a. 1-(4-fluorophenyl)-5-(2-hydroxy-1-(4-hydroxypiperidin-4-yl) ethyl)-1H-pyrazolo[3,4-d]pyrimidin-4(5H)-one hydrochloride

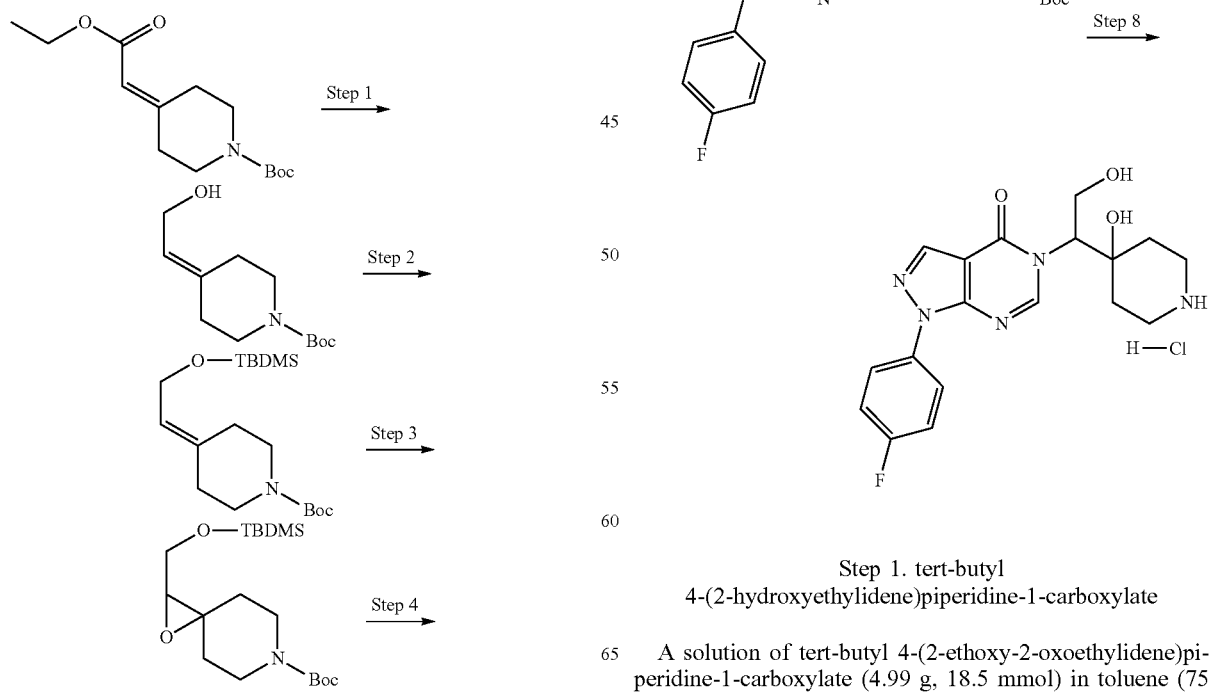

Step 1. tert-butyl 4-(2-hydroxyethylidene)piperidine-1-carboxylate

A solution of tert-butyl 4-(2-ethoxy-2-oxoethylidene)piperidine-1-carboxylate (4.99 g, 18.5 mmol) in toluene (75 ml) was placed under nitrogen in a 500 mL round-bottom flask and cooled on a dry ice/acetone bath at −77° C. Diisobutylaluminum hydride (1.0 M in heptane, 40 ml, 40.0 mmol) was added dropwise by syringe over 20 min. The solution was stirred for 2.5 hours before adding saturated aqueous NH$_4$Cl (12.5 mL) dropwise over 8 min. The sample warmed to 23° C. and stirred for 16 h. The mixture was shaken with water (100 mL). The resulting emulsion was filtered on a Buchner funnel and the filter cake was washed with EtOAc (50 mL). The layers were separated. The product was extracted with EtOAc (2×50 mL), then the combined organic extracts were dried over sodium sulfate, filtered and evaporated under reduced pressure to provide an oil. The material was dissolved in hexanes-EtOAc and purified by Biotage MPLC (100 g silica gel column, 10 to 60% EtOAc in hexanes) to provide tert-butyl 4-(2-hydroxyethylidene)piperidine-1-carboxylate (3.71 g, 88%). $^1$H NMR (300 MHz, CHLOROFORM-d) δ 5.50 (t, J=7.04 Hz, 1H), 4.15-4.23 (m, 2H), 3.36-3.50 (m, 4H), 2.27 (dd, J=5.70 Hz, 2H), 2.19 (dd, J=5.70 Hz, 2H), 1.48 (s, 9H). LCMS: (ESI) m/z 250 [M+Na].

Step 2. tert-butyl 4-(2-((tert-butyldimethylsilyl)oxy) ethylidene)piperidine-1-carboxylate A solution of tert-butyl 4-(2-hydroxyethylidene)piperidine-1-carboxylate (Step 1, 3.71 g, 16.3 mmol) in DMF (22 ml) was treated with imidazole (3.44 g, 50.5 mmol) and TBDMS-Cl (3.72 g, 24.7 mmol). The solution was stirred at 23° C. for 72 h. The yellow solution was diluted with EtOAc (250 mL), washed with water (3×250 mL) and brine (2×250 mL). The combined organic layers were dried over sodium sulfate, filtered, and evaporated to provide a colorless oil. The oil was dissolved in a few mL hexanes and purified by Biotage MPLC (100 g silica gel column, 0 to 6.5% EtOAc in hexanes) to provide tert-butyl 4-(2-((tert-butyldimethylsilyl)oxy)ethylidene)piperidine-1-carboxylate (5.37 g, 96%). $^1$H NMR (300 MHz, CDCl$_3$) δ 5.40 (t, J=6.45 Hz, 1H), 4.21 (d, J=6.45 Hz, 2H), 3.34-3.49 (m, 4H), 2.10-2.29 (m, 4H), 1.47 (s, 9H), 0.91 (s, 9H), 0.08 (s, 6H). LCMS: (ESI) m/z 342 [M+H].

Step 3. tert-butyl 2-((tert-butyldimethylsilyl)oxy) methyl)-1-oxa-6-azaspiro[2.5]octane-6-carboxylate A stirred solution of tert-butyl 4-(2-((tert-butyldimethylsilyl)oxy)ethylidene) piperidine-1-carboxylate (Step 2, 5.37 g, 15.7 mmol) in chloroform (200 mL) was cooled on an ice bath. To the reaction was added m-CPBA (<77%, 12.57 g, 56.1 mmol) before removing the ice bath. The reaction was stirred for 2 days resulting in formation of a white precipitate. The reaction was quenched with aqueous 10% sodium thiosulfate (250 mL) and aqueous saturated NaHCO$_3$ (250 mL). The mixture was shaken for 5 min and then partitioned. The product was extracted further with dichloromethane (2×400 mL). The combined organic layers were dried over magnesium sulfate and evaporated under reduced pressure to provide 5.74 g yellow liquid. The material was dissolved in a little hexanes/EtOAc and purified by Biotage MPLC (100 g silica gel column, 0 to 10% EtOAc in hexanes) to provide tert-butyl 2-(((tert-butyldimethylsilyl)oxy)methyl)-1-oxa-6-azaspiro[2.5]octane-6-carboxylate (2.55 g, 45%). $^1$H NMR (300 MHz, CDCl$_3$) δ 3.60-3.86 (m, 4H), 3.36-3.53 (m, 2H), 2.98 (t, J=5.57 Hz, 1H), 1.78 (ddd, J=13.49, 9.23, 4.25 Hz, 2H), 1.38-1.66 (m, 11H), 0.91 (s, 9H), 0.07-0.12 (m, 6H). LCMS: (ESI) m/z 358 [M+H].

Step 4. tert-butyl 4-(1-azido-2-((tert-butyldimethylsilyl)oxy)ethyl)-4-hydroxypiperidine-1-carboxylate A solution of tert-butyl 2-(((tert-butyldimethylsilyl)oxy) methyl)-1-oxa-6-azaspiro[2.5]octane-6-carboxylate (Step 3, 179 mg, 0.501 mmol) in DMF (4 ml) was treated with ammonium chloride (102 mg, 1.91 mmol) and sodium azide (153 mg, 2.35 mmol) and stirred at 90° C. for 5 h. The mixture was diluted with EtOAc (40 mL), washed with brine (2×40 mL) and water (3×40 mL). The combined organic layers were dried over sodium sulfate, filtered, and evaporated under reduced pressure. The residue was dissolved in hexanes/EtOAc and purified by Biotage MPLC eluting with EtOAc/Hexanes (10 g silica gel column, 0 to 17% v/v) to provide tert-butyl 4-(1-azido-2-((tert-butyldimethylsilyl) oxy)ethyl)-4-hydroxypiperidine-1-carboxylate (77.2 mg, 39% yield). $^1$H NMR (300 MHz, DMSO-d$_6$) δ 4.79 (s, 1H), 4.01 (dd, J=10.99, 3.08 Hz, 1H), 3.62-3.80 (m, 3H), 3.36 (dd, J=9.23, 3.08 Hz, 1H), 2.92 (br s, 2H), 1.33-1.52 (m, 13H), 0.88 (s, 9H), 0.08 (s, 6H). LCMS: (ESI) nm/z 401 [M+H].

Step 5. tert-butyl 4-(1-amino-2-((tert-butyldimethylsilyl)oxy)ethyl)-4-hydroxypiperidine-1-carboxylate In a 2-necked 50 mL round-bottom flask was added 10% Pd/C (49.0 mg, 0.046 mmol Pd) under nitrogen. Methanol (3 mL) was added carefully by syringe and then the apparatus was opened and a solution of tert-butyl 4-(1-azido-2-((tert-butyldimethylsilyl)oxy)ethyl)-4-hydroxypiperidine-1-carboxylate (Step 4, 1.15 g, 2.87 mmol) in MeOH (10 mL) was added by pipet followed by triethylamine (5 drops). The atmosphere was removed and replaced with hydrogen three times. The mixture was stirred under hydrogen (balloon, 1 atm) for 24 h. The sample was filtered through Celite 545 on a Buchner funnel, and the filter cake was washed with MeOH (40 mL). The filtrate was evaporated under reduced pressure to provide tert-butyl 4-(1-amino-2-((tert-butyldimethylsilyl)oxy)ethyl)-4-hydroxypiperidine-1-carboxylate (1.07 g, 99%). $^1$H NMR (300 MHz, DMSO-d$_6$) δ 4.25 (s, 1H), 3.63-3.80 (m, 3H), 3.40 (dd, J=9.97, 7.62 Hz, 1H), 2.96 (br s, 3H), 1.04-1.57 (m, 15H), 0.86 (s, 9H), 0.04 (s, 6H). LCMS: (ESI) m/z 375 [M+H].

Step 6. tert-butyl 4-(1-(5-amino-1-(4-fluorophenyl)-1H-pyrazole-4-carboxamido)-2-((tert-butyldimethylsilyl)oxy)ethyl)-4-hydroxypiperidine-1-carboxylate A solution of tert-butyl 4-(1-amino-2-((tert-butyldimethylsilyl)oxy)ethyl)-4-hydroxypiperidine-1-carboxylate (Step 5, 922 mg, 2.46 mmol) in dichloromethane (30 ml) was treated with 5-amino-1-(4-fluorophenyl)-1H-pyrazole-4-carboxylic acid (571 mg, 2.58 mmol), HATU (989 mg, 2.60 mmol), and triethylamine (1.72 mL, 12.3 mmol). The reaction was stirred at 23° C. for 4 days and diluted with EtOAc (250 mL). The organic layer was washed with saturated aqueous ammonium chloride (250 mL), brine (250 mL), and water (2×250 mL). The combined organic layers were dried over sodium sulfate, filtered, treated with silica gel, and evaporated under reduced pressure. The material was purified by Biotage MPLC eluting with EtOAc/Hexanes (50 g silica gel column, 0 to 50% v/v, isocratic elution at 42% EtOAc) to provide tert-butyl 4-(1-(5-amino-1-(4-fluorophenyl)-1H-pyrazole-4-carboxamido)-2-((tert-butyldimethylsilyl)oxy)ethyl)-4-hydroxypiperidine-1-carboxylate (841 mg, 59%). $^1$H NMR (300 MHz, DMSO-d$_6$) δ 8.01 (s, 1H), 7.53-7.63 (m, 2H), 7.25-7.41 (m, 3H), 6.35 (s, 2H), 4.62 (s, 1H), 3.91-4.08 (m, 2H), 3.59-3.77 (m, 3H), 2.99 (br s, 2H), 1.22-1.59 (m, 13H), 0.82 (s, 9H), 0.02 (d, J=4.40 Hz, 6H). LCMS: (ESI) m/z 578 [M+H].

Step 7. tert-butyl 4-(2-((tert-butyldimethylsilyl)oxy)-1-(1-(4-fluorophenyl)-4-oxo-1H-pyrazolo[3,4-d]pyrimidin-5(4H)-yl)ethyl)-4-hydroxypiperidine-1-carboxylate A solution of tert-butyl 4-(1-(5-amino-1-(4-fluorophenyl)-1H-pyrazole-4-carboxamido)-2-((tert-butyldimethylsilyl)oxy)ethyl)-4-hydroxypiperidine-1-carboxylate (Step 6, 180 mg, 0.311 mmol) and p-toluenesulfonic acid monohydrate (5.0 mg, 0.026 mmol) in triethyl orthoformate (5.4 mL, 32.4 mmol) was stirred at 23° C. for 3.5 hours. The reaction was quenched with triethylamine (12 drops). The sample was dissolved in EtOAc/hexanes material at the same stage from a previous run (20.1 mg, 0.035 mmol pyrazole starting material) was added. The sample was purified by Biotage MPLC (10 g silica gel column, 0 to 50% EtOAc in hexanes, with isocratic elution at 16% EtOAc) to provide tert-butyl 4-(2-((tert-butyldimethylsilyl)oxy)-1-(1-(4-fluorophenyl)-4-oxo-1H-pyrazolo[3,4-d]pyrimidin-5(4H)-yl)ethyl)-4-hydroxypiperidine-1-carboxylate (130 mg, 64%) and used without further purification. $^1$H NMR (300 MHz, DMSO-$d_6$) δ 8.45 (s, 1H), 8.39 (s, 1H), 7.99-8.13 (m, 2H), 7.38-7.51 (m, 2H), 5.22 (s, 1H), 5.06 (dd, J=10.11, 5.72 Hz, 1H), 4.14-4.25 (m, 1H), 4.03-4.13 (m, 1H), 3.53-3.80 (m, 3H), 3.06 (br s, 3H), 1.61-1.74 (m, 2H), 1.38 (s, 9H), 0.66 (s, 9H), −0.03 (d, J=9.67 Hz, 6H). LCMS: (ESI) m/z 588 [M+H].

Step 8. 1-(4-fluorophenyl)-5-(2-hydroxy-1-(4-hydroxypiperidin-4-yl)ethyl)-1H-pyrazolo[3,4-d]pyrimidin-4(5H)-one hydrochloride The title compound was prepared according to the procedure outlined in Example 2a utilizing tert-butyl 4-(2-((tert-butyldimethylsilyl)oxy)-1-(1-(4-fluorophenyl)-4-oxo-1H-pyrazolo[3,4-d]pyrimidin-5(4H)-yl)ethyl)-4-hydroxypiperidine-1-carboxylate (Step 7, 124.5 mg, 0.212 mmol) as starting material (83.7 mg, 96%). $^1$H NMR (300 MHz, DMSO-$d_6$) δ 8.85 (br s, 1H), 8.46-8.57 (m, 1H), 8.45 (s, 1H), 8.39 (s, 1H), 8.01-8.13 (m, 2H), 7.37-7.49 (m, 2H), 5.44-5.99 (m, 4H), 5.00 (dd, J=9.23, 5.42 Hz, 1H), 3.86-4.10 (m, 2H), 3.11-3.24 (m, 1H), 2.80-3.11 (m, 3H), 1.94 (br s, 2H), 1.57-1.74 (m, 1H), 1.28 (br d, J=14.07 Hz, 1H). LCMS: (ESI) m/z 374 [M+H].

Example 80: Intermediate 2-515a. 5-[(4-hydroxypiperidin-4-yl)methyl]-1-[4-(4-methyl-1H-pyrazol-1-yl)phenyl]-1H,4H,5H-pyrazolo[3,4-d]pyrimidin-4-one, TFA salt

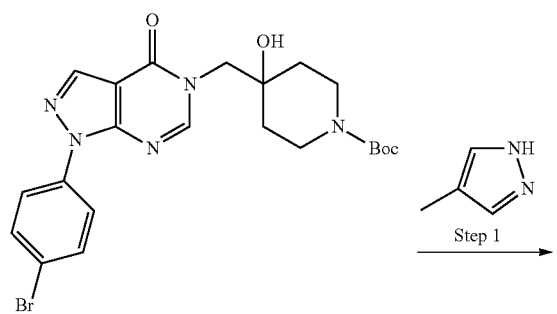

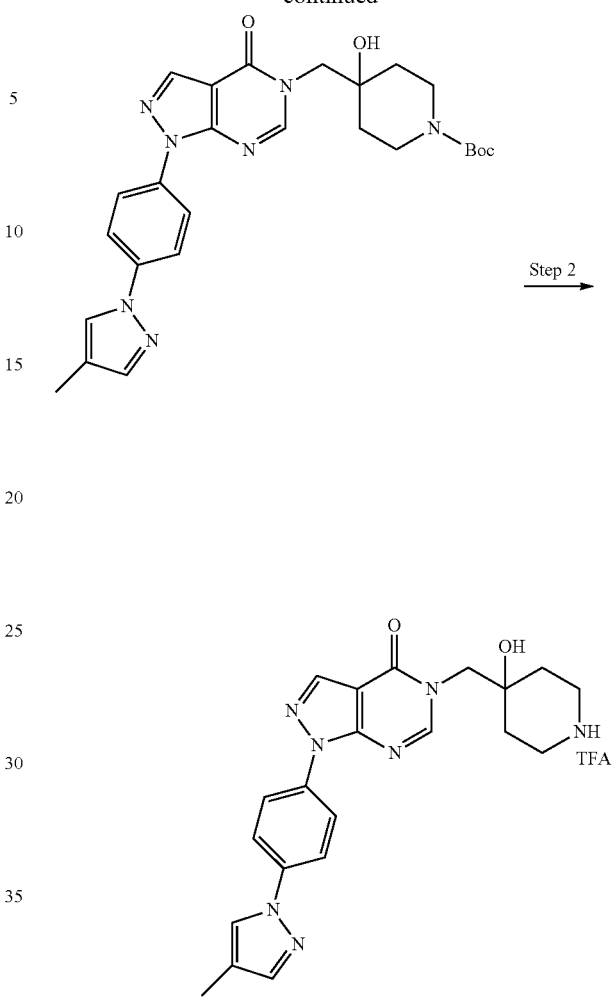

Step 1. Tert-butyl 4-hydroxy-4-([1-[4-(4-methyl-1H-pyrazol-1-yl)phenyl]-4-oxo-1H,4H,5H-pyrazolo[3,4-d]pyrimidin-5-yl]methyl)piperidine-1-carboxylate A 25-mL 3-necked round-bottom flask fitted with a nitrogen balloon, magnetic stir bar, condenser and thermometer was charged with tert-butyl 4-[[1-(4-bromophenyl)-4-oxo-1H,4H,5H-pyrazolo[3,4-d]pyrimidin-5-yl]methyl]-4-hydroxypiperidine-1-carboxylate (Intermediate 28x, 1.000 g, 1.98 mmol), 4-methyl-1H-pyrazole (1.30 g, 15.8 mmol), copper (I) iodide (0.754 g, 3.96 mmol), sodium carbonate (0.421 g, 3.97 mmol), (1S,2S)-cyclohexane-1,2-diamine (0.046 g, 0.40 mmol) and dioxane (7 mL). The resulting solution was stirred for 12 h at 120° C. under nitrogen. After cooling to 23° C., the mixture was diluted with water (10 mL). The product was extracted with dichloromethane (3×20 mL) and the organic layers were combined, washed with brine (20 mL), dried over anhydrous sodium sulfate, filtered and concentrated under vacuum. The residue was purified by column chromatography eluting with acetate/petroleum ether (35:65, v/v) to afford tert-butyl 4-hydroxy-4-([1-[4-(4-methyl-1H-pyrazol-1-yl)phenyl]-4-oxo-1H,4H,5H-pyrazolo[3,4-d]pyrimidin-5-yl]methyl)piperidine-1-carboxylate (0.140 g, 14%). LCMS: (ESI) m/z 506 [M+H].

Step 2. 5-[(4-hydroxypiperidin-4-yl)methyl]-1-[4-(4-methyl-1H-pyrazol-1-yl)phenyl]-1H,4H,5H-pyrazolo[3,4-d]pyrimidin-4-one, TFA salt The title compound was prepared according to the procedure outlined in Example 2, utilizing tert-butyl 4-hydroxy-4-([1-[4-(4-methyl-1H-pyrazol-1-yl)phenyl]-4-oxo-1H,4H,5H-pyrazolo[3,4-d]pyrimidin-5-yl]methyl)piperidine-1-carboxylate, Step 1, as starting material (0.112 g, 95%). LCMS: (ESI) m/z 406 [M+H].

The Intermediates in Table 35 were prepared according to the procedure outlined above.

TABLE 35

| Intermediate No.: | Precursor Used | MS (ESI, m/z) [M + H]. |
|---|---|---|
| Intermediate 2-517aa. 1-(4-(1H-pyrazol-1-yl)phenyl)-5-((4-hydroxypiperidin-4-yl)methyl)-1,5-dihydro-4H-pyrazolo[3,4-d]pyrimidin-4-one, TFA salt | tert-butyl 4-[[1-(4-bromophenyl)-4-oxo-1H,4H,5H-pyrazolo[3,4-d]pyrimidin-5-yl]methyl]-4-hydroxypiperidine-1-carboxylate and 1H-pyrazole | 392 |

Example 81: Intermediate 2-619a. 4-(4-Oxo-4,5-dihydropyrazolo[3,4-d]pyrimidin-1-yl)benzoic acid

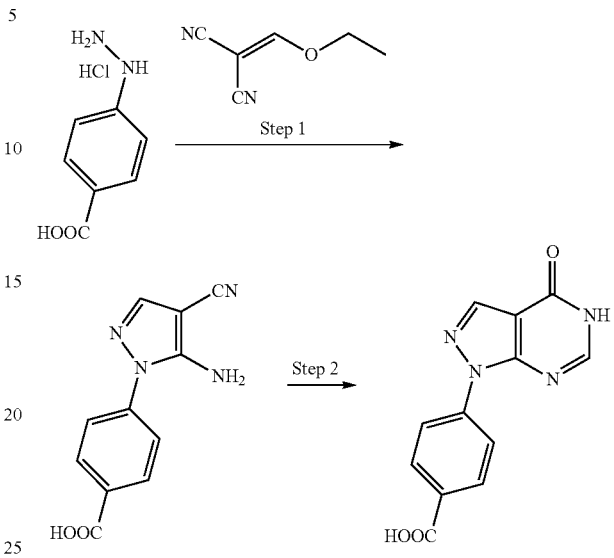

The title compound was prepared according to procedures outlined in Example 21, Step 1, Step 2, utilizing 4-hydrazinylbenzoic acid hydrochloride (4.95 g, 26.2 mmol) as starting material LCMS: (ES) m/z 257 [M+H].

The Intermediates in Table 36 were prepared according to the procedure outlined above:

TABLE 36

| Intermediate No.: | Precursor Used | MS (ESI, m/z) [M + H]. |
|---|---|---|
| Intermediate 2-537aa 1-(4-Methylphenyl)-1H,4H,5H-pyrazolo[3,4-d]pyrimidin-4-one | (4-methylphenyl)hydrazine hydrochloride | 227 |
| Intermediate 2-366a. 1-(4-(1H-1,2,3-triazol-1-yl)phenyl)-1H-pyrazolo[3,4-d]pyrimidin-4 (5H)-one and 1-(4-(2H-1,2,3-triazol-1-yl)phenyl)-1H-pyrazolo[3,4-d]pyrimidin-4 (5H)-one | 1-(4-hydrazinylphenyl)-1H-1,2,3-triazole hydrochloride and 2-(4-hydrazinylphenyl)-1H-1,2,3-triazole hydrochloride prepared from 4-(2H-1,2,3-triazol-2-yl)aniline and 4-(1H-1,2,3-triazol-2-yl)aniline | 280 |
| Intermediate 2-3111. 1-(4-bromo-3-methylphenyl)-1H-pyrazolo[3,4-d]pyrimidin-4 (5H)-one | (4-bromo-3-methylphenyl)hydrazine prepared according to procedure used for intermediate 2-28 from 4-bromo-3-methylaniline | 305, 307 |
| Intermediate 2-3112. 1-(4-fluoro-3-methylphenyl)-1H-pyrazolo[3,4-d]pyrimidin-4 (5H)-one | (4-fluoro-3-methylphenyl)hydrazine starting from 4-fluoro-3-methylbenzenamine as it is outlined in procedure used for intermediate 2-28 | 245 |

Example 82: Intermediate 332aa. 7-(4-fluorophenyl)-6-phenyl-3H-pyrrolo[2,3-d]pyrimidin-4 (7H)-one

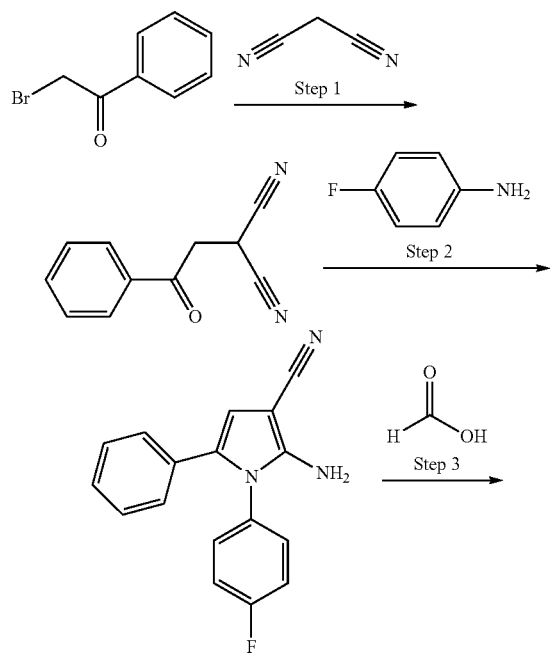

Step 1. 2-(2-oxo-2-phenylethyl(malononitrile

A 250-mL 3-necked round-bottom flask fitted with a magnetic stir bar was charged with propanedinitrile (1.39 g, 21.04 mmol), ethanol (100 mL) and 2-bromo-1-phenylethan-1-one (5 g, 25.1 mmol) followed by sodium hydroxide (1.26 g, 31.5 mmol) in ethanol (25 mL) added dropwise with stirring over 3 min. Stirring continued for 1 h at 23° C. before concentrating the reaction under vacuum. The residue was diluted with water (50 mL). The product was extracted with ethyl acetate (5×50 mL). The combined organic layers were dried over anhydrous sodium sulfate, filtered and concentrated. The residue was purified by column chromatography eluting with ethyl acetate/petroleum ether (1:1 v/v) to afford 2-(2-oxo-2-phenylethyl) malononitrile (1.2 g, 31%). LCMS: (ESI) m/z 185[M+H].

Step 2. 2-amino-1-(4-fluorophenyl)-5-phenyl-1H-pyrrole-3-carbonitrile

A 10-mL MW tube was charged with 2-(2-oxo-2-phenylethyl)malononitrile (Step 1, 340 mg, 1.85 mmol), 4-fluoroaniline (204 mg, 1.84 mmol), ethanol (3 mL), hydrochloric acid (0.1 mL, 12N). The reaction mixture was irradiated with a microwave for 1 h at 120° C. and cooled to 23° C. The pH was adjusted to 8 with saturated sodium carbonate and the product was extracted with ethyl acetate (5×30 mL). The combined organic layers were dried over anhydrous sodium sulfate, filtered and concentrated under vacuum. The residue was purified by column chromatography eluting with ethyl acetate/petroleum ether (1:1 v/v) to afford 2-amino-1-(4-fluorophenyl)-5-phenyl-1H-pyrrole-3-carbonitrile (180 mg, 35%). LCMS: (ESI) m/z 278 [M+H].

Step 3. 7-(4-fluorophenyl)-6-phenyl-3H-pyrrolo[2,3-d]pyrimidin-4 (7H)-one

A 50-mL 3-necked round-bottom flask fitted with a magnetic stir bar, thermometer and condenser was charged with 2-amino-1-(4-fluorophenyl)-5-phenyl-1H-pyrrole-3-carbonitrile (Step 2, 90 mg, 0.32 mmol), formic acid (10 mL) and water (0.5 mL). The resulting solution was stirred for 1.5 h at 100° C. and cooled to 23° C. The solvent was removed under vacuum and the residue was diluted with water (20 mL). The product was extracted with ethyl acetate (5×20 mL). The combined organic layers were dried over anhydrous sodium sulfate, filtered and concentrated to afford 7-(4-fluorophenyl)-6-phenyl-3H-pyrrolo[2,3-d]pyrimidin-4 (7H)-one (120 mg) and used without further purification. LCMS: (ESI) m/z 306[M+H].

Example 83: Intermediate 2-537a. 1-[4-(hydroxymethyl)phenyl]-1H,4H,5H-pyrazolo[3,4-d]pyrimidin-4-one

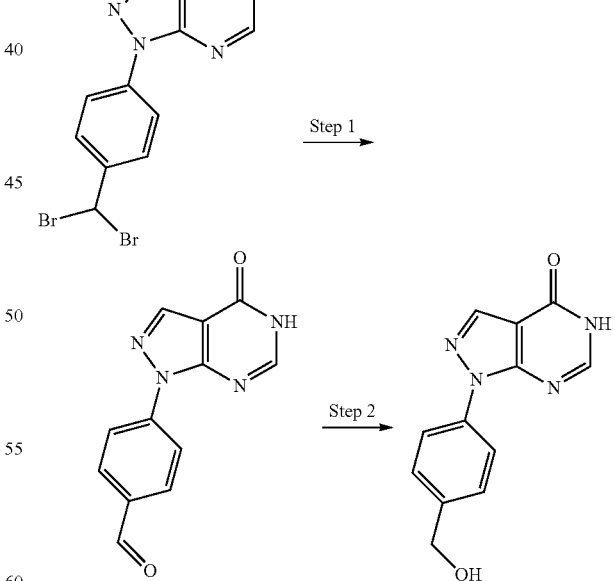

Step 1. 1-[4-(Dibromomethyl)phenyl]-1H,4H,5H-pyrazolo[3,4-d]pyrimidin-4-one

A 250-mL 3-necked round-bottom flask fitted with a magnetic stir bar, condenser and thermometer was charged with 1-(4-methylphenyl)-1H,4H,5H-pyrazolo[3,4-d]pyrimidin-4-one (900 mg, 3.98 mmol), tetrachloromethane (60 mL, 619 mmol), N-bromosuccinimide (2.25 g, 12.6 mmol), benzoyl peroxide (2.03 g, 7.90 mmol). The solution was stirred for 14 h at 80° C. in an oil bath After cooling to 25° C., the reaction was quenched with water (50 mL). The product was extracted with dichloromethane (4×40 mL). The combined organic layers were washed with brine (30 mL), dried over anhydrous sodium sulfate, filtered and concentrated under vacuum. The residue was purified by column chromatography eluting with dichloromethane/methanol (20:1, v/v) to give 1-[4-(dibromomethyl)phenyl]-1H,4H,5H-pyrazolo[3,4-d]pyrimidin-4-one as a yellow solid (1 g, 65%). LCMS: (ES) m/z 383, 385, 387 [M+H].

Step 2. 4-[4-oxo-1H,4H,5H-pyrazolo[3,4-d]pyrimidin-1-yl]benzaldehyde

A 100-mL 3-necked round-bottom flask fitted with a magnetic stir bar, condenser and thermometer was charged with 1-[4-(dibromomethyl)phenyl]-1H,4H,5H-pyrazolo[3,4-d]pyrimidin-4-one (Step 1, 1 g, 2.60 mmol), dioxane (20 mL), water (40 mL) and calcium carbonate (260 mg, 2.55 mmol). The resulting solution was stirred for 1 h at 100° C. in an oil bath. After cooling to 25° C., the reaction was with water (20 mL). The solids were collected by filtration, washed with water (2×20 mL) and dried in an oven to give 4-[4-oxo-1H,4H,5H-pyrazolo[3,4-d]pyrimidin-1-yl]benzaldehyde as a yellow solid (900 mg, >95%). LCMS: (ES) m/z 241 [M+H].

Step 3. 1-[4-(hydroxymethyl)phenyl]-1H,4H,5H-pyrazolo[3,4-d]pyrimidin-4-one

A 50-mL round-bottom flask fitted with a magnetic stir bar was charged with 4-[4-oxo-1H,4H,5H-pyrazolo[3,4-d]pyrimidin-1-yl]benzaldehyde (Step 2, 500 mg, 2.08 mmol) and tetrahydrofuran (20 mL). This was followed by the addition of sodium borohydride (463 mg, 12.2 mmol) in portions at 0° C. The solution was stirred for 4 h at 25° C. The reaction was quenched with water (10 mL) and the product was extracted with ethyl acetate (3×20 mL). The combined organic layers were dried over anhydrous sodium sulfate, filtered and concentrated under vacuum. The residue was purified by column chromatography eluting with dichloromethane/methanol (50:1-20:1, v/v) to afford 1-[4-(hydroxymethyl)phenyl]-1H,4H,5H-pyrazolo[3,4-d]pyrimidin-4-one as an off-white solid (100 mg, 20%). LCMS: (ES) m/z 243 [M+H].

Example 84: Intermediate 2-665a. 1-(4-cyclobutylphenyl)-5-[(4-hydroxypiperidin-4-yl)methyl]-1H,4H,5H-pyrazolo[3,4-d]pyrimidin-4-one TFA salt

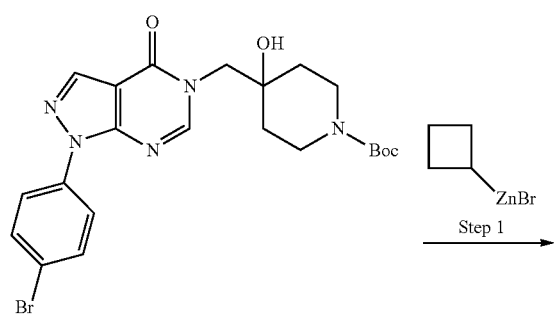

Step 1. Tert-butyl 4-[[1-(4-cyclobutylphenyl)-4-oxo-1H,4H,5H-pyrazolo[3,4-d]pyrimidin-5-yl]methyl]-4-hydroxypiperidine-1-carboxylate

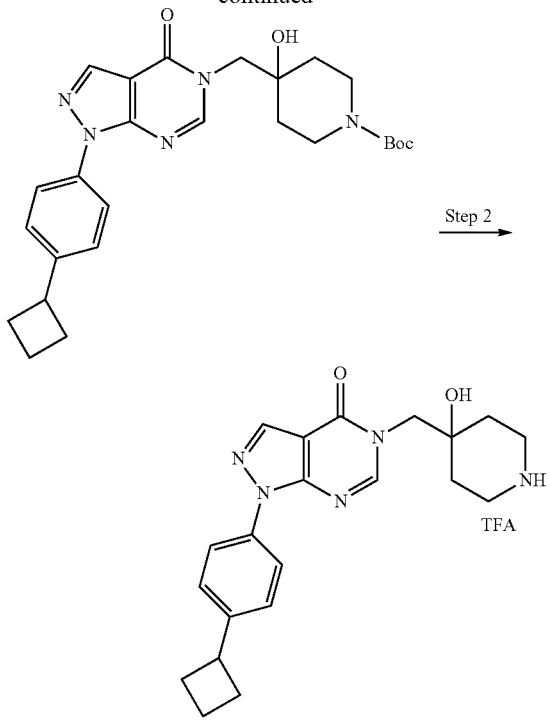

A 100-mL round-bottom flask fitted with a nitrogen balloon and magnetic stir bar was charged with tert-butyl 4-[[1-(4-bromophenyl)-4-oxo-1H,4H,5H-pyrazolo[3,4-d]pyrimidin-5-yl]methyl]-4-hydroxypiperidine-1-carboxylate (500 mg, 0.99 mmol), tetrahydrofuran (30 mL), palladium acetate (11.1 mg, 0.05 mmol), S-Phos (30.5 mg, 0.07 mmol), bromo(cyclobutyl)zinc (1.98 mL, 4.94 mmol). The reaction was stirred for 16 h at 25° C. under nitrogen and then quenched with water (50 mL). The product was extracted with ethyl acetate (3×40 mL). The combined organic layers were dried over anhydrous sodium sulfate, filtered and concentrated under vacuum. The residue was purified by column chromatography eluting with ethyl acetate/petroleum ether (1:1, v/v) to afford tert-butyl 4-[[1-(4-cyclobutylphenyl)-4-oxo-1H,4H,5H-pyrazolo[3,4-d]pyrimidin-5-yl]methyl]-4-hydroxypiperidine-1-carboxylate (50 mg, 11%). LCMS: (ES) m/z 480 [M+H].

Step 2 1-(4-cyclobutylphenyl)-5-[(4-hydroxypiperidin-4-yl)methyl]-1H,4H,5H-pyrazolo[3,4-d]pyrimidin-4-one, TFA salt The title compound was prepared according to the method outlined in Example 2 utilizing tert-butyl 4-[[1-(4-cyclobutylphenyl)-4-oxo-1H,4H,5H-pyrazolo[3,4-d]pyrimidin-5-yl] methyl]-4-hydroxypiperidine-1-carboxylate (Step 1, 50 mg, 0.10 mmol) as starting material (52 mg). LCMS: (ES) m/z 380 [M+H].

Example 85: Intermediate 2-869a. 4-[1-[2-(Benzyloxy)ethyl]-1H-pyrazol-4-yl]benzoic acid

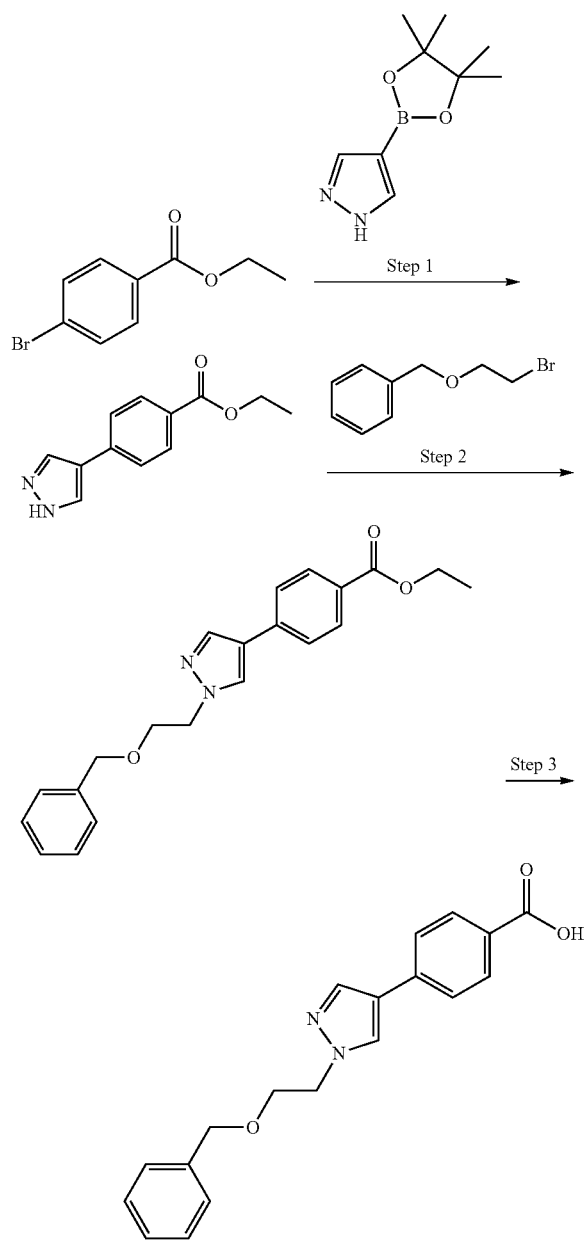

Step 1. Ethyl 4-(1H-pyrazol-4-yl)benzoate

A 500-mL 3-necked round-bottom flask fitted with a nitrogen balloon, magnetic stir bar, condenser and thermometer was charged with ethyl 4-bromobenzoate (2 g, 8.73 mmol), 4-(tetramethyl-1,3,2-dioxaborolan-2-yl)-1H-pyrazole (2 g, 10.3 mmol), Pd(dppf)Cl$_2$.CH$_2$Cl$_2$ (700 mg, 0.86 mmol), potassium carbonate (26.3 mg, 0.19 nmol), 1,4-dioxane (200 mL) and water (20 mL). The resulting solution was stirred for 10 h at 100° C. in an oil bath under nitrogen. After cooling to 25° C., the reaction was quenched with water (200 mL). The product was extracted with ethyl acetate (3×50 mL). The combined organic layers were dried over sodium sulfate, filtered and concentrated under vacuum. The residue was purified by column chromatography eluting with ethyl acetate/petroleum (4:1, v/v) to afford ethyl 4-(1H-pyrazol-4-yl)benzoate as a yellow solid (360 mg, 19%). LCMS: (ESI) m/z 217 [M+H].

Step 2. Ethyl 4-[1-[2-(benzyloxy)ethyl]-1H-pyrazol-4-yl]benzoate

The title compound as prepared according to the procedure outlined in Example 865, Step 1, utilizing ethyl 4-(1H-pyrazol-4-yl)benzoate (Step 1, 80 mg, 0.37 mmol), and [(2-bromoethoxy)methyl]benzene (240 mg, 1.12 mmol) as starting materials which was used in the next step without further purification (100 mg). LCMS: (ESI) m/z 351 [M+H]

Step 3. 4-[1-[2-(Benzyloxy)ethyl]-1H-pyrazol-4-yl]benzoic acid

The title compound as prepared according to the procedure outlined in Example 10, Step 2, utilizing ethyl 4-[1-[2-(benzyloxy)ethyl]-1H-pyrazol-4-yl]benzoate (Step 2, 100 mg, 0.29 mmol) as starting material LCMS: (ESI) m/v 323 [M+H].

Example 85a: Intermediate 2-131. trans-4-(difluoromethoxy)cyclohexane-1-carboxylic acid

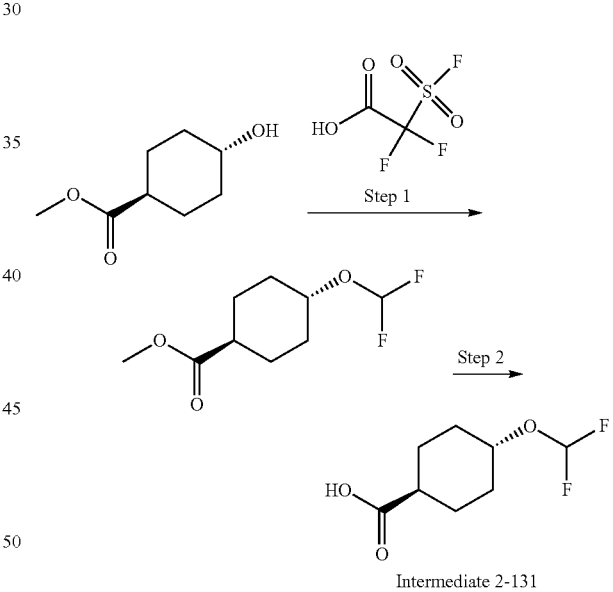

Intermediate 2-131

Step 1. Methyl (1r,4r)-4-(difluoromethoxy)cyclohexane-1-carboxylate

A 50-mL 3-necked round-bottom fitted with a nitrogen balloon, magnetic stir bar condenser and thermometer was charged with methyl trans-4-hydroxycyclohexane-1-carboxylate (200 mg, 1.26 mmol), acetonitrile (20 mL) and cuprous iodide (239 mg, 1.25 mmol). To the reaction was added 2,2-difluoro-2-(fluorosulfonyl)acetic acid (715 mg, 4.01 mmol) dropwise with stirring at 65° C. over 15 min. The solution was stirred for 1 h and cooled to 25° C. The reaction was quenched with water (15 mL). The product was extracted with ethyl acetate (3×30 mL). The organic layers were combined, washed with brine (3×20 mL), dried over anhydrous sodium sulfate, filtered and concentrated under vacuum. The residue was purified by column chromatography eluting with ethyl acetate/petroleum ether (1:10-1:5, v/v) to afford the title compound (200 mg). GCMS: m/z 208.

Step 2.
Trans-4-(Difluoromethoxy)cyclohexane-1-carboxylic acid

The title compound was prepared according to the procedure described in Example 10, Step 2, utilizing methyl (1r,4r)-4-(difluoromethoxy)cyclohexane-1-carboxylate (100 mg, 0.48 mmol), (Intermediate 2-131, 40 mg, 43%). LCMS: (ESI) m/z 193 [M−1]. *Column: XBridge Shield RP18 OBD Column, 5 μm, 19×150 mm. Mobile phase A: aqueous trifluoroacetic acid (0.1%)/Mobile phase B: acetonitrile. Gradient: 25% B to 45% B over 7 min. Detector: 220 and 254 nm.

Methods for the Synthesis of Compounds of Formula (I)
Method A

Example 86: 5-((4-Hydroxy-1-(3-phenylbutanoyl)piperidin-4-yl)methyl)-1-methyl-1,5-dihydro-4H-pyrazolo[3,4-d]pyrimidin-4-one (I-1)

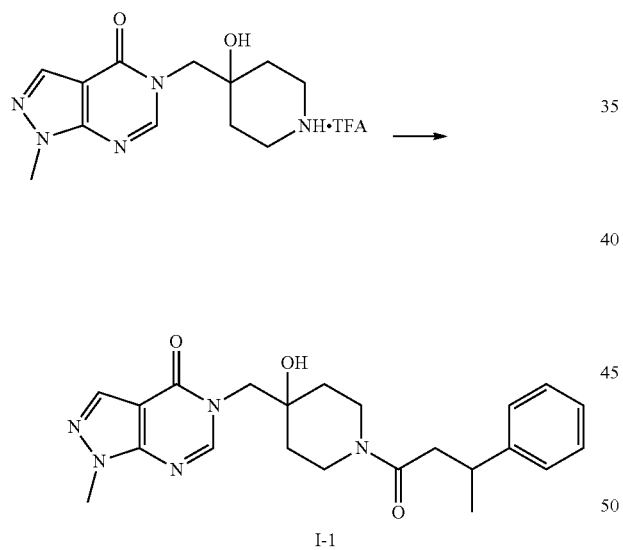

I-1

To a solution of 5-((4-hydroxypiperidin-4-yl)methyl)-1-methyl-1,5-dihydro-4H-pyrazolo[3,4-d]pyrimidin-4-one trifluoroacetic acid (Intermediate 2-2, 21 mg, 0.08 mmol) in 1,2-dichloroethane (0.2 mL) was added 3-phenylbutanoic acid (0.2 M in 1,2-dichloroethane, 0.480 mL, 0.096 mmol), DIPEA (0.070 mL, 0.4 mmol) and HATU (37 mg, 0.096 mmol). The reaction mixture was stirred at 50° C. for 16 h. The reaction mixture was cooled to room temperature, diluted with dichloromethane and washed with water. The crude product was purified by preparative HPLC (Method 6) to afford 5-((4-hydroxy-1-(3-phenylbutanoyl)piperidin-4-yl)methyl)-1-methyl-1,5-dihydro-4H-pyrazolo[3,4-d]pyrimidin-4-one (I-1, 13 mg, 38%). LCMS (ESI) m/z 410.23 [M+H]

Method D

Example 87: N-([1,1'-biphenyl]-4-yl)-4-hydroxy-N-methyl-4-({1-methyl-4-oxo-1,4-dihydro-5H-pyrazolo[3,4-d]pyrimidin-5-yl}methyl)piperidine-1-carboxamide (I-4)

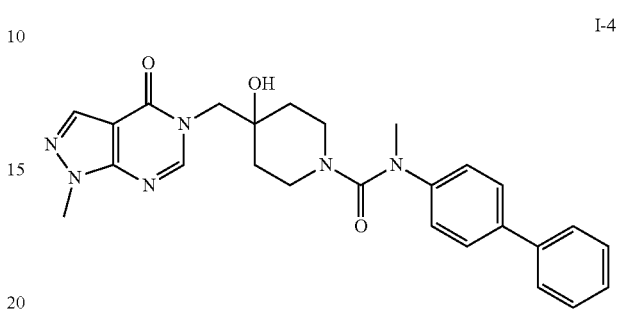

I-4

The [1,1'-biphenyl]-4-yl(methyl)carbamic chloride solution (prepared by the addition of triphosgene (3 mg, 11 μmol) to a solution of N-methyl-[1,1'-biphenyl]-4-amine (5.5 mg, 30 μmol) and DIPEA (11 μL, 60 μmol) in 1,2-dichloroethane (200 μL) and the resulting solution was stirred at room temperature for 2.5 h and used without further purification) was added to a suspension of 5-((4-hydroxypiperidin-4-yl)methyl)-1-methyl-1,5-dihydro-4H-pyrazolo[3,4-d]pyrimidin-4-one, hydrochloric acid salt (Intermediate 2-2a, 9 mg, 30 μmol) and DIPEA (11 μL, 60 μmol) in 1,4-dioxane (200 μL). The resulting solution was stirred for 16 h at room temperature, concentrated under reduced pressure and then partitioned between saturated aqueous sodium bicarbonate and ethyl acetate. The ethyl acetate was separated and combined with a second ethyl acetate extract. The combined extracts were concentrated under reduced pressure and the crude product was purified by preparative HPLC (Method 6) to afford N-([1,1'-biphenyl]-4-yl)-4-hydroxy-N-methyl-4-({1-methyl-4-oxo-1,4-dihydro-5H-pyrazolo[3,4-d]pyrimidin-5-yl}methyl)piperidine-1-carboxamide (I-4, 6.5 mg, 46%). LCMS: (ESI) m/z 473.06 [M+H].

Method E

Example 88: 1-(3-((Cyclohexyl(ethyl)amino)methyl)phenyl)-5-((1-(cyclopropane-carbonyl)-4-hydroxypiperidin-4-yl)methyl)-1,5-dihydro-4H-pyrazolo[3,4-d]pyrimidin-4-one (I-5)

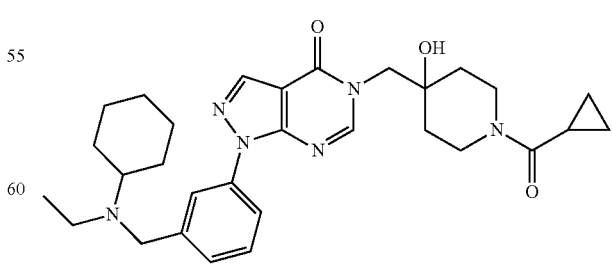

I-5

N-Ethylcyclohexanamine (0.2 M 1,4-dioxane, 180 μL, 36 μmol) was added to a suspension of potassium (bromomethyl)trifluoroborate (7 mg, 36 μmol) in 1,4-dioxane (162

μL) and water (18 μL). The resulting mixture was sealed and heated at 80° C. for 6 h. The reaction mixture was cooled to room temperature. 1-(3-bromophenyl)-5-((1-(cyclopropanecarbonyl)-4-hydroxypiperidin-4-yl)methyl)-1,5-dihydro-4H-pyrazolo[3,4-d]pyrimidin-4-one (Intermediate 2-31, 0.2 M solution in DMF, 15.0 μL, 30 μmol) and cesium carbonate (1.0M in methanol, 90 μL, 90 μmol) were added and nitrogen gas was bubbled through the resulting mixture. Chloro(2-dicyclohexylphosphino-2',4',6'-tri-iso-propyl-1,1'-biphenyl)[2-(2-aminoethyl)phenyl] palladium (II) methyl-tert-butyl ether adduct (0.01 M in 1,4-dioxane, 75 μL, 0.75 μmol) was added and the reaction mixture was heated at 100° C. for 16 h. The reaction mixture was diluted with brine (500 μL) and extracted with ethyl acetate (2×500 μL). The organic layers were combined, concentrated, and purified by preparative HPLC (Method 8) to afford 1-(3-((cyclohexyl (ethyl)amino)methyl)phenyl)-5-((1-(cyclopropanecarbonyl)-4-hydroxypiperidin-4-yl)methyl)-1,5-dihydro-4H-pyrazolo[3,4-d]pyrimidin-4-one (I-5, 3.1 mg, 19%). LCMS: (ESI) m/z 533.56 [M+H].

Method H

Example 89: 5-((1-(Cyclopropanecarbonyl)-4-hydroxypiperidin-4-yl)methyl)-1-(3'-(trifluoromethyl)-[1,1'-biphenyl]-4-yl)-1,5-dihydro-4H-pyrazolo[3,4-d]pyrimidin-4-one (I-8)

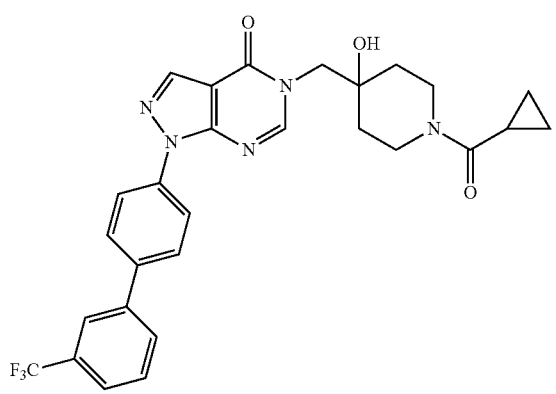

I-8

1-(4-Bromophenyl)-5-((1-(cyclopropanecarbonyl)-4-hydroxypiperidin-4-yl)methyl)-1,5-dihydro-4H-pyrazolo[3,4-d]pyrimidin-4-one (Intermediate 2-30, 0.05 M in 1:1 toluene:DMF, 600 μL, 30 μmol), (3-(trifluoromethyl)phenyl)boronic acid (0.2 M in 1,4-dioxane, 270 μL, 54 μmol), potassium carbonate (1.0 M aqueous, 90 μL, 90 μmol) and [1,1'-bis(diphenylphosphino)ferrocene]dichloropalladium (II), complex with dichloromethane (0.02 M in 1,2-dichloroethane, 150 μL, 3 μmol) were combined and heated at 80° C. under nitrogen for 14 h. The reaction mixture was cooled to room temperature. Ethyl acetate (500 μL) and sodium hydroxide (1.0 M aqueous, 400 μL) were added. The organic phase was separated and the aqueous layer was extracted with ethyl acetate (500 μL). The combined organic phases were concentrated and purified by preparative HPLC (Method 6) to give 5-((1-(cyclopropane carbonyl)-4-hydroxypiperidin-4-yl)methyl)-1-(3'-(trifluoromethyl)-[1,1'-biphenyl]-4-yl)-1,5-dihydro-4H-pyrazolo[3,4-d]pyrimidin-4-one (I-8, 3.2 mg, 20%). LCMS: (ESI) nm/z 538.37 [M+H].

Method I

Example 90: 5-((4-Hydroxy-1-(4-((pyrimidin-2-yloxy)methyl)benzoyl)piperidin-4-yl)methyl)-1-methyl-1,5-dihydro-4H-pyrazolo[3,4-d]pyrimidin-4-one (I-9)

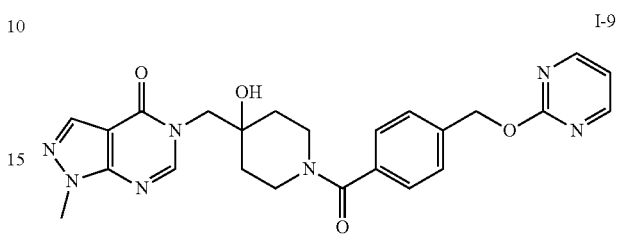

I-9

In a 20 mL vial was added 5-((4-hydroxy-1-(4-(hydroxymethyl)benzoyl)piperidin-4-yl)methyl)-1-methyl-1,5-dihydro-4H-pyrazolo[3,4-d]pyrimidin-4-one (Intermediate 2-7, 0.030 g, 0.075 mmol) and sodium hydride (60% in mineral oil, 6 mg, 0.151 mmol) in portions at 0° C. in DMF (0.503 mL). The reaction was stirred for 5 min and then 2-chloropyrimidine (0.09 g, 0.075 mmol) was added to give a brown suspension. The reaction was stirred at 23° C. for 16 h. The DMF was removed under reduced pressure and the crude material was purified by column chromatography (Biotage, 25 g column, eluting with 0-10% methanol/dichloromethane gradient) to provide 5-((4-hydroxy-1-(4-((pyrimidin-2-yloxy)methyl)benzoyl)piperidin-4-yl)methyl)-1-methyl-1,5-dihydro-4H-pyrazolo[3,4-d]pyrimidin-4-one (I-9, 8.2 mg, 23%). LCMS: (ESI) m/z 476.19 [M+H].

Method J

Example 91: 4-((4-(4-Hydroxy-4-({1-methyl-4-oxo-1,4-dihydro-5H-pyrazolo[3,4-d]pyrimidin-5-yl)methyl)piperidine-1-carbonyl)benzyl)oxy)benzonitrile (I-10)

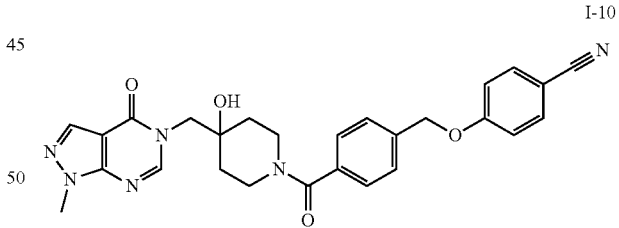

I-10

In a 20 mL vial was added 5-((4-hydroxy-1-(4-(hydroxymethyl)benzoyl)piperidin-4-yl)methyl)-1-methyl-1,5-dihydro-4H-pyrazolo[3,4-d]pyrimidin-4-one (Intermediate 2-7, 30 mg, 0.075 mmol), 4-hydroxybenzonitrile (9.89 mg, 0.083 mmol) and a solution of triphenylphosphine (0.022 g, 0.083 mmol) in tetrahydrofuran (0.503 mL). Diisopropyl azodicarboxylate (0.016 mL, 0.083 mmol) was added and the reaction was stirred for 3 h at 23° C. The solution was diluted with ethyl acetate (30 mL) and washed with saturated aqueous ammonium chloride (20 mL) and saturated aqueous sodium bicarbonate (20 mL). The organic layer was dried over magnesium sulfate, filtered and concentrated. The crude product was purified by preparative HPLC (Method 1) to provide 4-((4-(4-hydroxy-4-({1-methyl-4-oxo-1,4-dihydro-5H-pyrazolo[3,4-d]pyrimidin-5-yl)methyl)piperidine-1-carbonyl)benzyl)oxy) benzonitrile (I-10, 3.4 mg, 9%). LCMS: (ESI) m/z 499.23 [M+H].

Method K

Example 92: 2-(3-(5-((1-Benzoyl-4-hydroxypiperidin-4-yl)methyl)-4-oxo-4,5-dihydro-1H-pyrazolo[3,4-d]pyrimidin-1-yl)phenyl)acetic acid (I-11)

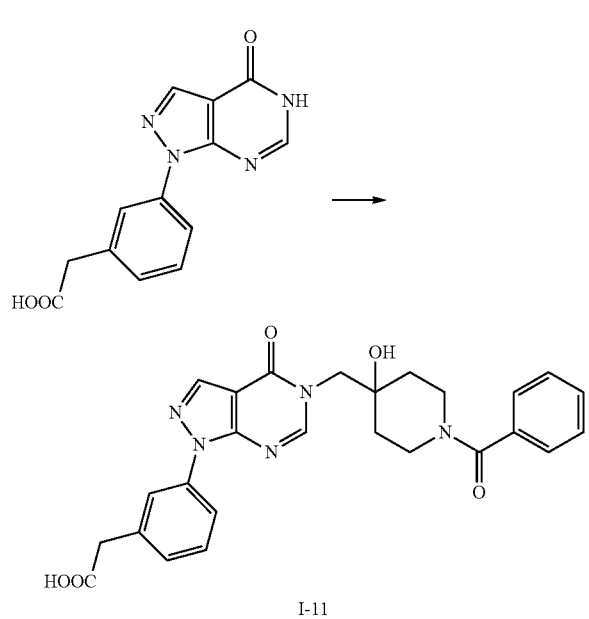

I-11

2-(3-(4-Oxo-4,5-dihydro-1H-pyrazolo[3,4-d]pyrimidin-1-yl)phenyl)acetic acid (prepared with a similar procedure outline in procedure used for intermediate 2-28 utilizing Methyl 2-(3-aminophenyl) acetate as starting material followed by procedure outlined in Example 21 utilizing Methyl 2-(3-hydrazinylphenyl)acetate as starting material which led to in situ hydrolysis of the methyl ester) (180 mg, 0.67 mmol), cesium carbonate (652 mg, 2.00 mmol), DMF (10 mL) and 6-benzoyl-1-oxa-6-azaspiro[2.5]octane (Intermediate 2-36, 174 mg, 0.80 mmol) were added to a 100-mL round-bottom flask fitted with magnetic stir bar, condenser and thermometer. The resulting solution was stirred for 3 h at 100° C. The reaction was then quenched by the addition of water (20 mL). The resulting solution was extracted with dichloromethane (5×20 mL) and the organic layers were combined, dried over anhydrous sodium sulfate, filtered and concentrated under vacuum. The residue was purified by preparative HPLC* to give 2-(3-(5-((I-benzoyl-4-hydroxypiperidin-4-yl)methyl)-4-oxo-4,5-dihydro-1H-pyrazolo[3,4-d]pyrimidin-1-yl)phenyl) acetic acid (I-11, 34 mg, 10%). $^1$H NMR (300 MHz, CD$_3$OD) δ 8.29-8.28 (m, 1H), 8.28-8.20 (m, 1H), 8.01 (s, 1H), 7.85-7.83 (m, 1H), 7.47-7.34 (m, 7H), 4.36-4.34 (m, 1H), 4.14 (s, 2H), 3.57-3.30 (m, 5H), 1.81-1.67 (m, 3H), 1.45-1.42 (m, 1H). LCMS: (ESI) m/z 488.39 [M+H]. *Column: Waters XBridge BEH Shield RP18 OBD Prep Column, 130 Å, 5 µm, 19 mm×150 mm. Mobile phase A: 0.05% aqueous ammonium bicarbonate/Mobile phase B: acetonitrile. Gradient: 3% B to 10% B over 8 min. Detector: 220 and 254 nm.

Method L

Example 93: 5-((1-(4-(3,4-Dihydroisoquinolin-2(1H)-yl)benzoyl)-4-hydroxypiperidin-4-yl)methyl)-1-methyl-1,5-dihydro-4H-pyrazolo[3,4-d]pyrimidin-4-one (I-12)

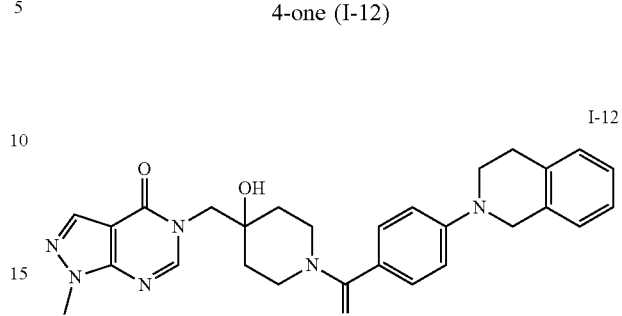

I-12

5-((1-(4-Bromobenzoyl)-4-hydroxypiperidin-4-yl)methyl)-1-methyl-1,5-dihydro-4H-pyrazolo[3,4-d]pyrimidin-4-one (Intermediate 2-3, 0.2 M solution in DMF, 150 µL, 30 µmol), 1,2,3,4-tetrahydroisoquinoline (0.2 M solution in 1,4-dioxane, 300 µL, 60 µmol) and cesium carbonate (39 mg, 120 µmol) were combined in a 2 mL reaction vial which was then purged with nitrogen. In a separate vessel, BINAP (0.05 M 1,4-dioxane, 4 mL) was combined with palladium (II) acetate (0.1 M 1,4-dioxane, 1.33 mL). The mixture was stirred at room temperature under nitrogen for 5 minutes. The preformed catalyst suspension (120 µL) was added to the reaction vial. The vial was sealed and heated at 100° C. for 16 h. The reaction mixture was partitioned between ethyl acetate (500 µL) and brine (500 µL). The organic layer was removed and concentrated. The crude product was purified by preparative HPLC (Method 3) to afford 5-((1-(4-(3,4-dihydroisoquinolin-2(1H)-yl)benzoyl)-4-hydroxypiperidin-4-yl)methyl)-1-methyl-1,5-dihydro-4H-pyrazolo[3,4-d]pyrimidin-4-one (I-12, 2 mg, 15%). LCMS: (ESI) m/z 499.17 [M+H].

Method R

Example 94: 5-((1-(2-Aminobenzoyl)-4-hydroxypiperidin-4-yl)methyl)-1-phenyl-1,5-dihydro-4H-pyrazolo[3,4-d]pyrimidin-4-one (I-17)

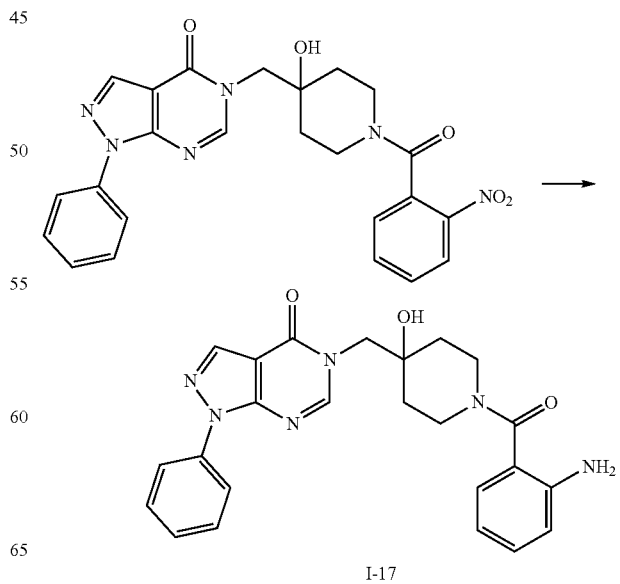

I-17

5-((4-Hydroxy-1-(2-nitrobenzoyl)piperidin-4-yl)methyl)-1-phenyl-1,5-dihydro-4H-pyrazolo[3,4-d]pyrimidin-4-one, utilizing 5-((4-Hydroxypiperidin-4-yl)methyl)-1-phenyl-1,5-dihydro-4H-pyrazolo[3,4-d]pyrimidin-4-one trifluoroacetic acid salt (Intermediate 2-18) and 2-nitrobenzoic acid as starting materials), (100 mg, 0.21 mmol), palladium on carbon (10% wt, 18 mg) and methanol (20 mL) were added to a 50-mL round-bottom flask fitted with a hydrogen balloon and a magnetic stir bar. The resulting solution was stirred for 16 h at room temperature and filtered to remove solids. The filtrate was concentrated under vacuum and the crude product was purified by preparative HPLC* to give 5-((1-(2-aminobenzoyl)-4-hydroxypiperidin-4-yl)methyl)-1-phenyl-1,5-dihydro-4H-pyrazolo[3,4-d]pyrimidin-4-one (I-17, 11 mg, 11%). $^1$H NMR (300 MHz, DMSO-d$_6$) δ 8.36 (s, 1H), 8.34 (s, 1H), 8.05 (d, 2H), 7.58 (t, 2H), 7.42 (t, 1H), 7.10-7.04 (m, 1H), 6.99-6.96 (m, 1H), 6.69 (d, 1H), 6.55 (t, 1H), 5.12 (br s, 2H), 4.96 (s, 1H), 4.05 (s, 2H), 3.32-3.15 (m, 4H), 1.66-1.40 (m, 4H) ppm. LCMS: (ESI) m/z 445.10 [M+H]. *Column: Waters XBridge BEH Shield RP18 OBD Prep Column, 130 Å, 5 μm, 19 mm×150 mm. Mobile phase A: 0.5% aqueous ammonium bicarbonate/Mobile phase B: acetonitrile. Gradient: 30% B to 70% B over 10 min. Flow rate: 20 mL/min. Detector: 254 nm.
Method S Example 95: 5-((1-Benzoyl-4-hydroxypiperidin-4-yl)methyl)-1-(2-hydroxyphenyl)-1,5-dihydro-4H-pyrazolo[3,4-d]pyrimidin-4-one (I-18)

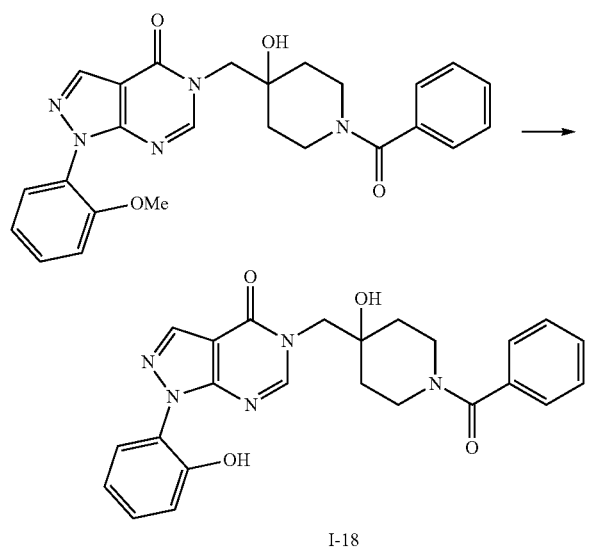

I-18

5-((1-Benzoyl-4-hydroxypiperidin-4-yl)methyl)-1-(2-methoxyphenyl)-1,5-dihydro-4H-pyrazolo[3,4-d]pyrimidin-4-one and dichloromethane (10 mL) were added to a 50-mL 3-necked round-bottom flask fitted with a magnetic stir bar and thermometer. This was followed by the addition of boron tribromide (0.22 mL, 2.00 equiv) at 5° C. The resulting solution was stirred for 30 min at room temperature. The reaction was then quenched by the addition of methanol and concentrated under vacuum. The residue was purified by column chromatography eluting with dichloromethane/methanol (30:1 v/v). The product was further purified by preparative HPLC* to give 5-((1-benzoyl-4-hydroxypiperidin-4-yl)methyl)-1-(2-hydroxyphenyl)-1,5-dihydro-4H-pyrazolo[3,4-d]pyrimidin-4-one (I-18, 9 mg, 9%). LCMS: (ESI) m/z 446.12.*Column: Waters XSelect CSH C18 OBD Prep Column, 130 Å, 5 μm, 19 mm×150 mm. Mobile phase A: 0.05% aqueous ammonium bicarbonate/Mobile phase B: acetonitrile. Gradient: 5% B to 49% B over 7 min. Detector: 220 and 254 nm.
Method W Example 96: 3-(5-((1-Benzoyl-4-hydroxypiperidin-4-yl)methyl)-4-oxo-4,5-dihydro-1H-pyrazolo[3,4-d]pyrimidin-1-yl)benzoic acid (I-22)

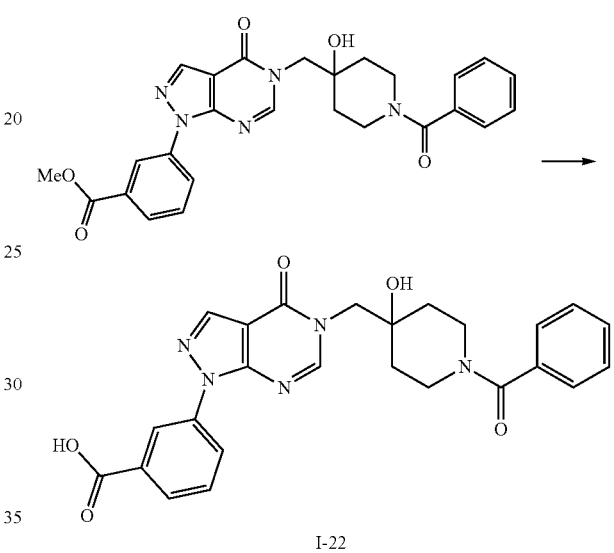

I-22

Methyl 3-(5-((1-benzoyl-4-hydroxypiperidin-4-yl)methyl)-4-oxo-4,5-dihydro-1H-pyrazolo [3,4-d]pyrimidin-1-yl)benzoate (prepared according to procedure outline in Method A utilizing Methyl 3-(5-((4-hydroxypiperidin-4-yl)methyl)-4-oxo-4,5-dihydro-1H-pyrazolo[3,4-d]pyrimidin-1-yl)benzoate trifluoroacetic acid salt (Intermediate 2-20) and benzoic acid (60 mg, 0.12 mmol), lithium hydroxide (6 mg, 0.26 mmol), water (5 mL) and tetrahydrofuran (10 mL) were added to a 100-mL round-bottom flask fitted with magnetic stir bar. The resulting solution was stirred for 16 h at room temperature. The pH value of the solution was adjusted to 2 with hydrochloric acid (6.0 M aqueous) and then extracted with ethyl acetate (3×30 mL). The organic layers were combined, dried over anhydrous sodium sulfate, filtered and concentrated under vacuum. The residue was purified by preparative HPLC* to give 3-(5-((1-benzoyl-4-hydroxypiperidin-4-yl)methyl)-4-oxo-4,5-dihydro-1H-pyrazolo[3,4-d]pyrimidin-1-yl)benzoic acid (I-22, 26 mg, 17%). $^1$H NMR (300 MHz, CD$_3$OD) δ 8.62 (s, 1H), 8.27 (s, 1H), 8.19 (s, 1H), 8.06 (d, 1H), 7.94 (d, 1H), 7.51-7.35 (m, 6H), 4.88 (s, 1H), 4.34-4.30 (m, 1H), 4.12-4.06 (m, 1H), 3.61-3.57 (m, 1H), 3.49-3.37 (m, 2H), 1.91-1.52 (m, 3H), 1.50-1.32 (m, 1H) ppm. LCMS: (ESI) m/z 474.22 [M+H]. *Column: Waters XBridge BEH Shield RP18 OBD Prep Column, 130 Å, 5 μm, 19 mm×150 mm. Mobile phase A: 10 mM aqueous ammonium bicarbonate/Mobile phase B: acetonitrile. Gradient: 10% B to 75% B over 10 min. Flow rate: 25 mL/min. Detector: 220 and 254 nm.

Method X

Example 97: 5-((1-(4-(Cyclopropylamino)benzoyl)-4-hydroxypiperidin-4-yl)methyl)-1-phenyl-1,5-dihydro-4H-pyrazolo[3,4-d]pyrimidin-4-one (I-23)

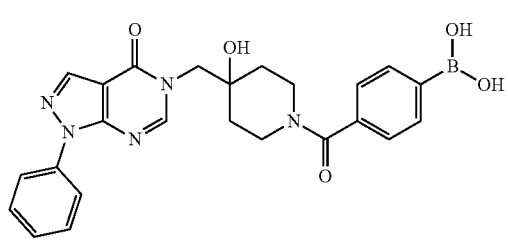

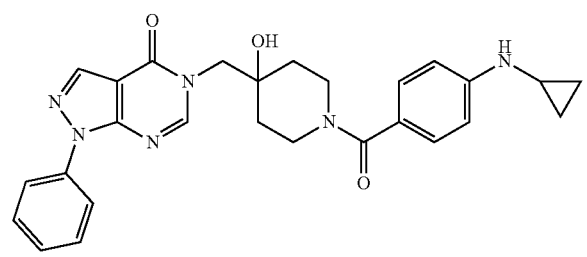

I-23

(4-(4-Hydroxy-4-((4-oxo-1-phenyl-1,4-dihydro-5H-pyrazolo[3,4-d]pyrimidin-5-yl)methyl)piperidine-1-carbonyl)phenyl)boronic acid (Prepared according to the procedure described in Method utilizing 5-((4-Hydroxypiperidin-4-yl)methyl)-1-phenyl-1,5-dihydro-4H-pyrazolo[3,4-d]pyrimidin-4-one trifluoroacetic acid salt (Intermediate 2-18) and 4-(dihydroxyboranyl)benzoic acid as starting materials) (250 mg, 0.53 mmol), cyclopropylamine (60 mg, 1.05 mmol), copper (II) acetate (240 mg, 0.53 mmol), pyridine (125 mg, 1.58 mmol), dichloromethane (30 mL) and 4 Å molecular sieves (200 mg) were added to a 100 mL round-bottom flask fitted with a magnetic stir bar. The resulting solution was stirred for 16 h at room temperature. The solids were filtered and the filtrate was concentrated under vacuum. The residue was first purified by silica gel column chromatography eluting with dichloromethane/methanol (20:1 v/v) and then further purified by preparative HPLC* to give 5-((1-(4-(cyclopropylamino)benzoyl)-4-hydroxypiperidin-4-yl)methyl)-1-phenyl-1,5-dihydro-4H-pyrazolo[3,4-d]pyrimidin-4-one (I-23, 11 mg, 4%). $^1$H NMR (300 MHz, CDCl$_3$) δ 8.27 (s, 1H), 8.07-7.93 (m, 3H), 7.64-7.26 (m, 5H), 6.75-6.73 (m, 2H), 4.23-3.98 (m, 3H), 3.48-3.08 (m, 3H), 2.55-2.31 (m, 1H), 2.08-1.40 (m, 4H), 0.90-0.65 (m, 2H), 0.65-0.40 (m, 2H) ppm. LCMS: (ESI) m/z 485.22 [M+H]. *Column: Waters XBridge BEH Shield RP18 OBD Prep Column, 130 Å, 5 μm, 19 mm×150 mm. Mobile phase A: 0.1% aqueous ammonium hydroxide/Mobile phase B: acetonitrile. Gradient: 25% B to 46% B over 8 min. Detector: 220 and 254 nm.

Method B

Example 98

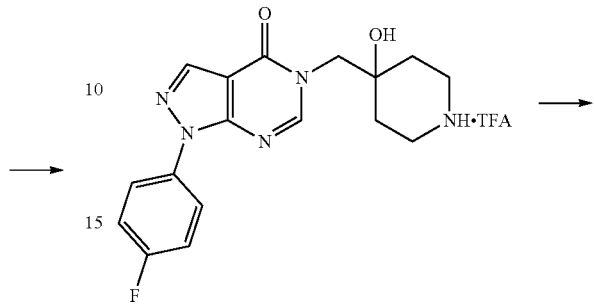

Intermediate 2-28

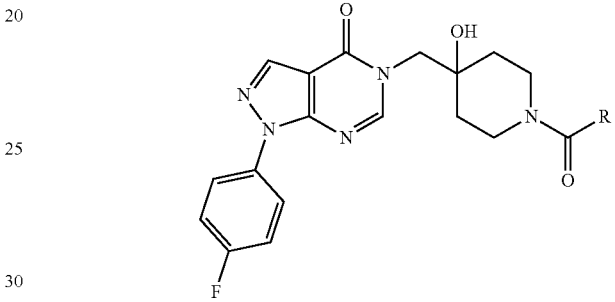

1-(4-fluorophenyl)-5-((4-hydroxypiperidin-4-yl)methyl)-1,5-dihydro-4H-pyrazolo[3,4-d]pyrimidin-4-one trifluoroacetic acid salt (Intermediate 2-28, 130 mg, 0.28 mmol), dichloromethane (150 mL) and triethylamine (152 mg, 1.50 mmol) were added to a 250-mL round-bottom flask fitted with a magnetic stir bar. The relevant carbamoyl or acid chloride (0.87 mmol) was added dropwise at 0° C. The resulting solution was stirred for 16 h at room temperature and then quenched by addition of water (20 mL). The organic layer was dried over anhydrous sodium sulfate, filtered and concentrated under vacuum. The crude product was purified by preparative HPLC with the following conditions: Column: Waters SunFire C18 OBD Prep Column, 100 Å, 5 μm, 19 mm×150 mm. Mobile phase A: 0.05% aqueous ammonium bicarbonate/Mobile phase B: acetonitrile. Detector: 220 and 254 nm.

Method C

Example 99: N-(4'-(4-Hydroxy-4-({1-methyl-4-oxo-1,4-dihydro-5H-pyrazolo[3,4-d]pyrimidin-5-yl)methyl)piperidine-1-carbonyl)-[1,1'-biphenyl]-2-yl)ethenesulfonamide (I-45)

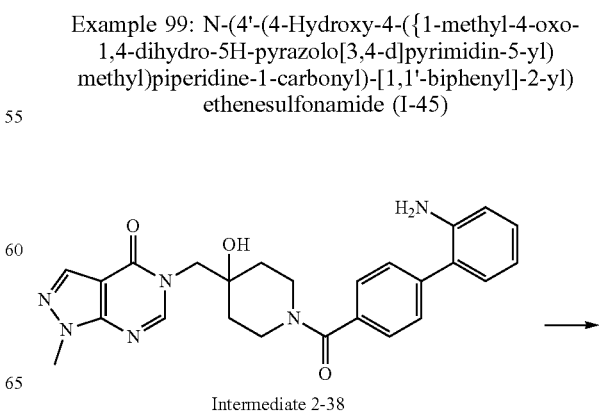

Intermediate 2-38

265
-continued

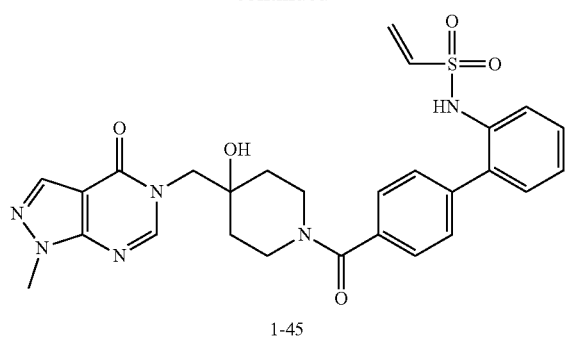

I-45

5-((1-(2'-Amino-[1,1'-biphenyl]-4-carbonyl)-4-hydroxypiperidin-4-yl)methyl)-1-methyl-1,5-dihydro-4H-pyrazolo[3,4-d]pyrimidin-4-one (Intermediate 2-38, 40 mg, 0.090 mmol), dichloromethane (10 mL) and triethylamine (30.7 mg, 0.30 mmol) were added to a 100-mL round-bottom flask fitted with a magnetic stir bar and thermometer. A solution of 2-chloroethane-1-sulfonyl chloride (17 mg, 0.10 mmol) in dichloromethane (5 mL) was added dropwise at 0° C. The resulting solution was stirred for 30 min at 0° C. The reaction was then quenched by the addition of water (10 mL). The resulting solution was extracted with dichloromethane (4×20 mL) and the organic layers were combined, dried over anhydrous sodium sulfate, filtered and concentrated under vacuum. The residue was purified by preparative HPLC* to afford N-(4'-(4-hydroxy-4-({1-methyl-4-oxo-1,4-dihydro-5H-pyrazolo[3,4-d]pyrimidin-5-yl)methyl)piperidine-1-carbonyl)-[1,1'-biphenyl]-2-yl)ethenesulfonamide (I-45. 11 mg, 23%). $^1$H NMR (400 MHz, CD$_3$OD) δ 8.28 (s, 1H), 8.07 (s, 1H), 7.56-7.46 (m, 5H), 7.40-7.31 (m, 3H), 6.57-6.51 (m, 1H), 6.04 (d, 1H), 5.87 (d, 1H), 4.42-4.38 (m, 1H), 4.22-4.12 (m, 2H), 4.00 (s, 3H), 3.72-3.69 (m, 1H), 3.52-3.46 (m, 2H), 3.46-3.32 (m, 1H), 1.87-1.65 (m, 3H), 1.50-1.47 (m, 1H) ppm. LCMS: (ESI) m/z 549.11 [M+H]. *Column: Waters XBridge BEH Shield RP18 OBD Prep Column, 130 Å, 5 μm, 19 mm×150 mm. Mobile phase A: 10 mM aqueous ammonium bicarbonate/Mobile phase B: acetonitrile. Gradient: 16% B to 42% B over 7 min. Detector: 220 and 254 nm.
Method F Example 100: (R)—N-(1-(4-Hydroxy-4-({1-methyl-4-oxo-1,4-dihydro-5H-pyrazolo[3,4-d]pyrimidin-5-yl)methyl)piperidin-1-yl)-1-oxo-3-phenylpropan-2-yl)ethenesulfonamide (I-46)

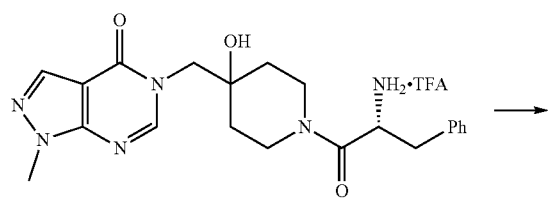

266
-continued

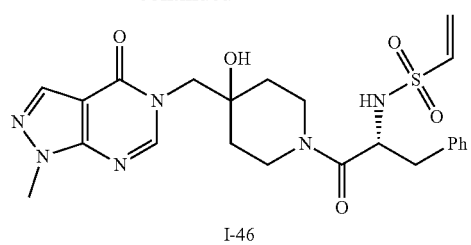

I-46

5-((1-(D-phenylalanyl)-4-hydroxypiperidin-4-yl)methyl)-1-methyl-1,5-dihydro-4H-pyrazolo[3,4-d]pyrimidin-4-one trifluoroacetic acid (prepared according to the procedure outlined in Example 20, using TFA than HCl in Step 2, utilizing 2S)-2-benzyl-3-[[(tert-butoxy)carbonyl]amino]propanoic acid and 5-((4-hydroxypiperidin-4-yl)methyl)-1-methyl-1H-pyrazolo[3,4-d]pyrimidin-4(5H)-one trifluoroacetic acid salt (Intermediate 2-2) as starting materials (200 mg, 0.49 mmol), dichloromethane (20 mL) and triethylamine (197 mg, 1.95 mmol) were added to a 100-mL round-bottom flask fitted with a magnetic stir bar and thermometer. A solution of 2-chloroethane-1-sulfonyl chloride (86 mg, 0.53 mmol) in dichloromethane (5 mL) was added at 0° C. The resulting solution was stirred for 2 h at 0° C. The reaction was then quenched by the addition of water (10 mL). The resulting solution was extracted with dichloromethane (3×20 mL) and the organic layers were combined, dried over anhydrous sodium sulfate, filtered and concentrated under vacuum. The residue was purified by preparative HPLC* to afford (R)—N-(1-(4-hydroxy-4-({1-methyl-4-oxo-1,4-dihydro-5H-pyrazolo[3,4-d]pyrimidin-5-yl)methyl)piperidin-1-yl)-1-oxo-3-phenylpropan-2-yl) ethenesulfonamide (I-46, 28 mg, 11%). LCMS: (ESI) m/z 501.09 [M+H]. *Column: Waters SunFire C18 OBD Prep Column, 100 Å, 5 μm, 19 mm×150 mm. Mobile phase A: 0.05% aqueous ammonium bicarbonate/Mobile phase B: acetonitrile. Gradient: 15% B to 60% B over 8 min then 100% B for 4 min. Detector: 220 and 254 nm.

Example 101: 4-(3-((1-(4-Fluorobenzoyl)-4-hydroxypiperidin-4-yl)methyl)-4-oxo-3,4-dihydro-7H-pyrrolo[2,3-d]pyrimidin-7-yl)-N-methylpiperidine-1-carboxamide (I-49)

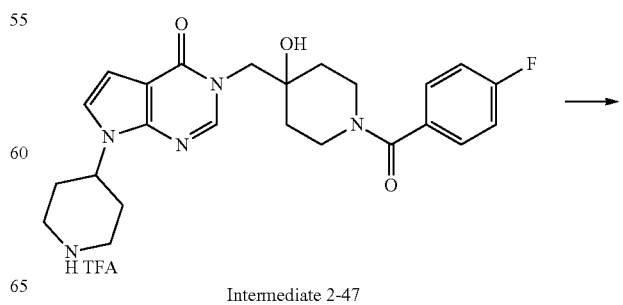

Intermediate 2-47

267

-continued

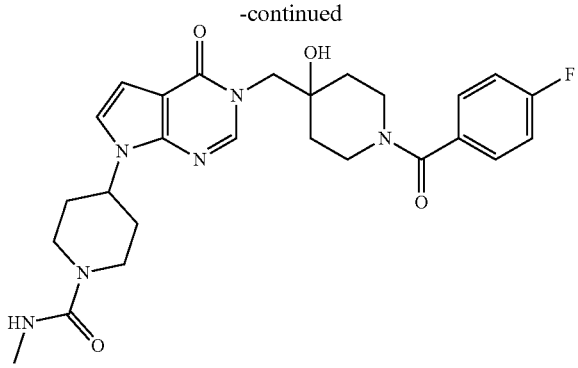

I-49

3-((1-(4-Fluorobenzoyl)-4-hydroxypiperidin-4-yl) methyl)-7-(piperidin-4-yl)-3,7-dihydro-4H-pyrrolo[2,3-d] pyrimidin-4-one trifluoroacetic acid salt (Intermediate 2-47, 100 mg, 0.18 mmol), triethylamine (36 mg, 0.36 mmol) and dichloromethane (20 mL) were added to a 50-mL round-bottom flask fitted with a nitrogen inlet and magnetic stir bar. A solution of methylcarbamic chloride (20 mg, 0.21 mmol) in dichloromethane (5 mL) was then added dropwise with stirring at room temperature. The resulting solution was stirred for 1 h at room temperature. The reaction was then quenched by the addition of water (10 mL) and extracted with ethyl acetate (4×20 mL). The organic layers were combined, dried over anhydrous sodium sulfate, filtered and concentrated under reduced pressure. The residue was purified by preparative HPLC* to afford 4-(3-((I-(4-fluorobenzoyl)-4-hydroxypiperidin-4-yl)methyl)-4-oxo-3,4-dihydro-7H-pyrrolo[2,3-d]pyrimidin-7-yl)-N-methylpiperidine-1-carboxamide (I-49, 35 mg, 39%). $^1$H NMR (400 MHz, DMSO-$d_6$) δ 8.10 (s, 1H), 7.48-7.44 (m, 2H), 7.29-7.24 (m, 3H), 6.51-6.48 (m, 2H), 6.05 (br s, 1H), 5.03-4.91 (m, 1H), 4.65-4.62 (m, 1H), 4.13-4.10 (m, 3H), 4.02 (s, 2H), 3.54-3.36 (m, 2H), 2.91-2.80 (m, 2H), 2.59 (d, 3H), 1.94-1.29 (m, 8H). LCMS: (ESI) m/z 511.36 [M+H]. *Column: Waters XBridge BEH Shield RP18 OBD Prep Column, 130 Å, 5 μm, 19 mm×150 mm. Mobile phase A: 0.05% aqueous ammonium bicarbonate/Mobile phase B: acetonitrile. Gradient: 20% B to 52% B over 18 min. Detector: 220 and 254 nm.

Method G

Example 102: 7-(3-(Aminomethyl)phenyl)-3-((1-(4-fluorobenzoyl)-4-hydroxypiperidin-4-yl)methyl)-3,7-dihydro-4H-pyrrolo[2,3-d]pyrimidin-4-one (I-51)

268

-continued

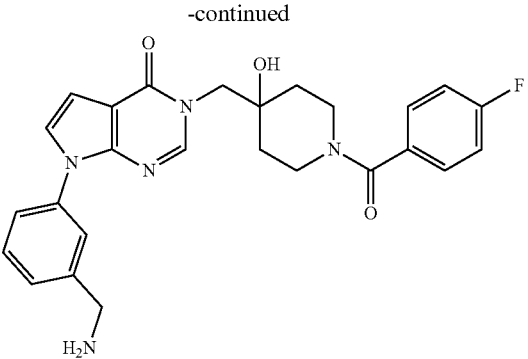

I-51

3-(3-((1-(4-(4-Fluorobenzoyl)-4-hydroxypiperidin-4-yl) methyl)-4-oxo-3,4-dihydro-7H-pyrrolo[2,3-d]pyrimidin-7-yl)benzonitrile (120 mg, 0.25 mmol), palladium on carbon (10% wt, 10 mg), Raney nickel (10 mg), lithium hydroxide (10 mg, 0.42 mmol) and methanol (10 mL) were added to a 25-mL pressure tank reactor (5 atm) fitted with a magnetic stir bar. The mixture was placed under a hydrogen atmosphere and stirred for 30 min at room temperature. The solids were removed by filtration and the filtrate was concentrated under reduced pressure. The residue was purified by preparative HPLC* to give 7-(3-(aminomethyl)phenyl)-3-((1-(4-fluorobenzoyl)-4-hydroxypiperidin-4-yl)methyl)-3,7-dihydro-4H-pyrrolo[2,3-d]pyrimidin-4-one (I-51, 26 mg, 21%). $^1$H NMR (400 MHz, DMSO-$d_6$) δ 8.13 (s, 1H), 7.65 (s, 1H), 7.57-7.50 (m, 1H), 7.48-7.44 (m, 4H), 7.37-7.35 (m, 1H), 7.30-7.24 (m, 2H), 6.69 (d, 1H), 4.97 (s, 1H), 4.23-4.12 (m, 1H), 4.05 (s, 2H), 3.79 (s, 2H), 3.52-3.37 (m, 2H), 3.32-3.01 (m, 2H), 1.74-1.23 (m, 4H) ppm. LCMS: (ESI) m/z 476.30 [M+H]. *Column: Waters XBridge BEH Shield RP18 OBD Prep Column, 130 Å, 5 μm, 19 mm×150 mm. Mobile phase A: 10 mM aqueous ammonium bicarbonate/Mobile phase B: acetonitrile. Gradient: 7% B to 35% B over 10 min. Flow rate: 25 mL/min. Detector: 220 and 254 nm.

Method O

Example 103: 4-({1-[4-(Benzyloxy)phenyl]-4-oxo-1H,4H,5H-pyrazolo[3,4-d]pyrimidin-5-yl}methyl)-4-hydroxy-N,N-dimethylpiperidine-1-carboxamide (I-474)

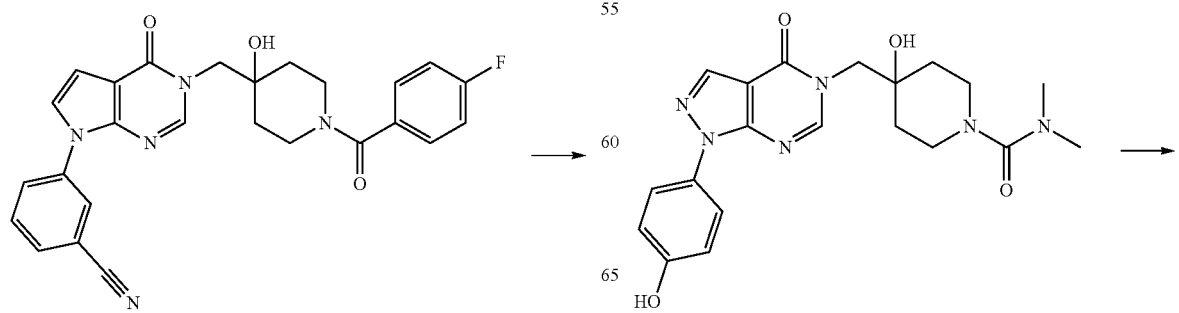

269
-continued

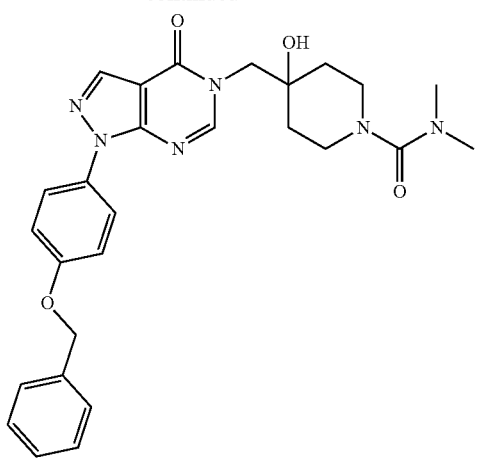

4-Hydroxy-4-((1-(4-hydroxyphenyl)-4-oxo-1,4-dihydro-5H-pyrazolo[3,4-d]pyrimidin-5-yl)methyl)-N,N-dimethylpiperidine-1-carboxamide (0.1 M in DMF, 300 μL, 30 μmol) was combined with benzyl bromide (0.2 M DMF, 225 μL, 45 μmol, 1.5 equivalents) over solid potassium carbonate (21 mg, 150 μmol, 5 equivalents). The mixture was agitated at 50° C. for 18 h. The volatiles were removed under a stream of nitrogen, and the solids were partitioned between ethyl acetate (1.0 mL) and water (0.5 mL). The organic layer was removed, concentrated, and purified by mass triggered preparative HPLC (Method 4) to afford 4-({1-[4-(benzyloxy)phenyl]-4-oxo-1H,4H,5H-pyrazolo[3,4-d]pyrimidin-5-yl}methyl)-4-hydroxy-N,N-dimethylpiperidine-1-carboxamide (5.5 mg, 37%). LCMS: (ESI) m/z 503.34 [M+H]

Method P

Example 104: 3-(Pyrrolidin-1-yl)propyl 4-((1-(4-fluorophenyl)-4-oxo-1,4-dihydro-5H-pyrazolo[3,4-d]pyrimidin-5-yl)methyl)-4-hydroxypiperidine-1-carboxylate (I-486)

270
-continued

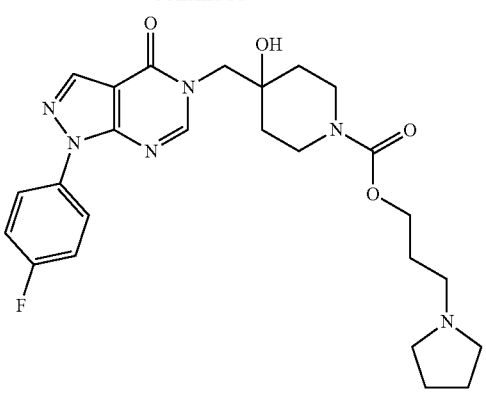

A 2 mL reaction vial was charged with 4-((1-(4-fluorophenyl)-4-oxo-1,4-dihydro-5H-pyrazolo[3,4-d]pyrimidin-5-yl)methyl)-4-hydroxypiperidine-1-carbonyl chloride (0.2M DMF, 150 μL, 30 μmol), N,N-diisopropylethylamine (26 μL, 150 μmol), and 2-(pyrrolidin-1-yl)ethanol (0.2M DMF, 225 μL, 45 μmol). The mixture was agitated at room temperature for 12-18 h. The resulting solution was concentrated, and the crude residue was diluted with brine (500 μL) and extracted with 3:1 ethyl acetate/methanol (2×500 μL). The organic layers were deposited onto a tosic acid cation exchange cartridge (500 mg) for solid phase extraction. The solid phase was washed with 3 mL of 3:1 ethyl acetate/methanol (3 mL), and product was released with 2M ammonia in methanol (3 mL). The methanolic eluent was collected, concentrated, and purified by mass triggered preparative HPLC (Method 6) to yield 3-(pyrrolidin-1-yl)propyl 4-((1-(4-fluorophenyl)-4-oxo-1,4-dihydro-5H-pyrazolo[3,4-d]pyrimidin-5-yl)methyl)-4-hydroxypiperidine-1-carboxylate (3.9 mg, 26%). LCMS: (ESI) m/z 499.24 [M+H]

Method Q

Example 105: 5-[(1-Cyclopropanecarbonyl-4-hydroxypiperidin-4-yl)methyl]-1-{4-[(methylsulfamoyl)amino]phenyl)-1H,4H,5H-pyrazolo[3,4-d]pyrimidin-4-one (I-504)

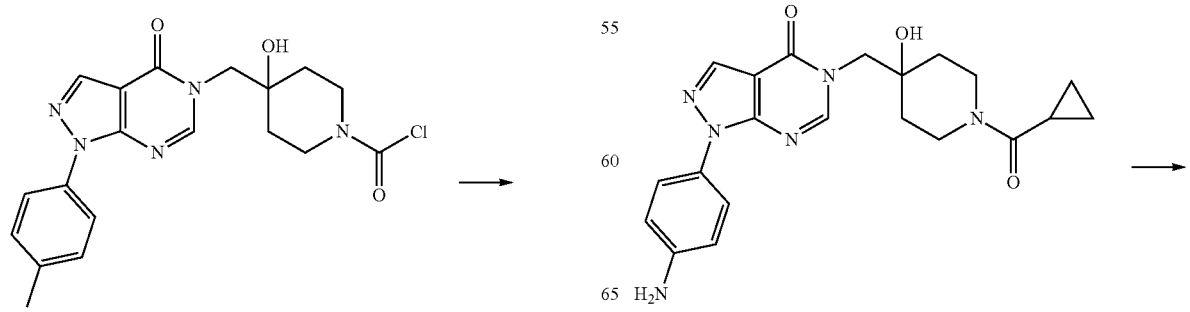

271

-continued

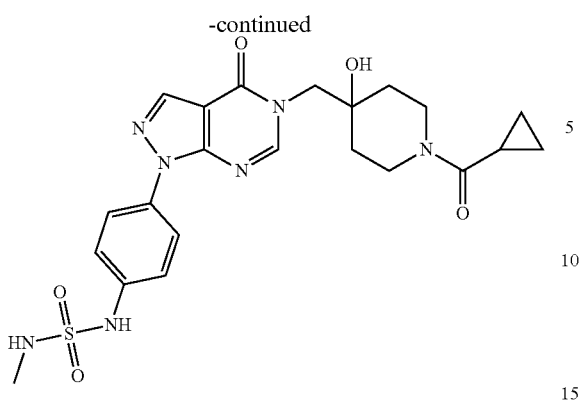

To a 2 mL vial was charged 1-(4-aminophenyl)-5-((1-(cyclopropanecarbonyl)-4-hydroxypiperidin-4-yl)methyl)-1,5-dihydro-4H-pyrazolo[3,4-d]pyrimidin-4-one (9.8 mg, 24 μmol), DMF (150 μL), N,N-diisopropylethylamine (21 μL, 120 μmol), and methylsulfamoyl chloride (6 μL, 72 μmol). The vial was sealed and heated at 50° C. for 2 h. Additional methylsulfamoyl chloride (6 μL, 72 μmol) was added, and the contents of the vial were heated at 50° C. overnight. The reaction was cooled, quenched with methanol (100 μL), and concentrated. The crude material was purified by mass triggered preparative HPLC (Method 6) to yield 5-[(1-cyclopropanecarbonyl-4-hydroxypiperidin-4-yl)methyl]-1-{4-[(methylsulfamoyl) amino]phenyl)-1H,4H,5H-pyrazolo[3,4-d]pyrimidin-4-one (singleton g, 1.0 mg, 8%). LCMS: (ESI) m/z 502.23 [M+H].
Method T Example 106

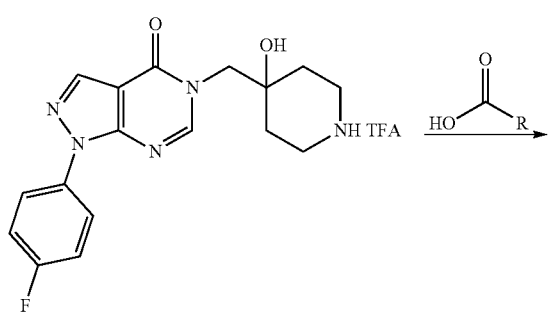

Intermediate 2-28

272

-continued

A 100-mL round-bottom flask was charged with TFA salt of 1-(4-fluorophenyl)-5-((4-hydroxypiperidin-4-yl)methyl)-1H-pyrazolo[3,4-d]pyrimidin-4 (5H)-one (1 mmol), N,N-diisopropylethylamine (1.60 mmol), dichloromethane (10 mL), N-(3-dimethylaminopropyl)-N'-ethylcarbodiimide hydrochloride (1.3 mmol), 1-hydroxybenzotriazole (1.3 mmol) and the acids (1.2 mmol). The resulting solution was stirred for 4 h at 23° C. The mixture was then quenched by the addition water (10 mL). The resulting solution was extracted with dichloromethane (3×20 mL). The combined organic layers were dried over anhydrous sodium sulfate, filtered and concentrated under vacuum. The residue was purified by pre-TLC eluting with 20/1-5/1 dichloromethane/methanol (20:1 v/v) to give desired product as a white or yellow solid.

Method U

Example 107: 1-(4-[4-[2-(benzyloxy)ethoxy]-1H-pyrazol-1-yl]phenyl)-5-([4-hydroxy-1-[(4-methylphenyl)carbonyl]piperidin-4-yl]methyl)-1H,4H,5H-pyrazolo[3,4-d]pyrimidin-4-one

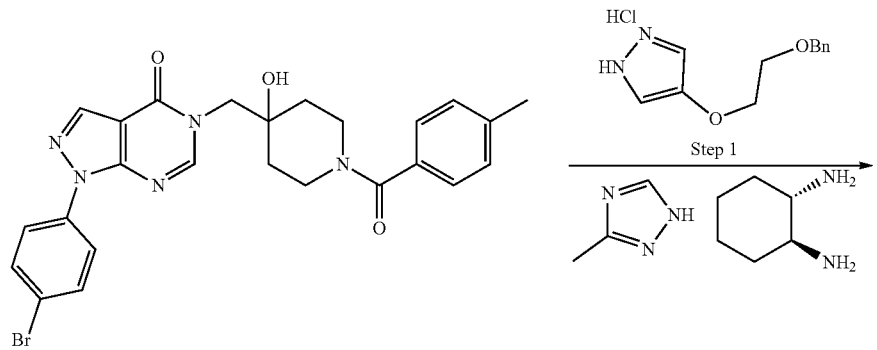

Step 1

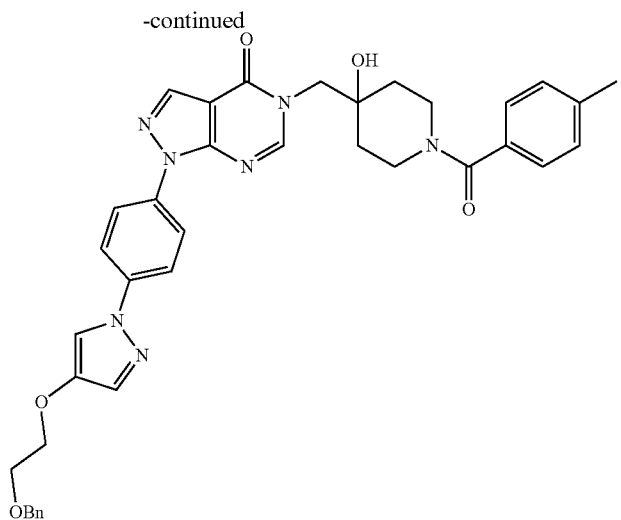

A 50-mL 3-necked round-bottom flask fitted with a nitrogen inlet, magnetic stir bar, condenser and thermometer was charged with 1-(4-bromophenyl)-5-([4-hydroxy-1-[(4-methylphenyl)carbonyl]piperidin-4-yl]methyl)-1H,4H,5H-pyrazolo[3,4-d]pyrimidin-4-one (130 mg, 0.25 mmol), cuprous iodide (2.5 mg, 0.01 mmol), 1,4-dioxane (20 mL), potassium carbonate (75.4 mg, 0.54 mmol), 4-[2-(benzyloxy)ethoxy]-1H-pyrazole hydrochloride (76 mg, 0.30 mmol) and (1R, 2R)-1-N,2-N-dimethylcyclohexane-1,2-diamine (7.4 mg, 0.05 mmol). The resulting solution was stirred for 16 h at 110° C. in an oil bath under nitrogen. After cooling to 25° C., the reaction was quenched with saturated ammonium chloride (10 mL). The product was extracted with ethyl acetate (3×20 mL) and the organic layers combined. The organic layer was washed with brine (20 mL), dried over anhydrous sodium sulfate and concentrated under vacuum. The residue was purified by preparatory TLC plate eluting with dichloromethane/ethyl acetate (1:1 v/v) to give 1-(4-[4-[2-(benzyloxy)ethoxy]-1H-pyrazol-1-yl]phenyl)-5-([4-hydroxy-1-[(4-methylphenyl)carbonyl]piperidin-4-yl]methyl)-1H,4H,5H-pyrazolo[3,4-d]pyrimidin-4-one (50 mg, 30%) as a yellow solid. LCMS: (ESI) m/z 660 [M+H].
Method V

Example 108: Methyl-4-(5-((1-(4-fluorobenzoyl)-4-hydroxypiperidin-4-yl)methyl)-4-oxo-4,5-dihydropyrazolo[3,4-d]pyrimidin-1-yl)benzoate

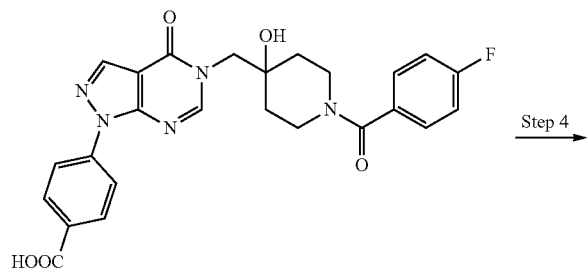

Step 4

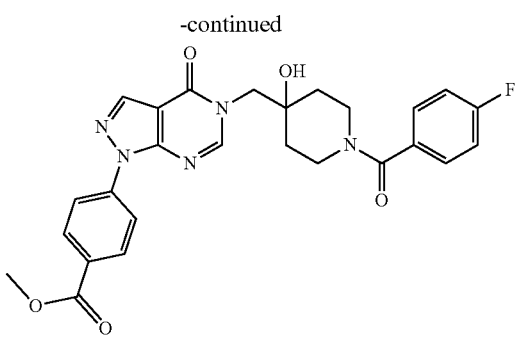

Step 4. Methyl 4-(5-((1-(4-fluorobenzoyl)-4-hydroxypiperidin-4-yl)methyl)-4-oxo-4,5-dihydropyrazolo[3,4-d]pyrimidin-1-yl)benzoate A 25-mL round-bottom flask fitted with a magnetic stir bar was charged with 4-[5-([1-[(4-fluorophenyl)carbonyl]-4-hydroxypiperidin-4-yl]methyl)-4-oxo1H,4H,5H-pyrazolo[3,4-d]pyrimidin-1-yl]benzoic acid ((prepared according to procedure outlined in Example 40x utilizing 6-[(4-fluorophenyl)carbonyl]-1-oxa-6-azaspiro[2.5]octane and 4-(4-oxo-4,5-dihydropyrazolo[3,4-d]pyrimidin-1-yl)benzoic acid as starting materials) (49.1 mg, 0.10 mmol), cesium carbonate (65.2 mg, 0.20 mmol) and N,N-dimethylformamide (5 mL) followed by iodomethane (28.4 mg, 0.20 mmol) added dropwise. The resulting solution was stirred for 2 h at 25° C. and quenched with water (20 mL). The product was extracted with ethyl acetate (5×20 mL). The combined organic layers were washed with brine (20 mL), dried over anhydrous sodium sulfate and concentrated under vacuum. The residue was washed with water (5 mL) and dried in an oven to afford methyl-4-(5-((1-(4-fluorobenzoyl)-4-hydroxypiperidin-4-yl)methyl)-4-oxo-4,5-dihydropyrazolo[3,4-d]pyrimidin-1-yl)benzoate (46.5 mg, 92%). LCMS: (ESI) m/z 506 [M+H].

Method Y

Example 109: 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one (Enantiomer A-I-301) and 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one (Enantiomer B-I-302)

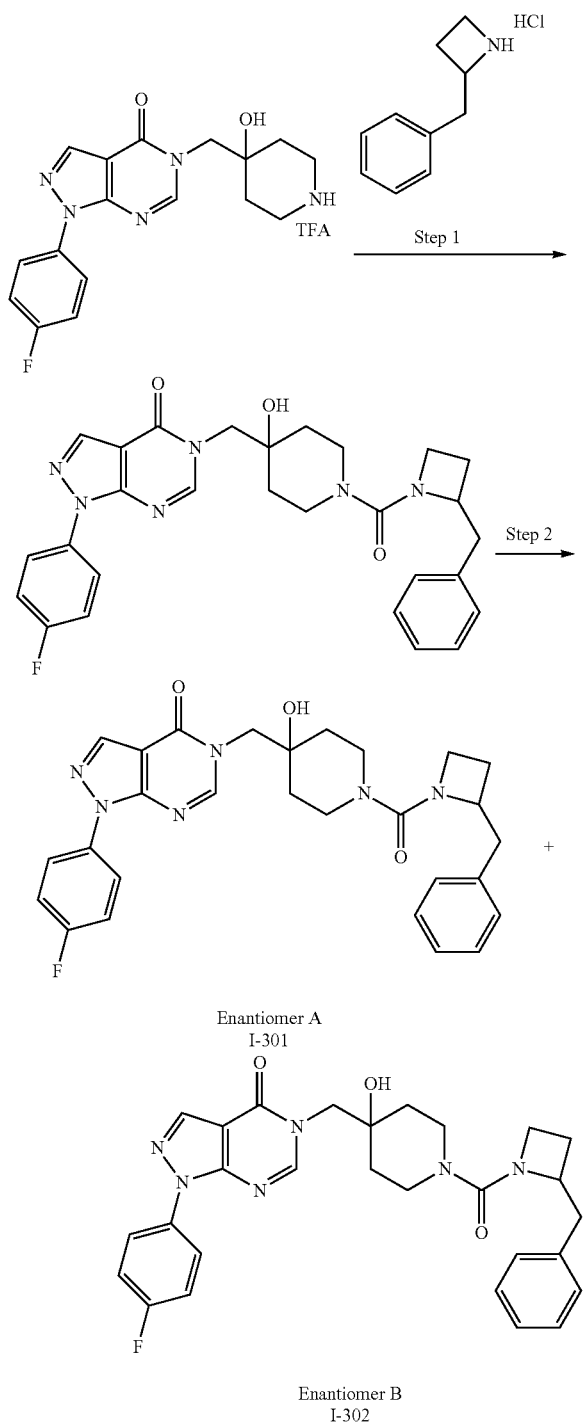

Enantiomer A
I-301

Enantiomer B
I-302

Step 1. 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one A 250-mL 3-necked round-bottom flask fitted with a magnetic stir bar and thermometer was charged with ditrichloromethyl carbonate (148 mg, 0.50 mmol), dichloromethane (50 mL), 2-benzylazetidine hydrochloride (183 mg, 1.24 mmol). To the reaction was added N,N-diisopropylethylamine (387 mg, 2.99 mmol) dropwise at 0° C. The resulting solution was stirred for 2 h at 0° C. before adding the TFA salt of 1-(4-fluorophenyl)-5-[(4-hydroxypiperidin-4-yl)methyl]-1H,4H,5H-pyrazolo[3,4-d]pyrimidin-4-one (343 mg, 1.00 mmol) and N,N-diisopropylethylamine (387 mg, 2.99 mmol) in dichloromethane (50 mL) dropwise at 0° C. After addition, the solution was stirred for 3 h at 0° C. and diluted with water (30 mL). The product was extracted with dichloromethane (3×30 mL). The combined organic layers were dried over anhydrous sodium sulfate, filtered and concentrated under vacuum. The residue was purified by preparatory HPLC* to give 5-([1-[(2-benzylazetidin-1-yl)carbonyl]-4-hydroxypiperidin-4-yl]methyl)-1-(4-fluorophenyl)-1H,4H,5H-pyrazolo[3,4-d]pyrimidin-4-one as a white solid (200 mg, 39%). LCMS: (ESI) m/z 517 [M+H]. *Column: Xbridge Prep $C_{18}$ OBD, 19×150 mm, 5 m. Mobile phase A: aqueous ammonium bicarbonate (0.05%)/Mobile phase B: acetonitrile. Gradient: 48% B to 53% B over 8 min. Detector: 220 and 254 nm.

Step 2. 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one The enantiomers were separated by SFC* to give 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one, enantiomer A (I-301) (29.5 mg, 15%, stereochemistry unconfirmed). $^1$H-NMR (300 MHz, DMSO-$d_6$) δ 1.30-1.62 (m, 4H), 1.76-1.95 (m, 1H), 1.98-2.15 (m, 1H), 2.65-2.83 (m, 1H), 2.89-3.17 (m, 3H), 3.41-3.69 (m, 3H), 3.79-3.93 (m, 1H), 4.02 (s, 2H), 4.32-4.59 (m, 1H), 4.90 (brs, 1H), 7.17-7.22 (m, 3H), 7.29 (t, J=7.5 Hz, 2H), 7.40-7.46 (m, 2H), 8.05-8.10 (m, 2H), 8.35 (s, 1H), 8.38 (s, 1H). LCMS: (ESI) m/z 517 [M+H] and 5-((1-(2-benzylazetidine-1-carbonyl)-4-hydroxypiperidin-4-yl)methyl)-1-(4-fluorophenyl)-1H-pyrazolo[3,4-d]pyrimidin-4(5H)-one, enantiomer B (I-302) (29.5 mg, 15%, stereochemistry unconfirmed). $^1$H-NMR (300 MHz, DMSO-$d_6$) δ 1.30-1.62 (m, 4H), 1.76-1.95 (m, 1H), 1.98-2.15 (m, 1H), 2.69-2.79 (m, 1H), 2.91-3.13 (m, 3H), 3.41-3.65 (m, 3H), 3.82-3.91 (m, 1H), 4.02 (s, 2H), 4.32-4.59 (m, 1H), 4.90 (brs, 1H), 7.17-7.22 (m, 3H), 7.29 (t, J=7.2 Hz, 2H), 7.40-7.46 (m, 2H), 8.05-8.10 (m, 2H), 8.35 (s, 1H), 8.38 (s, 1H). LCMS: (ESI) m/z 517 [M+H]. *Column: Chiralpak IC, 2×25 cm, 5 μm. Mobile Phase A: methanol/Mobile Phase B: dichloromethane. Flow rate: 17 mL/min. Gradient: 10% B to 100% B over 11 min. Detector: 254 and 220 nm. $RT_1$: 7.93 min; $RT_2$: 9.40 min.

Method Z

Example 110: 5-((4-Hydroxy-1-(4-(4-hydroxycyclo-hexyloxy)benzoyl)piperidin-4-yl)methyl)-1-p-tolyl-1H-pyrazolo[3,4-d]pyrimidin-4 (5H)-one (I-1141)

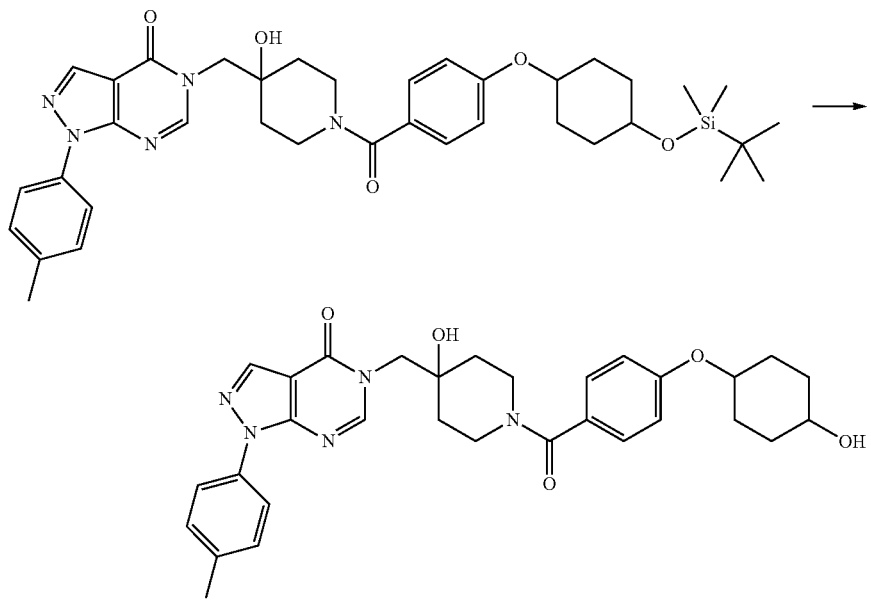

I-357

A 100-mL round-bottom flask was charged with 5-((1-(4-(4-(tert-butyldimethylsilyloxy)cyclohexyloxy)benzoyl)-4-hydroxypiperidin-4-yl)methyl)-1-p-tolyl-1H-pyrazolo[3,4-d]pyrimidin-4 (5H)-one (prepared by Step 1: procedure outlined in Method A utilizing 5-((4-hydroxypiperidin-4-yl)methyl)-1-p-tolyl-1H-pyrazolo[3,4-d]pyrimidin-4 (5H)-one and 4-hydroxybenzoic acid. Step 2: Procedure outlined in Experiment 172 utilizing 4-[(tert-butyldimethylsilyl)oxy]cyclohexan-1-ol) (50 mg, 0.07 mmol), tetrahydrofuran (5 mL) and tetrabutylammonium fluoride in tetrahydrofuran (1M, 1.5 mL). The resulting solution was stirred for 5 h at 40° C. in an oil bath. Upon cooling to 23° C., the reaction was quenched with water (20 mL). The product was extracted with ethyl acetate (5×10 mL). The combined organic layers were dried over anhydrous sodium sulfate, filtered and concentrated under vacuum. The residue was purified by preparative-HPLC* to afford 5-((4-hydroxy-1-(4-(4-hydroxycyclohexyloxy)benzoyl)piperidin-4-yl)methyl)-1-p-tolyl-1H-pyrazolo[3,4-d]pyrimidin-4 (5H)-one (2.4 mg, 6%) as an off-white solid. 1H NMR (300 MHz, CDCl$_3$) δ 1.23-1.45 (m, 5H), 1.57-1.64 (m, 5H), 1.81-1.85 (m, 2H), 1.99-2.01 (m, 1H), 2.38 (s, 3H), 3.16-3.31 (m, 2H), 3.50-3.62 (m, 2H), 4.06 (s, 2H), 4.36-4.60 (m, 2H), 4.98 (brs, 1H), 6.95-6.98 (m, 2H), 7.31-7.33 (m, 2H), 7.38 (d, J=8.4 Hz, 2H), 7.92 (d, J=8.4 Hz, 2H), 8.33 (s, 1H), 8.34 (s, 1H). LCMS: (ESI) m/z 558 [M+H]. *Column: X Bridge RP, 19×150 mm, 5 μm. Mobile phase A: aqueous ammonium bicarbonate (10 mM)/Mobile phase B: acetonitrile. Gradient: 15% B to 71% B over 7 min. Flow rate: 20 mL/min. Detector: 254 and 220 nm.

Method AA

Example 111: 5-((4-Hydroxy-1-(1-methylcyclopropanecarbonyl)piperidin-4-yl)methyl)-1-(4-((4-methoxycyclohexyl)oxy)phenyl)-1H-pyrazolo[3,4-d]pyrimidin-4(5H)-one, isomer A and isomer B

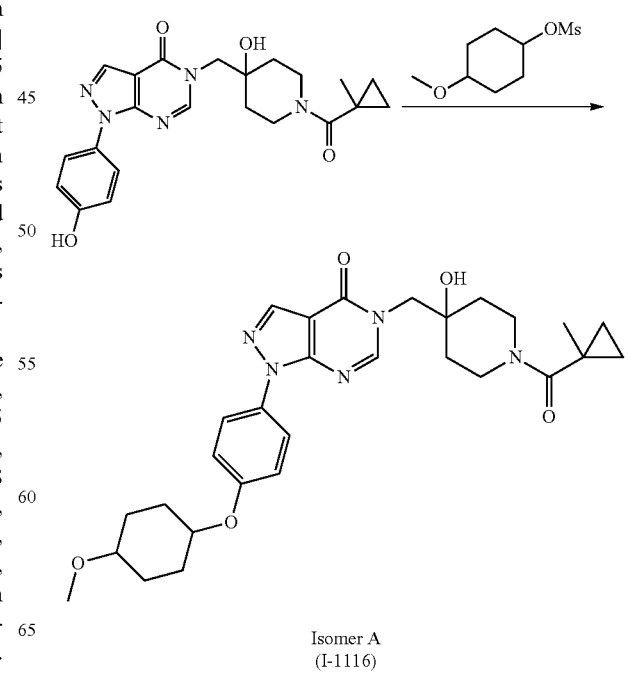

Isomer A
(I-1116)

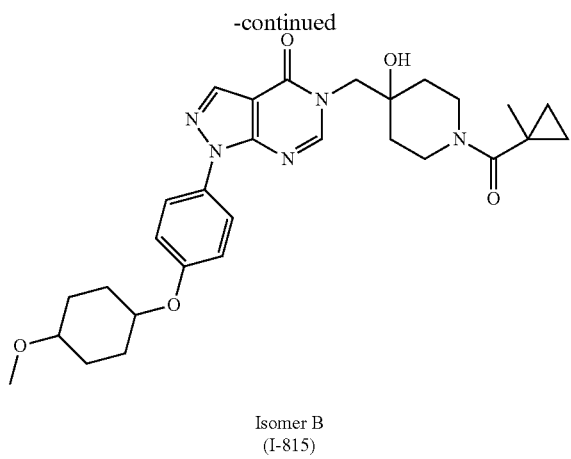

Isomer B
(I-815)

A 50-mL 3-necked round-bottom flask fitted with a magnetic stir bar, condenser and thermometer was charged with 5-([4-hydroxy-1-[(1-methylcyclopropyl)carbonyl]piperidin-4-yl]methyl)-1-(4-hydroxyphenyl)-1H,4H,5H-pyrazolo[3,4-d]pyrimidin-4-one (51 mg, 0.12 mmol), 4-methoxycyclohexyl methanesulfonate (25 mg, 0.12 mmol), potassium carbonate (34 mg, 0.25 mmol) and N,N-dimethylformamide (10 mL). The resulting solution was stirred for 24 h at 80° C. in an oil bath. After cooling to 23° C., the reaction was then quenched by the addition of water (20 mL). The resulting mixture was extracted with ethyl acetate (3×30 mL). The organic layers were combined, dried over anhydrous sodium sulfate, filtered and concentrated under vacuum. The residue was purified by preparatory HPLC* to give the racemic mixture (15 mg, 23%). LCMS: (ESI) m/z 536[M+H]. *Column: XBridge Prep C18 OBD Column, 5 μm, 19×150 mm. Mobile phase A: aqueous ammonium hydroxide (0.05%)/Mobile phase B: acetonitrile. Flow rate: 20 mL/min. Gradient: 25% B to 55% B in 7 min. Detector: 220 and 254 nm. The mixture (15 mg) was separated by chiral HPLC** to give 5-((4-Hydroxy-1-(1-methylcyclopropanecarbonyl)piperidin-4-yl)methyl)-1-(4-((4-methoxycyclohexyl)oxy)phenyl)-1H-pyrazolo[3,4-d]pyrimidin-4(5H)-one, isomer A (2.1 mg, 3%). $^1$H-NMR (300 MHz, CD$_3$OD) δ 0.56-0.64 (m, 2H), 0.85-0.89 (m, 2H), 1.25-1.28 (s, 4H), 1.48-1.58 (m, 2H), 1.60-1.96 (m, 10H), 3.27-3.36 (m, 4H), 4.05-4.16 (m, 4H), 4.42-4.75 (m, 2H), 7.06 (d, J=9.0 Hz, 2H), 7.83 (d, J=9.0 Hz, 2H), 8.19 (s, 1H), 8.26 (s, 1H). LCMS: (ESI) m/z 536[M+H], and 5-((4-Hydroxy-1-(1-methylcyclopropanecarbonyl)piperidin-4-yl)methyl)-1-(4-((4-methoxycyclohexyl) oxy)phenyl)-1H-pyrazolo[3,4-d]pyrimidin-4(5H)-one, isomer B (2.1 mg, 3%). $^1$H-NMR (400 MHz, CD$_3$OD) δ 0.56-0.63 (m, 2H), 0.85-0.89 (m, 2H), 1.26-1.28 (m, 4H), 1.38-1.72 (m, 8H), 2.01-2.15 (m, 4H), 3.05-3.35 (m, 4H), 4.07-4.47 (m, 4H), 4.36-4.43 (m, 1H), 4.52-4.56 (m, 1H), 7.05 (d, J=9.0 Hz, 2H), 7.83 (d, J=9.0 Hz, 2H), 8.19 (s, 1H), 8.26 (s, 1H). LCMS: (ESI) m/z 536[M+H].

**Column: Chiralpak IC Column, 5 μm, 2×25 cm. Mobile Phase: methanol (0.1% diethylamine). Flow rate: 18 mL/min over 24 min. Detector: 254 and 220 nm. RT$_1$: 16.2 min; RT$_2$: 20.5 min. #A similar method can be used for alkylation where the starting material is an epoxide such as 1,5-dioxaspiro[2.3]hexane and 5-(diphenylmethyl)-1-oxa-5-azaspiro[2.3]hexane (readily prepared from the corresponding ketone and trimethylsulfoxonium iodide)

Method AB

Example 112. 5-((1-(2'-aminobiphenylcarbonyl)-4-hydroxypiperidin-4-yl)methyl)-1-(4-ethynylphenyl)-1H-pyrazolo[3,4-d]pyrimidin-4(5H)-one

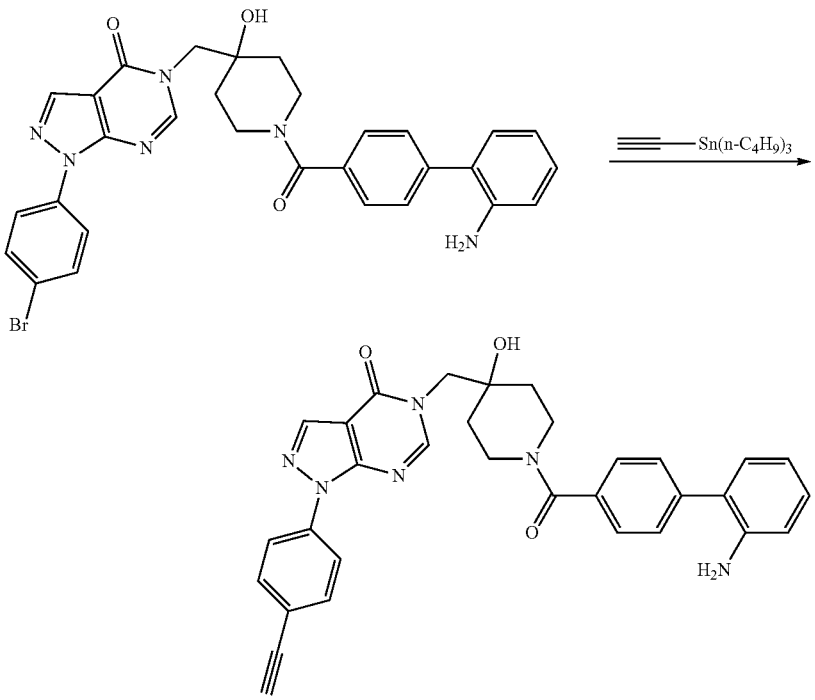

A 5-mL microwave tube fitted with a magnetic stir bar was charged with 5-((1-(2'-aminobiphenylcarbonyl)-4-hydroxypiperidin-4-yl)methyl)-1-(4-bromophenyl)-1H-pyrazolo[3,4-d]pyrimidin-4(5H)-one (prepared according to the procedure outlined in Method A, utilizing 1-(4-bromophenyl)-5-((4-hydroxypiperidin-4-yl)methyl)-1H-pyrazolo[3,4-d]pyrimidin-4(5H)-one and 4-(2-aminophenyl)benzoic acid as starting materials) (100 mg, 0.17 mmol), dioxane (2 mL), tributyl(ethynyl)stannane (64.5 mg, 0.20 mmol), 1,1'-bis(diphenylphosphino)ferrocene-palladium(II)dichloride dichloromethane complex (12.4 mg, 0.02 mmol) and 2-(dicyclohexylphosphino)-2',4',6'-tri-1-propyl-1,1'-biphenyl (16.2 mg, 0.03 mmol). The resulting solution was irradiated with a microwave for 1 h at 160° C. After cooling to 25° C., the reaction mixture was poured into water (20 mL). The product was extracted with ethyl acetate (5×20 mL). The combined organic layers were dried over anhydrous sodium sulfate, filtered and concentrated under vacuum. The residue was purified by column chromatography eluting with petroleum ether/ethyl acetate (7:1, v/v) to afford 5-((1-(2'-aminobiphenylcarbonyl)-4-hydroxypiperidin-4-yl)methyl)-1-(4-ethynylphenyl)-1H-pyrazolo[3,4-d]pyrimidin-4(5H)-one as a yellow oil (40 mg, 44%). LCMS: (ESI) m/z 545 [M+H].

Method M

Example 113: 5-((1-(cyclopropanecarbonyl)-4-hydroxypiperidin-4-yl)methyl)-1-(4-(piperidin-4-yl)phenyl)-1H-pyrazolo[3,4-d]pyrimidin-4(5H)-one (I-843)

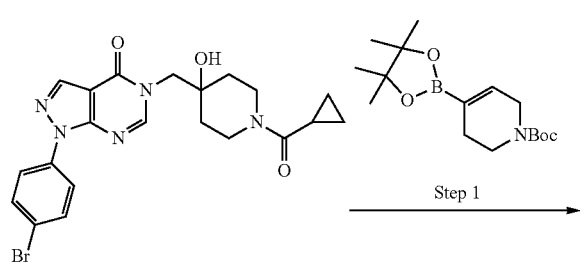

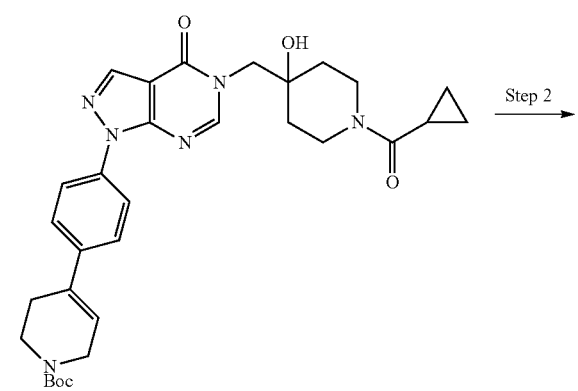

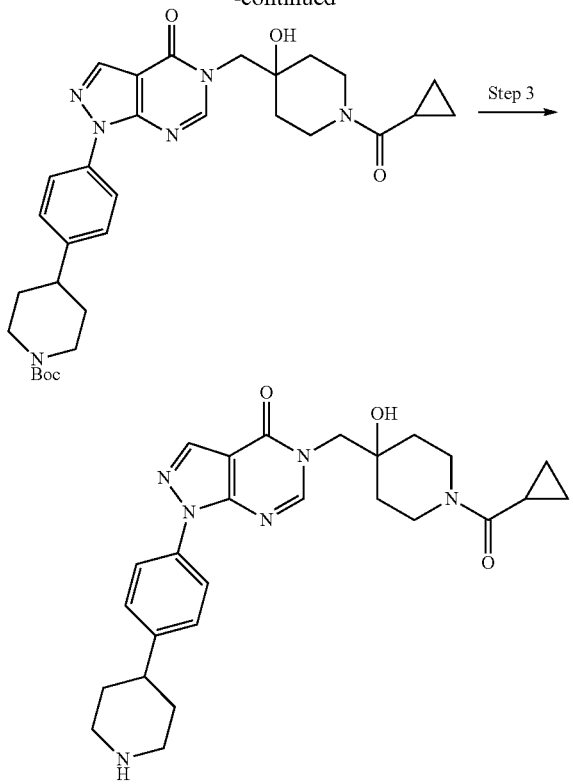

I-843

Step 1. Tert-butyl 4-(4-(5-((1-(cyclopropanecarbonyl)-4-hydroxypiperidin-4-yl)methyl)-4-oxo-4,5-dihydropyrazolo[3,4-d]pyrimidin-1-yl)phenyl)-5,6-dihydropyridine-1(2H)-carboxylate A 50-mL 3-necked round-bottom flask fitted with a nitrogen balloon, magnetic stir bar, condenser and thermometer was charged with 1-(4-bromophenyl)-5-[(1-cyclopropanecarbonyl-4-hydroxypiperidin-4-yl)methyl]-1H,4H,5H-pyrazolo[3,4-d]pyrimidin-4-one (500 mg, 1.06 mmol), Pd(dppf)Cl$_2$ (76 mg, 0.10 mmol), 1,4-dioxane (20 mL), water (2 mL), potassium carbonate (440 mg, 3.18 mmol) and 1-tert-butyl-6-(tetramethyl-1,3,2-dioxaborolan-2-yl)-3,4,7,8-tetrahydro-2H-1-3,3-oxazocin-2-one (393 mg, 1.27 mmol). The solution was stirred for 8 h at 100° C. and cooled to 25° C. The resulting solution was diluted with water (30 mL) and the product was extracted with dichloromethane (3×20 mL). The combined organic layers were dried over sodium sulfate, filtered and concentrated under vacuum. The residue was purified by preparative TLC eluting with dichloromethane/methanol (50:1, v/v) to afford tert-butyl 4-(4-(5-((1-(cyclopropanecarbonyl)-4-hydroxypiperidin-4-yl)methyl)-4-oxo-4,5-dihydropyrazolo[3,4-d]pyrimidin-1-yl)phenyl)-5,6-dihydropyridine-1(2H)-carboxylate as a yellow oil (0.45 g, 65%). LCMS: (ESI) m/z 575 [M+H].

Step 2. Tert-butyl4-(4-(5-((1-(cyclopropanecarbonyl)-4-hydroxypiperidin-4-yl) methyl)-4-oxo-4,5-dihydropyrazolo[3,4-d]pyrimidin-1-yl)phenyl)piperidine-1-carboxylate A 100-mL round-bottom flask fitted with a hydrogen balloon and magnetic stir bar was charged with tert-butyl4-

(4-(5-((1-(cyclopropanecarbonyl)-4-hydroxypiperidin-4-yl)methyl)-4-oxo-4,5-dihydropyridine-1(2H)-carboxylate (Step 1, 400 mg, 0.69 mmol), palladium on carbon (0.1 g, 10%) and N,N-dimethylformamide (20 mL). The solution was stirred for 3 h at 25° C. under hydrogen. The solids were removed by filtration and the filtrate was concentrated under vacuum to afford tert-butyl4-(4-(5-((1-(cyclopropanecarbonyl)-4-hydroxypiperidin-4-yl)methyl)-4-oxo-4,5-dihydropyrazolo[3,4-d]pyrimidin-1-yl)phenyl)piperidine-1-carboxylate (0.37 g). LCMS: (ESI) m/z 577 [M+H].

Step 3. 5-((1-(cyclopropanecarbonyl)-4-hydroxypiperidin-4-yl)methyl)-1-(4-(piperidin-4-yl)phenyl)-1H-pyrazolo[3,4-d]pyrimidin-4(5H)-one The title compound was prepared according to the procedure outlined in Example 2 utilizing tert-butyl4-(4-(5-((1-(cyclopropanecarbonyl)-4-hydroxypiperidin-4-yl)methyl)-4-oxo-4,5-dihydropyrazolo[3,4-d]pyrimidin-1-yl)phenyl)piperidine-1-carboxylate (Step 2, 400 mg, 0.69 mmol), as starting material and it was further purified by preparatory HPLC* (15 mg, 18%). $^1$H-NMR (300 MHz, CD$_3$OD) δ 0.72-0.92 (m, 4H), 1.57-1.83 (m, 6H), 1.87-2.01 (m, 3H), 2.84-2.87 (m, 3H), 3.08-3.24 (m, 3H), 3.52-3.59 (m, 1H), 4.01-4.23 (m, 4H), 7.45 (d, J=8.4 Hz, 2H), 8.00 (d, J=8.1 Hz, 2H), 8.25 (s, 1H), 8.33 (s, 1H). LCMS: (ESI) m/z 477 [M+H]. *Column, SunFire Prep C18, 19×150 mm. Mobile phase A: aqueous ammonium bicarbonate (0.05%)/Mobile phase B: acetonitrile. Flow rate: 20 mL/min. Gradient: 40% B to 60% B over 8 min. Detector: 254 and 220 nm.
Method AD Example 114: 4-{[1-(4-fluorophenyl)-4-oxo-1H,4H,5H-pyrazolo[3,4-d]pyrimidin-5-yl]methyl)-4-hydroxy-N-methylpiperidine-1-carboxamide (I-284)

A 250-mL 3-necked round-bottom flask fitted with a magnetic stir bar and thermometer was charged with the 1-(4-fluorophenyl)-5-((4-hydroxypiperidin-4-yl)methyl)-1H-pyrazolo[3,4-d]pyrimidin-4(5H)-one TFA salt (Intermediate 2-28, 95 mg, 0.21 mmol), dichloromethane (100 mL) and triethylamine (65 mg, 0.64 mmol). The reaction was treated with N-methylcarbamoyl chloride (45 mg, 0.48 mmol) in dichloromethane (1 mL) added in portions at 0° C. The resulting solution was warmed to 23° C. and stirred for 2 h. The reaction was quenched with water (20 mL) and the product was extracted with dichloromethane (3×30 mL). The combined organic layers were dried over anhydrous sodium sulfate, filtered and concentrated under vacuum. The residue was purified by preparatory HPLC* to give 4-((1-(4-fluorophenyl)-4-oxo-1H-pyrazolo[3,4-d]pyrimidin-5(4H)-yl)methyl)-4-hydroxy-N-methylpiperidine-1-carboxamide (16.5 mg, 20%). $^1$H NMR (300 MHz, DMSO-d$_6$) δ 1.25-1.57 (m, 4H), 2.54-2.59 (m, 3H), 2.95-3.05 (m, 2H), 3.54-3.68 (m, 2H), 4.02 (s, 2H), 4.86 (s, 1H), 6.33-6.41 (m, 1H), 7.39-7.51 (m, 2H), 8.01-8.12 (m, 2H), 8.34 (s, 1H), 8.38 (s, 1H). LCMS: (ESI) m/z 401 [M+H]. *Column: XBridge Prep C18 OBD Column, 5 μm, 19×150 mm. Mobile phase A: aqueous ammonium bicarbonate (0.05%)/ Mobile phase B: acetonitrile. Flow rate: 20 mL/min. Gradient: 25% B to 66% B over 10 min. Detector: 220 and 254 nm.
Method AE Example 115: 5-[(1-cyclopropanecarbonyl-4-hydroxypiperidin-4-yl)methyl]-1-{4-[4-(4-methylpiperazin-1-yl]-1H-pyrazol-1-yl]phenyl)-1H,4H,5H-pyrazolo[3,4-d]pyrimidin-4-one (I-975)

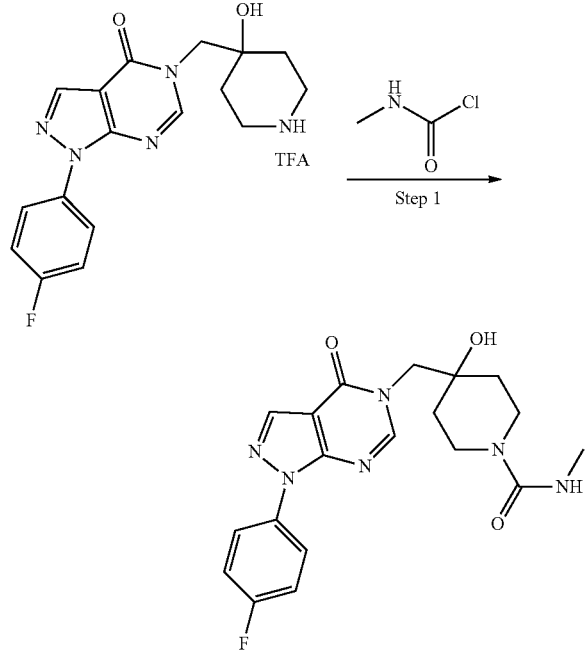

I-284

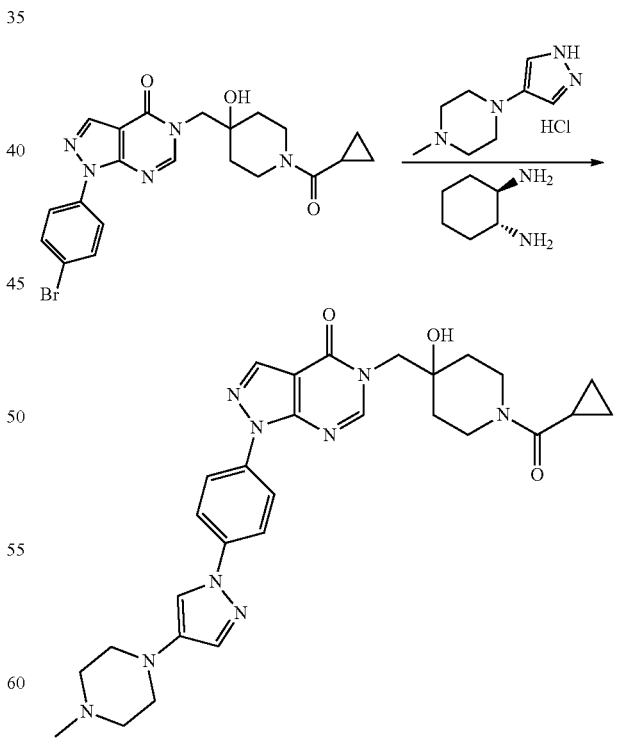

I-975

A 100-mL 3-necked round-bottom flask fitted with a nitrogen balloon, magnetic stir bar, condenser and thermometer was charged with 1-(4-bromophenyl)-5-[(1-cyclopropanecarbonyl-4-hydroxypiperidin-4-yl)methyl]-1H,4H,5H-pyrazolo[3,4-d]pyrimidin-4-one (100 mg, 0.21 mmol), 1-methyl-4-(1H-pyrazol-4-yl)piperazine (35 mg, 0.21 mmol), potassium carbonate (8.77 mg, 0.06 mmol), 1,4-dioxane (20 mL), (1S,2S)-cyclohexane-1,2-diamine (2.4 mg, 0.02 mmol) and cuprous iodide (4 mg, 0.02 mmol). The resulting solution was stirred for 16 h at 110° C. in an oil bath. After cooling to 25° C., the reaction was quenched with water (30 mL). The product was extracted with ethyl acetate (3×30 mL). The combined organic layers were dried over anhydrous sodium sulfate, filtered and concentrated under vacuum. The residue was purified by column chromatography eluting with dichloromethane/methanol (1:1, v/v). The product was further purified by preparative HPLC* to afford 5-[(1-cyclopropanecarbonyl-4-hydroxypiperidin-4-yl)methyl]-1-[4-[4-(4-methylpiperazin-1-yl)-1H-pyrazol-1-yl]phenyl]-1H,4H,5H-pyrazolo[3,4-d]pyrimidin-4-one as a white solid (8.7 mg, 7%) $^1$H NMR (300 MHz, DMSO-d$_6$) δ 0.66-0.71 (m, 4H), 1.40-1.60 (m, 4H), 1.95-1.99 (m, 1H), 2.23 (s, 3H), 2.44-2.48 (m, 4H), 2.98-3.01 (m, 5H), 3.35-3.42 (m, 1H), 3.99-4.10 (m, 4H), 4.98 (brs, 1H), 7.61 (s, 1H), 7.95 (d, J=9.0 Hz, 2H), 8.10 (s, 1H), 8.13 (d, J=9.0 Hz, 2H), 8.38 (s, 1H), 8.39 (s, 1H). LCMS: (ESI) m/z 558 [M+H]. *Column: XBridge Shield RP18 OBD Column, 5 μm, 19×150 mm. Mobile phase A: aqueous ammonium bicarbonate (10 mmol/L)/Mobile phase B: acetonitrile. Gradient: 18% B to 38% B over 8 min. Flow rate: 20 mL/min. Detector: 254 and 220.

Method AF

Example 116: 5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one, enantiomer A (I-995) and 5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one, enantiomer B (I-996)

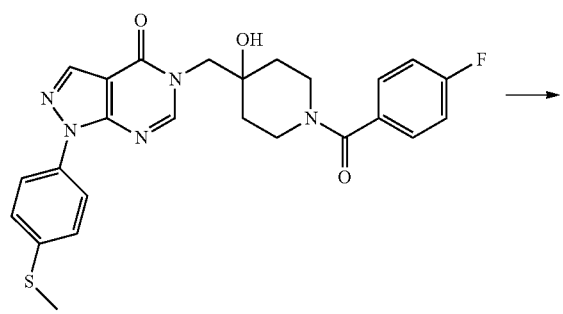

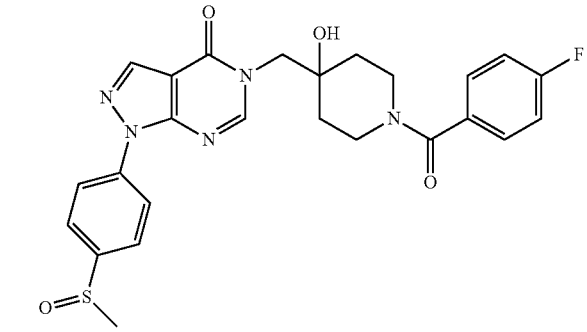

enantiomer A,
I-995

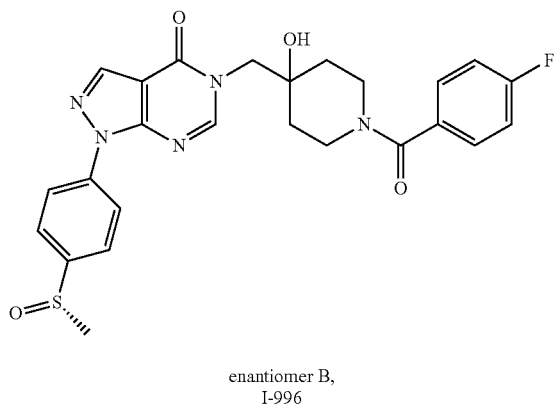

enantiomer B,
I-996

A 50-mL round-bottom flask fitted with a magnetic stir bar was charged with 5-((1-(4-fluorobenzoyl)-4-hydroxypiperidin-4-yl)methyl)-1-(4-(methylthio)phenyl)-1H-pyrazolo[3,4-d]pyrimidin-4(5H)-one (100 mg, 0.20 mmol), dichloromethane (15 mL) and mCPBA (34.4 mg, 0.20 mmol). The resulting solution was stirred at 0° C. for 10 min and then quenched with water (10 mL). The product was extracted with dichloromethane. (3×10 mL) and the combined organic layers were washed with brine (10 mL), dried over anhydrous sodium sulfate, filtered and concentrated under vacuum. The residue was purified by preparatory HPLC* to give 5-((1-(4-fluorobenzoyl)-4-hydroxypiperidin-4-yl)methyl)-1-(4-(methylsulfinyl) phenyl)-1H-pyrazolo[3,4-d]pyrimidin-4(5H)-one as a white solid (60 mg, 58%). LCMS: (ESI) m/z 510 [M+H]. *Column: XBridge Prep C18 OBD Column, 5 μm, 19×150 mm. Mobile phase A: aqueous ammonium bicarbonate (0.05%)/Mobile phase B: acetonitrile. Flow rate: 20 mL/min. Gradient: 25% to 50% B over 8 min Detector: 220 and 254 nm. 5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one (122 mg, 0.24 mmol) was separated by Chiral preparatory HPLC to give 5-((I-(4-fluorobenzoyl)-4-hydroxypiperidin-4-yl)methyl)-1-(4-(methylsulfinyl) phenyl)-1H-pyrazolo[3,4-d]pyrimidin-4(5H)-one, enantiomer A (I-995) (36.3 mg, 30%) and 5-((1-(4-fluorobenzoyl)-4-hydroxypiperidin-4-yl)methyl)-1-(4-(methylsulfin-yl)phenyl)-1H-pyrazolo[3,4-d]pyrimidin-4(5H)-one enantiomer B (I-996) (38.9 mg, 32%). A: $^1$H NMR (400 MHz, CD$_3$OD) δ 1.48-1.80 (m, 4H), 2.86 (s, 3H), 3.43-3.48 (m, 3H), 4.18 (s, 2H), 4.33-4.35 (m, 1H), 7.17-7.22 (m, 2H), 7.45-7.50 (m, 2H), 7.88 (d, J=8.8 Hz, 2H), 8.29 (s, 1H), 8.36 (s, 1H), 8.43 (d, J=8.8 Hz, 2H). B: $^1$H NMR (400 MHz, CD$_3$OD) δ 1.48-1.82 (m, 4H), 2.86 (s, 3H), 3.43-3.56 (m, 3H), 4.18 (s, 2H), 4.32-4.35 (m, 1H), 7.19 (d, J=8.8 Hz, 2H), 7.48 (d, J=8.4 Hz, 2H), 7.88 (d, J=8.8 Hz, 2H), 8.29 (s, 1H), 8.37 (s, 1H), 8.43 (d, J=8.8 Hz, 2H). LCMS: (ESI) m/z 510 [M+H]. Column: Chiralpak IC, 2×25 cm, 5 μm. Mobile Phase: methanol over 45 min. Detector: 220 and 254 nm. RT$_1$: 9.33 min; RT$_2$: 6.22 min.

Method AG

Example 117: 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one, enantiomer A(I-997) and 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one, enantiomer B(I-998)

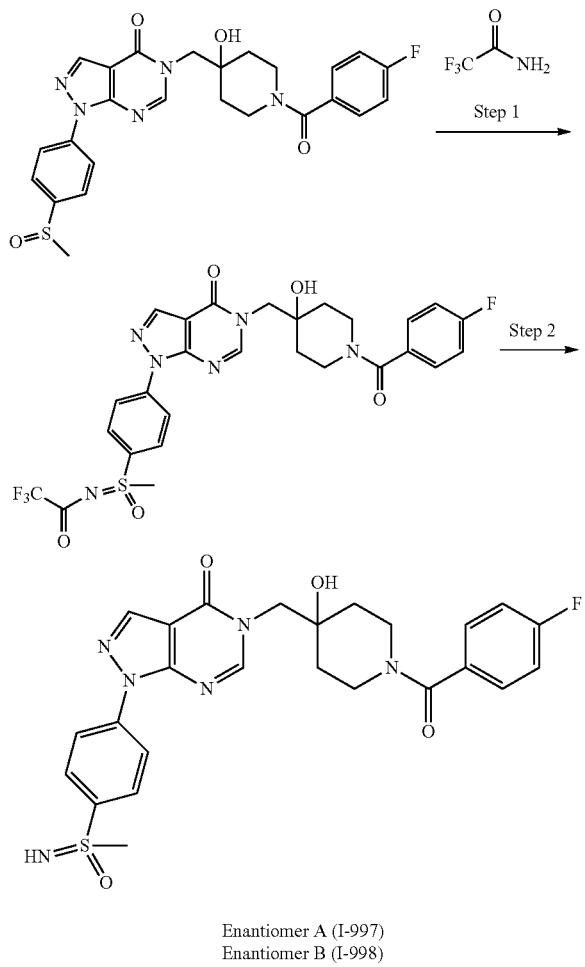

Enantiomer A (I-997)
Enantiomer B (I-998)

Step 1. 2,2,2-Trifluoro-N-([4-[5-([1-[(4-fluorophenyl)carbonyl]-4-hydroxypiperidin-4-yl]methyl)-4-oxo-1H,4H,5H-pyrazolo[3,4-d]pyrimidin-1-yl]benzene](methane)sulfinylidene)acetamide A 50-mL 3-necked round-bottom flask fitted with a magnetic stir bar, condenser and thermometer was charged with 5-((1-(4-fluorobenzoyl)-4-hydroxypiperidin-4-yl)methyl)-1-(4-(methylsulfinyl)phenyl)-1H-pyrazolo[3,4-d]pyrimidin-4(5H)-one (Example 116, 102 mg, 0.20 mmol), dichloromethane (20 mL), MgO (32 mg, 0.80 mmol), rhodium acetate dimer (3.8 mg, 0.02 mmol) and trifluoroacetamide (45.2 mg, 0.40 mmol) followed by iodobenzene diacetate (128 mg, 0.40 mmol) at 40° C. The resulting solution was stirred for 16 h and concentrated under vacuum. The residue was purified by preparative thin layer chromatography eluting with dichloromethane/methanol (20:1, v/v) to afford 2,2,2-trifluoro-N-([4-[5-([1-[(4-fluorophenyl)carbonyl]-4-hydroxypiperidin-4-yl]methyl)-4-oxo-1H,4H,5H-pyrazolo[3,4-d]pyrimidin-1-yl]benzene](methane)sulfinylidene)acetamide as a yellow solid (82 mg, 66%). LCMS: (ESI) m/z 621 [M+H].

Step 2. 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one A 50-mL round-bottom flask fitted with a magnetic stir bar was charged with 2,2,2-trifluoro-N-([4-[5-([1-[(4-fluorophenyl)carbonyl]-4-hydroxypiperidin-4-yl]methyl)-4-oxo-1H,4H,5H-pyrazolo[3,4-d]pyrimidin-1-yl]benzene](methane)sulfinylidene)acetamide (Step 1, 124 mg, 0.20 mmol), methanol (10 mL) and potassium carbonate (83 mg, 0.60 mmol). The resulting solution was stirred for 2 h at 27° C. The solids were removed by filtration and the filtrate was concentrated under vacuum. The residue was purified by preparative thin layer chromatography eluting with dichloromethane/methanol (20:1, v/v) to afford the title compound (95 mg, 91%). LCMS: (ESI) m/z 525 [M+H].

Step 3. Chiral separation of 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one (70 mg) was separated by Chiral preparatory HPLC to give (5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one, enantiomer A (I-997) (23.0 mg, 33%) and enantiomer B (I-998) 5-((1-(4-fluorobenzoyl)-4-hydroxypiperidin-4-yl)methyl)-1-(4-(S-methylsulfonimidoyl)phenyl)-1,5-dihydro-4H-pyrazolo[3,4-d]pyrimidin-4-one (22.0 mg, 33%). Enantiomer A: $^1$H NMR (300 MHz, CD$_3$OD) δ 1.30-1.68 (m, 4H), 3.29 (s, 3H), 3.44-3.53 (m, 3H), 4.09 (s, 2H), 4.22-4.24 (m, 1H), 7.12 (t, J=2.7 Hz, 2H), 7.36-7.42 (m, 2H), 8.11 (d, J=7.2 Hz, 2H), 8.22 (s, 1H), 8.29 (s, 1H), 8.49 (d, J=9.0 Hz, 2H). 0B: $^1$H NMR (300 MHz, CD$_3$OD) δ 1.39-1.68 (m, 4H), 3.14 (s, 3H), 3.30-3.45 (m, 3H), 4.08 (s, 2H), 4.21-4.23 (m, 11H), 7.10 (t, J=8.7 Hz, 2H), 7.36-7.41 (m, 2H), 8.11 (d, J=9.0 Hz, 2H), 8.21 (s, 1H), 8.28 (s, 1H), 8.41 (d, J=8.7 Hz, 2H). LCMS: (ESI) m/z 525 [M+H]. Column: Repaired IA, 21.2×150 mm, 5 μm. Mobile Phase A: MTBE/Mobile Phase B: methanol. Gradient: 20% B to 30% B over 24 min. Detector: 220 and 254 nm. RT$_1$: 13.917 min; RT$_2$: 20.080 min.

Method AH

Example 118: 2-(4-(4-(4-((1-(4-fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetamide (I-1002)

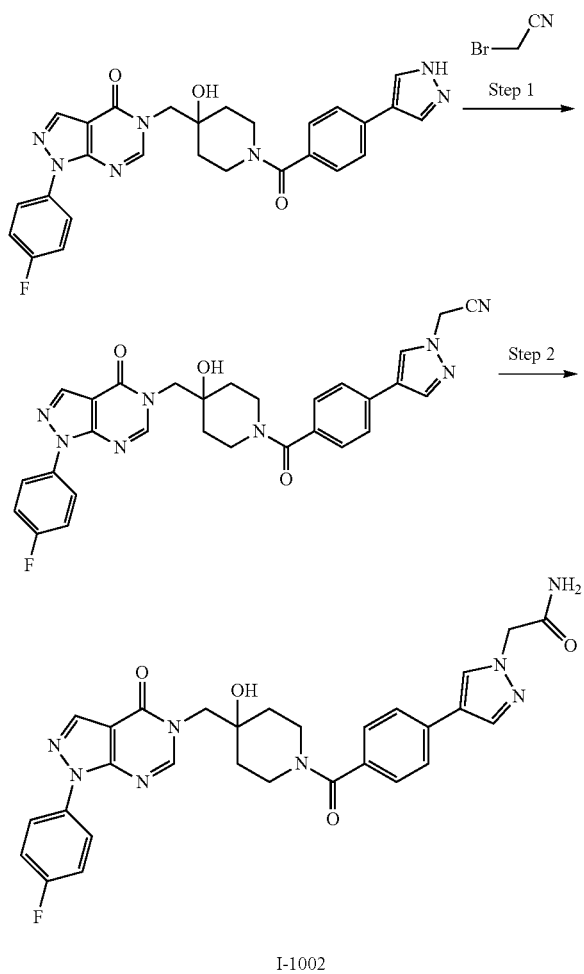

I-1002

Step 1. 2-(4-(4-(4-((1-(4-Fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetonitrile A 50-mL 3-necked round-bottom with fitted with a magnetic stir bar, condenser and thermometer was charged with 5-((1-(4-(1H-pyrazol-4-yl)benzoyl)-4-hydroxypiperidin-4-yl)methyl)-1-(4-fluorophenyl)-1H-pyrazolo[3,4-d]pyrimidin-4(5H)-one (prepared according to the procedure outlined in Method A utilizing 1-(4-fluorophenyl)-5-((4-hydroxypiperidin-4-yl)methyl)-1H-pyrazolo[3,4-d]pyrimidin-4(5H)-one TFA salt and 4-(1H-pyrazol-4-yl)benzoic acid) (100 mg, 0.19 mmol), N,N-dimethylformamide (10 mL), 2-bromoacetonitrile (150 mg, 1.25 mmol) and cesium carbonate (500 mg, 1.53 mmol). The resulting solution was stirred for 1 h at 120° C. After cooling to 23° C., the reaction was quenched with water (20 mL) and the resulting mixture was extracted with ethyl acetate (4×20 mL). The combined organic layers were dried over anhydrous sodium sulfate, filtered and concentrated under vacuum. The residue was purified by column chromatography eluting with dichloromethane/methanol (50/1-20/1, v/v) to afford 2-(4-(4-(4-((1-(4-fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetonitrile as a yellow solid (80 mg, 74%). LCMS: (ESI) m/z 553 [M+H].

Step 2. 2-(4-(4-(4-((1-(4-Fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetamide A 100-mL round-bottom flask was charged with 2-(4-(4-(4-((1-(4-fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetonitrile (60 mg, 0.11 mmol), DMSO (20 mL), ethanol (10 mL), potassium carbonate (250 mg, 1.81 mmol) and hydrogen peroxide (5 mL, 30%). The resulting solution was stirred for 1 h at 23° C. The reaction was quenched with saturated aqueous sodium thiosulfate (20 mL). The product was extracted with ethyl acetate (4×30 mL). The combined organic layers were dried over anhydrous sodium sulfate, filtered and concentrated under vacuum. The residue was purified by preparatory HPLC* to afford 1-(4-fluoro-3-(hydroxymethyl)phenyl)-5-((4-hydroxy-1-(4-(pyrimidin-2-yloxy)benzoyl)piperidin-4-yl)methyl)-1H-pyrazolo[3,4-d]pyrimidin-4(5H)-one (10 mg, 9%). $^1$H NMR (300 MHz, DMSO-$d_6$) δ 1.30-1.55 (m, 2H), 1.56-1.71 (m, 2H), 3.05-3.30 (m, 2H), 3.38-3.61 (m, 1H), 4.02-4.29 (m, 3H), 4.78 (s, 2H), 5.00 (brs, 1H), 7.29 (s, 1H), 7.32-7.49 (m, 4H), 7.52 (s, 1H), 7.64 (d, J=8.4 Hz, 2H), 7.95 (s, 1H), 8.01-8.11 (m, 2H), 8.19 (s, 1H), 8.36 (s, 1H), 8.37 (s, 1H). LCMS: (ESI) m/z 571 [M+H]. *Column: XBridge Prep C18 OBD Column, 5 μm, 19×150 mm. Mobile phase A: aqueous ammonium bicarbonate (0.05%)/Mobile phase B: acetonitrile. Flow rate: 20 mL/min. Gradient: 15% B to 48% B over 10 min. Detector: 220 and 254 nm.

Method AI

Example 119: 5-((1-(4-fluorobenzoyl)-4-hydroxypiperidin-4-yl)methyl)-1-(4-(2-(1-methylpiperidin-2-yl)ethyl)phenyl)-1H-pyrazolo[3,4-d]pyrimidin-4(5H)-one (I-1007)

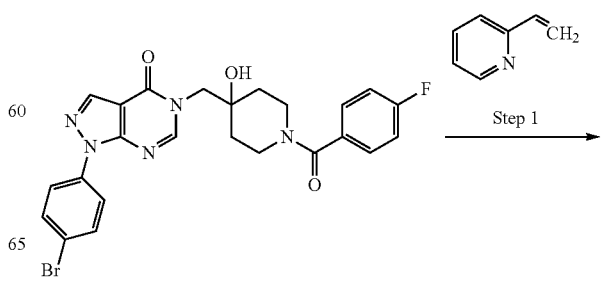

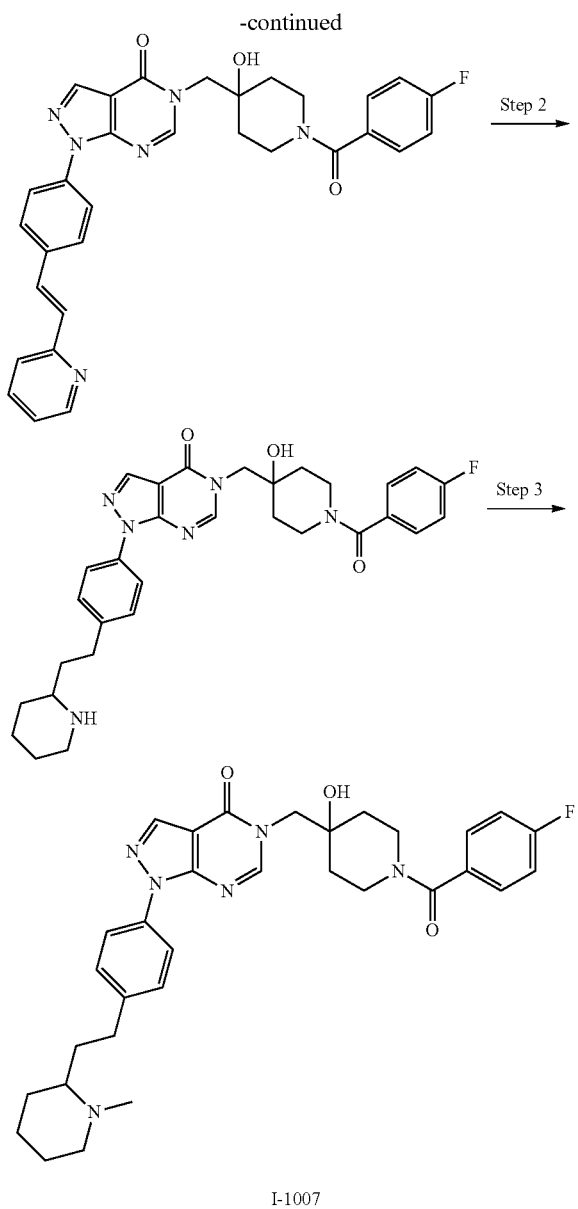

I-1007

Step 1. (E)-5-((1-(4-fluorobenzoyl)-4-hydroxypiperidin-4-yl)methyl)-1-(4-(2-(pyridin-2-yl)vinyl)phenyl)-1H-pyrazolo[3,4-d]pyrimidin-4(5H)-one A 100-mL 3-necked round-bottom flask fitted with a nitrogen balloon, magnetic stir bar, condenser and thermometer was charged with 1-(4-bromophenyl)-5-([1-[(4-fluorophenyl)carbonyl]-4-hydroxypiperidin-4-yl]methyl)-1H,4H,5H-pyrazolo[3,4-d]pyrimidin-4-one (200 mg, 0.38 mmol), 2-ethenylpyridine (210 mg, 2.00 mmol), palladium acetate (30 mg, 0.13 mmol), (+)-2,2'-Bis(diphenylphosphino)-1,1'-binaphthalene (30 mg, 0.05 mmol), potassium acetate (113 mg, 1.15 mmol) and N,N-dimethylformamide (20 mL). The resulting solution was stirred for 10 h at 100° C. in an oil bath and cooled to 25° C. The reaction was quenched with water (40 mL). The product was extracted with dichloromethane (3×40 mL). The combined organic layers were washed with brine (20 mL), dried over anhydrous sodium sulfate, filtered and concentrated under vacuum. The residue was purified by column chromatography eluting with ethyl acetate/petroleum ether (10:1, v:v) to afford the title compound (100 mg, 48%). LCMS: (ESI) m/z 551 [M+H].

Step 2. 5-((1-(4-fluorobenzoyl)-4-hydroxypiperidin-4-yl)methyl)-1-(4-(2-(piperidin-2-yl)ethyl)phenyl)-1H-pyrazolo[3,4-d]pyrimidin-4(5H)-one A 100-mL pressure tank reactor fitted with a magnetic stir bar was charged with (E)-5-((1-(4-fluorobenzoyl)-4-hydroxypiperidin-4-yl)methyl)-1-(4-(2-(pyridin-2-yl)vinyl)phenyl)-1H-pyrazolo[3,4-d]pyrimidin-4(5H)-one (Step 1, 150 mg, 0.27 mmol), methanol (20 mL) and platinum oxide (20 mg, 0.05 mmol). The resulting solution was stirred for 12 h under hydrogen (0.8 MPa) at 23° C. The solids were removed by filtration and the filtrate was concentrated under vacuum to afford the title compound (120 mg). LCMS: (ESI) m/z 559 [M+H].

Step 3. 5-((1-(4-fluorobenzoyl)-4-hydroxypiperidin-4-yl)methyl)-1-(4-(2-(1-methylpiperidin-2-yl)ethyl)phenyl)-1H-pyrazolo[3,4-d]pyrimidin-4(5H)-one A 100-mL round-bottom flask fitted with a magnetic stir bar was charged with 5-((1-(4-fluorobenzoyl)-4-hydroxypiperidin-4-yl)methyl)-1-(4-(2-(piperidin-2-yl)ethyl)phenyl)-1H-pyrazolo[3,4-d]pyrimidin-4(5H)-one (Step 2, 50 mg, 0.09 mmol), a solution of formaldehyde in water (2 mL, 37%), tetrahydrofuran (15 mL), sodium cyanoborohydride (17 mg, 0.3 mmol) and acetic acid (5 mg, 0.08 mmol). The solution was stirred for 2 h and concentrated under vacuum. The crude mixture was purified by preparatory HPLC* to afford the title compound (20 mg, 39%). $^1$H NMR (300 MHz, DMSO-d) δ 1.26-1.75 (m, 11H), 1.80-2.49 (m, 6H), 2.55-2.78 (m, 2H), 2.91-3.33 (m, 4H), 4.06 (s, 2H), 4.07-4.18 (m, 1H), 5.03 (brs, 1H), 7.24-7.30 (m, 2H), 7.40-7.49 (m, 4H), 7.91-7.94 (d, J=8.4 Hz, 2H), 8.34 (s, 2H). LCMS: (ESI) m/z 573 [M+H]. *Column: X Bridge C18, 19×150 mm, 5 μm. Mobile phase A: Water (0.05% ammonium bicarbonate)/Mobile phase B: acetonitrile. Flow rate: 20 mL/min. Gradient: 10% B to 80% B over 10 min). Detector: 220 and 254 nm.

Method AK

Example 120

Syn-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer A (I-1039a); and Anti-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer B (I-1039B)

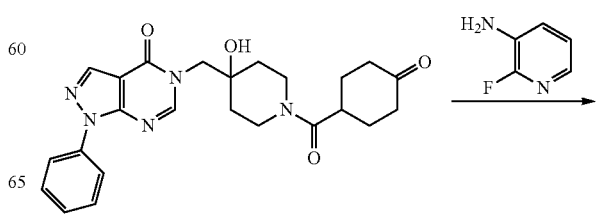

-continued

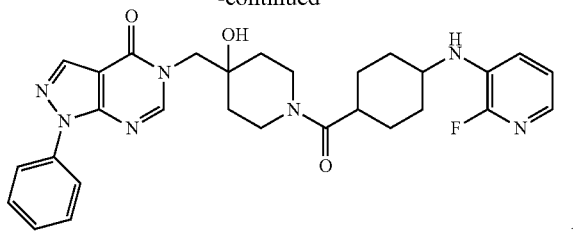

Isomer A (I-1039a)
Isomer B (I-1039B)

A 100-mL round-bottom flask fitted with a magnetic stir bar was charged with 5-((4-hydroxy-1-(4-oxocyclohexanecarbonyl)piperidin-4-yl)methyl)-1-phenyl-1H-pyrazolo[3,4-d]pyrimidin-4(5H)-one (220 mg, 0.5 mmol), dichloromethane (20 mL), 2-fluoropyridin-3-amine (70 mg, 0.6 mmol) and sodium triacetoxyborohydride (300 mg, 1.42 mmol). The resulting mixture was stirred for 1 h at 23° C. The reaction was quenched with water (30 mL) and the product was extracted with dichloromethane (4×20 mL). The combined organic layers were washed with brine (30 mL), dried over anhydrous sodium sulfate, filtered and concentrated under vacuum. The residue was purified by preparatory HPLC* to afford 5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer A (I-1039a); (12.5 mg, 5%). $^1$H-NMR (300 MHz, DMSO-$d_6$) δ 1.22-1.78 (m, 10H), 1.90-1.99 (m, 2H), 2.56-2.63 (m, 1H), 2.87-3.01 (m, 1H), 3.17-3.30 (m, 2H), 3.65-3.76 (m, 1H), 4.01-4.16 (m, 3H), 5.02 (brs, 1H), 5.46 (d, J=8.1 Hz, 1H), 7.05-7.09 (m, 1H), 7.13-7.19 (m, 1H), 7.25-7.32 (m, 1H), 7.43 (t, J=7.5 Hz, 1H), 7.59 (t, J=7.8 Hz, 2H), 8.07 (d, J=8.1 Hz, 2H), 8.37 (s, 1H), 8.38 (s, 1H). LCMS: (ESI) m/z 546[M+H] and 5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer B (I-1039b) (30.7 mg, 11%). $^1$H-NMR (300 MHz, DMSO-$d_6$) δ 1.35-1.88 (m, 12H), 2.67-2.78 (m, 1H), 2.87-3.01 (m, 1H), 3.17-3.30 (m, 1H), 3.48-3.58 (m, 1H), 3.67-3.75 (m, 1H), 3.95-4.16 (m, 3H), 4.98 (brs, 1H), 5.24 (d, J=5.7 Hz, 1H), 7.06-7.15 (m, 2H), 7.28-7.32 (m, 1H), 7.43 (t, J=7.5 Hz, 1H), 7.59 (t, J=8.1 Hz, 2H), 8.07 (d, J=7.8 Hz, 2H), 8.36 (s, 1H), 8.39 (s, 1H). LCMS: (ESI) m/z 546[M+H]. *Column: XBridge Prep C18 OBD Column, 5 μm, 19×150 mm. Mobile phase A: water (0.1% FA)/Mobile phase B: acetonitrile. Flow rate: 20 mL/min. Gradient: 18% B to 57% over 12.5 min. Detector: 220 and 254 nm.
Method AL Example 121: 1-(3-((3,3-difluorocyclobutyl)methoxy)phenyl)-5-((4-hydroxy-1-(1-methylcyclopropane-1-carbonyl)piperidin-4-yl)methyl)-1,5-dihydro-4H-pyrazolo[3,4-d]pyrimidin-4-one (I-1046)

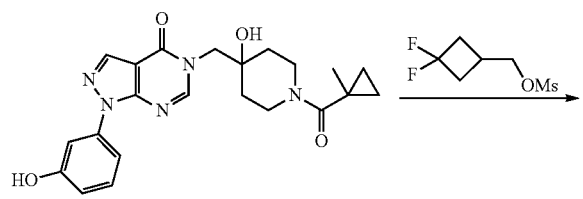

-continued

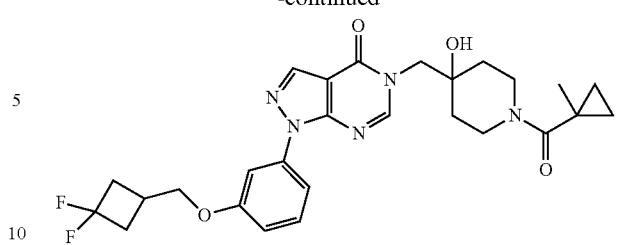

I-1046

A 100-mL 3-necked round-bottom fitted with a magnetic stir bar condenser and thermometer was charged with 5-([4-hydroxy-1-[(1-methylcyclopropyl)carbonyl]piperidin-4-yl]methyl)-1-(3-hydroxyphenyl)-1H,4H,5H-pyrazolo[3,4-d]pyrimidin-4-one (320 mg, 0.68 mmol), N,N-dimethylformamide (10 mL), (3,3-difluorocyclobutyl)methyl methanesulfonate (197 mg, 0.94 mmol) and potassium carbonate (313 mg, 2.24 mmol). The resulting mixture was stirred for 16 h at 120° C. in an oil bath. After cooling to 25° C., the reaction was quenched with water (20 mL). The resulting mixture was extracted with ethyl acetate (3×30 mL) and the combined organic layers were dried over anhydrous sodium sulfate, filtered and concentrated under vacuum. The residue was purified by preparative HPLC* to afford the title compound (13 mg, 4%). $^1$H-NMR (400 MHz, DMSO-$d_6$) δ 0.49-0.51 (m, 2H), 0.74-0.77 (m, 2H), 1.19 (s, 3H), 1.39-1.42 (m, 2H), 1.50-1.55 (m, 2H), 2.44-2.47 (m, 1H), 2.55-2.79 (m, 4H), 3.05-3.20 (m, 2H), 3.94-3.98 (m, 2H), 4.03 (s, 2H), 4.10 (d, J=6.4 Hz, 2H), 4.94 (brs, 1H), 6.98 (dd, J=1.6, 6.8 Hz, 1H), 7.47 (t, J=8.0 Hz, 1H), 7.65-7.69 (m, 2H), 8.34 (s, 1H), 8.35 (s, 1H). LCMS: (ESI) m/z 528[M+H]. *Column: XBridge Prep C18 OBD Column, 100 Å, 19×250 mm, 5 μm. Mobile phase A: 0.05% aqueous ammonium bicarbonate/Mobile phase B: acetonitrile. Gradient: 30% B to 41% B over 8 min. Flow rate: 20 mL/min. Detector: 254 and 220 nm.
Method AM Example 122: ((1-(cyclopropanecarbonyl)-4-hydroxypiperidin-4-yl)methyl)-1-(4-(6-(3-hydroxypyrrolidin-1-yl)pyridin-3-yl)phenyl)-1H-pyrazolo[3,4-d]pyrimidin-4(5H)-one (I-770)

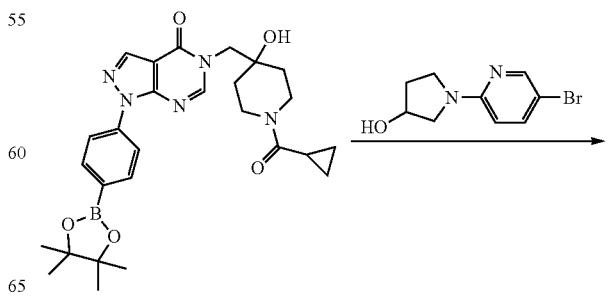

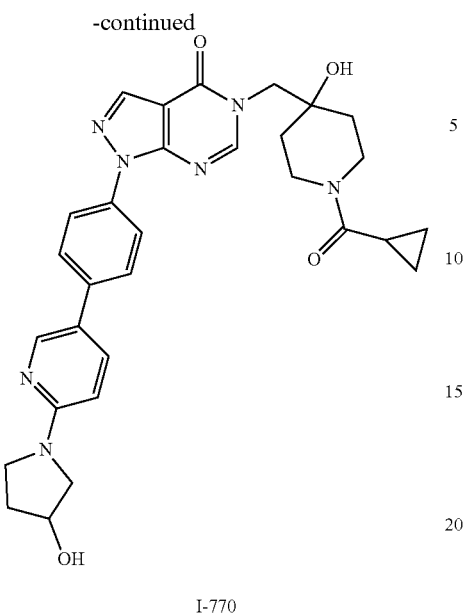

I-770

A 100-mL round-bottom flask fitted with a nitrogen balloon, magnetic stir bar, condenser and thermometer was charged with 1-(5-bromopyridin-2-yl)pyrrolidin-3-ol (Intermediate 2-7b, 85 mg, 0.35 mmol), 5-((1-(cyclopropanecarbonyl)-4-hydroxypiperidin-4-yl)methyl)-1-(4-(4,4,5,5-tetramethyl-1,3,2-dioxaborolan-2-yl)phenyl)-1H-pyrazolo[3,4-d]pyrimidin-4(5H)-one (Intermediate 2-149, 200 mg, 0.39 mmol), DMF (30 mL), water (3 mL), sodium carbonate (112 mg, 1.06 mmol) and [1,1'-bis(diphenylphosphino)ferrocene]dichloropalladium(II) (12 mg, 0.02 mmol). The resulting solution was stirred for 5 h at 100° C. in an oil bath. After cooling to 23° C., the reaction was quenched by the addition of water (60 mL). The resulting mixture was extracted with dichloromethane (5×40 mL). The organic layers were combined, dried over anhydrous sodium sulfate, filtered and concentrated under vacuum. The residue was further purified by preparative HPLC* to afford 5-((1-(cyclopropanecarbonyl)-4-hydroxypiperidin-4-yl)methyl)-1-(4-(6-(3-hydroxypyrrolidin-1-yl)pyridin-3-yl)phenyl)-1H-pyrazolo[3,4-d]pyrimidin-4(5H)-one (44 mg, 37%) as a light yellow solid. LCMS: (ES) m/z 556 [M+H]. ¹H-NMR (400 MHz, DMSO-d$_6$) δ 0.63-0.74 (m, 4H), 1.33-1.64 (m, 4H), 1.86-2.10 (m, 3H), 2.92-2.99 (m, 1H), 3.30-3.42 (m, 2H), 3.43-3.55 (m, 3H), 3.91-4.23 (m, 4H), 4.35-4.39 (m, 1H), 4.97 (brs, 2H), 6.54 (d, J=8.8 Hz, 1H), 7.79 (d, J=8.8 Hz, 2H), 7.88 (dd, J=2.8, 8.8 Hz, 1H), 8.08 (d, J=8.8 Hz, 2H), 8.36 (s, 1H), 8.37 (s, 1H), 8.49 (s, 1H). *Column: XBridge Prep C18 5 μm OBD 19×150 mm. Mobile phase A: 0.05% aqueous ammonium bicarbonate)/Mobile phase B: acetonitrile. Gradient: 30% B to 80% B over 20 min. Flow rate: 20 mL/min. Detector: UV 254/220 nm.

Method N

Example 123: (R)-5-((1-(4-fluorobenzoyl)-4-hydroxypiperidin-4-yl)methyl)-1-(4-(octahydro-2H-pyrido[1,2-a]pyrazin-2-yl)phenyl)-1,5-dihydro-4H-pyrazolo[3,4-d]pyrimidin-4-one (I-484)

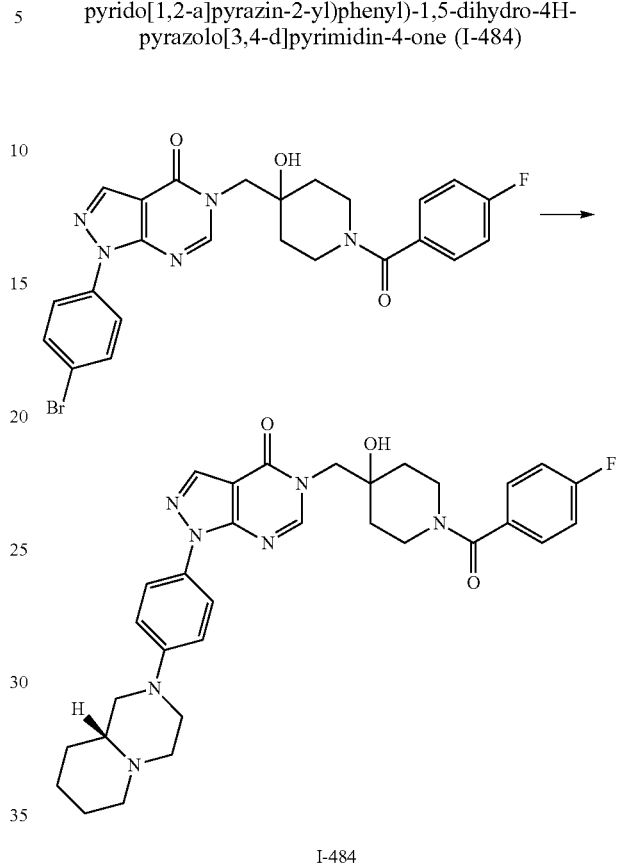

I-484

A reaction vial was charged with 1-(4-bromophenyl)-5-((1-(4-fluorobenzoyl)-4-hydroxypiperidin-4-yl)methyl)-1,5-dihydro-4H-pyrazolo[3,4-d]pyrimidin-4-one (15.8 mg), and (R)-octahydro-2H-pyrido[1,2-a]pyrazine. The reaction vial was flushed with nitrogen, and DMF, methanesulfonato(2-dicyclohexylphosphino-2',6'-di-1-propoxy-1,1'-biphenyl)(2'-methylamino-1,1'-biphenyl-2-yl)palladium(II) was introduced. The vial was sealed and heated at 120° C. for 8 h. The reaction mixture was concentrated, diluted with brine (500 μL), and extracted with ethyl acetate (2×500 μL). Purification by HPLC (Method 6) afforded the title compound. LCMS: (ES) m/z 586 [M+H]

Purification

Example 124: Chiral and Diastereomers Purification and Separation

The R and S enantiomers of racemic compounds and the diastereomers (including cis- and trans-) of compounds were separated using either Chiral SFC or Chiral HPLC or preparative HPLC or SFC utilizing different columns such as XBridge Shield RP18 OBD, (CHIRALCEL OJ, CHIRALCEL OD, ChiralPAK AD, (R,R)-WHELK-Ol-Kromasil, ChiralPAK IA, ChiralPAK IC, ChiralPAK ID, Lux Cellulose-4, SHIIADZU-SPD-20A, Phenomenex Lux, Cellulose-4, Anchintcq ACl Am-1 with different dimensions and diameter.

Columns were eluted with two mobile phases (Phase A and Phase B) with gradient from 0 to 100% for both phases.

Some examples of phases used but not limited: 0.1% diethylamine in MeOH, water (0.05% TFA), MeCN, Hexane (0.1% diethylamine or diisopropylamine), MeOH, dichloromethane, isopropanol, ethanol, MTBE, 0.2% isopropanol in EtOH, 0.1% isopropanol in hexane, 0.1% aqueous diethyl amine, 0.1% or 0.2% 2,6-diethylaniline in tert butyl methyl ether. Peaks were detected at 220 and 254 nm.

Biochemical Assays

Example 125: USP7 Assay A (Ubitquin-Rhodamine 110 Assay)

Each assay was performed in a final volume of 15 µL in assay buffer containing 20 mM Tris-HCl (pH 8.0, (1M Tris-HCl, pH 8.0 solution; Corning 46-031-CM)), 1 mM GSH (L-Glutathione reduced; Sigma #G4251), 0.03% BGG (0.22 µM filtered, Sigma, #G7516-25G), and 0.01% Triton X-100 (Sigma, #T9284-10L). Nanoliter quantities of either an 8-point or 10-point, 3-fold serial dilution in DMSO was pre-dispensed into assay plates (Perkin Elmer, ProxiPlate-384 F Plus, #6008269) for a final test concentration range of either 25 µM to 11 nM or 25 µM to 1.3 nM, respectively. The final concentration of the enzyme (USP7, construct USP7 (208-1102) 6*His, Viva Biotech) in the assay was 62.5 µM. Final substrate (Ub-Rh110; Ubiquitin-Rhodamine 110, R&D Systems #U-555) concentration was 25 nM with [Ub-Rh110]<<Km. 5 µL of 2× enzyme was added to assay plates (pre-stamped with compound) preincubated with USP7 for 30 minutes and then 5 µL of 2×Ub-Rh110 was added to assay plates. Plates were incubated stacked for 20 minutes at room temperature before 5 µL of stop solution (final concentration of 10 mM citric acid in assay buffer (Sigma, #251275-500G)). Fluorescence was read on the Envision (Excitation at 485 nm and Emission at 535 nm; Perkin Elmer) or on the PheraSTAR (Excitation at 485 nm and Emission at 535 nm; BMG Labtech).

Example 126: USP7 Assay B (Ubitquin-Rhodamine 110 Assay)

Each assay was performed in a final volume of 20 µL in assay buffer containing 20 mM Tris-HCl (pH 8.0, (1M Tris-HCl, pH 8.0 solution; Corning 46-031-CM)), 2 mM $CaCl_2$ (1M Calcium Chloride solution; Sigma #21114) 1 mM GSH (L-Glutathione reduced; Sigma #G4251), 0.01% Prionex (0.22 µM filtered, Sigma #G-0411), and 0.01% Triton X-100. Stock compound solutions were stored at −20° C. as 10 mM in DMSO. Up to 1 month prior to the assay, 2 mM test compounds were pre-dispensed into assay plates (Black, low volume; Corning #3820) and frozen at −20° C. Prestamped assay plates were allowed to come to room temperature on the day of the assay. For the screen, 100 nL of 2 mM was pre-dispensed for a final screening concentration of 10 µM ($DMSO_{(fc)}$=0.5%). For follow-up studies, 250 nL of an 8-point, 3-fold serial dilution in DMSO was pre-dispensed into assay plates for a final test concentration of 25 µM-11 nM (1.25% DMSO final concentration). Unless otherwise indicated, all follow-up assays were run on triplecate plates. Enzyme (USP7, construct Met (208-1102)-TEV-6*His; Viva Q93009-1) concentration and incubation times were optimized for the maximal signal-to-background while maintaining initial velocity conditions at a fixed substrate concentration. The final concentration of the enzyme in the assay was either 75 µM or 250 µM. Final substrate (Ub-Rh110; Ubiquitin-Rhodamine 110, R&D Systems (biotechne) #U-555) concentration was 25 nM with [Ub-Rh110]<<Km. Pre-stamped with compounds were either not preincubated or preincubated with USP7 between 30 to 120 minutes prior to the addition of 10 µL of 2×Ub-Rh110 to compound plates. Plates were incubated stacked for either 23 or 45 minutes at room temperature before fluorescence was read on the Envision (Excitation at 485 nm and Emission at 535 nm; Perkin Elmer) or on the PheraSTAR (Excitation at 485 nm and Emission at 535 nm; BMG Labtech).

Data from USP7 Assays A and B were reported as percent inhibition (inh) compared with control wells based on the following equation: % inh=1−((FLU−$Ave_{Low}$)/($Ave_{High}$−$Ave_{Low}$)) where FLU=measured Fluorescence (See Tables 6-10). $Ave_{Low}$=average Fluorescence of no enzyme control (n=16). $Ave_{High}$=average Fluorescence of DMSO control (n=16). $IC_{50}$ values were determined by curve fitting of the standard 4 parameter logistic fitting algorithm included in the Activity Base software package: IDBS XE Designer Model 205. Data is fitted using the Levenburg Marquardt algorithm. $IC_{50}$ data from USP7 Assays A-B for the compounds of the invention can be found in the Table below.

TABLE 37

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-1024 | AK | 564 | 1.4734 | ++++ |
| I-1023 | AK | 564 | 1.3952 | ++++ |
| I-1047 | AL | 542 | 1.4897 | ++++ |
| I-1046 | AL | 542 | 1.4357 | +++ |
| I-1016 | A | 562 | 0.9501 | +++ |
| I-1022 | A | 562 | 1.1794 | +++ |
| I-1015 | A | 562 | 1.3548 | +++ |
| I-1037 | A | 584 | 1.5436 | ++ |
| I-1036 | A | 584 | 1.5542 | ++++ |
| I-1018 | A | 602 | 1.2874 | ++++ |
| I-1035 | A | 518 | 0.7317 | +++ |
| I-1034 | A | 518 | 0.7343 | ++ |
| I-1033 | A | 536 | 0.9366 | ++ |
| I-1032 | A | 536 | 0.9096 | +++ |
| I-1031 | A | 518 | 0.7292 | +++ |
| I-1030 | A | 518 | 0.7317 | +++ |
| I-1014 | A, I | 572 | 1.4575 | +++ |
| I-1021 | A, | 548 | 1.2992 | +++ |
| I-1038 | A, | 546 | 1.2334 | ++++ |
| I-1042 | A | 492 | 1.3042 | +++ |
| I-1020 | A | 559 | 1.3817 | +++ |
| I-1019 | A | 559 | 1.4217 | +++ |
| I-1039 | AK | 546 | 1.2834 | +++ |
| I-1039b | AK | 546 | 1.3467 | ++++ |
| I-1041 | AK | 548 | 0.89 | +++ |
| I-1040 | AK | 548 | 0.8933 | ++ |
| I-1017 | A | 547 | 1.3283 | +++ |
| I-1112 | A | 520 | 1.375 | ++ |
| I-926 | A | 554 | 1.2733 | +++ |
| I-925 | A | 554 | 1.175 | ++ |
| I-1212 | A | 548 | 1.1083 | +++ |
| I-1113 | A | 548 | 1.2783 | ++++ |
| I-794 | A | 549 | 1.1617 | +++ |
| I-1114 | A | 549 | 1.1833 | ++ |
| I-1167 | A | 550 | 1.455 | ++ |
| I-1166 | A | 550 | 1.46 | ++++ |
| I-807 | AK | 550 | 1.2017 | ++ |
| I-806 | AK | 550 | 1.2333 | +++ |
| I-1067 | A | 549 | 1.1933 | +++ |
| I-791 | A | 597 | 1.5683 | +++ |
| I-790 | A | 597 | 1.5683 | ++++ |
| I-785 | A | 597 | 1.535 | +++ |
| I-784 | A | 597 | 1.5333 | ++++ |
| I-765 | AK | 549 | 0.845 | ++ |
| I-1075 | A, W | 537 | 1.0933 | ++ |
| I-1124 | A | 546 | 1.2917 | ++++ |

TABLE 37-continued

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-766 | AK | 549 | 0.9167 | +++ |
| I-1116 | AA | 536 | 1.3033 | +++ |
| I-815 | AA | 536 | 1.2967 | +++ |
| I-924 | A, W | 537 | 0.9783 | ++ |
| I-1029 | A | 498 | 1.2117 | ++ |
| I-1028 | A | 498 | 1.2083 | ++++ |
| I-1445 | N | 509 | 1.1583 | +++ |
| I-1561 | N | 509 | 1.2233 | ++++ |
| I-1570 | N | 547 | 1.2283 | +++ |
| I-1732 | N | 547 | 1.2833 | +++ |
| I-764 | AK | 549 | 0.91 | +++ |
| I-763 | AK | 549 | 0.8283 | ++ |
| I-748 | A | 548 | 1.166 | +++ |
| I-747 | A | 548 | 1.2083 | ++ |
| I-1728 | N | 527 | 1.3143 | +++ |
| I-1675 | N | 527 | 1.3433 | ++++ |
| I-1674 | N | 521 | 1.0417 | +++ |
| I-1676 | N | 521 | 1.0933 | ++++ |
| I-1677 | N | 479 | 0.8767 | +++ |
| I-1678 | N | 479 | 0.9232 | +++ |
| I-1679 | N | 481 | 1.1433 | +++ |
| I-1680 | N | 481 | 1.1867 | +++ |
| I-1636 | N | 548 | 0.6033 | +++ |
| I-1637 | N | 548 | 0.6317 | +++ |
| I-742 | A | 547 | 1.4783 | +++ |
| I-741 | A | 547 | 1.4867 | ++++ |
| I-789 | A | 601 | 1.2383 | ++++ |
| I-788 | A | 601 | 1.2367 | ++ |
| I-1126 | A | 533 | 1.2874 | ++++ |
| I-1125 | A | 533 | 1.2883 | +++ |
| I-1638 | N | 534 | 0.6067 | ++++ |
| I-1639 | N | 520 | 0.5883 | ++++ |
| I-1640 | N | 520 | 0.5883 | ++++ |
| I-1641 | N | 506 | 0.565 | ++++ |
| I-1642 | N | 547 | 0.8717 | +++ |
| I-1643 | N | 505 | 1.025 | +++ |
| I-1644 | N | 532 | 0.6467 | ++++ |
| I-1645 | N | 534 | 0.6383 | ++++ |
| I-1646 | N | 520 | 0.6183 | ++++ |
| I-1689 | N | 520 | 0.6167 | ++++ |
| I-1690 | N | 506 | 0.595 | ++++ |
| I-1691 | N | 547 | 0.96 | +++ |
| I-1692 | N | 505 | 1.07 | ++++ |
| I-1693 | N | 556 | 0.695 | +++ |
| I-1694 | N | 556 | 0.7217 | ++++ |
| I-1079 | A | 477 | 1.065 | +++ |
| I-1078 | A | 451 | 0.977 | +++ |
| I-1077 | A | 452 | 1.0183 | +++ |
| I-744 | A | 547 | 1.4367 | +++ |
| I-743 | A | 547 | 1.4433 | ++ |
| I-793 | A | 595 | 0.6433 | ++++ |
| I-792 | A | 595 | 0.6417 | +++ |
| I-746 | A | 561 | 1.4517 | ++ |
| I-745 | A | 561 | 1.4333 | ++ |
| I-740 | A | 565 | 1.5083 | +++ |
| I-739 | A | 565 | 1.5167 | ++++ |
| I-738 | A | 565 | 1.4733 | +++ |
| I-737 | A | 565 | 1.4783 | ++++ |
| I-752 | A | 547 | 0.74 | ++++ |
| I-751 | A | 547 | 0.8433 | ++ |
| I-1695 | A | 453 | 0.9433 | ++++ |
| I-1696 | A | 453 | 0.9433 | + |
| I-736 | A | 530 | 1.27 | + |
| I-735 | A | 530 | 1.27 | ++ |
| I-734 | A | 550, 552 | 1.3733 | + |
| I-733 | A | 550, 552 | 1.3683 | +++ |
| I-732 | A | 550, 552 | 1.3667 | ++ |
| I-731 | A | 550, 552 | 1.3683 | ++++ |
| I-728 | H, W, A | 534 | 1.1683 | +++ |
| I-727 | H, W, A | 534 | 1.2383 | +++ |
| I-1697 | A | 454 | 0.8917 | ++++ |
| I-1698 | A | 454 | 0.8917 | + |
| I-1700 | N | 548 | 0.62 | +++ |
| I-1701 | N | 548 | 0.5933 | +++ |
| I-1702 | N | 546 | 0.9517 | +++ |
| I-1747 | N | 546 | 0.9117 | +++ |
| I-1748 | N | 546 | 0.9533 | +++ |
| I-1749 | N | 546 | 0.9117 | +++ |
| I-1750 | N | 550 | 0.6283 | +++ |
| I-1751 | N | 516 | 1.155 | +++ |
| I-1752 | N | 516 | 1.1083 | +++ |
| I-797 | A | 530 | 1.37 | ++ |
| I-796 | A | 530 | 1.37 | ++++ |
| I-786 | N | 541 | 1.3067 | +++ |
| I-760 | Y | 517 | 1.4762 | ++ |
| I-759 | Y | 517 | 1.4767 | ++ |
| I-768 | AK | 545 | 1.1033 | ++++ |
| I-767 | AK | 545 | 0.935 | +++ |
| I-758 | A | 550 | 1.16 | +++ |
| I-757 | A | 550 | 1.17 | +++ |
| I-855 | AK, K, Example 2, A | 567 | 0.5967 | ++++ |
| I-1133 | AA | 528 | 1.4 | ++++ |
| I-770 | Example 2, A, S, AA | 581 | 1.39 | ++++ |
| I-1072 | A, AK | 509 | 0.7342 | ++ |
| I-769 | A, AK | 509 | 0.685 | +++ |
| I-756 | A | 551 | 1.355 | +++ |
| I-755 | A | 551 | 1.335 | +++ |
| I-853 | A, J | 559 | 1.03 | +++ |
| I-852 | A, J | 559 | 0.9383 | ++++ |
| I-1163 | A | 556 | 1.325 | ++ |
| I-1162 | A | 556 | 1.3233 | ++++ |
| I-1753 | A | 454 | 0.8983 | +++ |
| I-1754 | AE | 492 | 1.2583 | +++ |
| I-1710 | AE | 488 | 1.185 | +++ |
| I-1711 | A, AE | 504 | 1.0683 | ++ |
| I-799 | A | 475 | 1.2167 | +++ |
| I-981 | A, S, AA | 563 | 1.36 | ++++ |
| I-1508 | A, S, AA | 559 | 1.6483 | +++ |
| I-771 | A | 510 | 1.1817 | +++ |
| I-846 | A | 489 | 1.3952 | +++ |
| I-783 | A | 535 | 1.2334 | +++ |
| I-1135 | A, S, AA | 537 | 1.2717 | ++++ |
| I-772 | A | 468 | 1.1308 | +++ |
| I-762 | AH, Example 2, D | 507 | 1.058 | ++ |
| I-725 | A | 506 | 1.058 | ++ |
| I-761 | D | 493 | 0.6767 | ++++ |
| I-798 | A | 500 | 1.2603 | +++ |
| I-754 | A | 550 | 1.2 | +++ |
| I-753 | A | 550 | 1.2175 | +++ |
| I-750 | A | 547 | 0.8817 | +++ |
| I-749 | A | 547 | 0.8417 | ++++ |
| I-1025 | A | 556 | 1.3278 | +++ |
| I-1716 | N | 533 | 0.9467 | ++++ |
| I-1717 | AE | 556 | 1.5436 | ++++ |
| I-1043 | AE | 542 | 1.4357 | +++ |
| I-1045 | AE | 508 | 1.3548 | ++++ |
| I-724 | A | 492 | 0.95 | +++ |
| I-1136 | A, S, AA | 523 | 1.245 | ++++ |
| I-1118 | A, S, AA | 508 | 1.1333 | ++++ |
| I-923 | AA | 552 | 1.14 | ++ |
| I-835 | A | 598 | 1.08 | ++++ |
| I-847 | A | 516 | 1.5075 | +++ |
| I-726 | A | 478 | 1.085 | +++ |
| I-1137 | A, S, AA | 524 | 1.4842 | ++++ |
| I-1119 | S, AA | 510 | 1.3792 | ++++ |
| I-840 | A | 562 | 0.9906 | ++ |
| I-839 | A | 562 | 0.9906 | ++++ |
| I-838 | A | 562 | 0.9906 | ++ |
| I-837 | A | 562 | 0.9906 | ++++ |
| I-836 | A | 598 | 1.0825 | ++ |
| I-834 | A | 598 | 1.085 | ++ |
| I-833 | A | 598 | 1.745 | ++++ |

TABLE 37-continued

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-1718 | N | 581 | 1.4917 | ++++ |
| I-490 | N | 567 | 1.375 | +++ |
| I-1719 | H | 572 | 1.1983 | ++++ |
| I-1720 | H | 528 | 1.2733 | ++++ |
| I-1721 | H | 538 | 1.3267 | ++++ |
| I-1722 | H | 558 | 1.0933 | ++++ |
| I-1723 | H | 514 | 1.1617 | +++ |
| I-489 | H | 524 | 1.22 | +++ |
| I-781 | A | 474 | 1.1242 | +++ |
| I-782 | A | 488 | 1.2358 | ++++ |
| I-780 | AE, Example 2, A | 527 | 1.1242 | ++++ |
| I-778 | N, Example 2, A | 547 | 0.6264 | ++++ |
| I-777 | N, Example 2, A | 547 | 0.6264 | ++++ |
| I-822 | A | 582 | 0.9333 | +++ |
| I-821 | A | 582 | 0.9232 | ++ |
| I-818 | AE | 559 | 0.6399 | ++++ |
| I-975 | N, Example 2a, AE | 559 | 0.6128 | +++ |
| I-712 | H | 530 | 1.1367 | ++ |
| I-1117 | A, S, AA | 543 | 1.4583 | +++ |
| I-1134 | A, S, AA | 569 | 1.3548 | +++ |
| I-776 | H | 541 | 1.031 | ++++ |
| I-775 | H, Example 2, T | 488 | 1.031 | +++ |
| I-795 | A, W, J | 572 | 0.8675 | ++ |
| I-922 | Y | 552 | 1.3325 | ++ |
| I-1052 | A | 562 | 0.9892 | +++ |
| I-819 | AE | 546 | 1.0392 | +++ |
| I-817 | A, S, AA | 595 | 1.4492 | ++++ |
| I-1110 | A | 559 | 1.4357 | ++++ |
| I-987 | U | 528 | 0.6938 | ++ |
| I-988 | U | 528 | 0.68 | ++ |
| I-820 | AE | 570 | 1.2064 | +++ |
| I-976 | AE | 571 | 1.19 | ++ |
| I-1681 | N | 572 | 0.74 | ++ |
| I-1682 | N | 572 | 0.73 | ++ |
| I-1683 | N | 586 | 0.76 | ++ |
| I-553 | A | 584 | 1.1792 | +++ |
| I-1096 | A | 577 | 0.84 | ++ |
| I-672 | R | 571 | 1.1255 | +++ |
| I-1089 | A | 546 | 1.2675 | +++ |
| I-1684 | AE | 557 | 0.9092 | ++++ |
| I-1685 | AE | 595 | 1.4342 | ++++ |
| I-1686 | AE | 561 | 1.3548 | ++++ |
| I-779 | A | 541 | 1.2317 | ++++ |
| I-1687 | AE | 531 | 0.8133 | ++++ |
| I-1688 | AE | 569 | 1.34 | ++++ |
| I-1733 | AE | 535 | 1.2575 | ++++ |
| I-488 | AE | 515 | 1.1255 | ++++ |
| I-1734 | AE | 544 | 1.0175 | +++ |
| I-1735 | N | 572 | 0.7333 | ++ |
| I-487 | N | 572 | 0.7343 | ++ |
| I-921 | A | 532 | 1.02 | ++ |
| I-557 | A | 529 | 1.39 | +++ |
| I-1164 | A | 543 | 1.39 | ++++ |
| I-1161 | A | 542 | 1.24 | ++++ |
| I-687 | L, AM | 556 | 0.63 | +++ |
| I-686 | L, AM | 556 | 0.63 | +++ |
| I-685 | N, H, Example 2a | 569 | 0.5 | ++++ |
| I-684 | N, H, Example 2a | 569 | 0.5 | ++++ |
| I-977 | AE, R | 520 | 0.92 | ++ |
| I-985 | N | 538 | 0.77 | +++ |
| I-920 | I, A | 564 | 0.8 | ++ |
| I-1736 | H | 510 | 1.2033 | +++ |
| I-1737 | H | 539 | 1.3526 | ++ |
| I-1738 | H | 511 | 1.1567 | ++ |
| I-1739 | N | 533 | 0.7283 | ++ |
| I-1740 | N | 601 | 0.9486 | +++ |
| I-1741 | N | 547 | 0.785 | +++ |
| I-699 | N | 580 | 1.32 | +++ |
| I-551 | T | 570 | 1.2 | +++ |
| I-543 | A | 534 | 1.32 | +++ |
| I-542 | A | 534 | 1.32 | ++++ |
| I-1092 | A | 494 | 0.82 | ++ |
| I-673 | AE | 529 | 1.08 | ++ |
| I-983 | H | 528 | 0.69 | ++ |
| I-984 | H | 542 | 0.69 | ++ |
| I-919 | A | 531 | 1.11 | ++ |
| I-552 | A | 569 | 0.99 | +++ |
| I-549 | A | 520 | 1.21 | ++ |
| I-548 | A | 521 | 1.1933 | ++ |
| I-832 | A, Example 2, A | 561 | 0.48 | ++++ |
| I-561 | A | 545 | 1.53 | +++ |
| I-560 | A | 545 | 1.54 | +++ |
| I-559 | A | 563 | 1.51 | ++ |
| I-558 | A | 545 | 1.53 | +++ |
| I-845 | N, H, Example 2a | 569 | 0.5 | ++++ |
| I-1093 | A | 494 | 1.31 | ++ |
| I-1091 | A | 496 | 1.33 | ++ |
| I-696 | A, S, AA | 550 | 1.49 | +++ |
| I-692 | A, S, AA, | 533 | 0.66 | ++++ |
| I-1101 | H | 558 | 0.83 | ++ |
| I-1090 | A | 531 | 1.23 | +++ |
| I-1744 | H | 646 | 1.14 | +++ |
| I-1745 | H | 618 | 1.18 | +++ |
| I-1746 | H | 554 | 1.29 | +++ |
| I-1614 | H | 598 | 1.21 | +++ |
| I-1615 | H | 570 | 1.14 | +++ |
| I-1616 | H | 586 | 1.18 | +++ |
| I-1617 | H | 586 | 1.14 | +++ |
| I-1095 | A | 494 | 1.2333 | +++ |
| I-556 | A | 480 | 1.17 | ++ |
| I-693 | A, S, AA | 580 | 1.31 | +++ |
| I-1099 | H | 558 | 0.83 | ++ |
| I-1087 | A | 532 | 1.27 | +++ |
| I-1621 | A | 614 | 0.68 | ++++ |
| I-1622 | A | 560 | 0.56 | ++++ |
| I-1755 | N | 503 | 1.11 | ++ |
| I-1756 | O | 548 | 1.26 | +++ |
| I-486 | P | 499 | 0.71 | ++ |
| I-612 | A, AE | 544 | 1.06 | ++ |
| I-613 | AE, W, T, R | 543 | 0.71 | ++ |
| I-550 | A | 556 | 1.18 | +++ |
| I-546 | A | 548 | 1.3283 | +++ |
| I-545 | A | 547 | 1.24 | +++ |
| I-544 | A | 547 | 1.24 | ++ |
| I-918 | A | 534 | 1.3 | + |
| I-1159 | A | 534 | 1.3 | ++++ |
| I-660 | A, Example 2, B | 553 | 1.38 | +++ |
| I-850 | A | 492 | 1.15 | +++ |
| I-849 | A | 478 | 1.13 | ++++ |
| I-1010 | A | 508 | 0.6 | ++ |
| I-629 | A | 501 | 1.33 | ++++ |
| I-816 | S, AA, R, AK | 563 | 0.65 | ++++ |
| I-1088 | A | 530 | 0.81 | +++ |
| I-697 | D, AA | 586 | 0.91 | + |
| I-646 | A | 574 | 1.52 | ++ |
| I-645 | A | 574 | 1.52 | +++ |
| I-1006 | A, H, R | 558 | 1.07 | ++ |
| I-1002 | A, H, AH | 571 | 1.02 | ++ |
| I-1001 | A | 569 | 0.72 | ++ |
| I-1000 | A | 569 | 0.72 | ++ |
| I-611 | A | 555 | 0.71 | ++ |
| I-917 | A | 515 | 1.34 | ++ |
| I-1160 | A | 597 | 1.21 | +++ |
| I-831 | A, Example 2, A | 561 | 0.52 | ++++ |
| I-1009 | A | 490 | 0.59 | ++ |
| I-830 | A | 596 | 0.64 | +++ |
| I-829 | A | 597 | 0.635 | ++++ |
| I-915 | A | 538 | 0.96 | ++ |
| I-1140 | A | 493 | 1.4 | +++ |
| I-1086 | A | 548 | 1.22 | ++ |
| I-547 | A | 542 | 1.23 | ++ |
| I-610 | Y | 548 | 1.33 | ++ |
| I-827 | A | 596 | 0.6 | ++ |
| I-826 | A | 597 | 0.6117 | ++++ |

TABLE 37-continued

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-825 | A | 596 | 0.61 | ++++ |
| I-1132 | A | 532 | 1.33 | +++ |
| I-1131 | A | 532 | 1.33 | ++ |
| I-604 | A | 558 | 0.72 | ++ |
| I-1005 | A, Example 2 | 544 | 0.71 | ++ |
| I-643 | A | 582 | 1.36 | +++ |
| I-555 | A | 524 | 1.04 | +++ |
| I-1764 | H | 524 | 1.29 | ++ |
| I-1768 | H | 510 | 0.65 | +++ |
| I-1725 | H | 485 | 0.79 | ++ |
| I-1726 | H | 485 | 0.92 | +++ |
| I-554 | A | 497 | 1.33 | ++ |
| I-1085 | A | 553 | 0.76 | ++ |
| I-1108 | A | 511 | 1.27 | + |
| I-912 | A | 534 | 1.27 | ++ |
| I-913 | A | 534 | 1.27 | ++ |
| I-1727 | N | 526 | 0.66 | ++ |
| I-1729 | N | 580 | 0.77 | ++ |
| I-562 | AA, W, A | 544 | 1.22 | ++ |
| I-563 | AA, T | 545 | 1.35 | ++ |
| I-1673 | H | 516 | 1 | ++ |
| I-1672 | H | 528 | 1.15 | ++ |
| I-603 | A, R | 528 | 1.16 | ++++ |
| I-1178 | N | 570 | 1 | ++ |
| I-1176 | N | 584 | 1 | ++ |
| I-1170 | N | 569 | 0.71 | +++ |
| I-1168 | N | 547 | 1.14 | +++ |
| I-1657 | N | 493 | 0.98 | ++ |
| I-1434 | N | 533 | 1.07 | ++ |
| I-1655 | N | 479 | 0.9 | ++ |
| I-1654 | N | 569 | 1.05 | +++ |
| I-1632 | N | 442 | 1.29 | ++ |
| I-541 | A | 528 | 1.29 | +++ |
| I-1003 | A, R, B | 495 | 1.01 | ++ |
| I-680 | H, S, J | 569 | 0.87 | +++ |
| I-679 | H, S, J | 569 | 0.87 | ++++ |
| I-484 | N | 586 | 0.88 | ++++ |
| I-720 | A | 496 | 1.18 | ++ |
| I-1625 | A | 401 | 1.14 | + |
| I-1623 | AE | 528 | 1.31 | ++ |
| I-690 | N, AM, Example 2 | 568 | 0.88 | +++ |
| I-689 | N, H, Example 2a | 568 | 0.76 | ++++ |
| I-842 | H, AA, Example 2 | 555 | 0.85 | +++ |
| I-841 | H, AA, Example 2 | 555 | 0.85 | +++ |
| I-856 | A, H, S, I | 557 | 0.94 | +++ |
| I-972 | K, Example 2, A, L | 525 | 1.3 | ++ |
| I-971 | K, Example 2, A, L | 525 | 1.29 | +++ |
| I-719 | A | 544 | 1.2 | ++ |
| I-605 | A, H, R, Example 2, AK | 545 | 0.89 | + |
| I-911 | T | 530 | 1.09 | ++ |
| I-536 | A | 522 | 1.21 | ++ |
| I-678 | H, AA | 569 | 0.87 | +++ |
| I-675 | H, AA, Example 2 | 555 | 0.85 | +++ |
| I-601 | W, T, AK | 561 | 0.88 | + |
| I-1667 | O | 494 | 1.05 | ++ |
| I-1666 | AE | 497 | 1.26 | + |
| I-537 | L, W, T | 564 | 0.89 | ++ |
| I-1129 | A | 531 | 1.4 | ++ |
| I-688 | N, AM, Example 2 | 568 | 0.88 | +++ |
| I-701 | N | 526 | 0.75 | ++ |
| I-633 | N | 525 | 1.3 | ++ |
| I-691 | H, Example 2a | 541 | 0.8 | ++ |
| I-698 | L, H, Example 2 | 554 | 0.95 | +++ |
| I-1659 | A | 537 | 1.44 | +++ |
| I-482 | AD | 469 | 1.3 | + |
| I-1584 | N | 532 | 0.71 | +++ |
| I-535 | A | 514 | 1.21 | +++ |
| I-1128 | A | 531 | 1.22 | +++ |
| I-970 | N | 546 | 0.8 | ++ |
| I-638 | N | 511 | 1.05 | +++ |
| I-637 | N | 511 | 1.05 | +++ |
| I-528 | A | 560 | 1.27 | ++ |
| I-527 | A | 560 | 1.27 | ++ |
| I-634 | N | 546 | 0.81 | ++ |
| I-533 | A | 561 | 0.9 | ++ |
| I-657 | A, Example 2, B | 539 | 1.29 | +++ |
| I-636 | N | 511 | 1.05 | +++ |
| I-529 | AK, A | 531 | 0.88 | ++ |
| I-1127 | AK, A | 547 | 1.03 | ++ |
| I-843 | H, R, Example 2 | 477 | 0.69 | +++ |
| I-526 | A | 560 | 1.27 | ++ |
| I-580 | A, Example 2, B | 495 | 1.01 | +++ |
| I-713 | K, Example 10 | 504 | 1.07 | ++ |
| I-525 | A | 523 | 0.98 | + |
| I-524 | A | 523 | 0.99 | ++ |
| I-1142 | A, AA, Example 2, AK | 529 | 0.94 | ++ |
| I-1007 | AI | 573 | 0.92 | ++ |
| I-1576 | AD | 534 | 0.98 | ++ |
| I-1437 | A | 529 | 1.36 | ++ |
| I-1526 | AE | 531 | 1.34 | ++ |
| I-508 | N, Example 2a | 549 | 0.69 | +++ |
| I-523 | A | 523 | 0.98 | + |
| I-522 | A | 520 | 1.22 | + |
| I-521 | A | 520 | 1.22 | + |
| I-520 | A | 520 | 1.2 | + |
| I-519 | A | 520 | 1.2 | + |
| I-998 | AG | 525 | 0.88 | ++ |
| I-997 | AG | 525 | 0.88 | ++ |
| I-1544 | N | 494 | 1.4 | ++ |
| I-1543 | N | 523 | 0.68 | +++ |
| I-654 | A | 556 | 1.41 | + |
| I-653 | A | 556 | 1.41 | +++ |
| I-652 | A | 556 | 1.41 | +++ |
| I-518 | A | 516 | 1.16 | ++++ |
| I-517 | A | 516 | 1.16 | ++ |
| I-1061 | A | 512 | 1.22 | ++ |
| I-1060 | A | 512 | 1.23 | ++++ |
| I-704 | A | 514 | 1.3 | ++ |
| I-952 | A, Example 2, T | 493 | 1.04 | +++ |
| I-1525 | N | 535 | 0.7 | ++ |
| I-707 | A, Example 2, A, R, AK | 491 | 1.23 | +++ |
| I-705 | A | 526 | 1.11 | ++ |
| I-996 | AF | 510 | 0.92 | ++ |
| I-995 | AF | 510 | 0.92 | ++ |
| I-1141 | Z | 558 | 1.2 | ++ |
| I-507 | AD | 466 | 0.79 | ++ |
| I-506 | AD | 466 | 0.76 | ++ |
| I-505 | Q | 516 | 0.94 | ++ |
| I-504 | Q | 502 | 0.83 | ++ |
| I-1535 | A | 515 | 1.08 | +++ |
| I-606 | A | 546 | 0.86 | ++ |
| I-538 | AA, T | 541 | 1.28 | ++ |
| I-1528 | A | 558 | 1.26 | ++ |
| I-1527 | A | 496 | 1.16 | ++ |
| I-1569 | A | 510 | 1.2 | ++ |
| I-1130 | A | 495 | 1.26 | +++ |
| I-1524 | A | 469 | 1.19 | ++ |
| I-1523 | A | 496 | 1.5 | ++ |
| I-1521 | A | 506 | 1.36 | ++ |
| I-1519 | A | 557 | 1.42 | ++ |
| I-1063 | AA, W, T | 538 | 1.17 | +++ |
| I-1542 | A | 475 | 1.17 | +++ |
| I-1514 | A | 449 | 1.11 | +++ |
| I-1510 | A | 537 | 1.34 | +++ |
| I-1145 | A, Example 2 | 543 | 0.94 | ++ |
| I-1104 | A | 508 | 1.37 | ++ |
| I-1103 | A | 508 | 1.37 | ++++ |
| I-992 | H, R, Example 2 | 522 | 0.73 | ++ |
| I-1102 | A | 508 | 1.36 | ++++ |
| I-1138 | N | 496 | 1.08 | ++ |
| I-974 | N | 500 | 0.94 | ++ |

TABLE 37-continued

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-851 | K, Example 2, A | 526 | 1.04 | +++ |
| I-635 | N, R | 481 | 1.07 | ++ |
| I-539 | AA, W, T | 542 | 1.11 | ++ |
| I-658 | A, Example 2, A | 551 | 1.33 | ++ |
| I-650 | A | 538 | 1.4 | ++ |
| I-649 | A | 538 | 1.4 | +++ |
| I-1144 | A | 544 | 1.3 | ++ |
| I-576 | A, B | 523 | 1.04 | ++ |
| I-1461 | N | 516 | 1.23 | ++ |
| I-648 | A | 538 | 1.4 | ++ |
| I-515 | A | 480 | 1.07 | ++ |
| I-514 | A | 480 | 1.07 | +++ |
| I-513 | A | 480 | 1.07 | +++ |
| I-967 | AD, N, Example 2 | 481 | 0.63 | ++ |
| I-655 | K, Example 2, AD | 477 | 1.29 | ++ |
| I-803 | A, Example 2, T | 479 | 0.97 | +++ |
| I-574 | A, Example 2, B | 481 | 0.95 | +++ |
| I-824 | A, N, Example 2a | 550 | 0.84 | +++ |
| I-639 | N | 551 | 1.24 | ++ |
| I-1501 | AD | 480 | 1.3 | ++ |
| I-1499 | AD | 506 | 0.9 | ++ |
| I-1496 | A | 548 | 0.63 | ++ |
| I-1493 | A | 520 | 1.02 | ++ |
| I-1492 | A | 531 | 1.19 | ++ |
| I-1490 | A | 513 | 1.15 | ++ |
| I-1487 | A | 508 | 0.64 | +++ |
| I-1058 | A | 510 | 1.39 | +++ |
| I-572 | A, Example 2, B | 481 | 0.96 | + |
| I-589 | AH, W, A, Example 2, T | 507 | 1.07 | ++ |
| I-703 | A | 452 | 0.89 | ++ |
| I-641 | Example 83, A | 544 | 1.12 | ++ |
| I-1708 | AD | 464 | 0.85 | ++ |
| I-1468 | I-1468 | 548 | 0.65 | ++ |
| I-993 | H, R, Example 2 | 531 | 0.84 | ++ |
| I-640 | Example 83, A | 496 | 1.03 | ++ |
| I-664 | D, Example 2 | 532 | 1.12 | ++ |
| I-663 | D, Example 2 | 532 | 1.12 | + |
| I-492 | AD | 480 | 0.81 | ++ |
| I-1448 | AD | 529 | 0.74 | ++ |
| I-1433 | C | 581 | 1.16 | ++ |
| I-1432 | C | 513 | 0.94 | ++ |
| I-1431 | C | 487 | 0.84 | ++ |
| I-1428 | C | 583 | 1.23 | ++ |
| I-1425 | C | 563 | 1.17 | ++ |
| I-1422 | C | 583 | 1.24 | ++ |
| I-1421 | C | 568 | 1.09 | ++ |
| I-1417 | C | 487 | 0.87 | ++ |
| I-1406 | C | 583 | 1.25 | ++ |
| I-1400 | C | 554 | 0.76 | ++ |
| I-1395 | A | 521 | 0.85 | ++ |
| I-1383 | A | 514 | 1.08 | ++ |
| I-1380 | A | 531 | 1.12 | ++ |
| I-1377 | A | 477 | 0.93 | ++ |
| I-965 | A, R | 409 | 0.73 | ++ |
| I-964 | A, R | 409 | 0.79 | ++ |
| I-989 | A | 526 | 1.07 | ++ |
| I-665 | Example 38, A | 536 | 1.29 | ++ |
| I-662 | D, Example 2 | 532 | 1.11 | + |
| I-1325 | O | 562 | 1.35 | ++ |
| I-1324 | O | 562 | 1.3 | ++ |
| I-1363 | O | 522 | 1.16 | ++ |
| I-1320 | O | 503 | 1.16 | ++ |
| I-1318 | O | 579 | 1.42 | ++ |
| I-1314 | O | 575 | 0.9 | +++ |
| I-1313 | O | 575 | 0.87 | +++ |
| I-1307 | O | 521 | 0.91 | ++ |
| I-1295 | O | 481 | 1.44 | ++ |
| I-475 | H | 509 | 1.43 | ++ |
| I-1289 | O | 467 | 1.3 | ++ |
| I-823 | N | 548 | 0.85 | +++ |
| I-632 | S | 482 | 1.06 | ++ |
| I-1285 | O | 554 | 1.57 | ++ |
| I-1800 | H | 524 | 1.2198 | ++++ |
| I-1801 | A, S, AL | 514 | 1.3533 | ++++ |
| I-814 | F | 563 | 1.27 | +++ |
| I-627 | A | 496 | 1.26 | ++ |
| I-1257 | N | 542 | 1.16 | +++ |
| I-1277 | N | 511 | 1.09 | ++ |
| I-1191 | N | 516 | 1.09 | ++ |
| I-1234 | N | 570 | 1.09 | ++ |
| I-950 | T, Example 2, T | 493 | 1 | ++ |
| I-621 | A | 478 | 1.25 | ++ |
| I-510 | A | 531 | 0.9 | + |
| I-706 | AD | 490 | 1.33 | ++ |
| I-1232 | N | 486 | 0.71 | ++ |
| I-500 | X | 489 | 1.39 | + |
| I-511 | A, Example 2 | 517 | 0.9 | + |
| I-531 | A | 453 | 1.05 | ++ |
| I-624 | A | 492 | 1.29 | +++ |
| I-625 | A | 504 | 1.27 | ++ |
| I-499 | N, Example 2a | 478 | 0.64 | +++ |
| I-498 | N, Example 2a | 478 | 0.68 | ++++ |
| I-1216 | N | 533 | 1.2 | ++ |
| I-1082 | N | 525 | 1.59 | ++ |
| I-1211 | N | 520 | 0.85 | ++ |
| I-1209 | N | 520 | 0.72 | +++ |
| I-1208 | N | 534 | 0.81 | ++ |
| I-1205 | N | 553 | 1.62 | ++ |
| I-1202 | N | 477 | 1.2 | ++ |
| I-1200 | N | 463 | 1.32 | +++ |
| I-1199 | N | 463 | 1.29 | ++ |
| I-1197 | N | 520 | 0.74 | +++ |
| I-1196 | N | 495 | 1.19 | ++ |
| I-1194 | N | 522 | 0.68 | ++ |
| I-1158 | N | 500 | 0.77 | ++ |
| I-1155 | N | 499 | 1.31 | +++ |
| I-1402 | N | 507 | 1.01 | ++ |
| I-1151 | N | 520 | 0.71 | +++ |
| I-1149 | N | 495 | 1.15 | ++ |
| I-1146 | N | 520 | 0.69 | +++ |
| I-1187 | N | 513 | 1.37 | ++ |
| I-615 | A | 492 | 1.32 | +++ |
| I-614 | AD | 429 | 1.14 | + |
| I-620 | A | 478 | 1.21 | +++ |
| I-469 | A | 448 | 1.25 | ++ |
| I-467 | A | 486 | 1.25 | ++ |
| I-464 | A | 440 | 1.24 | +++ |
| I-452 | E | 493 | 0.76 | ++ |
| I-449 | E | 495 | 0.68 | ++ |
| I-446 | E | 516 | 0.69 | ++ |
| I-443 | E | 547 | 0.68 | ++ |
| I-440 | E | 556 | 0.73 | ++ |
| I-437 | E | 539 | 0.83 | ++ |
| I-434 | E | 495 | 0.66 | ++ |
| I-431 | E | 491 | 0.69 | ++ |
| I-425 | AD | 459 | 1.3 | ++ |
| I-11 | K | 488 | 0.99 | + |
| I-423 | A | 506 | 1.41 | ++ |
| I-422 | A | 517 | 1.31 | + |
| I-419 | A | 534 | 1.09 | ++ |
| I-416 | E | 533 | 0.85 | ++ |
| I-51 | G | 476 | 0.76 | ++ |
| I-409 | H | 557 | 0.97 | ++ |
| I-406 | H | 509 | 1.32 | ++ |
| I-403 | H | 518 | 1.2 | ++ |
| I-401 | H | 557 | 1.19 | ++ |
| I-399 | H | 539 | 1.73 | ++ |
| I-393 | H | 509 | 1.29 | + |
| I-390 | H | 518 | 1.19 | ++ |
| I-387 | H | 489 | 1.14 | ++ |
| I-385 | H | 486 | 1.17 | ++ |
| I-844 | H, N | 568 | 0.72 | ++++ |
| I-369 | H | 557 | 0.85 | ++ |

TABLE 37-continued

USP7 activity of compounds of the invention in USP7 assay A and B.

| Compounds No.: | Method | LCMS: (ESI) m/z [M + H] | HPLC retention time/ mins | USP7_IC50 |
|---|---|---|---|---|
| I-1214 | H | 471 | 0.89 | ++ |
| I-362 | H | 513 | 1.46 | + |
| I-359 | H | 495 | 1.32 | ++ |
| I-350 | H | 541 | 1.11 | ++ |
| I-347 | H | 504 | 1.59 | ++ |
| I-333 | H | 567 | 1.18 | ++ |
| I-330 | H | 488 | 1.48 | ++ |
| I-50 | AD | 511 | 0.85 | + |
| I-44 | E | 480 | 1.34 | ++ |
| I-317 | A | 516 | 1.78 | +++ |
| I-315 | A | 482 | 1.75 | ++ |
| I-314 | A | 479 | 1.15 | +++ |
| I-312 | A | 453 | 1.75 | ++ |
| I-309 | A | 484 | 1.94 | ++ |
| I-306 | A | 514 | 1.33 | ++ |
| I-304 | A | 488 | 1.6 | ++ |
| I-303 | A | 482 | 1.55 | ++ |
| I-302 | A | 482 | 1.54 | +++ |
| I-296 | A | 486 | 1.61 | ++ |
| I-294 | A | 494 | 1.42 | ++ |
| I-49 | A | 461 | 1.3 | +++ |
| I-291 | A | 542 | 1.3 | ++ |
| I-290 | K, Example 2, A | 488 | 1.44 | ++ |
| I-289 | K, Example 2, A | 420 | 1.24 | +++ |
| I-287 | A | 465 | 1.15 | ++ |
| I-284 | AD | 401 | 0.96 | ++ |
| I-283 | A | 504 | 1.41 | ++ |
| I-282 | A | 515 | 1.29 | ++ |
| I-281 | A | 460 | 0.98 | ++ |
| I-280 | K, Example 2, A | 464 | 1.41 | ++ |
| I-279 | AD | 415 | 1.06 | ++ |
| I-278 | P | 430 | 1.34 | + |
| I-277 | A | 462 | 1.24 | ++ |
| I-48 | A | 447 | 1.2 | ++ |
| I-276 | A | 470 | 1.45 | ++ |
| I-274 | A | 496 | 1.29 | ++ |
| I-272 | A | 474 | 1.01 | ++ |
| I-271 | A | 408 | 1.08 | ++ |
| I-268 | A | 466 | 1.25 | ++ |
| I-31 | A | 472 | 0.9 | ++ |
| I-26 | A | 436 | 1.19 | + |
| I-267 | A | 478 | 1.24 | +++ |
| I-266 | A | 448 | 1.23 | ++ |
| I-35 | A | 428 | 1.25 | ++ |
| I-28 | A | 462 | 1.35 | ++ |
| I-1139 | A | 486 | 1.46 | ++++ |
| I-34 | A | 462 | 1.33 | + |
| I-264 | A | 462 | 1.17 | + |
| I-27 | A | 436 | 1.3 | ++ |
| I-259 | A, Example 2, A | 475 | 0.95 | ++ |
| I-33 | A | 462 | 1.43 | ++ |
| I-30 | A | 395 | 0.76 | ++ |
| I-29 | A | 400 | 1.11 | + |
| I-38 | A | 412 | 1.02 | ++ |
| I-25 | A | 450 | 1.49 | +++ |
| I-252 | A | 497 | 1.29 | +++ |
| I-23 | X | 485 | 1.3 | +++ |
| I-233 | K, Example 2, A | 479 | 1.27 | +++ |
| I-232 | A | 479 | 1.29 | +++ |
| I-230 | K, Example 2, A | 465 | 1.05 | ++ |
| I-229 | K, Example 2, A | 448 | 1.04 | ++ |
| I-227 | K, Example 2, A | 446 | 1 | + |
| I-226 | K, Example 2, A | 494 | 1.34 | ++ |
| I-224 | A | 498 | 1.66 | +++ |
| I-223 | K, Example 2, A | 498 | 1.39 | +++ |
| I-221 | K, Example 2, A | 490 | 1.21 | ++ |
| I-218 | K, Example 2, A | 494 | 1.32 | ++ |
| I-214 | K, Example 2, A | 494 | 1.3 | +++ |
| I-213 | K, Example 2, A | 498 | 1.52 | ++ |
| I-212 | K, Example 2, A | 478 | 1.43 | +++ |
| I-211 | K, Example 2, A | 478 | 1.42 | +++ |
| I-210 | K, Example 2, A | 482 | 1.36 | ++ |
| I-209 | K, Example 2, A | 466 | 1.26 | ++ |
| I-206 | K, Example 2, A | 462 | 1.31 | ++ |
| I-203 | K, Example 2, A | 490 | 1.26 | + |
| I-200 | K, Example 2, A | 458 | 1.37 | ++ |
| I-197 | K, Example 2, A | 458 | 1.39 | ++ |
| I-195 | K, Example 2, A | 422 | 1.24 | +++ |
| I-194 | K, Example 2, A | 408 | 1.15 | ++ |
| I-191 | K, Example 2, A | 431 | 0.92 | ++ |
| I-190 | A | 448 | 1.23 | +++ |
| I-189 | K, Example 2, A | 436 | 1.32 | +++ |
| I-20 | A, Example 2a | 459 | 0.81 | ++ |
| I-184 | A | 487 | 0.95 | +++ |
| I-182 | A | 523 | 1.07 | ++ |
| I-19 | A, S | 446 | 1.02 | ++ |
| I-181 | A | 487 | 1.01 | ++ |
| I-179 | A | 473 | 0.92 | +++ |
| I-178 | A | 461 | 1.23 | ++ |
| I-177 | A | 461 | 1.29 | ++++ |
| I-176 | A | 462 | 1.04 | ++ |
| I-175 | A | 462 | 1.04 | ++++ |
| I-173 | A | 535 | 1.11 | +++ |
| I-172 | A | 473 | 0.93 | ++ |
| I-18 | S | 446 | 0.98 | + |
| I-170 | F | 515 | 0.93 | + |
| I-164 | A, C | 523 | 1.03 | +++ |
| I-160 | A | 447 | 0.84 | +++ |
| I-158 | A | 394 | 1.04 | ++ |
| I-157 | A | 460 | 1.21 | +++ |
| I-156 | A | 470 | 1.38 | +++ |
| I-155 | A | 434 | 0.83 | ++ |
| I-154 | A | 368 | 0.9 | ++ |
| I-153 | A | 430 | 1.2 | ++ |
| I-152 | A | 486 | 1.26 | ++ |
| I-150 | A | 509 | 1.44 | ++++ |
| I-147 | A | 446 | 1.0237 | ++ |
| I-145 | A | 540 | 1.5492 | ++++ |
| I-144 | A | 540 | 1.54 | ++ |
| I-861 | A | 464 | 1.1238 | + |
| I-143 | A | 464 | 1.1238 | ++ |
| I-142 | A | 526 | 1.4591 | ++++ |
| I-141 | A | 526 | 1.4591 | ++ |
| I-45 | C | 549 | 1.04 | +++ |
| I-121 | L | 501 | 0.7002 | + |
| I-119 | L | 487 | 0.7118 | +++ |
| I-13 | L | 459 | 1.08 | ++ |
| I-115 | A | 499 | 1.2061 | ++ |
| I-111 | A | 523 | 0.9237 | ++ |
| I-108 | A | 501 | 0.9267 | ++ |
| I-106 | A | 523 | 0.9933 | ++ |
| I-105 | A | 399 | 0.8414 | +++ |
| I-102 | A | 482 | 0.7118 | + |
| I-4 | D | 473 | 1.29 | + |
| I-83 | A | 483 | 1.1 | ++ |
| I-78 | A | 428 | 1.058 | +++ |
| I-73 | A | 522 | 1.4567 | +++ |
| I-72 | A | 472 | 1.35 | ++++ |
| I-70 | K, Example 2, A | 473 | 1.08 | +++ |
| I-69 | A | 536 | 1.59 | +++ |
| I-68 | A | 486 | 1.46 | ++++ |
| I-67 | K, Example 2, A | 540 | 1.62 | ++++ |
| I-66 | A | 540 | 1.54 | +++ |
| I-65 | K, Example 2, A | 490 | 1.43 | ++++ |
| I-62 | K, Example 2, A | 488 | 1.35 | + |
| I-61 | K, Example 2, A | 438 | 1.19 | +++ |
| I-60 | K, Example 2, A | 502 | 1.51 | + |
| I-59 | K, Example 2, A | 452 | 1.35 | +++ |
| I-57 | A | 410 | 1 | +++ |

TABLE 37-continued

USP7 activity of compounds of the
invention in USP7 assay A and B.

| Compounds No.: | Method | LCMS: (ESI) m/z [M + H] | HPLC retention time/ mins | USP7_IC50 |
|---|---|---|---|---|
| I-55 | A | 589 | 1.14 | ++ |
| I-1 | A | 410 | 1.03 | +++ |

++++ indicates an $IC_{50}$ of less than about 0.2 μM,
+++ indicates an $IC_{50}$ between about 0.2 μM and about 1 μM,
++ indicates an $IC_{50}$ between about 1 μM and about 10 μM, and
+ indicates an $IC_{50}$ greater than 10 μM.

EQUIVALENTS

Those skilled in the art will recognize, or be able to ascertain, using no more than routine experimentation, numerous equivalents to the specific embodiments described specifically herein, Such equivalents are intended to be encompassed in the scope of the following claims.

The invention claimed is:
1. A method of inhibiting USP7 comprising administering to a patient in need thereof an effective amount of a compound of Formula (I):

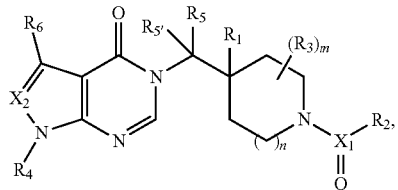

or a pharmaceutically acceptable salt thereof, wherein:
$X_1$ is C, S, or S(O);
$X_2$ is $CR_7$ or N;
$R_1$ is OH;
$R_2$ is $(C_1-C_8)$ alkyl, aryl, heteroaryl, $(C_3-C_8)$ cycloalkyl, heterocyclyl, $—NR_{10}R_{11}$, or $—OR_{10}$, wherein alkyl, aryl, cycloalkyl, and heterocyclyl are optionally substituted with one or more $R_8$;
each $R_3$ is independently at each occurrence selected from D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, aryl, heteroaryl, $(C_3-C_8)$ cycloalkyl, heterocyclyl, $—CN$, $—OH$, $—C(O)R_{17}$, $C(O)OR_{17}$, $—OC(O)OR_{17}$, $—OC(O)NR_{17}R_{18}$, $—NR_{17}R_{18}$, $—NR_{17}C(O)R_{18}$, $—NR_{17}C(O)OR_{18}$, $—C(O)NR_{17}R_{18}$, $—NR_{17}C(O)NR_{17}R_{18}$, $—S(O)_qNR_{17}R_{18}$, $—S(O)_qR_{17}R_{18}$, $—NR_{17}S(O)_qR_{17}R_{18}$, or halogen, wherein the alkyl is optionally substituted with one or more substituents independently selected from $—OH$ or $—NH_2$;
or two $R_3$ together when on adjacent carbons form a $(C_3-C_8)$ cycloalkyl optionally substituted with one or more $R_{19}$; or two $R_3$ together form a $(C_3-C_8)$ spirocycloalkyl optionally substituted with one or more $R_{19}$; or two $R_3$ together form a spiroheterocyclyl optionally substituted with one or more $R_{19}$; or two $R_3$ together when on adjacent carbons form an aryl ring optionally substituted with one or more $R_{19}$; or two $R_3$ together when on adjacent carbons form an heteroaryl ring optionally substituted with one or more $R_{19}$;
$R_4$ is $(C_1-C_6)$ alkyl or aryl, wherein aryl is optionally substituted with one or more $R_{12}$;
$R_5$ and $R_{5'}$ are H;
$R_6$ is H;
$R_7$ is H, D, $(C_1-C_6)$ alkyl, $(C_2-C_6)$ alkenyl, $(C_2-C_6)$ alkynyl, $(C_1-C_6)$ alkoxy, $(C_1-C_6)$ haloalkyl, $(C_1-C_6)$ haloalkoxy, halogen, aryl, heteroaryl, $—CN$, or $—NR_{10}R_{11}$, wherein the aryl and heteroaryl is optionally substituted with one or more $R_{10}$;
each $R_8$ is independently at each occurrence selected from D, $(C_1-C_6)$ alkyl, $(C_1-C_6)$ alkoxy, $(C_1-C_6)$ haloalkyl, $(C_1-C_6)$ haloalkoxy, $—(C_1-C_3)$-alkylene-O($C_1-C_6$) alkyl, $—(C_0-C_4)$-alkylene-aryl, $—(C_0-C_4)$-alkylene-heteroaryl, $(C_3-C_{10})$ cycloalkyl, heterocyclyl, $—(C_0-C_4)$-alkylene-O-aryl, $—(C_0-C_4)$-alkylene-O-heteroaryl, $—O—(C_3-C_8)$cycloalkyl, $—S$-heteroaryl, halogen, $—CN$, $—C(O)R_{10}$, $—CO(O)R_{10}$, $—C(O)NR_{10}R_{11}$, $—S(O)_qR_{10}$, $—S(O)gNR_{10}R_{11}$, $—NR_{10}S(O)_qR_{11}$, $—(C_0-C_3)$-alkylene-$NR_{10}R_{11}$, $—NR_{10}C(O)R_{11}$, $—NR_{10}C(O)C(O)R_{11}$, $—NR_{10}C(O)NR_{10}R_{11}$, $—P(O)((C_1-C_6)$alkyl$)_2$, $—P(O)(aryl)_2$, $—SiMe_3$, $SF_5$, or $—OH$, wherein alkyl, alkylene, aryl, heteroaryl, and heterocyclyl are optionally substituted with one or more $R_9$;
or two $R_8$ together when on adjacent carbons form an aryl ring optionally substituted with one or more $R_9$; or two $R_8$ together when on adjacent carbons form a heteroaryl ring optionally substituted with one or more $R_9$; or two $R_8$ together when on adjacent carbons form a heterocyclyl ring optionally substituted with one or more $R_9$;
each $R_9$ is independently at each occurrence selected from D, $(C_1-C_6)$ alkyl, $(C_1-C_6)$ alkoxy, $(C_3-C_8)$ cycloalkyl, halogen, aryl, $—OH$, $—CN$, $—C(O)R_{10}$, $—C(O)NR_{10}R_{11}$, $—NR_{10}C(O)R_{11}$, $—NR_{10}R_{11}$, $—S(O)_qR_{10}$, $—S(O)_qNR_{10}R_{11}$, $—NR_{10}S(O)_qR_{11}$, $—P(O)((C_1-C_6)$ alkyl$)_2$, $—P(O)(aryl)_2$, $—SiMe_3$, $SF_5$, $—O$-aryl, CN, or $—O$-heteroaryl, wherein alkyl, aryl, and cycloalkyl are optionally substituted with one or more substituents independently selected from $(C_1-C_6)$ alkyl, $(C_1-C_6)$ alkoxy, $(C_1-C_6)$ haloalkyl, halogen, aryl, $—NR_{14}C(O)R_{15}$, $—NR_{14}S(O)_qR_{15}$, $—OH$ or $—CN$;
or two $R_9$ together when on adjacent carbons form an aryl ring; or two $R_9$ together when on adjacent carbons form a heteroaryl ring; or two $R_9$ together when on adjacent carbons form a $(C_3-C_{10})$ cycloalkyl ring;
each $R_{10}$ and $R_{11}$ is independently at each occurrence selected from H, $(C_1-C_6)$ alkyl, $(C_2-C_6)$ alkenyl, $(C_2-C_6)$ alkynyl, $—(C_0-C_3)$ alkylene-aryl, $—(C_0-C_4)$ alkylene-$(C_3-C_8)$ cycloalkyl, $—(C_0-C_4)$ alkylene-heterocyclyl, $—(C_0-C_4)$ alkylene-heteroaryl, or $—CN$, wherein the alkyl, alkenyl, alkynyl, alkylene, cycloalkyl, heterocyclyl, aryl, and heteroaryl are optionally substituted with one or more substituents independently selected from $(C_1-C_6)$ alkyl, $(C_1-C_6)$ alkoxy, $(C_1-C_6)$ haloalkyl, $(C_1-C_6)$ haloalkoxy, $(C_3-C_8)$ cycloalkyl, heterocyclyl, aryl, $—S(O)_q(C_1-C_3)$ alkyl, $—S(O)gNR_{14}R_{15}$, $—NR_{14}R_{15}$, $—NR_{14}C(O)R_{15}$, halogen, $—OH$, or $—CN$;
or $R_{10}$ and $R_{11}$ together form a heterocyclyl ring optionally substituted with one or more substituents selected from $—C(O)(C_1-C_3)$ alkyl or $—NR_{14}NR_{15}$;
each $R_{12}$ is independently at each occurrence selected from D, $(C_1-C_6)$ alkyl, $(C_1-C_6)$ alkoxy, $(C_1-C_6)$ haloalkyl, $(C_3-C_8)$ cycloalkyl, aryl, heteroaryl, $—O$-aryl, $—O$-heteroaryl, $—O$-heterocyclyl, $—O—(C_3-C_8)$cycloalkyl, —S(O)$_q$R$_{10}$, —(CH$_2$)$_p$C(O)OR$_{10}$, —C(O) NR$_{14}$R$_{15}$, —S(O)$_q$NR$_{14}$R$_{15}$, —NR$_{14}$R$_{15}$, —NR$_{14}$C(O) NR$_{14}$R$_{15}$, —NR$_{14}$C(O)OR$_{10}$, —NR$_{14}$SO$_q$R$_{10}$, —NR$_{14}$COR$_{10}$, halogen, —P(O)((C$_1$-C$_6$)alkyl)$_2$, —P(O)(aryl)$_2$, —SiMe$_3$, SF$_5$ or —OH, wherein the alkyl, aryl, heteroaryl, heterocyclyl, and cycloalkyl are optionally substituted with one or more R$_{13}$;

each R$_{13}$ is independently at each occurrence selected from D, (C$_1$-C$_6$) alkyl, (C$_1$-C$_6$) haloalkyl, (C$_1$-C$_6$) alkoxy, halogen, (C$_1$-C$_6$) haloalkoxy, (C$_1$-C$_6$) hydroxyalkyl, heterocyclyl, heteroaryl, aryl, —OR$_{14}$, —C(O) R$_{14}$, —C(O)NR$_{14}$R$_{15}$, —NR$_{14}$R$_{15}$, —S(O)$_q$R$_{14}$, —NR$_{14}$S(O)$_q$R$_{15}$, —S(O)$_q$NR$_{14}$R$_{15}$, —NR$_{14}$C(O) NR$_{14}$R$_{15}$, —NR$_{14}$C(O)OR$_{15}$, —P(O)((C$_1$-C$_6$)alkyl)$_2$, —P(O)(aryl)$_2$, —SiMe$_3$, SF$_5$ or —CN, wherein alkyl, cycloalkyl, aryl, heterocyclyl, and heteroaryl are substituted with one or more substituents independently selected from (C$_1$-C$_6$) alkyl, —NR$_{14}$C(O)R$_{15}$, —OH, —CN, —C(O)R$_{14}$, or —NR$_{14}$R$_{15}$;

or two R$_{13}$ together when on adjacent carbons form a heterocyclyl ring optionally substituted with one or more R$_{16}$; or two R$_{13}$ together when on adjacent carbons form a heteroaryl ring optionally substituted with one or more R$_{16}$; or two R$_{13}$ together with the carbon to which they are attached can form a spiroheterocyclyl optionally substituted with one or more R$_{16}$;

each R$_{14}$ and R$_{15}$ are independently at each occurrence selected from H, (C$_1$-C$_6$) alkyl, (C$_2$-C$_6$) alkenyl, (C$_2$-C$_6$) alkynyl, —(C$_1$-C$_4$) alkylene-(C$_3$-C$_8$) cycloalkyl, —(C$_0$-C$_4$) alkylene-heterocyclyl, —(C$_0$-C$_4$) alkylene-aryl, —(C$_0$-C$_4$) alkylene-heteroaryl, or —CN, wherein alkyl, alkenyl, alkynyl, alkylene, cycloalkyl, heterocyclyl, aryl, and heteroaryl are optionally substituted with one or more R$_{16}$;

or R$_{14}$ and R$_{15}$ together form a heterocyclyl ring optionally substituted with one or more R$_{16}$;

each R$_{16}$ is independently at each occurrence selected from D, (C$_1$-C$_6$) alkyl, (C$_2$-C$_6$) alkenyl, (C$_2$-C$_6$) alkynyl, (C$_1$-C$_6$) haloalkyl, (C$_1$-C$_6$) alkoxy, (C$_1$-C$_6$) haloalkoxy, —C(O)(C$_1$-C$_3$) alkyl, —NHC(O)(C$_1$-C$_4$) alkyl, —CN, —CH$_2$CN, oxo, —S(O)$_q$(C$_1$-C$_6$) alkyl, - or —OH;

or two R$_{16}$ together when on adjacent carbons form an aryl ring; or two R$_{16}$ together when on adjacent carbons form a spiroheterocyclyl ring;

each R$_{17}$ and R$_{18}$ is at each occurrence independently H or (C$_1$-C$_6$) alkyl;

R$_{19}$ is independently at each occurrence H, D, (C$_1$-C$_6$) alkyl, (C$_2$-C$_6$) alkenyl, (C$_2$-C$_6$) alkynyl, (C$_1$-C$_6$) alkoxy, (C$_1$-C$_6$) haloalkyl, (C$_1$-C$_6$) haloalkoxy, halogen, —CN, or —NR$_{17}$R$_{18}$;

m is 0, 1 or 2;

n is 1;

p is 0, 1, or 2; and each q is 0, 1, or 2.

2. The method of claim 1, wherein:

each aryl ring is independently selected from the group consisting of phenyl, biphenyl, naphthyl, anthracenyl, phenalenyl, phenanthrenyl, indanyl, indenyl, tetrahydronaphthalenyl, and tetrahydrobenzoannulenyl;

each heterocycloalkyl ring is independently selected from the group consisting of oxetanyl, azetadinyl, tetrahydrofuranyl, tetrahydropyranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, oxazolidinonyl, and homotropanyl; and each heteroaryl ring is independently selected from the group consisting of furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b] pyrazinyl, quinazolinyl, tetrazolo[1,5-a]pyridinyl, [1,2,4]triazolo[4,3-a]pyridinyl, isoindolyl, pyrrolo[2,3-b] pyridinyl, pyrrolo[3,4-b]pyridinyl, pyrrolo[3,2-b] pyridinyl, imidazo[5,4-b]pyridinyl, pyrrolo[1,2-a] pyrimidinyl, tetrahydro pyrrolo[1,2-a]pyrimidinyl, 3,4-dihydro-2H-1λ$^2$-pyrrolo[2,1-b]pyrimidine, dibenzo[b, d] thiophene, pyridin-2-one, furo[3,2-c]pyridinyl, furo [2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno [2,3-b]pyrrolyl, 3H-indolyl, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

3. The method of claim 2, wherein X$_1$ is C or S(O).

4. The method of claim 2, wherein R$_3$ is halogen or (C$_1$-C$_6$) alkoxy.

5. The method of claim 2, wherein R$_7$ is H (C$_1$-C$_6$) alkyl or aryl.

6. The method of claim 2, wherein the compound is of Formula (Ie) or Formula (Ig):

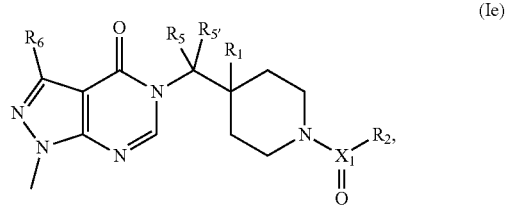

(Ie)

-continued

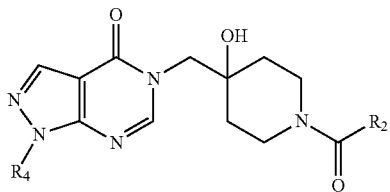
(Ig)

or a pharmaceutically acceptable salt thereof.

7. The method of claim 2, wherein the compound is of Formula (Ic) or Formula (Ii):

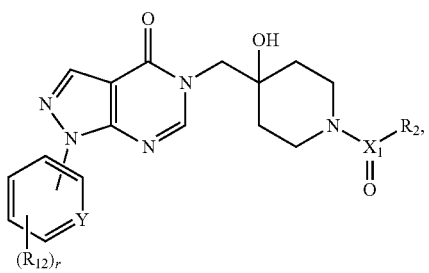
(Ic)

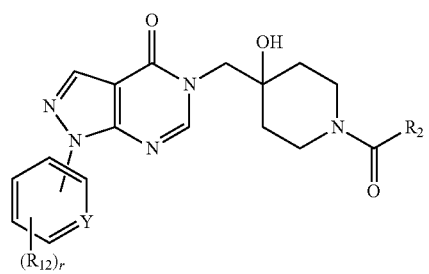
(Ii)

or a pharmaceutically acceptable salt thereof.

8. The method of claim 2, wherein the compound is of Formula (Ib), Formula (If), or Formula (Ih):

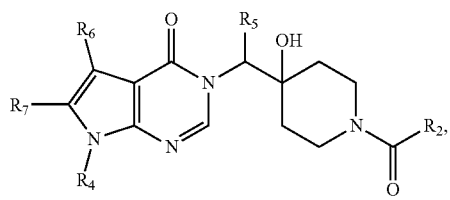
(Ib)

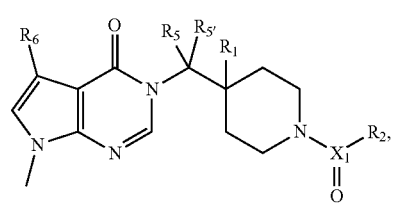
(If)

-continued

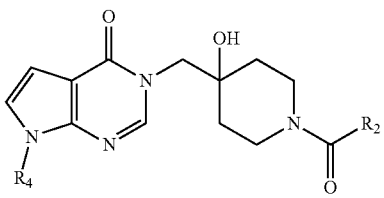
(Ih)

or a pharmaceutically acceptable salt thereof.

9. The method of claim 2, wherein the compound is of Formula (Id) or Formula (Ij):

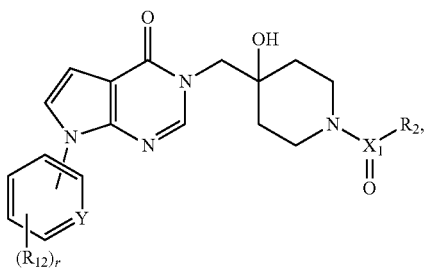
(Id)

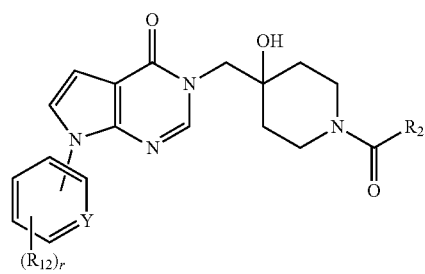
(Ij)

or a pharmaceutically acceptable salt thereof.

10. A method of inhibiting USP7 comprising administering to a patient in need thereof an effective amount of a compound selected from:
- 5-{[4-hydroxy-1-(3-phenylbutanoyl)piperidin-4-yl] methyl}-1-methyl-1H,4H,5H-pyrazolo[3,4-d]pyrimidin-4-one;
- 4-({4-[4-hydroxy-4-({1-methyl-4-oxo-1H,4H,5H-pyrazolo[3,4-d]pyrimidin-5-yl}methyl)piperidine-1-carbonyl]phenyl}methoxy)benzonitrile;
- 1-(4-fluorophenyl)-5-((4-hydroxy-1-(4-(5-methyl-5,6-dihydropyrrolo [3,4-c]pyrazol-1(4H)-yl)benzoyl)piperidin-4-yl)methyl)-1H-pyrazolo[3,4-d]pyrimidin-4(5H)-one;
- 1-(4-fluorophenyl)-5-{[4-hydroxy-1-(4-{5-methyl-2H,4H,5H,6H-pyrrolo[3,4-c]pyrazol-2-yl}benzoyl)piperidin-4-yl]methyl}-1H,4H,5H-pyrazolo[3,4-d]pyrimidin-4-one;
- 2-(4-(4-(4-((1-(4-fluorophenyl)-4-oxo-1H-pyrazolo[3,4-d]pyrimidin-5(4H)-yl)methyl)-4-hydroxypiperidine-1-carbonyl)phenyl)-1H-pyrazol-1-yl)acetamide;
- 5-((1-((2R,4S)-1-acryloyl-4-methylazetidine-2-carbonyl)-4-hydroxypiperidin-4-yl)methyl)-1-(4-fluorophenyl)-1H-pyrazolo[3,4-d]pyrimidin-4(5H)-one;
- 5-{[1-(4-{2,5-diazabicyclo[2.2.1]heptan-2-yl}benzoyl)-4-hydroxypiperidin-4-yl]methyl}-1-(4-fluorophenyl)-1H,4H,5H-pyrazolo[3,4-d]pyrimidin-4-one;
- 1-(4-fluorophenyl)-5-[(4-hydroxy-1-{4-[1-(2-hydroxyethyl)-1H-pyrazol-4-yl]benzoyl}piperidin-4-yl) methyl]-1H,4H,5H-pyrazolo[3,4-d]pyrimidin-4-one;

5-((1-(4-fluorobenzoyl)-4-hydroxypiperidin-4-yl)methyl)-1-(4-(2-(1-methylpiperidin-2-yl)ethyl) phenyl)-1H-pyrazolo[3,4-d]pyrimidin-4(5H)-one;

1-(3-(3-(dimethylamino)propyl)phenyl)-5-((1-(4-fluorobenzoyl)-4-hydroxypiperidin-4-yl) methyl)-1H-pyrazolo[3,4-d]pyrimidin-4(5H)-one;

3-((1-(cyclopropanecarbonyl)-4-hydroxypiperidin-4-yl)methyl)-7-(3-(piperidin-1-ylmethyl) phenyl)-3H-pyrrolo[2,3-d]pyrimidin-4(7H)-one;

3-[(1-cyclopropanecarbonyl-4-hydroxypiperidin-4-yl)methyl]-7-[4-fluoro-3-(piperidin-1-ylmethyl)phenyl]-3H,4H,7H-pyrrolo[2,3-d]pyrimidin-4-one;

(S)-5-(1-(1-(4-Fluorobenzoyl)-4-hydroxypiperidin-4-yl)ethyl)-1-(4-fluorophenyl)-1H-pyrazolo[3,4-d]pyrimidin-4(5H)-one;

6-{[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]oxy}pyridine-3-carbonitrile;

1-(4-fluorophenyl)-5-({4-hydroxy-1-[(1r,4r)-4-[(6-methylpyrazin-2-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(2-methylpyrimidin-4-yl)oxy]cyclohexanecarbonyl]piperidin-4-yl}methyl)-1H,4H,5H-pyrazolo[3,4-d]pyrimidin-4-one;

5-({4-hydroxy-1-[(1r,4r)-4-[(2-fluoropyridin-3-yl)oxy]cyclohexanecarbonyl]piperidin-4-yl}methyl)-1-phenyl-1H,4H,5H-pyrazolo[3,4-d]pyrimidin-4-one;

1-(4-fluorophenyl)-5-({4-hydroxy-1-[(1r,4r)-4-{[6-(azetidin-1-yl)pyridin-2-yl]oxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(5-methoxypyridin-2-yl)oxy]cyclohexanecarbonyl]piperidin-4-yl}methyl)-1H,4H,5H-pyrazolo[3,4-d]pyrimidin-4-one;

5-({4-hydroxy-1-[(1r,4r)-4-[(5-methoxypyridin-2-yl)oxy]cyclohexanecarbonyl]piperidin-4-yl}methyl)-1-phenyl-1H,4H,5H-pyrazolo[3,4-d]pyrimidin-4-one;

1-(4-fluorophenyl)-5-({4-hydroxy-1-[(1s,4s)-4-(pyrazin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(2-methylpyrimidin-5-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-[(6-fluoropyridin-2-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(6-fluoropyridin-2-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[1-methyl-3-(1-phenylethyl)-1H-pyrazole-4-carbonyl]piperidin-4-yl}methyl)-1H,4H,5H-pyrazolo[3,4-d]pyrimidin-4-one;

5-({1-[(3R)-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

5-({1-[(3S)-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

5-({4-hydroxy-1-[2-(1,2,3,4-tetrahydronaphthalen-1-yl)acetyl]piperidin-4-yl}methyl)-1-methyl-1H,4H,5H-pyrazolo[3,4-d]pyrimidin-4-one;

1-(4-fluorophenyl)-5-({4-hydroxy-1-[(1s,3s)-3-[(pyridin-3-yl)amino]cyclobutanecarbonyl]piperidin-4-yl}methyl)-1H,4H,5H-pyrazolo[3,4-d]pyrimidin-4-one;

1-(4-fluorophenyl)-5-({4-hydroxy-1-[(1r,3r)-3-[(pyridin-3-yl)amino]cyclobutanecarbonyl]piperidin-4-yl}methyl)-1H,4H,5H-pyrazolo[3,4-d]pyrimidin-4-one;

1-(4-fluorophenyl)-5-({4-hydroxy-1-[(1s,3s)-3-[(5-fluoropyridin-2-yl)amino]cyclobutanecarbonyl]piperidin-4-yl}methyl)-1H,4H,5H-pyrazolo[3,4-d]pyrimidin-4-one;

1-(4-fluorophenyl)-5-({4-hydroxy-1-[(1r,3r)-3-[(5-fluoropyridin-2-yl)amino]cyclobutanecarbonyl]piperidin-4-yl}methyl)-1H,4H,5H-pyrazolo[3,4-d]pyrimidin-4-one;

1-(4-fluorophenyl)-5-({4-hydroxy-1-[(1s,3s)-3-[(pyridin-2-yl)amino]cyclobutanecarbonyl]piperidin-4-yl}methyl)-1H,4H,5H-pyrazolo[3,4-d]pyrimidin-4-one;

1-(4-fluorophenyl)-5-({4-hydroxy-1-[(1r,3r)-3-[(pyridin-2-yl)amino]cyclobutanecarbonyl]piperidin-4-yl}methyl)-1H,4H,5H-pyrazolo[3,4-d]pyrimidin-4-one;

5-({1-[(3R)-4,4-difluoro-3-(3-fluoro-1H-pyrazol-1-yl)butanoyl]-4-hydroxypiperidin-4-yl}methyl)-1-[4-(trifluoromethyl)phenyl]-1H,4H,5H-pyrazolo[3,4-d]pyrimidin-4-one;

5-({1-[(3S)-4,4-difluoro-3-(3-fluoro-1H-pyrazol-1-yl)butanoyl]-4-hydroxypiperidin-4-yl}methyl)-1-[4-(trifluoromethyl)phenyl]-1H,4H,5H-pyrazolo[3,4-d]pyrimidin-4-one;

7-(4-fluorophenyl)-3-({4-hydroxy-1-[(1s,4s)-4-(pyridin-2-yloxy)cyclohexanecarbonyl]piperidin-4-yl}methyl)-3H,4H,7H-pyrrolo[2,3-d]pyrimidin-4-one;

Syn-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer A (I-1039a);

Anti-5-((1-(4-((2-fluoropyridin-3-yl)amino)cyclohexane-1-carbonyl)-4-hydroxypiperidin-4-yl)methyl)-1-phenyl-1,5-dihydro-4H-pyrazolo[3,4-d]pyrimidin-4-one, isomer B (I-1039b);

5-({4-hydroxy-1-[4-(phenoxymethyl)benzoyl]piperidin-4-yl)methyl)-1-methyl-1H,4H,5H-pyrazolo[3,4-d]pyrimidin-4-one;

7-(4-fluorophenyl)-3-({4-hydroxy-1-[(1s,4s)-4-[(1-methyl-1H-pyrazol-3-yl)amino]cyclohexanecarbonyl]piperidin-4-yl}methyl)-3H,4H,7H-pyrrolo[2,3-d]pyrimidin-4-one;

7-(4-fluorophenyl)-3-({4-hydroxy-1-[(1r,4r)-4-[(1-methyl-1H-pyrazol-3-yl)amino]cyclohexanecarbonyl]piperidin-4-yl}methyl)-3H,4H,7H-pyrrolo[2,3-d]pyrimidin-4-one;

1-[3-(3-fluoro-1H-pyrazol-1-yl)phenyl]-5-{[4-hydroxy-1-(1-methylcyclopropanecarbonyl) piperidin-4-yl]methyl}-1H,4H,5H-pyrazolo[3,4-d]pyrimidin-4-one;

5-{[4-hydroxy-1-(1-methylcyclopropanecarbonyl)piperidin-4-yl]methyl}-1-{4-[4-(trifluoromethyl)-1H-pyrazol-1-yl]phenyl}-1H,4H,5H-pyrazolo[3,4-d]pyrimidin-4-one;

1-[4-(4-chloro-1H-pyrazol-1-yl)phenyl]-5-{[4-hydroxy-1-(1-methylcyclopropanecarbonyl) piperidin-4-yl]methyl}-1H,4H,5H-pyrazolo[3,4-d]pyrimidin-4-one;

1-(3-((3,3-difluorocyclobutyl)methoxy)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;
1-{3-[(4,4-difluorocyclohexyl)oxy]phenyl)-5-{[4-hydroxy-1-(1-methylcyclopropanecarbonyl)piperidin-4-yl]methyl)-1H,4H,5H-pyrazolo[3,4-d]pyrimidin-4-one;
5-({4-hydroxy-1-[3-(1H-pyrrol-1-yl)butanoyl]piperidin-4-yl}methyl)-1-methyl-1H,4H,5H-pyrazolo[3,4-d]pyrimidin-4-one;
5-({4-hydroxy-1-[(3S)-3-(1H-pyrazol-1-yl)butanoyl]piperidin-4-yl}methyl)-1-{4-[(3R)-3-hydroxy-3-methylpyrrolidin-1-yl]phenyl}-1H,4H,5H-pyrazolo[3,4-d]pyrimidin-4-one;
5-({1-[4-(difluoromethoxy)benzoyl]-4-hydroxypiperidin-4-yl}methyl)-1-(4-methylphenyl)-1H,4H,5H-pyrazolo[3,4-d]pyrimidin-4-one;
5-[(4-hydroxy-1-{4-[(1-methylpyrrolidin-3-yl)oxy]benzoyl}piperidin-4-yl)methyl]-1-(4-methylphenyl)-1H,4H,5H-pyrazolo[3,4-d]pyrimidin-4-one;
4-[4-hydroxy-4-({1-methyl-4-oxo-1H,4H,5H-pyrazolo[3,4-d]pyrimidin-5-yl}methyl)piperidine-1-carbonyl]-N-phenylbenzene-1-sulfonamide;
5-({1-[(3R)-4,4-difluoro-3-(1H-pyrazol-1-yl)butanoyl]-4-hydroxypiperidin-4-yl}methyl)-1-(4-methylphenyl)-1H,4H,5H-pyrazolo[3,4-d]pyrimidin-4-one;
5-({1-[(3S)-4,4-difluoro-3-(1H-pyrazol-1-yl)butanoyl]-4-hydroxypiperidin-4-yl}methyl)-1-(4-methylphenyl)-1H,4H,5H-pyrazolo[3,4-d]pyrimidin-4-one;
5-[(4-hydroxy-1-{4-[(1-methylpiperidin-4-yl)oxy]benzoyl}piperidin-4-yl)methyl]-1-(4-methylphenyl)-1H,4H,5H-pyrazolo[3,4-d]pyrimidin-4-one;
5-({4-hydroxy-1-[4-(pyrimidin-2-yloxy)benzoyl]piperidin-4-yl}methyl)-1-(4-methylphenyl)-1H,4H,5H-pyrazolo[3,4-d]pyrimidin-4-one;
5-({4-hydroxy-1-[(1s,3s)-3-(pyridin-2-yloxy)cyclobutanecarbonyl]piperidin-4-yl}methyl)-1-(4-methylphenyl)-1H,4H,5H-pyrazolo[3,4-d]pyrimidin-4-one;
1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-cyclopropylurea;
4-[1-{5-[(cyclopropylmethyl)amino]pyridin-3-yl}-4-oxo-1H,4H,5H-pyrazolo[3,4-d]pyrimidin-5-yl)methyl]-4-hydroxy-N,N-dimethylpiperidine-1-carboxamide;
7-(4-fluorophenyl)-3-({4-hydroxy-1-[(1r,4r)-4-[(1-methyl-1H-pyrazol-3-yl)oxy]cyclohexanecarbonyl]piperidin-4-yl}methyl)-3H,4H,7H-pyrrolo[2,3-d]pyrimidin-4-one;
N-[(1r,4r)-4-[(4-[[1-(4-fluorophenyl)-4-oxo-1H,4H,5H-pyrazolo[3,4-d]pyrimidin-5-yl]methyl]-4-hydroxypiperidin-1-yl)carbonyl]cyclohexyl]acetamide;
5-((4-hydroxy-1-((1r,4r)-4-(pyridin-2-yloxy)cyclohexanecarbonyl) piperidin-4-yl)methyl)-1-(4-(hydroxymethyl)phenyl)-1H-pyrazolo[3,4-d]pyrimidin-4(5H)-one;
4-[4-hydroxy-4-({1-methyl-4-oxo-1H,4H,5H-pyrazolo[3,4-d]pyrimidin-5-yl}methyl)piperidine-1-carbonyl]-N-methyl-N-phenylbenzene-1-sulfonamide;
1-(4-bromophenyl)-5-{[1-(4-fluorobenzoyl)-4-hydroxypiperidin-4-yl]methyl}-1H,4H,5H-pyrazolo[3,4-d]pyrimidin-4(5H)-one;
5-{[4-hydroxy-1-(6-methoxypyridine-3-carbonyl)piperidin-4-yl]methyl}-1-[4-(trifluoromethyl)phenyl]-1H,4H,5H-pyrazolo[3,4-d]pyrimidin-4-one;
1-(4-fluorophenyl)-5-({4-hydroxy-1-[(1s,4s)-4-(cyclopropylamino)cyclohexanecarbonyl] piperidin-4-yl}methyl)-1H,4H,5H-pyrazolo[3,4-d]pyrimidin-4-one;
1-(4-fluorophenyl)-5-({4-hydroxy-1-[(1r,4r)-4-[(cyclopropylmethyl)amino]cyclohexanecarbonyl]piperidin-4-yl}methyl)-1H,4H,5H-pyrazolo[3,4-d]pyrimidin-4-one;
1-(4-fluorophenyl)-5-({4-hydroxy-1-[(1s,4s)-4-[(cyclopropylmethyl)amino]cyclohexanecarbonyl]piperidin-4-yl}methyl)-1H,4H,5H-pyrazolo[3,4-d]pyrimidin-4-one;
N-[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]cyclopropanecarboxamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-3-carboxamide;
7-(4-fluorophenyl)-3-{[4-hydroxy-1-(2-methyl-1,3-oxazole-5-carbonyl)piperidin-4-yl]methyl}-3H,4H,7H-pyrrolo[2,3-d]pyrimidin-4-one;
7-(4-fluorophenyl)-3-{[4-hydroxy-1-(1-methyl-1H-pyrazole-4-carbonyl)piperidin-4-yl]methyl}-3H,4H,7H-pyrrolo[2,3-d]pyrimidin-4-one;
3-{[1-(1-cyclopropyl-1H-pyrazole-4-carbonyl)-4-hydroxypiperidin-4-yl]methyl}-7-(4-fluorophenyl)-3H,4H,7H-pyrrolo[2,3-d]pyrimidin-4-one;
4-[4-hydroxy-4-({1-methyl-4-oxo-1H,4H,5H-pyrazolo[3,4-d]pyrimidin-5-yl}methyl)piperidine-1-carbonyl]-N-methyl-N-phenylbenzamide;
1-[3-(4-acetylpiperazin-1-yl)phenyl]-5-[(1-cyclopropanecarbonyl-4-hydroxypiperidin-4-yl)methyl]-1H,4H,5H-pyrazolo[3,4-d]pyrimidin-4-one;
4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1λ6,4-thiomorpholine-1,1-dione;
5-[(1-cyclopropanecarbonyl-4-hydroxypiperidin-4-yl)methyl]-1-[4-(1,2,3,4-tetrahydroquinolin-1-yl)phenyl]-1H,4H,5H-pyrazolo[3,4-d]pyrimidin-4-one;
5-[(1-cyclopropanecarbonyl-4-hydroxypiperidin-4-yl)methyl]-1-[3-(1,2,3,4-tetrahydroquinolin-1-yl)phenyl]-1H,4H,5H-pyrazolo[3,4-d]pyrimidin-4-one;
2-[1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)piperidin-3-yl]acetonitrile;
1-(4-chlorophenyl)-5-({4-hydroxy-1-[2-(4-methylpiperazin-1-yl)-1,3-oxazole-5-carbonyl]piperidin-4-yl}methyl)-1H,4H,5H-pyrazolo[3,4-d]pyrimidin-4-one;
1-(4-chlorophenyl)-5-({4-hydroxy-1-[2-(pyridin-2-yloxy)-1,3-oxazole-5-carbonyl]piperidin-4-yl}methyl)-1H,4H,5H-pyrazolo[3,4-d]pyrimidin-4-one;
1-(4-chlorophenyl)-5-({4-hydroxy-1-[4-(1H-1,2,3,4-tetrazol-1-yl)benzoyl]piperidin-4-yl}methyl)-1H,4H,5H-pyrazolo[3,4-d]pyrimidin-4-one;
1-(4-chlorophenyl)-5-({4-hydroxy-1-[4-(1H-imidazol-1-yl)benzoyl]piperidin-4-yl}methyl)-1H,4H,5H-pyrazolo[3,4-d]pyrimidin-4-one;
1-(4-chlorophenyl)-5-({4-hydroxy-1-[4-(5-methyl-1H-1,2,3,4-tetrazol-1-yl)benzoyl]piperidin-4-yl}methyl)-1H,4H,5H-pyrazolo[3,4-d]pyrimidin-4-one;
4-[4-hydroxy-4-({1-methyl-4-oxo-1H,4H,5H-pyrazolo[3,4-d]pyrimidin-5-yl}methyl)piperidine-1-carbonyl]-N-phenylbenzamide;

1-(4-chlorophenyl)-5-({4-hydroxy-1-[4-(1H-1,2,4-triazol-1-yl)benzoyl]piperidin-4-yl}methyl)-1H,4H,5H-pyrazolo[3,4-d]pyrimidin-4-one;
1-(4-chlorophenyl)-5-{[1-(5-cyclopropyl-1,3,4-oxadiazole-2-carbonyl)-4-hydroxypiperidin-4-yl]methyl)-1H,4H,5H-pyrazolo[3,4-d]pyrimidin-4-one;
1-(4-chlorophenyl)-5-{[1-(1-cyclopropyl-1H-imidazole-4-carbonyl)-4-hydroxypiperidin-4-yl]methyl)-1H,4H,5H-pyrazolo[3,4-d]pyrimidin-4-one;
1-(4-chlorophenyl)-5-{[1-(1-cyclopropyl-1H-pyrazole-3-carbonyl)-4-hydroxypiperidin-4-yl]methyl)-1H,4H,5H-pyrazolo[3,4-d]pyrimidin-4-one;
1-(4-chlorophenyl)-5-{[1-(1-cyclopropyl-1H-pyrazole-4-carbonyl)-4-hydroxypiperidin-4-yl]methyl)-1H,4H,5H-pyrazolo[3,4-d]pyrimidin-4-one;
1-(4-chlorophenyl)-5-[(4-hydroxy-1-{4-[(1-methylpiperidin-4-yl)oxy]benzoyl}piperidin-4-yl)methyl]-1H,4H,5H-pyrazolo[3,4-d]pyrimidin-4-one;
1-(4-chlorophenyl)- 5-[[1-([3-[2-(dimethylamino)ethoxy]phenyl]carbonyl)-4-hydroxypiperidin-4-yl]methyl]-1H,4H,5H-pyrazolo[3,4-d]pyrimidin-4-one;
1-(4-chlorophenyl)-5-[(1-{3-[3-(dimethylamino)propoxy]benzoyl}-4-hydroxypiperidin-4-yl)methyl]-1H,4H,5H-pyrazolo[3,4-d]pyrimidin-4-one;
1-(4-chlorophenyl)-5-[(1-[[4-(1,5-dimethyl-1H-imidazol-2-yl)phenyl]carbonyl]-4-hydroxypiperidin-4-yl)methyl]-1H,4H,5H-pyrazolo[3,4-d]pyrimidin-4-one;
2-(3-{5-[(1-benzoyl-4-hydroxypiperidin-4-yl)methyl]-4-oxo-1H,4H,5H-pyrazolo[3,4-d]pyrimidin-1-yl}phenyl) acetic acid;
N-{4-[4-hydroxy-4-({1-methyl-4-oxo-1H,4H,5H-pyrazolo[3,4-d]pyrimidin-5-yl}methyl)piperidine-1-carbonyl]phenyl}benzamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methylpyrazine-2-carboxamide;
1-(4-chlorophenyl)-5-({1-[4-(1,2-dimethyl-1H-imidazol-5-yl}benzoyl]-4-hydroxypiperidin-4-yl}methyl)-1H,4H,5H-pyrazolo[3,4-d]pyrimidin-4-one;
5-{[1-(4,4-difluoro-3-phenylbutanoyl)-4-hydroxypiperidin-4-yl]methyl}-1-phenyl-1H,4H,5H-pyrazolo[3,4-d]pyrimidin-4-one;
5-({1-[(3S)-4,4-difluoro-3-phenylbutanoyl]-4-hydroxypiperidin-4-yl}methyl)-1-phenyl-1H,4H,5H-pyrazolo[3,4-d]pyrimidin-4-one;
5-({1-[(3R)-4,4-difluoro-3-phenylbutanoyl]-4-hydroxypiperidin-4-yl}methyl)-1-phenyl-1H,4H,5H-pyrazolo[3,4-d]pyrimidin-4-one;
5-{[1-(4-benzyl-1,3-oxazole-5-carbonyl)-4-hydroxypiperidin-4-yl]methyl}-1-phenyl-1H,4H,5H-pyrazolo[3,4-d]pyrimidin-4-one;
N-{4-[4-hydroxy-4-({1-methyl-4-oxo-1H,4H,5H-pyrazolo[3,4-d]pyrimidin-5-yl}methyl)piperidine-1-carbonyl]phenyl}benzenesulfonamide;
5-{[1-(3-benzyl-5-methyl-1,2-thiazole-4-carbonyl)-4-hydroxypiperidin-4-yl]methyl}-1-(4-fluorophenyl)-1H,4H,5H-pyrazolo[3,4-d]pyrimidin-4-one;
1-(4-fluorophenyl)-5-({4-hydroxy-1-[(1r,4r)-4-(difluoromethoxy)cyclohexanecarbonyl] piperidin-4-yl}methyl)-1H,4H,5H-pyrazolo[3,4-d]pyrimidin-4-one;
1-(4-fluorophenyl)-5-({4-hydroxy-1-[(1r,4r)-4-(pyrazin-2-yloxy)cyclohexanecarbonyl]piperidin-4-yl}methyl)-1H,4H,5H-pyrazolo[3,4-d]pyrimidin-4-one
1-(4-fluorophenyl)-5-({4-hydroxy-1-[(1r,4r)-4-[(1-methyl-1H-pyrazol-5-yl)oxy]cyclohexanecarbonyl]piperidin-4-yl}methyl)-1H,4H,5H-pyrazolo[3,4-d]pyrimidin-4-one;
1-(4-fluorophenyl)-5-({4-hydroxy-1-[(1s,4s)-4-methoxycyclohexanecarbonyl]piperidin-4-yl}methyl)-1H,4H,5H-pyrazolo[3,4-d]pyrimidin-4-one;
5-{[4-hydroxy-1-(1-methylcyclopropanecarbonyl)piperidin-4-yl]methyl}-1-(4-([(1r,4r)-4-methoxycyclohexyl]oxy}phenyl)-1H,4H,5H-pyrazolo[3,4-d]pyrimidin-4-one;
Syn-5-((4-Hydroxy-1-(1-methylcyclopropanecarbonyl)piperidin-4-yl}methyl)-1-(4-((4-methoxycyclohexyl)oxy)phenyl)-1H-pyrazolo[3,4-d]pyrimidin-4(5H)-one;
Anti-5-((4-Hydroxy-1-(1-methylcyclopropanecarbonyl)piperidin-4-yl}methyl)-1-(4-((4-methoxycyclohexyl)oxy)phenyl)-1H-pyrazolo[3,4-d]pyrimidin-4(5H)-one;
1-{4-[(4,4-difluorocyclohexyl)oxy]phenyl)-5-{[4-hydroxy-1-(1-methylcyclopropanecarbonyl)piperidin-4-yl]methyl}-1H,4H,5H-pyrazolo[3,4-d]pyrimidin-4-one;
5-{[4-hydroxy-1-(1-methylcyclopropanecarbonyl)piperidin-4-yl]methyl}-1-{4-[(3-methyloxetan-3-yl)methoxy]phenyl}-1H,4H,5H-pyrazolo[3,4-d]pyrimidin-4-one;
1-{4-[(1-fluorocyclobutyl)methoxy]phenyl}-5-{[4-hydroxy-1-(1-methylcyclopropanecarbonyl) piperidin-4-yl]methyl}-1H,4H,5H-pyrazolo[3,4-d]pyrimidin-4-one;
5-({4-hydroxy-1-[3-(1,3-thiazol-2-yl)butanoyl]piperidin-4-yl}methyl)-1-methyl-1H,4H,5H-pyrazolo[3,4-d]pyrimidin-4-one;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methylbenzamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-fluorobenzamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-fluorobenzamide;
7-(4-fluorophenyl)-3-({4-hydroxy-1-[(1r,4r)-4-(pyridin-2-yloxy)cyclohexanecarbonyl]piperidin-4-yl}methyl)-3H,4H,7H-pyrrolo[2,3-d]pyrimidin-4-one;
3-({1-[(3R)-4,4-difluoro-3-(3-fluoro-1H-pyrazol-1-yl)butanoyl]-4-hydroxypiperidin-4-yl}methyl)-7-(4-fluorophenyl)-3H,4H,7H-pyrrolo[2,3-d]pyrimidin-4-one;
3-({1-[(3S)-4,4-difluoro-3-(3-fluoro-1H-pyrazol-1-yl)butanoyl]-4-hydroxypiperidin-4-yl}methyl)-7-(4-fluorophenyl)-3H,4H,7H-pyrrolo[2,3-d]pyrimidin-4-one;
1-(4-chlorophenyl)-5-({4-hydroxy-1-[3-(pyrrolidin-1-ylmethyl}benzoyl]piperidin-4-yl}methyl)-1H,4H,5H-pyrazolo[3,4-d]pyrimidin-4-one;
1-(4-chlorophenyl)-5-({4-hydroxy-1-[4-(1H-1,2,3-triazol-1-yl)benzoyl]piperidin-4-yl}methyl)-1H,4H,5H-pyrazolo[3,4-d]pyrimidin-4-one;
1-(4-chlorophenyl)-5-({4-hydroxy-1-[4-(2H-1,2,3-triazol-2-yl)benzoyl]piperidin-4-yl}methyl)-1H,4H,5H-pyrazolo[3,4-d]pyrimidin-4-one;
5-{[1-(2-chloro-4-phenoxybenzoyl)-4-hydroxypiperidin-4-yl]methyl}-1-methyl-1H,4H,5H-pyrazolo[3,4-d]pyrimidin-4-one;

1-(4-chlorophenyl)-5-{[1-(2-cyclopropyl-1,3-oxazole-5-carbonyl)-4-hydroxypiperidin-4-yl]methyl)-1H,4H,5H-pyrazolo[3,4-d]pyrimidin-4-one;

1-(4-chlorophenyl)-5-({1-[(3R)-4,4-difluoro-3-(1H-pyrazol-1-yl)butanoyl]-4-hydroxypiperidin-4-yl}methyl)-1H,4H,5H-pyrazolo[3,4-d]pyrimidin-4-one;

1-(4-chlorophenyl)-5-({1-[(3S)-4,4-difluoro-3-(1H-pyrazol-1-yl)butanoyl]-4-hydroxypiperidin-4-yl}methyl)-1H,4H,5H-pyrazolo[3,4-d]pyrimidin-4-one;

1-{4-[(3,3-difluorocyclobutyl)methoxy]phenyl}-5-{[4-hydroxy-1-(1-methylcyclopropanecarbonyl)piperidin-4-yl]methyl)-1H,4H,5H-pyrazolo[3,4-d]pyrimidin-4-one;

1-{4-[(4,4-difluorocyclohexyl)oxy]phenyl}-5-{[4-hydroxy-1-(2-methyl-1,3-oxazole-5-carbonyl)piperidin-4-yl]methyl)-1H,4H,5H-pyrazolo[3,4-d]pyrimidin-4-one;

1-{4-[(1-fluorocyclobutyl)methoxy]phenyl}-5-{[4-hydroxy-1-(2-methyl-1,3-oxazole-5-carbonyl)piperidin-4-yl]methyl)-1H,4H,5H-pyrazolo[3,4-d]pyrimidin-4-one;

5-{[4-hydroxy-1-(1-methylcyclobutanecarbonyl)piperidin-4-yl]methyl}-1-{4-[(3-methyloxetan-3-yl)methoxy]phenyl)-1H,4H,5H-pyrazolo[3,4-d]pyrimidin-4-one;

1-{4-[(1-fluorocyclobutyl)methoxy]phenyl}-5-{[4-hydroxy-1-(1-methylcyclobutanecarbonyl)piperidin-4-yl]methyl)-1H,4H,5H-pyrazolo[3,4-d]pyrimidin-4-one;

4-hydroxy-4-[(1-{4-[(3R)-3-methoxypyrrolidin-1-yl]phenyl}-4-oxo-1H,4H,5H-pyrazolo[3,4-d]pyrimidin-5-yl)methyl]-N,N-dimethylpiperidine-1-carboxamide;

5-({4-hydroxy-1-[(3S)-3-phenylbutanoyl]piperidin-4-yl}methyl)-1-(4-methylphenyl)-1H,4H,5H-pyrazolo[3,4-d]pyrimidin-4-one;

5-{[1-(2-amino-4-chlorobenzoyl)-4-hydroxypiperidin-4-yl]methyl}-1-(4-methylphenyl)-1H,4H,5H-pyrazolo[3,4-d]pyrimidin-4-one;

5-((4-Hydroxy-1-(4-(4-hydroxycyclohexyloxy)benzoyl}piperidin-4-yl}methyl)-1-p-tolyl-1H-pyrazolo[3,4-d]pyrimidin-4 (5H)-one;

5-((4-hydroxy-1-(4-(1-methylazetidin-3-yloxy)benzoyl}piperidin-4-yl}methyl)-1-p-tolyl-1H-pyrazolo[3,4-d]pyrimidin-4 (5H)-one;

5-((4-Hydroxy-1-(4-(oxetan-3-yloxy)benzoyl}piperidin-4-yl}methyl)-1-p-tolyl-1H-pyrazolo[3,4-d]pyrimidin-4 (5H)-one;

5-({4-hydroxy-1-[4-(oxan-4-yloxy)benzoyl]piperidin-4-yl}methyl)-1-(4-methylphenyl)-1H,4H,5H-pyrazolo[3,4-d]pyrimidin-4-one;

5-((4-hydroxy-1-(4-(piperidin-4-yloxy)benzoyl}piperidin-4-yl}methyl)-1-p-tolyl-1H-pyrazolo[3,4-d]pyrimidin-4 (5H)-one;

5-[(1-cyclopropanecarbonyl-4-hydroxypiperidin-4-yl)methyl]-1-(4-{[2-(piperidin-1-yl)ethyl]amino}phenyl)-1H,4H,5H-pyrazolo[3,4-d]pyrimidin-4-one;

5-[(1-cyclopropanecarbonyl-4-hydroxypiperidin-4-yl)methyl]-1-(4-{[2-(morpholin-4-yl)ethyl]amino}phenyl)-1H,4H,5H-pyrazolo[3,4-d]pyrimidin-4-one;

5-[(1-cyclopropanecarbonyl-4-hydroxypiperidin-4-yl)methyl]-1-{4-[(2-ethylbutyl)amino]phenyl}-1H,4H,5H-pyrazolo[3,4-d]pyrimidin-4-one;

5-[(1-cyclopropanecarbonyl-4-hydroxypiperidin-4-yl)methyl]-1-(4-{[2-(propan-2-yloxy)ethyl]amino}phenyl)-1H,4H,5H-pyrazolo[3,4-d]pyrimidin-4-one;

5-{[4-hydroxy-1-(2-phenyl-1,2,3,4-tetrahydroisoquinoline-6-carbonyl)piperidin-4-yl]methyl}-1-methyl-1H,4H,5H-pyrazolo[3,4-d]pyrimidin-4-one;

5-[(1-cyclopropanecarbonyl-4-hydroxypiperidin-4-yl)methyl]-1-{4-[(cyclopropylmethyl)amino]phenyl}-1H,4H,5H-pyrazolo[3,4-d]pyrimidin-4-one;

5-[(1-cyclopropanecarbonyl-4-hydroxypiperidin-4-yl)methyl]-1-(4-{[(1-methylpiperidin-3-yl)methyl]amino)phenyl)-1H,4H,5H-pyrazolo[3,4-d]pyrimidin-4-one;

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzene-1-sulfonamide;

5-[(1-cyclopropanecarbonyl-4-hydroxypiperidin-4-yl)methyl]-1-[3-(cyclopropylamino)phenyl]-1H,4H,5H-pyrazolo[3,4-d]pyrimidin-4-one;

1-[3-(cyclohexylamino)phenyl]-5-[(1-cyclopropanecarbonyl-4-hydroxypiperidin-4-yl)methyl]-1H,4H,5H-pyrazolo[3,4-d]pyrimidin-4-one;

1-[3-(benzylamino)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-{3-[(2-phenylethyl)amino]phenyl)-1H,4H,5H-pyrazolo[3,4-d]pyrimidin-4-one;

5-[(1-cyclopropanecarbonyl-4-hydroxypiperidin-4-yl)methyl]-1-{3-[(2,2-dimethylpropyl)amino]phenyl)-1H,4H,5H-pyrazolo[3,4-d]pyrimidin-4-one;

5-[(1-cyclopropanecarbonyl-4-hydroxypiperidin-4-yl)methyl]-1-{3-[(pyridin-3-ylmethyl)amino]phenyl)-1H,4H,5H-pyrazolo[3,4-d]pyrimidin-4-one;

5-({1-[(3R)-4,4-difluoro-3-(4-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

5-[(1-{3-[benzyl(methyl)amino]benzoyl}-4-hydroxypiperidin-4-yl)methyl]-1-methyl-1H,4H,5H-pyrazolo[3,4-d]pyrimidin-4-one;

5-{[4-hydroxy-1-(4-{[5-(2-hydroxyethoxy)pyridin-2-yl]oxy)benzoyl}piperidin-4-yl]methyl}-1-(4-methylphenyl)-1H,4H,5H-pyrazolo[3,4-d]pyrimidin-4-one;

5-{[1-(3-benzyl-1-methyl-1H-pyrazole-4-carbonyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-[(4-hydroxy-1-{1-methyl-3-[(1R)-1-phenylethyl]-1H-pyrazole-4-carbonyl)piperidin-4-yl]methyl]-1H,4H,5H-pyrazolo[3,4-d]pyrimidin-4-one;

1-(4-fluorophenyl)-5-[(4-hydroxy-1-{1-methyl-3-[(1S)-1-phenylethyl]-1H-pyrazole-4-carbonyl)piperidin-4-yl]methyl]-1H,4H,5H-pyrazolo[3,4-d]pyrimidin-4-one;

5-([1-(3-benzyl-5-methyl-1,2-oxazole-4-carbonyl)-4-hydroxypiperidin-4-yl]methyl}-1-(4-fluorophenyl)-1H,4H,5H-pyrazolo[3,4-d]pyrimidin-4-one;

5-{[4-hydroxy-1-(1-methylcyclopropanecarbonyl)piperidin-4-yl]methyl}-1-{4-[4-(2-methoxyethyl)piperazin-1-yl]phenyl)-1H,4H,5H-pyrazolo[3,4-d]pyrimidin-4-one;

1-(4-chlorophenyl)-5-((1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

1-(4-chlorophenyl)-5-((1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

5-{[1-(4-fluorobenzoyl)-4-hydroxypiperidin-4-yl]
methyl}-1-[4-(3-hydroxy-3-methylpyrrolidin-1-yl)
phenyl]-1H,4H,5H-pyrazolo[3,4-d]pyrimidin-4-one;

5-[(1-cyclopropanecarbonyl-4-hydroxypiperidin-4-yl)
methyl]-1-(4-{5H,6H,7H,8H-imidazo[1,2-a]pyrimidin-8-yl}phenyl)-1H,4H,5H-pyrazolo[3,4-d]pyrimidin-4-one;

5-({4-hydroxy-1-[3-(1,2,3,4-tetrahydroquinolin-1-yl)
benzoyl]piperidin-4-yl}methyl)-1-methyl-1H,4H,5H-pyrazolo[3,4-d]pyrimidin-4-one;

5-{[1-(4-fluorobenzoyl)-4-hydroxypiperidin-4-yl]
methyl}-1-(4-{5H,6H,7H,8H-imidazo[1,2-a]pyrimidin-8-yl}phenyl)-1H,4H,5H-pyrazolo[3,4-d]pyrimidin-4-one;

5-[(1-cyclopropanecarbonyl-4-hydroxypiperidin-4-yl)
methyl]-1-[4-(1,2,3,4-tetrahydroquinoxalin-1-yl)phenyl]-1H,4H,5H-pyrazolo[3,4-d]pyrimidin-4-one;

5-{[1-(4-fluorobenzoyl)-4-hydroxypiperidin-4-yl]
methyl}-1-[4-(1,2,3,4-tetrahydroquinoxalin-1-yl)phenyl]-1H,4H,5H-pyrazolo[3,4-d]pyrimidin-4-one;

5-[(1-cyclopropanecarbonyl-4-hydroxypiperidin-4-yl)
methyl]-1-(4-{4H,5H,6H,7H-[1,2,4]triazolo[1,5-a]pyrimidin-4-yl}phenyl)-1H,4H,5H-pyrazolo[3,4-d]pyrimidin-4-one;

5-{[1-(4-fluorobenzoyl)-4-hydroxypiperidin-4-yl]
methyl}-1-(4-{4H,5H,6H,7H-[1,2,4]triazolo[1,5-a]pyrimidin-4-yl}phenyl)-1H,4H,5H-pyrazolo[3,4-d]pyrimidin-4-one;

5-[(1-cyclopropanecarbonyl-4-hydroxypiperidin-4-yl)
methyl]-1-(4-{2-methyl-5H,6H,7H,8H-[1,2,4]triazolo[1,5-a]pyrazin-7-yl}phenyl)-1H,4H,5H-pyrazolo[3,4-d]pyrimidin-4-one;

5-{[1-(4-fluorobenzoyl)-4-hydroxypiperidin-4-yl]
methyl}-1-(4-{2-methyl-5H,6H,7H,8H-[1,2,4]triazolo[1,5-a]pyrazin-7-yl}phenyl)-1H,4H,5H-pyrazolo[3,4-d]pyrimidin-4-one;

5-[(1-cyclopropanecarbonyl-4-hydroxypiperidin-4-yl)
methyl]-1-(4-{5H,6H,7H,8H-[1,2,4]triazolo[1,5-a]pyrazin-7-yl}phenyl)-1H,4H,5H-pyrazolo[3,4-d]pyrimidin-4-one;

5-({1-(4-fluorobenzoyl)-4-hydroxypiperidin-4-yl]
methyl}-1-(4-{5H,6H,7H,8H-[1,2,4]triazolo[1,5-a]pyrazin-7-yl}phenyl)-1H,4H,5H-pyrazolo[3,4-d]pyrimidin-4-one;

5-{[1-(4-fluorobenzoyl)-4-hydroxypiperidin-4-yl]
methyl}-1-[4-(4-methyl-1,2,3,4-tetrahydroquinoxalin-1-yl)phenyl]-1H,4H,5H-pyrazolo[3,4-d]pyrimidin-4-one;

5-{[1-(1-acetylpiperidine-4-carbonyl)-4-hydroxypiperidin-4-yl]methyl}-1-(4-fluorophenyl)-1H,4H,5H-pyrazolo[3,4-d]pyrimidin-4-one;

5-[(1-{bicyclo[1.1.1]pentane-1-carbonyl}-4-hydroxypiperidin-4-yl)methyl]-1-(4-fluorophenyl)-1H,4H,5H-pyrazolo[3,4-d]pyrimidin-4-one;

1-[4-(cyclopentylamino)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)
methyl]-1-[4-(morpholin-4-yl)phenyl]-1H,4H,5H-pyrazolo[3,4-d]pyrimidin-4-one;

1-(4-fluorophenyl)-5-{[4-hydroxy-1-(5-methoxypyridine-2-carbonyl)piperidin-4-yl]methyl}-1H,4H,5H-pyrazolo[3,4-d]pyrimidin-4-one;

5-[(1-{3-aminobicyclo[1.1.1]pentane-1-carbonyl}-4-hydroxypiperidin-4-yl)methyl]-1-(4-fluorophenyl)-1H,4H,5H-pyrazolo[3,4-d]pyrimidin-4-one;

1-[4-(cyclohexylamino)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)
methyl]-1-{4-[(2-phenylethyl)amino]phenyl)-1H,4H,5H-pyrazolo[3,4-d]pyrimidin-4-one;

5-[(1-cyclopropanecarbonyl-4-hydroxypiperidin-4-yl)
methyl]-1-{4-[(2,2-dimethylpropyl)amino]phenyl)-1H,4H,5H-pyrazolo[3,4-d]pyrimidin-4-one;

5-[(1-cyclopropanecarbonyl-4-hydroxypiperidin-4-yl)
methyl]-1-{4-[(pyridin-3-ylmethyl)amino]phenyl)-1H,4H,5H-pyrazolo[3,4-d]pyrimidin-4-one;

5-[(1-{4-[benzyl(methyl)amino]benzoyl}-4-hydroxypiperidin-4-yl)methyl]-1-methyl-1H,4H,5H-pyrazolo[3,4-d]pyrimidin-4-one;

5-[(1-cyclopropanecarbonyl-4-hydroxypiperidin-4-yl)
methyl]-1-{4-[(1H-pyrazol-3-yl)amino]phenyl)-1H,4H,5H-pyrazolo[3,4-d]pyrimidin-4-one;

5-[(1-cyclopropanecarbonyl-4-hydroxypiperidin-4-yl)
methyl]-1-{4-[(6-methoxypyridin-3-yl)amino]phenyl)-1H,4H,5H-pyrazolo[3,4-d]pyrimidin-4-one;

5-[(1-cyclopropanecarbonyl-4-hydroxypiperidin-4-yl)
methyl]-1-{4-[(2-methoxypyridin-3-yl)amino]phenyl)-1H,4H,5H-pyrazolo[3,4-d]pyrimidin-4-one;

5-[(1-cyclopropanecarbonyl-4-hydroxypiperidin-4-yl)
methyl]-1-{4-[(5-methyl-1,3,4-thiadiazol-2-yl)amino]
phenyl)-1H,4H,5H-pyrazolo[3,4-d]pyrimidin-4-one;

5-[(1-cyclopropanecarbonyl-4-hydroxypiperidin-4-yl)
methyl]-1-(3-{[2-(morpholin-4-yl)ethyl]amino)phenyl)-1H,4H,5H-pyrazolo[3,4-d]pyrimidin-4-one;

5-[(1-cyclopropanecarbonyl-4-hydroxypiperidin-4-yl)
methyl]-1-{3-[(2-ethylbutyl)amino]phenyl)-1H,4H,5H-pyrazolo[3,4-d]pyrimidin-4-one;

5-[(1-cyclopropanecarbonyl-4-hydroxypiperidin-4-yl)
methyl]-1-(3-{[2-(propan-2-yloxy)ethyl]amino)phenyl)-1H,4H,5H-pyrazolo[3,4-d]pyrimidin-4-one;

5-[(1-cyclopropanecarbonyl-4-hydroxypiperidin-4-yl)
methyl]-1-(3-{[(1-methylpiperidin-3-yl)methyl]
amino)phenyl)-1H,4H,5H-pyrazolo[3,4-d]pyrimidin-4-one;

5-[(1-cyclopropanecarbonyl-4-hydroxypiperidin-4-yl)
methyl]-1-{3-[(oxan-4-ylmethyl)amino]phenyl)-1H,4H,5H-pyrazolo[3,4-d]pyrimidin-4-one;

5-[(1-cyclopropanecarbonyl-4-hydroxypiperidin-4-yl)
methyl]-1-[4-(pyrrolidin-1-yl)phenyl]-1H,4H,5H-pyrazolo[3,4-d]pyrimidin-4-one;

5-({4-hydroxy-1-[4-(1,2,3,4-tetrahydroisoquinolin-2-yl)
benzoyl]piperidin-4-yl}methyl)-1-methyl-1H,4H,5H-pyrazolo[3,4-d]pyrimidin-4-one;

5-[(1-cyclopropanecarbonyl-4-hydroxypiperidin-4-yl)
methyl]-1-[3-(pyrrolidin-1-yl)phenyl]-1H,4H,5H-pyrazolo[3,4-d]pyrimidin-4-one;

5-[(1-cyclopropanecarbonyl-4-hydroxypiperidin-4-yl)
methyl]-1-[4-(piperidin-1-yl)phenyl]-1H,4H,5H-pyrazolo[3,4-d]pyrimidin-4-one;

5-[(1-cyclopropanecarbonyl-4-hydroxypiperidin-4-yl)
methyl]-1-[3-(piperidin-1-yl)phenyl]-1H,4H,5H-pyrazolo[3,4-d]pyrimidin-4-one;

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)piperidine-4-carbonitrile;

1-{4-[benzyl(methyl)amino]phenyl}-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)
methyl]-1-[3-(4-phenylpiperidin-1-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-[(2-methoxyethylxmethyl)amino]phenyl)-1H,4H,5H-pyrazolo[3,4-d]pyrimidin-4-one;
5-[(1-cyclopropanecarbonyl-4-hydroxypiperidin-4-yl)methyl]-1-{3-[(2-methoxyethylxmethyl)amino]phenyl)-1H,4H,5H-pyrazolo[3,4-d]pyrimidin-4-one;
N-[1-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)piperidin-4-yl]acetamide;
5-[(1-cyclopropanecarbonyl-4-hydroxypiperidin-4-yl)methyl]-1-{3-[4-(dimethylamino)piperidin-1-yl]phenyl)-1H,4H,5H-pyrazolo[3,4-d]pyrimidin-4-one;
5-[(1-cyclopropanecarbonyl-4-hydroxypiperidin-4-yl)methyl]-1-[3-(1,2,3,4-tetrahydroisoquinolin-2-yl)phenyl]-1H,4H,5H-pyrazolo[3,4-d]pyrimidin-4-one;
1-[4-(4-acetylpiperazin-1-yl)phenyl]-5-[(1-cyclopropanecarbonyl-4-hydroxypiperidin-4-yl)methyl]-1H,4H,5H-pyrazolo[3,4-d]pyrimidin-4-one;
1-(4-fluorophenyl)-5-({4-hydroxy-1-[(1r,4r)-4-(pyridazin-3-yloxy)cyclohexanecarbonyl]piperidin-4-yl}methyl)-1H,4H,5H-pyrazolo[3,4-d]pyrimidin-4-one;
5-[(1-cyclopropanecarbonyl-4-hydroxypiperidin-4-yl)methyl]-1-[4-(2,4-dichlorophenyl)phenyl]-1H,4H,5H-pyrazolo[3,4-d]pyrimidin-4-one;
5-[(1-cyclopropanecarbonyl-4-hydroxypiperidin-4-yl)methyl]-1-[4-(pyridin-2-yl)phenyl]-1H,4H,5H-pyrazolo[3,4-d]pyrimidin-4-one;
5-[(1-cyclopropanecarbonyl-4-hydroxypiperidin-4-yl)methyl]-1-[4-(1H-indazol-4-yl)phenyl]-1H,4H,5H-pyrazolo[3,4-d]pyrimidin-4-one;
5-[(1-cyclopropanecarbonyl-4-hydroxypiperidin-4-yl)methyl]-1-(4-{8-oxa-2-azaspiro[4.5]decan-2-yl)phenyl)-1H,4H,5H-pyrazolo[3,4-d]pyrimidin-4-one;
5-[(1-cyclopropanecarbonyl-4-hydroxypiperidin-4-yl)methyl]-1-(3-{8-oxa-2-azaspiro[4.5]decan-2-yl)phenyl)-1H,4H,5H-pyrazolo[3,4-d]pyrimidin-4-one;
5-([1-(1-cyclopropylpiperidine-4-carbonyl)-4-hydroxypiperidin-4-yl]methyl}-1-(4-fluorophenyl)-1H,4H,5H-pyrazolo[3,4-d]pyrimidin-4-one;
1-(4-fluorophenyl)-5-[(4-hydroxy-1-{3-phenylbicyclo[1.1.1]pentane-1-carbonyl)piperidin-4-yl)methyl]-1H,4H,5H-pyrazolo[3,4-d]pyrimidin-4-one;
5-[(1-{4-[(4aR,8aS)-decahydroisoquinolin-2-yl]benzoyl}-4-hydroxypiperidin-4-yl)methyl]-1-methyl-1H,4H,5H-pyrazolo[3,4-d]pyrimidin-4-one;
1-(4-fluorophenyl)-5-[(4-hydroxy-1-{pyrazolo[1,5-a]pyridine-3-carbonyl)piperidin-4-yl)methyl]-1H,4H,5H-pyrazolo[3,4-d]pyrimidin-4-one;
5-({1-[5-(difluoromethoxy)pyridine-2-carbonyl]-4-hydroxypiperidin-4-yl}methyl)-1-(4-fluorophenyl)-1H,4H,5H-pyrazolo[3,4-d]pyrimidin-4-one;
5-[(1-{6-aminospiro[3.3]heptane-2-carbonyl)-4-hydroxypiperidin-4-yl)methyl]-1-(4-fluorophenyl)-1H,4H,5H-pyrazolo[3,4-d]pyrimidin-4-one;
1-(4-fluorophenyl)-5-[(4-hydroxy-1-{2H,3H-pyrazolo[3,2-b][1,3]oxazole-6-carbonyl)piperidin-4-yl)methyl]-1H,4H,5H-pyrazolo[3,4-d]pyrimidin-4-one;
1-(4-fluorophenyl)-5-({4-hydroxy-1-[(3S)-piperidine-3-carbonyl]piperidin-4-yl}methyl)-1H,4H,5H-pyrazolo[3,4-d]pyrimidin-4-one;
1-(4-fluorophenyl)-5-({4-hydroxy-1-[(3S)-pyrrolidine-3-carbonyl]piperidin-4-yl}methyl)-1H,4H,5H-pyrazolo[3,4-d]pyrimidin-4-one;
1-(4-fluorophenyl)-5-({4-hydroxy-1-[(3R)-piperidine-3-carbonyl]piperidin-4-yl}methyl)-1H,4H,5H-pyrazolo[3,4-d]pyrimidin-4-one;
1-(4-fluorophenyl)-5-({4-hydroxy-1-[(3R)-pyrrolidine-3-carbonyl]piperidin-4-yl}methyl)-1H,4H,5H-pyrazolo[3,4-d]pyrimidin-4-one;
5-({4-hydroxy-1-[4-(1,2,3,4-tetrahydroquinolin-1-yl)benzoyl]piperidin-4-yl}methyl)-1-methyl-1H,4H,5H-pyrazolo[3,4-d]pyrimidin-4-one;
5-[(1-cyclopropanecarbonyl-4-hydroxypiperidin-4-yl)methyl]-1-[3-(phenylamino)phenyl]-1H,4H,5H-pyrazolo[3,4-d]pyrimidin-4-one
5-[(1-cyclopropanecarbonyl-4-hydroxypiperidin-4-yl)methyl]-1-[4-(phenylamino)phenyl]-1H,4H,5H-pyrazolo[3,4-d]pyrimidin-4-one;
5-[(1-cyclopropanecarbonyl-4-hydroxypiperidin-4-yl)methyl]-1-{3-[(pyridin-4-yl)amino]phenyl)-1H,4H,5H-pyrazolo[3,4-d]pyrimidin-4-one;
5-[(1-cyclopropanecarbonyl-4-hydroxypiperidin-4-yl)methyl]-1-{4-[(pyridin-2-yl)amino]phenyl)-1H,4H,5H-pyrazolo[3,4-d]pyrimidin-4-one;
5-[(1-cyclopropanecarbonyl-4-hydroxypiperidin-4-yl)methyl]-1-(4-{[4-(morpholin-4-yl)phenyl]amino}phenyl)-1H,4H,5H-pyrazolo[3,4-d]pyrimidin-4-one;
5-[(1-cyclopropanecarbonyl-4-hydroxypiperidin-4-yl)methyl]-1-(4-{[1-(pyridin-3-ylmethyl)-1H-pyrazol-3-yl]amino}phenyl)-1H,4H,5H-pyrazolo[3,4-d]pyrimidin-4-one;
5-[(1-cyclopropanecarbonyl-4-hydroxypiperidin-4-yl)methyl]-1-(4-{[1-(pyridin-2-ylmethyl)-1H-pyrazol-3-yl]amino}phenyl)-1H,4H,5H-pyrazolo[3,4-d]pyrimidin-4-one;
1-{4-[(2,1,3-benzoxadiazol-4-yl)amino]phenyl)-5-[(1-cyclopropanecarbonyl-4-hydroxypiperidin-4-yl)methyl]-1H,4H,5H-pyrazolo[3,4-d]pyrimidin-4-one;
5-[(1-cyclopropanecarbonyl-4-hydroxypiperidin-4-yl)methyl]-1-{4-[(5-cyclopropyl-1,3,4-thiadiazol-2-yl)amino]phenyl)-1H,4H,5H-pyrazolo[3,4-d]pyrimidin-4-one;
5-[(1-cyclopropanecarbonyl-4-hydroxypiperidin-4-yl)methyl]-1-{4-[(3-phenyl-1,2,4-thiadiazol-5-yl)amino]phenyl)-1H,4H,5H-pyrazolo[3,4-d]pyrimidin-4-one;
5-{[4-hydroxy-1-(4-{methyl[(2-methylphenyl}methyl]amino)benzoyl}piperidin-4-yl]methyl}-1-methyl-1H,4H,5H-pyrazolo[3,4-d]pyrimidin-4-one;
5-[(1-cyclopropanecarbonyl-4-hydroxypiperidin-4-yl)methyl]-1-{4-[(1,3-thiazol-2-yl)amino]phenyl)-1H,4H,5H-pyrazolo[3,4-d]pyrimidin-4-one;
5-[(1-cyclopropanecarbonyl-4-hydroxypiperidin-4-yl)methyl]-1-{4-[(5-methyl-1,2-oxazol-3-yl)amino]phenyl)-1H,4H,5H-pyrazolo[3,4-d]pyrimidin-4-one;
1-{4-[(4-tert-butyl-1,3-thiazol-2-yl)amino]phenyl)-5-[(1-cyclopropanecarbonyl-4-hydroxypiperidin-4-yl)methyl]-1H,4H,5H-pyrazolo[3,4-d]pyrimidin-4-one;
1-{4-[(1,3-benzothiazol-6-yl)amino]phenyl)-5-[(1-cyclopropanecarbonyl-4-hydroxypiperidin-4-yl)methyl]-1H,4H,5H-pyrazolo[3,4-d]pyrimidin-4-one;
1-{4-[(5-tert-butyl-1H-pyrazol-3-yl)amino]phenyl)-5-[(1-cyclopropanecarbonyl-4-hydroxypiperidin-4-yl)methyl]-1H,4H,5H-pyrazolo[3,4-d]pyrimidin-4-one;
5-[(1-cyclopropanecarbonyl-4-hydroxypiperidin-4-yl)methyl]-1-(4-([1-(4-fluorophenyl)-1H-pyrazol-3-yl]amino)phenyl)-1H,4H,5H-pyrazolo[3,4-d]pyrimidin-4-one;
5-[(1-cyclopropanecarbonyl-4-hydroxypiperidin-4-yl)methyl]-1-{3-[(pyridin-2-yl)amino]phenyl)-1H,4H,5H-pyrazolo[3,4-d]pyrimidin-4-one;
5-[(1-cyclopropanecarbonyl-4-hydroxypiperidin-4-yl)methyl]-1-(3-{[4-(morpholin-4-yl)phenyl]amino}phenyl)-1H,4H,5H-pyrazolo[3,4-d]pyrimidin-4-one;

5-[(1-cyclopropanecarbonyl-4-hydroxypiperidin-4-yl)methyl]-1-{3-[(1H-pyrazol-3-yl)amino]phenyl)-1H,4H,5H-pyrazolo[3,4-d]pyrimidin-4-one;

5-[(1-cyclopropanecarbonyl-4-hydroxypiperidin-4-yl)methyl]-1-{3-[(6-methoxypyridin-3-yl)amino]phenyl)-1H,4H,5H-pyrazolo[3,4-d]pyrimidin-4-one;

5-({4-hydroxy-1-[4-(thiomorpholin-4-yl)benzoyl]piperidin-4-yl}methyl)-1-methyl-1H,4H,5H-pyrazolo[3,4-d]pyrimidin-4-one;

5-[(1-cyclopropanecarbonyl-4-hydroxypiperidin-4-yl)methyl]-1-{3-[(2-methoxypyridin-3-yl)amino]phenyl)-1H,4H,5H-pyrazolo[3,4-d]pyrimidin-4-one;

5-[(1-cyclopropanecarbonyl-4-hydroxypiperidin-4-yl)methyl]-1-{3-[(5-methyl-1,3,4-thiadiazol-2-yl)amino]phenyl)-1H,4H,5H-pyrazolo[3,4-d]pyrimidin-4-one;

5-[(1-cyclopropanecarbonyl-4-hydroxypiperidin-4-yl)methyl]-1-(3-{[3-(morpholin-4-yl)phenyl]amino}phenyl)-1H,4H,5H-pyrazolo[3,4-d]pyrimidin-4-one;

5-[(1-cyclopropanecarbonyl-4-hydroxypiperidin-4-yl)methyl]-1-(3-{[2-(morpholin-4-yl)phenyl]amino}phenyl)-1H,4H,5H-pyrazolo[3,4-d]pyrimidin-4-one;

6-[(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-3-carbonitrile;

4-({1-[4-(cyanomethoxy)phenyl]-4-oxo-1H,4H,5H-pyrazolo[3,4-d]pyrimidin-5-yl}methyl)-4-hydroxy-N,N-dimethylpiperidine-1-carboxamide;

4-hydroxy-4-({1-[4-(2-methoxyethoxy)phenyl]-4-oxo-1H,4H,5H-pyrazolo[3,4-d]pyrimidin-5-yl}methyl)-N,N-dimethylpiperidine-1-carboxamide;

1-{3-[(1,3-benzothiazol-6-yl)amino]phenyl}-5-[(1-cyclopropanecarbonyl-4-hydroxypiperidin-4-yl)methyl]-1H,4H,5H-pyrazolo[3,4-d]pyrimidin-4-one;

1-{3-[(5-tert-butyl-1H-pyrazol-3-yl)amino]phenyl}-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-(3-([1-(4-fluorophenyl)-1H-pyrazol-3-yl]amino)phenyl)-1H,4H,5H-pyrazolo[3,4-d]pyrimidin-4-one;

5-({4-hydroxy-1-[4-(1-phenoxyethyl)benzoyl]piperidin-4-yl}methyl)-1-methyl-1H,4H,5H-pyrazolo[3,4-d]pyrimidin-4-one;

5-[(1-cyclopropanecarbonyl-4-hydroxypiperidin-4-yl)methyl]-1-{3-[4-(2-hydroxyethyl)piperazin-1-yl]phenyl}-1H,4H,5H-pyrazolo[3,4-d]pyrimidin-4-one;

4-(({1-[5-(cyclopentylamino)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-hydroxy-N,N-dimethyl-4-[(4-oxo-1-{5-[(2-phenylethyl)amino]pyridin-3-yl}-1H,4H,5H-pyrazolo[3,4-d]pyrimidin-5-yl}methyl]piperidine-1-carboxamide;

4-hydroxy-N,N-dimethyl-4-{[1-(5-{[2-(morpholin-4-yl)ethyl]amino}pyridin-3-yl)-4-oxo-1H,4H,5H-pyrazolo[3,4-d]pyrimidin-5-yl]methyl}piperidine-1-carboxamide;

4-hydroxy-N,N-dimethyl-4-({1-[5-(morpholin-4-yl)pyridin-3-yl]-4-oxo-1H,4H,5H-pyrazolo[3,4-d]pyrimidin-5-yl}methyl)piperidine-1-carboxamide;

4-({1-[5-(4-cyanopiperidin-1-yl)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-hydroxy-N,N-dimethyl-4-[(1-{5-[4-(morpholin-4-yl)piperidin-1-yl]pyridin-3-yl}-4-oxo-1H,4H,5H-pyrazolo[3,4-d]pyrimidin-5-yl)methyl]piperidine-1-carboxamide;

4-({1-[5-(1,1-dioxo-1λ6,4-thiomorpholin-4-yl)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-hydroxy-N,N-dimethyl-4-{[1-(5-{8-oxa-2-azaspiro[4.5]decan-2-yl}pyridin-3-yl)-4-oxo-1H,4H,5H-pyrazolo[3,4-d]pyrimidin-5-yl]methyl}piperidine-1-carboxamide;

4-hydroxy-N,N-dimethyl-4-({4-oxo-1-[5-(piperazin-1-yl)pyridin-3-yl]-1H,4H,5H-pyrazolo[3,4-d]pyrimidin-5-yl}methyl)piperidine-1-carboxamide;

5-[(1-{4-[1-(4-fluorophenoxy)ethyl]benzoyl}-4-hydroxypiperidin-4-yl)methyl]-1-methyl-1H,4H,5H-pyrazolo[3,4-d]pyrimidin-4-one;

4-({1-[5-(3-fluorophenyl)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-({1-[5-(4-fluorophenyl)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-[(1-{5-[4-(dimethylcarbamoyl)phenyl]pyridin-3-yl}-4-oxo-1H,4H,5H-pyrazolo[3,4-d]pyrimidin-5-yl)methyl]-4-hydroxy-N,N-dimethylpiperidine-1-carboxamide;

4-hydroxy-N,N-dimethyl-4-[(4-oxo-1-{5-[4-(pyrrolidine-1-carbonyl)phenyl]pyridin-3-yl}-1H,4H,5H-pyrazolo[3,4-d]pyrimidin-5-yl}methyl]piperidine-1-carboxamide;

4-({1-[5-(3,4-dimethoxyphenyl)pyridin-3-yl]-4-oxo-1H,4H,5H-pyrazolo[3,4-d]pyrimidin-5-yl}methyl)-4-hydroxy-N,N-dimethylpiperidine-1-carboxamide;

4-hydroxy-N,N-dimethyl-4-({4-oxo-1-[5-(pyridin-3-yl)pyridin-3-yl]-1H,4H,5H-pyrazolo[3,4-d]pyrimidin-5-yl}methyl)piperidine-1-carboxamide;

5-[(1-cyclopropanecarbonyl-4-hydroxypiperidin-4-yl)methyl]-1-(4-{[3-(morpholin-4-yl)phenyl]amino}phenyl)-1H,4H,5H-pyrazolo[3,4-d]pyrimidin-4-one;

6-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-3-carbonitrile;

5-[(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)amino]pyridine-2-carbonitrile;

6-({4-[4-hydroxy-4-({1-methyl-4-oxo-1H,4H,5H-pyrazolo[3,4-d]pyrimidin-5-yl}methyl)piperidine-1-carbonyl]phenyl}methoxy)pyridine-2-carbonitrile;

4-[(1-{5-[3-(dimethylcarbamoyl)phenyl]pyridin-3-yl}-4-oxo-1H,4H,5H-pyrazolo[3,4-d]pyrimidin-5-yl)methyl]-4-hydroxy-N,N-dimethylpiperidine-1-carboxamide;

4-hydroxy-N,N-dimethyl-4-[(1-{5-[3-(methylcarbamoyl)phenyl]pyridin-3-yl}-4-oxo-1H,4H,5H-pyrazolo[3,4-d]pyrimidin-5-yl)methyl]piperidine-1-carboxamide;

4-hydroxy-4-{[1-(5-{3-[(2-hydroxyethyl)carbamoyl]phenyl}pyridin-3-yl)-4-oxo-1H,4H,5H-pyrazolo[3,4-d]pyrimidin-5-yl]methyl}-N,N-dimethylpiperidine-1-carboxamide;

4-hydroxy-N,N-dimethyl-4-({1-[5-(1-methyl-1H-indazol-5-yl)pyridin-3-yl]-4-oxo-1H,4H,5H-pyrazolo[3,4-d]pyrimidin-5-yl}methyl)piperidine-1-carboxamide;

1-[4-(benzyloxy)phenyl]-5-{[1-(4-fluorobenzoyl)-4-hydroxypiperidin-4-yl]methyl}-1H,4H,5H-pyrazolo[3,4-d]pyrimidin-4-one;

1-[3-(benzyloxy)phenyl]-5-{[1-(4-fluorobenzoyl)-4-hydroxypiperidin-4-yl]methyl}-1H,4H,5H-pyrazolo[3,4-d]pyrimidin-4-one;

4-({1-[4-(cyclopentyloxy)phenyl]-4-oxo-1H,4H,5H-pyrazolo[3,4-d]pyrimidin-5-yl}methyl)-4-hydroxy-N,N-dimethylpiperidine-1-carboxamide;

1-[4-(cyclopentyloxy)phenyl]-5-{[1-(4-fluorobenzoyl)-4-hydroxypiperidin-4-yl]methyl}-1H,4H,5H-pyrazolo[3,4-d]pyrimidin-4-one;

1-[3-(cyclopentyloxy)phenyl]-5-{[1-(4-fluorobenzoyl)-4-hydroxypiperidin-4-yl]methyl}-1H,4H,5H-pyrazolo[3,4-d]pyrimidin-4-one;

4-({1-[4-(cyclopropylmethoxy)phenyl]-4-oxo-1H,4H,5H-pyrazolo[3,4-d]pyrimidin-5-yl}methyl)-4-hydroxy-N,N-dimethylpiperidine-1-carboxamide;

6-({4-[4-hydroxy-4-({1-methyl-4-oxo-1H,4H,5H-pyrazolo[3,4-d]pyrimidin-5-yl}methyl)piperidine-1-carbonyl]phenyl}methoxy)pyrazine-2-carbonitrile;

1-[4-(cyclopropylmethoxy)phenyl]-5-{[1-(4-fluorobenzoyl)-4-hydroxypiperidin-4-yl]methyl}-1H,4H,5H-pyrazolo[3,4-d]pyrimidin-4-one;

1-[3-(cyclopropylmethoxy)phenyl]-5-{[1-(4-fluorobenzoyl)-4-hydroxypiperidin-4-yl]methyl}-1H,4H,5H-pyrazolo[3,4-d]pyrimidin-4-one;

4-({1-[4-fluoro-3-(1-methyl-1H-pyrazol-4-yl)phenyl]-4-oxo-1H,4H,5H-pyrazolo[3,4-d]pyrimidin-5-yl}methyl)-4-hydroxy-N,N-dimethylpiperidine-1-carboxamide;

4-hydroxy-4-[(1-{4-[2-(1H-imidazol-1-yl)ethoxy]phenyl}-4-oxo-1H,4H,5H-pyrazolo[3,4-d]pyrimidin-5-yl)methyl]-N,N-dimethylpiperidine-1-carboxamide;

4-({1-[4-(carbamoylmethoxy)phenyl]-4-oxo-1H,4H,5H-pyrazolo[3,4-d]pyrimidin-5-yl}methyl)-4-hydroxy-N,N-dimethylpiperidine-1-carboxamide;

4-({1-[4-(cyclobutylmethoxy)phenyl]-4-oxo-1H,4H,5H-pyrazolo[3,4-d]pyrimidin-5-yl}methyl)-4-hydroxy-N,N-dimethylpiperidine-1-carboxamide;

4-hydroxy-N,N-dimethyl-4-({1-[4-(3-methylbutoxy)phenyl]-4-oxo-1H,4H,5H-pyrazolo[3,4-d]pyrimidin-5-yl}methyl)piperidine-1-carboxamide;

4-hydroxy-N,N-dimethyl-4-({4-oxo-1-[4-(2,2,2-trifluoroethoxy)phenyl]-1H,4H,5H-pyrazolo[3,4-d]pyrimidin-5-yl}methyl)piperidine-1-carboxamide;

4-hydroxy-N,N-dimethyl-4-[(1-{4-[(1-methylpiperidin-2-yl)methoxy]phenyl}-4-oxo-1H,4H,5H-pyrazolo[3,4-d]pyrimidin-5-yl)methyl]piperidine-1-carboxamide;

4-[(1-{4-[(4-cyanophenyl)methoxy]phenyl}-4-oxo-1H,4H,5H-pyrazolo[3,4-d]pyrimidin-5-yl)methyl]-4-hydroxy-N,N-dimethylpiperidine-1-carboxamide;

5-({4-hydroxy-1-[4-(phenylamino)benzoyl]piperidin-4-yl}methyl)-1-methyl-1H,4H,5H-pyrazolo[3,4-d]pyrimidin-4-one;

4-[(1-{4-[(3-cyanophenyl)methoxy]phenyl}-4-oxo-1H,4H,5H-pyrazolo[3,4-d]pyrimidin-5-yl)methyl]-4-hydroxy-N,N-dimethylpiperidine-1-carboxamide;

4-hydroxy-N,N-dimethyl-4-({4-oxo-1-[4-(pyridin-3-ylmethoxy)phenyl]-1H,4H,5H-pyrazolo[3,4-d]pyrimidin-5-yl}methyl)piperidine-1-carboxamide;

4-hydroxy-N,N-dimethyl-4-({4-oxo-1-[4-(pyridin-2-ylmethoxy)phenyl]-1H,4H,5H-pyrazolo[3,4-d]pyrimidin-5-yl}methyl)piperidine-1-carboxamide;

4-hydroxy-N,N-dimethyl-4-({1-[4-(oxan-4-ylmethoxy)phenyl]-4-oxo-1H,4H,5H-pyrazolo[3,4-d]pyrimidin-5-yl}methyl)piperidine-1-carboxamide;

4-hydroxy-N,N-dimethyl-4-[(1-{4-[2-(morpholin-4-yl)-2-oxoethoxy]phenyl}-4-oxo-1H,4H,5H-pyrazolo[3,4-d]pyrimidin-5-yl)methyl]piperidine-1-carboxamide;

5-{[1-(4-fluorobenzoyl)-4-hydroxypiperidin-4-yl]methyl}-1-{4-[2-(1H-imidazol-1-yl)ethoxy]phenyl}-1H,4H,5H-pyrazolo[3,4-d]pyrimidin-4-one;

5-{[1-(4-fluorobenzoyl)-4-hydroxypiperidin-4-yl]methyl}-1-{3-[2-(1H-imidazol-1-yl)ethoxy]phenyl}-1H,4H,5H-pyrazolo[3,4-d]pyrimidin-4-one;

2-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetamide;

2-[3-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetamide;

1-[4-(cyclobutylmethoxy)phenyl]-5-{[1-(4-fluorobenzoyl)-4-hydroxypiperidin-4-yl]methyl}-1H,4H,5H-pyrazolo[3,4-d]pyrimidin-4-one;

5-[(1-{4-[4-(dimethylamino)piperidin-1-yl]benzoyl}-4-hydroxypiperidin-4-yl)methyl]-1-methyl-1H,4H,5H-pyrazolo[3,4-d]pyrimidin-4-one;

1-[3-(cyclobutylmethoxy)phenyl]-5-{[1-(4-fluorobenzoyl)-4-hydroxypiperidin-4-yl]methyl}-1H,4H,5H-pyrazolo[3,4-d]pyrimidin-4-one;

5-{[1-(4-fluorobenzoyl)-4-hydroxypiperidin-4-yl]methyl}-1-[3-(3-methylbutoxy)phenyl]-1H,4H,5H-pyrazolo[3,4-d]pyrimidin-4-one;

1-[3-(2,2-dimethylpropoxy)phenyl]-5-{[1-(4-fluorobenzoyl)-4-hydroxypiperidin-4-yl]methyl}-1H,4H,5H-pyrazolo[3,4-d]pyrimidin-4-one;

5-{[1-(4-fluorobenzoyl)-4-hydroxypiperidin-4-yl]methyl}-1-{4-[(1-methylpiperidin-2-yl)methoxy]phenyl}-1H,4H,5H-pyrazolo[3,4-d]pyrimidin-4-one;

5-{[1-(4-fluorobenzoyl)-4-hydroxypiperidin-4-yl]methyl}-1-{3-[(1-methylpiperidin-2-yl)methoxy]phenyl}-1H,4H,5H-pyrazolo[3,4-d]pyrimidin-4-one;

4-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxymethyl]benzonitrile;

4-[3-(5-{[1-(4-fluorobenzoyl)-4-hydroxypiperidin-4-yl]methyl)-4-oxo-1H,4H,5H-pyrazolo[3,4-d]pyrimidin-1-yl)phenoxymethyl]benzonitrile;

1-{3-[(4-chlorophenyl)methoxy]phenyl}-5-{[1-(4-fluorobenzoyl)-4-hydroxypiperidin-4-yl]methyl}-1H,4H,5H-pyrazolo[3,4-d]pyrimidin-4-one;

3-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxymethyl]benzonitrile;

3-[3-(5-{[1-(4-fluorobenzoyl)-4-hydroxypiperidin-4-yl]methyl)-4-oxo-1H,4H,5H-pyrazolo[3,4-d]pyrimidin-1-yl)phenoxymethyl]benzonitrile;

2-[4-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetonitrile;

2-[3-(5-{[1-(4-fluorobenzoyl)-4-hydroxypiperidin-4-yl]methyl)-4-oxo-1H,4H,5H-pyrazolo[3,4-d]pyrimidin-1-yl)phenoxy]acetonitrile;

4-hydroxy-N,N-dimethyl-4-[(1-{5-[4-(methylcarbamoyl)phenyl]pyridin-3-yl}-4-oxo-1H,4H,5H-pyrazolo[3,4-d]pyrimidin-5-yl)methyl]piperidine-1-carboxamide;

5-({1-(4-fluorobenzoyl)-4-hydroxypiperidin-4-yl]methyl}-1-[4-(oxan-4-ylmethoxy)phenyl]-1H,4H,5H-pyrazolo[3,4-d]pyrimidin-4-one;

5-{[1-(4-fluorobenzoyl)-4-hydroxypiperidin-4-yl]methyl}-1-[3-(oxan-4-ylmethoxy)phenyl]-1H,4H,5H-pyrazolo[3,4-d]pyrimidin-4-one;

5-{[1-(4-fluorobenzoyl)-4-hydroxypiperidin-4-yl]methyl}-1-{4-[2-(morpholin-4-yl)-2-oxoethoxy]phenyl}-1H,4H,5H-pyrazolo[3,4-d]pyrimidin-4-one;

5-{[1-(4-fluorobenzoyl)-4-hydroxypiperidin-4-yl]methyl}-1-{3-[2-(morpholin-4-yl)-2-oxoethoxy]phenyl}-1H,4H,5H-pyrazolo[3,4-d]pyrimidin-4-one;

5-{[1-(4-fluorobenzoyl)-4-hydroxypiperidin-4-yl] methyl}-1-{3-[(2-phenyl-1,3-thiazol-4-yl)methoxy] phenyl)-1H,4H,5H-pyrazolo[3,4-d]pyrimidin-4-one;

4-({1-[6-(3-cyanophenyl)pyridin-3-yl]-4-oxo-1H,4H,5H-pyrazolo[3,4-d]pyrimidin-5-yl}methyl)-4-hydroxy-N,N-dimethylpiperidine-1-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)benzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-phenylacetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(3-methyl-1,2-oxazol-5-yl)acetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-methoxybenzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-fluorobenzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-methoxybenzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)pyridine-4-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-methyl-1,3-thiazole-4-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(oxan-4-yl)acetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-methoxyacetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)cyclopropanecarboxamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-1,3-dimethyl-1H-pyrazole-5-carboxamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-methyl-1,3-thiazole-5-carboxamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(dimethylamino)acetamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-6-methylpyridine-3-carboxamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-5-fluoropyridine-2-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)pyridine-2-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-methyl-1,2,3-thiadiazole-5-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(methylamino)benzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-(methylamino)benzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-methoxypyridine-3-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-1,3-dimethyl-1H-pyrazole-5-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-4-methyl-1,3-thiazole-5-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(dimethylamino)acetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-6-methylpyridine-3-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-5-fluoropyridine-2-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(1,1-dioxo-1¿6,4-thiomorpholin-4-yl)acetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(morpholin-4-yl)acetamide;

(2S)—N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-1-methylpyrrolidine-2-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-1-methylpiperidine-2-carboxamide;

5-({4-hydroxy-1-[(3R)-3-methoxy-3-phenylpropanoyl] piperidin-4-yl}methyl)-1-methyl-1H,4H,5H-pyrazolo [3,4-d]pyrimidin-4-one;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)oxane-4-carboxamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(1H-pyrazol-1-yl)acetamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-3,3-difluorocyclobutane-1-carboxamide;

5-([1-(4-fluorobenzoyl)-4-hydroxypiperidin-4-yl] methyl}-1-[4-(2-methoxyethoxy)phenyl]-1H,4H,5H-pyrazolo[3,4-d]pyrimidin-4-one;

5-([1-(4-fluorobenzoyl)-4-hydroxypiperidin-4-yl] methyl}-1-[3-(2-methoxyethoxy)phenyl]-1H,4H,5H-pyrazolo[3,4-d]pyrimidin-4-one;

5-([1-(4-fluorobenzoyl)-4-hydroxypiperidin-4-yl] methyl}-1-[3-(pyridin-3-ylmethoxy)phenyl]-1H,4H,5H-pyrazolo[3,4-d]pyrimidin-4-one;

5-([1-(4-fluorobenzoyl)-4-hydroxypiperidin-4-yl] methyl}-1-[3-(pyridin-4-ylmethoxy)phenyl]-1H,4H,5H-pyrazolo[3,4-d]pyrimidin-4-one;

5-([1-(4-fluorobenzoyl)-4-hydroxypiperidin-4-yl]
methyl}-1-[4-(pyridin-2-ylmethoxy)phenyl]-1H,4H,
5H-pyrazolo[3,4-d]pyrimidin-4-one;
5-([1-(4-fluorobenzoyl)-4-hydroxypiperidin-4-yl]
methyl}-1-[3-(pyridin-2-ylmethoxy)phenyl]-1H,4H,
5H-pyrazolo[3,4-d]pyrimidin-4-one;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(3-methyl-1,2-oxazol-5-yl)acetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-fluorobenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxybenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-4-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methyl-1,3-thiazole-4-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(oxan-4-yl)acetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxyacetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanecarboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methylbenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-fluorobenzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-3-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methylpyrazine-2-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyridine-2-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(methylamino)benzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-(methylamino)benzamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methoxypyridine-3-carboxamide;
5-[(1-cyclopropanecarbonyl-4-hydroxypiperidin-4-yl)methyl]-1-(3-{[1-(pyridin-3-ylmethyl)-1H-pyrazol-3-yl]amino}phenyl)-1H,4H,5H-pyrazolo[3,4-d]pyrimidin-4-one;
5-[(1-cyclopropanecarbonyl-4-hydroxypiperidin-4-yl)methyl]-1-(3-{[1-(pyridin-2-ylmethyl)-1H-pyrazol-3-yl]amino}phenyl)-1H,4H,5H-pyrazolo[3,4-d]pyrimidin-4-one;
5-[(1-cyclopropanecarbonyl-4-hydroxypiperidin-4-yl)methyl]-1-{3-[(1,3-thiazol-2-yl)amino]phenyl}-1H,4H,5H-pyrazolo[3,4-d]pyrimidin-4-one;
5-([1-(1-benzyl-1,2,3,4-tetrahydroquinoline-6-carbonyl)-4-hydroxypiperidin-4-yl]methyl}-1-methyl-1H,4H,5H-pyrazolo[3,4-d]pyrimidin-4-one;
5-[(1-cyclopropanecarbonyl-4-hydroxypiperidin-4-yl)methyl]-1-{3-[(5-methyl-1,2-oxazol-3-yl)amino]phenyl}-1H,4H,5H-pyrazolo[3,4-d]pyrimidin-4-one;
N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-(1,1-dioxo-1¿6,4-thiomorpholin-4-yl)acetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(morpholin-4-yl)acetamide;
(2S)—N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpyrrolidine-2-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-methylpiperidine-2-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)oxane-4-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-(1H-pyrazol-1-yl)acetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,3-difluorocyclobutane-1-carboxamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-[methyl(phenyl)amino]acetamide;
N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methyl-2-(morpholin-4-yl)propanamide;
5-{[(3S,4R)-1-benzoyl-4-hydroxy-3-methoxypiperidin-4-yl]methyl}-1-phenyl-1H,4H,5H-pyrazolo[3,4-d]pyrimidin-4-one;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-5-methyl-1,2-oxazole-4-sulfonamide;
4-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide;
5-[(1-cyclopropanecarbonyl-4-hydroxypiperidin-4-yl)methyl]-1-{4-[(oxan-4-ylmethyl)amino]phenyl}-1H,4H,5H-pyrazolo[3,4-d]pyrimidin-4-one;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methylbenzene-1-sulfonamide;
2-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide;
N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzene-1-sulfonamide;

3-chloro-N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)benzene-1-sulfonamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-3-fluorobenzene-1-sulfonamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-3-methylbenzene-1-sulfonamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-[methyl(phenyl)amino]acetamide;

5-({4-hydroxy-1-[(3R)-4,4,4-trifluoro-3-phenylbutanoyl]piperidin-4-yl}methyl)-1-phenyl-1H,4H,5H-pyrazolo[3,4-d]pyrimidin-4-one;

N-(3-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-methyl-2-(morpholin-4-yl)propanamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)acetamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)benzamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl)phenyl)-2-phenylacetamide;

3-{5-[(1-cyclopropanecarbonyl-4-hydroxypiperidin-4-yl)methyl]-4-oxo-1H,4H,5H-pyrazolo[3,4-d]pyrimidin-1-yl)-N-(oxetan-3-yl)benzamide;

3-{5-[(1-cyclopropanecarbonyl-4-hydroxypiperidin-4-yl)methyl]-4-oxo-1H,4H,5H-pyrazolo[3,4-d]pyrimidin-1-yl)-N-phenylbenzamide;

3-{5-[(1-cyclopropanecarbonyl-4-hydroxypiperidin-4-yl)methyl]-4-oxo-1H,4H,5H-pyrazolo[3,4-d]pyrimidin-1-yl)-N-(pyridin-3-yl)benzamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)methanesulfonamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanesulfonamide;

N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)oxane-4-sulfonamide;

5-({4-hydroxy-1-[(3S)-4,4,4-trifluoro-3-phenylbutanoyl]piperidin-4-yl}methyl)-1-phenyl-1H,4H,5H-pyrazolo[3,4-d]pyrimidin-4-one;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzenesulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,5-dimethyl-1,2-oxazole-4-sulfonamide;

4-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methoxybenzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-4-methylbenzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-2-methylbenzene-1-sulfonamide;

2-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methoxybenzene-1-sulfonamide;

3-chloro-N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-fluorobenzene-1-sulfonamide;

5-({4-hydroxy-1-[(3R)-4,4,4-trifluoro-3-phenylbutanoyl]piperidin-4-yl}methyl)-1-methyl-1H,4H,5H-pyrazolo[3,4-d]pyrimidin-4-one;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-methylbenzene-1-sulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)methanesulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)cyclopropanesulfonamide;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(4-fluorophenyl)methanesulfonamide;

5-{[1-(4-fluorobenzoyl)-4-hydroxypiperidin-4-yl]methyl}-1-{4-[(3S)-3-hydroxypyrrolidin-1-yl]phenyl}-1H,4H,5H-pyrazolo[3,4-d]pyrimidin-4-one;

3-cyclopentyl-1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;

5-{[1-(2-amino-4-fluorobenzoyl)-4-hydroxypiperidin-4-yl]methyl}-1-[4-(trifluoromethyl)phenyl]-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-[4-(trifluoromethyl)phenyl]-1H,4H,5H-pyrazolo[3,4-d]pyrimidin-4-one;

3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-phenylurea;

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-phenylurea;

5-({4-hydroxy-1-[(3R)-4,4,4-trifluoro-3-phenylbutanoyl]piperidin-4-yl}methyl)-1-(4-methylphenyl)-1H,4H,5H-pyrazolo[3,4-d]pyrimidin-4-one;

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(4-fluorophenyl)urea;

1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(4-methylphenyl)urea;

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(3-methoxypropyl)urea;

1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(3-methoxypropyl)urea;

1-[4-(4-fluoropiperidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one;
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-cyclopropylurea;
3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(pyridin-3-yl)urea;
3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(pyridin-3-yl)urea;
1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(thiophen-3-yl)urea;
5-({4-hydroxy-1-[(3S)-4,4,4-trifluoro-3-phenylbutanoyl]piperidin-4-yl}methyl)-1-(4-methylphenyl)-1H,4H,5H-pyrazolo[3,4-d]pyrimidin-4-one;
5-[(1-cyclopropanecarbonyl-4-hydroxypiperidin-4-yl)methyl]-1-[3-(4-hydroxypiperidine-1-carbonyl)phenyl]-1H,4H,5H-pyrazolo[3,4-d]pyrimidin-4-one;
5-[(1-cyclopropanecarbonyl-4-hydroxypiperidin-4-yl)methyl]-1-[3-(3-hydroxyazetidine-1-carbonyl)phenyl]-1H,4H,5H-pyrazolo[3,4-d]pyrimidin-4-one;
3-{5-[(1-cyclopropanecarbonyl-4-hydroxypiperidin-4-yl)methyl]-4-oxo-1H,4H,5H-pyrazolo[3,4-d]pyrimidin-1-yl}-N-methylbenzamide;
N-benzyl-3-{5-[(1-cyclopropanecarbonyl-4-hydroxypiperidin-4-yl)methyl]-4-oxo-1H,4H,5H-pyrazolo[3,4-d]pyrimidin-1-yl)benzamide;
N-cyclobutyl-3-{5-[(1-cyclopropanecarbonyl-4-hydroxypiperidin-4-yl)methyl]-4-oxo-1H,4H,5H-pyrazolo[3,4-d]pyrimidin-1-yl)benzamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-[(4-fluorophenyl}methyl]benzamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-[2-(dimethylamino)ethyl]benzamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-[(3-methyloxetan-3-yl}methyl]benzamide;
4-({1-[4-fluoro-3-(3-fluoroazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide;
4-({1-[4-fluoro-3-(3-hydroxyazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide;
1-(4-fluorophenyl)-5-{[4-hydroxy-1-(1-methyl-1H-indazole-6-carbonyl)piperidin-4-yl]methyl}-1H,4H,5H-pyrazolo[3,4-d]pyrimidin-4-one;
4-({1-[4-(4,4-difluoropiperidin-1-yl)phenyl]-4-oxo-1H,4H,5H-pyrazolo[3,4-d]pyrimidin-5-yl}methyl)-4-hydroxy-N,N-dimethylpiperidine-1-carboxamide;
4-hydroxy-N,N-dimethyl-4-{[4-oxo-1-(4-{[2-(propan-2-yloxy)ethyl]amino}phenyl)-1H,4H,5H-pyrazolo[3,4-d]pyrimidin-5-yl]methyl}piperidine-1-carboxamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-(4-fluorophenyl)benzamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-(1,3-thiazol-2-yl)benzamide;
3-{5-[(1-cyclopropanecarbonyl-4-hydroxypiperidin-4-yl)methyl]-4-oxo-1H,4H,5H-pyrazolo[3,4-d]pyrimidin-1-yl)-N-(5-methyl-1,2-oxazol-3-yl)benzamide;
5-[(1-cyclopropanecarbonyl-4-hydroxypiperidin-4-yl)methyl]-1-[3-(pyrrolidine-1-carbonyl)phenyl]-1H,4H,5H-pyrazolo[3,4-d]pyrimidin-4-one;
5-[(1-cyclopropanecarbonyl-4-hydroxypiperidin-4-yl)methyl]-1-[3-(morpholine-4-carbonyl)phenyl]-1H,4H,5H-pyrazolo[3,4-d]pyrimidin-4-one;
5-[(1-cyclopropanecarbonyl-4-hydroxypiperidin-4-yl)methyl]-1-{3-[4-(dimethylamino)piperidine-1-carbonyl]phenyl}-1H,4H,5H-pyrazolo[3,4-d]pyrimidin-4-one;
5-[(1-cyclopropanecarbonyl-4-hydroxypiperidin-4-yl)methyl]-1-[3-(4-methylpiperazine-1-carbonyl)phenyl]-1H,4H,5H-pyrazolo[3,4-d]pyrimidin-4-one;
5-({1-(4,4-difluoro-3-phenylbutanoyl)-4-hydroxypiperidin-4-yl]methyl}-1-methyl-1H,4H,5H-pyrazolo[3,4-d]pyrimidin-4-one;
5-[(1-cyclopropanecarbonyl-4-hydroxypiperidin-4-yl)methyl]-1-[3-(3-fluoroazetidine-1-carbonyl)phenyl]-1H,4H,5H-pyrazolo[3,4-d]pyrimidin-4-one;
1-(4-fluorophenyl)-5-[(4-hydroxy-1-{imidazo[1,2-a]pyrazine-2-carbonyl}piperidin-4-yl)methyl]-1H,4H,5H-pyrazolo[3,4-d]pyrimidin-4-one;
1-(4-fluorophenyl)-5-{[4-hydroxy-1-(1H-indole-5-carbonyl)piperidin-4-yl]methyl}-1H,4H,5H-pyrazolo[3,4-d]pyrimidin-4-one;
1-(4-fluorophenyl)-5-{[4-hydroxy-1-(1H-indole-2-carbonyl)piperidin-4-yl]methyl}-1H,4H,5H-pyrazolo[3,4-d]pyrimidin-4-one;
1-(4-fluorophenyl)-5-{[4-hydroxy-1-(4,4,4-trifluorobutanoyl)piperidin-4-yl]methyl}-1H,4H,5H-pyrazolo[3,4-d]pyrimidin-4-one;
5-{[1-(2,3-dihydro-1-benzofuran-5-carbonyl)-4-hydroxypiperidin-4-yl]methyl}-1-(4-fluorophenyl)-1H,4H,5H-pyrazolo[3,4-d]pyrimidin-4-one;
5-{[1-(1H-1,2,3-benzotriazole-5-carbonyl)-4-hydroxypiperidin-4-yl]methyl}-1-(4-fluorophenyl)-1H,4H,5H-pyrazolo[3,4-d]pyrimidin-4-one;
1-(4-fluorophenyl)-5-{[4-hydroxy-1-(1H-indole-6-carbonyl)piperidin-4-yl]methyl}-1H,4H,5H-pyrazolo[3,4-d]pyrimidin-4-one;
5-{[1-(1,3-benzothiazole-6-carbonyl)-4-hydroxypiperidin-4-yl]methyl}-1-(4-fluorophenyl)-1H,4H,5H-pyrazolo[3,4-d]pyrimidin-4-one;
N-tert-butyl-4-{[1-(4-fluorophenyl)-4-oxo-1H,4H,5H-pyrazolo[3,4-d]pyrimidin-5-yl]methyl}-4-hydroxypiperidine-1-carboxamide;
3-cyclopentyl-1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;
1-cyclohexyl-3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;
1-cyclohexyl-3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;
1-benzyl-3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;
1-benzyl-3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)urea;
4-{5-[(1-cyclopropanecarbonyl-4-hydroxypiperidin-4-yl)methyl]-4-oxo-1H,4H,5H-pyrazolo[3,4-d]pyrimidin-1-yl}-N-methylbenzamide;
4-{5-[(1-cyclopropanecarbonyl-4-hydroxypiperidin-4-yl)methyl]-4-oxo-1H,4H,5H-pyrazolo[3,4-d]pyrimidin-1-yl}-N-[(4-fluorophenyl}methyl]benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-[2-(dimethylamino)ethyl]benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-[(3-methyloxetan-3-yl)methyl]benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-(oxetan-3-yl)benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-phenylbenzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-(pyridin-3-yl)benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-(4-fluorophenyl)benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-(1,3-thiazol-2-yl)benzamide;

4-{5-[(1-cyclopropanecarbonyl-4-hydroxypiperidin-4-yl) methyl]-4-oxo-1H,4H,5H-pyrazolo[3,4-d]pyrimidin-1-yl)-N-(5-methyl-1,2-oxazol-3-yl)benzamide;

5-[(1-cyclopropanecarbonyl-4-hydroxypiperidin-4-yl) methyl]-1-[4-(morpholine-4-carbonyl)phenyl]-1H,4H,5H-pyrazolo[3,4-d]pyrimidin-4-one;

5-[(1-cyclopropanecarbonyl-4-hydroxypiperidin-4-yl) methyl]-1-{4-[4-(dimethylamino)piperidine-1-carbonyl]phenyl}-1H,4H,5H-pyrazolo[3,4-d]pyrimidin-4-one 5-[(1-cyclopropanecarbonyl-4-hydroxypiperidin-4-yl) methyl]-1-[4-(4-methylpiperazine-1-carbonyl)phenyl]-1H,4H,5H-pyrazolo[3,4-d]pyrimidin-4-one;

5-[(1-cyclopropanecarbonyl-4-hydroxypiperidin-4-yl) methyl]-1-[4-(3,3-difluoropyrrolidine-1-carbonyl)phenyl]-1H,4H,5H-pyrazolo[3,4-d]pyrimidin-4-one;

N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)pyrrolidine-1-carboxamide;

5-([1-(1-benzyl-1H-pyrrole-2-carbonyl)-4-hydroxypiperidin-4-yl}methyl}-1-phenyl-1H,4H,5H-pyrazolo[3,4-d]pyrimidin-4-one;

3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-1-(oxan-4-yl)urea;

1-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3,3-dimethylurea;

propan-2-yl N-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)carbamate;

4-[(1-{4-[(8aS)-octahydropyrrolo[1,2-a]piperazin-2-yl] phenyl)-4-oxo-1H,4H,5H-pyrazolo[3,4-d]pyrimidin-5-yl)methyl]-4-hydroxy-N,N-dimethylpiperidine-1-carboxamide;

4-hydroxy-4-({1-[4-(4-hydroxy-4-methylpiperidin-1-yl) phenyl]-4-oxo-1H,4H,5H-pyrazolo[3,4-d]pyrimidin-5-yl}methyl)-N,N-dimethylpiperidine-1-carboxamide;

5-{[1-(2,3-dihydro-1,4-benzodioxine-6-carbonyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-{[4-hydroxy-1-(5-methoxy-1-methyl-1H-pyrazole-3-carbonyl)piperidin-4-yl] methyl)-1H,4H,5H-pyrazolo[3,4-d]pyrimidin-4-one;

5-{[1-(3,4-dihydro-2H-1-benzopyran-6-carbonyl)-4-hydroxypiperidin-4-yl]methyl}-1-(4-fluorophenyl)-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-{4-[(1-methylcyclobutyl)methoxy]phenyl}-1H,4H,5H-pyrazolo[3,4-d] pyrimidin-4-one;

4-hydroxy-4-[(1-{4-[(3S)-3-methoxypyrrolidin-1-yl]phenyl)-4-oxo-1H,4H,5H-pyrazolo[3,4-d]pyrimidin-5-yl) methyl]-N,N-dimethylpiperidine-1-carboxamide;

5-([1-(4-fluoro-3-phenylbutanoyl)-4-hydroxypiperidin-4-yl]methyl}-1-methyl-1H,4H,5H-pyrazolo[3,4-d]pyrimidin-4-one;

5-((4-hydroxy-1-[4-(pyridin-2-yloxy)benzoyl]piperidin-4-yl}methyl)-1-(4-methylphenyl)-1H,4H,5H-pyrazolo [3,4-d]pyrimidin-4-one;

5-{[4-hydroxy-1-(4,4,4-trifluorobutanoyl)piperidin-4-yl] methyl}-1-(4-methylphenyl)-1H,4H,5H-pyrazolo[3,4-d]pyrimidin-4-one;

5-([1-(2,3-dihydro-1-benzofuran-5-carbonyl)-4-hydroxypiperidin-4-yl]methyl}-1-(4-methylphenyl)-1H,4H,5H-pyrazolo[3,4-d]pyrimidin-4-one;

5-{[4-hydroxy-1-(1,2,3-thiadiazole-4-carbonyl)piperidin-4-yl]methyl}-1-(4-methylphenyl)-1H,4H,5H-pyrazolo [3,4-d]pyrimidin-4-one;

5-{[4-hydroxy-1-(2-methyl-1,3-oxazole-5-carbonyl)piperidin-4-yl]methyl}-1-(4-methylphenyl)-1H,4H,5H-pyrazolo[3,4-d]pyrimidin-4-one;

5-[(4-hydroxy-1-{5H,6H,7H-pyrazolo[3,2-b][1,3] oxazine-2-carbonyl)piperidin-4-yl)methyl]-1-(4-methylphenyl)-1H,4H,5H-pyrazolo[3,4-d]pyrimidin-4-one;

5-[(4-hydroxy-1-{2H,3H-pyrazolo[3,2-b][1,3]oxazole-6-carbonyl)piperidin-4-yl)methyl]-1-(4-methylphenyl)-1H,4H,5H-pyrazolo[3,4-d]pyrimidin-4-one;

5-{[4-hydroxy-1-(5-methyl-1,2,3-thiadiazole-4-carbonyl) piperidin-4-yl]methyl}-1-(4-methylphenyl)-1H,4H, 5H-pyrazolo[3,4-d]pyrimidin-4-one;

1-(4-chlorophenyl)-5-({4-hydroxy-1-[4-(pyridin-2-yloxy)benzoyl]piperidin-4-yl}methyl)-1H,4H,5H-pyrazolo[3,4-d]pyrimidin-4-one;

1-cyclopropyl-5-{[4-hydroxy-1-(4-phenoxybenzoyl}piperidin-4-yl]methyl)-1H,4H,5H-pyrazolo[3,4-d]pyrimidin-4-one;

1-(4-chlorophenyl)-5-{[4-hydroxy-1-(4,4,4-trifluorobutanoyl)piperidin-4-yl]methyl}-1H,4H,5H-pyrazolo[3,4-d]pyrimidin-4-one;

1-(4-chlorophenyl)-5-{[1-(2,3-dihydro-1-benzofuran-5-carbonyl)-4-hydroxypiperidin-4-yl]methyl}-1H,4H, 5H-pyrazolo[3,4-d]pyrimidin-4-one;

1-(4-chlorophenyl)-5-{[4-hydroxy-1-(1,2,3-thiadiazole-4-carbonyl)piperidin-4-yl]methyl}-1H,4H,5H-pyrazolo[3,4-d]pyrimidin-4-one;

1-(4-chlorophenyl)-5-{[1-(3-fluoro-4-methylbenzoyl)-4-hydroxypiperidin-4-yl]methyl)-1H,4H,5H-pyrazolo[3, 4-d]pyrimidin-4-one;

1-(4-chlorophenyl)-5-{[4-hydroxy-1-(2-methyl-1,3-oxazole-5-carbonyl)piperidin-4-yl]methyl}-1H,4H,5H-pyrazolo[3,4-d]pyrimidin-4-one;

4-[(1-{4-[(9aS)-octahydro-1H-pyrido[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide;

4-hydroxy-N,N-dimethyl-4-[(4-oxo-1-{4-[4-(trifluoromethyl)-1H-pyrazol-1-yl]phenyl)-1H,4H,5H-pyrazolo[3, 4-d]pyrimidin-5-yl}methyl]piperidine-1-carboxamide;

1-(4-chlorophenyl)-5-[(4-hydroxy-1-{2H,3H-pyrazolo[3,2-b][1,3]oxazole-6-carbonyl}piperidin-4-yl)methyl]-1H,4H,5H-pyrazolo[3,4-d]pyrimidin-4-one;

1-(4-chlorophenyl)-5-({4-hydroxy-1-[4-(pyrimidin-2-yloxy)benzoyl]piperidin-4-yl}methyl)-1H,4H,5H-pyrazolo[3,4-d]pyrimidin-4-one;

1-(4-chlorophenyl)-5-{[4-hydroxy-1-(5-methyl-1,2,3-thiadiazole-4-carbonyl)piperidin-4-yl]methyl)-1H,4H,5H-pyrazolo[3,4-d]pyrimidin-4-one;

5-[(1-benzoyl-4-hydroxypiperidin-4-yl)methyl]-1-phenyl-1H,4H,5H-pyrazolo[3,4-d]pyrimidin-4-one;

1-(4-fluorophenyl)-5-{[4-hydroxy-1-(1,2,3-thiadiazole-4-carbonyl)piperidin-4-yl]methyl}-1H,4H,5H-pyrazolo[3,4-d]pyrimidin-4-one;

5-{[1-(3-fluoro-4-methylbenzoyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-{[4-hydroxy-1-(4,4,4-trifluoro-3-methylbutanoyl)piperidin-4-yl]methyl}-1H,4H,5H-pyrazolo[3,4-d]pyrimidin-4-one;

5-{[1-(4,4-difluorobutanoyl)-4-hydroxypiperidin-4-yl]methyl}-1-(4-fluorophenyl)-1H,4H,5H-pyrazolo[3,4-d]pyrimidin-4-one;

2-[4-(4-{[1-(4-fluorophenyl)-4-oxo-1H,4H,5H-pyrazolo[3,4-d]pyrimidin-5-yl]methyl)-4-hydroxypiperidine-1-carbonyl)phenyl]-1-6,2-thiazolidine-1,1-dione;

1-(4-fluorophenyl)-5-({4-hydroxy-1-[4-(1H-1,2,3-triazol-1-yl)benzoyl]piperidin-4-yl}methyl)-1H,4H,5H-pyrazolo[3,4-d]pyrimidin-4-one;

1-(4-fluorophenyl)-5-({4-hydroxy-1-[4-(4-hydroxypiperidin-1-yl)benzoyl]piperidin-4-yl}methyl)-1H,4H,5H-pyrazolo[3,4-d]pyrimidin-4-one;

5-({1-[2-(difluoromethoxy)acetyl]-4-hydroxypiperidin-4-yl}methyl)-1-(4-fluorophenyl)-1H,4H,5H-pyrazolo[3,4-d]pyrimidin-4-one;

4-hydroxy-N,N-dimethyl-4-({4-oxo-1-[4-(1H-pyrazol-1-yl)phenyl]-1H,4H,5H-pyrazolo[3,4-d]pyrimidin-5-yl}methyl)piperidine-1-carboxamide;

4-hydroxy-N,N-dimethyl-4-({1-[4-(4-methyl-1H-pyrazol-1-yl)phenyl]-4-oxo-1H,4H,5H-pyrazolo[3,4-d]pyrimidin-5-yl}methyl)piperidine-1-carboxamide;

5-[(1-acetyl-4-hydroxypiperidin-4-yl)methyl]-1-phenyl-1H,4H,5H-pyrazolo[3,4-d]pyrimidin-4-one;

5-[(1-cyclopropanecarbonyl-4-hydroxypiperidin-4-yl)methyl]-1-[3-(4-methyl-1H-pyrazol-1-yl)phenyl]-1H,4H,5H-pyrazolo[3,4-d]pyrimidin-4-one;

4-[(1-{4-[(9aR)-octahydro-1H-pyrido[1,2-a]piperazin-2-yl]phenyl)-4-oxo-1H,4H,5H-pyrazolo[3,4-d]pyrimidin-5-yl)methyl]-4-hydroxy-N,N-dimethylpiperidine-1-carboxamide;

5-{[1-(2-cyclopropyl-1,3-oxazole-5-carbonyl)-4-hydroxypiperidin-4-yl]methyl}-1-(4-methylphenyl)-1H,4H,5H-pyrazolo[3,4-d]pyrimidin-4-one;

4-hydroxy-N,N-dimethyl-4-{[4-oxo-1-(4-{[2-(piperidin-1-yl)ethyl]amino}phenyl)-1H,4H,5H-pyrazolo[3,4-d]pyrimidin-5-yl]methyl}piperidine-1-carboxamide;

4-[(1-{4-[(3,3-dimethylcyclobutyl)amino]phenyl}-4-oxo-1H,4H,5H-pyrazolo[3,4-d]pyrimidin-5-yl)methyl]-4-hydroxy-N,N-dimethylpiperidine-1-carboxamide;

1-(4-fluorophenyl)-5-{[4-hydroxy-1-(4,4,4-trifluoro-3-hydroxy-3-methylbutanoyl)piperidin-4-yl]methyl}-1H,4H,5H-pyrazolo[3,4-d]pyrimidin-4-one;

4-[(1-{4-[(8aR)-octahydropyrrolo[1,2-a]piperazin-2-yl]phenyl}-4-oxo-1H,4H,5H-pyrazolo[3,4-d]pyrimidin-5-yl)methyl]-4-hydroxy-N,N-dimethylpiperidine-1-carboxamide;

5-{[4-hydroxy-1-(pyridine-4-carbonyl)piperidin-4-yl]methyl}-1-(4-phenylphenyl)-1H,4H,5H-pyrazolo[3,4-d]pyrimidin-4-one;

4-hydroxy-N,N-dimethyl-4-[(4-oxo-1-{4-[4-(1H-pyrazol-1-yl)piperidin-1-yl]phenyl)-1H,4H,5H-pyrazolo[3,4-d]pyrimidin-5-yl}methyl]piperidine-1-carboxamide;

5-[(1-acetyl-4-hydroxypiperidin-4-yl)methyl]-1-[4-(trifluoromethyl)phenyl]-1H,4H,5H-pyrazolo[3,4-d]pyrimidin-4-one;

5-{[4-hydroxy-1-(1-methyl-1H-imidazole-4-carbonyl)piperidin-4-yl]methyl}-1-phenyl-1H,4H,5H-pyrazolo[3,4-d]pyrimidin-4-one;

5-[(1-benzoyl-4-hydroxypiperidin-4-yl)methyl]-1-[4-(trifluoromethyl)phenyl]-1H,4H,5H-pyrazolo[3,4-d]pyrimidin-4-one;

5-{[4-hydroxy-1-(4-methoxybenzoyl)piperidin-4-yl]methyl}-1-[4-(trifluoromethyl)phenyl]-1H,4H,5H-pyrazolo[3,4-d]pyrimidin-4-one;

5-{[1-(4-fluorobenzoyl)-4-hydroxypiperidin-4-yl]methyl}-1-[4-(trifluoromethyl)phenyl]-1H,4H,5H-pyrazolo[3,4-d]pyrimidin-4-one;

5-{[4-hydroxy-1-(pyridine-4-carbonyl)piperidin-4-yl]methyl}-1-[4-(trifluoromethyl)phenyl]-1H,4H,5H-pyrazolo[3,4-d]pyrimidin-4-one;

5-({4-hydroxy-1-[2-(oxan-4-yl)acetyl]piperidin-4-yl}methyl)-1-[4-(trifluoromethyl)phenyl]-1H,4H,5H-pyrazolo[3,4-d]pyrimidin-4-one;

5-({4-hydroxy-1-[4-(pyridin-2-yloxy)benzoyl]piperidin-4-yl}methyl)-1-[4-(trifluoromethyl)phenyl]-1H,4H,5H-pyrazolo[3,4-d]pyrimidin-4-one;

5-{[1-(3-ethoxypropanoyl)-4-hydroxypiperidin-4-yl]methyl}-1-[4-(trifluoromethyl)phenyl]-1H,4H,5H-pyrazolo[3,4-d]pyrimidin-4-one;

5-[(1-cyclobutanecarbonyl-4-hydroxypiperidin-4-yl)methyl]-1-[4-(trifluoromethyl)phenyl]-1H,4H,5H-pyrazolo[3,4-d]pyrimidin-4-one;

5-{[1-(2,3-dihydro-1-benzofuran-5-carbonyl)-4-hydroxypiperidin-4-yl]methyl}-1-[4-(trifluoromethyl)phenyl]-1H,4H,5H-pyrazolo[3,4-d]pyrimidin-4-one;

5-{[4-hydroxy-1-(pyridine-3-carbonyl)piperidin-4-yl]methyl}-1-[4-(trifluoromethyl)phenyl]-1H,4H,5H-pyrazolo[3,4-d]pyrimidin-4-one;

5-{[1-(4-cyclopropylbenzoyl)-4-hydroxypiperidin-4-yl]methyl}-1-phenyl-1H,4H,5H-pyrazolo[3,4-d]pyrimidin-4-one;

5-{[1-(1,5-dimethyl-1H-pyrazole-3-carbonyl)-4-hydroxypiperidin-4-yl]methyl}-1-[4-(trifluoromethyl)phenyl]-1H,4H,5H-pyrazolo[3,4-d]pyrimidin-4-one;

1-[3-(4-fluoropiperidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one;

5-({1-(2-aminobenzoyl)-4-hydroxypiperidin-4-yl]methyl}-1-[4-(trifluoromethyl)phenyl]-1H,4H,5H-pyrazolo[3,4-d]pyrimidin-4-one;

5-{[4-hydroxy-1-(5-methyl-1,2-oxazole-3-carbonyl)piperidin-4-yl]methyl}-1-[4-(trifluoromethyl)phenyl]-1H,4H,5H-pyrazolo[3,4-d]pyrimidin-4-one;

5-{[4-hydroxy-1-(1H-indole-6-carbonyl)piperidin-4-yl]methyl}-1-[4-(trifluoromethyl)phenyl]-1H,4H,5H-pyrazolo[3,4-d]pyrimidin-4-one;

5-{[4-hydroxy-1-(1-methylpiperidine-4-carbonyl)piperidin-4-yl]methyl}-1-[4-(trifluoromethyl)phenyl]-1H,4H,5H-pyrazolo[3,4-d]pyrimidin-4-one;

5-{[4-hydroxy-1-(oxane-4-carbonyl)piperidin-4-yl]methyl}-1-[4-(trifluoromethyl)phenyl]-1H,4H,5H-pyrazolo[3,4-d]pyrimidin-4-one;

5-{[1-(4,4-difluorocyclohexanecarbonyl)-4-hydroxypiperidin-4-yl]methyl}-1-[4-(trifluoromethyl)phenyl]-1H,4H,5H-pyrazolo[3,4-d]pyrimidin-4-one;

5-{[1-(3,3-difluorocyclobutanecarbonyl)-4-hydroxypiperidin-4-yl]methyl}-1-[4-(trifluoromethyl)phenyl]-1H,4H,5H-pyrazolo[3,4-d]pyrimidin-4-one;

1-(4-chlorophenyl)-5-[(4-hydroxy-1-{5H,6H,7H-pyrazolo[3,2-b][1,3]oxazine-2-carbonyl}piperidin-4-yl)methyl]-1H,4H,5H-pyrazolo[3,4-d]pyrimidin-4-one;

5-{[4-hydroxy-1-(4-methoxybenzoyl)piperidin-4-yl]methyl}-1-phenyl-1H,4H,5H-pyrazolo[3,4-d]pyrimidin-4-one;

5-{[4-hydroxy-1-(1-methylcyclopropanecarbonyl)piperidin-4-yl]methyl}-1-{4-[3-(oxan-4-yl)azetidin-1-yl]phenyl)-1H,4H,5H-pyrazolo[3,4-d]pyrimidin-4-one;

5-[(4-hydroxy-1-{5H,6H,7H-pyrazolo[3,2-b][1,3]oxazine-2-carbonyl}piperidin-4-yl)methyl]-1-[4-(trifluoromethyl)phenyl]-1H,4H,5H-pyrazolo[3,4-d]pyrimidin-4-one;

5-[(4-hydroxy-1-{imidazo[1,5-a]pyridine-6-carbonyl}piperidin-4-yl)methyl]-1-[4-(trifluoromethyl)phenyl]-1H,4H,5H-pyrazolo[3,4-d]pyrimidin-4-one;

5-[(4-hydroxy-1-{2H,3H-pyrazolo[3,2-b][1,3]oxazole-6-carbonyl}piperidin-4-yl)methyl]-1-[4-(trifluoromethyl)phenyl]-1H,4H,5H-pyrazolo[3,4-d]pyrimidin-4-one;

5-({4-hydroxy-1-[4-(pyrimidin-2-yloxy)benzoyl]piperidin-4-yl}methyl)-1-[4-(trifluoromethyl)phenyl]-1H,4H,5H-pyrazolo[3,4-d]pyrimidin-4-one;

1-[4-(5-{[1-(4-fluorobenzoyl)-4-hydroxypiperidin-4-yl]methyl}-4-oxo-1H,4H,5H-pyrazolo[3,4-d]pyrimidin-1-yl)phenyl]-3,3-dimethylurea;

5-[(1-cyclopropanecarbonyl-4-hydroxypiperidin-4-yl)methyl]-1-{3-[4-(trifluoromethyl)-1H-pyrazol-1-yl]phenyl}-1H,4H,5H-pyrazolo[3,4-d]pyrimidin-4-one;

5-[(1-cyclopropanecarbonyl-4-hydroxypiperidin-4-yl)methyl]-1-{4-[4-(trifluoromethyl)-1H-pyrazol-1-yl]phenyl}-1H,4H,5H-pyrazolo[3,4-d]pyrimidin-4-one;

5-[(1-cyclopropanecarbonyl-4-hydroxypiperidin-4-yl)methyl]-1-(4-{[5-(trifluoromethyl)pyridin-2-yl]oxy}phenyl)-1H,4H,5H-pyrazolo[3,4-d]pyrimidin-4-one;

5-[(1-cyclopropanecarbonyl-4-hydroxypiperidin-4-yl)methyl]-1-phenyl-1H,4H,5H-pyrazolo[3,4-d]pyrimidin-4-one;

5-[(1-cyclopropanecarbonyl-4-hydroxypiperidin-4-yl)methyl]-1-(4-{[4-(trifluoromethyl)pyrimidin-2-yl]oxy}phenyl)-1H,4H,5H-pyrazolo[3,4-d]pyrimidin-4-one;

5-[(1-cyclopropanecarbonyl-4-hydroxypiperidin-4-yl)methyl]-1-{4-[4-(1H-pyrazol-1-yl)piperidin-1-yl]phenyl}-1H,4H,5H-pyrazolo[3,4-d]pyrimidin-4-one;

5-[(1-cyclopropanecarbonyl-4-hydroxypiperidin-4-yl)methyl]-1-{4-[4-(1H-1,2,3-triazol-1-yl)piperidin-1-yl]phenyl}-1H,4H,5H-pyrazolo[3,4-d]pyrimidin-4-one;

4-hydroxy-N,N-dimethyl-4-[(4-oxo-1-{4-[4-(1H-1,2,3-triazol-1-yl)piperidin-1-yl]phenyl}-1H,4H,5H-pyrazolo[3,4-d]pyrimidin-5-yl)methyl]piperidine-1-carboxamide;

1-{4-[(9aR)-octahydro-1H-pyrido[1,2-a]piperazin-2-yl]phenyl}-5-[(1-cyclopropanecarbonyl-4-hydroxypiperidin-4-yl)methyl]-1H,4H,5H-pyrazolo[3,4-d]pyrimidin-4-one;

1-(4-fluorophenyl)-5-({4-hydroxy-1-[4-(1H-1,2,3-triazol-1-yl)piperidine-1-carbonyl]piperidin-4-yl}methyl)-1H,4H,5H-pyrazolo[3,4-d]pyrimidin-4-one;

1-[3-(4-chloro-1H-pyrazol-1-yl)phenyl]-5-[(1-cyclopropanecarbonyl-4-hydroxypiperidin-4-yl)methyl]-1H,4H,5H-pyrazolo[3,4-d]pyrimidin-4-one;

1-[4-(4-chloro-1H-pyrazol-1-yl)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-[4-(oxetan-3-yloxy)phenyl]-1H,4H,5H-pyrazolo[3,4-d]pyrimidin-4-one;

5-{[4-hydroxy-1-(3-hydroxybenzoyl)piperidin-4-yl]methyl}-1-phenyl-1H,4H,5H-pyrazolo[3,4-d]pyrimidin-4-one;

5-[(1-cyclopropanecarbonyl-4-hydroxypiperidin-4-yl)methyl]-1-[4-(oxan-4-ylmethoxy)phenyl]-1H,4H,5H-pyrazolo[3,4-d]pyrimidin-4-one;

5-[(1-acetyl-4-hydroxypiperidin-4-yl)methyl]-1-(4-phenylphenyl)-1H,4H,5H-pyrazolo[3,4-d]pyrimidin-4-one;

1-(4-chlorophenyl)-5-{[4-hydroxy-1-(1H-indole-6-carbonyl)piperidin-4-yl]methyl}-1H,4H,5H-pyrazolo[3,4-d]pyrimidin-4-one;

1-(4-chlorophenyl)-5-({4-hydroxy-1-[3-(1H-1,2,3,4-tetrazol-1-yl)propanoyl]piperidin-4-yl}methyl)-1H,4H,5H-pyrazolo[3,4-d]pyrimidin-4-one;

1-(4-chlorophenyl)-5-{[4-hydroxy-1-(oxane-4-carbonyl)piperidin-4-yl]methyl}-1H,4H,5H-pyrazolo[3,4-d]pyrimidin-4-one;

1-(4-chlorophenyl)-5-[(4-hydroxy-1-{pyrazolo[1,5-a]pyridine-2-carbonyl}piperidin-4-yl)methyl]-1H,4H,5H-pyrazolo[3,4-d]pyrimidin-4-one;

1-(4-chlorophenyl)-5-{[1-(4,4-difluorocyclohexanecarbonyl)-4-hydroxypiperidin-4-yl]methyl}-1H,4H,5H-pyrazolo[3,4-d]pyrimidin-4-one;

1-(4-chlorophenyl)-5-{[4-hydroxy-1-(3-methyloxetane-3-carbonyl)piperidin-4-yl]methyl}-1H,4H,5H-pyrazolo[3,4-d]pyrimidin-4-one;

1-(4-chlorophenyl)-5-{[1-(3,3-difluorocyclobutanecarbonyl)-4-hydroxypiperidin-4-yl]methyl}-1H,4H,5H-pyrazolo[3,4-d]pyrimidin-4-one;

5-[4-hydroxy-4-({4-oxo-1-phenyl-1H,4H,5H-pyrazolo[3,4-d]pyrimidin-5-yl}methyl)piperidine-1-carbonyl]-1,2-dihydropyridin-2-one;

1-(4-chlorophenyl)-5-{[4-hydroxy-1-(3-hydroxy-3-methylbutanoyl)piperidin-4-yl]methyl}-1H,4H,5H-pyrazolo[3,4-d]pyrimidin-4-one;

1-(4-chlorophenyl)-5-{[4-hydroxy-1-(4-methyl-1,3-oxazole-5-carbonyl)piperidin-4-yl]methyl}-1H,4H,5H-pyrazolo[3,4-d]pyrimidin-4-one;

5-{[1-(3-ethoxypropanoyl)-4-hydroxypiperidin-4-yl]methyl}-1-(4-phenylphenyl)-1H,4H,5H-pyrazolo[3,4-d]pyrimidin-4(5H)-one;

5-[(1-cyclobutanecarbonyl-4-hydroxypiperidin-4-yl)methyl]-1-(4-phenylphenyl)-1H,4H,5H-pyrazolo[3,4-d]pyrimidin-4-one;

5-({1-(2,3-dihydro-1-benzofuran-5-carbonyl)-4-hydroxypiperidin-4-yl]methyl)-1-(4-phenylphenyl)-1H,4H,5H-pyrazolo[3,4-d]pyrimidin-4-one;

5-{[4-hydroxy-1-(pyridine-3-carbonyl)piperidin-4-yl]methyl}-1-(4-phenylphenyl)-1H,4H,5H-pyrazolo[3,4-d]pyrimidin-4-one;

5-({1-(1,5-dimethyl-1H-pyrazole-3-carbonyl)-4-hydroxypiperidin-4-yl]methyl}-1-(4-phenylphenyl)-1H,4H,5H-pyrazolo[3,4-d]pyrimidin-4-one;

5-([1-(dimethyl-1,3-thiazole-5-carbonyl)-4-hydroxypiperidin-4-yl]methyl}-1-(4-phenylphenyl)-1H,4H,5H-pyrazolo[3,4-d]pyrimidin-4-one;
5-([1-(2-aminobenzoyl)-4-hydroxypiperidin-4-yl]methyl}-1-(4-phenylphenyl)-1H,4H,5H-pyrazolo[3,4-d]pyrimidin-4-one;
5-{[4-hydroxy-1-(1H-indole-6-carbonyl)piperidin-4-yl]methyl}-1-(4-phenylphenyl)-1H,4H,5H-pyrazolo[3,4-d]pyrimidin-4-one;
5-{[4-hydroxy-1-(1H-indazole-3-carbonyl)piperidin-4-yl]methyl}-1-phenyl-1H,4H,5H-pyrazolo[3,4-d]pyrimidin-4-one;
5-{[4-hydroxy-1-(oxane-4-carbonyl)piperidin-4-yl]methyl}-1-(4-phenylphenyl)-1H,4H,5H-pyrazolo[3,4-d]pyrimidin-4-one;
5-{[1-(3,3-difluorocyclobutanecarbonyl)-4-hydroxypiperidin-4-yl]methyl}-1-(4-phenylphenyl)-1H,4H,5H-pyrazolo[3,4-d]pyrimidin-4-one;
5-{[1-(2-amino-4-fluorobenzoyl)-4-hydroxypiperidin-4-yl]methyl}-1-(4-phenylphenyl)-1H,4H,5H-pyrazolo[3,4-d]pyrimidin-4-one;
5-{[4-hydroxy-1-(2-methyl-1,3-oxazole-5-carbonyl)piperidin-4-yl]methyl}-1-(4-phenylphenyl)-1H,4H,5H-pyrazolo[3,4-d]pyrimidin-4-one;
5-{[1-(4-fluorobenzoyl)-4-hydroxypiperidin-4-yl]methyl}-1-{4-[1-(oxan-4-yl)-1H-pyrazol-4-yl]phenyl)-1H,4H,5H-pyrazolo[3,4-d]pyrimidin-4-one;
5-{[1-(4-fluorobenzoyl)-4-hydroxypiperidin-4-yl]methyl}-1-{4-[1-(oxetan-3-yl)-1H-pyrazol-4-yl]phenyl)-1H,4H,5H-pyrazolo[3,4-d]pyrimidin-4-one;
5-([1-(4-fluorobenzoyl)-4-hydroxypiperidin-4-yl]methyl}-1-{4-[1-(1-hydroxy-2-methylpropan-2-yl)-1H-pyrazol-4-yl]phenyl)-1H,4H,5H-pyrazolo[3,4-d]pyrimidin-4-one;
5-([1-(4-fluorobenzoyl)-4-hydroxypiperidin-4-yl]methyl}-1-{4-[1-(2-hydroxy-2-methylpropyl)-1H-pyrazol-4-yl]phenyl)-1H,4H,5H-pyrazolo[3,4-d]pyrimidin-4-one;
1-(4-{7-azaspiro[3.5]nonan-7-yl}phenyl)-5-[(1-cyclopropanecarbonyl-4-hydroxypiperidin-4-yl)methyl]-1H,4H,5H-pyrazolo[3,4-d]pyrimidin-4-one;
1-(4-{3-azaspiro[5.5]undecan-3-yl}phenyl)-5-{[1-(4-fluorobenzoyl)-4-hydroxypiperidin-4-yl]methyl)-1H,4H,5H-pyrazolo[3,4-d]pyrimidin-4-one;
5-{[1-(3-aminobenzoyl)-4-hydroxypiperidin-4-yl]methyl}-1-phenyl-1H,4H,5H-pyrazolo[3,4-d]pyrimidin-4-one;
1-(4-{3-azaspiro[5.5]undecan-3-yl}phenyl)-5-[(1-cyclopropanecarbonyl-4-hydroxypiperidin-4-yl)methyl]-1H,4H,5H-pyrazolo[3,4-d]pyrimidin-4-one;
5-{[1-(4-fluorobenzoyl)-4-hydroxypiperidin-4-yl]methyl}-1-(4-{9-methyl-3,9-diazaspiro[5.5]undecan-3-yl}phenyl)-1H,4H,5H-pyrazolo[3,4-d]pyrimidin-4-one;
5-[(1-cyclopropanecarbonyl-4-hydroxypiperidin-4-yl)methyl]-1-(4-{9-methyl-3,9-diazaspiro[5.5]undecan-3-yl}phenyl)-1H,4H,5H-pyrazolo[3,4-d]pyrimidin-4-one;
5-{[1-(4-fluorobenzoyl)-4-hydroxypiperidin-4-yl]methyl}-1-[4-(4-methyl-1H-pyrazol-1-yl)phenyl]-1H,4H,5H-pyrazolo[3,4-d]pyrimidin-4-one;
5-{[1-(4-fluorobenzoyl)-4-hydroxypiperidin-4-yl]methyl}-1-{4-[4-(trifluoromethyl)-1H-pyrazol-1-yl]phenyl)-1H,4H,5H-pyrazolo[3,4-d]pyrimidin-4-one;
5-[(1-acetyl-4-hydroxypiperidin-4-yl)methyl]-1-(4-chlorophenyl)-1H,4H,5H-pyrazolo[3,4-d]pyrimidin-4-one;

1-(4-chlorophenyl)-5-{[4-hydroxy-1-(1H-pyrazole-3-carbonyl)piperidin-4-yl]methyl}-1H,4H,5H-pyrazolo[3,4-d]pyrimidin-4-one;
1-(4-chlorophenyl)-5-{[1-(5-cyclopropyl-1H-pyrazole-3-carbonyl)-4-hydroxypiperidin-4-yl]methyl)-1H,4H,5H-pyrazolo[3,4-d]pyrimidin-4-one;
1-(4-chlorophenyl)-5-{[4-hydroxy-1-(3-methyl-1,2-oxazole-5-carbonyl)piperidin-4-yl]methyl}-1H,4H,5H-pyrazolo[3,4-d]pyrimidin-4-one;
1-(4-chlorophenyl)-5-[(4-hydroxy-1-{imidazo[1,2-a]pyridine-6-carbonyl}piperidin-4-yl)methyl]-1H,4H,5H-pyrazolo[3,4-d]pyrimidin-4-one;
1-(4-chlorophenyl)-5-[(1-cyclobutanecarbonyl-4-hydroxypiperidin-4-yl)methyl]-1H,4H,5H-pyrazolo[3,4-d]pyrimidin-4-one;
1-(4-chlorophenyl)-5-{[4-hydroxy-1-(1-methylcyclopropanecarbonyl)piperidin-4-yl]methyl}-1H,4H,5H-pyrazolo[3,4-d]pyrimidin-4-one;
1-(4-chlorophenyl)-5-{[4-hydroxy-1-(5-methyl-1,2-oxazole-3-carbonyl)piperidin-4-yl]methyl}-1H,4H,5H-pyrazolo[3,4-d]pyrimidin-4-one;
1-(4-chlorophenyl)-5-{[4-hydroxy-1-(5-methyl-1H-pyrazole-3-carbonyl)piperidin-4-yl]methyl}-1H,4H,5H-pyrazolo[3,4-d]pyrimidin-4-one;
1-(4-chlorophenyl)-5-{[1-(1,3-dimethyl-1H-pyrazole-5-carbonyl)-4-hydroxypiperidin-4-yl]methyl}-1H,4H,5H-pyrazolo[3,4-d]pyrimidin-4-one;
5-{[4-hydroxy-1-(1-methylcyclopropanecarbonyl)piperidin-4-yl]methyl}-1-{4-[3-(morpholin-4-yl)azetidin-1-yl]phenyl)-1H,4H,5H-pyrazolo[3,4-d]pyrimidin-4-one;
5-{[4-hydroxy-1-(1-methylcyclopropanecarbonyl)piperidin-4-yl]methyl}-1-{3-[3-(morpholin-4-yl)azetidin-1-yl]phenyl)-1H,4H,5H-pyrazolo[3,4-d]pyrimidin-4-one;
rel-5-{[4-hydroxy-1-(1-methylcyclopropanecarbonyl)piperidin-4-yl]methyl}-1-{4-[(3R,5S)-3,4,5-trimethylpiperazin-1-yl]phenyl)-1H,4H,5H-pyrazolo[3,4-d]pyrimidin-4-one;
1-{4-[(3S)-3,4-dimethylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;
N-{4-[4-hydroxy-4-({4-oxo-1-phenyl-1H,4H,5H-pyrazolo[3,4-d]pyrimidin-5-yl}methyl)piperidine-1-carbonyl]phenyl}methanesulfonamide;
1-{4-[(3R)-3,4-dimethylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one
5-{[4-hydroxy-1-(1-methylcyclopropanecarbonyl)piperidin-4-yl]methyl}-1-[4-(4-methylpiperazin-1-yl)phenyl]-1H,4H,5H-pyrazolo[3,4-d]pyrimidin-4-one;
5-{[4-hydroxy-1-(1-methylcyclopropanecarbonyl)piperidin-4-yl]methyl}-1-{4-[4-(oxetan-3-yl)piperidin-1-yl]phenyl)-1H,4H,5H-pyrazolo[3,4-d]pyrimidin-4-one;
5-{[4-hydroxy-1-(1-methylcyclopropanecarbonyl)piperidin-4-yl]methyl}-1-(4-{6-oxa-3-azabicyclo[3.1.1]heptan-3-yl}phenyl)-1H,4H,5H-pyrazolo[3,4-d]pyrimidin-4-one;
5-{[4-hydroxy-1-(1-methylcyclopropanecarbonyl)piperidin-4-yl]methyl}-1-(3-{8-methyl-3,8-diazabicyclo[3.2.1]octan-3-yl}phenyl)-1H,4H,5H-pyrazolo[3,4-d]pyrimidin-4-one;
5-{[4-hydroxy-1-(1-methylcyclopropanecarbonyl)piperidin-4-yl]methyl}-1-[3-(3,4,5-trimethylpiperazin-1-yl)phenyl]-1H,4H,5H-pyrazolo[3,4-d]pyrimidin-4-one;

1-{3-[(3S)-3,4-dimethylpiperazin-1-yl]phenyl}-5-{[4-hydroxy-1-(1-methylcyclopropanecarbonyl)piperidin-4-yl]methyl}-1H,4H,5H-pyrazolo[3,4-d]pyrimidin-4-one;

1-(4-chlorophenyl)-5-{[4-hydroxy-1-(6-methoxypyridine-3-carbonyl)piperidin-4-yl]methyl}-1H,4H,5H-pyrazolo[3,4-d]pyrimidin-4-one;

1-(4-chlorophenyl)-5-{[1-(6-fluoropyridine-3-carbonyl)-4-hydroxypiperidin-4-yl]methyl}-1H,4H,5H-pyrazolo[3,4-d]pyrimidin-4-one;

1-(4-chlorophenyl)-5-[(4-hydroxy-1-{imidazo[1,5-a]pyridine-6-carbonyl)piperidin-4-yl)methyl]-1H,4H,5H-pyrazolo[3,4-d]pyrimidin-4-one;

1-(4-chlorophenyl)-5-({4-hydroxy-1-[4-(4-hydroxypiperidin-1-yl)benzoyl]piperidin-4-yl}methyl)-1H,4H,5H-pyrazolo[3,4-d]pyrimidin-4-one;

1-(4-chlorophenyl)-5-{[4-hydroxy-1-(4,4,4-trifluoro-3-hydroxy-3-methylbutanoyl)piperidin-4-yl]methyl}-1H,4H,5H-pyrazolo[3,4-d]pyrimidin-4-one;

5-{[1-(2-amino-4-fluorobenzoyl)-4-hydroxypiperidin-4-yl]methyl}-1-(4-chlorophenyl)-1H,4H,5H-pyrazolo[3,4-d]pyrimidin-4-one;

5-[(1-cyclopropanecarbonyl-4-hydroxypiperidin-4-yl)methyl]-1-(4-{4H,5H,6H,7H-pyrazolo[1,5-a]pyrimidin-4-yl}phenyl)-1H,4H,5H-pyrazolo[3,4-d]pyrimidin-4-one;

5-{[1-(4-fluorobenzoyl)-4-hydroxypiperidin-4-yl]methyl}-1-(4-{4H,5H,6H,7H-pyrazolo[1,5-a]pyrimidin-4-yl}phenyl)-1H,4H,5H-pyrazolo[3,4-d]pyrimidin-4-one;

5-[(1-cyclopropanecarbonyl-4-hydroxypiperidin-4-yl)methyl]-1-{4-[(3S)-3-hydroxypyrrolidin-1-yl]phenyl}-1H,4H,5H-pyrazolo[3,4-d]pyrimidin-4-one;

1-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-3-(propan-2-yl)urea;

5-[(1-cyclopropanecarbonyl-4-hydroxypiperidin-4-yl)methyl]-1-[4-(3-hydroxy-3-methylpyrrolidin-1-yl)phenyl]-1H,4H,5H-pyrazolo[3,4-d]pyrimidin-4-one;

5-{[4-hydroxy-1-(4-methyl-1,3-oxazole-5-carbonyl)piperidin-4-yl]methyl}-1-(4-phenylphenyl)-1H,4H,5H-pyrazolo[3,4-d]pyrimidin-4-one;

5-([1-(2-cyclopropyl-1,3-oxazole-5-carbonyl)-4-hydroxypiperidin-4-yl]methyl}-1-(4-phenylphenyl)-1H,4H,5H-pyrazolo[3,4-d]pyrimidin-4-one;

5-({4-hydroxy-1-[3-(hydroxymethyl)benzoyl]piperidin-4-yl}methyl)-1-phenyl-1H,4H,5H-pyrazolo[3,4-d]pyrimidin-4-one;

5-{[4-hydroxy-1-(5-methoxypyridine-2-carbonyl)piperidin-4-yl]methyl}-1-(4-phenylphenyl)-1H,4H,5H-pyrazolo[3,4-d]pyrimidin-4-one;

5-{[4-hydroxy-1-(6-methoxypyridine-3-carbonyl)piperidin-4-yl]methyl}-1-(4-phenylphenyl)-1H,4H,5H-pyrazolo[3,4-d]pyrimidin-4-one;

5-{[1-(6-fluoropyridine-3-carbonyl)-4-hydroxypiperidin-4-yl]methyl}-1-(4-phenylphenyl)-1H,4H,5H-pyrazolo[3,4-d]pyrimidin-4-one;

5-[(4-hydroxy-1-{5H,6H,7H-pyrazolo[3,2-b][1,3]oxazine-2-carbonyl)piperidin-4-yl)methyl]-1-(4-phenylphenyl)-1H,4H,5H-pyrazolo[3,4-d]pyrimidin-4-one;

5-[(4-hydroxy-1-{imidazo[1,5-a]pyridine-6-carbonyl)piperidin-4-yl)methyl]-1-(4-phenylphenyl)-1H,4H,5H-pyrazolo[3,4-d]pyrimidin-4-one;

5-({4-hydroxy-1-[4-(1H-1,2,3-triazol-1-yl)benzoyl]piperidin-4-yl}methyl)-1-(4-phenylphenyl)-1H,4H,5H-pyrazolo[3,4-d]pyrimidin-4-one;

4-({1-[3-(4-chloro-1H-pyrazol-1-yl)phenyl]-4-oxo-1H,4H,5H-pyrazolo[3,4-d]pyrimidin-5-yl}methyl)-4-hydroxy-N,N-dimethylpiperidine-1-carboxamide;

5-[(1-cyclopropanecarbonyl-4-hydroxypiperidin-4-yl)methyl]-1-[4-(oxan-4-yloxy)phenyl]-1H,4H,5H-pyrazolo[3,4-d]pyrimidin-4-one;

5-{[1-(4-fluorobenzoyl)-4-hydroxypiperidin-4-yl]methyl}-1-[4-(1H-pyrazol-1-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-[3-(trifluoromethyl)-5H,6H,7H,8H-[1,2,4]triazolo[4,3-a]pyrimidin-8-yl]phenyl}-1H,4H,5H-pyrazolo[3,4-d]pyrimidin-4-one;

5-{[4-hydroxy-1-(2-hydroxybenzoyl)piperidin-4-yl]methyl}-1-phenyl-1H,4H,5H-pyrazolo[3,4-d]pyrimidin-4-one;

5-({1-(4-fluorobenzoyl)-4-hydroxypiperidin-4-yl]methyl}-1-[4-(pyridin-3-yl)phenyl]-1H,4H,5H-pyrazolo[3,4-d]pyrimidin-4-one;

5-({1-(4-fluorobenzoyl)-4-hydroxypiperidin-4-yl]methyl}-1-[4-(pyrimidin-5-yl)phenyl]-1H,4H,5H-pyrazolo[3,4-d]pyrimidin-4-one;

5-{[1-(4-fluorobenzoyl)-4-hydroxypiperidin-4-yl]methyl}-1-[4-(1-methyl-1H-pyrazol-4-yl)phenyl]-1H,4H,5H-pyrazolo[3,4-d]pyrimidin-4-one;

5-[(1-cyclopropanecarbonyl-4-hydroxypiperidin-4-yl)methyl]-1-(4-{4H,6H,7H-pyrazolo[3,2-c][1,4]oxazin-3-yl}phenyl)-1H,4H,5H-pyrazolo[3,4-d]pyrimidin-4-one;

5-{[4-hydroxy-1-(1-methylcyclopropanecarbonyl)piperidin-4-yl]methyl}-1-{4-[3-(2-hydroxypropan-2-yl)azetidin-1-yl]phenyl}-1H,4H,5H-pyrazolo[3,4-d]pyrimidin-4-one;

1-[3-(4,4-difluoropiperidin-1-yl)phenyl]-5-{[4-hydroxy-1-(1-methylcyclopropanecarbonyl) piperidin-4-yl]methyl)-1H,4H,5H-pyrazolo[3,4-d]pyrimidin-4-one;

5-{[4-hydroxy-1-(1-methylcyclopropanecarbonyl)piperidin-4-yl]methyl}-1-{3-[3-(2-hydroxypropan-2-yl)azetidin-1-yl]phenyl}-1H,4H,5H-pyrazolo[3,4-d]pyrimidin-4-one;

5-{[4-hydroxy-1-(1-methylcyclopropanecarbonyl)piperidin-4-yl]methyl}-1-[4-(3-hydroxyazetidin-1-yl)phenyl]-1H,4H,5H-pyrazolo[3,4-d]pyrimidin-4-one;

5-{[4-hydroxy-1-(1-methylcyclopropanecarbonyl)piperidin-4-yl]methyl}-1-[3-(3-hydroxyazetidin-1-yl)phenyl]-1H,4H,5H-pyrazolo[3,4-d]pyrimidin-4-one;

1-[4-(3-fluoroazetidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one;

5-{[4-hydroxy-1-(1H-pyrazole-3-carbonyl)piperidin-4-yl]methyl}-1-phenyl-1H,4H,5H-pyrazolo[3,4-d]pyrimidin-4-one;

1-[3-(3-fluoroazetidin-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one;

1-(4-fluorophenyl)-5-{[4-hydroxy-1-(4-{3-methyl-3,8-diazabicyclo[3.2.1]octan-8-yl}benzoyl)piperidin-4-yl]methyl)-1H,4H,5H-pyrazolo[3,4-d]pyrimidin-4-one;

5-{[1-(4-{1,4-diazabicyclo[3.2.2]nonan-4-yl}benzoyl)-4-hydroxypiperidin-4-yl]methyl}-1-(4-fluorophenyl)-1H,4H,5H-pyrazolo[3,4-d]pyrimidin-4-one;

5-[(1-{4-[(9aS)-octahydro-1H-pyrrolo[1,2-a][1,4]diazepin-2-yl]benzoyl}-4-hydroxypiperidin-4-yl)methyl]-1-(4-fluorophenyl)-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-{4-[4-(hydroxymethyl)-1H-pyrazol-1-yl]phenyl)-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-{4-[4-(trifluoromethyl)-1H-pyrazol-1-yl]phenyl)-1H,4H,5H-pyrazolo[3,4-d]pyrimidin-4-one;

1-[4-(4-chloro-1H-pyrazol-1-yl)phenyl]-5-{[1-(2-cyclopropyl-1,3-oxazole-5-carbonyl)-4-hydroxypiperidin-4-yl]methyl)-1H,4H,5H-pyrazolo[3,4-d]pyrimidin-4-one;

5-{[4-hydroxy-1-(2-methyl-1,3-oxazole-5-carbonyl)piperidin-4-yl]methyl}-1-{4-[4-(hydroxymethyl)-1H-pyrazol-1-yl]phenyl)-1H,4H,5H-pyrazolo[3,4-d]pyrimidin-4-one;

5-{[4-hydroxy-1-(2-methyl-1,3-oxazole-5-carbonyl)piperidin-4-yl]methyl}-1-{4-[4-(trifluoromethyl)-1H-pyrazol-1-yl]phenyl)-1H,4H,5H-pyrazolo[3,4-d]pyrimidin-4-one;

1-{3-[(3R)-3,4-dimethylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

5-{[4-hydroxy-1-(1H-indazole-6-carbonyl)piperidin-4-yl]methyl}-1-phenyl-1H,4H,5H-pyrazolo[3,4-d]pyrimidin-4-one;

5-{[4-hydroxy-1-(1-methylcyclopropanecarbonyl)piperidin-4-yl]methyl}-1-[3-(4-methylpiperazin-1-yl)phenyl]-1H,4H,5H-pyrazolo[3,4-d]pyrimidin-4-one;

5-{[4-hydroxy-1-(1-methylcyclopropanecarbonyl)piperidin-4-yl]methyl}-1-{3-[4-(oxetan-3-yl)piperidin-1-yl]phenyl)-1H,4H,5H-pyrazolo[3,4-d]pyrimidin-4-one;

5-{[4-hydroxy-1-(1-methylcyclopropanecarbonyl)piperidin-4-yl]methyl}-1-(3-{6-oxa-3-azabicyclo[3.1.1]heptan-3-yl}phenyl)-1H,4H,5H-pyrazolo[3,4-d]pyrimidin-4-one;

1-{4-[3-(difluoromethyl)-4-methylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

1-{3-[3-(difluoromethyl)-4-methylpiperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

rel-3-({1-[(3R)-4,4-difluoro-3-(3-fluoro-1H-pyrazol-1-yl)butanoyl]-4-hydroxypiperidin-4-yl}methyl)-7-methyl-3H,4H,7H-pyrrolo[2,3-d]pyrimidin-4-one;

rel-3-({1-[(3R)-4,4-difluoro-3-(3-fluoro-1H-pyrazol-1-yl)butanoyl]-4-hydroxypiperidin-4-yl}methyl)-7-methyl-3H,4H,7H-pyrrolo[2,3-d]pyrimidin-4-one;

rel-5-({1-[(3R)-4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one;

rel-5-({1-[(3R)-4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one;

1-{3-[4-(2,2-difluoroethyl)piperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

5-{[1-(2-aminobenzoyl)-4-hydroxypiperidin-4-yl]methyl}-1-phenyl-1H,4H,5H-pyrazolo[3,4-d]pyrimidin-4-one;

N-[(2R)-2-benzyl-3-[4-hydroxy-4-({1-methyl-4-oxo-1H,4H,5H-pyrazolo[3,4-d]pyrimidin-5-yl}methyl)piperidin-1-yl]-3-oxopropyl]ethene-1-sulfonamide;

5-{[4-hydroxy-1-(1-methylcyclopropanecarbonyl)piperidin-4-yl]methyl}-1-{3-[4-(oxetan-3-yl)piperazin-1-yl]phenyl)-1H,4H,5H-pyrazolo[3,4-d]pyrimidin-4-one;

5-{[4-hydroxy-1-(1-methylcyclopropanecarbonyl)piperidin-4-yl]methyl}-1-{4-[4-(oxetan-3-yl)piperazin-1-yl]phenyl)-1H,4H,5H-pyrazolo[3,4-d]pyrimidin-4-one;

1-{3-[(1S,4S)-5-acetyl-2,5-diazabicyclo[2.2.1]heptan-2-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

4-{[1-(4-fluorophenyl)-4-oxo-1H,4H,5H-pyrazolo[3,4-d]pyrimidin-5-yl]methyl}-N-[(4-fluorophenyl}methyl]-4-hydroxypiperidine-1-carboxamide;

4-{[1-(4-fluorophenyl)-4-oxo-1H,4H,5H-pyrazolo[3,4-d]pyrimidin-5-yl]methyl)-4-hydroxy-N-phenylpiperidine-1-carboxamide;

N-(4-fluorophenyl)-4-{[1-(4-fluorophenyl)-4-oxo-1H,4H,5H-pyrazolo[3,4-d]pyrimidin-5-yl]methyl}-4-hydroxypiperidine-1-carboxamide;

4-{[1-(4-fluorophenyl)-4-oxo-1H,4H,5H-pyrazolo[3,4-d]pyrimidin-5-yl]methyl}-4-hydroxy-N-(3-methoxypropyl)piperidine-1-carboxamide;

N-cyclopropyl-4-{[1-(4-fluorophenyl)-4-oxo-1H,4H,5H-pyrazolo[3,4-d]pyrimidin-5-yl]methyl}-4-hydroxypiperidine-1-carboxamide;

4-{[1-(4-fluorophenyl)-4-oxo-1H,4H,5H-pyrazolo[3,4-d]pyrimidin-5-yl]methyl}-4-hydroxy-N-(pyridin-3-yl)piperidine-1-carboxamide;

5-[(1-cyclopropanecarbonyl-4-hydroxypiperidin-4-yl)methyl]-1-[4-(3-hydroxyazetidine-1-carbonyl)phenyl]-1H,4H,5H-pyrazolo[3,4-d]pyrimidin-4-one;

N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]ethene-1-sulfonamide;

5-{[4-hydroxy-1-(1-methylcyclopropanecarbonyl)piperidin-4-yl]methyl}-1-[4-(3-methyl-1H-pyrazol-1-yl)phenyl]-1H,4H,5H-pyrazolo[3,4-d]pyrimidin-4-one;

5-{[4-hydroxy-1-(3-methyloxetane-3-carbonyl)piperidin-4-yl]methyl}-1-[4-(3-methyl-1H-pyrazol-1-yl)phenyl]-1H,4H,5H-pyrazolo[3,4-d]pyrimidin-4-one;

1-{4-[4-(2,2-difluoroethyl)piperazin-1-yl]phenyl)-5-{[4-hydroxy-1-(1-methylcyclopropanecarbonyl)piperidin-4-yl]methyl)-1H,4H,5H-pyrazolo[3,4-d]pyrimidin-4-one;

5-{[4-hydroxy-1-(3-methyloxetane-3-carbonyl)piperidin-4-yl]methyl}-1-[4-(1H-pyrazol-1-yl)phenyl]-1H,4H,5H-pyrazolo[3,4-d]pyrimidin-4-one;

5-{[4-hydroxy-1-(1-methylcyclopropanecarbonyl)piperidin-4-yl]methyl}-1-(4-{3-oxa-9-azaspiro[5.5]undecan-9-yl}phenyl)-1H,4H,5H-pyrazolo[3,4-d]pyrimidin-4-one;

5-{[4-hydroxy-1-(1-methylcyclopropanecarbonyl)piperidin-4-yl]methyl}-1-(4-{1-oxa-8-azaspiro[4.5]decan-8-yl}phenyl)-1H,4H,5H-pyrazolo[3,4-d]pyrimidin-4-one;

5-{[4-hydroxy-1-(1-methylcyclopropanecarbonyl)piperidin-4-yl]methyl}-1-(4-{2-oxa-7-azaspiro[3.5]nonan-7-yl}phenyl)-1H,4H,5H-pyrazolo[3,4-d]pyrimidin-4-one;

5-{[4-hydroxy-1-(1-methylcyclobutanecarbonyl)piperidin-4-yl]methyl}-1-{4-[4-(trifluoromethyl)-1H-pyrazol-1-yl]phenyl)-1H,4H,5H-pyrazolo[3,4-d]pyrimidin-4-one;

1-(4-{2,2-difluoro-7-azaspiro[3.5]nonan-7-yl}phenyl)-5-{[4-hydroxy-1-(1-methylcyclobutanecarbonyl)piperidin-4-yl]methyl)-1H,4H,5H-pyrazolo[3,4-d]pyrimidin-4-one;

5-{[4-hydroxy-1-(1-methylcyclobutanecarbonyl)piperidin-4-yl]methyl}-1-{4-[1-(oxan-4-yl)-1H-pyrazol-4-yl]phenyl}-1H,4H,5H-pyrazolo[3,4-d]pyrimidin-4-one;

3-[4-hydroxy-4-({4-oxo-1-phenyl-1H,4H,5H-pyrazolo[3,4-d]pyrimidin-5-yl}methyl)piperidine-1-carbonyl]benzamide;

1-[4-(1-cyclopropyl-1H-pyrazol-4-yl)phenyl]-5-{[4-hydroxy-1-(1-methylcyclobutanecarbonyl)piperidin-4-yl]methyl}-1H,4H,5H-pyrazolo[3,4-d]pyrimidin-4-one;

1-{4-[1-(difluoromethyl)-1H-pyrazol-4-yl]phenyl}-5-{[4-hydroxy-1-(1-methylcyclobutanecarbonyl)piperidin-4-yl]methyl}-1H,4H,5H-pyrazolo[3,4-d]pyrimidin-4-one;

5-{[4-hydroxy-1-(1-methylcyclopropanecarbonyl)piperidin-4-yl]methyl}-1-{4-[1-(oxan-4-yl)-1H-pyrazol-4-yl]phenyl}-1H,4H,5H-pyrazolo[3,4-d]pyrimidin-4-one;

1-[4-(1-cyclopropyl-1H-pyrazol-4-yl)phenyl]-5-{[4-hydroxy-1-(1-methylcyclopropanecarbonyl) piperidin-4-yl]methyl}-1H,4H,5H-pyrazolo[3,4-d]pyrimidin-4-one;

1-(4-fluorophenyl)-5-{[4-hydroxy-1-(4-{1-methyl-octahydro-1H-pyrrolo[3,4-b]pyridin-6-yl}benzoyl)piperidin-4-yl]methyl)-1H,4H,5H-pyrazolo[3,4-d]pyrimidin-4-one;

5-[(1-cyclopropanecarbonyl-4-hydroxypiperidin-4-yl)methyl]-1-[4-(4-methylpyridin-2-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(5-methylpyridin-2-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(1,2,3,4-tetrahydro-1,5-naphthyridin-1-yl)phenyl]-1H,4H,5H-pyrazolo[3,4-d]pyrimidin-4-one;

1-[4-(4,4-difluoropiperidin-1-yl)phenyl]-5-{[4-hydroxy-1-(1-methylcyclopropanecarbonyl) piperidin-4-yl]methyl}-1H,4H,5H-pyrazolo[3,4-d]pyrimidin-4-one;

5-{[1-(4-fluorobenzoyl)-4-hydroxypiperidin-4-yl]methyl}-1-[4-(1,2,3,4-tetrahydro-1,6-naphthyridin-1-yl)phenyl]-1H,4H,5H-pyrazolo[3,4-d]pyrimidin-4-one;

N-{4-[4-hydroxy-4-({4-oxo-1-phenyl-1H,4H,5H-pyrazolo[3,4-d]pyrimidin-5-yl}methyl)piperidine-1-carbonyl]phenyl}ethene-1-sulfonamide;

5-{[1-(4-fluorobenzoyl)-4-hydroxypiperidin-4-yl]methyl}-1-[4-(1,2,3,4-tetrahydro-1,5-naphthyridin-1-yl)phenyl]-1H,4H,5H-pyrazolo[3,4-d]pyrimidin-4-one;

5-{[4-hydroxy-1-(1-methylcyclopropanecarbonyl)piperidin-4-yl]methyl}-1-{3-[3-(oxan-4-yl)azetidin-1-yl]phenyl}-1H,4H,5H-pyrazolo[3,4-d]pyrimidin-4-one;

1-[4-(4-chloro-1H-pyrazol-1-yl)phenyl]-5-{[4-hydroxy-1-(2-methyl-1,3-oxazole-5-carbonyl)piperidin-4-yl]methyl}-1H,4H,5H-pyrazolo[3,4-d]pyrimidin-4-one;

5-{[1-(4-fluorobenzoyl)-4-hydroxypiperidin-4-yl]methyl}-1-{4-[4-(hydroxymethyl)-1H-pyrazol-1-yl]phenyl}-1H,4H,5H-pyrazolo[3,4-d]pyrimidin-4-one;

5-[(1-{4-[(8aS)-octahydropyrrolo[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one;

5-[(1-cyclopropanecarbonyl-4-hydroxypiperidin-4-yl)methyl]-1-(4-{pyrazolo[1,5-a]pyridin-3-yl}phenyl)-1H,4H,5H-pyrazolo[3,4-d]pyrimidin-4-one;

5-[(1-cyclopropanecarbonyl-4-hydroxypiperidin-4-yl)methyl]-1-{4-[5-(trifluoromethyl)pyridin-3-yl]phenyl}-1H,4H,5H-pyrazolo[3,4-d]pyrimidin-4-one;

1-[4-(1,2-benzoxazol-4-yl)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-(4-{2-hydroxy-7-azaspiro[3.5]nonan-7-yl}phenyl)-1H,4H,5H-pyrazolo[3,4-d]pyrimidin-4-one;

5-{[1-(4-fluorobenzoyl)-4-hydroxypiperidin-4-yl]methyl}-1-{4-[2-(hydroxymethyl)-7-azaspiro[3.5]nonan-7-yl]phenyl}-1H,4H,5H-pyrazolo[3,4-d]pyrimidin-4-one;

5-[(1-cyclopropanecarbonyl-4-hydroxypiperidin-4-yl)methyl]-1-{4-[2-(hydroxymethyl)-7-azaspiro[3.5]nonan-7-yl]phenyl}-1H,4H,5H-pyrazolo[3,4-d]pyrimidin-4-one;

5-[(1-cyclopropanecarbonyl-4-hydroxypiperidin-4-yl)methyl]-1-(4-{2,2-difluoro-7-azaspiro[3.5]nonan-7-yl}phenyl)-1H,4H,5H-pyrazolo[3,4-d]pyrimidin-4-one;

1-{4-[1-(difluoromethyl)-1H-pyrazol-4-yl]phenyl}-5-{[1-(4-fluorobenzoyl)-4-hydroxypiperidin-4-yl]methyl}-1H,4H,5H-pyrazolo[3,4-d]pyrimidin-4-one;

4-{4-[4-(5-{[1-(4-fluorobenzoyl)-4-hydroxypiperidin-4-yl]methyl)-4-oxo-1H,4H,5H-pyrazolo[3,4-d]pyrimidin-1-yl]phenyl}-1H-pyrazol-1-yl}-1λ6-thiane-1,1-dione;

3-{4-[4-(5-{[1-(4-fluorobenzoyl)-4-hydroxypiperidin-4-yl]methyl)-4-oxo-1H,4H,5H-pyrazolo[3,4-d]pyrimidin-1-yl]phenyl}-1H-pyrazol-1-yl}-1λ6-thietane-1,1-dione;

1-[4-(1-cyclopropyl-1H-pyrazol-4-yl)phenyl]-5-{[1-(4-fluorobenzoyl)-4-hydroxypiperidin-4-yl]methyl)-1H,4H,5H-pyrazolo[3,4-d]pyrimidin-4-one;

1-{4-[(1S,4S)-5-acetyl-2,5-diazabicyclo[2.2.1]heptan-2-yl]phenyl}-5-{[4-hydroxy-1-(1-methylcyclopropanecarbonyl)piperidin-4-yl]methyl}-1H,4H,5H-pyrazolo[3,4-d]pyrimidin-4-one;

1-{3-[(1R,4R)-5-acetyl-2,5-diazabicyclo[2.2.1]heptan-2-yl]phenyl}-5-{[4-hydroxy-1-(1-methylcyclopropanecarbonyl)piperidin-4-yl]methyl}-1H,4H,5H-pyrazolo[3,4-d]pyrimidin-4-one;

1-{4-[(1R,4R)-5-acetyl-2,5-diazabicyclo[2.2.1]heptan-2-yl]phenyl}-5-{[4-hydroxy-1-(1-methylcyclopropanecarbonyl)piperidin-4-yl]methyl}-1H,4H,5H-pyrazolo[3,4-d]pyrimidin-4-one;

5-({4-hydroxy-1-[(3R)-3-(1H-pyrazol-1-yl)butanoyl]piperidin-4-yl}methyl)-1-phenyl-1H,4H,5H-pyrazolo[3,4-d]pyrimidin-4-one;

5-{[4-hydroxy-1-(1-methylcyclopropanecarbonyl)piperidin-4-yl]methyl}-1-{3-[4-(2-methoxyethyl)piperazin-1-yl]phenyl}-1H,4H,5H-pyrazolo[3,4-d]pyrimidin-4-one;

1-[3-(5-{[4-hydroxy-1-(1-methylcyclopropanecarbonyl)piperidin-4-yl]methyl)-4-oxo-1H,4H,5H-pyrazolo[3,4-d]pyrimidin-1-yl)phenyl]piperidine-4-carbonitrile;

1-[4-(5-{[4-hydroxy-1-(1-methylcyclopropanecarbonyl)piperidin-4-yl]methyl)-4-oxo-1H,4H,5H-pyrazolo[3,4-d]pyrimidin-1-yl)phenyl]piperidine-4-carbonitrile;

5-({1-[4,4-difluoro-3-(3-fluoro-1H-pyrazol-1-yl)butanoyl]-4-hydroxypiperidin-4-yl}methyl)-1-methyl-1H,4H,5H-pyrazolo[3,4-d]pyrimidin-4-one  1-[4-(3-fluoro-1H-pyrazol-1-yl)phenyl]-5-{[4-hydroxy-1-(1-methylcyclopropanecarbonyl)piperidin-4-yl]methyl)-1H,4H,5H-pyrazolo[3,4-d]pyrimidin-4-one;

1-(4-{6-azaspiro[2.5]octan-6-yl}phenyl)-5-[(1-cyclopropanecarbonyl-4-hydroxypiperidin-4-yl)methyl]-1H,4H,5H-pyrazolo[3,4-d]pyrimidin-4-one;

5-{[1-(4-fluorobenzoyl)-4-hydroxypiperidin-4-yl]methyl}-1-{4-[(3-methyloxetan-3-yl)methoxy]phenyl}-1H,4H,5H-pyrazolo[3,4-d]pyrimidin-4-one;

2-[2-(dimethylamino)ethoxy]ethyl 4-{[1-(4-fluorophenyl)-4-oxo-1H,4H,5H-pyrazolo[3,4-d]pyrimidin-5-yl]methyl)-4-hydroxypiperidine-1-carboxylate;

2-(1H-imidazol-1-yl)ethyl 4-{[1-(4-fluorophenyl)-4-oxo-1H,4H,5H-pyrazolo[3,4-d]pyrimidin-5-yl]methyl)-4-hydroxypiperidine-1-carboxylate;

5-({4-hydroxy-1-[(3S)-3-(1H-pyrazol-1-yl)butanoyl]piperidin-4-yl}methyl)-1-phenyl-1H,4H,5H-pyrazolo[3,4-d]pyrimidin-4-one;

1-methylpiperidin-4-yl 4-{[1-(4-fluorophenyl)-4-oxo-1H,4H,5H-pyrazolo[3,4-d]pyrimidin-5-yl]methyl)-4-hydroxypiperidine-1-carboxylate;

5-[(1-cyclopropanecarbonyl-4-hydroxypiperidin-4-yl)methyl]-1-[4-(3-methyl-1,2-benzoxazol-5-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(1-methyl-1H-indazol-6-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(3-methyl-1H-indazol-7-yl)phenyl]-1H,4H,5H-pyrazolo[3,4-d]pyrimidin-4-one;

1-[4-(1,2-benzoxazol-5-yl)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-(4-{5H,6H,7H,8H-[1,2,4]triazolo[4,3-a]pyridin-3-yl}phenyl)-1H,4H,5H-pyrazolo[3,4-d]pyrimidin-4-one;

5-[(1-cyclopropanecarbonyl-4-hydroxypiperidin-4-yl)methyl]-1-(4-{1H-pyrrolo[3,2-b]pyridin-5-yl}phenyl)-1H,4H,5H-pyrazolo[3,4-d]pyrimidin-4-one;

5-[(1-cyclopropanecarbonyl-4-hydroxypiperidin-4-yl)methyl]-1-{4-[2-(trifluoromethyl)pyrimidin-4-yl]phenyl}-1H,4H,5H-pyrazolo[3,4-d]pyrimidin-4-one;

(S)-3-((1-(4,4-difluoro-3-(3-fluoro-1H-pyrazol-1-yl)butanoyl)-4-hydroxypiperidin-4-yl}methyl)-7-(4-fluorophenyl)-6-methyl-3,7-dihydro-4H-pyrrolo[2,3-d]pyrimidin-4-one;

(R)-3-((1-(4,4-difluoro-3-(3-fluoro-1H-pyrazol-1-yl)butanoyl)-4-hydroxypiperidin-4-yl}methyl)-7-(4-fluorophenyl)-6-methyl-3,7-dihydro-4H-pyrrolo[2,3-d]pyrimidin-4-one;

7-(4-fluorophenyl)-3-((4-hydroxy-1-((1r,4r)-4-({1-methyl-1H-pyrazol-3-yl)oxy)cyclohexane-1-carbonyl)piperidin-4-yl}methyl)-6-methyl-3,7-dihydro-4H-pyrrolo[2,3-d]pyrimidin-4-one;

7-(4-fluorophenyl)-3-((4-hydroxy-1-((1s,4s)-4-({1-methyl-1H-pyrazol-3-yl)oxy)cyclohexane-1-carbonyl)piperidin-4-yl}methyl)-6-methyl-3,7-dihydro-4H-pyrrolo[2,3-d]pyrimidin-4-one;

(S)-3-((1-(4,4-difluoro-3-(3-fluoro-1H-pyrazol-1-yl)butanoyl)-4-hydroxypiperidin-4-yl}methyl)-7-(4-morpholinophenyl)-3,7-dihydro-4H-pyrrolo[2,3-d]pyrimidin-4-one;

(S)-3-((1-(4,4-difluoro-3-(3-fluoro-1H-pyrazol-1-yl)butanoyl)-4-hydroxypiperidin-4-yl}methyl)-7-(3-morpholinophenyl)-3,7-dihydro-4H-pyrrolo[2,3-d]pyrimidin-4-one;

(R)-3-((1-(4,4-difluoro-3-(3-fluoro-1H-pyrazol-1-yl)butanoyl)-4-hydroxypiperidin-4-yl}methyl)-7-(4-morpholinophenyl)-3,7-dihydro-4H-pyrrolo[2,3-d]pyrimidin-4-one;

(R)-3-((1-(4,4-difluoro-3-(3-fluoro-1H-pyrazol-1-yl)butanoyl)-4-hydroxypiperidin-4-yl}methyl)-7-(3-morpholinophenyl)-3,7-dihydro-4H-pyrrolo[2,3-d]pyrimidin-4-one;

1-(4-((3,3-difluoro-1-methylcyclobutyl)methoxy)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;

(S)—N-(2-benzyl-3-(4-hydroxy-4-((4-oxo-1-phenyl-1,4-dihydro-5H-pyrazolo[3,4-d]pyrimidin-5-yl}methyl)piperidin-1-yl)-3-oxopropyl)ethenesulfonamide;

1-(4-(1-(difluoromethyl)-1H-pyrazol-4-yl)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;

1-(4-(3,3-difluorocyclobutoxy)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;

5-({4-hydroxy-1-[(3R)-3-(1H-pyrrol-1-yl)butanoyl]piperidin-4-yl}methyl)-1-phenyl-1H,4H,5H-pyrazolo[3,4-d]pyrimidin-4-one;

5-({4-hydroxy-1-[(3S)-3-(1H-pyrrol-1-yl)butanoyl]piperidin-4-yl}methyl)-1-phenyl-1H,4H,5H-pyrazolo[3,4-d]pyrimidin-4-one;

4-[4-hydroxy-4-({4-oxo-1-phenyl-1H,4H,5H-pyrazolo[3,4-d]pyrimidin-5-yl}methyl)piperidine-1-carbonyl]benzamide;

5-[(1-benzoyl-4-hydroxypiperidin-4-yl)methyl]-1-(2-hydroxyphenyl)-1H,4H,5H-pyrazolo[3,4-d]pyrimidin-4-one;

5-({4-hydroxy-1-[4-(methoxymethyl)benzoyl]piperidin-4-yl}methyl)-1-phenyl-1H,4H,5H-pyrazolo[3,4-d]pyrimidin-4-one;

N-{3-[4-hydroxy-4-({4-oxo-1-phenyl-1H,4H,5H-pyrazolo[3,4-d]pyrimidin-5-yl}methyl)piperidine-1-carbonyl]phenyl}acetamide;

4-[4-hydroxy-4-({4-oxo-1-phenyl-1H,4H,5H-pyrazolo[3,4-d]pyrimidin-5-yl}methyl)piperidine-1-carbonyl]-N-methylbenzene-1-sulfonamide;

4-[4-hydroxy-4-({4-oxo-1-phenyl-1H,4H,5H-pyrazolo[3,4-d]pyrimidin-5-yl}methyl)piperidine-1-carbonyl]-N-methylbenzamide;

5-[(1-cyclohexanecarbonyl-4-hydroxypiperidin-4-yl)methyl]-1-phenyl-1H,4H,5H-pyrazolo[3,4-d]pyrimidin-4-one;

5-[(1-benzoyl-4-hydroxypiperidin-4-yl)methyl]-1-(3-hydroxyphenyl)-1H,4H,5H-pyrazolo[3,4-d]pyrimidin-4-one;

5-([1-(4-fluorobenzoyl)-4-hydroxypiperidin-4-yl]methyl}-1-phenyl-1H,4H,5H-pyrazolo[3,4-d]pyrimidin-4-one;

5-{[4-hydroxy-1-(pyridine-4-carbonyl)piperidin-4-yl]methyl}-1-phenyl-1H,4H,5H-pyrazolo[3,4-d]pyrimidin-4-one;

5-{[4-hydroxy-1-(4,4,4-trifluorobutanoyl)piperidin-4-yl]methyl}-1-phenyl-1H,4H,5H-pyrazolo[3,4-d]pyrimidin-4-one;

5-{[1-(3-ethoxypropanoyl)-4-hydroxypiperidin-4-yl]methyl}-1-phenyl-1H,4H,5H-pyrazolo[3,4-d]pyrimidin-4-one;

5-[(1-cyclobutanecarbonyl-4-hydroxypiperidin-4-yl)methyl]-1-phenyl-1H,4H,5H-pyrazolo[3,4-d]pyrimidin-4-one;

5-[(1-cyclopentanecarbonyl-4-hydroxypiperidin-4-yl)methyl]-1-phenyl-1H,4H,5H-pyrazolo[3,4-d]pyrimidin-4-one;

5-{[1-(2,2-dimethylpropanoyl)-4-hydroxypiperidin-4-yl]methyl}-1-phenyl-1H,4H,5H-pyrazolo[3,4-d]pyrimidin-4-one;

5-{[1-(3,5-dimethylbenzoyl)-4-hydroxypiperidin-4-yl]methyl}-1-phenyl-1H,4H,5H-pyrazolo[3,4-d]pyrimidin-4-one;

5-{[4-hydroxy-1-(3-methylbenzoyl}piperidin-4-yl]methyl}-1-phenyl-1H,4H,5H-pyrazolo[3,4-d]pyrimidin-4-one;

5-{[4-hydroxy-1-(4-methylbenzoyl}piperidin-4-yl]methyl}-1-phenyl-1H,4H,5H-pyrazolo[3,4-d]pyrimidin-4-one;

5-{[1-(2-fluoro-4-phenylbenzoyl)-4-hydroxypiperidin-4-yl]methyl}-1-methyl-1H,4H,5H-pyrazolo[3,4-d]pyrimidin-4-one;

5-({1-[3-(aminomethyl}benzoyl]-4-hydroxypiperidin-4-yl}methyl)-1-phenyl-1H,4H,5H-pyrazolo[3,4-d]pyrimidin-4-one;

5-([1-(3,4-dimethylbenzoyl)-4-hydroxypiperidin-4-yl]methyl}-1-phenyl-1H,4H,5H-pyrazolo[3,4-d]pyrimidin-4-one;

5-([1-(3-fluoro-4-methoxybenzoyl)-4-hydroxypiperidin-4-yl]methyl}-1-phenyl-1H,4H,5H-pyrazolo[3,4-d]pyrimidin-4-one;

5-([1-(2,3-dihydro-1-benzofuran-5-carbonyl)-4-hydroxypiperidin-4-yl]methyl}-1-phenyl-1H,4H,5H-pyrazolo[3,4-d]pyrimidin-4-one;

5-([1-(3,5-dimethoxybenzoyl)-4-hydroxypiperidin-4-yl]methyl}-1-phenyl-1H,4H,5H-pyrazolo[3,4-d]pyrimidin-4-one;

5-([1-(3-fluorobenzoyl)-4-hydroxypiperidin-4-yl]methyl}-1-phenyl-1H,4H,5H-pyrazolo[3,4-d]pyrimidin-4-one;

5-([1-(2-fluorobenzoyl)-4-hydroxypiperidin-4-yl]methyl}-1-phenyl-1H,4H,5H-pyrazolo[3,4-d]pyrimidin-4-one;

5-([1-(2-fluoro-3-methylbenzoyl)-4-hydroxypiperidin-4-yl]methyl}-1-phenyl-1H,4H,5H-pyrazolo[3,4-d]pyrimidin-4-one;

5-([1-(3,4-difluorobenzoyl)-4-hydroxypiperidin-4-yl]methyl}-1-phenyl-1H,4H,5H-pyrazolo[3,4-d]pyrimidin-4-one;

5-([1-(2,5-difluorobenzoyl)-4-hydroxypiperidin-4-yl]methyl}-1-phenyl-1H,4H,5H-pyrazolo[3,4-d]pyrimidin-4-one;

5-([1-(2,4-difluorobenzoyl)-4-hydroxypiperidin-4-yl]methyl}-1-phenyl-1H,4H,5H-pyrazolo[3,4-d]pyrimidin-4-one;

5-([1-(3-chloro-4-fluorobenzoyl)-4-hydroxypiperidin-4-yl]methyl}-1-phenyl-1H,4H,5H-pyrazolo[3,4-d]pyrimidin-4-one;

5-([1-(3-chloro-4-methylbenzoyl)-4-hydroxypiperidin-4-yl]methyl}-1-phenyl-1H,4H,5H-pyrazolo[3,4-d]pyrimidin-4-one;

5-([1-(4-chloro-3-methylbenzoyl)-4-hydroxypiperidin-4-yl]methyl}-1-phenyl-1H,4H,5H-pyrazolo[3,4-d]pyrimidin-4-one;

5-([1-(3,4-dichlorobenzoyl)-4-hydroxypiperidin-4-yl]methyl}-1-phenyl-1H,4H,5H-pyrazolo[3,4-d]pyrimidin-4-one;

5-([1-(3-chloro-4-methoxybenzoyl)-4-hydroxypiperidin-4-yl]methyl}-1-phenyl-1H,4H,5H-pyrazolo[3,4-d]pyrimidin-4-one;

5-{[4-hydroxy-1-(2-methylbenzoyl}piperidin-4-yl]methyl}-1-phenyl-1H,4H,5H-pyrazolo[3,4-d]pyrimidin-4-one;

5-([1-(2,5-dimethylbenzoyl)-4-hydroxypiperidin-4-yl]methyl}-1-phenyl-1H,4H,5H-pyrazolo[3,4-d]pyrimidin-4-one;

5-{[1-(2,4-dimethylbenzoyl)-4-hydroxypiperidin-4-yl]methyl}-1-phenyl-1H,4H,5H-pyrazolo[3,4-d]pyrimidin-4-one;

5-{[1-(5-chloro-2-methoxybenzoyl)-4-hydroxypiperidin-4-yl]methyl}-1-phenyl-1H,4H,5H-pyrazolo[3,4-d]pyrimidin-4-one;

5-{[1-(4-chloro-2-methoxybenzoyl)-4-hydroxypiperidin-4-yl]methyl}-1-phenyl-1H,4H,5H-pyrazolo[3,4-d]pyrimidin-4-one;

3-{5-[(1-benzoyl-4-hydroxypiperidin-4-yl)methyl]-4-oxo-1H,4H,5H-pyrazolo[3,4-d]pyrimidin-1-yl}benzoic acid;

5-{[1-(2,3-dimethoxybenzoyl)-4-hydroxypiperidin-4-yl]methyl}-1-phenyl-1H,4H,5H-pyrazolo[3,4-d]pyrimidin-4-one;

5-{[1-(2,5-dimethoxybenzoyl)-4-hydroxypiperidin-4-yl]methyl}-1-phenyl-1H,4H,5H-pyrazolo[3,4-d]pyrimidin-4-one;

5-{[1-(2,4-dimethoxybenzoyl)-4-hydroxypiperidin-4-yl]methyl}-1-phenyl-1H,4H,5H-pyrazolo[3,4-d]pyrimidin-4-one;

5-{[1-(2,5-dichlorobenzoyl)-4-hydroxypiperidin-4-yl]methyl}-1-phenyl-1H,4H,5H-pyrazolo[3,4-d]pyrimidin-4-one;

5-{[1-(2,4-dichlorobenzoyl)-4-hydroxypiperidin-4-yl]methyl}-1-phenyl-1H,4H,5H-pyrazolo[3,4-d]pyrimidin-4-one;

5-{[4-hydroxy-1-(pyridine-3-carbonyl)piperidin-4-yl]methyl}-1-phenyl-1H,4H,5H-pyrazolo[3,4-d]pyrimidin-4-one;

5-{[1-(4-chloro-3-methoxybenzoyl)-4-hydroxypiperidin-4-yl]methyl}-1-phenyl-1H,4H,5H-pyrazolo[3,4-d]pyrimidin-4-one;

5-{[4-hydroxy-1-(5-methylpyrazine-2-carbonyl)piperidin-4-yl]methyl}-1-phenyl-1H,4H,5H-pyrazolo[3,4-d]pyrimidin-4-one;

5-{[4-hydroxy-1-(pyridine-2-carbonyl)piperidin-4-yl]methyl}-1-phenyl-1H,4H,5H-pyrazolo[3,4-d]pyrimidin-4-one;

5-{[1-(1,5-dimethyl-1H-pyrazole-3-carbonyl)-4-hydroxypiperidin-4-yl]methyl}-1-phenyl-1H,4H,5H-pyrazolo[3,4-d]pyrimidin-4-one;

5-((1-[4-(cyclopropylamino)benzoyl]-4-hydroxypiperidin-4-yl}methyl)-1-phenyl-1H,4H,5H-pyrazolo[3,4-d]pyrimidin-4-one;

5-{[1-(dimethyl-1,3-thiazole-5-carbonyl)-4-hydroxypiperidin-4-yl]methyl}-1-phenyl-1H,4H,5H-pyrazolo[3,4-d]pyrimidin-4-one;

5-{[4-hydroxy-1-(1,2,3-thiadiazole-4-carbonyl)piperidin-4-yl]methyl}-1-phenyl-1H,4H,5H-pyrazolo[3,4-d]pyrimidin-4-one;

5-{[1-(2-amino-4-chlorobenzoyl)-4-hydroxypiperidin-4-yl]methyl}-1-phenyl-1H,4H,5H-pyrazolo[3,4-d]pyrimidin-4-one;

5-{[1-(2-amino-5-chlorobenzoyl)-4-hydroxypiperidin-4-yl]methyl}-1-phenyl-1H,4H,5H-pyrazolo[3,4-d]pyrimidin-4-one;

5-{[1-(2-amino-3-methylbenzoyl)-4-hydroxypiperidin-4-yl]methyl}-1-phenyl-1H,4H,5H-pyrazolo[3,4-d]pyrimidin-4-one;
5-{[4-hydroxy-1-(5-methyl-1,2-oxazole-3-carbonyl)piperidin-4-yl]methyl}-1-phenyl-1H,4H,5H-pyrazolo[3,4-d]pyrimidin-4-one;
5-{[4-hydroxy-1-(5-methyl-1H-pyrazole-3-carbonyl)piperidin-4-yl]methyl}-1-phenyl-1H,4H,5H-pyrazolo[3,4-d]pyrimidin-4-one;
5-{[4-hydroxy-1-(4-methyl-1,3-thiazole-5-carbonyl)piperidin-4-yl]methyl}-1-phenyl-1H,4H,5H-pyrazolo[3,4-d]pyrimidin-4-one;
5-{[4-hydroxy-1-(6-methylpyridine-3-carbonyl)piperidin-4-yl]methyl}-1-phenyl-1H,4H,5H-pyrazolo[3,4-d]pyrimidin-4-one;
5-({4-hydroxy-1-[2-(trifluoromethyl)pyrimidine-5-carbonyl]piperidin-4-yl}methyl)-1-phenyl-1H,4H,5H-pyrazolo[3,4-d]pyrimidin-4-one;
5-([1-(5-fluoropyridine-2-carbonyl)-4-hydroxypiperidin-4-yl]methyl}-1-phenyl-1H,4H,5H-pyrazolo[3,4-d]pyrimidin-4-one;
5-([1-(5-ethyl-1,3-oxazole-4-carbonyl)-4-hydroxypiperidin-4-yl]methyl}-1-phenyl-1H,4H,5H-pyrazolo[3,4-d]pyrimidin-4-one;
5-([1-(3-fluoro-4-methylbenzoyl)-4-hydroxypiperidin-4-yl]methyl}-1-phenyl-1H,4H,5H-pyrazolo[3,4-d]pyrimidin-4-one;
5-([1-(3-fluoro-2-methylbenzoyl)-4-hydroxypiperidin-4-yl]methyl}-1-phenyl-1H,4H,5H-pyrazolo[3,4-d]pyrimidin-4-one;
5-([1-(5-fluoro-2-methylbenzoyl)-4-hydroxypiperidin-4-yl]methyl}-1-phenyl-1H,4H,5H-pyrazolo[3,4-d]pyrimidin-4-one;
5-([1-(dimethyl-1,2-oxazole-4-carbonyl)-4-hydroxypiperidin-4-yl]methyl}-1-phenyl-1H,4H,5H-pyrazolo[3,4-d]pyrimidin-4-one;
5-([1-(2,3-difluorobenzoyl)-4-hydroxypiperidin-4-yl]methyl}-1-phenyl-1H,4H,5H-pyrazolo[3,4-d]pyrimidin-4-one;
5-{[4-hydroxy-1-(1H-indole-4-carbonyl)piperidin-4-yl]methyl}-1-phenyl-1H,4H,5H-pyrazolo[3,4-d]pyrimidin-4-one;
5-([1-(4,4-dimethylpentanoyl)-4-hydroxypiperidin-4-yl]methyl}-1-phenyl-1H,4H,5H-pyrazolo[3,4-d]pyrimidin-4-one;
5-{[4-hydroxy-1-(oxane-4-carbonyl)piperidin-4-yl]methyl}-1-phenyl-1H,4H,5H-pyrazolo[3,4-d]pyrimidin-4-one;
1-(4-tert-butylphenyl)-5-[(1-cyclopropanecarbonyl-4-hydroxypiperidin-4-yl)methyl]-1H,4H,5H-pyrazolo[3,4-d]pyrimidin-4-one;
5-{[4-hydroxy-1-(1-methyl-1H-pyrrole-2-carbonyl)piperidin-4-yl]methyl}-1-phenyl-1H,4H,5H-pyrazolo[3,4-d]pyrimidin-4-one;
5-{[1-(3,3-difluorocyclobutanecarbonyl)-4-hydroxypiperidin-4-yl]methyl}-1-phenyl-1H,4H,5H-pyrazolo[3,4-d]pyrimidin-4-one;
5-{[4-hydroxy-1-(2-phenyl-1,3-oxazole-5-carbonyl)piperidin-4-yl]methyl}-1-phenyl-1H,4H,5H-pyrazolo[3,4-d]pyrimidin-4-one;
N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]prop-2-ynamide;
5-[(1-cyclopropanecarbonyl-4-hydroxypiperidin-4-yl)methyl]-1-(2,4,6-trimethylphenyl)-1H,4H,5H-pyrazolo[3,4-d]pyrimidin-4-one;
5-[(1-cyclopropanecarbonyl-4-hydroxypiperidin-4-yl)methyl]-1-(2,4-dichlorophenyl)-1H,4H,5H-pyrazolo[3,4-d]pyrimidin-4-one;
5-[(1-benzoyl-4-hydroxypiperidin-4-yl)methyl]-1-(4-fluorophenyl)-1H,4H,5H-pyrazolo[3,4-d]pyrimidin-4-one;
1-(4-fluorophenyl)-5-{[4-hydroxy-1-(4-methoxybenzoyl)piperidin-4-yl]methyl}-1H,4H,5H-pyrazolo[3,4-d]pyrimidin-4-one;
5-([1-(4-fluorobenzoyl)-4-hydroxypiperidin-4-yl]methyl}-1-(4-fluorophenyl)-1H,4H,5H-pyrazolo[3,4-d]pyrimidin-4-one;
5-[(1-cyclopropanecarbonyl-4-hydroxypiperidin-4-yl)methyl]-1-[4-(propan-2-yl)phenyl]-1H,4H,5H-pyrazolo[3,4-d]pyrimidin-4-one;
5-{[4-hydroxy-1-(1-methylcyclopropanecarbonyl)piperidin-4-yl]methyl}-1-phenyl-1H,4H,5H-pyrazolo[3,4-d]pyrimidin-4-one;
4-[4-hydroxy-4-({4-oxo-1-phenyl-1H,4H,5H-pyrazolo[3,4-d]pyrimidin-5-yl}methyl)piperidine-1-carbonyl]benzoic acid;
5-({4-hydroxy-1-[4-(trifluoromethoxy)benzoyl]piperidin-4-yl}methyl)-1-phenyl-1H,4H,5H-pyrazolo[3,4-d]pyrimidin-4-one;
5-({1-[4-(difluoromethoxy)benzoyl]-4-hydroxypiperidin-4-yl}methyl)-1-phenyl-1H,4H,5H-pyrazolo[3,4-d]pyrimidin-4-one;
5-[(1-cyclopropanecarbonyl-4-hydroxypiperidin-4-yl)methyl]-1-(4-phenylphenyl)-1H,4H,5H-pyrazolo[3,4-d]pyrimidin-4-one;
5-({4-hydroxy-1-[1-(trifluoromethyl)cyclopropanecarbonyl]piperidin-4-yl}methyl)-1-phenyl-1H,4H,5H-pyrazolo[3,4-d]pyrimidin-4-one;
4-{[1-(4-fluorophenyl)-4-oxo-1H,4H,5H-pyrazolo[3,4-d]pyrimidin-5-yl]methyl}-4-hydroxy-N,N-dimethylpiperidine-1-carboxamide;
5-[(1-cyclopropanecarbonyl-4-hydroxypiperidin-4-yl)methyl]-1-[4-(trifluoromethyl)phenyl]-1H,4H,5H-pyrazolo[3,4-d]pyrimidin-4-one;
5-([1-(4-chlorobenzoyl)-4-hydroxypiperidin-4-yl]methyl}-1-phenyl-1H,4H,5H-pyrazolo[3,4-d]pyrimidin-4-one;
5-[(1-benzoyl-4-hydroxypiperidin-4-yl)methyl]-1-[3-(hydroxymethyl)phenyl]-1H,4H,5H-pyrazolo[3,4-d]pyrimidin-4-one;
5-([1-(4-chloroquinoline-7-carbonyl)-4-hydroxypiperidin-4-yl]methyl}-1-phenyl-1H,4H,5H-pyrazolo[3,4-d]pyrimidin-4-one;
5-([1-(4-cyclopropoxybenzoyl)-4-hydroxypiperidin-4-yl]methyl}-1-(4-fluorophenyl)-1H,4H,5H-pyrazolo[3,4-d]pyrimidin-4-one;
4-([1-(4-fluorophenyl)-4-oxo-1H,4H,5H-pyrazolo[3,4-d]pyrimidin-5-yl]methyl}-4-hydroxy-N-methylpiperidine-1-carboxamide;
5-([1-(2-chloropyridine-4-carbonyl)-4-hydroxypiperidin-4-yl]methyl}-1-phenyl-1H,4H,5H-pyrazolo[3,4-d]pyrimidin-4-one;
5-([1-(2,5-dichloropyridine-4-carbonyl)-4-hydroxypiperidin-4-yl]methyl}-1-phenyl-1H,4H,5H-pyrazolo[3,4-d]pyrimidin-4-one;
5-[(1-{bicyclo[1.1.1]pentane-1-carbonyl}-4-hydroxypiperidin-4-yl)methyl]-1-phenyl-1H,4H,5H-pyrazolo[3,4-d]pyrimidin-4-one;
1-cyclohexyl-5-[(1-cyclopropanecarbonyl-4-hydroxypiperidin-4-yl)methyl]-1H,4H,5H-pyrazolo[3,4-d]pyrimidin-4-one;

5-({4-hydroxy-1-[3-(trifluoromethyl)bicyclo[1.1.1]pentane-1-carbonyl]piperidin-4-yl}methyl)-1-phenyl-1H,4H,5H-pyrazolo[3,4-d]pyrimidin-4-one;
5-({4-hydroxy-1-[4-(1,1,1-trifluoro-2-hydroxypropan-2-yl)benzoyl]piperidin-4-yl}methyl)-1-phenyl-1H,4H,5H-pyrazolo[3,4-d]pyrimidin-4-one;
2-cyano-N-[(1r,3r)-3-[4-hydroxy-4-({4-oxo-1-phenyl-1H,4H,5H-pyrazolo[3,4-d]pyrimidin-5-yl}methyl)piperidine-1-carbonyl]cyclobutyl]acetamide;
5-({1-[4-(1,1-difluoroethyl}benzoyl]-4-hydroxypiperidin-4-yl}methyl)-1-phenyl-1H,4H,5H-pyrazolo[3,4-d]pyrimidin-4-one;
5-[(1-cyclopropanecarbonyl-4-hydroxypiperidin-4-yl)methyl]-1-(4-phenoxyphenyl)-1H,4H,5H-pyrazolo[3,4-d]pyrimidin-4-one;
5-({4-hydroxy-1-[4-(4-methylphenoxy)benzoyl]piperidin-4-yl}methyl)-1-methyl-1H,4H,5H-pyrazolo[3,4-d]pyrimidin-4-one;
5-[(1-cyclopropanecarbonyl-4-hydroxypiperidin-4-yl)methyl]-1-(pyridin-3-yl}-1H,4H,5H-pyrazolo[3,4-d]pyrimidin-4-one;
(R)-5-((1-(2-benzylazetidine-1-carbonyl)-4-hydroxypiperidin-4-yl}methyl)-1-(4-fluorophenyl)-1H-pyrazolo[3,4-d]pyrimidin-4(5H)-one;
(S)-5-((1-(2-benzylazetidine-1-carbonyl)-4-hydroxypiperidin-4-yl}methyl)-1-(4-fluorophenyl)-1H-pyrazolo[3,4-d]pyrimidin-4(5H)-one;
5-((1-(2-benzylazetidine-1-carbonyl)-4-hydroxypiperidin-4-yl}methyl)-1-(4-fluorophenyl)-1H-pyrazolo[3,4-d]pyrimidin-4(5H)-one;
5-([1-(4-chlorobenzoyl)-4-hydroxypiperidin-4-yl]methyl}-1-(4-fluorophenyl)-1H,4H,5H-pyrazolo[3,4-d]pyrimidin-4-one;
5-([1-(3-chlorobenzoyl)-4-hydroxypiperidin-4-yl]methyl}-1-(4-fluorophenyl)-1H,4H,5H-pyrazolo[3,4-d]pyrimidin-4-one;
5-([1-(4-cyclopropylbenzoyl)-4-hydroxypiperidin-4-yl]methyl}-1-(4-fluorophenyl)-1H,4H,5H-pyrazolo[3,4-d]pyrimidin-4-one;
5-([1-(3-chloro-1-methyl-1H-pyrazole-4-carbonyl)-4-hydroxypiperidin-4-yl]methyl}-1-phenyl-1H,4H,5H-pyrazolo[3,4-d]pyrimidin-4-one;
5-({1-[4-(difluoromethoxy)benzoyl]-4-hydroxypiperidin-4-yl}methyl)-1-(4-fluorophenyl)-1H,4H,5H-pyrazolo[3,4-d]pyrimidin-4-one;
1-(4-fluorophenyl)-5-{[4-hydroxy-1-(4-methylbenzoyl}piperidin-4-yl]methyl}-1H,4H,5H-pyrazolo[3,4-d]pyrimidin-4-one;
5-([1-(3-fluoro-4-methoxybenzoyl)-4-hydroxypiperidin-4-yl]methyl}-1-(4-fluorophenyl)-1H,4H,5H-pyrazolo[3,4-d]pyrimidin-4-one;
5-([1-(3,4-difluorobenzoyl)-4-hydroxypiperidin-4-yl]methyl}-1-(4-fluorophenyl)-1H,4H,5H-pyrazolo[3,4-d]pyrimidin-4-one;
5-[(1-cyclopropanecarbonyl-4-hydroxypiperidin-4-yl)methyl]-1-(4-methanesulfonylphenyl)-1H,4H,5H-pyrazolo[3,4-d]pyrimidin-4-one;
5-{[1-(2,4-difluorobenzoyl)-4-hydroxypiperidin-4-yl]methyl}-1-(4-fluorophenyl)-1H,4H,5H-pyrazolo[3,4-d]pyrimidin-4-one;
5-{[1-(3-chloro-4-methoxybenzoyl)-4-hydroxypiperidin-4-yl]methyl}-1-(4-fluorophenyl)-1H,4H,5H-pyrazolo[3,4-d]pyrimidin-4-one;
1-(4-fluorophenyl)-5-{[4-hydroxy-1-(4-methyl-1,3-oxazole-5-carbonyl)piperidin-4-yl]methyl}-1H,4H,5H-pyrazolo[3,4-d]pyrimidin-4-one;
5-{[1-(dimethyl-1,3-oxazole-5-carbonyl)-4-hydroxypiperidin-4-yl]methyl}-1-(4-fluorophenyl)-1H,4H,5H-pyrazolo[3,4-d]pyrimidin-4-one;
5-{[1-(2-cyclopropyl-1,3-oxazole-5-carbonyl)-4-hydroxypiperidin-4-yl]methyl}-1-(4-fluorophenyl)-1H,4H,5H-pyrazolo[3,4-d]pyrimidin-4-one;
5-{{1-[2-(dimethylamino)-1,3-oxazole-5-carbonyl]-4-hydroxypiperidin-4-yl}methyl)-1-(4-fluorophenyl)-1H,4H,5H-pyrazolo[3,4-d]pyrimidin-4-one;
5-[(1-benzoyl-4-hydroxypiperidin-4-yl)methyl]-1-(4-phenoxyphenyl)-1H,4H,5H-pyrazolo[3,4-d]pyrimidin-4-one;
5-{[1-(2,4-dichlorobenzoyl)-4-hydroxypiperidin-4-yl]methyl}-1-(4-fluorophenyl)-1H,4H,5H-pyrazolo[3,4-d]pyrimidin-4-one;
5-[(1-cyclopropanecarbonyl-4-hydroxypiperidin-4-yl)methyl]-1-(pyridin-4-yl}-1H,4H,5H-pyrazolo[3,4-d]pyrimidin-4-one;
5-[(1-cyclopropanecarbonyl-4-hydroxypiperidin-4-yl)methyl]-1-(3,4-dichlorophenyl)-1H,4H,5H-pyrazolo[3,4-d]pyrimidin-4-one;
5-[(1-cyclopropanecarbonyl-4-hydroxypiperidin-4-yl)methyl]-1-[4-(3-fluorophenyl)phenyl]-1H,4H,5H-pyrazolo[3,4-d]pyrimidin-4-one;
4-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzamide;
5-[(1-cyclopropanecarbonyl-4-hydroxypiperidin-4-yl)methyl]-1-{4-[4-(pyrrolidine-1-carbonyl)phenyl]phenyl)-1H,4H,5H-pyrazolo[3,4-d]pyrimidin-4-one;
5-[(1-cyclopropanecarbonyl-4-hydroxypiperidin-4-yl)methyl]-1-[4-(3,4-dimethoxyphenyl)phenyl]-1H,4H,5H-pyrazolo[3,4-d]pyrimidin-4-one;
5-[(1-cyclopropanecarbonyl-4-hydroxypiperidin-4-yl)methyl]-1-[4-(2,4-difluorophenyl)phenyl]-1H,4H,5H-pyrazolo[3,4-d]pyrimidin-4-one;
5-[(1-cyclopropanecarbonyl-4-hydroxypiperidin-4-yl)methyl]-1-[4-(3,5-difluorophenyl)phenyl]-1H,4H,5H-pyrazolo[3,4-d]pyrimidin-4-one;
3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile;
5-[(1-cyclopropanecarbonyl-4-hydroxypiperidin-4-yl)methyl]-1-[3-(trifluoromethyl)phenyl]-1H,4H,5H-pyrazolo[3,4-d]pyrimidin-4-one;
4-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile;
5-[(1-cyclopropanecarbonyl-4-hydroxypiperidin-4-yl)methyl]-1-[3-(4-methoxyphenyl)phenyl]-1H,4H,5H-pyrazolo[3,4-d]pyrimidin-4-one;
5-[(1-cyclopropanecarbonyl-4-hydroxypiperidin-4-yl)methyl]-1-[3-(3-phenylphenyl)phenyl]-1H,4H,5H-pyrazolo[3,4-d]pyrimidin-4-one;
1-[3-(2-chlorophenyl)phenyl]-5-[(1-cyclopropanecarbonyl-4-hydroxypiperidin-4-yl)methyl]-1H,4H,5H-pyrazolo[3,4-d]pyrimidin-4-one;
5-[(1-cyclopropanecarbonyl-4-hydroxypiperidin-4-yl)methyl]-1-[3-(3-fluorophenyl)phenyl]-1H,4H,5H-pyrazolo[3,4-d]pyrimidin-4-one;
1-[3-(3-chlorophenyl)phenyl]-5-[(1-cyclopropanecarbonyl-4-hydroxypiperidin-4-yl)methyl]-1H,4H,5H-pyrazolo[3,4-d]pyrimidin-4-one;
5-[(1-cyclopropanecarbonyl-4-hydroxypiperidin-4-yl)methyl]-1-[3-(4-fluorophenyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(4-methanesulfonylphenyl)phenyl]-1H,4H,5H-pyrazolo[3,4-d]pyrimidin-4-one;

1-(4-chlorophenyl)-5-[(1-cyclopropanecarbonyl-4-hydroxypiperidin-4-yl)methyl]-1H,4H,5H-pyrazolo[3,4-d]pyrimidin-4-one;

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzamide;

5-[(1-cyclopropanecarbonyl-4-hydroxypiperidin-4-yl)methyl]-1-{3-[4-(pyrrolidine-1-carbonyl)phenyl]phenyl}-1H,4H,5H-pyrazolo[3,4-d]pyrimidin-4-one;

5-[(1-cyclopropanecarbonyl-4-hydroxypiperidin-4-yl)methyl]-1-[3-(3,4-dimethoxyphenyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(2,4-difluorophenyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(3,4-difluorophenyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(3,5-difluorophenyl)phenyl]-1H,4H,5H-pyrazolo[3,4-d]pyrimidin-4-one;

3-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile;

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)benzonitrile;

5-[(1-cyclopropanecarbonyl-4-hydroxypiperidin-4-yl)methyl]-1-{4-[3-(dimethylamino)phenyl]phenyl}-1H,4H,5H-pyrazolo[3,4-d]pyrimidin-4-one;

5-[(1-cyclopropanecarbonyl-4-hydroxypiperidin-4-yl)methyl]-1-{4-[2-methyl-4-(1H-pyrazol-1-yl)phenyl]phenyl}-1H,4H,5H-pyrazolo[3,4-d]pyrimidin-4-one;

5-[(1-cyclopropanecarbonyl-4-hydroxypiperidin-4-yl)methyl]-1-[4-(dimethyl-1,2-oxazol-4-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(pyridin-3-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(pyrimidin-5-yl)phenyl]-1H,4H,5H-pyrazolo[3,4-d]pyrimidin-4-one;

5-[(1-cyclopropanecarbonyl-4-hydroxypiperidin-4-yl)methyl]-1-[4-(1-methyl-1H-pyrazol-4-yl)phenyl]-1H,4H,5H-pyrazolo[3,4-d]pyrimidin-4-one;

5-[(1-cyclopropanecarbonyl-4-hydroxypiperidin-4-yl)methyl]-1-(4-{4-[2-(morpholin-4-yl)ethoxy]phenyl}phenyl)-1H,4H,5H-pyrazolo[3,4-d]pyrimidin-4-one;

5-[(1-cyclopropanecarbonyl-4-hydroxypiperidin-4-yl)methyl]-1-(4-{4-[2-(dimethylamino)ethoxy]phenyl}phenyl)-1H,4H,5H-pyrazolo[3,4-d]pyrimidin-4-one;

N-[2-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)phenyl]methanesulfonamide;

5-[(1-cyclopropanecarbonyl-4-hydroxypiperidin-4-yl)methyl]-1-[4-(2-methanesulfonylphenyl)phenyl]-1H,4H,5H-pyrazolo[3,4-d]pyrimidin-4-one;

5-[(1-cyclopropanecarbonyl-4-hydroxypiperidin-4-yl)methyl]-1-[4-(3-hydroxyphenyl)phenyl]-1H,4H,5H-pyrazolo[3,4-d]pyrimidin-4-one;

5-[(1-cyclopropanecarbonyl-4-hydroxypiperidin-4-yl)methyl]-1-[4-(5-fluoropyridin-3-yl)phenyl]-1H,4H,5H-pyrazolo[3,4-d]pyrimidin-4-one;

5-[(1-cyclopropanecarbonyl-4-hydroxypiperidin-4-yl)methyl]-1-{3-[3-(dimethylamino)phenyl]phenyl}-1H,4H,5H-pyrazolo[3,4-d]pyrimidin-4-one;

5-[(1-cyclopropanecarbonyl-4-hydroxypiperidin-4-yl)methyl]-1-{3-[4-(dimethylamino)phenyl]phenyl}-1H,4H,5H-pyrazolo[3,4-d]pyrimidin-4-one;

5-[(1-cyclopropanecarbonyl-4-hydroxypiperidin-4-yl)methyl]-1-[3-(dimethyl-1,2-oxazol-4-yl)phenyl]-1H,4H,5H-pyrazolo[3,4-d]pyrimidin-4-one;

5-[(1-cyclopropanecarbonyl-4-hydroxypiperidin-4-yl)methyl]-1-[3-(pyridin-3-yl)phenyl]-1H,4H,5H-pyrazolo[3,4-d]pyrimidin-4-one;

5-[(1-cyclopropanecarbonyl-4-hydroxypiperidin-4-yl)methyl]-1-[3-(pyrimidin-5-yl)phenyl]-1H,4H,5H-pyrazolo[3,4-d]pyrimidin-4-one;

5-[(1-cyclopropanecarbonyl-4-hydroxypiperidin-4-yl)methyl]-1-(4-fluorophenyl)-1H,4H,5H-pyrazolo[3,4-d]pyrimidin-4-one;

5-[(1-cyclopropanecarbonyl-4-hydroxypiperidin-4-yl)methyl]-1-[3-(1-methyl-1H-pyrazol-4-yl)phenyl]-1H,4H,5H-pyrazolo[3,4-d]pyrimidin-4-one;

4-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N-methylbenzamide;

5-[(1-cyclopropanecarbonyl-4-hydroxypiperidin-4-yl)methyl]-1-{3-[5-hydroxy-2-(trifluoromethoxy)phenyl]phenyl}-1H,4H,5H-pyrazolo[3,4-d]pyrimidin-4-one;

N-[2-(3-{5-[(1-cyclopropanecarbonyl-4-hydroxypiperidin-4-yl)methyl]-4-oxo-1H,4H,5H-pyrazolo[3,4-d]pyrimidin-1-yl}phenyl)phenyl]methanesulfonamide;

5-[(1-cyclopropanecarbonyl-4-hydroxypiperidin-4-yl)methyl]-1-[3-(2-methanesulfonylphenyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(3-hydroxyphenyl)phenyl]-1H,4H,5H-pyrazolo[3,4-d]pyrimidin-4-one;

5-[(1-cyclopropanecarbonyl-4-hydroxypiperidin-4-yl)methyl]-1-{3-[6-(dimethylamino)pyridin-3-yl]phenyl}-1H,4H,5H-pyrazolo[3,4-d]pyrimidin-4-one;

5-[(1-cyclopropanecarbonyl-4-hydroxypiperidin-4-yl)methyl]-1-[3-(5-fluoropyridin-3-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-[3-(morpholine-4-carbonyl)phenyl]phenyl}-1H,4H,5H-pyrazolo[3,4-d]pyrimidin-4-one;

5-[(1-cyclopropanecarbonyl-4-hydroxypiperidin-4-yl)methyl]-1-[4-(3,5-dimethyl-1H-pyrazol-4-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-[5-fluoro-2-(hydroxymethyl)phenyl]phenyl}-1H,4H,5H-pyrazolo[3,4-d]pyrimidin-4-one;

5-[(1-cyclopropanecarbonyl-4-hydroxypiperidin-4-yl)methyl]-1-[4-(3-fluoro-5-methoxyphenyl)phenyl]-1H,4H,5H-pyrazolo[3,4-d]pyrimidin-4-one;

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzene-1-sulfonamide;

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N,N-dimethylbenzamide;

3-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)-N-(2-hydroxyethyl)benzamide;

5-[(1-cyclopropanecarbonyl-4-hydroxypiperidin-4-yl)methyl]-1-[4-(1-methyl-1H-indazol-5-yl)phenyl]-1H,4H,5H-pyrazolo[3,4-d]pyrimidin-4-one;

5-[(1-cyclopropanecarbonyl-4-hydroxypiperidin-4-yl)
methyl]-1-{4-[3-(cyclopropylmethoxy)phenyl]phe-
nyl)-1H,4H,5H-pyrazolo[3,4-d]pyrimidin-4-one;
5-[(1-cyclopropanecarbonyl-4-hydroxypiperidin-4-yl)
methyl]-1-{4-[3-(pyrrolidin-1-yl)phenyl]phenyl)-1H,
4H,5H-pyrazolo[3,4-d]pyrimidin-4-one;
4-hydroxy-N-methyl-4-({1-methyl-4-oxo-1H,4H,5H-
pyrazolo[3,4-d]pyrimidin-5-yl}methyl)-N-(4-phe-
nylphenyl)piperidine-1-carboxamide;
N-[(1r,3r)-3-[4-hydroxy-4-({4-oxo-1-phenyl-1H,4H,5H-
pyrazolo[3,4-d]pyrimidin-5-yl}methyl)piperidine-1-
carbonyl]cyclobutyl]ethane-1-sulfonamide;
5-[(1-cyclopropanecarbonyl-4-hydroxypiperidin-4-yl)
methyl]-1-{3-[2-(dimethylamino)pyrimidin-5-yl]phe-
nyl)-1H,4H,5H-pyrazolo[3,4-d]pyrimidin-4-one;
5-[(1-cyclopropanecarbonyl-4-hydroxypiperidin-4-yl)
methyl]-1-{3-[2-(morpholin-4-yl)pyrimidin-5-yl]phe-
nyl)-1H,4H,5H-pyrazolo[3,4-d]pyrimidin-4-one;
1-[3-(5-chloropyridin-3-yl)phenyl]-5-[(1-cyclopropan-
ecarbonyl-4-hydroxypiperidin-4-yl)methyl]-1H,4H,
5H-pyrazolo[3,4-d]pyrimidin-4-one;
5-[(1-cyclopropanecarbonyl-4-hydroxypiperidin-4-yl)
methyl]-1-{3-[3-(morpholine-4-carbonyl)phenyl]phe-
nyl)-1H,4H,5H-pyrazolo[3,4-d]pyrimidin-4-one;
5-[(1-cyclopropanecarbonyl-4-hydroxypiperidin-4-yl)
methyl]-1-{3-[5-fluoro-2-(hydroxymethyl)phenyl]phe-
nyl)-1H,4H,5H-pyrazolo[3,4-d]pyrimidin-4-one;
5-[(1-cyclopropanecarbonyl-4-hydroxypiperidin-4-yl)
methyl]-1-[3-(3-fluoro-5-methoxyphenyl)phenyl]-1H,
4H,5H-pyrazolo[3,4-d]pyrimidin-4-one;
3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzene-1-sulfona-
mide;
5-[(1-cyclopropanecarbonyl-4-hydroxypiperidin-4-yl)
methyl]-1-[3-(1H-indol-4-yl)phenyl]-1H,4H,5H-pyra-
zolo[3,4-d]pyrimidin-4-one;
3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N,N-dimethylbenzamide;
3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N-methylbenzamide;
3-(3-{5-[(1-cyclopropanecarbonyl-4-hydroxypiperidin-4-
yl)methyl]-4-oxo-1H,4H,5H-pyrazolo[3,4-d]pyrimi-
din-1-yl}phenyl)-N-(2-hydroxyethyl)benzamide;
5-[(1-cyclopropanecarbonyl-4-hydroxypiperidin-4-yl)
methyl]-1-[3-(1-methyl-1H-indazol-5-yl)phenyl]-1H,
4H,5H-pyrazolo[3,4-d]pyrimidin-4-one;
5-[(1-cyclopropanecarbonyl-4-hydroxypiperidin-4-yl)
methyl]-1-{3-[3-(cyclopropylmethoxy)phenyl]phe-
nyl)-1H,4H,5H-pyrazolo[3,4-d]pyrimidin-4-one;
5-[(1-cyclopropanecarbonyl-4-hydroxypiperidin-4-yl)
methyl]-1-{3-[3-(pyrrolidin-1-yl)phenyl]phenyl)-1H,
4H,5H-pyrazolo[3,4-d]pyrimidin-4-one;
5-[(1-cyclopropanecarbonyl-4-hydroxypiperidin-4-yl)
methyl]-1-[3-(morpholin-4-ylmethyl)phenyl]-1H,4H,
5H-pyrazolo[3,4-d]pyrimidin-4-one;
1-(4-{[cyclohexyl(ethyl)amino]methyl}phenyl)-5-[(1-cy-
clopropanecarbonyl-4-hydroxypiperidin-4-yl)methyl]-
1H,4H,5H-pyrazolo[3,4-d]pyrimidin-4-one;
5-[(1-cyclopropanecarbonyl-4-hydroxypiperidin-4-yl)
methyl]-1-[4-(morpholin-4-ylmethyl)phenyl]-1H,4H,
5H-pyrazolo[3,4-d]pyrimidin-4-one;
1-(4-fluorophenyl)-5-{[4-hydroxy-1-(pyridine-4-carbo-
nyl)piperidin-4-yl]methyl)-1H,4H,5H-pyrazolo[3,4-d]
pyrimidin-4-one;
1-(4-fluorophenyl)-5-({4-hydroxy-1-[6-(morpholin-4-yl)
pyridine-3-carbonyl]piperidin-4-yl}methyl)-1H,4H,
5H-pyrazolo[3,4-d]pyrimidin-4-one;
1-(4-fluorophenyl)-5-({4-hydroxy-1-[6-(2,2,2-
trifluoroethoxy)pyridine-3-carbonyl]piperidin-4-
yl}methyl)-1H,4H,5H-pyrazolo[3,4-d]pyrimidin-4-
one;
1-(4-fluorophenyl)-5-{[4-hydroxy-1-(pyridine-3-carbo-
nyl)piperidin-4-yl]methyl)-1H,4H,5H-pyrazolo[3,4-d]
pyrimidin-4-one;
1-(4-fluorophenyl)-5-({4-hydroxy-1-[6-(trifluoromethyl)
pyridine-3-carbonyl]piperidin-4-yl}methyl)-1H,4H,
5H-pyrazolo[3,4-d]pyrimidin-4-one;
1-(4-fluorophenyl)-5-({4-hydroxy-1-[3-(trifluoromethyl)
bicyclo[1.1.1]pentane-1-carbonyl]piperidin-4-
yl}methyl)-1H,4H,5H-pyrazolo[3,4-d]pyrimidin-4-
one;
4-hydroxy-N-methyl-4-{[4-oxo-1-(4-phenylphenyl)-1H,
4H,5H-pyrazolo[3,4-d]pyrimidin-5-yl]methyl)piperi-
dine-1-carboxamide;
5-{[(3S,4S)-1-benzoyl-3-fluoro-4-hydroxypiperidin-4-yl]
methyl}-1-phenyl-1H,4H,5H-pyrazolo[3,4-d]pyrimi-
din-4-one;
5-[(1-cyclopropanecarbonyl-4-hydroxypiperidin-4-yl)
methyl]-1-[4-({[2-(dimethylamino)ethyl](methyl)
amino}methyl)phenyl]-1H,4H,5H-pyrazolo[3,4-d]py-
rimidin-4-one;
N-{1-[(4-{5-[(1-cyclopropanecarbonyl-4-hydroxypiperi-
din-4-yl)methyl]-4-oxo-1H,4H,5H-pyrazolo[3,4-d]py-
rimidin-1-yl}phenyl}methyl]piperidin-4-yl)acetamide;
5-[(1-cyclopropanecarbonyl-4-hydroxypiperidin-4-yl)
methyl]-1-[4-(pyrrolidin-1-ylmethyl)phenyl]-1H,4H,
5H-pyrazolo[3,4-d]pyrimidin-4-one;
5-[(1-cyclopropanecarbonyl-4-hydroxypiperidin-4-yl)
methyl]-1-[4-(piperidin-1-ylmethyl)phenyl]-1H,4H,
5H-pyrazolo[3,4-d]pyrimidin-4-one;
1-[(4-{5-[(1-cyclopropanecarbonyl-4-hydroxypiperidin-
4-yl)methyl]-4-oxo-1H,4H,5H-pyrazolo[3,4-d]pyrimi-
din-1-yl}phenyl}methyl]piperidine-4-carbonitrile;
1-(4-{[benzyl(methyl)amino]methyl}phenyl)-5-[(1-cy-
clopropanecarbonyl-4-hydroxypiperidin-4-yl)methyl]-
1H,4H,5H-pyrazolo[3,4-d]pyrimidin-4-one;
5-[(1-cyclopropanecarbonyl-4-hydroxypiperidin-4-yl)
methyl]-1-(4-{[(2-methoxyethylxmethyl)amino]
methyl}phenyl)-1H,4H,5H-pyrazolo[3,4-d]pyrimidin-
4-one;
5-[(1-cyclopropanecarbonyl-4-hydroxypiperidin-4-yl)
methyl]-1-(4-{[4-(dimethylamino)piperidin-1-yl]
methyl}phenyl)-1H,4H,5H-pyrazolo[3,4-d]pyrimidin-
4-one;
5-[(1-cyclopropanecarbonyl-4-hydroxypiperidin-4-yl)
methyl]-1-(4-{[methyl(2-methylpropyl)amino]methyl}
phenyl)-1H,4H,5H-pyrazolo[3,4-d]pyrimidin-4-one;
5-[(1-cyclopropanecarbonyl-4-hydroxypiperidin-4-yl)
methyl]-1-[4-(1,2,3,4-tetrahydroisoquinolin-2-ylm-
ethyl)phenyl]-1H,4H,5H-pyrazolo[3,4-d]pyrimidin-4-
one;
1-{4-[(4-acetylpiperazin-1-yl)methyl]phenyl}-5-[(1-cy-
clopropanecarbonyl-4-hydroxypiperidin-4-yl)methyl]-
1H,4H,5H-pyrazolo[3,4-d]pyrimidin-4-one;
4-[(4-{5-[(1-cyclopropanecarbonyl-4-hydroxypiperidin-
4-yl)methyl]-4-oxo-1H,4H,5H-pyrazolo[3,4-d]pyrimi-
din-1-yl}phenyl}methyl]-1l6,4-thiomorpholine-1,1-di-
one;
5-[(1R)-1-[1-(4-fluorobenzoyl)-4-hydroxypiperidin-4-yl]
ethyl]-1-(4-fluorophenyl)-1H,4H,5H-pyrazolo[3,4-d]
pyrimidin-4-one;

5-[(1-cyclopropanecarbonyl-4-hydroxypiperidin-4-yl)methyl]-1-[4-({[(6-ethylpyridin-3-yl}methyl](methyl)amino)methyl)phenyl]-1H,4H,5H-pyrazolo[3,4-d]pyrimidin-4-one;

2-{1-[(4-5-[(1-cyclopropanecarbonyl-4-hydroxypiperidin-4-yl)methyl]-4-oxo-1H,4H,5H-pyrazolo[3,4-d]pyrimidin-1-yl)phenyl}methyl]piperidin-3-yl)acetonitrile;

5-[(1-cyclopropanecarbonyl-4-hydroxypiperidin-4-yl)methyl]-1-(4-{[cyclopropyl(oxan-4-yl)amino]methyl}phenyl)-1H,4H,5H-pyrazolo[3,4-d]pyrimidin-4-one;

5-[(1-cyclopropanecarbonyl-4-hydroxypiperidin-4-yl)methyl]-1-(4-{8-oxa-2-azaspiro[4.5]decan-2-ylmethyl}phenyl)-1H,4H,5H-pyrazolo[3,4-d]pyrimidin-4-one;

5-[(1-cyclopropanecarbonyl-4-hydroxypiperidin-4-yl)methyl]-1-[3-(pyrrolidin-1-ylmethyl)phenyl]-1H,4H,5H-pyrazolo[3,4-d]pyrimidin-4-one;

5-[(1-cyclopropanecarbonyl-4-hydroxypiperidin-4-yl)methyl]-1-[3-(piperidin-1-ylmethyl)phenyl]-1H,4H,5H-pyrazolo[3,4-d]pyrimidin-4-one;

1-[(3-{5-[(1-cyclopropanecarbonyl-4-hydroxypiperidin-4-yl)methyl]-4-oxo-1H,4H,5H-pyrazolo[3,4-d]pyrimidin-1-yl)phenyl}methyl]piperidine-4-carbonitrile;

1-(3-{[benzyl(methyl)amino]methyl}phenyl)-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl)methyl]-1-[3-(f[2-(dimethylamino)ethyl](methyl)amino)methyl)phenyl]-1H,4H,5H-pyrazolo[3,4-d]pyrimidin-4-one;

5-[(1-cyclopropanecarbonyl-4-hydroxypiperidin-4-yl)methyl]-1-(3-{[(2-methoxyethylxmethyl)amino]methyl}phenyl)-1H,4H,5H-pyrazolo[3,4-d]pyrimidin-4-one;

N-(2-{4-[4-hydroxy-4-(f1-methyl-4-oxo-1H,4H,5H-pyrazolo[3,4-d]pyrimidin-5-yl}methyl)piperidine-1-carbonyl]phenyl}phenyl)ethene-1-sulfonamide;

N-{1-[(3-{5-[(1-cyclopropanecarbonyl-4-hydroxypiperidin-4-yl)methyl]-4-oxo-1H,4H,5H-pyrazolo[3,4-d]pyrimidin-1-yl)phenyl}methyl]piperidin-4-yl)acetamide;

5-[(1-cyclopropanecarbonyl-4-hydroxypiperidin-4-yl)methyl]-1-(3-{[4-(dimethylamino)piperidin-1-yl]methyl}phenyl)-1H,4H,5H-pyrazolo[3,4-d]pyrimidin-4-one;

5-[(1-cyclopropanecarbonyl-4-hydroxypiperidin-4-yl)methyl]-1-(3-{[methyl(2-methylpropyl)amino]methyl}phenyl)-1H,4H,5H-pyrazolo[3,4-d]pyrimidin-4-one;

5-[(1-cyclopropanecarbonyl-4-hydroxypiperidin-4-yl)methyl]-1-(3-(1,2,3,4-tetrahydroisoquinolin-2-ylmethyl)phenyl]-1H,4H,5H-pyrazolo[3,4-d]pyrimidin-4-one;

1-{3-[(4-acetylpiperazin-1-yl]methyl]phenyl)-5-[(1-cyclopropanecarbonyl-4-hydroxypiperidin-4-yl)methyl]-1H,4H,5H-pyrazolo[3,4-d]pyrimidin-4-one;

4-[(3-{5-[(1-cyclopropanecarbonyl-4-hydroxypiperidin-4-yl)methyl]-4-oxo-1H,4H,5H-pyrazolo[3,4-d]pyrimidin-1-yl)phenyl}methyl]-1l6,4-thiomorpholine-1,1-dione;

2-{1-[(3-5-[(1-cyclopropanecarbonyl-4-hydroxypiperidin-4-yl)methyl]-4-oxo-1H,4H,5H-pyrazolo[3,4-d]pyrimidin-1-yl)phenyl}methyl]piperidin-3-yl)acetonitrile;

5-[(1-cyclopropanecarbonyl-4-hydroxypiperidin-4-yl)methyl]-1-(3-{8-oxa-2-azaspiro[4.5]decan-2-ylmethyl}phenyl)-1H,4H,5H-pyrazolo[3,4-d]pyrimidin-4-one;

1-(4-fluorophenyl)-5-(f4-hydroxy-1-[2-(oxan-4-yl)acetyl]piperidin-4-yl}methyl)-1H,4H,5H-pyrazolo[3,4-d]pyrimidin-4-one;

1-(4-fluorophenyl)-5-{[4-hydroxy-1-(2-methoxyacetyl)piperidin-4-yl]methyl}-1H,4H,5H-pyrazolo[3,4-d]pyrimidin-4-one;

N-[(2R)-1-[4-hydroxy-4-(f1-methyl-4-oxo-1H,4H,5H-pyrazolo[3,4-d]pyrimidin-5-yl}methyl)piperidin-1-yl]-1-oxo-3-phenylpropan-2-yl]ethene-1-sulfonamide;

3-[1-(4-{[1-(4-fluorophenyl)-4-oxo-1H,4H,5H-pyrazolo[3,4-d]pyrimidin-5-yl]methyl)-4-hydroxypiperidin-1-yl}-1-oxopropan-2-yl]-1,3-oxazolidin-2-one;

5-{[1-(4,4-difluorocyclohexanecarbonyl)-4-hydroxypiperidin-4-yl]methyl}-1-(4-fluorophenyl)-1H,4H,5H-pyrazolo[3,4-d]pyrimidin-4-one;

5-{[1-(2-cyclopropylacetyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-{[4-hydroxy-1-(1-methylcyclobutanecarbonyl)piperidin-4-yl]methyl}-1H,4H,5H-pyrazolo[3,4-d]pyrimidin-4-one;

1-(4-fluorophenyl)-5-{[4-hydroxy-1-(6-methoxypyridine-3-carbonyl)piperidin-4-yl]methyl}-1H,4H,5H-pyrazolo[3,4-d]pyrimidin-4-one;

1-(4-fluorophenyl)-5-{[1-(6-fluoropyridine-3-carbonyl)-4-hydroxypiperidin-4-yl]methyl}-1H,4H,5H-pyrazolo[3,4-d]pyrimidin-4-one;

5-{(4-hydroxy-1-[4-(1-hydroxycyclopropyl}benzoyl]piperidin-4-yl}methyl)-1-phenyl-1H,4H,5H-pyrazolo[3,4-d]pyrimidin-4-one;

1-(4-fluorophenyl)-5-((4-hydroxy-1-[4-(1-hydroxycyclopropyl}benzoyl]piperidin-4-yl}methyl)-1H,4H,5H-pyrazolo[3,4-d]pyrimidin-4-one;

5-{[(3R,4S)-1-benzoyl-3-fluoro-4-hydroxypiperidin-4-yl]methyl}-1-phenyl-1H,4H,5H-pyrazolo[3,4-d]pyrimidin-4-one;

5-{[1-(3-chloro-1H-pyrazole-4-carbonyl)-4-hydroxypiperidin-4-yl]methyl}-1-phenyl-1H,4H,5H-pyrazolo[3,4-d]pyrimidin-4-one;

4-hydroxy-N-methyl-4-([4-oxo-1-(6-phenylpyridin-3-yl)-1H,4H,5H-pyrazolo[3,4-d]pyrimidin-5-yl]methyl)piperidine-1-carboxamide;

1-[3-(Cyclopentylamino)phenyl]-5-[(1-cyclopropanecarbonyl-4-hydroxypiperidin-4-yl)methyl]-1H,4H,5H-pyrazolo[3,4-d]pyrimidin-4-one;

5-[(1-Cyclopropanecarbonyl-4-hydroxypiperidin-4-yl)methyl]-1-[3-(morpholin-4-yl)phenyl]-1H,4H,5H-pyrazolo[3,4-d]pyrimidin-4-one;

1-(4-Fluorophenyl)-5-[(4-hydroxy-1-{8-oxabicyclo[3.2.1]octane-3-carbonyl)piperidin-4-yl)methyl]-1H,4H,5H-pyrazolo[3,4-d]pyrimidin-4-one;

4-((1-[4-(Benzyloxy)phenyl]-4-oxo-1H,4H,5H-pyrazolo[3,4-d]pyrimidin-5-yl}methyl)-4-hydroxy-N,N-dimethylpiperidine-1-carboxamide;

4-((1-(4',6-Difluoro-[1,1'-biphenyl]-3-yl)-4-oxo-1,4-dihydro-5H-pyrazolo[3,4-d]pyrimidin-5-yl}methyl)-4-hydroxy-N,N-dimethylpiperidine-1-carboxamide;

N-(3-(5-((1-(Cyclopropanecarbonyl)-4-hydroxypiperidin-4-yl}methyl)-4-oxo-4,5-dihydro-1H-pyrazolo[3,4-d]pyrimidin-1-yl)phenyl)acetamide;

N-(3-(5-((1-(Cyclopropanecarbonyl)-4-hydroxypiperidin-4-yl}methyl)-4-oxo-4,5-dihydro-1H-pyrazolo[3,4-d]pyrimidin-1-yl)phenyl)-3,5-dimethylisoxazole-4-sulfonamide;

1-(3-(5-((1-(Cyclopropanecarbonyl)-4-hydroxypiperidin-4-yl}methyl)-4-oxo-4,5-dihydro-1H-pyrazolo[3,4-d]pyrimidin-1-yl)phenyl)-3-isopropylurea;

5-{(1-(Cyclopropanecarbonyl)-4-hydroxypiperidin-4-yl}methyl)-1-(3-(3,3-difluoropyrrolidine-1-carbonyl)phenyl)-1,5-dihydro-4H-pyrazolo[3,4-d]pyrimidin-4-one;

3-[(1-benzoyl-4-hydroxypiperidin-4-yl)methyl]-7-(4-fluorophenyl)-3H,4H,7H-pyrrolo[2,3-d]pyrimidin-4-one;

1-(4-Fluorophenyl)-5-((4-hydroxy-1-(1H-pyrrolo[3,2-c]pyridine-2-carbonyl)piperidin-4-yl}methyl)-1,5-dihydro-4H-pyrazolo[3,4-d]pyrimidin-4-one;

4-{[1-(4-Fluorophenyl)-4-oxo-1H,4H,5H-pyrazolo[3,4-d]pyrimidin-5-yl]methyl)-4-hydroxy-N-(propan-2-yl)piperidine-1-carboxamide;

N-(3,3-Dimethylcyclobutyl)-4-((1-(4-fluorophenyl)-4-oxo-1,4-dihydro-5H-pyrazolo[3,4-d]pyrimidin-5-yl}methyl)-4-hydroxypiperidine-1-carboxamide;

1-(4-Chlorophenyl)-5-{[4-hydroxy-1-(1H-indole-2-carbonyl)piperidin-4-yl]methyl}-1H,4H,5H-pyrazolo[3,4-d]pyrimidin-4-one;

(R)-5-((1-(4-fluorobenzoyl)-4-hydroxypiperidin-4-yl}methyl)-1-(4-(octahydro-2H-pyrido[1,2-a]pyrazin-2-yl)phenyl)-1,5-dihydro-4H-pyrazolo[3,4-d]pyrimidin-4-one;

5-[(1-Cyclopropanecarbonyl-4-hydroxypiperidin-4-yl)methyl]-1-(4-{imidazo[1,2-a]pyridin-8-yl}phenyl)-1H,4H,5H-pyrazolo[3,4-d]pyrimidin-4-one;

3-(Pyrrolidin-1-yl)propyl 4-((1-(4-fluorophenyl)-4-oxo-1,4-dihydro-5H-pyrazolo[3,4-d]pyrimidin-5-yl}methyl)-4-hydroxypiperidine-1-carboxylate;

5-[(1-{4-[(8aR)-octahydropyrrolo[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one;

5-{[4-Hydroxy-1-(2-methyl-1,3-oxazole-5-carbonyl)piperidin-4-yl]methyl}-1-[4-(4-methyl-1H-pyrazol-1-yl)phenyl]-1H,4H,5H-pyrazolo[3,4-d]pyrimidin-4-one;

1-{4-[1-(Difluoromethyl)-1H-pyrazol-4-yl]phenyl}-5-{[4-hydroxy-1-(1-methylcyclopropanecarbonyl)piperidin-4-yl]methyl}-1H,4H,5H-pyrazolo[3,4-d]pyrimidin-4-one;

3-[(1-benzoyl-4-hydroxypiperidin-4-yl)methyl]-7-(4-fluorophenyl)-6-methyl-3H,4H,7H-pyrrolo[2,3-d]pyrimidin-4-one;

1-(4-{2,2-Difluoro-7-azaspiro[3.5]nonan-7-yl)phenyl]-5-{[4-hydroxy-1-(1-methylcyclopropanecarbonyl)piperidin-4-yl]methyl}-1H,4H,5H-pyrazolo[3,4-d]pyrimidin-4-one;

1-{4-[(5-Chloropyridin-2-yl)oxy]phenyl}-5-[(1-cyclopropanecarbonyl-4-hydroxypiperidin-4-yl)methyl]-1H,4H,5H-pyrazolo[3,4-d]pyrimidin-4-one;

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3,3-dimethylurea;

Propan-2-yl N-(4-{5-[(1-cyclopropanecarbonyl-4-hydroxypiperidin-4-yl)methyl]-4-oxo-1H,4H,5H-pyrazolo[3,4-d]pyrimidin-1-yl}phenyl)carbamate;

3-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-1-(oxan-4-yl)urea;

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-(oxetan-3-yl)urea;

4-({1-[4-(3,3-dimethylazetidin-1-yl)phenyl]-4-oxo-1H,4H,5H-pyrazolo[3,4-d]pyrimidin-5-yl}methyl)-4-hydroxy-N,N-dimethylpiperidine-1-carboxamide;

5-[(1-Cyclopropanecarbonyl-4-hydroxypiperidin-4-yl)methyl]-1-[3-(1H-pyrazol-1-yl)phenyl]-1H,4H,5H-pyrazolo[3,4-d]pyrimidin-4-one;

5-[(1-Cyclopropanecarbonyl-4-hydroxypiperidin-4-yl)methyl]-1-[3-(piperazin-1-yl)phenyl]-1H,4H,5H-pyrazolo[3,4-d]pyrimidin-4-one;

5-[(1-Cyclopropanecarbonyl-4-hydroxypiperidin-4-yl)methyl]-1-[4-(piperazin-1-yl)phenyl]-1H,4H,5H-pyrazolo[3,4-d]pyrimidin-4-one;

1-(3-{[cyclohexyl(ethyl)amino]methyl}phenyl)-5-[(1-cyclopropanecarbonyl-4-hydroxypiperidin-4-yl)methyl]-1H,4H,5H-pyrazolo[3,4-d]pyrimidin-4-one;

4-Hydroxy-N,N-dimethyl-4-{[4-oxo-1-(4-phenoxyphenyl)-1H,4H,5H-pyrazolo[3,4-d]pyrimidin-5-yl]methyl}piperidine-1-carboxamide;

4-{[1-(4-Fluorophenyl)-4-oxo-1H,4H,5H-pyrazolo[3,4-d]pyrimidin-5-yl]methyl)-4-hydroxy-N-(oxan-4-yl)piperidine-1-carboxamide;

(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)urea;

(3-{5-[(1-Cyclopropanecarbonyl-4-hydroxypiperidin-4-yl)methyl]-4-oxo-1H,4H,5H-pyrazolo[3,4-d]pyrimidin-1-yl}phenyl)urea;

5-[(1-Cyclopropanecarbonyl-4-hydroxypiperidin-4-yl)methyl]-1-{4-[(methylsulfamoyl)amino]phenyl}-1H,4H,5H-pyrazolo[3,4-d]pyrimidin-4-one;

5-[(1-Cyclopropanecarbonyl-4-hydroxypiperidin-4-yl)methyl]-1-{4-[(dimethylsulfamoyl)amino]phenyl}-1H,4H,5H-pyrazolo[3,4-d]pyrimidin-4-one;

1-(4-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-methylurea;

1-(3-{5-[(1-Cyclopropanecarbonyl-4-hydroxypiperidin-4-yl)methyl]-4-oxo-1H,4H,5H-pyrazolo[3,4-d]pyrimidin-1-yl}phenyl)-3-methylurea;

4-{[1-(4-{3,9-Diazaspiro[5.5]undecan-3-yl}phenyl)-4-oxo-1H,4H,5H-pyrazolo[3,4-d]pyrimidin-5-yl]methyl)-4-hydroxy-N,N-dimethylpiperidine-1-carboxamide;

1-(4-Fluorophenyl)-5-[(4-hydroxy-1-{4-[(3S)-3-hydroxypyrrolidin-1-yl]benzoyl}piperidin-4-yl)methyl]-1H,4H,5H-pyrazolo[3,4-d]pyrimidin-4-one;

7-[3-(aminomethyl)phenyl]-3-{[1-(4-fluorobenzoyl)-4-hydroxypiperidin-4-yl]methyl}-3H,4H,7H-pyrrolo[2,3-d]pyrimidin-4-one;

1-(4-fluorophenyl)-5-({4-hydroxy-1-[3-(pyrrolidin-1-ylmethyl}benzoyl]piperidin-4-yl}methyl)-1H,4H,5H-pyrazolo[3,4-d]pyrimidin-4-one;

1-(4-fluorophenyl)-5-({4-hydroxy-1-[3-(1H-pyrazol-1-yl)butanoyl]piperidin-4-yl}methyl)-1H,4H,5H-pyrazolo[3,4-d]pyrimidin-4-one;

1-(4-fluorophenyl)-5-({4-hydroxy-1-[(3S)-3-(1H-pyrazol-1-yl)butanoyl]piperidin-4-yl}methyl)-1H,4H,5H-pyrazolo[3,4-d]pyrimidin-4-one;

1-(4-fluorophenyl)-5-({4-hydroxy-1-[(3R)-3-(1H-pyrazol-1-yl)butanoyl]piperidin-4-yl}methyl)-1H,4H,5H-pyrazolo[3,4-d]pyrimidin-4-one;

5-{{1-[3-(difluoromethoxy)cyclobutanecarbonyl]-4-hydroxypiperidin-4-yl}methyl)-1-(4-fluorophenyl)-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl]-1-(4-fluorophenyl)-1H,4H,5H-pyrazolo[3,4-d]pyrimidin-4-one;

5-{{1-[(3S)-4,4-difluoro-3-(1H-pyrazol-1-yl)butanoyl]-4-hydroxypiperidin-4-yl}methyl]-1-(4-fluorophenyl)-1H,4H,5H-pyrazolo[3,4-d]pyrimidin-4-one;

5-{{1-[(3S)-3-{2H,4H,5H,6H-cyclopenta[c]pyrazol-2-yl}butanoyl]-4-hydroxypiperidin-4-yl}methyl)-1-(4-fluorophenyl)-1H,4H,5H-pyrazolo[3,4-d]pyrimidin-4-one;

3-([1-(4-fluorobenzoyl)-4-hydroxypiperidin-4-yl]methyl}-7-(5-fluoropyridin-2-yl)-3H,4H,7H-pyrrolo[2,3-d]pyrimidin-4-one;

5-{(1-[(3R)-3-(2H,4H,5H,6H-cyclopenta[c]pyrazol-2-yl}butanoyl]-4-hydroxypiperidin-4-yl}methyl)-1-(4-fluorophenyl)-1H,4H,5H-pyrazolo[3,4-d]pyrimidin-4-one;

5-{(1-[(3S)-3-(1H,4H,5H,6H-cyclopenta[c]pyrazol-1-yl}butanoyl]-4-hydroxypiperidin-4-yl}methyl)-1-(4-fluorophenyl)-1H,4H,5H-pyrazolo[3,4-d]pyrimidin-4-one;

5-{(1-[(3R)-3-(1H,4H,5H,6H-cyclopenta[c]pyrazol-1-yl}butanoyl]-4-hydroxypiperidin-4-yl}methyl)-1-(4-fluorophenyl)-1H,4H,5H-pyrazolo[3,4-d]pyrimidin-4-one;

1-(4-fluorophenyl)-5-([4-hydroxy-1-(3-{octahydrocyclopenta[c]pyrrol-2-yl}butanoyl)piperidin-4-yl]methyl)-1H,4H,5H-pyrazolo[3,4-d]pyrimidin-4-one;

1-(4-fluorophenyl)-5-((4-hydroxy-1-[(3S)-3-(octahydrocyclopenta[c]pyrrol-2-yl}butanoyl]piperidin-4-yl}methyl)-1H,4H,5H-pyrazolo[3,4-d]pyrimidin-4-one;

1-(4-fluorophenyl)-5-((4-hydroxy-1-[(3R)-3-(octahydrocyclopenta[c]pyrrol-2-yl}butanoyl]piperidin-4-yl}methyl)-1H,4H,5H-pyrazolo[3,4-d]pyrimidin-4-one;

1-(4-fluorophenyl)-5-((4-hydroxy-1-[4-(1,1,1-trifluoro-2-hydroxypropan-2-yl)benzoyl]piperidin-4-yl}methyl)-1H,4H,5H-pyrazolo[3,4-d]pyrimidin-4-one;

1-(4-fluorophenyl)-5-[(4-hydroxy-1-{4-[(2R)-1,1,1-trifluoro-2-hydroxypropan-2-yl]benzoyl}piperidin-4-yl)methyl]-1H,4H,5H-pyrazolo[3,4-d]pyrimidin-4-one;

1-(4-fluorophenyl)-5-[(4-hydroxy-1-{4-[(2S)-1,1,1-trifluoro-2-hydroxypropan-2-yl]benzoyl}piperidin-4-yl)methyl]-1H,4H,5H-pyrazolo[3,4-d]pyrimidin-4-one;

1-(4-fluorophenyl)-5-((4-hydroxy-1-[4-(pyrrolidin-1-ylmethyl}benzoyl]piperidin-4-yl}methyl)-1H,4H,5H-pyrazolo[3,4-d]pyrimidin-4-one;

1-(4-fluorophenyl)-5-({4-hydroxy-1-[4-(morpholin-4-ylmethyl}benzoyl]piperidin-4-yl}methyl)-1H,4H,5H-pyrazolo[3,4-d]pyrimidin-4-one;

1-(4-fluorophenyl)-5-{[4-hydroxy-1-(2-methyl-1,3-oxazole-5-carbonyl)piperidin-4-yl]methyl}-1H,4H,5H-pyrazolo[3,4-d]pyrimidin-4-one;

1-(4-fluorophenyl)-5-[(4-hydroxy-1-{5H,6H,7H-pyrazolo[3,2-b][1,3]oxazine-2-carbonyl}piperidin-4-yl)methyl]-1H,4H,5H-pyrazolo[3,4-d]pyrimidin-4-one;

1-(4-fluorophenyl)-5-[(4-hydroxy-1-{4-[(1-methylpiperidin-4-yl)oxy]benzoyl}piperidin-4-yl)methyl]-1H,4H,5H-pyrazolo[3,4-d]pyrimidin-4-one;

1-(4-fluorophenyl)-5-({4-hydroxy-1-[5-(piperidin-1-yl)-1,3,4-oxadiazole-2-carbonyl]piperidin-4-yl}methyl)-1H,4H,5H-pyrazolo[3,4-d]pyrimidin-4-one;

1-(4-fluorophenyl)-5-({4-hydroxy-1-[4-(1H-pyrazol-1-yl)benzoyl]piperidin-4-yl}methyl)-1H,4H,5H-pyrazolo[3,4-d]pyrimidin-4-one;

1-(4-fluorophenyl)-5-({4-hydroxy-1-[2-(piperidin-1-yl)-1,3-oxazole-5-carbonyl]piperidin-4-yl}methyl)-1H,4H,5H-pyrazolo[3,4-d]pyrimidin-4-one;

5-{{1-[3-fluoro-4-(4-methylpiperazin-1-yl)benzoyl]-4-hydroxypiperidin-4-yl}methyl)-1-(4-fluorophenyl)-1H,4H,5H-pyrazolo[3,4-d]pyrimidin-4-one;

1-(4-fluorophenyl)-5-({4-hydroxy-1-[4-(pyridin-2-yloxy)benzoyl]piperidin-4-yl}methyl)-1H,4H,5H-pyrazolo[3,4-d]pyrimidin-4-one;

1-(4-fluorophenyl)-5-({4-hydroxy-1-[4-(pyrimidin-2-yloxy)benzoyl]piperidin-4-yl}methyl)-1H,4H,5H-pyrazolo[3,4-d]pyrimidin-4-one;

4-{3-chloro-4-[4-hydroxy-4-({1-methyl-4-oxo-1H,4H,5H-pyrazolo[3,4-d]pyrimidin-5-yl}methyl)piperidine-1-carbonyl]phenyl)-N,N-dimethylbenzamide;

5-{[1-(1-benzyl-1H-indole-2-carbonyl)-4-hydroxypiperidin-4-yl]methyl}-1-(4-fluorophenyl)-1H,4H,5H-pyrazolo[3,4-d]pyrimidin-4-one;

5-{[1-(1-benzyl-1H-pyrazole-5-carbonyl)-4-hydroxypiperidin-4-yl]methyl}-1-(4-fluorophenyl)-1H,4H,5H-pyrazolo[3,4-d]pyrimidin-4-one;

5-{{1-[(3S)-4,4-difluoro-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

5-{{1-[(3R)-4,4-difluoro-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

1-(4-fluorophenyl)-5-({4-hydroxy-1-[4-(pyridin-2-yloxy)cyclohexanecarbonyl]piperidin-4-yl}methyl)-1H,4H,5H-pyrazolo[3,4-d]pyrimidin-4-one;

1-(4-fluorophenyl))-5-({4-hydroxy-1-[(1s,4s)-4-(pyridin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(pyridin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[5-(pyridin-2-yloxy}pyridine-2-carbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(1H-pyrazol-1-yl)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-(1H-pyrazol-1-yl)cyclohexanecarbonyl]piperidin-4-yl}methyl)-1H,4H,5H-pyrazolo[3,4-d]pyrimidin-4-one;

5-[(1-{2-chloro-4-[4-(piperidine-1-carbonyl)phenyl]benzoyl}-4-hydroxypiperidin-4-yl)methyl]-1-methyl-1H,4H,5H-pyrazolo[3,4-d]pyrimidin-4-one;

1-(4-fluorophenyl)-5-{[4-hydroxy-1-(4-{2H,3H-pyrazolo[3,2-b][1,3]oxazol-7-yl}benzoyl)piperidin-4-yl]methyl)-1H,4H,5H-pyrazolo[3,4-d]pyrimidin-4-one;

1-(4-fluorophenyl)-5-{[4-hydroxy-1-(4-{5H,6H,7H-pyrazolo[3,2-b][1,3]oxazin-3-yl}benzoyl)piperidin-4-yl]methyl}-1H,4H,5H-pyrazolo[3,4-d]pyrimidin-4-one;

1-(4-fluorophenyl)-5-{[4-hydroxy-1-(4-{4H,5H,6H,7H-pyrazolo[1,5-a]pyrimidin-3-yl}benzoyl)piperidin-4-yl]methyl}-1H,4H,5H-pyrazolo[3,4-d]pyrimidin-4-one;

1-(4-fluorophenyl)-5-{[4-hydroxy-1-(4-{4-methyl-4H,5H,6H,7H-pyrazolo[1,5-a]pyrimidin-3-yl}benzoyl)piperidin-4-yl]methyl}-1H,4H,5H-pyrazolo[3,4-d]pyrimidin-4-one;

5-{[1-(2-amino-4-chlorobenzoyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-({4-hydroxy-1-[2-(morpholin-4-yl)-1,3-oxazole-5-carbonyl]piperidin-4-yl}methyl)-1H,4H,5H-pyrazolo[3,4-d]pyrimidin-4-one;

5-{[1-(5-cyclopropyl-1,3,4-oxadiazole-2-carbonyl)-4-hydroxypiperidin-4-yl]methyl}-1-(4-fluorophenyl)-1H,4H,5H-pyrazolo[3,4-d]pyrimidin-4-one;

5-{[1-(5-benzyl-1,3-oxazole-4-carbonyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-[(1-{1-[(4-fluorophenyl]methyl]-1H-pyrrole-2-carbonyl}-4-hydroxypiperidin-4-yl)methyl]-1H,4H,5H-pyrazolo[3,4-d]pyrimidin-4-one;

5-[(1-{1-[(2,6-difluorophenyl)methyl]-1H-pyrrole-2-carbonyl}-4-hydroxypiperidin-4-yl)methyl]-1-(4-fluorophenyl)-1H,4H,5H-pyrazolo[3,4-d]pyrimidin-4-one;

5-{[4-hydroxy-1-(4-phenoxybenzoyl)piperidin-4-yl]methyl}-1-methyl-1H,4H,5H-pyrazolo[3,4-d]pyrimidin-4-one;

1-(4-fluorophenyl)-5-[(1-{1-[(3-fluorophenyl)methyl]-1H-pyrrole-2-carbonyl}-4-hydroxypiperidin-4-yl)methyl]-1H,4H,5H-pyrazolo[3,4-d]pyrimidin-4-one;

1-(4-fluorophenyl)-5-[(1-{1-[(2-fluorophenyl)methyl]-1H-pyrrole-2-carbonyl}-4-hydroxypiperidin-4-yl)methyl]-1H,4H,5H-pyrazolo[3,4-d]pyrimidin-4-one;

1-(4-fluorophenyl)-5-[(4-hydroxy-1-{4-[(1-methyl-1H-pyrazol-4-yl)oxy]benzoyl}piperidin-4-yl)methyl]-1H,4H,5H-pyrazolo[3,4-d]pyrimidin-4-one;

1-(4-fluorophenyl)-5-[(4-hydroxy-1-{4-[(5-methyl-1,2-oxazol-3-yl)oxy]benzoyl}piperidin-4-yl)methyl]-1H,4H,5H-pyrazolo[3,4-d]pyrimidin-4-one;

1-[4-(4-fluorophenyl)phenyl]-5-{[4-hydroxy-1-(piperazine-1-carbonyl)piperidin-4-yl]methyl}-1H,4H,5H-pyrazolo[3,4-d]pyrimidin-4-one;

N-[(1s,3s)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]prop-2-enamide;

N-[(1S,3R)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclopentyl]prop-2-enamide;

5-{{4-hydroxy-1-[(3R)-3-phenylbutanoyl]piperidin-4-yl}methyl)-1-methyl-1H,4H,5H-pyrazolo[3,4-d]pyrimidin-4-one;

N-[(1R,3S)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclopentyl]prop-2-enamide;

1-(4-fluorophenyl)-5-({4-hydroxy-1-[(2R)-1-(prop-2-enoyl)azetidine-2-carbonyl]piperidin-4-yl}methyl)-1H,4H,5H-pyrazolo[3,4-d]pyrimidin-4-one;

N-[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]prop-2-enamide;

N-[(1s,4s)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]prop-2-enamide;

N-[(1s,3s)-3-[2-(4-({1-(4-fluorophenyl)-4-oxo-1H,4H,5H-pyrazolo[3,4-d]pyrimidin-5-yl]methyl}-4-hydroxypiperidin-1-yl)-2-oxoethyl]cyclobutyl]prop-2-ynamide;

1-(4-fluorophenyl)-5-({4-hydroxy-1-[(2S)-2-methyl-1-(prop-2-enoyl)azetidine-2-carbonyl]piperidin-4-yl}methyl)-1H,4H,5H-pyrazolo[3,4-d]pyrimidin-4-one;

1-benzyl-5-({4-hydroxy-1-[(3R)-3-phenylbutanoyl]piperidin-4-yl}methyl)-1H,4H,5H-pyrazolo[3,4-d]pyrimidin-4-one;

1-(4-fluorophenyl)-5-({4-hydroxy-1-[(2R)-2-methyl-1-(prop-2-enoyl)azetidine-2-carbonyl]piperidin-4-yl}methyl)-1H,4H,5H-pyrazolo[3,4-d]pyrimidin-4-one;

N-[(1r,3r)-3-(4-{[1-(4-fluorophenyl)-4-oxo-1H,4H,5H-pyrazolo[3,4-d]pyrimidin-5-yl]methyl}-4-hydroxypiperidine-1-carbonyl)cyclobutyl]acetamide;

5-{(1-(3-(aminomethyl}benzoyl)-4-hydroxypiperidin-4-yl) methyl)-1-(4-fluorophenyl)-1H-pyrazolo[3,4-d]pyrimidin-4 (5H)-one;

5-{(1-(4-(1-(aminomethyl)cyclopropyl}benzoyl)-4-hydroxypiperidin-4-yl}methyl)-1-(4-fluorophenyl)-1H-pyrazolo[3,4-d]pyrimidin-4 (5H)-one hydrochloride;

N-((1-(4-(4-((1-(4-fluorophenyl)-4-oxo-1H-pyrazolo[3,4-d]pyrimidin-5 (4H)-yl]methyl)-4-hydroxypiperidine-1-carbonyl)phenyl)cyclopropyl}methyl)acetamide;

N-methyl-N-[(1r,3r)-3-(4-{[1-(4-fluorophenyl)-4-oxo-1H,4H,5H-pyrazolo[3,4-d]pyrimidin-5-yl]methyl)-4-hydroxypiperidine-1-carbonyl)cyclobutyl]prop-2-ynamide;

1-tert-butyl-5-({4-hydroxy-1-[(3R)-3-phenylbutanoyl]piperidin-4-yl}methyl)-1H,4H,5H-pyrazolo[3,4-d]pyrimidin-4-one;

1-tert-butyl-5-{[4-hydroxy-1-(4-phenoxybenzoyl}piperidin-4-yl]methyl)-1H,4H,5H-pyrazolo[3,4-d]pyrimidin-4-one;

N-methyl-N-[(1s,3s)-3-(4-{[1-(4-fluorophenyl)-4-oxo-1H,4H,5H-pyrazolo[3,4-d]pyrimidin-5-yl]methyl)-4-hydroxypiperidine-1-carbonyl)cyclobutyl]prop-2-ynamide;

1-(4-fluorophenyl)-5-((4-hydroxy-1-(3-((3-hydroxy-3-methyl- pyrrolidin-1-yl}methyl}benzoyl}piperidin-4-yl}methyl)-1H-pyrazolo[3,4-d]pyrimidin-4 (5H)-one;

1-(4-fluorophenyl)-5-[(4-hydroxy-1-{3-[1-(pyrrolidin-1-yl)ethyl]benzoyl}piperidin-4-yl)methyl]-1H,4H,5H-pyrazolo[3,4-d]pyrimidin-4-one;

5-{[1-[(5-benzyl-1H-pyrazol-4-yl)carbonyl]-4-hydroxypiperidin-4-yl] methyl)-1-(4-fluorophenyl)-1H,4H,5H-pyrazolo[3,4-d]pyrimidin-4-one;

1-(4-fluorophenyl)-5-{[4-hydroxy-1-(4-{5-methyl-2,5-diazabicyclo[2.2.1]heptan-2-yl}benzoyl)piperidin-4-yl]methyl)-1H,4H,5H-pyrazolo[3,4-d]pyrimidin-4-one;

1-(4-fluorophenyl)-5-((4-hydroxy-1-(4-(1-methylpiperidin-4-yl) benzoyl}piperidin-4-yl}methyl)-1H-pyrazolo[3,4-d]pyrimidin-4 (5H)-one;

1-(4-fluorophenyl)-5-[(4-hydroxy-1-[[4-(4-methylpiperazin-1-yl) phenyl]carbonyl]piperidin-4-yl)methyl]-1H,4H,5H-pyrazolo[3,4-d]pyrimidin-4-one;

1-(4-fluorophenyl)-5-{[4-hydroxy-1-(4-{octahydro-1H-pyrido[1,2-a]piperazin-2-yl}benzoyl)piperidin-4-yl]methyl)-1H,4H,5H-pyrazolo[3,4-d]pyrimidin-4-one;

5-[(1-{4-[(9aR)-octahydro-1H-pyrido[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one;

5-[(1-{4-[(9aS)-octahydro-1H-pyrido[1,2-a]piperazin-2-yl]benzoyl}-4-hydroxypiperidin-4-yl)methyl]-1-(4-fluorophenyl)-1H,4H,5H-pyrazolo[3,4-d]pyrimidin-4-one;

5-{{4-hydroxy-1-[(3R)-3-phenylbutanoyl]piperidin-4-yl}methyl)-1-(propan-2-yl}-1H,4H,5H-pyrazolo[3,4-d]pyrimidin-4-one;

1-(4-fluorophenyl)-5-[(4-hydroxy-1-[[4-(pyridin-2-yloxy)piperidin-1-yl]carbonyl]piperidin-4-yl)methyl]-1H,4H,5H-pyrazolo[3,4-d]pyrimidin-4-one;

5-{(1-(4-(5,6-dihydropyrrolo[3,4-c]pyrazol-1 (4H)-yl}benzoyl)-4-hydroxypiperidin-4-yl}methyl)-1-(4-fluorophenyl)-1H-pyrazolo[3,4-d]pyrimidin-4 (5H)-one;

1-(4-fluorophenyl)-5-[(4-hydroxy-1-{4-[4-(hydroxymethyl)-1H-pyrazol-1-yl]benzoyl}piperidin-4-yl)methyl]-1H,4H,5H-pyrazolo[3,4-d]pyrimidin-4-one;

5-{(1-(4-(4-(aminomethyl)-1H-pyrazol-1-yl}benzoyl)-4-hydroxypiperidin-4-yl}methyl)-1-(4-fluorophenyl)-1H-pyrazolo[3,4-d]pyrimidin-4 (5H)-one;

1-(4-fluorophenyl)-5-(1-[4-hydroxy-1-[(4-methoxyphenyl)carbonyl] piperidin-4-yl]ethyl)-1H,4H,5H-pyrazolo[3,4-d]pyrimidin-4-one;

1-(4-fluorophenyl)-5-(1-[4-hydroxy-1-[(4-methoxyphenyl)carbonyl] piperidin-4-yl]ethyl)-1H,4H,5H-pyrazolo[3,4-d]pyrimidin-4-one;

5-{1-(1-(3-(aminomethyl}benzoyl)-4-hydroxypiperidin-4-yl)ethyl)-1-(4-fluorophenyl)-1H-pyrazolo[3,4-d]pyrimidin-4 (5H)-one hydrochloride;

5-[(4-hydroxypiperidin-4-yl)methyl]-1-(4-methoxyphenyl)-1H,4H,5H-pyrazolo[3,4-d]pyrimidin-4-one;

4-Hydroxy-4-[[1-(4-methoxyphenyl)-4-oxo-1H,4H,5H-pyrazolo[3,4-d]pyrimidin-5-yl]methyl]-N,N-dimethylpiperidine-1-carboxamide;

4-Hydroxy-4-[[1-(4-hydroxyphenyl)-4-oxo-1H,4H,5H-pyrazolo [3,4-d]pyrimidin-5-yl]methyl]-N,N-dimethylpiperidine-1-carboxamide;

5-{[4-hydroxy-1-(4-phenoxybenzoyl}piperidin-4-yl]methyl}-1-(propan-2-yl)-1H,4H,5H-pyrazolo[3,4-d]pyrimidin-4-one;

5-{[1-(4-fluorobenzoyl)-4-hydroxypiperidin-4-yl]methyl}-1-(4-methoxyphenyl)-1H,4H,5H-pyrazolo[3,4-d]pyrimidin-4-one;

5-{[1-(4-fluorobenzoyl)-4-hydroxypiperidin-4-yl]methyl}-1-(3-methoxyphenyl)-1H,4H,5H-pyrazolo[3,4-d]pyrimidin-4-one;

5-{[1-(4-fluorobenzoyl)-4-hydroxypiperidin-4-yl]methyl}-1-(4-hydroxyphenyl)-1H,4H,5H-pyrazolo[3,4-d]pyrimidin-4-one;

5-{[1-(4-fluorobenzoyl)-4-hydroxypiperidin-4-yl]methyl}-1-(3-hydroxyphenyl)-1H,4H,5H-pyrazolo[3,4-d]pyrimidin-4-one;

5-{1-(1-(4-fluorobenzoyl)-4-hydroxypiperidin-4-yl)ethyl)-1-(4-methoxyphenyl)-1H-pyrazolo[3,4-d]pyrimidin-4 (5H)-one;

5-{1-[4-hydroxy-1-(4-methoxybenzoyl}piperidin-4-yl]ethyl}-1-(4-methoxyphenyl)-1H,4H,5H-pyrazolo[3,4-d]pyrimidin-4-one;

1-(3-bromo-4-fluorophenyl)-5-{[1-(4-fluorobenzoyl)-4-hydroxypiperidin-4-yl]methyl)-1H-pyrazolo[3,4-d]pyrimidin-4-one;

1-(4-fluoro-3-methoxyphenyl)-5-([1-(4-fluorobenzoyl)-4-hydroxypiperidin-4-yl]methyl}-1H,4H,5H-pyrazolo[3,4-d]pyrimidin-4-one;

5-{[1-(4-fluorobenzoyl)-4-hydroxypiperidin-4-yl]methyl}-1-(6-fluoropyridin-3-yl)-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-(4-cyclopropylphenyl)-1H,4H,5H-pyrazolo[3,4-d]pyrimidin-4-one;

5-{{4-hydroxy-1-[(3R)-3-phenylbutanoyl]piperidin-4-yl}methyl)-3-methyl-1-phenyl-1H,4H,5H-pyrazolo[3,4-d]pyrimidin-4-one;

1-(4-bromophenyl)-5-[(1-cyclopropanecarbonyl-4-hydroxypiperidin-4-yl)methyl]-1H,4H,5H-pyrazolo[3,4-d]pyrimidin-4-one;

1-(3-bromo-4-chlorophenyl)-5-[(1-cyclopropanecarbonyl-4-hydroxypiperidin-4-yl)methyl]-1H,4H,5H-pyrazolo[3,4-d]pyrimidin-4-one;

1-(4-fluoro-3-hydroxyphenyl)-5-([1-[(4-fluorophenyl)carbonyl]-4-hydroxypiperidin-4-yl]methyl}-1H,4H,5H-pyrazolo[3,4-d]pyrimidin-4-one;

5-[(1-cyclopropanecarbonyl-4-hydroxypiperidin-4-yl)methyl]-1-[4-fluoro-3-(3-methoxy-3-methylpyrrolidin-1-yl)phenyl]-1H,4H,5H-pyrazolo[3,4-d]pyrimidin-4-one;

5-{(1-benzoyl-4-hydroxypiperidin-4-yl}methyl)-1-(4-fluoro-3-(4-methylpiperazin-1-yl)phenyl)-1H-pyrazolo[3,4-d]pyrimidin-4 (5H)-one;

1-(3-Amino-4-fluorophenyl)-5-([1-[(4-fluorophenyl)carbonyl]-4-hydroxypiperidin-4-yl]methyl}-1H,4H,5H-pyrazolo[3,4-d]pyrimidin-4-one;

5-[(1-cyclopropanecarbonyl-4-hydroxypiperidin-4-yl)methyl]-1-[4-fluoro-3-(3-hydroxy-3-methylpyrrolidin-1-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-fluoro-3-[(3S)-3-hydroxy-3-methylpyrrolidin-1-yl]phenyl}-1H,4H,5H-pyrazolo[3,4-d]pyrimidin-4-one;

5-[(1-cyclopropanecarbonyl-4-hydroxypiperidin-4-yl)methyl]-1-{4-fluoro-3-[(3R)-3-hydroxy-3-methylpyrrolidin-1-yl]phenyl}-1H,4H,5H-pyrazolo[3,4-d]pyrimidin-4-one;

1-[4-fluoro-3-(morpholin-4-yl)phenyl]-5-{[1-(4-fluorobenzoyl)-4-hydroxypiperidin-4-yl]methyl}-1H,4H,5H-pyrazolo[3,4-d]pyrimidin-4-one;

5-{[4-hydroxy-1-(4-phenoxybenzoyl}piperidin-4-yl]methyl}-3-methyl-1-phenyl-1H,4H,5H-pyrazolo[3,4-d]pyrimidin-4-one;

1-(4-fluoro-3-(hydroxymethyl)phenyl)-5-((1-(4-fluorobenzoyl)-4-hydroxypiperidin-4-yl}methyl)-1H-pyrazolo[3,4-d]pyrimidin-4 (5H)-one;

5-{{1-[4-(difluoromethoxy)benzoyl]-4-hydroxypiperidin-4-yl}methyl)-1-[4-fluoro-3-(hydroxymethyl)phenyl]-1H,4H,5H-pyrazolo[3,4-d]pyrimidin-4-one;

1-[4-fluoro-3-(hydroxymethyl)phenyl]-5-({4-hydroxy-1-[4-(pyridin-2-yloxy)benzoyl]piperidin-4-yl}methyl)-1H,4H,5H-pyrazolo[3,4-d]pyrimidin-4-one;

1-(Biphenyl-4-yl)-5-((4-hydroxy-1-(2-morpholinooxazole-5-carbonyl) piperidin-4-yl}methyl)-1H-pyrazolo [3,4-d]pyrimidin-4 (5H)-one;

5-{{1-[4,4-difluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one;

5-{{1-[(3S)-4,4-difluoro-3-(1H-pyrazol-1-yl)butanoyl]-4-hydroxypiperidin-4-yl}methyl)-1-(4-phenylphenyl)-1H,4H,5H-pyrazolo[3,4-d]pyrimidin-4-one;

5-{{4-hydroxy-1-[3-(1H-pyrazol-1-yl)butanoyl]piperidin-4-yl}methyl)-1-(4-phenylphenyl)-1H,4H,5H-pyrazolo[3,4-d]pyrimidin-4-one;

5-{{4-hydroxy-1-[(3S)-3-(1H-pyrazol-1-yl)butanoyl]piperidin-4-yl}methyl)-1-(4-phenylphenyl)-1H,4H,5H-pyrazolo[3,4-d]pyrimidin-4-one;

1-(4-fluorophenyl)-5-({4-hydroxy-1-[(3R)-3-phenylbutanoyl]piperidin-4-yl}methyl)-1H,4H,5H-pyrazolo[3,4-d]pyrimidin-4-one;

5-{{4-hydroxy-1-[(3R)-3-(1H-pyrazol-1-yl)butanoyl]piperidin-4-yl}methyl)-1-(4-phenylphenyl)-1H,4H,5H-pyrazolo[3,4-d]pyrimidin-4-one;

1-[4-(4-fluorophenyl)phenyl]-5-({4-hydroxy-1-[3-(1H-pyrazol-1-yl)butanoyl]piperidin-4-yl}methyl)-1H,4H,5H-pyrazolo[3,4-d]pyrimidin-4-one;

1-[4-(4-fluorophenyl)phenyl]-5-({4-hydroxy-1-[(3R)-3-(1H-pyrazol-1-yl)butanoyl]piperidin-4-yl}methyl)-1H,4H,5H-pyrazolo[3,4-d]pyrimidin-4-one;

1-[4-(4-fluorophenyl)phenyl]-5-({4-hydroxy-1-[(3S)-3-(1H-pyrazol-1-yl)butanoyl]piperidin-4-yl}methyl)-1H,4H,5H-pyrazolo[3,4-d]pyrimidin-4-one;

4-([1-[4-(4-fluorophenyl)phenyl]-4-oxo-1H,4H,5H-pyrazolo[3,4-d]pyrimidin-5-yl]methyl)-4-hydroxy-N-methylpiperidine-1-carboxamide;

5-{(1-(1-acryloylazetidine-2-carbonyl)-4-hydroxypiperidin-4-yl) methyl)-1-(biphenyl-4-yl}-1H-pyrazolo[3,4-d]pyrimidin-4 (5H)-one;

N-[(1r,3r)-3-(4-hydroxy-4-{[4-oxo-1-(4-phenylphenyl)-1H,4H,5H-pyrazolo[3,4-d]pyrimidin-5-yl]methyl)piperidine-1-carbonyl)cyclobutyl]prop-2-ynamide;

5-{{4-hydroxy-1-[(2S)-2-methyl-1-(prop-2-enoyl)azetidine-2-carbonyl]piperidin-4-yl}methyl)-1-(4-phenylphenyl)-1 H,4H,5H-pyrazolo[3,4-d]pyrimidin-4-one;

1-(4-fluorophenyl)-5-{[4-hydroxy-1-(4-phenoxybenzoyl}piperidin-4-yl]methyl)-1H,4H,5H-pyrazolo[3,4-d]pyrimidin-4-one;

5-{{4-hydroxy-1-[(2R)-2-methyl-1-(prop-2-enoyl)azetidine-2-carbonyl]piperidin-4-yl}methyl)-1-(4-phenylphenyl)-1 H,4H,5H-pyrazolo[3,4-d]pyrimidin-4-one;

pyrrolidin-3-ylmethyl 4-hydroxy-4-{[4-oxo-1-(4-phenylphenyl)-1H,4H,5H-pyrazolo[3,4-d]pyrimidin-5-yl] methyl)piperidine-1-carboxylate;

N-(4-fluoropyrrolidin-3-yl)-4-hydroxy-4-{[4-oxo-1-(4-phenylphenyl)-1H,4H,5H-pyrazolo[3,4-d]pyrimidin-5-yl]methyl)piperidine-1-carboxamide;

N-[(3R)-4-fluoropyrrolidin-3-yl]-4-hydroxy-4-{[4-oxo-1-(4-phenylphenyl)-1H,4H,5H-pyrazolo[3,4-d]pyrimidin-5-yl]methyl)piperidine-1-carboxamide;

N-[(3S)-4-fluoropyrrolidin-3-yl]-4-hydroxy-4-{[4-oxo-1-(4-phenylphenyl)-1H,4H,5H-pyrazolo[3,4-d]pyrimidin-5-yl]methyl)piperidine-1-carboxamide;

5-{(1-benzoyl-4-hydroxypiperidin-4-yl}methyl)-1-(2-(hydroxymethyl) biphenyl-4-yl}-1H-pyrazolo[3,4-d]pyrimidin-4 (5H)-one;

5-[(1-cyclopropanecarbonyl-4-hydroxypiperidin-4-yl) methyl]-1-[3-(hydroxymethyl)-4-phenylphenyl]-1H,4H,5H-pyrazolo[3,4-d]pyrimidin-4-one;

5-{[4-hydroxy-1-[(morpholin-4-yl)carbonyl]piperidin-4-yl]methyl) -1-[3-(hydroxymethyl)-4-phenylphenyl]-1 H,4H,5H-pyrazolo[3,4-d]pyrimidin-4-one;

1-[3-(Aminomethyl)-4-phenylphenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl) methyl]-1-{3-[(dimethylamino)methyl]-4-phenylphenyl)-1H,4H,5H-pyrazolo[3,4-d]pyrimidin-4-one;

5-{{4-hydroxy-1-[(3R)-3-phenylbutanoyl]piperidin-4-yl}methyl)-1-[3-(trifluoromethyl)phenyl]-1H,4H,5H-pyrazolo[3,4-d]pyrimidin-4-one;

5-{[1-[(4-fluorophenyl)carbonyl]-4-hydroxypiperidin-4-yl]methyl}-1-(4-[[2-(propan-2-yloxy)ethyl]amino] phenyl)-1H,4H,5H-pyrazolo[3,4-d]pyrimidin-4-one;

5-[(1-benzoyl-4-hydroxypiperidin-4-yl)methyl]-1-(4-{[2-(propan-2-yloxy)ethyl]amino}phenyl)-1H,4H,5H-pyrazolo[3,4-d]pyrimidin-4-one;

5-{[4-hydroxy-1-[(4-methylphenyl)carbonyl]piperidin-4-yl]methyl}-1-[4-[4-(2-hydroxyethoxy)-1H-pyrazol-1-yl]phenyl]-1H,4H,5H-pyrazolo[3,4-d]pyrimidin-4-one;

5-{[1-(4-fluorobenzoyl)-4-hydroxypiperidin-4-yl] methyl}-1-[4-(3-methyl-1H-1,2,4-triazol-1-yl)phenyl]-1H,4H,5H-pyrazolo[3,4-d]pyrimidin-4-one;

5-{(1-(cyclopropanecarbonyl)-4-hydroxypiperidin-4-yl}methyl)-1-(2'-(2-(dimethylamino)ethylamino)biphenyl-4-yl}-1H-pyrazolo[3,4-d]pyrimidin-4 (5H)-one;

5-[(1-cyclopropanecarbonyl-4-hydroxypiperidin-4-yl) methyl]-1-[4-[4-(pyrrolidin-3-yloxy)phenyl]phenyl]-1H,4H,5H-pyrazolo[3,4-d]pyrimidin-4-one;

5-[(1-cyclopropanecarbonyl-4-hydroxypiperidin-4-yl) methyl]-1-(4-{4-[2-(dimethylamino)ethoxy]-3-fluorophenyl}phenyl)-1H,4H,5H-pyrazolo[3,4-d]pyrimidin-4-one;

5-[(1-cyclopropanecarbonyl-4-hydroxypiperidin-4-yl) methyl]-1-(4-{2-[2-(dimethylamino)ethoxy] phenyl}phenyl)-1H,4H,5H-pyrazolo[3,4-d]pyrimidin-4-one;

5-[(1-cyclopropanecarbonyl-4-hydroxypiperidin-4-yl) methyl]-1-(4-[4-[(1-methylpyrrolidin-3-yl)oxy]phenyl]phenyl)-1H,4H,5H-pyrazolo[3,4-d]pyrimidin-4-one;

5-[(1-cyclopropanecarbonyl-4-hydroxypiperidin-4-yl) methyl]-1-[4-(4-{[(3R)-1-methylpyrrolidin-3-yl]oxy}phenyl)phenyl]-1H,4H,5H-pyrazolo[3,4-d]pyrimidin-4-one;

5-{{4-hydroxy-1-[(3R)-3-phenylbutanoyl]piperidin-4-yl}methyl)-1-(4-methylphenyl)-1H-pyrazolo[3,4-d]pyrimidin-4-one;

5-[(1-cyclopropanecarbonyl-4-hydroxypiperidin-4-yl) methyl]-1-[4-(4-{[(3S)-1-methylpyrrolidin-3-yl]oxy}phenyl)phenyl]-1H,4H,5H-pyrazolo[3,4-d]pyrimidin-4-one;

5-{(1-(cyclopropanecarbonyl)-4-hydroxypiperidin-4-yl}methyl)-1-(4-(1-(2,2-difluoroethyl)piperidin-4-yl) phenyl)-1H-pyrazolo[3,4-d]pyrimidin-4 (5H)-one;

4-hydroxy-N,N-dimethyl-4-({1-[4-(oxan-4-yl)phenyl]-4-oxo-1H,4H,5H-pyrazolo[3,4-d]pyrimidin-5-yl}methyl)piperidine-1-carboxamide;

4-[(1-{4-[1-(2,2-difluoroethyl)piperidin-4-yl]phenyl}-4-oxo-1H,4H,5H-pyrazolo[3,4-d]pyrimidin-5-yl) methyl]-4-hydroxy-N,N-dimethylpiperidine-1-carboxamide;

5-[(1-cyclopropanecarbonyl-4-hydroxypiperidin-4-yl) methyl]-1-(4-{6-[(3S)-3-(methylamino)pyrrolidin-1-yl]pyridin-3-yl)phenyl)-1H,4H,5H-pyrazolo[3,4-d]pyrimidin-4-one;

5-{(1-(cyclopropanecarbonyl)-4-hydroxypiperidin-4-yl}methyl)-1-(4-(6-(3-(methylamino)pyrrolidin-1-yl)pyridin-3-yl)phenyl)-1H-pyrazolo[3,4-d]pyrimidin-4 (5H)-one;

5-[(1-cyclopropanecarbonyl-4-hydroxypiperidin-4-yl) methyl]-1-(4-{6-[(3S)-3-hydroxypyrrolidin-1-yl]pyridin-3-yl)phenyl)-1H,4H,5H-pyrazolo[3,4-d]pyrimidin-4-one;

5-[(1-cyclopropanecarbonyl-4-hydroxypiperidin-4-yl) methyl]-1-(4-{6-[(3R)-3-hydroxypyrrolidin-1-yl]pyridin-3-yl)phenyl)-1H,4H,5H-pyrazolo[3,4-d]pyrimidin-4-one;

5-[(1-cyclopropanecarbonyl-4-hydroxypiperidin-4-yl) methyl]-1-(4-{4-[3-(methylamino)pyrrolidin-1-yl]phenyl)phenyl)-1H,4H,5H-pyrazolo[3,4-d]pyrimidin-4-one;

5-[(1-cyclopropanecarbonyl-4-hydroxypiperidin-4-yl) methyl]-1-(4-{4-[(3S)-3-(methylamino)pyrrolidin-1-yl]phenyl)phenyl)-1H,4H,5H-pyrazolo[3,4-d]pyrimidin-4-one;

5-{[4-hydroxy-1-(4-phenoxybenzoyl}piperidin-4-yl] methyl}-1-(4-methylphenyl)-1H,4H,5H-pyrazolo[3,4-d]pyrimidin-4-one;

5-[(1-cyclopropanecarbonyl-4-hydroxypiperidin-4-yl) methyl]-1-(4-{4-[(3R)-3-(methylamino)pyrrolidin-1-yl]phenyl}phenyl)-1H,4H,5H-pyrazolo[3,4-d]pyrimidin-4-one;

1-[4-[3-(3-aminooxetan-3-yl)phenyl]phenyl]-5-[(1-cyclopropanecarbonyl-4-hydroxypiperidin-4-yl)methyl]-1H,4H,5H-pyrazolo[3,4-d]pyrimidin-4-one;

5-{[1-[(4-fluorophenyl)carbonyl]-4-hydroxypiperidin-4-yl]methyl}-1-[4-[(1-methylazetidin-3-yl)oxy]phenyl]-1H,4H,5H-pyrazolo[3,4-d]pyrimidin-4-one;

5-{[1-(4-fluorobenzoyl)-4-hydroxypiperidin-4-yl] methyl}-1-{4-[(4-fluorooxan-4-yl)methoxy]phenyl)-1H,4H,5H-pyrazolo[3,4-d]pyrimidin-4-one;

1-{4-[(4,4-difluorocyclohexyl)oxy]phenyl)-5-{[1-(4-fluorobenzoyl)-4-hydroxypiperidin-4-yl]methyl)-1H,4H,5H-pyrazolo[3,4-d]pyrimidin-4-one;

5-[(1-cyclopropanecarbonyl-4-hydroxypiperidin-4-yl) methyl]-1-{4-[(4,4-difluorocyclohexyl)oxy]phenyl}-1H,4H,5H-pyrazolo[3,4-d]pyrimidin-4-one;

5-{[1-(4-fluorobenzoyl)-4-hydroxypiperidin-4-yl] methyl}-1-{4-[(1-fluorocyclobutyl)methoxy]phenyl)-1H,4H,5H-pyrazolo[3,4-d]pyrimidin-4-one;

1-(4-(4,4-difluorocyclohexyloxy)phenyl)-5-((4-hydroxy-1-(4-methylpiperazine-1-carbonyl)piperidin-4-yl}methyl)-1H-pyrazolo[3,4-d]pyrimidin-4 (5H)-one;

5-{(1-(cyclopropanecarbonyl)-4-hydroxypiperidin-4-yl}methyl)-1-(2-(piperazin-1-yl)biphenyl-4-yl)-1H-pyrazolo[3,4-d]pyrimidin-4 (5H)-one;

5-{[1-(2-cyclopropyl-1,3-oxazole-5-carbonyl)-4-hydroxypiperidin-4-yl]methyl}-1-[4-(4,4-difluoropiperidin-1-yl)phenyl]-1H,4H,5H-pyrazolo[3,4-d]pyrimidin-4-one;

5-{{4-hydroxy-1-[(3R)-3-phenylbutanoyl]piperidin-4-yl}methyl)-1-(pyridin-2-yl)-1H,4H,5H-pyrazolo[3,4-d]pyrimidin-4-one;

1-[4-(4,4-difluoropiperidin-1-yl)phenyl]-5-{[4-hydroxy-1-(4-methylbenzoyl)piperidin-4-yl]methyl)-1H,4H,5H-pyrazolo[3,4-d]pyrimidin-4-one;

1-[3-chloro-4-(4-methylpiperazin-1-yl)phenyl]-5-[(1-cyclopropanecarbonyl-4-hydroxypiperidin-4-yl)methyl]-1H,4H,5H-pyrazolo[3,4-d]pyrimidin-4-one;

5-[(1-cyclopropanecarbonyl-4-hydroxypiperidin-4-yl) methyl]-1-[3-(morpholin-4-yl)-4-phenylphenyl]-1H,4H,5H-pyrazolo[3,4-d]pyrimidin-4-one;

5-{[1-[(4-fluorophenyl)carbonyl]-4-hydroxypiperidin-4-yl]methyl}-1-(1-methyl-1H-pyrazol-4-yl)-1H,4H,5H-pyrazolo[3,4-d]pyrimidin-4-one;

5-{[1-(4-fluorobenzoyl)-4-hydroxypiperidin-4-yl] methyl}-1-(1-phenyl-1H-pyrazol-4-yl)-1H,4H,5H-pyrazolo[3,4-d]pyrimidin-4-one;

1-(1-cyclopropyl-1H-pyrazol-4-yl)-5-({1-[4-(difluoromethoxy)benzoyl]-4-hydroxypiperidin-4-yl}methyl)-1H,4H,5H-pyrazolo[3,4-d]pyrimidin-4-one;

4-((7-(4-fluorophenyl)-4-oxo-6-phenyl-4H-pyrrolo[2,3-d]pyrimidin-3 (7H)-yl}methyl)-4-hydroxy-N,N-dimethylpiperidine-1-carboxamide;

1-[4-(dimethylamino)phenyl]-5-({1-[(4-fluorophenyl)carbonyl]-4-hydroxypiperidin-4-yl}methyl}-1H,4H,5H-pyrazolo[3,4-d]pyrimidin-4-one;

5-{[4-hydroxy-1-(4-phenoxybenzoyl}piperidin-4-yl] methyl}-1-(pyridin-2-yl)-1H,4H,5H-pyrazolo[3,4-d]pyrimidin-4-one;

1-(4-(1H-1,2,3-triazol-1-yl)phenyl)-5-((1-(4-fluorobenzoyl)-4-hydroxypiperidin-4-yl}methyl)-1H-pyrazolo[3,4-d]pyrimidin-4(5H)-one;

5-{[1-(4-fluorobenzoyl)-4-hydroxypiperidin-4-yl] methyl}-1-[4-(5-methyl-1,3,4-oxadiazol-2-yl)phenyl]-1H,4H,5H-pyrazolo[3,4-d]pyrimidin-4-one;

5-{[1-[(4-Fluorophenyl)carbonyl]-4-hydroxypiperidin-4-yl]methyl}-1-[4-(1-hydroxycyclopropyl)phenyl]-1H,4H,5H-pyrazolo[3,4-d]pyrimidin-4-one;

5-{[(3R,4R)-1-benzoyl-3-fluoro-4-hydroxypiperidin-4-yl]methyl}-1-phenyl-1H,4H,5H-pyrazolo[3,4-d]pyrimidin-4-one;

5-{[(3S,4R)-1-benzoyl-3-fluoro-4-hydroxypiperidin-4-yl]methyl}-1-phenyl-1H,4H,5H-pyrazolo[3,4-d]pyrimidin-4-one;

1-(4-fluorophenyl)-5-((4-hydroxy-1-(4-({1-methyl-1H-pyrazol-3-yl)oxy)benzoyl}piperidin-4-yl}methyl)-1H-pyrazolo[3,4-d]pyrimidin-4(5H)-one;

5-{(4-hydroxy-1-[(3R)-3-phenylbutanoyl]piperidin-4-yl}methyl)-1-phenyl-1H,4H,5H-pyrazolo[3,4-d]pyrimidin-4-one;

5-{1-(1-(4-fluorobenzoyl)-4-hydroxypiperidin-4-yl)-2-hydroxyethyl)-1-(4-fluorophenyl)-1H-pyrazolo[3,4-d]pyrimidin-4(5H)-one;

8-((1-(4-fluorophenyl)-4-oxo-1,4-dihydro-5H-pyrazolo[3,4-d]pyrimidin-5-yl}methyl)-8-hydroxyoctahydro-4H-quinolizin-4-one;

1-(4-fluorophenyl)-5-((4-hydroxy-1-[(1r,4r)-4-methoxycyclohexanecarbonyl]piperidin-4-yl}methyl)-1H,4H,5H-pyrazolo[3,4-d]pyrimidin-4-one;

4-(4-{[1-(4-fluorophenyl)-4-oxo-1H,4H,5H-pyrazolo[3,4-d]pyrimidin-5-yl]methyl}-4-hydroxypiperidine-1-carbonyl)-1 v-thiane-1,1-dione;

1-(4-fluorophenyl)-5-{[4-hydroxy-1-(4,5,6,7-tetrahydro-1H-indazole-6-carbonyl)piperidin-4-yl]methyl}-1H,4H,5H-pyrazolo[3,4-d]pyrimidin-4-one;

1-(4-fluorophenyl)-5-{[4-hydroxy-1-(1-methyl-4,5,6,7-tetrahydro-1H-indazole-6-carbonyl)piperidin-4-yl] methyl)-1H,4H,5H-pyrazolo[3,4-d]pyrimidin-4-one;

5-{[1-(1-cyclopropyl-1H-pyrazole-4-carbonyl)-4-hydroxypiperidin-4-yl]methyl}-1-(4-fluorophenyl)-1H,4H,5H-pyrazolo[3,4-d]pyrimidin-4-one;

1-(4-fluorophenyl)-5-((4-hydroxy-1-[(1r,4r)-4-(1-methyl-1H-pyrazol-4-yl)cyclohexanecarbonyl]piperidin-4-yl}methyl)-1H,4H,5H-pyrazolo[3,4-d]pyrimidin-4-one;

1-(4-fluorophenyl)-5-((4-hydroxy-1-[(1s,4s)-4-(1-methyl-1H-pyrazol-4-yl)cyclohexanecarbonyl]piperidin-4-yl}methyl)-1H,4H,5H-pyrazolo[3,4-d]pyrimidin-4-one;

5-{[4-hydroxy-1-(4-phenoxybenzoyl}piperidin-4-yl] methyl}-1-phenyl-1H,4H,5H-pyrazolo[3,4-d]pyrimidin-4-one;

5-{(1-[(3R)-3-(3-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one;

5-{(1-[(3S)-3-(3-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one;

5-{(1-[(3R)-3-(4-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one;

5-{(1-[(3S)-3-(4-chloro-1H-pyrazol-1-yl)-4,4-difluorobutanoyl]-4-hydroxypiperidin-4-yl}methyl)-1-(4-fluorophenyl)-1H,4H,5H-pyrazolo[3,4-d]pyrimidin-4-one;

5-{(1-[(3R)-4,4-difluoro-3-(4-methyl-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

5-{(1-[(3S)-4,4-difluoro-3-(4-methyl-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

1-(4-fluorophenyl)-5-[(4-hydroxy-1-[[(1r,4r)-4-[(5-fluoropyridin-2-yl)oxy]cyclohexyl]carbonyl]piperidin-4-yl)methyl]-1H,4H,5H-pyrazolo[3,4-d]pyrimidin-4-one;

1-(4-fluorophenyl)-5-[(4-hydroxy-1-[[(1s,4s)-4-[(5-fluoropyridin-2-yl) oxy]cyclohexyl]carbonyl]piperidin-4-yl)methyl]-1H,4H,5H-pyrazolo[3,4-d]pyrimidin-4-one;

1-(4-fluorophenyl)-5-((4-hydroxy-1-[(1r,4r)-4-[(6-fluoropyridin-2-yl)oxy]cyclohexanecarbonyl]piperidin-4-yl}methyl)-1H,4H,5H-pyrazolo[3,4-d]pyrimidin-4-one;

5-{{4-hydroxy-1-[4-(1H-imidazol-1-ylmethyl}benzoyl]piperidin-4-yl}methyl)-1-methyl-1H,4H,5H-pyrazolo[3,4-d]pyrimidin-4-one;

1-(4-fluorophenyl)-5-({4-hydroxy-1-[(1s,4s)-4-[(6-fluoropyridin-2-yl)oxy]cyclohexanecarbonyl]piperidin-4-yl}methyl)-1H,4H,5H-pyrazolo[3,4-d]pyrimidin-4-one;

5-{{4-hydroxy-1-[(1r,4r)-4-[(6-fluoropyridin-2-yl)oxy]cyclohexanecarbonyl]piperidin-4-yl}methyl)-1-phenyl-1H,4H,5H-pyrazolo[3,4-d]pyrimidin-4-one;

5-{{4-hydroxy-1-[(1s,4s)-4-[(6-fluoropyridin-2-yl)oxy]cyclohexanecarbonyl]piperidin-4-yl}methyl)-1-phenyl-1H,4H,5H-pyrazolo[3,4-d]pyrimidin-4-one;

5-{{4-hydroxy-1-[(1r,4r)-4-[(5-fluoropyridin-2-yl)oxy]cyclohexanecarbonyl]piperidin-4-yl}methyl)-1-phenyl-1H,4H,5H-pyrazolo[3,4-d]pyrimidin-4-one;

5-{{4-hydroxy-1-[(1s,4s)-4-[(5-fluoropyridin-2-yl)oxy]cyclohexanecarbonyl]piperidin-4-yl}methyl)-1-phenyl-1H,4H,5H-pyrazolo[3,4-d]pyrimidin-4-one;

1-(4-fluorophenyl)-5-({4-hydroxy-1-[(1s,4s)-1-methyl-4-(pyridin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-1-methyl-4-(pyridin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-(pyrimidin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(pyrimidin-2-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-(pyridin-3-yloxy)cyclohexanecarbonyl]piperidin-4-yl}methyl)-1H,4H,5H-pyrazolo[3,4-d]pyrimidin-4-one;

5-{{4-hydroxy-1-[4-(1H-1,2,3,4-tetrazol-1-ylmethyl}benzoyl]piperidin-4-yl}methyl)-1-methyl-1H,4H,5H-pyrazolo[3,4-d]pyrimidin-4-one;

1-(4-fluorophenyl)-5-({4-hydroxy-1-[(1r,4r)-4-(pyridin-3-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-(pyridin-4-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(pyridin-4-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-[(1-methyl-1H-pyrazol-3-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(1-methyl-1H-pyrazol-3-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-[(5-methyl-1,2-oxazol-3-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(5-methyl-1,2-oxazol-3-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-[(1-methyl-1H-pyrazol-4-yl)oxy]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(1-methyl-1H-pyrazol-4-yl)oxy]cyclohexanecarbonyl]piperidin-4-yl}methyl)-1H,4H,5H-pyrazolo[3,4-d]pyrimidin-4-one;

5-{(1-(2-benzylazetidine-1-carbonyl)-4-hydroxypiperidin-4-yl}methyl)-1-(4-fluorophenyl)-1H-pyrazolo[3,4-d]pyrimidin-4(5H)-one;

5-{[1-(2-benzylbenzoyl)-4-hydroxypiperidin-4-yl]methyl}-1-methyl-1H,4H,5H-pyrazolo[3,4-d]pyrimidin-4-one;

5-{{1-[(2R)-2-benzylazetidine-1-carbonyl]-4-hydroxypiperidin-4-yl}methyl)-1-(4-fluorophenyl)-1H,4H,5H-pyrazolo[3,4-d]pyrimidin-4-one;

1-(4-fluorophenyl)-5-[(4-hydroxy-1-{1H,4H,5H,6H,7H-pyrazolo[3,4-c]pyridine-6-carbonyl}piperidin-4-yl)methyl]-1H,4H,5H-pyrazolo[3,4-d]pyrimidin-4-one;

1-(4-fluorophenyl)-5-[(4-hydroxy-1-{1-methyl-1H,4H,5H,6H,7H-pyrazolo[3,4-c]pyridine-6-carbonyl}piperidin-4-yl)methyl]-1H,4H,5H-pyrazolo[3,4-d]pyrimidin-4-one;

1-(4-fluorophenyl)-5-({4-hydroxy-1-[(1s,4s)-4-[(1-methyl-1H-pyrazol-5-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(1-methyl-1H-pyrazol-5-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-[(1-methyl-1H-pyrazol-3-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-[(1-methyl-1H-pyrazol-3-yl)amino]cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1s,4s)-4-(phenylamino)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(phenylamino)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(cyclopropylamino)cyclohexanecarbonyl] piperidin-4-yl}methyl)-1H,4H,5H-pyrazolo[3,4-d]pyrimidin-4-one;

5-{{1-[3-(3-fluorophenyl)butanoyl]-4-hydroxypiperidin-4-yl}methyl)-1-methyl-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-{4-[(3,3-difluorocyclobutyl)methoxy]phenyl)-1H,4H,5H-pyrazolo[3,4-d]pyrimidin-4-one;

1-(4-chlorophenyl)-5-[(1-[[2-(cyclopropylamino)-1,3-oxazol-5-yl]carbonyl]-4-hydroxypiperidin-4-yl)methyl]-1H,4H,5H-pyrazolo[3,4-d]pyrimidin-4-one;

1-(4-chlorophenyl)-5-{[4-hydroxy-1-(1-methyl-1H-pyrazole-4-carbonyl)piperidin-4-yl]methyl}-1H,4H,5H-pyrazolo[3,4-d]pyrimidin-4-one;

5-{(1-(3-(3-aminopropoxy)benzoyl)-4-hydroxypiperidin-4-yl}methyl)-1-(4-chlorophenyl)-1H-pyrazolo[3,4-d]pyrimidin-4(5H)-one;

5-{(4-hydroxy-1-(1-methylcyclopropanecarbonyl)piperidin-4-yl) methyl)-1-(4-(1-methyl-1H-pyrazol-4-yl)phenyl)-1H-pyrazolo[3,4-d]pyrimidin-4(5H)-one;

5-{[1-[(2-Cyclopropyl-1,3-oxazol-5-yl)carbonyl]-4-hydroxypiperidin-4-yl]methyl}-1-[4-(1-methyl-1H-pyrazol-4-yl)phenyl]-1H,4H,5H-pyrazolo[3,4-d]pyrimidin-4-one;

(S)-1-(4-(hexahydro-1H-pyrido[1,2-a]pyrazin-2(6H)-yl)phenyl)-5-((4-hydroxy-1-(1-methylcyclopropanecarbonyl)piperidin-4-yl) methyl)-1H-pyrazolo[3,4-d]pyrimidin-4(5H)-one;

(R)-1-(4-(hexahydro-1H-pyrido [1,2-a]pyrazin-2(6H)-yl)phenyl)-5-((4-hydroxy-1-(1-methylcyclopropanecarbonyl)piperidin-4-yl}methyl)-1H-pyrazolo[3,4-d]pyrimidin-4(5H)-one;

5-{[1-[(2-cyclopropyl-1,3-oxazol-5-yl)carbonyl]-4-hydroxypiperidin-4-yl]methyl}-1-[4-(4-methyl-1H-pyrazol-1-yl)phenyl]-1H,4H,5H-pyrazolo[3,4-d]pyrimidin-4-one;

5-{{1-[3-(4-fluorophenyl)butanoyl]-4-hydroxypiperidin-4-yl}methyl)-1-methyl-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-[4-(1H-pyrazol-1-yl)phenyl]-1H,4H,5H-pyrazolo[3,4-d]pyrimidin-4-one;

5-{[4-hydroxy-1-(1-methylcyclopropanecarbonyl)piperidin-4-yl]methyl}-1-[4-(1H-pyrazol-1-yl)phenyl]-1H,4H,5H-pyrazolo[3,4-d]pyrimidin-4-one;

5-{[4-hydroxy-1-(1-methylcyclobutanecarbonyl)piperidin-4-yl]methyl}-1-[4-(1H-pyrazol-1-yl)phenyl]-1H,4H,5H-pyrazolo[3,4-d]pyrimidin-4-one;

(R)-5-((1-(cyclohexanecarbonyl)-4-hydroxypiperidin-4-yl}methyl)-1-(4-(3-hydroxy-3-methylpyrrolidin-1-yl)phenyl)-1H-pyrazolo[3,4-d]pyrimidin-4(5H)-one;

1-(4-{3-azabicyclo[3.1.0]hexan-3-yl}phenyl)-5-({1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

1-(4-{3-azabicyclo[3.1.0]hexan-3-yl}phenyl)-5-({1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

1-(4-(4,4-Difluorocyclohexylamino)phenyl)-5-((4-hydroxy-1-methylcyclopropanecarbonyl)piperidin-4-yl}methyl)-1H-pyrazolo[3,4-d]pyrimidin-4(5H)-one;

N-(4'-(4-((1-(4-ethynylphenyl)-4-oxo-1H-pyrazolo[3,4-d]pyrimidin- 5(4H)-yl}methyl)-4-hydroxypiperidine-1-carbonyl)biphenyl-2-yl)ethenesulfonamide;

5-{[1-[(3R)-4,4-difluoro-3-(3-fluoro-1H-pyrazol-1-yl)butanoyl]-4-hydroxypiperidin-4-yl]methyl}-1-[3-(morpholin-4-yl)phenyl]-1H,4H,5H-pyrazolo[3,4-d]pyrimidin-4-one;

5-{[1-[(3S)-4,4-difluoro-3-(3-fluoro-1H-pyrazol-1-yl)butanoyl]-4-hydroxypiperidin-4-yl]methyl}-1-[3-(morpholin-4-yl)phenyl]-1H,4H,5H-pyrazolo[3,4-d]pyrimidin-4-one;

5-{[4-hydroxy-1-(2-methyl-4-phenylbutanoyl)piperidin-4-yl]methyl}-1-methyl-1H,4H,5H-pyrazolo[3,4-d]pyrimidin-4-one;

1-(3-{3-azabicyclo[3.1.0]hexan-3-yl}phenyl)-5-({1-[(3S)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

1-(3-{3-azabicyclo[3.1.0]hexan-3-yl}phenyl)-5-({1-[(3R)-4,4-difluoro-3-(3-fluoro-1H-pyrazol-1-yl)butanoyl]-4-hydroxypiperidin-4-yl}methyl)-1H,4H,5H-pyrazolo[3,4-d]pyrimidin-4-one;

(R)-3-((1-(4,4-difluoro-3-(1H-pyrazol-1-yl)butanoyl)-4-hydroxypiperidin-4-yl}methyl)-7-(3-(4-methylpiperazin-1-yl)phenyl)-3H-pyrrolo[2,3-d]pyrimidin-4(7H)-one;

(S)-3-((1-(4,4-difluoro-3-(1H-pyrazol-1-yl)butanoyl)-4-hydroxypiperidin-4-yl}methyl)-7-(3-(4-methylpiperazin-1-yl)phenyl)-3H-pyrrolo[2,3-d]pyrimidin-4(7H)-one;

7-(4-fluorophenyl)-3-((4-hydroxy-1-(trans-4-({1-methyl-1H-pyrazol-5-yl)oxy)cyclohexanecarbonyl)piperidin-4-yl}methyl)-3H-pyrrolo[2,3-d]pyrimidin-4(7H)-one;

1-(4-ethylphenyl)-5-((4-hydroxy-1-(4-(1-methylpiperidin-4-yloxy)benzoyl}piperidin-4-yl}methyl)-1H-pyrazolo[3,4-d]pyrimidin-4(5H)-one;

(R)-5-((1-(4,4-difluoro-3-(3-fluoro-1H-pyrazol-1-yl)butanoyl)-4-hydroxypiperidin-4-yl}methyl)-1-p-tolyl-1H-pyrazolo[3,4-d]pyrimidin-4(5H)-one;

(S)-5-((1-(4,4-difluoro-3-(3-fluoro-1H-pyrazol-1-yl)butanoyl)-4-hydroxypiperidin-4-yl}methyl)-1-p-tolyl-1H-pyrazolo[3,4-d]pyrimidin-4(5H)-one;

5-{[1-[(1-cyclopropyl-1H-pyrazol-4-yl)carbonyl]-4-hydroxypiperidin-4-yl]methyl}-1-(4-cyclopropylphenyl)-1H,4H,5H-pyrazolo[3,4-d]pyrimidin-4-one;

1-(4-cyclopropylphenyl)-5-((4-hydroxy-1-(2-methyloxazole-5-carbonyl)piperidin-4-yl}methyl)-1H-pyrazolo[3,4-d]pyrimidin-4(5H)-one;

5-{[1-(2-benzylcyclopropanecarbonyl)-4-hydroxypiperidin-4-yl]methyl}-1-methyl-1H,4H,5H-pyrazolo[3,4-d]pyrimidin-4-one;

1-(4-fluorophenyl)-5-({4-hydroxy-1-[(2S)-1-(prop-2-ynoyl)azetidine-2-carbonyl]piperidin-4-yl}methyl)-1H,4H,5H-pyrazolo[3,4-d]pyrimidin-4-one;

1-(4-Fluorophenyl)-5-((4-hydroxy-1-(trans-4-(5-methylisoxazol-3-ylamino)cyclohexanecarbonyl)piperidin-4-yl}methyl)-1H-pyrazolo[3,4-d]pyrimidin-4(5H)-one;

1-(4-Fluorophenyl)-5-((4-hydroxy-1-(cis-4-(5-methylisoxazol-3-ylamino)cyclohexanecarbonyl)piperidin-4-yl}methyl)-1H-pyrazolo[3,4-d]pyrimidin-4(5H)-one;

5-{[4-hydroxy-1-(2-methoxy-3-phenylpropanoyl)piperidin-4-yl]methyl}-1-methyl-1H,4H,5H-pyrazolo[3,4-d]pyrimidin-4-one;

4-([1-(3-bromo-4-fluorophenyl)-4-oxo-1H,4H,5H-pyrazolo[3,4-d]pyrimidin-5-yl]methyl)-4-hydroxy-N,N-dimethylpiperidine-1-carboxamide;

4-([1-(3-bromophenyl)-4-oxo-1H,4H,5H-pyrazolo[3,4-d]pyrimidin-5-yl]methyl)-4-hydroxy-N,N-dimethylpiperidine-1-carboxamide;

4-(5-((1-(cyclopropanecarbonyl)-4-hydroxypiperidin-4-yl}methyl) -4-oxo-4,5-dihydropyrazolo[3,4-d]pyrimidin-1-yl)benzoic acid;

N-[(2R)-1-[4-hydroxy-4-((4-oxo-1-phenyl-1H,4H,5H-pyrazolo[3,4-d]pyrimidin-5-yl]methyl)piperidin-1-yl]-1-oxo-3-phenylpropan-2-yl]ethene-1-sulfonamide;

Anti-5-((4-Hydroxy-1-(1-methylcyclopropanecarbonyl) piperidin-4-yl}methyl)-1-(4-((4-methoxycyclohexyl)oxy)phenyl)-1H-pyrazolo[3,4-d]pyrimidin-4(5H)-one;

Syn-5-((4-Hydroxy-1-(1-methylcyclopropanecarbonyl) piperidin-4-yl}methyl)-1-(4-((4-methoxycyclohexyl)oxy)phenyl)-1H-pyrazolo[3,4-d]pyrimidin-4(5H)-one;

5-{(1-(4-fluorobenzoyl)-4-hydroxypiperidin-4-yl}methyl)-1-(4-((3-hydroxy-1-methylazetidin-3-yl)methoxy)phenyl)-1H-pyrazolo[3,4-d]pyrimidin-4 (5H)-one;

5-{[1-(2-cyclopropyl-1,3-oxazole-5-carbonyl)-4-hydroxypiperidin-4-yl]methyl}-1-{4-[(4,4-difluorocyclohexyl)oxy]phenyl}-1H,4H,5H-pyrazolo[3,4-d]pyrimidin-4-one;

5-[(1-cyclopropanecarbonyl-4-hydroxypiperidin-4-yl)methyl]-1-{4-[3-(4-methylpiperazin-1-yl}-1H-pyrazol-1-yl]phenyl)-1H,4H,5H-pyrazolo[3,4-d]pyrimidin-4-one;

5-[(1-cyclopropanecarbonyl-4-hydroxypiperidin-4-yl)methyl]-1-{4-[4-(morpholin-4-yl}-1H-pyrazol-1-yl]phenyl)-1H,4H,5H-pyrazolo[3,4-d]pyrimidin-4-one;

5-{[4-hydroxy-1-(4,4,4-trifluoro-3-phenylbutanoyl)piperidin-4-yl]methyl}-1-methyl-1H,4H,5H-pyrazolo[3,4-d]pyrimidin-4-one;

5-{[1-(4-fluorobenzoyl)-4-hydroxypiperidin-4-yl]methyl}-1-(4-{1H,4H,6H,7H-pyrano[4,3-c]pyrazol-1-yl}phenyl)-1H,4H,5H-pyrazolo[3,4-d]pyrimidin-4-one;

5-{[1-[(3R)-4,4-difluoro-3-(1H-pyrazol-1-yl)butanoyl]-4-hydroxypiperidin-4-yl]methyl}-1-[4-(piperidin-1-yl)phenyl]-1H,4H,5H-pyrazolo[3,4-d]pyrimidin-4-one;

5-{[1-[(3S)-4,4-difluoro-3-(1H-pyrazol-1-yl)butanoyl]-4-hydroxypiperidin-4-yl]methyl}-1-[4-(piperidin-1-yl)phenyl]-1H,4H,5H-pyrazolo[3,4-d]pyrimidin-4-one;

1-(3-{[2-(dimethylamino)ethyl](methyl)amino}phenyl)-5-{[1-(4-fluorobenzoyl)-4-hydroxypiperidin-4-yl]methyl)-1H,4H,5H-pyrazolo[3,4-d]pyrimidin-4-one;

1-[4-fluoro-3-(piperazin-1-yl)phenyl]-5-{[1-(4-fluorobenzoyl)-4-hydroxypiperidin-4-yl]methyl}-1H,4H,5H-pyrazolo[3,4-d]pyrimidin-4-one;

5-{{1-[4,4-difluoro-3-(1H-pyrazol-1-yl)butanoyl]-4-hydroxypiperidin-4-yl}methyl)-1-[4-(4-methylpiperazin-1-yl)phenyl]-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl]-1-[4-(4-methylpiperazin-1-yl)phenyl]-1H,4H,5H-pyrazolo[3,4-d]pyrimidin-4-one;

5-{{1-[(3S)-4,4-difluoro-3-(1H-pyrazol-1-yl)butanoyl]-4-hydroxypiperidin-4-yl}methyl]-1-[4-(4-methylpiperazin-1-yl)phenyl]-1H,4H,5H-pyrazolo[3,4-d]pyrimidin-4-one;

5-{{1-[4,4-difluoro-3-(1H-pyrazol-1-yl)butanoyl]-4-hydroxypiperidin-4-yl}methyl)-1-[3-(4-methylpiperazin-1-yl)phenyl]-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl)-1-[3-(4-methylpiperazin-1-yl)phenyl]-1H,4H,5H-pyrazolo[3,4-d]pyrimidin-4-one;

2-(2-{4-[4-hydroxy-4-({1-methyl-4-oxo-1H,4H,5H-pyrazolo[3,4-d]pyrimidin-5-yl}methyl)piperidine-1-carbonyl]phenyl}phenyl)acetonitrile;

5-{{1-[(3S)-4,4-difluoro-3-(1H-pyrazol-1-yl)butanoyl]-4-hydroxypiperidin-4-yl}methyl)-1-[3-(4-methylpiperazin-1-yl)phenyl]-1H,4H,5H-pyrazolo[3,4-d]pyrimidin-4-one;

5-{{4-hydroxy-1-[1-(prop-2-enoyl)azetidine-2-carbonyl]piperidin-4-yl}methyl)-1-[3-(4-methylpiperazin-1-yl)phenyl]-1H,4H,5H-pyrazolo[3,4-d]pyrimidin-4-one;

5-{{4-hydroxy-1-[1-(prop-2-enoyl)azetidine-2-carbonyl]piperidin-4-yl}methyl)-1-[4-(4-methylpiperazin-1-yl)phenyl]-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl)-1-{4-[(3S)-3-hydroxy-3-methylpyrrolidin-1-yl]phenyl}-1H,4H,5H-pyrazolo[3,4-d]pyrimidin-4-one;

5-{{1-[(3R)-4,4-difluoro-3-(1H-pyrazol-1-yl)butanoyl]-4-hydroxypiperidin-4-yl}methyl)-1-{4-[(3R)-3-hydroxy-3-methylpyrrolidin-1-yl]phenyl}-1H,4H,5H-pyrazolo[3,4-d]pyrimidin-4-one;

5-{{1-[(3S)-4,4-difluoro-3-(1H-pyrazol-1-yl)butanoyl]-4-hydroxypiperidin-4-yl}methyl)-1-{4-[(3S)-3-hydroxy-3-methylpyrrolidin-1-yl]phenyl}-1H,4H,5H-pyrazolo[3,4-d]pyrimidin-4-one;

5-{{1-[(3S)-4,4-difluoro-3-(1H-pyrazol-1-yl)butanoyl]-4-hydroxypiperidin-4-yl}methyl)-1-{4-[(3R)-3-hydroxy-3-methylpyrrolidin-1-yl]phenyl}-1H,4H,5H-pyrazolo[3,4-d]pyrimidin-4-one;

5-{{4-hydroxy-1-[(3S)-3-(1H-pyrazol-1-yl)butanoyl]piperidin-4-yl}methyl)-1-{4-[(3S)-3-hydroxy-3-methylpyrrolidin-1-yl]phenyl)-1H,4H,5H-pyrazolo[3,4-d]pyrimidin-4-one;

5-{{4-hydroxy-1-[(3S)-3-(1H-pyrazol-1-yl)butanoyl]piperidin-4-yl}methyl)-1-{4-[(3R)-3-hydroxy-3-methylpyrrolidin-1-yl]phenyl)-1H,4H,5H-pyrazolo[3,4-d]pyrimidin-4-one;

5-{{4-hydroxy-1-[(3R)-3-(1H-pyrazol-1-yl)butanoyl]piperidin-4-yl}methyl)-1-{4-[(3S)-3-hydroxy-3-methylpyrrolidin-1-yl]phenyl)-1H,4H,5H-pyrazolo[3,4-d]pyrimidin-4-one;

1-(2-{4-[4-hydroxy-4-({1-methyl-4-oxo-1H,4H,5H-pyrazolo[3,4-d]pyrimidin-5-yl}methyl)piperidine-1-carbonyl]phenyl}phenyl)cyclopropane-1-carbonitrile;

5-{{4-hydroxy-1-[(3R)-3-(1H-pyrazol-1-yl)butanoyl]piperidin-4-yl}methyl)-1-{4-[(3R)-3-hydroxy-3-methylpyrrolidin-1-yl]phenyl)-1H,4H,5H-pyrazolo[3,4-d]pyrimidin-4-one;

5-[(1-cyclopropanecarbonyl-4-hydroxypiperidin-4-yl)methyl]-1-(4-[4-[(3S)-pyrrolidin-3-yloxy]phenyl]phenyl)-1H,4H,5H-pyrazolo[3,4-d]pyrimidin-4-one;

5-[(1-cyclopropanecarbonyl-4-hydroxypiperidin-4-yl)methyl]-1-(4-[4-[(3R)-pyrrolidin-3-yloxy]phenyl]phenyl)-1H,4H,5H-pyrazolo[3,4-d]pyrimidin-4-one;

5-{(1-(cyclopropanecarbonyl)-4-hydroxypiperidin-4-yl}methyl)-1-(4-(piperidin-4-yl)phenyl)-1H-pyrazolo[3,4-d]pyrimidin-4(5H)-one;

5-[(1-cyclopropanecarbonyl-4-hydroxypiperidin-4-yl)methyl]-1-{4-[4-(4-methylpiperazin-1-yl)phenyl]phenyl)-1H,4H,5H-pyrazolo[3,4-d]pyrimidin-4-one;

5-[(1-cyclopropanecarbonyl-4-hydroxypiperidin-4-yl)methyl]-1-(4-{6-[3-(methylamino)pyrrolidin-1-yl]pyridin-3-yl}phenyl)-1H,4H,5H-pyrazolo[3,4-d]pyrimidin-4-one;

1-(4-cyclobutylphenyl)-5-{[4-hydroxy-1-(2-methyl-1,3-oxazole-5-carbonyl)piperidin-4-yl]methyl}-1H,4H,5H-pyrazolo[3,4-d]pyrimidin-4-one;

1-(4-cyclobutylphenyl)-5-{[1-(2-cyclopropyl-1,3-oxazole-5-carbonyl)-4-hydroxypiperidin-4-yl]methyl-1H,4H,5H-pyrazolo[3,4-d]pyrimidin-4-one;

3-{[1-(2-cyclopropyl-1,3-oxazole-5-carbonyl)-4-hydroxypiperidin-4-yl]methyl}-7-(4-fluorophenyl)-3H,4H,7H-pyrrolo[2,3-d]pyrimidin-4-one;

5-{{1-[4-(4-chlorophenoxy)benzoyl]-4-hydroxypiperidin-4-yl}methyl)-1-methyl-1H,4H,5H-pyrazolo[3,4-d]pyrimidin-4-one;

3-({1-[2-(cyclopropyl-1,3-oxazole-5-carbonyl)-4-hydroxypiperidin-4-yl]methyl}-7-(4-fluorophenyl)-6-methyl-3H,4H,7H-pyrrolo[2,3-d]pyrimidin-4-one;

5-{(1-[4-(difluoromethoxy)benzoyl]-4-hydroxypiperidin-4-yl}methyl)-1-[4-(hydroxymethyl)phenyl]-1H,4H,5H-pyrazolo[3,4-d]pyrimidin-4-one;

5-{(4-hydroxy-1-[(1r,4r)-4-(pyridin-2-yloxy)cyclohexanecarbonyl]piperidin-4-yl}methyl)-1-[4-(hydroxymethyl)phenyl]-1H,4H,5H-pyrazolo[3,4-d]pyrimidin-4-one;

5-{(4-hydroxy-1-[(1s,4s)-4-(pyridin-2-yloxy)cyclohexanecarbonyl]piperidin-4-yl}methyl)-1-[4-(hydroxymethyl)phenyl]-1H,4H,5H-pyrazolo[3,4-d]pyrimidin-4-one;

1-[4-(azetidin-1-ylmethyl)phenyl]-5-({1-[(3S)-4,4-difluoro-3-(1H-pyrazol-1-yl)butanoyl]-4-hydroxypiperidin-4-yl}methyl)-1H,4H,5H-pyrazolo[3,4-d]pyrimidin-4-one;

1-[4-(azetidin-1-ylmethyl)phenyl]-5-({1-[(3R)-4,4-difluoro-3-(1H-pyrazol-1-yl)butanoyl]-4-hydroxypiperidin-4-yl}methyl)-1H,4H,5H-pyrazolo[3,4-d]pyrimidin-4-one;

5-[(1-cyclopropanecarbonyl-4-hydroxypiperidin-4-yl)methyl]-1-[3-[2-(dimethylamino)ethoxy]-4-phenylphenyl]-1H,4H,5H-pyrazolo[3,4-d]pyrimidin-4-one;

5-{(1-[4-(4-fluorophenoxy)benzoyl]-4-hydroxypiperidin-4-yl}methyl)-1-methyl-1H,4H,5H-pyrazolo[3,4-d]pyrimidin-4-one;

5-{(4-hydroxy-1-[(3S)-4,4,4-trifluoro-3-phenylbutanoyl]piperidin-4-yl}methyl)-1-methyl-1H,4H,5H-pyrazolo[3,4-d]pyrimidin-4-one;

5-{(1-[4-(4-bromophenoxy)benzoyl]-4-hydroxypiperidin-4-yl}methyl)-1-methyl-1H,4H,5H-pyrazolo[3,4-d]pyrimidin-4-one;

5-{(4-hydroxy-1-[4-(4-hydroxyphenoxy)benzoyl]piperidin-4-yl}methyl)-1-methyl-1H,4H,5H-pyrazolo[3,4-d]pyrimidin-4-one;

5-{{4-hydroxy-1-[4-(3-hydroxyphenoxy)benzoyl]piperidin-4-yl}methyl)-1-methyl-1H,4H,5H-pyrazolo[3,4-d]pyrimidin-4-one;

5-[(4-hydroxy-1-{4-[(pyrimidin-2-yloxy)methyl]benzoyl}piperidin-4-yl)methyl]-1-methyl-1H,4H,5H-pyrazolo[3,4-d]pyrimidin-4-one;

5-{{1-[4-(3-chlorophenoxy)benzoyl]-4-hydroxypiperidin-4-yl}methyl)-1-methyl-1H,4H,5H-pyrazolo[3,4-d]pyrimidin-4-one;

5-{(1-[4-(3-bromophenoxy)benzoyl]-4-hydroxypiperidin-4-yl}methyl)-1-methyl-1H,4H,5H-pyrazolo[3,4-d]pyrimidin-4-one;

1-(1-cyclopropyl-1H-pyrazol-4-yl)-5-{[1-(4-fluorobenzoyl)-4-hydroxypiperidin-4-yl]methyl}-1H,4H,5H-pyrazolo[3,4-d]pyrimidin-4-one;

1-(4-fluorophenyl)-5-({4-hydroxy-1-[4-(5-methyl-1,3,4-oxadiazol-2-yl)benzoyl]piperidin-4-yl}methyl)-1H,4H,5H-pyrazolo[3,4-d]pyrimidin-4-one;

1-(4-fluorophenyl)-5-({4-hydroxy-1-[(3S)-4,4,4-trifluoro-3-(1H-pyrazol-1-yl)butanoyl]piperidin-4-yl}methyl)-1H,4H,5H-pyrazolo[3,4-d]pyrimidin-4-one;

1-(4-fluorophenyl)-5-({4-hydroxy-1-[(3R)-4,4,4-trifluoro-3-(1H-pyrazol-1-yl)butanoyl]piperidin-4-yl}methyl)-1H,4H,5H-pyrazolo[3,4-d]pyrimidin-4-one;

1-(4-fluorophenyl)-5-({4-hydroxy-1-[2-(4-hydroxypiperidin-1-yl)-1,3-oxazole-5-carbonyl]piperidin-4-yl}methyl)-1H,4H,5H-pyrazolo[3,4-d]pyrimidin-4-one;

5-{{4-hydroxy-1-[2-(4-hydroxypiperidin-1-yl)-1,3-oxazole-5-carbonyl]piperidin-4-yl}methyl)-1-(4-phenylphenyl)-1H,4H,5H-pyrazolo[3,4-d]pyrimidin-4-one;

5-{{4-hydroxy-1-[(1r,3r)-3-(pyridin-2-yloxy)cyclobutanecarbonyl]piperidin-4-yl}methyl)-1-(4-methylphenyl)-1H,4H,5H-pyrazolo[3,4-d]pyrimidin-4-one;

5-{(1-[(3S)-4,4-difluoro-3-(4-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one;

1-(4-chlorophenyl)-5-((4-hydroxy-1-[4-(4H-1,2,4-triazol-4-yl)benzoyl]piperidin-4-yl}methyl)-1H,4H,5H-pyrazolo[3,4-d]pyrimidin-4-one;

5-{[4-hydroxy-1-(4-{[5-(trifluoromethyl)pyridin-2-yl]oxy)benzoyl}piperidin-4-yl]methyl}-1-methyl-1H,4H,5H-pyrazolo[3,4-d]pyrimidin-4-one;

1-(4-chlorophenyl)-5-[(4-hydroxy-1-{6-[(1-methylpyrrolidin-3-yl)oxy]pyridine-3-carbonyl)piperidin-4-yl)methyl]-1H,4H,5H-pyrazolo[3,4-d]pyrimidin-4-one;

1-(4-fluorophenyl)-5-({4-hydroxy-1-[1-methyl-3-(1H-pyrazol-1-ylmethyl)-1H-pyrazole-4-carbonyl]piperidin-4-yl}methyl)-1H,4H,5H-pyrazolo[3,4-d]pyrimidin-4-one;

1-(4-fluorophenyl)-5-[(4-hydroxy-1-{4-[(5-methyl-1,2-oxazol-3-yl)oxy]piperidine-1-carbonyl}piperidin-4-yl)methyl]-1H,4H,5H-pyrazolo[3,4-d]pyrimidin-4-one;

1-(4-fluorophenyl)-5-[(4-hydroxy-1-{4-[(1-methyl-1H-pyrazol-4-yl)oxy]piperidine-1-carbonyl}piperidin-4-yl)methyl]-1H,4H,5H-pyrazolo[3,4-d]pyrimidin-4-one;

N-[(1r,4r)-4-(4-{[1-(4-fluorophenyl)-4-oxo-1H,4H,5H-pyrazolo[3,4-d]pyrimidin-5-yl]methyl}-4-hydroxypiperidine-1-carbonyl)cyclohexyl]acetamide;

1-(4-fluorophenyl)-5-({4-hydroxy-1-[(1s,4s)-4-(oxan-4-yloxy)cyclohexanecarbonyl]piperidin-4-yl}methyl)-1H,4H,5H-pyrazolo[3,4-d]pyrimidin-4-one;

1-(4-fluorophenyl)-5-({4-hydroxy-1-[(1r,4r)-4-(oxan-4-yloxy)cyclohexanecarbonyl]piperidin-4-yl}methyl)-1H,4H,5H-pyrazolo[3,4-d]pyrimidin-4-one;

4-{[1-(4-bromophenyl)-4-oxo-1H,4H,5H-pyrazolo[3,4-d]pyrimidin-5-yl]methyl}-4-hydroxy-N,N-dimethylpiperidine-1-carboxamide;

5-{{4-hydroxy-1-[4-(pyridin-3-yloxy)benzoyl]piperidin-4-yl}methyl)-1-methyl-1H,4H,5H-pyrazolo[3,4-d]pyrimidin-4-one;

5-{{4-hydroxy-1-[4-(4-methoxyphenoxy)benzoyl]piperidin-4-yl}methyl)-1-methyl-1H,4H,5H-pyrazolo[3,4-d]pyrimidin-4-one;

5-{{4-hydroxy-1-[4-(3-methylphenoxy)benzoyl]piperidin-4-yl}methyl)-1-methyl-1H,4H,5H-pyrazolo[3,4-d]pyrimidin-4-one;

N-[(1r,3r)-3-(4-{[1-(4-fluorophenyl)-4-oxo-1H,4H,5H-pyrazolo[3,4-d]pyrimidin-5-yl]methyl)-4-hydroxypiperidine-1-carbonyl)cyclobutyl]prop-2-ynamide;

N-[(1R,2S)-2-(4-{[1-(4-fluorophenyl)-4-oxo-1H,4H,5H-pyrazolo[3,4-d]pyrimidin-5-yl]methyl)-4-hydroxypiperidine-1-carbonyl)cyclobutyl]prop-2-ynamide;

N-[(1r,3r)-3-[2-(4-{[1-(4-fluorophenyl)-4-oxo-1H,4H,5H-pyrazolo[3,4-d]pyrimidin-5-yl]methyl)-4-hydroxypiperidin-1-yl)-2-oxoethyl]cyclobutyl]prop-2-ynamide;

4-{4-[4-hydroxy-4-({1-methyl-4-oxo-1H,4H,5H-pyrazolo[3,4-d]pyrimidin-5-yl}methyl)piperidine-1-carbonyl]phenoxy)benzonitrile;

1-(3-aminophenyl)-5-((1-(cyclopropanecarbonyl)-4-hydroxypiperidin-4-yl}methyl)-1H-pyrazolo[3,4-d]pyrimidin-4(5H)-one;

1-(4-aminophenyl)-5-[(1-cyclopropanecarbonyl)-4-hydroxypiperidin-4-yl)methyl]-1H,4H,5H-pyrazolo[3,4-d]pyrimidin-4-one;

4-((1-(4-fluoro-3-(piperazin-1-yl)phenyl)-4-oxo-1H-pyrazolo[3,4-d] pyrimidin-5(4H)-yl}methyl)-4-hydroxy-N,N-dimethylpiperidine-1-carboxamide;

4-hydroxy-N,N-dimethyl-4-({4-oxo-1-[4-(piperazin-1-yl)phenyl]-1H,4H,5H-pyrazolo[3,4-d]pyrimidin-5-yl}methyl)piperidine-1-carboxamide;

4-[(1-{4-[(3R,4R)-3-fluoro-4-hydroxypyrrolidin-1-yl]phenyl)-4-oxo-1H,4H,5H-pyrazolo[3,4-d]pyrimidin-5-yl)methyl]-4-hydroxy-N,N-dimethylpiperidine-1-carboxamide;

1-[4-chloro-3-(morpholin-4-yl)phenyl]-5-{[1-(4-fluorobenzoyl)-4-hydroxypiperidin-4-yl]methyl}-1H,4H,5H-pyrazolo[3,4-d]pyrimidin-4-one;

5-{{1-[4-(3,4-dimethylphenoxy)benzoyl]-4-hydroxypiperidin-4-yl}methyl)-1-methyl-1H,4H,5H-pyrazolo[3,4-d]pyrimidin-4-one;

5-[(1-benzoyl-4-hydroxypiperidin-4-yl)methyl]-1-[3-fluoro-4-(4-methylpiperazin-1-yl)phenyl]-1H,4H,5H-pyrazolo[3,4-d]pyrimidin-4-one;

5-[(1-cyclopropanecarbonyl-4-hydroxypiperidin-4-yl)methyl]-1-{4-fluoro-3-[(3S)-3-methoxy-3-methylpyrrolidin-1-yl]phenyl)-1H,4H,5H-pyrazolo[3,4-d]pyrimidin-4-one;

5-[(1-cyclopropanecarbonyl-4-hydroxypiperidin-4-yl)methyl]-1-{4-fluoro-3-[(3R)-3-methoxy-3-methylpyrrolidin-1-yl]phenyl)-1H,4H,5H-pyrazolo[3,4-d]pyrimidin-4-one;

5-{5-[(1-cyclopropanecarbonyl-4-hydroxypiperidin-4-yl)methyl]-4-oxo-1H,4H,5H-pyrazolo[3,4-d]pyrimidin-1-yl)-2-(4-methylpiperazin-1-yl)benzonitrile;

4-((1-(3-((3R,4R)-3-fluoro-4-hydroxypyrrolidin-1-yl)phenyl)-4-oxo-1H-pyrazolo[3,4-d]pyrimidin-5(4H)-yl}methyl)-4-hydroxy-N,N-dimethylpiperidine-1-carboxamide;

5-[(1-cyclopropanecarbonyl-4-hydroxypiperidin-4-yl)methyl]-1-{4-[4-(4-methylpiperazin-1-yl]-1H-pyrazol-1-yl]phenyl)-1H,4H,5H-pyrazolo[3,4-d]pyrimidin-4-one;

5-{[1-(4-fluorobenzoyl)-4-hydroxypiperidin-4-yl]methyl}-1-(4-{2H,4H,6H,7H-pyrano[4,3-c]pyrazol-2-yl)phenyl)-1H,4H,5H-pyrazolo[3,4-d]pyrimidin-4-one;

5-[(1-cyclopropanecarbonyl-4-hydroxypiperidin-4-yl)methyl]-1-{4-[4-(2-hydroxyethoxy)-1H-pyrazol-1-yl]phenyl)-1H,4H,5H-pyrazolo[3,4-d]pyrimidin-4-one;

5-[(1-cyclopropanecarbonyl-4-hydroxypiperidin-4-yl)methyl]-1-{4-[3-(morpholin-4-yl)-1H-pyrazol-1-yl]phenyl)-1H,4H,5H-pyrazolo[3,4-d]pyrimidin-4-one;

5-[(1-cyclopropanecarbonyl-4-hydroxypiperidin-4-yl)methyl]-1-(4-hydroxyphenyl)-1H,4H,5H-pyrazolo[3,4-d]pyrimidin-4-one;

5-{[1-(2-cyclopropyl-1,3-oxazole-5-carbonyl)-4-hydroxypiperidin-4-yl]methyl}-1-{4-[(1-fluorocyclobutyl)methoxy]phenyl)-1H,4H,5H-pyrazolo[3,4-d]pyrimidin-4-one;

5-{(1-(4-fluorobenzoyl)-4-hydroxypiperidin-4-yl}methyl)-1-(4-((1-hydroxycyclobutyl)methoxy)phenyl)-1H-pyrazolo[3,4-d]pyrimidin-4(5H)-one;

5-{(1-(4-fluorobenzoyl)-4-hydroxypiperidin-4-yl}methyl)-1-(4-(2-methyl-1H-imidazol-4-yl)phenyl)-1H-pyrazolo[3,4-d]pyrimidin-4(5H)-one;

1-[4-(1,5-dimethyl-1H-imidazol-2-yl)phenyl]-5-([1-[(4-fluorophenyl)carbonyl]-4-hydroxypiperidin-4-yl]methyl)-1H,4H,5H-pyrazolo[3,4-d]pyrimidin-4-one;

5-{(1-(2-Cyclopropyloxazole-5-carbonyl)-4-hydroxypiperidin-4-yl) methyl)-1-(4-(pyridin-3-yl)phenyl)-1H-pyrazolo[3,4-d]pyrimidin-4(5H)-one;

5-{[1-[(4-fluorophenyl)carbonyl]-4-hydroxypiperidin-4-yl]methyl) -1-[4-(4-methyl-1H-imidazol-1-yl)phenyl]-1H,4H,5H-pyrazolo[3,4-d]pyrimidin-4-one;

5-{[1-(4-fluorobenzoyl)-4-hydroxypiperidin-4-yl]methyl}-1-[4-(2-methyl-1H-imidazol-1-yl)phenyl]-1H,4H,5H-pyrazolo[3,4-d]pyrimidin-4-one;

5-{(1-(4-(difluoromethoxy)benzoyl)-4-hydroxypiperidin-4-yl}methyl) -1-(3-(hydroxymethyl)phenyl)-1H-pyrazolo[3,4-d]pyrimidin-4(5H)-one;

5-{[1-(3-cyclopropyl-3-phenylpropanoyl)-4-hydroxypiperidin-4-yl]methyl}-1-methyl-1H,4H,5H-pyrazolo[3,4-d]pyrimidin-4-one;

1-(4-fluoro-3-(hydroxymethyl)phenyl)-5-((4-hydroxy-1-(4-(pyrimidin-2-yloxy)benzoyl)piperidin-4-yl}methyl)-1H-pyrazolo[3,4-d]pyrimidin-4(5H)-one;

4-hydroxy-4-((1-(4-(1-isopropylpiperidin-4-yl)phenyl)-4-oxo-1H-pyrazolo[3,4-d]pyrimidin-5(4H)-yl}methyl)-N,N-dimethylpiperidine-1-carboxamide;

5-{[1-(4-fluorobenzoyl)-4-hydroxypiperidin-4-yl]methyl}-1-[3-(piperidin-4-yl)phenyl]-1H,4H,5H-pyrazolo[3,4-d]pyrimidin-4-one;

4-hydroxy-N,N-dimethyl-4-({4-oxo-1-[4-(piperidin-4-yl)phenyl]-1H,4H,5H-pyrazolo[3,4-d]pyrimidin-5-yl}methyl)piperidine-1-carboxamide;

(R)-5-((1-(4-fluorobenzoyl)-4-hydroxypiperidin-4-yl}methyl)-1-(4-(methylsulfinyl)phenyl)-1H-pyrazolo[3,4-d]pyrimidin-4(5H)-one;

(S)-5-((1-(4-fluorobenzoyl)-4-hydroxypiperidin-4-yl}methyl)-1-(4-(methylsulfinyl)phenyl)-1H-pyrazolo[3,4-d]pyrimidin-4(5H)-one;

5-{(1-(4-fluorobenzoyl)-4-hydroxypiperidin-4-yl}methyl)-1-(4-(methylsulfinyl)phenyl)-1H-pyrazolo[3,4-d]pyrimidin-4(5H)-one;

(S)-5-((1-(4-fluorobenzoyl)-4-hydroxypiperidin-4-yl}methyl)-1-(4-(S-methylsulfonimidoyl) phenyl)-1,5-dihydro-4H-pyrazolo[3,4-d]pyrimidin-4-one;

(R)-5-((1-(4-fluorobenzoyl)-4-hydroxypiperidin-4-yl}methyl)-1-(4-(S-methylsulfonimidoyl) phenyl)-1,5-dihydro-4H-pyrazolo[3,4-d]pyrimidin-4-one;

5-{(1-(4-fluorobenzoyl)-4-hydroxypiperidin-4-yl}methyl)-1-(4-(S-methylsulfonimidoyl)phenyl)-1,5-dihydro-4H-pyrazolo[3,4-d]pyrimidin-4-one; and 1-[4-[(4-{[1-(4-fluorophenyl)-4-oxo-1H,4H,5H-pyrazolo[3,4-d]pyrimidin-5-yl]methyl}-4-hydroxypiperidin-1-yl)carbonyl]phenyl]-1H-pyrazole-4-carboxylic acid;

or a pharmaceutically acceptable salt thereof.

11. The method of claim 10, wherein the compound is 1-(4-(3,3-difluorocyclobutoxy)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one, or a pharmaceutically acceptable salt thereof.

12. The method of claim 10, wherein the compound is:
- 1-(4-(1-(difluoromethyl)-1H-pyrazol-4-yl)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;
- 1-(4-((3,3-difluoro-1-methylcyclobutyl)methoxy)phenyl)-5-((4-hydroxy-1-(1-methylcyclopropane-1-carbonyl)piperidin-4-yl}methyl)-1,5-dihydro-4H-pyrazolo[3,4-d]pyrimidin-4-one;
- 1-[4-(3-fluoro-1H-pyrazol-1-yl)phenyl]-5-{[4-hydroxy-1-(1-methylcyclopropanecarbonyl) piperidin-4-yl]methyl)-1H,4H,5H-pyrazolo[3,4-d]pyrimidin-4-one; or
- 1-[4-(5-([4-hydroxy-1-(1-methylcyclopropanecarbonyl) piperidin-4-yl]methyl)-4-oxo-1H,4H,5H-pyrazolo[3,4-d]pyrimidin-1-yl)phenyl]piperidine-4-carbonitrile;

or a pharmaceutically acceptable salt thereof.

13. The method of claim 10, wherein the compound is 5-((1-(1-acryloylazetidine-2-carbonyl)-4-hydroxypiperidin-4-yl) methyl)-1-(biphenyl-4-yl}-1H-pyrazolo[3,4-d]pyrimidin-4 (5H)-one, or a pharmaceutically acceptable salt thereof.

14. The method of claim 10, wherein the compound is:
N-(2-(4-[4-hydroxy-4-({1-methyl-4-oxo-1H,4H,5H-pyrazolo[3,4-d]pyrimidin-5-yl}methyl)piperidine-1-carbonyl]phenyl)phenyl)ethene-1-sulfonamide, or a pharmaceutically acceptable salt thereof.

15. The method of claim 10, wherein the compound is 5-((1-[(3S)-4,4-difluoro-3-(3-fluoro-1H-pyrazol-1-yl)butanoyl]-4-hydroxypiperidin-4-yl}methyl)-1-(4-fluorophenyl)-1H,4H,5H-pyrazolo[3,4-d]pyrimidin-4-one, or a pharmaceutically acceptable salt thereof.

16. The method of claim 10, wherein the compound is 1-(4-fluorophenyl)-5-((4-hydroxy-1-[(1r,4r)-4-[(1-methyl-1H-pyrazol-3-yl)oxy]cyclohexanecarbonyl]piperidin-4-yl}methyl)-1H,4H,5H-pyrazolo[3,4-d]pyrimidin-4-one, or a pharmaceutically acceptable salt thereof.

\* \* \* \* \*

UNITED STATES PATENT AND TRADEMARK OFFICE
CERTIFICATE OF CORRECTION

PATENT NO. : 12,018,030 B2
APPLICATION NO. : 17/186915
DATED : June 25, 2024
INVENTOR(S) : Stephanos Ioannidis et al.

Page 1 of 1

It is certified that error appears in the above-identified patent and that said Letters Patent is hereby corrected as shown below:

In the Claims

Claim 1, Column 309, Line 44, delete "R1 is OH" and insert --R1 is –OH--

Claim 1, Column 310, Line 20, delete "–S(O)gNR10R11" and insert -- –S(O)qNR10R11--

Claim 1, Column 310, Line 59, delete "–S(O)gNR14R15" and insert -- –S(O)qNR14R15--

Claim 5, Column 312, Line 51, delete "wherein R7 is H (C1-C6) or aryl." and insert --wherein R7 is H, (C1-C6), alkyl, or aryl.--

Signed and Sealed this
Twenty-seventh Day of August, 2024

Katherine Kelly Vidal
*Director of the United States Patent and Trademark Office*